US008193183B2

(12) United States Patent
Lim et al.

(10) Patent No.: US 8,193,183 B2
(45) Date of Patent: Jun. 5, 2012

(54) 2,6-SUBSTITUTED-4-MONOSUBSTITUTEDAMINO-PYRIMIDINE AS PROSTAGLANDIN D2 RECEPTOR ANTAGONISTS

(75) Inventors: Sungtaek Lim, Flemington, NJ (US); Keith John Harris, Chester, NJ (US); David Stefany, Hillsborough, NJ (US); Charles J. Gardner, Royersford, PA (US); Bin Cao, Bedminster, NJ (US); Ray Boffey, Harlow (GB); Timothy A. Gillespy, Hillsborough, NJ (US); Joacy C. Aguiar, Newark, NJ (US); Hazel J. Dyke, Harlow (GB); Elsa A. Dechaux, Harlow (GB)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 1011 days.

(21) Appl. No.: 11/735,751

(22) Filed: Apr. 16, 2007

(65) Prior Publication Data

US 2007/0244131 A1    Oct. 18, 2007

Related U.S. Application Data

(63) Continuation of application No. PCT/US2005/037148, filed on Oct. 14, 2005.

(60) Provisional application No. 60/619,272, filed on Oct. 15, 2004.

(51) Int. Cl.
| | |
|---|---|
| C07D 239/47 | (2006.01) |
| C07D 413/12 | (2006.01) |
| A61K 31/505 | (2006.01) |
| A61K 31/5355 | (2006.01) |
| A61P 37/00 | (2006.01) |
| A61P 37/08 | (2006.01) |
| A61P 17/00 | (2006.01) |

(52) U.S. Cl. .................... 514/235.8; 514/274; 544/123; 544/317

(58) Field of Classification Search .................. 544/310, 544/312, 317, 319, 328, 326; 514/274, 269, 514/256

See application file for complete search history.

(56) References Cited

U.S. PATENT DOCUMENTS

| | | | | |
|---|---|---|---|---|
| 3,503,963 | A | * | 3/1970 | Schweizer .................... 544/296 |
| 3,624,084 | A | * | 11/1971 | Mathieu .................... 544/326 |
| 6,169,086 | B1 | | 1/2001 | Ejima et al. |
| 6,380,263 | B1 | | 4/2002 | Pruche et al. |
| 7,183,313 | B2 | | 2/2007 | Makriyannis et al. |
| 2003/0187007 | A1 | | 10/2003 | Cao et al. |
| 2004/0087590 | A1 | | 5/2004 | Makriyannis et al. |
| 2007/0155701 | A1 | | 7/2007 | Makriyannis et al. |
| 2008/0194600 | A1 | | 8/2008 | Langevin |

FOREIGN PATENT DOCUMENTS

| | | |
|---|---|---|
| DE | 4031798 | 4/1992 |
| GB | 1143167 | 2/1969 |
| WO | WO 99/50251 | 10/1999 |
| WO | WO 0105783 | * 1/2001 |
| WO | WO 01/58871 | 8/2001 |
| WO | WO 02/08186 | 1/2002 |
| WO | WO 02092090 | * 11/2002 |
| WO | WO 03/031406 | 4/2003 |
| WO | WO 03/062200 | 7/2003 |
| WO | WO 2005092899 | * 3/2004 |
| WO | WO 2005095400 | * 3/2004 |
| WO | WO 2004/043926 | 5/2004 |
| WO | WO 2004043926 | * 5/2004 |
| WO | WO 2006034473 | * 9/2004 |
| WO | WO 2006058074 | * 11/2004 |
| WO | WO 2005/011758 | 2/2005 |
| WO | WO 2006100212 | * 3/2005 |
| WO | WO 2007047378 | * 10/2005 |

OTHER PUBLICATIONS

Wikipedia, Esters, 2010.*
Tullos, et al., Macromolecul., 1999, 32, 3598-3612.*
Zeng, et al., Europ. Polymer J., 45 #4, Apr. 2009, 1328-1335.*

(Continued)

*Primary Examiner* — James O Wilson
*Assistant Examiner* — Cecilia M Jaisle
(74) *Attorney, Agent, or Firm* — Ronald G. Ort

(57) ABSTRACT

The present invention is directed to a compound of Formula (I)

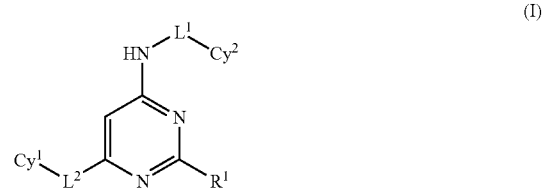

(I)

wherein $Cy^1$, $Cy^2$, $L^1$, $L^2$, and $R^1$ are as defined herein, a pharmaceutical composition comprising a pharmaceutically effective amount of one or more compounds according to Formula (I) in admixture with a pharmaceutically acceptable carrier, and a method of treating a patient suffering from a PGD2-mediated disorder including, but not limited to, allergic disease (such as allergic rhinitis, allergic conjunctivitis, atopic dermatitis, bronchial asthma and food allergy), systemic mastocytosis, disorders accompanied by systemic mast cell activation, anaphylaxis shock, bronchoconstriction, bronchitis, urticaria, eczema, diseases accompanied by itch (such as atopic dermatitis and urticaria), diseases (such as cataract, retinal detachment, inflammation, infection and sleeping disorders) which is generated secondarily as a result of behavior accompanied by itch (such as scratching and beating), inflammation, chronic obstructive pulmonary diseases, ischemic reperfusion injury, cerebrovascular accident, chronic rheumatoid arthritis, pleurisy, ulcerative colitis and the like by administering to said patient a pharmaceutically effective amount of a compound according to Formula (I).

40 Claims, No Drawings

OTHER PUBLICATIONS

Parshikov, et al., Chem. Het. Compounds, vol. 28, #2, 159-162, 1992.*

Arimura, et al., Prevention of Allergic Inflammation by a Novel Prostaglandin Receptor Antagonist, S-5751, The Journal of Pharmacology and Experimental Therapeutics, (2001) vol. 298, No. 2.

Ding, et al., N4-(4-methoxy-benzyl)-6-(3-methoxy-phenyl)-pyrimidine-2,4-diamine, Database Beilstein, BRNs 9073007, 9075686, 2002.

Kabashima, K., et al., The DP receptor, allergic inflammation and asthma, Prostaglandins, Leukotrienes and Essential Fatty Actids 69 (2003) 187-194.

Ma, Y., et al., Combinatorial Synthesis of Substituted Biaryls and Heterocyclic Arylamines, J. Comb. Chem. 2004, 6, 426-430.

Trantolo, et al., Inhibitors of *Bacillus subtilis* DNA Polymerase III. Influence of Modifications in the Pyrimidine Ring of Anilino-and (Benzylamino) pyrimidines, J. Med. Chem. (1986) 29, 676-681.

Ulrich, Crystallization: 4. Crystal Characteristics, Kirk-Othmer Encyclopedia of Chemical Technology, Aug. 2002.

Vippagunta, et al., Crystalline Solids, Advanced Drug Delivery Reviews 48 (2001) 3-26.

Vishwakarma, J., et al., Reactions of Polarized Keten S, N-Acetals with Guanidine: A Facile General Route to Novel 5,6-Substituted 2-Amino-4-N-alkyl/aryl/N-azacycloalkylaminopyrimidines, Indian Journal of Chemistry, (1985), vol. 24B, pp. 466-471.

Wade, J., et al., Suzuki Cross-Coupling of Solid-Supported Chloropyrimidines with Arylboronic Acids, J. Comb. Chem. 2003, 5, 267-272.

West, Solid Solutions, Chapter 10, pp. 358 and 365, 1998.

Ding, et. al., A Combinatorial Scaffold Approach toward Kinase-Directed Heterocycle Libraries, J. Am. Chem. Soc., (2002) vol. 124, No. 8 pp. 1594-1596.

* cited by examiner

2,6-SUBSTITUTED-4-MONOSUBSTITUTEDAMINO-PYRIMIDINE AS PROSTAGLANDIN D2 RECEPTOR ANTAGONISTS

This application is a Continuation of International Application No. PCT/US2005/037148, filed Oct. 14, 2005, which claims the benefit of U.S. Provisional Application No. 60/619,272, filed Oct. 15, 2004 now expired.

FIELD OF THE INVENTION

The present invention is directed to pyrimidine compounds, their preparation, pharmaceutical compositions containing these compounds, and their pharmaceutical use in the treatment of disease states capable of being modulated by the inhibition of prostaglandin D2 receptor.

BACKGROUND OF THE INVENTION

Local allergen challenge in patients with allergic rhinitis, bronchial asthma, allergic conjunctivitis and atopic dermatitis as been shown to result in rapid elevation of prostaglandin D2 "(PGD2)" levels in nasal and bronchial lavage fluids, tears and skin chamber fluids. PGD2 has many inflammatory actions, such as increasing vascular permeability in the conjunctiva and skin, increasing nasal airway resistance, airway narrowing and eosinophil infiltration into the conjunctiva and trachea.

PGD2 is the major cyclooxygenase product of arachidonic acid production from mast cells on immunological challenge [Lewis, R A, Soter N A, Diamond P T, Austen K F, Oates J A, Roberts I. J II, prostaglandin D2 generation after activation of rat and human mast cells with anti-IgE, *J. Immunol.* 129, 1627-1631, 1982]. Activated mast cells, a major source of PGD2, are one of the key players in driving the allergic response in conditions such as asthma, allergic rhinitis, allergic conjunctivitis, allergic dermatitis and other diseases [Brightling C E, Bradding P, Pavord I D, Wardlaw A J, New Insights into the role of the mast cell in asthma, *Clin Exp Allergy* 33, 550-556, 2003].

Many of the actions of PGD2 are mediated through its action on the D-type prostaglandin ("DP") receptor, a G protein-coupled receptor expressed on epithelium and smooth muscle.

In asthma, the respiratory epithelium has long been recognized as a key source of inflammatory cytokines and chemokines that drive the progression of the disease [Holgate S, Lackie P, Wilson S, Roche W, Davies D, Bronchial Epithelium as a Key Regulator of Airway Allergen Sensisitzation and Remodelling in Asthma, *Am J Respir Crit Care Med.* 162, 113-117, 2000]. In an experimental murine model of asthma, the DP receptor is dramatically up-regulated on airway epithelium on antigen challenge [Matsuoka T, Hirata M, Tanaka H, Takahashi Y, Murata T, Kabashima K, Sugimoto Y, Kobayashi T, Ushikubi F, Aze Y, Eguchi N, Urade Y, Yoshida N, Kimura K, Mizoguchi A, Honda Y, Nagai H, Narumiya S, prostaglandin D2 as a mediator of allergic asthma, *Science* 287, 2013-2017, 2000]. In knockout mice, lacking the DP receptor, there is a marked reduction in airway hyperreactivity and chronic inflammation [Matsuoka T, Hirata M, Tanaka H, Takahashi Y, Murata T, Kabashima K, Sugimoto Y, Kobayashi T, Ushikubi F, Aze Y, Eguchi N, Urade Y, Yoshida N, Kimura K, Mizoguchi A, Honda Y, Nagai H, Narumiya S, Prostaglandin D2 as a mediator of allergic asthma, *Science* 287, 2013-2017, 2000]; two of the cardinal features of human asthma.

The DP receptor is also thought to be involved in human allergic rhinitis, a frequent allergic disease that is characterized by the symptoms of sneezing, itching, rhinorea and nasal congestion. Local administration of PGD2 to the nose causes a dose dependent increase in nasal congestion [Doyle W J, Boehm S, Skoner D P, Physiologic responses to intranasal dose-response challenges with histamine, methacholine, bradykinin, and prostaglandin in adult volunteers with and without nasal allergy, *J Allergy Clin Immunol.* 86(6 Pt 1), 924-35, 1990].

DP receptor antagonists have been shown to reduce airway inflammation in a guinea pig experimental asthma model [Arimura A, Yasui K, Kishino J, Asanuma F, Hasegawa H, Kakudo S, Ohtani M, Arita H (2001), Prevention of allergic inflammation by a novel prostaglandin receptor antagonist, S-5751, *J Pharmacol Exp Ther.* 298(2), 411-9, 2001]. PGD2, therefore appears to act on the DP receptor and plays an important role in elicitation of certain key features of allergic asthma.

DP antagonists have been shown to be effective at alleviating the symptoms of allergic rhinitis in multiple species, and more specifically have been shown to inhibit the antigen-induced nasal congestion, the most manifest symptom of allergic rhinitis [Jones, T. R., Savoie, C., Robichaud, A., Sturino, C., Scheigetz, J., Lachance, N., Roy, B., Boyd, M., Abraham, W., Studies with a DP receptor antagonist in sheep and guinea pig models of allergic rhinitis, *Am. J. Resp. Crit. Care Med.* 167, A218, 2003; and Arimura A, Yasui K, Kishino J, Asanuma F, Hasegawa H, Kakudo S, Ohtani M, Arita H Prevention of allergic inflammation by a novel prostaglandin receptor antagonist, S-5751. *J Pharmacol Exp Ther.* 298(2), 411-9, 2001].

DP antagonists are also effective in experimental models of allergic conjunctivitis and allergic dermatitis [Arimura A, Yasui K, Kishino J, Asanuma F, Hasegawa H, Kakudo S, Ohtani M, Arita H, Prevention of allergic inflammation by a novel prostaglandin receptor antagonist, S-5751. *J Pharmacol Exp Ther.* 298(2), 411-9, 2001; and Torisu K, Kobayashi K, Iwahashi M, Nakai Y, Onoda T, Nagase T, Sugimoto I, Okada Y, Matsumoto R, Nanbu F, Ohuchida S, Nakai H, Toda M, Discovery of a new class of potent, selective, and orally active prostaglandin $D_2$ receptor antagonists, *Bioorg. & Med. Chem.* 12, 5361-5378, 2004].

Applicants herein disclose a novel 2,6-substituted-4-monosubstitutedaminopyrimidine compound having valuable pharmaceutical properties; particularly the ability to associate with and regulate the DP receptor.

SUMMARY OF THE INVENTION

The present invention is directed to a 2,6-substituted-4-monosubstitutedamino-pyrimidine compound of Formula (I)

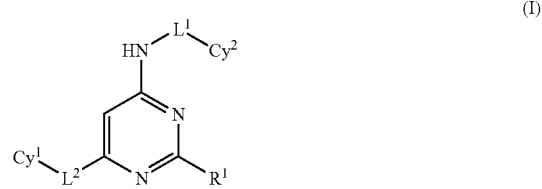

wherein:
(A) $Cy^1$ is cycloalkyl, heterocyclyl, cycloalkenyl, heterocyclenyl, heteroaryl, aryl, or multicyclic alkaryl, each of which is optionally substituted by one to three of same or different following $Cy^1$ substituent groups consisting of:

acyl, cyano, halogen, nitro, carboxy, hydroxy, alkylthio, alkylsulfonyl, alkylsulfinyl, cycloalkyl, heterocyclyl, cycloalkenyl, heterocyclenyl, aryl, heteroaryl, multicyclic alkaryl, aroyl, arylalkoxycarbonyl, arylalkylthio, aryloxy, aryloxycarbonyl, arylsulfinyl, arylsulfonyl, arylthio, heteroaryloxy, heteroarylalkoxycarbonyl, N-methoxysulfamoyl, $R^2$—C(=N—$OR^3$)—, $Y^1Y^2N$—, $Y^1Y^2NC$(=O)—, $Y^1Y^2NC$(=O)—O—, $Y^1Y^2NSO_2$—, alkyl-O—C(=O)—($C_2$-$C_6$)-alkylene-$Z^1$—, $Y^1Y^2N$—C(=O)—($C_1$-$C_6$)-alkylene-$Z^1$—, $Y^1Y^2N$—($C_2$-$C_6$)alkylene-$Z^1$—, alkyl-C(=O)—N($R^5$)—$SO_2$—, alkyl-O—C(=O)—N($R^5$)—, alkyl-O—C(=O)—N($R^5$)—$SO_2$—, alkyl-O—N($R^5$)—$SO_2$—, alkyl-O—N($R^5$)—C(=O)—, alkyl-$SO_2$—N($R^5$)—C(=O)—, aryl-$SO_2$—N($R^5$)—C(=O)—, alkyl-$SO_2$—N($R^5$)—, $R^6$—C(=O)—N($R^5$)—, $R^7$—NH—C(=O)—NH—;

alkenyl, which is optionally substituted by alkoxy or hydroxy;

alkoxycarbonyl, which is optionally substituted by $Y^1Y^2N$—;

alkynyl, which is optionally substituted by hydroxy or alkoxy;

alkyl, which is optionally substituted by one to three of same or different of halogen, carboxy, cyano, hydroxy, $Y^1Y^2N$—, $Y^1Y^2N$—C(=O)—, $H_2N$—C(=NH)—NH—O—, $R^6$—C(=O)—N($R^5$)—, alkyl-O—C(=O)—N($R^5$)—, alkyl-$SO_2$—N($R^5$)—, $R^8$—$SO_2$—N($R^5$)—C(=O)—, aryl-N($R^5$)—C(=O)—, heteroaryl-N($R^5$)—C(=O)—, heterocyclyl-N($R^5$)—C(=O)—, alkoxycarbonyl, cycloalkyl, heterocyclyl, cycloalkenyl, heterocyclenyl, aryl, heteroaryl, multicyclic alkaryl; alkoxy, which is optionally substituted by carboxy, aryl or heteroaryl; or alkoxycarbonyl, which is optionally substituted by $Y^1Y^2N$—; and alkoxy, which is optionally substituted by one to three of same of different of carboxy, alkoxycarbonyl, cyano, halogen, —$NY^1Y^2$, $Y^1Y^2N$—C(=O)—, cycloalkyl, heterocyclyl, cycloalkenyl, heterocyclenyl, aryl, heteroaryl, or multicyclic alkaryl;

wherein the aryl or heteroaryl moieties in the $Cy^1$ substituent groups are optionally independently substituted by hydroxy, amino, alkyl, alkoxy, carboxy, alkoxycarbonyl or $R^8$—$SO_2$—N($R^5$)—C(=O)—;

and, wherein the cycloalkyl, cycloalkenyl, heterocyclyl, heterocyclenyl or multicyclic alkaryl moieties in the $Cy^1$ substituent groups independently is optionally substituted by hydroxy, amino, alkyl, alkoxy, oxo, carboxy, alkoxycarbonyl or $R^8$—$SO_2$—N($R^5$)—C(=O)—;

and further provided that when $Cy^1$ is cycloalkyl, cycloalkenyl, heterocyclyl, heterocyclenyl or multicyclic alkaryl, each of which independently may also be substituted by oxo;

(B) $Cy^2$ is cycloalkenyl, heterocyclenyl, aryl, heteroaryl, or multicyclic alkaryl, each of which independently is optionally substituted by one to three of same or different of same or different of alkoxy, ($C_1$-$C_3$)-alkyl, hydroxy, cyano, halogen, haloalkoxy, haloalkyl, nitro, $Y^1Y^2N$—, $Y^1Y^2N$—$SO_2$—, aryl or heteroaryl, wherein the aryl is optionally substituted by alkyl or hydroxyalkyl, and the heteroaryl is optionally substituted by alkyl;

(C) $L^1$ is a straight- or branched-chain alkylene containing from 1 to about 6 carbon atoms and is optionally substituted by carboxy or hydroxy; or $L^1$ is —$CH_2$—($C_1$-$C_5$)haloalkylene, or $L^1$ is cycloalkylene containing from 1 to about 7 carbon atoms and is optionally substituted by hydroxy; or $L^1$ and $Cy^2$ together represent arylcycloalkyl or cycloalkylaryl;

(D) $R^1$ is ($C_1$-$C_4$)-alkylthio, $Y^4Y^5N$—; ($C_1$-$C_4$)-alkoxy which is optionally substituted by one to three halogen; or ($C_1$-$C_4$)-alkyl, which is optionally substituted by one to three of halogen, hydroxy or alkoxy;

(E) $L^2$ is bond, —O— or —$CH_2$—O—;

and wherein:

$R^2$, $R^3$, $R^4$ and $R^5$ are each independently H or alkyl, $R^6$ is alkyl, which is optionally substituted by hydroxy or alkoxy;

$R^7$ is H or alkyl;

$R^8$ is alkyl, aryl, arylalkyl, heteroaryl, heteroarylalkyl, wherein the aryl or heteroaryl moiety is optionally substituted by halogen;

$Y^1$ and $Y^2$ are each independently hydrogen, or alkyl, which is optionally substituted by one to three of same or different of carboxy, alkoxycarbonyl, alkoxy, hydroxy, amino, alkylamino, dialkylamino, cycloalkyl, cycloalkenyl, heterocyclyl, heterocyclenyl, aryl, heteroaryl or multicyclic alkaryl; wherein the aryl and heteroaryl independently is optionally substituted by hydroxy, amino, alkyl or alkoxy, and wherein the cycloalkyl, heterocyclyl, cycloalkenyl, heterocyclenyl and multicyclic alkaryl independently is optionally substituted by hydroxy, amino, alkyl, alkoxy or oxo; or $Y^1$ and $Y^2$ taken together with the nitrogen atom to which they are attached, form a nitrogen-containing three to seven member saturated heterocyclyl that optionally contains a further heteroatom selected from O, S, or $NY^3$, wherein $Y^3$ is hydrogen or alkyl, and wherein the heterocyclyl is optionally substituted by one to three of same or different of carboxy, hydroxy, hydroxyalkyl, oxo, amino, alkylamino or dialkylamino;

$Y^4$ and $Y^5$ are each independently H or ($C_1$-$C_4$)-alkyl;

$Z^1$ is C(=O)—N($R^4$), $NR^4$ or $S(O)_n$; and n is 0, 1 or 2;

provided that when $R^1$ is methoxy, $L^1$ is —$CH_2$—$CH_2$—, $L^2$ is a bond and $Cy^2$ is 2,4-dichlorophenyl, then $Cy^1$ is not 1-methyl-2-ethyloxycarbonyl-indol-5-yl;

or an N-oxide thereof, or an ester prodrug thereof, or a pharmaceutically acceptable salt, hydrate, or solvate thereof.

Another aspect of the present invention is a pharmaceutical composition comprising, a pharmaceutically effective amount of one or more compounds according to Formula (I) in admixture with a pharmaceutically acceptable carrier.

Another aspect of the present invention is a method of treating a patient suffering from a PGD2-mediated disorder including, but not limited to, allergic disease (such as allergic rhinitis, allergic conjunctivitis, atopic dermatitis, bronchial asthma and food allergy), systemic mastocytosis, disorders accompanied by systemic mast cell activation, anaphylaxis shock, bronchoconstriction, bronchitis, urticaria, eczema, diseases accompanied by itch (such as atopic dermatitis and urticaria), diseases (such as cataract, retinal detachment, inflammation, infection and sleeping disorders) which is generated secondarily as a result of behavior accompanied by itch (such as scratching and beating), inflammation, chronic obstructive pulmonary diseases, ischemic reperfusion injury, cerebrovascular accident, chronic rheumatoid arthritis, pleurisy, ulcerative colitis and the like by administering to said patient a pharmaceutically effective amount of a compound according to Formula (I).

DETAILED DESCRIPTION OF THE INVENTION

As used above, and throughout the description of the invention, the following terms, unless otherwise indicated, shall be understood to have the following meanings:

"Acyl" means H—CO— or (aliphatic or cyclyl)-CO—. Preferred acyl includes lower alkanoyl that contains a lower alkyl. Exemplary acyl includes formyl, acetyl, propanoyl, 2-methylpropanoyl, butanoyl, palmitoyl, acryloyl, propynoyl, and cyclohexylcarbonyl.

"Aliphatic" means alkyl, alkenyl or alkynyl.

"Alkenyl" means a straight or branched aliphatic hydrocarbon group containing a carbon-carbon double bond and having 2 to about 15 carbon atoms. Preferred alkenyl has 2 to about 12 carbon atoms. More preferred alkenyl has 2 to about 4 carbon atoms. Branched means that one or more lower alkyl groups such as methyl, ethyl or propyl are attached to a linear alkenyl chain. "Lower alkenyl" means about 2 to about 4 carbon atoms in the chain that may be straight or branched. Exemplary alkenyl includes ethenyl, propenyl, n-butenyl, i-butenyl, 3-methylbut-2-enyl, n-pentenyl, heptenyl, octenyl, cyclohexylbutenyl, and decenyl.

"Alkoxy" means alkyl-O—. Exemplary alkoxy includes methoxy, ethoxy, n-propoxy, i-propoxy, n-butoxy, and heptoxy.

"Alkoxyalkylene" means alkyl-O-alkylene. Exemplary alkoxyalkylene includes methoxymethylene and ethoxymethylene.

"Alkoxycarbonyl" means alkyl-O—CO—. Exemplary alkoxycarbonyl includes methoxycarbonyl, ethoxycarbonyl, and t-butyloxycarbonyl.

"Alkyl" means straight or branched aliphatic hydrocarbon having 1 to about 20 carbon atoms. Preferred alkyl has 1 to about 12 carbon atoms. More preferred is lower alkyl. Branched means that one or more lower alkyl groups such as methyl, ethyl or propyl are attached to a linear alkyl chain. "Lower alkyl" means 1 to about 4 carbon atoms in a linear alkyl chain that may be straight or branched.

"Alkylamino" means alkyl-NH—. Preferred alkylamino is ($C_1$-$C_6$)-alkylamino. Exemplary alkylamino includes methylamino and ethylamino.

"Alkylene" means a straight or branched bivalent hydrocarbon having from 1 to about 15 carbon atoms. Preferred alkylene is the lower alkylene having from 1 to about 6 carbon atoms. Exemplary alkenylene includes methylene, ethylene, propylene, and butylene.

"Alkylsulfinyl" means alkyl-SO—. Preferred alkylsulfinyl is ($C_1$-$C_6$)-alkylsulfinyl. Exemplary alkylsulfinyl groups include $CH_3$—SO—.

"Alkylsulfonyl" means alkyl-$SO_2$—. Preferred alkylsulfonyl is ($C_1$-$C_6$)-alkylsulfonyl. Exemplary alkylsulfonyl includes $CH_3$—$SO_2$—, and $CH_3CH_2$—$SO_2$—.

"Alkylthio" means an alkyl-S—. Exemplary alkylthio includes $CH_3$—S—.

"Alkynyl" means straight or branched aliphatic hydrocarbon containing a carbon-carbon triple bond and having 2 to about 15 carbon atoms. Preferred alkynyl has 2 to about 12 carbon atoms. More preferred alkynyl has 2 to about 6 carbon atoms. Branched means that one or more lower alkyl such as methyl, ethyl or propyl are attached to a linear alkynyl chain. "Lower alkynyl" means 2 to about 4 carbon atoms in a linear alkynyl chain that may be straight or branched. Exemplary alkynyl includes ethynyl, propynyl, n-butynyl, 2-butynyl, 3-methylbutynyl, n-pentynyl, heptynyl, octynyl, and decynyl.

"Aroyl" means aryl-CO—. Exemplary aroyl includes benzoyl, and 1- and 2-naphthoyl.

"Aryl" means an aromatic monocyclic or multicyclic ring system of about 6 to about 14 carbon atoms. Preferred aryl include about 6 to about 10 carbon atoms. Exemplary aryl include phenyl and naphthyl.

"Arylalkyl" means aryl-alkyl-. Preferred arylalkyl contains a ($C_1$-$C_6$)-alkyl moiety. Exemplary arylalkyl includes benzyl, 2-phenethyl and naphthalenemethyl.

"Arylalkoxy" means arylalkyl-O—. Exemplary arylalkoxy includes benzyloxy and 1- or 2-naphthalenemethoxy.

"Arylalkoxycarbonyl" means arylalkyl-O—CO—. Exemplary arylalkoxycarbonyl includes phenoxycarbonyl and naphthoxycarbonyl.

"Arylalkylthio" means arylalkyl-S—. Exemplary arylalkylthio includes benzylthio.

"Arylcycloalkenyl" means a fused aryl and cycloalkenyl. Preferred arylcycloalkenyl is one wherein the aryl thereof is phenyl and the cycloalkenyl consists of about 5 to about 7 ring atoms. An arylcycloalkenyl is bonded through any atom of the cycloalkenyl moiety thereof capable of such bonding. Exemplary arylcycloalkenyl includes 1,2-dihydronaphthylene and indene.

"Arylcycloalkyl" means a fused aryl and cycloalkyl. Preferred arylcycloalkyl is one wherein the aryl thereof is phenyl and the cycloalkyl consists of about 5 to about 6 ring atoms. An arylcycloalkyl is bonded through any atom of the cycloalkyl moiety thereof capable of such bonding. Exemplary arylcycloalkyl includes 1,2,3,4-tetrahydro-naphthylene.

"Arylheterocyclenyl" means a fused aryl and heterocyclenyl. Preferred arylheterocyclenyl is one wherein the aryl thereof is phenyl and the heterocyclenyl consists of about 5 to about 6 ring atoms. An arylheterocyclenyl is bonded through any atom of the heterocyclenyl thereof capable of such bonding. The designation of the aza, oxa or thio as a prefix before the heterocyclenyl portion of the arylheterocyclenyl defines that at least a nitrogen, oxygen or sulfur atom is present, respectively, as a ring atom. The nitrogen atom of an arylheterocyclenyl may be a basic nitrogen atom. The nitrogen or sulfur atom of the heterocyclenyl portion of the arylheterocyclenyl may also be optionally oxidized to the corresponding N-oxide, S-oxide or S,S-dioxide. Exemplary arylheterocyclenyl includes 3H-indolinyl, 1H-2-oxoquinolyl, 2H-1-oxoisoquinolyl, 1,2-di-hydroquinolinyl, 3,4-dihydroquinolinyl, 1,2-dihydroisoquinolinyl, and 3,4-dihydroisoquinolinyl.

"Arylheterocyclyl" means a fused aryl and heterocyclyl. Preferred heterocyclylaryl is one wherein the aryl thereof is phenyl and the heterocyclyl consists of about 5 to about 6 ring atoms. An arylheterocyclyl is bonded through any atom of the heterocyclyl moiety thereof capable of such bonding. The designation of the aza, oxa or thio as a prefix before heterocyclyl portion of the arylheterocyclyl defines that at least a nitrogen, oxygen or sulfur atom is present, respectively, as a ring atom. The nitrogen atom of an arylheterocyclyl may be a basic nitrogen atom. The nitrogen or sulfur atom of the heterocyclyl portion of the arylheterocyclyl may also be optionally oxidized to the corresponding N-oxide, S-oxide or S,S-dioxide. Exemplary arylheterocyclyl includes indolinyl, 1,2,3,4-tetrahydroisoquinoline, 1,2,3,4-tetrahydroquinoline, 1H-2,3-dihydroisoindol-2-yl, 2,3-dihydrobenz[f]isoindol-2-yl, and 1,2,3,4-tetrahydrobenz[g]-isoquinolin-2-yl.

"Aryloxy" means an aryl-O—. Exemplary aryloxy includes phenoxy and naphthoxy.

"Aryloxycarbonyl" means aryl-O—CO—. Exemplary aryloxycarbonyl includes phenoxycarbonyl and naphthoxycarbonyl.

"Arylsulfinyl" means aryl-SO—. Exemplary arylsulfinyl includes phenylsulfinyl and naphthylsulfinyl.

"Arylsulfonyl" means aryl-$SO_2$—. Exemplary arylsulfonyl includes phenylsulfonyl and naphthylsulfonyl.

"Arylthio" means aryl-S—. Exemplary arylthio includes phenylthio and naphthylthio.

"Compounds of the present invention", and equivalent expressions, are meant to embrace compounds of Formula (I) as hereinbefore described, which expression includes the ester prodrugs, the pharmaceutically acceptable salts, and the solvates, e.g., hydrates, where the context so permits. Similarly, reference to intermediates, whether or not they themselves are claimed, is meant to embrace their salts, and solvates, where the context so permits.

"Cycloalkenyl" means a non-aromatic mono- or multicyclic ring system of about 3 to about 10 carbon atoms, preferably of about 5 to about 10 carbon atoms, and which contains at least one carbon-carbon double bond. Preferred rings of the ring system include about 5 to about 6 ring atoms; and such preferred ring sizes are also referred to as "lower". Exemplary monocyclic cycloalkenyl includes cyclopentenyl, cyclohexenyl, and cycloheptenyl. An exemplary multicyclic cycloalkenyl is norbornylenyl.

"Cycloalkenylaryl" means a fused aryl and cycloalkenyl. Preferred cycloalkenylaryl is one wherein the aryl thereof is phenyl and the cycloalkenyl consists of about 5 to about 6 ring atoms. A cycloalkenylaryl is bonded through any atom of the aryl moiety thereof capable of such bonding. Exemplary cycloalkenylaryl includes 1,2-dihydronaphthylene and indene.

"Cycloalkenylheteroaryl" means a fused heteroaryl and cycloalkenyl. Preferred cycloalkenylheteroaryl is one wherein the heteroaryl thereof consists of about 5 to about 6 ring atoms and the cycloalkenyl consists of about 5 to about 6 ring atoms. A cycloalkenylheteroaryl is bonded through any atom of the heteroaryl thereof capable of such bonding. The designation of the aza, oxa or thio as a prefix before heteroaryl portion of the cycloalkenylheteroaryl defines that at least a nitrogen, oxygen or sulfur atom is present, respectively, as a ring atom. The nitrogen atom of a cycloalkenylheteroaryl may be a basic nitrogen atom. The nitrogen atom of the heteroaryl portion of the cycloalkenylheteroaryl may also be optionally oxidized to the corresponding N-oxide. Exemplary cycloalkenylheteroaryl includes 5,6-dihydroquinolyl, 5,6-dihydroisoquinolyl, 5,6-dihydroquinoxalinyl, 5,6-dihydroquinazolyl, 4,5-dihydro-1H-benzimidazolyl, and 4,5-dihydrobenzoxazolyl.

"Cycloalkyl" means a non-aromatic mono- or multicyclic saturated ring system of about 3 to about 10 carbon atoms, preferably of about 5 to about 10 carbon atoms. Preferred ring systems include about 5 to about 7 ring atoms; and such preferred ring systems are also referred to as "lower". Exemplary monocyclic cycloalkyl includes cyclopentyl, cyclohexyl, and cycloheptyl. Exemplary multicyclic cycloalkyl includes 1-decalin, norbornyl, and adamant-(1- or 2-)yl.

"Cycloalkylaryl" means a fused aryl and cycloalkyl. Preferred cycloalkylaryl is one wherein the aryl thereof is phenyl and the cycloalkyl consists of about 5 to about 6 ring atoms. A cycloalkylaryl is bonded through any atom of the cycloalkyl moiety thereof capable of such bonding. Exemplary cycloalkylaryl includes 1,2,3,4-tetrahydro-naphthylene.

"Cycloalkylene" means a bivalent cycloalkyl group having about 4 to about 8 carbon atoms. Preferred cycloalkylene includes about 5 to about 7 ring atoms; and such preferred ring systems are also referred to as "lower". The points of binding on the cycloalkylene group include 1,1-, 1,2-, 1,3-, or 1,4-binding patterns, and where applicable the stereochemical relationship of the points of binding is either cis or trans. Exemplary monocyclic cycloalkylene includes (1,1-, 1,2-, or 1,3-)cyclohexylene and (1,1- or 1,2-)cyclopentylene.

"Cycloalkylheteroaryl" means a fused heteroaryl and cycloalkyl. Preferred cycloalkylheteroaryl is one wherein the heteroaryl thereof consists of about 5 to about 6 ring atoms and the cycloalkyl consists of about 5 to about 6 ring atoms. A cycloalkylheteroaryl is bonded through any atom of the heteroaryl thereof capable of such bonding. The designation of the aza, oxa or thio as a prefix before heteroaryl portion of the fused cycloalkylheteroaryl defines that at least a nitrogen, oxygen or sulfur atom is present, respectively, as a ring atom. The nitrogen atom of a cycloalkylheteroaryl may be a basic nitrogen atom. The nitrogen atom of the heteroaryl portion of the cycloalkylheteroaryl may also be optionally oxidized to the corresponding N-oxide. Exemplary cycloalkylheteroaryl includes 5,6,7,8-tetrahydroquinolinyl, 5,6,7,8-tetrahydroisoquinolyl, 5,6,7,8-tetrahydroquinoxalinyl, 5,6,7,8-tetrahydroquinazolyl, 4,5,6,7-tetrahydro-1H-benzimidazolyl, and 4,5,6,7-tetrahydrobenzoxazolyl.

"Cyclyl" means cycloalkyl, cycloalkenyl, heterocyclyl or heterocyclenyl.

"Dialkylamino" means (alkyl)$_2$-N—. Preferred dialkylamino is ($C_1$-$C_6$alkyl)$_2$-N—. Exemplary dialkylamino groups include dimethylamino, diethylamino and methylethylamino.

"Halo" or "halogen" means fluoro, chloro, bromo, or iodo. Preferred are fluoro or chloro.

"Haloalkoxy" means alkoxy substituted by one to three halo groups. Preferred are loweralkoxy substituted by one to three halogens. Most preferred are loweralkoxy substituted by one halogen.

"Haloalkyl" means alkyl substituted by one to three halo groups. Preferred are loweralkyl substituted by one to three halogens. Most preferred are loweralkyl substituted by one halogen.

"Haloalkylene" means alkylene substituted by one to three halo groups. Preferred are loweralkylene substituted by one to three halogens. Most preferred are loweralkyl substituted by one halogen. Exemplary haloalkylene includes —CHF—, —$CF_2$—, —$CH_2$—CHF— and —$CH_2$—$CF_2$—.

"Heteroaroyl" means heteroaryl-CO—. Exemplary heteroaroyl includes thiophenoyl, nicotinoyl, pyrrol-2-ylcarbonyl, 1- and 2-naphthoyl, and pyridinoyl.

"Heteroaryl" means an aromatic monocyclic or multicyclic ring system of about 5 to about 14 carbon atoms, in which one or more of the carbon atoms in the ring system is/are hetero element(s) other than carbon, for example nitrogen, oxygen or sulfur. Preferably aromatic ring systems include about 5 to about 10 carbon atoms, and include 1 to 3 heteroatoms. Most preferred ring sizes of rings of the ring system include about 5 to about 6 ring atoms. The designation of the aza, oxa or thio as a prefix before heteroaryl defines that at least a nitrogen, oxygen or sulfur atom is present, respectively, as a ring atom. A nitrogen atom of an heteroaryl may be a basic nitrogen atom and may also be optionally oxidized to the corresponding N-oxide. When a heteroaryl is substituted by a hydroxy group, it also includes its corresponding tautomer where such hydroxy substituted heteroaryl is capable of such. Exemplary heteroaryl includes pyrazinyl, thienyl, isothiazolyl, oxazolyl, pyrazolyl, furazanyl, pyrrolyl, 1,2,4-thiadiazolyl, pyridazinyl, quinoxalinyl, phthalazinyl, imidazo[1,2-a]pyridine, imidazo[2,1-b]thiazolyl, benzofurazanyl, azaindolyl, benzimidazolyl, benzothienyl, thienopyridyl, thienopyrimidyl, pyrrolopyridyl, imidazopyridyl, benzoazaindolyl, 1,2,4-triazinyl, benzthiazolyl, furanyl, imidazolyl, indolyl, indolizinyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl, and triazolyl.

"Heteroarylalkyl" means heteroaryl-alkyl-. Preferred heteroarylalkyl contains a $C_{1-4}$alkyl moiety. Exemplary heteroarylalkyl includes tetrazol-5-ylmethyl.

"Heteroarylalkoxy" means heteroaryl-alkyl-O—.

"Heteroarylalkoxycarbonyl" means heteroarylalkyl-O—CO—.

"Heteroarylcycloalkenyl" means a fused heteroaryl and cycloalkenyl. Preferred heteroarylcycloalkenyl is one wherein the heteroaryl thereof consists of about 5 to about 6 ring atoms and the cycloalkenyl consists of about 5 to about 6 ring atoms. A heteroarylcycloalkenyl is bonded through any atom of the cycloalkenyl thereof capable of such bonding. The designation of the aza, oxa or thio as a prefix before heteroaryl portion of the heteroarylcycloalkenyl defines that at least a nitrogen, oxygen or sulfur atom is present, respectively, as a ring atom. The nitrogen atom of a heteroarylcycloalkenyl may be a basic nitrogen atom. The nitrogen atom of the heteroaryl portion of the heteroarylcycloalkenyl may also be optionally oxidized to the corresponding N-oxide. Exemplary heteroarylcycloalkenyl includes 5,6-dihydroquinolyl, 5,6-dihydroisoquinolyl, 5,6-dihydroquinoxalinyl, 5,6-dihydroquinazolinyl, 4,5-dihydro-1H-benzimidazolyl, and 4,5-di-hydrobenzoxazolyl.

"Heteroarylcycloalkyl" means a fused heteroaryl and cycloalkyl. Preferred heteroarylcycloalkyl is one wherein the heteroaryl thereof consists of about 5 to about 6 ring atoms and the cycloalkyl consists of about 5 to about 6 ring atoms. A heteroarylcycloalkyl is bonded through any atom of the cycloalkyl thereof capable of such bonding. The designation of the aza, oxa or thio as a prefix before heteroaryl portion of the fused heteroarylcycloalkyl defines that at least a nitrogen, oxygen or sulfur atom is present, respectively, as a ring atom. The nitrogen atom of a heteroarylcycloalkyl may be a basic nitrogen atom. The nitrogen atom of the heteroaryl portion of the heteroarylcycloalkyl may also be optionally oxidized to the corresponding N-oxide. Exemplary heteroarylcycloalkyl includes 5,6,7,8-tetrahydroquinolinyl, 5,6,7,8-tetra-hydroisoquinolyl, 5,6,7,8-tetrahydroquinoxalinyl, 5,6,7,8-tetrahydroquinazolyl, 4,5,6,7-tetrahydro-1H-benzimidazolyl, and 4,5,6,7-tetrahydrobenzoxazolyl "Heteroarylheterocyclenyl" means a fused heteroaryl and heterocyclenyl. Preferred heteroarylheterocyclenyl is one wherein the heteroaryl thereof consists of about 5 to about 6 ring atoms and the heterocyclenyl consists of about 5 to about 6 ring atoms. A heteroarylheterocyclenyl is bonded through any atom of the heterocyclenyl thereof capable of such bonding. The designation of the aza, oxa or thio as a prefix before the heteroaryl or heterocyclenyl portion of the heteroarylheterocyclenyl defines that at least a nitrogen, oxygen or sulfur atom is present, respectively, as a ring atom. The nitrogen atom of a heteroarylazaheterocyclenyl may be a basic nitrogen atom. The nitrogen or sulfur atom of the heteroaryl portion of the heteroarylheterocyclyl may also be optionally oxidized to the corresponding N-oxide. The nitrogen or sulfur atom of the heteroaryl or heterocyclyl portion of the heteroarylheterocyclyl may also be optionally oxidized to the corresponding N-oxide, S-oxide or S,S-dioxide. Exemplary heteroarylheterocyclenyl includes 7,8-dihydro[1,7]naphthyridinyl, 1,2-dihydro[2,7]-naphthyridinyl, 6,7-dihydro-3H-imidazo[4,5-c]pyridyl, 1,2-dihydro-1,5-naphthyridinyl, 1,2-dihydro-1,6-naphthyridinyl, 1,2-dihydro-1,7-naphthyridinyl, 1,2-dihydro-1,8-naphthyridinyl, and 1,2-dihydro-2,6-naphthyridinyl.

"Heteroarylheterocyclyl" means a fused heteroaryl and heterocyclyl. Preferred heteroarylheterocyclyl is one wherein the heteroaryl thereof consists of about 5 to about 6 ring atoms and the heterocyclyl consists of about 5 to about 6 ring atoms. A heteroarylheterocyclyl is bonded through any atom of the heterocyclyl thereof capable of such bonding. The designation of the aza, oxa or thio as a prefix before the heteroaryl or heterocyclyl portion of the fused heteroarylheterocyclyl defines that at least a nitrogen, oxygen or sulfur atom is present, respectively, as a ring atom. The nitrogen atom of a fused heteroarylheterocyclyl may be a basic nitrogen atom. The nitrogen or sulfur atom of the heteroaryl portion of the heteroarylheterocyclyl may also be optionally oxidized to the corresponding N-oxide. The nitrogen or sulfur atom of the heteroaryl or heterocyclyl portion of the heteroarylheterocyclyl may also be optionally oxidized to the corresponding N-oxide, S-oxide or S,S-dioxide. Exemplary heteroarylheterocyclyl includes 2,3-dihydro-1H-pyrrol[3,4-b]quinolin-2-yl, 1,2,3,4-tetrahydrobenz[b][1,7]naphthyridin-2-yl, 1,2,3,4-tetrahydrobenz[b][1,6]naphthyridin-2-yl, 1,2,3,4-tetrahydro-9H-pyrido[3,4-b]indol-2-yl, 1,2,3,4-tetrahydro-9H-pyrido[4,3-b]indol-2-yl, 2,3-dihydro-1H-pyrrolo[3,4-b]indol-2-yl, 1H-2,3,4,5-tetrahydroazepino[3,4-b]indol-2-yl, 1H-2,3,4,5-tetra-hydroazepino[4,3-b]indol-3-yl, 1H-2,3,4,5-tetrahydroazepino[4,5-b]indol-2 yl, 5,6,7,8-tetra-hydro[1,7]naphthyridyl, 1,2,3,4-tetrahydro[2,7]naphthyridyl, 2,3-dihydro[1,4]dioxino[2,3-b]pyridyl, 2,3-dihydro-[1,4]dioxino[2,3-b]pyridyl, 3,4-dihydro-2H-1-oxa[4,6]diazanaphthalenyl, 4,5,6,7-tetrahydro-3H-imidazo[4,5-c]pyridyl, 6,7-dihydro[5,8]diazanaphthalenyl, 1,2,3,4-tetrahydro[1,5]-naphthyridinyl, 1,2,3,4-tetrahydro[1,6]naphthyridinyl, 1,2,3,4-tetrahydro[1,7]naphthyridinyl, 1,2,3,4-tetrahydro[1,8] naphthyridinyl, and 1,2,3,4-tetra-hydro[2,6]naphthyridinyl.

"Heteroaryloxy" means heteroaryl-O—. Exemplary heteroaryloxy includes pyridyloxy.

"Heterocyclenyl" means a non-aromatic monocyclic or multicyclic hydrocarbon ring system of about 3 to about 10 carbon atoms, in which one or more of the carbon atoms in the ring system is/are hetero element(s) other than carbon, for example nitrogen, oxygen or sulfur atoms, and which contains at least one carbon-carbon double bond or carbon-nitrogen double bond. Preferably, the non-aromatic ring system includes about 5 to about 10 carbon atoms, and 1 to 3 heteroatoms. Most preferred ring sizes of rings of the ring system include about 5 to about 6 ring atoms; and such preferred ring sizes are also referred to as "lower". The designation of the aza, oxa or thio as a prefix before heterocyclenyl defines that at least a nitrogen, oxygen or sulfur atom is present, respectively, as a ring atom. The nitrogen atom of a heterocyclenyl may be a basic nitrogen atom. The nitrogen or sulfur atom of the heterocyclenyl may also be optionally oxidized to the corresponding N-oxide, S-oxide or S,S-dioxide. Exemplary monocyclic azaheterocyclenyl includes 1,2,3,4-tetrahydrohydropyridine, 1,2-dihydropyridyl, 1,4-dihydropyridyl, 1,2,3,6-tetra-hydropyridine, 1,4,5,6-tetrahydro-pyrimidine, 2-pyrrolinyl, 3-pyrrolinyl, 2-imidazolinyl, and 2-pyrazolinyl. Exemplary oxaheterocyclenyl includes 3,4-dihydro-2H-pyran, dihydrofuranyl, and fluorodihydro-furanyl. An exemplary multicyclic oxaheterocyclenyl is 7-oxabicyclo[2.2.1] heptenyl. Exemplary monocyclic thioheterocyclenyl includes dihydrothiophenyl and dihydrothiopyranyl.

"Heterocyclenylaryl" means a fused aryl and heterocyclenyl. Preferred heterocyclenylaryl is one wherein the aryl thereof is phenyl and the heterocyclenyl consists of about 5 to about 6 ring atoms. A heterocyclenylaryl is bonded through any atom of the aryl thereof capable of such bonding. The designation of the aza, oxa or thio as a prefix before heterocyclenyl portion of the fused heterocyclenylaryl defines that at least a nitrogen, oxygen or sulfur atom is present, respectively, as a ring atom. The nitrogen atom of a heterocyclenylaryl may be a basic nitrogen atom. The nitrogen or sulfur atom of the heterocyclenyl portion of the heterocyclenylaryl may also be optionally oxidized to the corresponding N-oxide, S-oxide or S,S-dioxide. Exemplary heterocyclenylaryl include 3H-indolinyl, IH-2-oxoquinolyl, 2H-1-oxoisoquinolyl, 1,2-di-hydroquinolinyl, 3,4-dihydroquinolinyl, 1,2-dihydroisoquinolinyl, and 3,4-dihydroisoquinolinyl.

"Heterocyclenylheteroaryl" means a fused heteroaryl and heterocyclenyl. Preferred heterocyclenylheteroaryl is one wherein the heteroaryl thereof consists of about 5 to about 6 ring atoms and the heterocyclenyl consists of about 5 to about 6 ring atoms. A heterocyclenylheteroaryl is bonded through any atom of the heteroaryl thereof capable of such bonding. The designation of the aza, oxa or thio as a prefix before the heteroaryl or heterocyclenyl portion of the heterocyclenylheteroaryl define that at least a nitrogen, oxygen or sulfur atom is present, respectively, as a ring atom. The nitrogen atom of an azaheterocyclenylheteroaryl may be a basic nitrogen atom. The nitrogen or sulfur atom of the heteroaryl portion of the heterocyclenylheteroaryl may also be optionally oxidized to the corresponding N-oxide. The nitrogen or sulfur atom of the heteroaryl or heterocyclyl portion of the heterocyclenylheteroaryl may also be optionally oxidized to the corresponding N-oxide, S-oxide or S,S-dioxide. Exemplary heterocyclenylheteroaryl includes 7,8-dihydro[1,7]naphthyridinyl, 1,2-dihydro[2,7]-naphthyridinyl, 6,7-dihydro-3H-imidazo[4,5-c]pyridyl, 1,2-dihydro-1,5-naphthyridinyl, 1,2-dihydro-1,6-naphthyridinyl, 1,2-dihydro-1,7-naphthyridinyl, 1,2-dihydro-1,8-naphthyridinyl and 1,2-dihydro-2,6-naphthyridinyl.

"Heterocyclyl" means a non-aromatic saturated monocyclic or multicyclic ring system of about 3 to about 10 carbon atoms, in which one or more of the atoms in the ring system is/are hetero element(s) other than carbon, for example nitrogen, oxygen or sulfur. Preferably, the ring system contains about 5 to about 10 carbon atoms, and from 1 to 3 heteroatoms. Preferred ring sizes of rings of the ring system include about 5 to about 6 ring atoms; and such preferred ring sizes are also referred to as "lower". The designation of the aza, oxa or thio as a prefix before heterocyclyl define that at least a nitrogen, oxygen or sulfur atom is present respectively as a ring atom. The nitrogen atom of a heterocyclyl may be a basic nitrogen atom. The nitrogen or sulfur atom of the heterocyclyl may also be optionally oxidized to 20 the corresponding N-oxide, S-oxide or S,S-dioxide. Exemplary monocyclic heterocyclyl includes piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, and tetrahydrothiopyranyl.

"Heterocyclylaryl" means a fused aryl and heterocyclyl. Preferred heterocyclylaryl is one wherein the aryl thereof is phenyl and the heterocyclyl consists of about 5 to about 6 ring atoms. A heterocyclylaryl is bonded through any atom of the aryl moiety thereof capable of such bonding. The designation of the aza, oxa or thio as a prefix before heterocyclyl portion of the heterocyclylaryl defines that at least a nitrogen, oxygen or sulfur atom is present, respectively, as a ring atom. The nitrogen atom of a heterocyclylaryl may be a basic nitrogen atom. The nitrogen or sulfur atom of the heterocyclyl portion of the heterocyclylaryl may also be optionally oxidized to the corresponding N-oxide, S-oxide or S,S-dioxide. Exemplary heterocyclylaryl includes indolinyl, 1,2,3,4-tetrahydroisoquinoline, 1,2,3,4-tetrahydroquinoline, 1H-2,3-dihydroisoindol-2-yl, and 2,3-dihydrobenz[f]isoindol-2-yl, and 1,2,3,4-tetrahydrobenz[g]-isoquinolin-2-yl.

"Heterocyclylheteroaryl" means a fused heteroaryl and heterocyclyl. Preferred heterocyclylheteroaryl is one wherein the heteroaryl thereof consists of about 5 to about 6 ring atoms and the heterocyclyl consists of about 5 to about 6 ring atoms. A heterocyclylheteroaryl is bonded through any atom of the heterocyclyl thereof capable of such bonding. The designation of the aza, oxa or thio as a prefix before the heteroaryl or heterocyclyl portion of the heterocyclylheteroaryl defines that at least a nitrogen, oxygen or sulfur atom is present, respectively, as a ring atom. The nitrogen atom of a heterocyclylheteroaryl may be a basic nitrogen atom. The nitrogen or sulfur atom of the heteroaryl portion of the heterocyclylheteroaryl may also be optionally oxidized to the corresponding N-oxide. The nitrogen or sulfur atom of the heteroaryl or heterocyclyl portion of the heterocyclylheteroaryl may also be optionally oxidized to the corresponding N-oxide, S-oxide or S,S-dioxide. Exemplary heterocyclylheteroaryl includes 2,3-dihydro-1H-pyrrol[3,4-b]quinolin-2-yl, 1,2,3,4-tetrahydrobenz[b][1,7]naphthyridin-2-yl, 1,2,3,4-tetrahydrobenz[b][1,6]naphthyridin-2-yl, 1,2,3,4-tetra-hydro-9H-pyrido[3,4-b]indol-2-yl, 1,2,3,4-tetrahydro-9H-pyrido[4,3-b]indol-2-yl, 2,3-dihydro-1H-pyrrolo[3,4-b ]indol-2-yl, 1H-2,3,4,5-tetrahydroazepino[3,4-b]indol-2-yl, 1H-2,3,4,5-tetra-hydroazepino[4,3-b]indol-3-yl, 1H-2,3,4,5-tetrahydroazepino[4,5-b]indol-2-yl, 5,6,7,8-tetra-hydro[1,7]naphthyridyl, 1,2,3,4-tetrahydro[2,7]naphthyridyl, 2,3-dihydro[1,4]dioxino[2,3-b]pyridyl, 2,3-dihydro-[1,4]dioxino[2,3-b]pyridyl, 3,4-dihydro-2H-1-oxa[4,6]diazanaphthalenyl, 4,5,6,7-tetrahydro-3H-imidazo[4,5-c]pyridyl, 6,7-dihydro[5,8]diazanaphthalenyl, 1,2,3,4-tetrahydro[1,5]-naphthyridinyl, 1,2,3,4-tetrahydro[1,6]naphthyridinyl, 1,2,3,4-tetrahydro[1,7]naphthyridinyl, 1,2,3,4-tetrahydro[1,8]naphthyridinyl, and 1,2,3,4-tetra-hydro[2,6]naphthyridinyl.

"Hydroxyalkyl" means a HO-alkylene-. Exemplary hydroxyalkyl include HO—$CH_2$— and HO—$CH_2$—$CH_2$—.

"Multicyclic alkaryl" means a multicyclic ring system including at least one aromatic ring fused to at least one non-aromatic ring that may be saturated or unsaturated, and may also contain in the ring system one or more heteroatoms, such as nitrogen, oxygen or sulfur. Exemplary multicyclic alkaryl includes arylcycloalkenyl, arylcycloalkyl, arylheterocyclenyl, arylheterocyclyl, cycloalkenylaryl, cycloalkylaryl, cycloalkenylheteroaryl, cycloalkylheteroaryl, heteroarylcycloalkenyl, heteroarylcycloalkyl, heteroarylheterocyclenyl, heteroarylheterocyclyl, heterocyclenylaryl, heterocyclenylheteroaryl, heterocyclylaryl, and heterocyclylheteroaryl. Preferred multicyclic alkaryl groups are bicyclic rings that include one aromatic ring fused to one non-aromatic ring and that also may contain in the ring system one or more heteroatoms, such as nitrogen, oxygen or sulfur.

"Patient" includes human and other mammals.

"Pharmaceutically acceptable prodrugs" as used herein refers to those prodrugs of the compounds of the present invention which are, within the scope of sound medical judgment, suitable for use in contact with the tissues of patients with undue toxicity, irritation, allergic response commensurate with a reasonable benefit/risk ratio, and effective for their intended use of the compounds of the invention. The term "prodrug" refers to compounds that are transformed in vivo to yield a parent compound of the present invention, for example by hydrolysis in blood. Functional groups that may be rapidly transformed, by metabolic cleavage, in vivo form a class of groups reactive with the carboxyl group of the compounds of this invention. They include, but are not limited to such groups as alkanoyl (such as acetyl, propanoyl, butanoyl, and the like), unsubstituted and substituted aroyl (such as benzoyl and substituted benzoyl), alkoxycarbonyl (such as ethoxycarbonyl), trialkylsilyl (such as trimethyl and triethysilyl), and monoesters formed with dicarboxylic acids (such as succinyl). Because of the ease with which the metabolically cleavable groups of the compounds of this invention are cleaved in vivo, the compounds bearing such groups act as pro-drugs. The compounds bearing the metabolically cleavable groups have the advantage that they may exhibit improved bioavailability as a result of enhanced solubility and/or rate of absorption conferred upon the parent compound by virtue of the presence of the metabolically cleavable group. A thorough discussion is provided in Design of Prodrugs, H. Bundgaard, ed., Elsevier (1985); Methods in Enzymology; K. Widder et al, Ed., Academic Press, 42, 309-396 (1985); A Textbook of Drug Design and Development, Krogsgaard-Larsen and H. Bandaged, ed., Chapter 5; "Design and Applications of Prodrugs" 113-191 (1991); Advanced Drug Delivery Reviews, H. Bundgard, 8, 1-38, (1992); J. Pharm. Sci., 77, 285 (1988); Chem. Pharm. Bull., N. Nakeya et al, 32, 692 (1984); Prodrugs as Novel Delivery Systems, T. Higuchi and V. Stella, 14 A.C.S. Symposium Series, and Bioreversible Carriers in Drug Design, E. B. Roche, ed., American Pharmaceutical Association and Pergamon Press, 1987, which are incorporated herein by reference.

"Ester prodrug" means a compound that is convertible in vivo by metabolic means (e.g., by hydrolysis) to a compound of Formula (I). For example an ester of a compound of Formula (I) containing a hydroxy group may be convertible by hydrolysis in vivo to the parent molecule. Alternatively an ester of a compound of Formula (I) containing a carboxy group may be convertible by hydrolysis in vivo to the parent molecule. Exemplary ester prodrugs are:

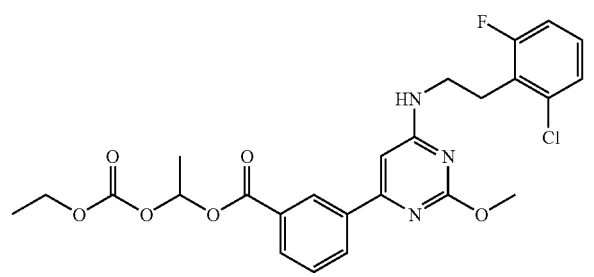

3-{6-[2-(2-chloro-6-fluoro-phenyl)-ethylamino]-2-methoxy-pyrimidin-4-yl}-benzoic acid, 1-ethoxycarbonyloxy-ethyl ester, and its enantiomers thereof;

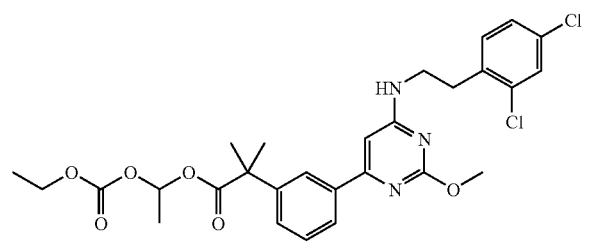

2-(3-{6-[2-(2,4-dichloro-phenyl)-ethylamino]-2-methoxy-pyrimidin-4-yl}-phenyl)-2-methyl-propionic acid, 1-ethoxycarbonyloxy-ethyl ester, and its enantiomers thereof;

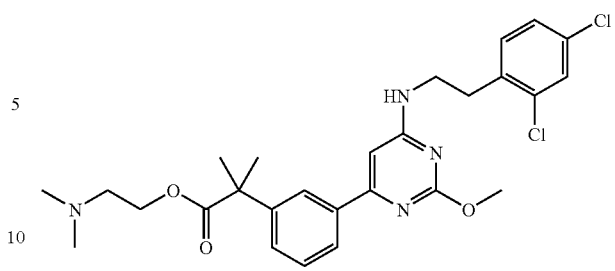

2-(3-{6-[2-(2,4-dichloro-phenyl)-ethylamino]-2-methoxy-pyrimidin-4-yl}-phenyl)-2-methyl-propionic acid, 2-dimethylamino-ethyl ester; and

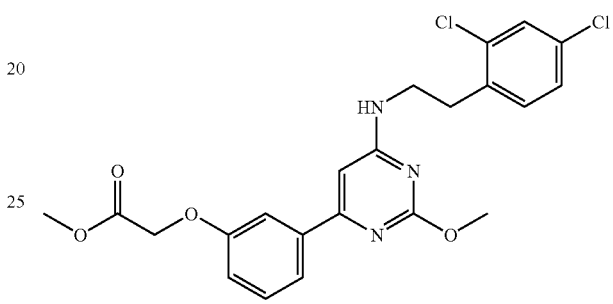

(3-{6-[2-(2,4-dichloro-phenyl)-ethylamino]-2-methoxy-pyrimidin-4-yl}-phenoxy)-acetic acid, methyl ester.

"Pharmaceutically acceptable salts" refers to the non-toxic, inorganic and organic acid addition salts, and base addition salts, of compounds of the present invention. These salts can be prepared in situ during the final isolation and purification of the compounds.

An exemplary N-oxide is:

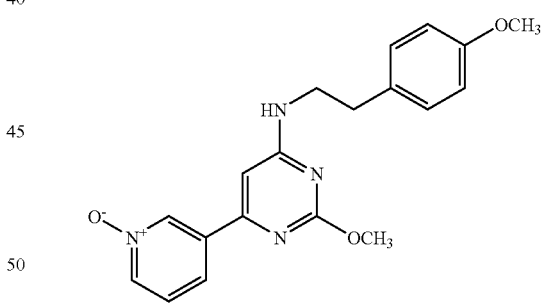

[2-methoxy-6-(1-oxy-pyridin-3-yl)-pyrimidin-4-yl]-[2-(4-methoxy-phenyl)-ethyl]-amine.

"Solvate" means a physical association of a compound of this invention with one or more solvent molecules. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Representative solvates include hydrates, ethanolates and methanolates.

Suitable esters of compounds of Formula (I) containing a hydroxy group, are for example acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methanesulfonates, ethanesulfonates, benzenesulfonates, p-toluenesulfonates, cyclohexylsulfamates and quinates.

Suitable esters of compounds of Formula (I) containing a carboxy group, are for example those described by F. J. Leinweber, Drug Metab. Res., 1987, 18, page 379.

An especially useful class of esters of compounds of Formula (I) containing a hydroxy group, may be formed from acid moieties selected from those described by Bundgaard et. al., J. Med. Chem., 1989, 32, pages 2503-2507, and include substituted (aminomethyl)-benzoates, for example dialkylamino-methylbenzoates in which the two alkyl groups may be joined together and/or interrupted by an oxygen atom or by an optionally substituted nitrogen atom, e.g., an alkylated nitrogen atom, more especially (morpholino-methyl)benzoates, e.g., 3- or 4-(morpholinomethyl)-benzoates, and (4-alkylpiperazin-1-yl)benzoates, e.g., 3- or 4-(4-alkylpiperazin-1-yl)benzoates.

Some of the compounds of the present invention are basic, and such compounds are useful in the form of the free base or in the form of a pharmaceutically acceptable acid addition salt thereof.

Acid addition salts are a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. In particular, acid addition salts can be prepared by separately reacting the purified compound in its free base form with a suitable organic or inorganic acid and isolating the salt thus formed. Pharmaceutically acceptable salts within the scope of the invention include those derived from mineral acids and organic acids. Exemplary acid addition salts include the hydrobromide hydrochloride, sulfate, bisulfate, phosphate, nitrate, acetate, oxalate, valerate, oleate, palmitate, quinates, stearate, laurate, borate, benzoate, lactate, phosphate, tosylate, citrate, maleate, fumarate, succinate, tartrate, naphthylate, mesylate, glucoheptonate, lactiobionate, sulfamates, malonates, salicylates, propionates, methylene-bis-β-hydroxynaphthoates, gentisates, isethionates, di-p-toluoyltartrates, methanesulfonates, ethanesulfonates, benzenesulfonates, p-toluenesulfonates, cyclohexylsulfamates and laurylsulfonate salts. See, for example S. M. Berge, et al., "Pharmaceutical Salts," *J. Pharm. Sci.,* 66. 1-19 (1977), which is incorporated herein by reference.

Where the compound of the invention is substituted with an acidic moiety, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the patient in pharmaceutical doses of the salts, so that the beneficial inhibitory effects inherent in the free base are not vitiated by side effects ascribable to the cations. Base addition salts can also be prepared by separately reacting the purified compound in its acid form with a suitable organic or inorganic base derived from alkali and alkaline earth metal salts and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which have sufficient basicity to form a stable salt, and preferably include those amines which are frequently used in medicinal chemistry because of their low toxicity and acceptability for medical use. Ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

It will be appreciated that compounds of the present invention may contain asymmetric centers. These asymmetric centers may independently be in either the R or S configuration. It will be apparent to those skilled in the art that certain compounds of the invention may also exhibit geometrical isomerism. It is to be understood that the present invention includes individual geometrical isomers and stereoisomers and mixtures thereof, including racemic mixtures, of compounds of Formula (I) hereinabove. Such isomers can be separated from their mixtures, by the application or adaptation of known methods. Chiral chromatography techniques represent one means for separating isomers from mixtures thereof. Chiral recrystallization techniques may be tried as an alternative means for separating isomers from mixtures thereof. Individual isomeric compounds can also be prepared by employing, where applicable, chiral precursors.

Regarding a more detailed description of the preferred compounds of the present invention, one particular embodiment of the invention is a compound of Formula (I) wherein $R^1$ is amino, dimethylamino, methoxy, ethoxy, ethyl, methylthio, methylamino, or 2,2,2-trifluoroethoxy; or an N-oxide thereof, or an ester prodrug thereof, or a pharmaceutically acceptable salt, hydrate, or solvate thereof.

Another particular embodiment of the invention is a compound of Formula (I) wherein $Cy^1$ is phenyl, benzimidazolyl, benzo[1,3]dioxolyl, benzothiazolyl, benzo[b]thiophenyl, 1H-benzotriazolyl, 2,3-dihydro-benzo[1,4]dioxanyl, 2,3-dihydro-benzofuranyl, 3,4-dihydro-2H-benzo[1,4]oxazinyl, furanyl, imidazolyl, 1H-indazolyl, indolinyl, indolyl, isoquinolinyl, isoxazolyl, oxadiazolyl, oxazolyl, 2-oxo-1H-pyridinyl, phenyl, pyrazolyl, pyridyl, thiazolyl, quinolinyl, thienyl or piperidinyl, wherein each of which independently is optionally substituted by one to three of the same or different Cy¹ substituent groups; or an N-oxide thereof, or an ester prodrug thereof, or a pharmaceutically acceptable salt, hydrate, or solvate thereof.

Another particular embodiment of the invention is a compound of Formula (I) wherein Cy¹ is phenyl, benzimidazol-2-yl, benzimidazol-5-yl, benzo[1,3]dioxol-5-yl, benzothiazol-6-yl, benzo[b]thiophen-2-yl, benzo[b]thiophen-3-yl, 1H-benzotriazol-6-yl, 2,3-dihydro-benzo[1,4]dioxin-6-yl, 2,3-dihydrobenzofuran-5-yl, 3,4-dihydro-2H-benzo[1,4]oxazin-7-yl, furan-2-yl, furan-3-yl, imidazol-1-yl, 1H-indazol-6-yl, indolin-5-yl, indol-3-yl, indol-5-yl, indol-6-yl isoquinolin-5-yl, isoxazol-4-yl, [1,2,4]oxadiazol-5-yl, [1,3,4]oxadiazol-2-yl, oxazol-5-yl, 2-oxo-1H-pyridin-5-yl, phenyl, pyrazol-1-yl, pyrazol-3-yl, pyrazol-4-yl, pyrid-3-yl, pyrid-4-yl, thiazol-2-yl, quinolin-3-yl, quinolin-6-yl, quinolin-8-yl, thien-2-yl, thien-3-yl or piperidin-1-yl, each of which is optionally substituted by one to three of the same or different Cy¹ substituent groups; or an N-oxide thereof, or an ester prodrug thereof, or a pharmaceutically acceptable salt, hydrate, or solvate thereof.

Another particular embodiment of the invention is a compound of Formula (I) wherein Cy² is phenyl, cyclohexenyl, benzo[1,3]dioxolyl, benzofuranyl, 2,3-dihydro-benzofuranyl, 3,4-dihydro-2H-benzo[1,4]oxazinyl, benzo[b]thiophenyl, imidazolyl, indolyl, isochromanyl, phenyl, naphthalenyl, pyridyl, or thienyl, each of which is optionally substituted by one to three of same or different substituents of alkoxy, (C₁-C₃)-alkyl, hydroxy, cyano, halogen, haloalkoxy, haloalkyl, nitro, Y¹Y²N—, Y¹Y²N—SO₂—, aryl or heteroaryl, wherein the aryl is optionally substituted by alkyl or hydroxyalkyl, and the heteroaryl is optionally substituted by alkyl; or an N-oxide thereof, or an ester prodrug thereof, or a pharmaceutically acceptable salt, hydrate, or solvate thereof.

Another particular embodiment of the invention is a compound of Formula (I) wherein Cy² is phenyl, cyclohex-1-enyl, benzo[1,3]dioxol-5-yl, benzofuran-6-yl, 2,3-dihydro-benzofuran-2-yl, 3,4-dihydro-2H-benzo[1,4]oxazin-2-yl, benzo[b]thiophen-2-yl, imidazol-4-yl, 1H-indol-3-yl, 1H-indol-5-yl, naphthalene-2-yl, isochroman-1-yl, pyridin-2-yl, pyridin-3-yl, pyridin-4-yl, or thien-2-yl, each of which is optionally substituted by one to three of the same or different substituents of alkoxy, (C₁-C₃)-alkyl, hydroxy, cyano, halogen, haloalkoxy, haloalkyl, nitro, Y¹Y²N—, Y¹Y²N—SO₂—, aryl or heteroaryl, wherein the aryl is optionally substituted by alkyl or hydroxyalkyl, and the heteroaryl is optionally substituted by alkyl; or an N-oxide thereof, or an ester prodrug thereof, or a pharmaceutically acceptable salt, hydrate, or solvate thereof.

Another particular embodiment of the invention is a compound of Formula (I) wherein: L¹ is —CH₂—, —CH₂—CH₂—, —CH₂—CH₂—CH₂—, —CH₂—CH₂—CH₂—CH₂—, —CH₂—CH(CH₃)—, —CH₂—C(CH₃)₂—, —CH(CH₃)—CH₂—, —CH₂—CH(OH)—, —CH(CO₂H)—CH₂—, —CH₂—CF₂—,

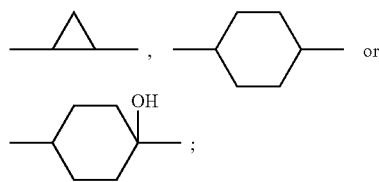

or an N-oxide thereof, or an ester prodrug thereof, or a pharmaceutically acceptable salt, hydrate, or solvate thereof.

Another particular embodiment of the invention is a compound of Formula (I) wherein L¹ and Cy² together represent indan-1-yl or indan-2-yl; or an N-oxide thereof, or an ester prodrug thereof, or a pharmaceutically acceptable salt, hydrate, or solvate thereof.

Another particular embodiment of the invention is a compound of Formula (I) wherein L¹ is —CH₂—CH₂—; or an N-oxide thereof, or an ester prodrug thereof, or a pharmaceutically acceptable salt, hydrate, or solvate thereof.

Another particular embodiment of the invention is a compound of Formula (I) wherein L¹ is —CH₂—CF₂—; or an N-oxide thereof, or an ester prodrug thereof, or a pharmaceutically acceptable salt, hydrate, or solvate thereof.

Another particular embodiment of the invention is a compound of Formula (I) wherein Cy¹ is unsubstituted phenyl or phenyl substituted by one to three of same or different substituent groups of acyl, alkylsulfinyl, alkylsulfonyl, carboxy, cyano, halo, heteroaroyl, heterocyclenyl, hydroxy, nitro, R²—C(=N—OR³)—, Y¹Y²N—, Y¹Y²NC(=O)—, Y¹Y²NC(=O)—O—, Y¹Y²NSO₂—, Y¹Y²N—C(=O)—(C₁-C₆)-alkylene-Z¹—, alkyl-C(=O)—N(R⁵)—SO₂—, alkyl-O—C(=O)—N(R⁵)—, alkyl-O—C(=O)—N(R⁵)—SO₂—, alkyl-O—N(R⁵)—C(=O)—, alkyl-O—N(R⁵)—SO₂—, alkyl-SO₂—N(R⁵)—C(=O)—, aryl-SO₂—N(R⁵)—C(=O)—, alkyl-SO₂—N(R⁵)—, R⁶—C(=O)—N(R⁵)— alkyl-NH—C(=O)—NH—;

alkoxy, which is optionally substituted by one to three of same or different of carboxy or heteroaryl; or alkyl, which is optionally substituted by one to three of same or different of halogen, carboxy, aryl, heteroaryl multicyclic alkaryl, cyano, hydroxy, Y¹Y²N—, H₂N—C(=NH)—NH—O—, R⁶—C(=O)—N(R⁵)—, R⁶—N(R⁵)—C=O)—, alkyl-O—C(=O)—N(R⁵)—, alkyl-SO₂—N(R⁵)—, R⁸—SO₂—N(R⁵)—C(=O)—, H₂N—C(=NH)—NH—O—; or alkoxy, which is optionally substituted by carboxy or heteroaryl;

wherein the aryl or heteroaryl moieties in the substituent groups are optionally independently substituted by hydroxy, amino, alkyl, alkoxy, carboxy, alkoxycarbonyl or R⁸—SO₂—N(R⁵)—C(=O)—;

and, wherein the heterocyclenyl or multicyclic alkaryl moieties in the substituent groups independently is optionally substituted by hydroxy, amino, alkyl, alkoxy, carboxy, alkoxycarbonyl, R⁸—SO₂—N(R⁵)—C(=O)— or oxo;

or an N-oxide thereof, or an ester prodrug thereof, or a pharmaceutically acceptable salt, hydrate, or solvate thereof.

Another particular embodiment of the invention is a compound of Formula (I) wherein Cy¹ is benzimidazol-2-yl, benzimidazol-5-yl, benzo[1,3]dioxol-5-yl, benzothiazol-6-yl, benzo[b]thiophen-2-yl, benzo[b]thiophen-3-yl, 1H-benzotriazol-6-yl, 2,3-dihydro-benzo[1,4]dioxin-6-yl, 2,3-dihydrobenzofuran-5-yl, 3,4-dihydro-2H-benzo[1,4]oxazin-7-yl, furan-2-yl, furan-3-yl, imidazol-1-yl, 1H-indazol-6-yl, indolin-5-yl, indol-3-yl, indol-5-yl, indol-6-yl isoquinolin-5-yl, isoxazol-4-yl, [1,2,4]oxadiazol-5-yl, [1,3,4]oxadiazol-2-yl, oxazol-5-yl, 2-oxo-1H-pyridin-5-yl), phenyl, pyrazol-1-yl, pyrazol-3-yl, pyrazol-4-yl, pyrid-3-yl, pyrid-4-yl, thiazol-2-yl, quinolin-3-yl, quinolin-6-yl, quinolin-8-yl, thien-2-yl, thien-3-yl or piperidin-1-yl, each of which is optionally substituted by one to three of the same or different substituent groups of lower alkanoyl, lower alkoxy, carboxy, cyano, halogen, R²—C(=N—OR³)—Y¹Y²N—, Y¹Y²NC(=O)—, heteroaryl; or loweralkyl, which is optionally substituted by one to three of same or different of halogen, carboxy, heteroaryl, hydroxy, or $Y^1Y^2N—$; wherein the heteroaryl moieties in substituent groups are optionally independently substituted by hydroxy, amino, alkyl or alkoxy; or an N-oxide thereof, or an ester prodrug thereof, or a pharmaceutically acceptable salt, hydrate, or solvate thereof.

Another particular embodiment of the invention is a compound of Formula (I) wherein $Cy^1$ is benzimidazol-2-yl, benzimidazol-5-yl, benzo[1,3]dioxol-5-yl, benzothiazol-6-yl, benzo[b]thiophen-2-yl, benzo[b]thiophen-3-yl, 1H-benzotriazol-6-yl, 2,3-dihydro-benzo[1,4]dioxin-6-yl, 2,3-dihydrobenzofuran-5-yl, 3,4-dihydro-2H-benzo[1,4]oxazin-7-yl, furan-2-yl, furan-3-yl, imidazol-1-yl, 1H-indazol-6-yl, indolin-5-yl, indol-3-yl, indol-5-yl, indol-6-yl isoquinolin-5-yl, isoxazol-4-yl, [1,2,4]oxadiazol-5-yl, [1,3,4]oxadiazol-2-yl, oxazol-5-yl, 2-oxo-1H-pyridin-5-yl), phenyl, pyrazol-1-yl, pyrazol-3-yl, pyrazol-4-yl, pyrid-3-yl, pyrid-4-yl, thiazol-2-yl, quinolin-3-yl, quinolin-6-yl, quinolin-8-yl, thien-2-yl, thien-3-yl or piperidin-1-yl, each of which is optionally substituted by one to three of the same or different substituent groups of formyl, acetyl, methoxy, carboxy, cyano, chloro, methyl, —CHF$_2$—, oxazol-5-yl, tetrazol-5-yl, HO$_2$C—CH$_2$—, HOCH$_2$—, HO—CH(CH$_3$)—, H—C(=N—OH)—, H—C(=N—OCH$_3$)—, CH$_3$—C(=N—OH)—, CH$_3$—C(=N—OCH$_3$)—, H$_2$N—CH$_2$—, CH$_3$NHCH$_2$—, CH$_3$OCH$_2$CH$_2$NHCH$_2$—, CH$_3$NH—C(=O)—,

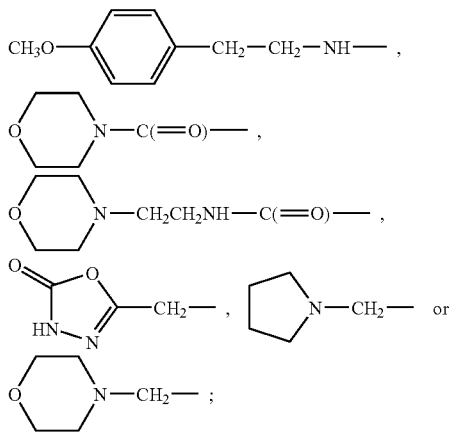

or an N-oxide thereof, or an ester prodrug thereof, or a pharmaceutically acceptable salt, hydrate, or solvate thereof.

Another particular embodiment of the invention is a compound of Formula (I) wherein $Cy^1$ is phenyl or phenyl substituted by one to three of the same or different groups of formyl, acetyl, methoxy, chloro, fluoro, hydroxy, nitro, cyano, carboxy, CH$_3$O—CH=CH—, CH$_3$—SO—, CH$_3$SO$_2$—, CH$_3$CH$_2$SO$_2$—, HO$_2$C—CH$_2$—O—, HO$_2$C—C(CH$_3$)$_2$—O—, 5-amino-[1,3,4]oxadiazol-2-yl, 3-methyl-isoxazol-5-yl, 3-methyl-[1,2,4]oxadiazol-5-yl, 5-methyl-[1,3,4]oxadiazol-2-yl, 2-methyl-2H-tetrazol-5-yl, 1-methyl-1H-tetrazol-5-yl, 5-methyl-2H-[1,2,4]triazol-3-yl, 3H-[1,3,4]oxadiazol-2-one, oxazol-5-yl, tetrazol-5-yl, 1H-tetrazol-5-ylmethyl, 1-methyl-1-(1H-tetrazol-5-yl)-ethyl, 3H-[1,3,4]oxadiazol-2-one, H—C(=N—OH)—, CH$_3$—C(=N—OH)—, H$_2$N—, (CH$_3$)$_2$N—, HO$_2$C—CF$_2$—, CH$_3$CH$_2$SO$_2$NHC(=O)—C(CH$_3$)$_2$—, PhCH$_2$SO$_2$NHC(=O)—C(CH$_3$)$_2$—, CH$_3$CH$_2$SO$_2$NHC(=O)—CF$_2$—, H$_2$N—C(=O)—, CH$_3$NHC(=O)—, (CH$_3$)$_2$NC(=O)—, (CH$_3$)$_2$NCH$_2$CH$_2$NH—C(=O)—, HO$_2$CCH$_2$NH—C(=O)—, HO$_2$CCH(CH$_3$)NH—C(=O)—, HO$_2$CCH(CH{CH$_3$}$_2$)NH—C(=O)—, HO$_2$CCH(CH$_2$CH{CH$_3$}$_2$)NH—C(=O)—, CH$_3$CH$_2$NH—C(=O)—O—, H$_2$N—SO$_2$—, CH$_3$NHSO$_2$—, CH$_3$CH$_2$NHSO$_2$—, (CH$_3$)$_2$CHNH—SO$_2$—, CH$_3$CH$_2$NH—C(=O)—CH$_2$—O—, (CH$_3$)$_2$CHNH—C(=O)—CH$_2$—O—, (CH$_3$)$_2$NCH$_2$CH$_2$NH—C(=O)—C(CH$_3$)$_2$—O—, CH$_3$—C(=O)—NH—SO$_2$—, CH$_3$CH$_2$—

O—C(=O)—NH—, CH₃—O—C(=O)—NH—SO₂—, CH₃—O—N(CH₃)—C(=O)—, CH₃—O—NH—SO₂—, CH₃—SO₂—NH—C(=O)—, CH₃—SO₂—N(CH₃)—C(=O)—,

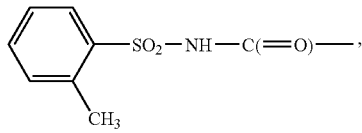

CH₃—SO₂—NH—, CH₃—C(=O)—NH—, CH₃O—CH₂—C(=O)—NH—, CH₃CH₂NH—C(=O)—NH—, HO₂C—CH₂CH₂—, HO₂C—CH(CH₃)—, HO₂C—C(CH₃)₂—, HO₂C—CH₂—O—CH₂—, benzyl, NC—CH₂—,

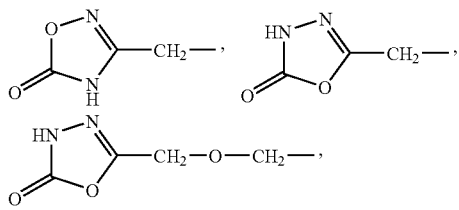

HOCH₂—, HOCH₂CH₂—, HO—CH(CH₃)—, HO—C(CH₃)₂—, H₂NCH₂—, (CH₃)₂NCH₂CH₂NHCH₂—, HO₂C—CH(CH₂Ph)—NHCH₂—, HO₂C—CH(CH₂OH)—NHCH₂—,

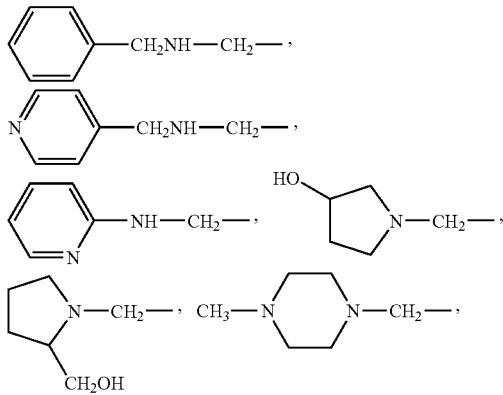

H₂N—C(=NH)—NH—O—CH₂—, CH₃OCH₂—C(=O)—NH—CH₂—, HOCH₂—NH—C(=O)—CH₂—, CH₃—C(=O)—NH—CH₂—, CH₃—C(=O)—NH—CH₂CH₂—, HOCH₂CH₂—NH—C(=O)—CH₂CH₂—, CH₃—O—C(=O)—NH—CH₂—, CH₃SO₂—NH—CH₂—, H₂N—C(=NH)—NH—O—CH₂—,

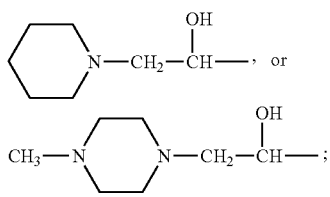

or an N-oxide thereof, or an ester prodrug thereof, or a pharmaceutically acceptable salt, hydrate, or solvate thereof.

Another particular embodiment of the invention is a compound of Formula (I) wherein $Cy^2$ is cyclohex-1-enyl; or an N-oxide thereof, or an ester prodrug thereof, or a pharmaceutically acceptable salt, hydrate, or solvate thereof.

Another particular embodiment of the invention is a compound of Formula (I) wherein $Cy^2$ is naphthyl or phenyl, each of which is optionally substituted by one to three of the same or different groups of alkoxy, $(C_1-C_3)$-alkyl, hydroxy, cyano, halogen, haloalkoxy, haloalkyl, nitro, $Y^1Y^2N$—, $Y^1Y^2N$—SO₂—, aryl or heteroaryl, wherein the aryl is optionally substituted by alkyl or hydroxyalkyl, and the heteroaryl is optionally substituted by alkyl; or an N-oxide thereof, or an ester prodrug thereof, or a pharmaceutically acceptable salt, hydrate, or solvate thereof.

Another particular embodiment of the invention is a compound of Formula (I) wherein $Cy^2$ is naphthyl or phenyl, each of which is optionally substituted by one to three of same or different groups of methoxy, ethoxy, methyl, ethyl, bromo, chloro, fluoro, F₂HCO—, F₃CO—, F₃C—, amino, H₂N—SO₂—, cyano, hydroxy, nitro or 5-methyl-[1,3,4]oxadiazol-2-yl; or an N-oxide thereof, or an ester prodrug thereof, or a pharmaceutically acceptable salt, hydrate, or solvate thereof.

Another particular embodiment of the invention is a compound of Formula (I) wherein $Cy^2$ is benzo[1,3]dioxol-5-yl, 1H-indol-3-yl, 1H-indol-5-yl, imidazol-4-yl, 1H-indol-3-yl, pyridin-2-yl, pyridin-3-yl, pyridin-4-yl, or thien-2-yl, each of which is optionally substituted by one to three of same or different groups of alkoxy, halo, or hydroxy; or an N-oxide thereof, or an ester prodrug thereof, or a pharmaceutically acceptable salt, hydrate, or solvate thereof.

Another particular embodiment of the invention is a compound of Formula (I) wherein $L^2$ is a bond.

Another particular embodiment of the invention is a compound of Formula (II)

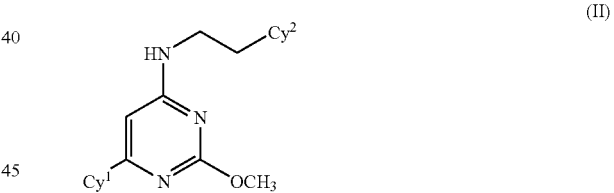

wherein $Cy^1$ and $Cy^2$ are as defined hereinabove, or a N-oxide thereof, or a ester prodrug thereof, or a pharmaceutically acceptable salt, hydrate or solvate thereof.

Another particular embodiment of the invention is a compound of Formula (II) wherein $Cy^1$ is phenyl or phenyl substituted by one to three of same or different substituent groups of:

acyl, alkylsulfonyl, carboxy, cyano, halo, heteroaryl, hydroxy, heterocyclyl, $R^2$—C(=N—OR³)—, $Y^1Y^2N$—, $Y^1Y^2NC(=O)$—, $Y^1Y^2NC(=O)$—O—, $Y^1Y^2N$—SO₂—, $Y^1Y^2N$—C(=O)—$(C_1-C_6)$-alkylene-$Z^1$—, alkyl-C(=O)—N(R⁵)—SO₂—, alkyl-O—C(=O)—N(R⁵)—SO₂—, alkyl-O—N(R⁵)—SO₂—, alkyl-SO₂—N(R⁵)—C(=O)—, alkyl-SO₂—N(R⁵)—, $R^6$—C(=O)—N(R⁵)—, alkyl-NH—C(=O)—NH—;

alkenyl, which is optionally substituted by alkoxy;

alkoxy, which is optionally substituted by carboxy or heteroaryl; or alkyl, which is optionally substituted by halogen, carboxy, cyano, heteroaryl, hydroxy, $R^6$—C(=O)—N(R⁵)—, R⁸—SO₂—N(R⁵)—C(=O)—; or alkoxy, which is optionally substituted by carboxy;

wherein the heterocyclyl moieties in the substituent groups are optionally independently substituted by hydroxy, amino, alkyl, alkoxy, oxo, carboxy, alkoxycarbonyl or R⁸—SO₂—N(R⁵)—C(=O)—; and the heteroaryl moieties in the substituent groups are optionally independently substituted by hydroxy, amino, alkyl, alkoxy, carboxy, alkoxycarbonyl or R⁸—SO₂—N(R⁵)—C(=O)—;

or an N-oxide thereof, or an ester prodrug thereof, or a pharmaceutically acceptable salt, hydrate, or solvate thereof.

Another particular embodiment of the invention is a compound of Formula (II) wherein Cy¹ is phenyl or phenyl substituted by one to three of same or different substituent groups of formyl, acetyl, cyano, methoxy, chloro, fluoro, hydroxy, carboxy, 5-amino-[1,3,4]oxadiazol-2-yl, 3-methyl-isoxazol-5-yl, 3-methyl-[1,2,4]oxadiazol-5-yl, 5-methyl-[1,3,4]oxadiazol-2-yl, 2-methyl-2H-tetrazol-5-yl, 5-methyl-2H-[1,2,4]triazol-3-yl, oxazol-5-yl, tetrazol-5-yl, 1H-tetrazol-5-ylmethyl, 1-methyl-1-(1H-tetrazol-5-yl)-ethyl, H₂N—, CH₃—NHC(=O)—, CH₃CH₂NH—C(=O)—O—CH₃O—CH=CH—, CH₃SO₂—, CH₃CH₂SO₂—, HO₂C—CH₂—O—, HO₂C—C(CH₃)₂—O—, H—C(=N—OH)—, CH₃—C(=N—OH)—, CH₃OCH₂CH₂NH—, H₂N—SO₂—, CH₃NHSO₂—, CH₃CH₂NHSO₂—, (CH₃)₂CHNH—SO₂—, CH₃CH₂NH—C(=O)—CH₂—O—, (CH₃)₂CHNH—C(=O)—CH₂—O—, CH₃—C(=O)—NH—SO₂—, CH₃—O—C(=O)—NH—SO₂—, CH₃—O—NH—SO₂—, CH₃—SO₂—NH—C(=O)—, CH₃—SO₂—N(CH₃)—C(=O)—, CH₃—SO₂—NH—, CH₃—C(=O)—NH—, CH₃O—CH₂—C(=O)—NH—, CH₃CH₂NH—C(=O)—NH—, HO₂C—CH₂CH₂—, HO₂C—CH(CH₃)—, HO₂C—C(CH₃)₂—, HO₂C—CH₂—O—CH₂—, HOCH₂—, HO—CH(CH₃)—, HO—C(CH₃)₂—, NC—CH₂—, CH₃OCH₂—C(=O)—NH—CH₂—,

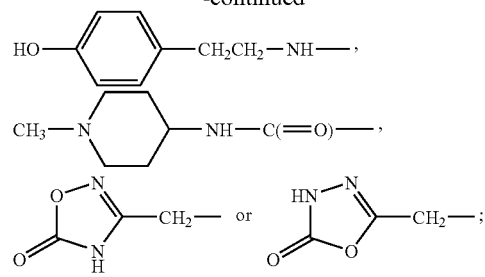

HO₂C—CF₂—, CH₃CH₂SO₂NHC(=O)—C(CH₃)₂—, PhCH₂SO₂NHC(=O)—C(CH₃)₂—, CH₃CH₂SO₂NHC(=O)—CF₂—,

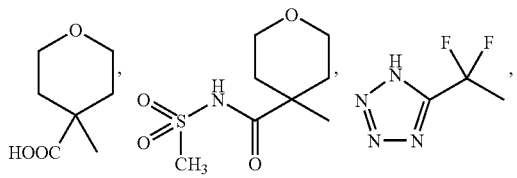

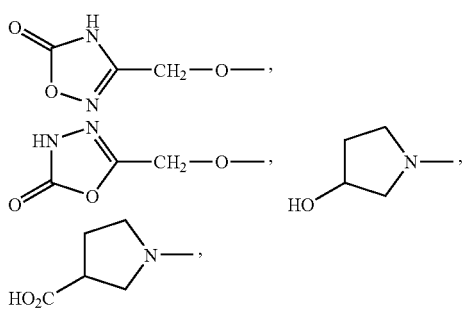

-continued

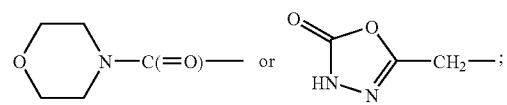

or an N-oxide thereof, or an ester prodrug thereof, or a pharmaceutically acceptable salt, hydrate, or solvate thereof.

Another particular embodiment of the invention is a compound of Formula (II) wherein Cy¹ is benzimidazol-2-yl, benzimidazol-5-yl, benzo[1,3]dioxol-5-yl, benzothiazol-6-yl, benzo[b]thiophen-2-yl, benzo[b]thiophen-3-yl, 1H-benzotriazol-6-yl, 2,3-dihydro-benzo[1,4]dioxin-6-yl, 2,3-dihydrobenzofuran-5-yl, 3,4-dihydro-2H-benzo[1,4]oxazin-7-yl, furan-2-yl, furan-3-yl, imidazol-1-yl, 1H-indazol-6-yl, indolin-5-yl, indol-3-yl, indol-5-yl, indol-6-yl isoquinolin-5-yl, isoxazol-4-yl, [1,2,4]oxadiazol-5-yl, [1,3,4]oxadiazol-2-yl, oxazol-5-yl, 2-oxo-1H-pyridin-5-yl), phenyl, pyrazol-1-yl, pyrazol-3-yl, pyrazol-4-yl, pyrid-3-yl, pyrid-4-yl, thiazol-2-yl, quinolin-3-yl, quinolin-6-yl, quinolin-8-yl, thien-2-yl, thien-3-yl or piperidin-1-yl, each of which is optionally substituted with one to three of same or different substituent groups of:

acyl, carboxy, heteroaryl, R²—C(=N—OR³)—, Y¹Y²NC(=O)—; or alkyl, which is optionally substituted by carboxy, heteroaryl or hydroxy;

wherein the heteroaryl moieties in the substituent groups are optionally independently substituted by hydroxy, amino, alkyl or alkoxy, or an N-oxide thereof, or an ester prodrug thereof, or a pharmaceutically acceptable salt, hydrate, or solvate thereof.

Another particular embodiment of the invention is a compound of Formula (II) wherein Cy¹ is benzimidazol-2-yl, benzimidazol-5-yl, benzo[1,3]dioxol-5-yl, benzothiazol-6-yl, benzo[b]thiophen-2-yl, benzo[b]thiophen-3-yl, 1H-benzotriazol-6-yl, 2,3-dihydro-benzo[1,4]dioxin-6-yl, 2,3-dihydrobenzofuran-5-yl, 3,4-dihydro-2H-benzo[1,4]oxazin-7-yl, furan-2-yl, furan-3-yl, imidazol-1-yl, 1H-indazol-6-yl, indolin-5-yl, indol-3-yl, indol-5-yl, indol-6-yl isoquinolin-5-yl, isoxazol-4-yl, [1,2,4]oxadiazol-5-yl, [1,3,4]oxadiazol-2-yl, oxazol-5-yl, 2-oxo-1H-pyridin-5-yl), phenyl, pyrazol-1-yl, pyrazol-3-yl, pyrazol-4-yl, pyrid-3-yl, pyrid-4-yl, thiazol-2-yl, quinolin-3-yl, quinolin-6-yl, quinolin-8-yl, thien-2-yl, thien-3-yl or piperidin-1-yl, each of which is optionally substituted with one to three of same or different substituent groups of formyl, acetyl, methyl, methoxy, carboxy, oxazol-5-yl, tetrazol-5-yl, HO₂C—CH₂—, HOCH₂—, HO—CH(CH₃)—, H—C(=N—OH)—, H—C(=N—OCH₃)—, CH₃—C(=N—OH)—, CH₃—C(=N—OCH₃)—, CH₃NH—C(=O)—, or an N-oxide thereof, or an ester prodrug thereof, or a pharmaceutically acceptable salt, hydrate, or solvate thereof.

Another particular embodiment of the invention is a compound of Formula (II) wherein Cy² is naphthyl or phenyl, each of which is optionally substituted with one to three of same or different substituent groups of alkoxy, (C₁-C₃)-alkyl, hydroxy, cyano, halogen, haloalkoxy, haloalkyl, nitro, Y¹Y²N—, Y¹Y²N—SO₂—, aryl or heteroaryl, wherein the aryl is optionally substituted by alkyl or hydroxyalkyl, and the heteroaryl is optionally substituted by alkyl; or an N-oxide thereof, or an ester prodrug thereof, or a pharmaceutically acceptable salt, hydrate, or solvate thereof.

Another particular embodiment of the invention is a compound of Formula (II) wherein Cy² is naphthyl or phenyl, each of which is optionally substituted with one to three of same or different substituent groups of methoxy, methyl, ethyl, cyano, bromo, chloro, fluoro, F₂HCO—, F₃CO—, F₃C—, nitro or 5-methyl-[1,3,4]oxadiazol-2-yl; or an N-oxide thereof, or an ester prodrug thereof, or a pharmaceutically acceptable salt, hydrate, or solvate thereof.

Another particular embodiment of the invention is a compound of Formula (II) wherein Cy² is cyclohex-1-enyl, benzo[1,3]dioxol-5-yl, benzofuran-6-yl, 2,3-dihydro-benzofuran-2-yl, 3,4-dihydro-2H-benzo[1,4]oxazin-2-yl, benzo[b]thiophen-2-yl, imidazol-4-yl, 1H-indol-3-yl, 1H-indol-5-yl, naphthalene-2-yl, isochroman-1-yl, pyridin-2-yl, pyridin-3-yl, pyridin-4-yl, or thien-2-yl; or an N-oxide thereof, or an ester prodrug thereof, or a pharmaceutically acceptable salt, hydrate, or solvate thereof.

Another particular embodiment of the invention is a compound of Formula (II) wherein Cy² is benzo[1,3]dioxol-5-yl, 2,2-difluoro-benzo[1,3]dioxol-5-yl pyridin-4-yl or thien-2-yl; or an N-oxide thereof, or an ester prodrug thereof, or a pharmaceutically acceptable salt, hydrate, or solvate thereof.

Another particular embodiment of the invention is a compound of Formula (II) wherein Cy¹ is phenyl, which is optionally substituted with one to three of same or different substituent groups of:
  acyl, carboxy, cyano, halo, heteroaryl, heterocyclyl, hydroxy, R²—C(=N—OR³)—, Y¹Y²NC(=O)—, Y¹Y²NC(=O)—O—, alkyl-O—C(=O)—N(R⁵)—SO₂—, alkyl-SO₂—N(R⁵)—C(=O)—;
  alkoxy, which is optionally substituted by carboxy or heteroaryl; or
  alkyl, which is optionally substituted by halogen, carboxy, heteroaryl, hydroxy, R⁶—C(=O)—N(R⁵)—, R⁸—SO₂—N(R⁵)—C(=O)—; or alkoxy, which is optionally substituted by carboxy;
  wherein
  the heterocyclyl moieties in the substituent groups are optionally independently substituted by hydroxy, amino, alkyl, alkoxy, oxo, carboxy, alkoxycarbonyl or R⁸—SO₂—N(R⁵)—C(=O)—;
  the heteroaryl moieties in the substituent groups are optionally independently substituted by hydroxy, amino, alkyl, alkoxy, carboxy, alkoxycarbonyl or R⁸—SO₂—N(R⁵)—C(=O)—;
or an N-oxide thereof, or an ester prodrug thereof, or a pharmaceutically acceptable salt, hydrate, or solvate thereof.

Another particular embodiment of the invention is a compound of Formula (II) wherein Cy¹ is phenyl, which is optionally substituted with one to three of same or different substituent groups of formyl, methoxy, carboxy, chloro, fluoro, cyano, tetrazol-5-yl, 1H-tetrazol-5-ylmethyl, HO₂C—CH₂—O—, HO₂C—C(CH₃)₂—O—, H—C(=N—OH)—, CH₃NHC(=O)—, CH₃CH₂NH—C(=O)—O—, CH₃—O—C(=O)—NH—SO₂—, CH₃—SO₂—NH—C(=O)—, HO₂C—CH(CH₃)—, HO₂C—C(CH₃)₂—, HO₂C—CH₂—O—CH₂—, HOCH₂—,

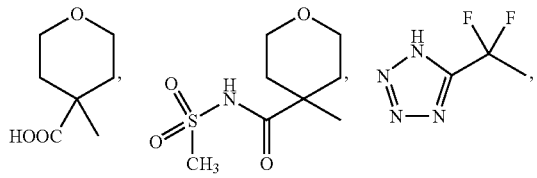

HO₂C—CF₂—, CH₃CH₂SO₂NHC(=O)—C(CH₃)₂—, PhCH₂SO₂NHC(=O)—C(CH₃)₂—, CH₃CH₂SO₂NHC(=O)—CF₂—,

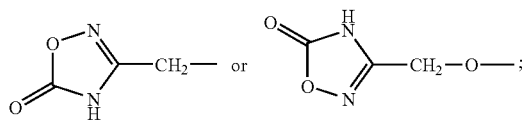

or an N-oxide thereof, or an ester prodrug thereof, or a pharmaceutically acceptable salt, hydrate, or solvate thereof.

Another particular embodiment of the invention is a compound of Formula (II) wherein Cy¹ is:

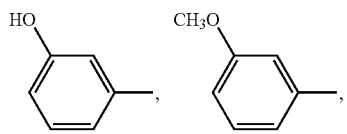

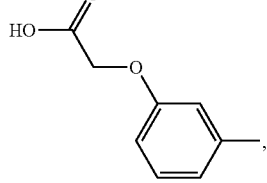

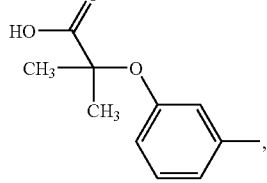

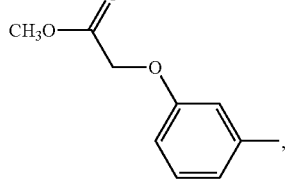

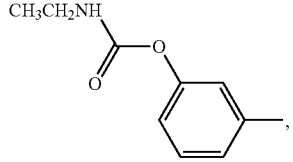

27
-continued
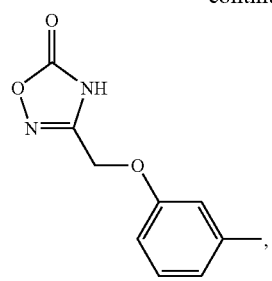
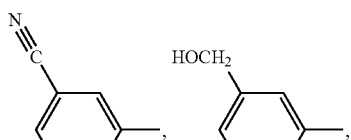
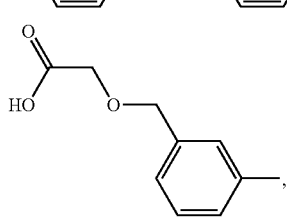
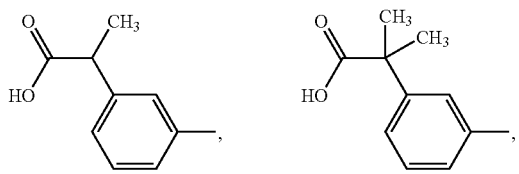
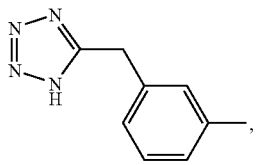
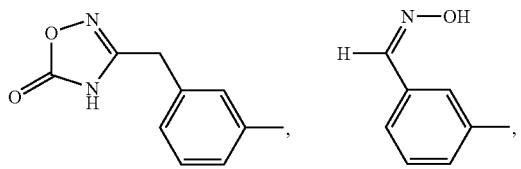
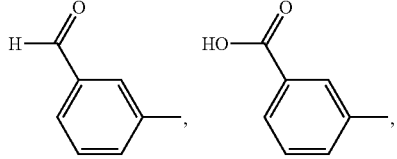
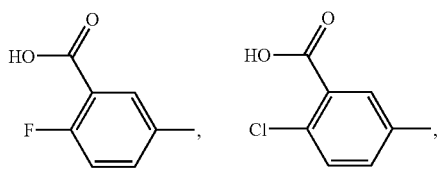
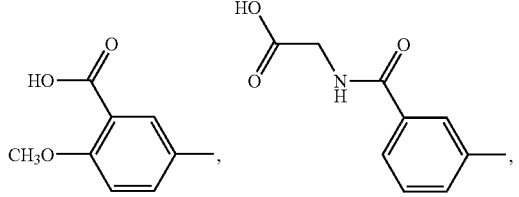
28
-continued
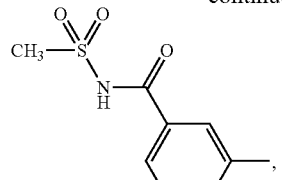
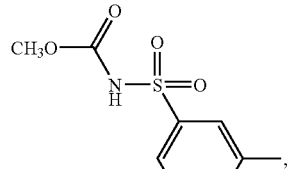
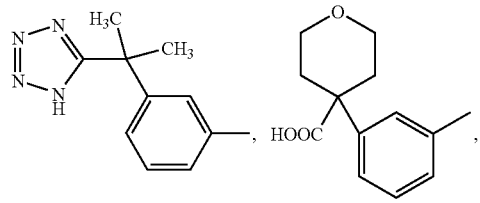
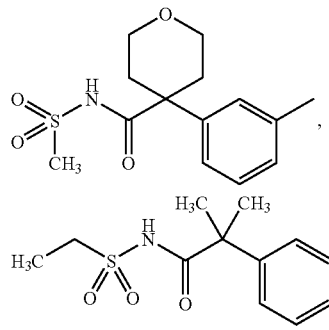
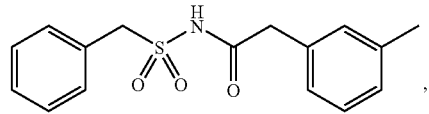
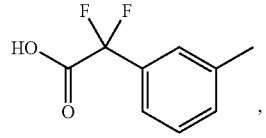
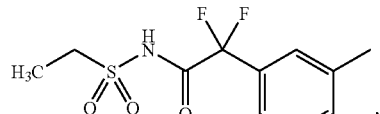
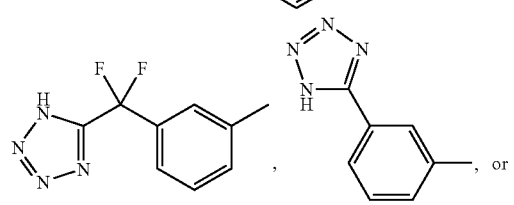; or
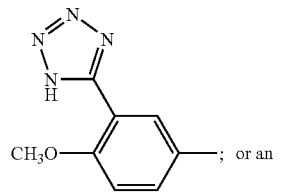; or an N-oxide thereof, or an ester prodrug thereof, or a pharmaceutically acceptable salt, hydrate, or solvate thereof.

Another particular embodiment of the invention is a compound of Formula (II) wherein $Cy^1$ is 1H-benzotriazol-6-yl, 1H-indazol-6-yl, indol-5-yl, indol-6-yl, 2-oxo-1H-pyridin-5-yl, quinolin-6-yl, quinolin-3-yl, thien-2-yl, thien-3-yl or 1-piperidin-1-yl, each of which is optionally substituted by one to three of same or different groups of acyl, carboxy, tetrazol-5-yl; $R^2$—C(=N—$OR^3$)—, $Y^1Y^2$NC(=O)—; or alkyl, which is optionally substituted by carboxy or hydroxy; or an N-oxide thereof, or an ester prodrug thereof, or a pharmaceutically acceptable salt, hydrate, or solvate thereof.

Another particular embodiment of the invention is a compound of Formula (II) wherein $Cy^1$ is 1H-benzotriazol-6-yl, 1H-indazol-6-yl, indol-5-yl, indol-6-yl, 2-oxo-1H-pyridin-5-yl, quinolin-6-yl, quinolin-3-yl, thien-2-yl, thien-3-yl or 1-piperidin-1-yl, each of which is optionally substituted by one to three of same or different groups of formyl, carboxy, tetrazol-5-yl, H—C(=N—OH)—, $CH_3$—C(=N—OH)—, $CH_3$—NH—C(=O)—, $HO_2C$—$CH_2$—, or HO—$CH_2$—.

Another particular embodiment of the invention is a compound of Formula (II) wherein $Cy^1$ is:

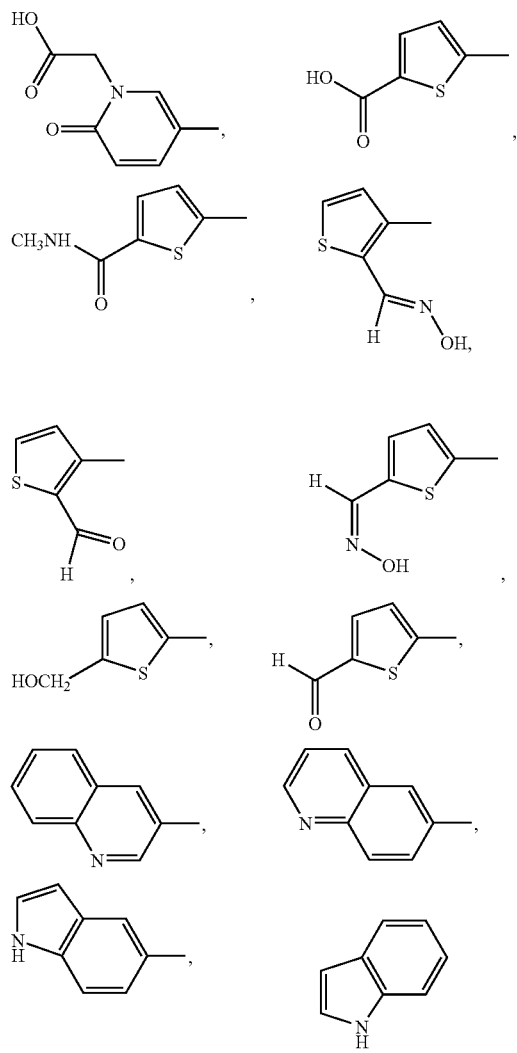

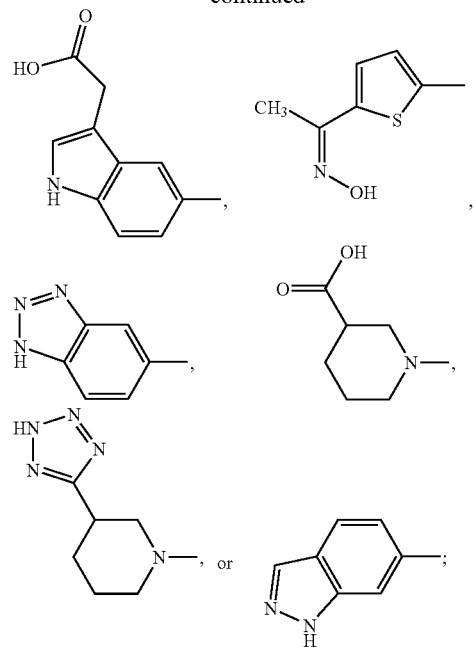

or an N-oxide thereof, or an ester prodrug thereof, or a pharmaceutically acceptable salt, hydrate, or solvate thereof.

Another particular embodiment of the invention is a compound of Formula (II) wherein $Cy^2$ is 4-chlorophenyl, 2,4-dichlorophenyl, 2,6-dichlorophenyl, 2,6-difluorophenyl, 2-fluoro-6-chlorophenyl, 3-fluoro-4-methoxyphenyl, 4-fluorophenyl, 2-fluoro-4-trifluoromethylphenyl, 4-methoxyphenyl, 4-nitrophenyl, 2,2-difluoro-benzo[1,3]dioxol-5-yl or 4-trifluoromethoxyphenyl; or an N-oxide thereof, or an ester prodrug thereof, or a pharmaceutically acceptable salt, hydrate, or solvate thereof.

Another particular embodiment of the invention is a compound of Formula (I), which is 3{-6-[2-(3-fluoro-4-methoxy-phenyl)-ethylamino]-2-methoxy-pyrimidin-4-yl}-benzonitrile,

[6-(3-amino-phenyl)-2-methoxy-pyrimidin-4-yl]-[2-(4-methoxy-phenyl)-ethyl]amine, 3-{2-methoxy-6-[2-(4-methoxy-phenyl)-ethylamino]-pyrimidin-4-yl}-benzenesulfonamide, 3-{2-methoxy-6-[2-(4-methoxy-phenyl)-ethyl amino]-pyrimidin-4-yl}-N-methyl-benzenesulfonamide, N-ethyl-3-{2-methoxy-6-[2-(4-methoxy-phenyl)-ethylamino]-pyrimidin-4-yl}-benzenesulfonamide, N-methoxycarbonyl-3-{2-methoxy-6-[2-(4-methoxy-phenyl)-ethylamino]-pyrimidin-4-yl}-benzenesulfonamide, 6-(3-amino-phenyl)-2-methoxy-pyrimidin-4-yl]-[2-(4-trifluoromethoxy-phenyl)-ethyl]-amine, N-(3-{2-methoxy-6-[2-(4-trifluoromethoxy-phenyl)-ethylamino]-pyrimidin-4-yl}-phenyl)-acetamide, N-(3-{2-methoxy-6-[2-(4-methoxy-phenyl)-ethylamino]-pyrimidin-4-yl}-phenyl)-acetamide, (3-{2-methoxy-6-[2-(4-methoxy-phenyl)-ethylamino]-pyrimidin-4-yl}-phenyl)-carbamic acid ethyl ester, 3-{6-[2-(2,4-difluoro-phenyl)-ethylamino]-2-methoxy-pyrimidin-4-yl}-benzoic acid, 5-{2-methoxy-6-[2-(4-methoxy-phenyl)-ethylamino]-pyrimidin-4-yl}-thiophene-2-carboxylic acid 5-{2-methoxy-6-[2-(4-methoxy-phenyl)-ethylamino]-pyrimidin-4-yl}-thiophene-2-carbaldehyde, 4-{2-methoxy-6-[2-(4-methoxy-phenyl)-ethylamino]-pyrimidin-4-yl}-thiophene-2-carbaldehyde,
[6-(3,5-dimethyl-isoxazol-4-yl)-2-methoxy-pyrimidin-4-yl]-[2-(4-methoxy-phenyl)-ethyl]-amine,
[2-methoxy-6-(5-methyl-thiophen-2-yl)-pyrimidin-4-yl]-[2-(4-methoxy-phenyl)-ethyl]-amine,
[2-(4-methoxy-phenyl)-ethyl]-[2-methoxy-6-(1H-pyrazol-4-yl)-pyrimidin-4-yl]-amine,
(6-isoquinolin-5-yl-2-methoxy-pyrimidin-4-yl)-[2-(4-methoxy-phenyl)-ethyl]-amine,
(5-{2-methoxy-6-[2-(4-methoxy-phenyl)-ethylamino]-pyrimidin-4-yl}-thiophen-2-yl)-methanol,
(3-{2-methoxy-6-[2-(4-methoxy-phenyl)-ethylamino]-pyrimidin-4-yl}-thiophen-2-yl)-methanol,
(3-{2-methoxy-6-[2-(4-methoxy-phenyl)-ethylamino]-pyrimidin-4-yl}-phenyl)-methanol,
(3-{6-[2-(2-chloro-6-fluoro-phenyl)-ethylamino]-2-methoxy-pyrimidin-4-yl}-phenyl)-methanol,
[2-(4-methoxy-phenyl)-ethyl]-(2-methoxy-6-quinolin-6-yl-pyrimidin-4-yl)-amine,
[2-(4-methoxy-phenyl)-ethyl]-(2-methoxy-6-quinolin-3-yl-pyrimidin-4-yl)-amine,
[6-(1H-indol-5-yl)-2-methoxy-pyrimidin-4-yl]-[2-(4-methoxy-phenyl)-ethyl]-amine,
N-(2-{2-methoxy-6-[2-(4-methoxy-phenyl)-ethylamino]-pyrimidin-4-yl}-phenyl)-methanesulfonamide,
4-{2-methoxy-6-[2-(4-methoxy-phenyl)-ethylamino]-pyrimidin-4-yl}-benzamide,
[2-methoxy-6-(1-methyl-1H-indol-5-yl)-pyrimidin-4-yl]-[2-(4-methoxy-phenyl)-ethyl]-amine,
(6-benzo[b]thiophen-2-yl-2-methoxy-pyrimidin-4-yl)-[2-(4-methoxy-phenyl)-ethyl]-amine,
1-(4-{2-methoxy-6-[2-(4-methoxy-phenyl)-ethylamino]-pyrimidin-4-yl}-phenyl)-ethanone,
[6-(3-methanesulfonyl-phenyl)-2-methoxy-pyrimidin-4-yl]-[2-(4-methoxy-phenyl)-ethyl]-amine,
[6-(2,3-dihydro-benzofuran-5-yl)-2-methoxy-pyrimidin-4-yl]-[2-(4-methoxy-phenyl)-ethyl]-amine,
[2-methoxy-6-(4-morpholin-4-yl-phenyl)-pyrimidin-4-yl]-[2-(4-methoxy-phenyl)-ethyl]-amine,
[6-(4-dimethylamino-phenyl)-2-methoxy-pyrimidin-4-yl]-[2-(4-methoxy-phenyl)-ethyl]-amine,
2,2'-dimethoxy-N*6*,N*6'*-bis-[2-(4-methoxy-phenyl)-ethyl]-[4,4']bipyrimidinyl-6,6'-diamine,
[2-methoxy-6-(5-oxazol-5-yl-thiophen-2-yl)-pyrimidin-4-yl]-[2-(4-methoxy-phenyl)-ethyl]-amine,
[2-methoxy-6-(3-oxazol-5-yl-phenyl)-pyrimidin-4-yl]-[2-(4-methoxy-phenyl)-ethyl]-amine,
[6-(5-difluoromethyl-thiophen-2-yl)-2-methoxy-pyrimidin-4-yl]-[2-(4-methoxy-phenyl)-ethyl]-amine,
[2-(4-methoxy-phenyl)-ethyl]-[2-methoxy-6-(5-pyrrolidin-1-ylmethyl-thiophen-2-yl)-pyrimidin-4-yl]-amine,
6-{4-fluoro-3-[(2-methoxy-ethylamino)-methyl]-phenyl}-2-methoxy-pyrimidin-4-yl)-[2-(4-methoxy-phenyl)-ethyl]-amine,
4-[2-(3-{2-methoxy-6-[2-(4-methoxy-phenyl)-ethylamino]-pyrimidin-4-yl}-benzylamino)-ethyl]-phenol,
N-(2-fluoro-5-{2-methoxy-6-[2-(4-methoxy-phenyl)-ethylamino]-pyrimidin-4-yl}-benzyl)-N',N'-dimethyl-ethane-1,2-diamine,
[6-(1H-benzoimidazol-5-yl)-2-methoxy-pyrimidin-4-yl]-[2-(4-methoxy-phenyl)-ethyl]-amine,
[6-(1H-benzotriazol-5-yl)-2-methoxy-pyrimidin-4-yl]-[2-(4-methoxy-phenyl)-ethyl]-amine,
6-{2-methoxy-6-[2-(4-methoxy-phenyl)-ethylamino]-pyrimidin-4-yl}-3H-benzooxazol-2-one,
[2-(3,4-dimethoxy-phenyl)-ethyl]-[6-(3,4-dimethoxy-phenyl)-2-methylsulfanyl-pyrimidin-4-yl]-amine,
3-{6-[2-(3,4-dimethoxy-phenyl)-ethylamino]-2-methylsulfanyl-pyrimidin-4-yl}-benzoic acid,
[2-(4-methoxy-phenyl)-ethyl]-[6-(3-methoxy-phenyl)-2-methylsulfanyl-pyrimidin-4-yl]-amine,
[2-(3,4-dimethoxy-phenyl)-ethyl]-[6-(3,4-dimethoxy-phenyl)-2-isopropoxy-pyrimidin-4-yl]-amine,
[6-(3,4-dimethoxy-phenyl)-2-ethoxy-pyrimidin-4-yl]-[2-(3,4-dimethoxy-phenyl)-ethyl]-amine,
[2-ethyl-6-(3-methoxy-phenyl)-pyrimidin-4-yl]-[2-(4-methoxy-phenyl)-ethyl]-amine,
6-(3-methoxy-phenyl)-N*4*-[2-(4-methoxy-phenyl)-ethyl]-N*2*,N*2*-dimethyl-pyrimidine-2,4-diamine,
2-fluoro-5-{2-methoxy-6-[2-(4-methoxy-phenyl)-ethylamino]-pyrimidin-4-yl}-benzoic acid,
3-{6-[2-(2-chloro-6-fluoro-phenyl)-ethylamino]-2-methoxy-pyrimidin-4-yl}-benzoic acid,
2-methoxy-5-{2-methoxy-6-[2-(4-methoxy-phenyl)-ethylamino]-pyrimidin-4-yl}-benzoic acid,
[2-methoxy-6-(1-oxy-pyridin-3-yl)-pyrimidin-4-yl]-[2-(4-methoxy-phenyl)-ethyl]-amine,
[2-(2,2-difluoro-benzo[1,3]dioxol-5-yl)-ethyl]-[2-methoxy-6-(1-oxy-pyridin-3-yl)-pyrimidin-4-yl]-amine,
2-(3-{2-methoxy-6-[2-(4-methoxy-phenyl)-ethylamino]-pyrimidin-4-yl}-phenoxy)-2-methyl-propionic acid ethyl ester,
(3-{2-methoxy-6-[2-(4-methoxy-phenyl)-ethylamino]-pyrimidin-4-yl}-phenoxy)-acetic acid methyl ester,
(3-{6-[2-(2,4-dichloro-phenyl)-ethylamino]-2-methoxy-pyrimidin-4-yl}-phenoxy)-acetic acid methyl ester,
(5-{6-[2-(2-chloro-6-fluoro-phenyl)-ethylamino]-2-methoxy-pyrimidin-4-yl}-2-oxo-2H-pyridin-1-yl)-acetic acid methyl ester,
(3-{6-[2-(2,4-dichloro-phenyl)-ethylamino]-2-methoxy-pyrimidin-4-yl}-phenoxy)-acetonitrile,
(3-{6-[2-(2-chloro-6-fluoro-phenyl)-ethylamino]-2-methoxy-pyrimidin-4-yl}-phenoxy)-acetonitrile,
2-(3-{2-methoxy-6-[2-(4-methoxy-phenyl)-ethylamino]-pyrimidin-4-yl}-phenoxy)-2-methyl-propionic acid,
(3-{2-methoxy-6-[2-(4-methoxy-phenyl)-ethylamino]-pyrimidin-4-yl}-phenoxy)-acetic acid,
(5-{6-[2-(2-chloro-6-fluoro-phenyl)-ethylamino]-2-methoxy-pyrimidin-4-yl}-2-oxo-2H-pyridin-1-yl)-acetic acid,
2-(3-{6-[2-(2,4-dichloro-phenyl)-ethylamino]-2-methoxy-pyrimidin-4-yl}-phenoxy)-2-methyl-propionic acid,
2-chloro-5-{2-methoxy-6-[2-(4-methoxy-phenyl)-ethylamino]-pyrimidin-4-yl}-benzoic acid,
[2-(4-methoxy-phenyl)-ethyl]-{2-methoxy-6-[3-(1H-tetrazol-5-yl)-phenyl]-pyrimidin-4-yl}-amine,
[2-(4-methoxy-phenyl)-ethyl]-{2-methoxy-6-[3-(1H-tetrazol-5-ylmethyl)-phenyl]-pyrimidin-4-yl}-amine,
{2-methoxy-6-[4-methoxy-3-(1H-tetrazol-5-yl)-phenyl]-pyrimidin-4-yl}-[2-(4-methoxy-phenyl)-ethyl]-amine,
N-(3-{2-methoxy-6-[2-(4-methoxy-phenyl)-ethylamino]-pyrimidin-4-yl}-benzoyl)-methanesulfonamide,
3-{6-[2-(3,4-dimethoxy-phenyl)-ethylamino]-2-methoxy-pyrimidin-4-yl}-N-(2-pyrrolidin-1-yl-ethyl)-benzamide,
2-fluoro-5-{2-methoxy-6-[2-(4-methoxy-phenyl)-ethylamino]-pyrimidin-4-yl}-benzaldehyde oxime,
3-{2-methoxy-6-[2-(4-methoxy-phenyl)-ethylamino]-pyrimidin-4-yl}-benzaldehyde oxime,
2-methoxy-5-{2-methoxy-6-[2-(4-methoxy-phenyl)-ethylamino]-pyrimidin-4-yl}-benzaldehyde oxime,
3-{2-methoxy-6-[2-(4-methoxy-phenyl)-ethylamino]-pyrimidin-4-yl}-thiophene-2-carbaldehyde oxime, 1-(5-{2-methoxy-6-[2-(4-methoxy-phenyl)-ethylamino]-pyrimidin-4-yl}-thiophen-2-yl)-ethanone oxime,
5-{2-methoxy-6-[2-(4-methoxy-phenyl)-ethylamino]-pyrimidin-4-yl}-thiophene-2-carbaldehyde oxime,
[6-(3-aminomethyl-4-fluoro-phenyl)-2-methoxy-pyrimidin-4-yl]-[2-(4-methoxy-phenyl)-ethyl]-amine,
N-(2-Fluoro-5-{2-methoxy-6-[2-(4-methoxy-phenyl)-ethylamino]-pyrimidin-4-yl}-benzyl)-2-methoxy-acetamide,
[2-methoxy-6-(3-methoxy-phenyl)-pyrimidin-4-yl]-[2-(4-methoxy-phenyl)-2-methyl-propyl]-amine,
[2-(2-chloro-6-fluoro-phenyl)-ethyl]-[6-(6-methoxy-pyridin-3-yl)-2-methylsulfanyl-pyrimidin-4-yl]-amine,
5-{6-[2-(2-chloro-6-fluoro-phenyl)-ethylamino]-2-methylsulfanyl-pyrimidin-4-yl}-1H-pyridin-2-one,
5-{6-[2-(2-chloro-6-fluoro-phenyl)-ethylamino]-2-methoxy-pyrimidin-4-yl}-1H-pyridin-2-one,
5-{6-[2-(2-chloro-6-fluoro-phenyl)-ethylamino]-2-methoxy-pyrimidin-4-yl}-1-(5-oxo-4,5-dihydro-[1,3,4]oxadiazol-2-ylmethyl)-1H-pyridin-2-one,
3-(3-{6-[2-(2,4-dichloro-phenyl)-ethylamino]-2-methoxy-pyrimidin-4-yl-phenoxymethyl)-4H-[1,2,4]oxadiazol-5-one,
3-(3-{6-[2-(2-chloro-6-fluoro-phenyl)-ethylamino]-2-methoxy-pyrimidin-4-yl}-benzyl)-4H-[1,2,4]oxadiazol-5-one,
3-(3-{6-[2-(2-chloro-6-fluoro-phenyl)-ethylamino]-2-methoxy-pyrimidin-4-yl}-phenoxymethyl)-4H-[1,2,4]oxadiazol-5-one,
3-{2-methoxy-6-[2-(4-methoxy-phenyl)-ethylamino]-pyrimidin-4-yl}-benzoic acid,
3-{2-methoxy-6-[2-(4-trifluoromethoxy-phenyl)-ethylamino]-pyrimidin-4-yl}-benzoic acid,
[2-(3,4-dimethoxy-phenyl)-ethyl]-(2-methoxy-6-thiophen-2-yl-pyrimidin-4-yl)amine,
[2-(3,4-dimethoxy-phenyl)-ethyl]-(6-furan-2-yl-2-methoxy-pyrimidin-4-yl)-amine,
(6-biphenyl-4-yl-2-methoxy-pyrimidin-4-yl)-[2-(3,4-dimethoxy-phenyl)-ethyl]-amine,
3-{6-[2-(4-fluoro-phenyl)-ethylamino]-2-methoxy-pyrimidin-4-yl}-benzoic acid,
3-{2-methoxy-6-[2-(4-methoxy-phenyl)-ethylamino]-pyrimidin-4-yl}-benzamide,
1-(3-{2-methoxy-6-[2-(4-methoxy-phenyl)-ethylamino]-pyrimidin-4-yl}-phenyl)-ethanone,
3-{6-[2-(2,4-dichloro-phenyl)-ethylamino]-2-methoxy-pyrimidin-4-yl}-phenol,
2-fluoro-5-{2-methoxy-6-[2-(4-methoxy-phenyl)-ethylamino]-pyrimidin-4-yl}-benzaldehyde,
3-{6-[2-(3,4-dimethoxy-phenyl)-ethylamino]-2-methoxy-pyrimidin-4-yl}-benzoic acid,
3-{2-methoxy-6-[2-(4-methoxy-phenyl)-ethylamino]-pyrimidin-4-yl}-thiophene-2-carbaldehyde,
1-(5-{2-methoxy-6-[2-(4-methoxy-phenyl)-ethylamino]-pyrimidin-4-yl}-thiophen-2-yl)-ethanone,
3-{6-[2-(4-chlorophenyl)-ethylamino]-2-methoxy-pyrimidin-4-yl}-benzoic acid,
[2-methoxy-6-(6-methoxy-pyridin-3-yl)-pyrimidin-4-yl]-[2-(4-methoxy-phenyl)-ethyl]-amine,
3-{2-methoxy-6-[2-(4-methoxy-phenyl)-ethylamino]-pyrimidin-4-yl}-phenol,
[2-(4-methoxy-phenyl)-ethyl]-(2-methoxy-6-pyridin-4-yl-pyrimidin-4-yl)-amine,
2-{2-methoxy-6-[2-(4-methoxy-phenyl)-ethylamino]-pyrimidin-4-yl}-phenol,
(3-{2-methoxy-6-[2-(4-methoxy-phenyl)-ethylamino]-pyrimidin-4-yl}-phenyl)-acetonitrile,
3-{2-methoxy-6-[2-(4-methoxy-phenyl)-ethylamino]-pyrimidin-4-yl}-benzonitrile,
3-{2-methoxy-6-[2-(4-methoxy-phenyl)-ethylamino]-pyrimidin-4-yl}-benzaldehyde,
3-{6-[2-(2-chloro-6-fluoro-phenyl)-ethylamino]-2-methoxy-pyrimidin-4-yl}-benzaldehyde,
3-{6-[2-(2,4-dichloro-phenyl)-ethylamino]-2-methoxy-pyrimidin-4-yl}-benzoic acid,
[2-methoxy-6-(pyridin-3-yl)-pyrimidin-4-yl]-[2-(4-methoxy-phenyl)-ethyl]-amine,
2-methoxy-5-{2-methoxy-6-[2-(4-methoxy-phenyl)-ethylamino]-pyrimidin-4-yl}-benzaldehyde,
2-chloro-5-{2-methoxy-6-[2-(4-methoxy-phenyl)-ethylamino]-pyrimidin-4-yl}-benzoic acid ethyl ester,
{2-methoxy-6-[3-(3-methyl-[1,2,4]oxadiazol-5-yl)-phenyl]-pyrimidin-4-yl}-[2-(4-methoxy-phenyl)-ethyl]-amine,
{2-methoxy-6-[3-(5-methyl-2H-[1,2,4]triazol-3-yl)-phenyl]-pyrimidin-4-yl}-[2-(4-methoxy-phenyl)-ethyl]-amine,
{2-methoxy-6-[3-(3-methyl-isoxazol-5-yl)-phenyl]-pyrimidin-4-yl}-[2-(4-methoxy-phenyl)-ethyl]-amine,
{2-methoxy-6-[3-(5-methyl-2H-pyrazol-3-yl)-phenyl]-pyrimidin-4-yl}-[2-(4-methoxy-phenyl)-ethyl]-amine,
[2-(3-fluoro-4-methoxy-phenyl)-ethyl]-{2-methoxy-6-[3-(2H-tetrazol-5-yl)-phenyl]-pyrimidin-4-yl}-amine,
1-ethyl-3-(3-{2-methoxy-6-[2-(4-methoxy-phenyl)-ethylamino]-pyrimidin-4-yl}-phenyl)-urea,
2-(3-{6-[2-(2,4-dichloro-phenyl)-ethylamino]-2-methoxy-pyrimidin-4-yl}-phenoxy)-2-methyl-propionic acid ethyl ester,
[2-(4-chloro-phenyl)-1-methyl-ethyl]-[6-(3,4-dimethoxy-phenyl)-2-methoxy-pyrimidin-4-yl]-amine,
[2-methoxy-6-(3-methoxy-phenyl)-pyrimidin-4-yl]-[2-(4-nitro-phenyl)-ethyl]-amine,
[2-methoxy-6-(3-methoxy-phenyl)-pyrimidin-4-yl]-[2-(4-trifluoromethoxy-phenyl)-ethyl]-amine,
[2-(2-chloro-6-fluoro-phenyl)-ethyl]-[2-methoxy-6-(3-methoxy-phenyl)-pyrimidin-4-yl]-amine,
[2-methoxy-6-(3-methoxy-phenyl)-pyrimidin-4-yl]-(2-thiophen-2-yl-ethyl)-amine,
3-{2-[2-methoxy-6-(3-methoxy-phenyl)-pyrimidin-4-ylamino]-ethyl}-1H-indol-5-ol,
[2-(6-methoxy-1H-indol-3-yl)-ethyl]-[2-methoxy-6-(3-methoxy-phenyl)-pyrimidin-4-yl]-amine,
[2-(5-methoxy-1H-indol-3-yl)-ethyl]-[2-methoxy-6-(3-methoxy-phenyl)-pyrimidin-4-yl]-amine,
[2-methoxy-6-(3-methoxy-phenyl)-pyrimidin-4-yl]-(2-pyridin-3-yl-ethyl)-amine,
[2-(4-amino-phenyl)-ethyl]-[2-methoxy-6-(3-methoxy-phenyl)-pyrimidin-4-yl]-amine,
(4-methoxy-benzyl)-[2-methoxy-6-(3-methoxy-phenyl)-pyrimidin-4-yl]-amine,
[2-methoxy-6-(3-methoxy-phenyl)-pyrimidin-4-yl]-(3-phenyl-propyl)-amine,
[2-(1H-imidazol-4-yl)-ethyl]-[2-methoxy-6-(3-methoxy-phenyl)-pyrimidin-4-yl]-amine,
(2S)-2-[2-methoxy-6-(3-methoxy-phenyl)-pyrimidin-4-ylamino]-3-(4-methoxy-phenyl)-propionic acid,
[2-methoxy-6-(3-methoxy-phenyl)-pyrimidin-4-yl]-[2-(4-methoxy-phenyl)-ethyl]-amine,
[2-methoxy-6-(5-methyl-[1,3,4]oxadiazol-2-yl)-pyrimidin-4-yl]-[2-(4-methoxy-phenyl)-ethyl]-amine,
(2-methoxy-6-oxazol-5-yl-pyrimidin-4-yl)-[2-(4-methoxy-phenyl)-ethyl]-amine, Example 45;
3-{6-[2-(2,2-difluoro-benzo[1,3]dioxol-5-yl)-ethylamino]-2-methoxy-pyrimidin-4-yl}-benzoic acid,
[2-(2,2-difluoro-benzo[1,3]dioxol-5-yl)-ethyl]-(2-methoxy-6-pyridin-3-yl-pyrimidin-4-yl)-amine, N-(3-{6-[2-(4-difluoromethoxy-phenyl)-ethylamino]-2-methoxy-pyrimidin-4-yl}-phenyl)-acetamide,
[2-(4-difluoromethoxy-phenyl)-ethyl]-[6-(3-methanesulfonyl-phenyl)-2-methoxy-pyrimidin-4-yl]-amine,
3-{6-[2-(2-chloro-6-fluoro-phenyl)-ethylamino]-2-methoxy-pyrimidin-4-yl}-phenol,
[2-(2,4-dichloro-phenyl)-ethyl]-(2-methyl-6-{3-[1-methyl-1-(1H-tetrazol-5-yl)-ethyl]-phenyl}-pyrimidin-4-yl)-amine,
[2-Methoxy-6-(2-methoxy-benzyloxy)-pyrimidin-4-yl]-[2-(4-methoxy-phenyl)-ethyl]-amine,
2-(3-{6-[2-(2,4-dichloro-phenyl)-ethylamino]-2-methoxy-pyrimidin-4-yl}-phenyl)-propionic acid,
2-(3-{6-[2-(2,4-dichloro-phenyl)-ethylamino]-2-methoxy-pyrimidin-4-yl}-phenyl)-2-methyl-propionic acid,
2-(3-{6-[2-(2,4-dichloro-phenyl)-ethylamino]-2-methoxy-pyrimidin-4-yl}-phenyl)-2-methyl-propionic acid 1-ethoxycarbonyloxy-ethyl ester,
2-(3-{6-[2-(2,4-dichloro-phenyl)-ethylamino]-2-methoxy-pyrimidin-4-yl}-phenyl)-2-methyl-propionic acid 2-dimethylamino-ethyl ester,
(5-{6-[2-(2-fluoro-4-trifluoromethyl-phenyl)-ethylamino]-2-methoxy-pyrimidin-4-yl}-1H-indol-3-yl)-acetic acid,
[6-(1H-indol-6-yl)-2-methoxy-pyrimidin-4-yl]-[2-(4-methoxy-phenyl)-ethyl]-ammonium,
[6-(1H-indazol-6-yl)-2-methoxy-pyrimidin-4-yl]-[2-(4-methoxy-phenyl)-ethyl]-amine,
3-{6-[2-(2,6-dichloro-phenyl)-ethylamino]-2-methoxy-pyrimidin-4-yl}-benzoic acid,
2-methoxy-5-{2-methoxy-6-[2-(4-methoxy-phenyl)-ethylamino]-pyrimidin-4-yl}-benzonitrile,
(3-{6-[2-(2-chloro-6-fluoro-phenyl)-ethylamino]-2-methoxy-pyrimidin-4-yl}-benzyloxy)-acetic acid,
(3-{6-[2-(2,4-dichloro-phenyl)-ethylamino]-2-methoxy-pyrimidin-4-yl}-benzoylamino)-acetic acid ethyl ester,
(3-{6-[2-(2,4-dichloro-phenyl)-ethylamino]-2-methoxy-pyrimidin-4-yl}-benzoylamino)-acetic acid, ethyl-carbamic acid 3-{6-[2-(2,4-dichloro-phenyl)-ethylamino]-2-methoxy-pyrimidin-4-yl}-ester,
5-{2-methoxy-6-[2-(4-methoxy-phenyl)-ethylamino]-pyrimidin-4-yl}-thiophene-2-carboxylic acid,
5-{2-methoxy-6-[2-(4-methoxy-phenyl)-ethylamino]-pyrimidin-4-yl}-thiophene-2-carboxylic acid methylamide,
(3-{6-[2-(3,4-dimethoxy-phenyl)-ethylamino]-2-methoxy-pyrimidin-4-yloxy}-benzoic acid methyl ester,
N-[2-(3-{6-[2-(2-fluoro-4-trifluoromethyl-phenyl)-ethylamino]-2-methoxy-pyrimidin-4-yl}-phenyl)-ethyl]-2-methoxy-acetamide,
N-[2-(3-{6-[2-(2-fluoro-4-trifluoromethyl-phenyl)-ethylamino]-2-methoxy-pyrimidin-4-yl}-phenyl)-ethyl]-acetamide,
[2-(2-fluoro-4-trifluoromethyl-phenyl)-ethyl]-[2-methoxy-6-(3-oxiranylmethoxy-phenyl)-pyrimidin-4-yl]-amine,
2-{3-[6-(2,2-difluoro-2-phenyl-ethylamino)-2-methoxy-pyrimidin-4-yl]-phenyl}-2-methyl-propionic acid,
2-[3-(2-methoxy-6-{2-[4-(5-methyl-[1,3,4]oxadiazol-2-yl)-phenyl]-ethylamino}-pyrimidin-4-yl)-phenyl]-2-methyl-propionic acid,
5-(3-{6-[2-(3,4-difluoro-phenyl)-ethylamino]-2-methoxy-pyrimidin-4-yl}-phenoxymethyl)-1-ethyl-2,4-dihydro-[1,2,4]triazol-3-one,
2-(2-fluoro-5-{2-methoxy-6-[2-(4-trifluoromethoxy-phenyl)-ethylamino]-pyrimidin-4-yl}-phenyl)-2-methyl-propionic acid,
2-(3-{2-methoxy-6-[(thiophen-3-ylmethyl)-amino]-pyrimidin-4-yl}-phenyl)-2-methyl-propionic acid,
2-(3-{6-[(benzo[b]thiophen-2-ylmethyl)-amino]-2-methyl-pyrimidin-4-yl}-phenyl)-2-methyl-propionic acid,
1-{6-[2-(2,4-dichloro-phenyl)-ethylamino]-2-methoxy-pyrimidin-4-yl}-piperidine-3-carboxylic acid,
1-(3-{6-[2-(2,4-dichloro-phenyl)-ethylamino]-2-methoxy-pyrimidin-4-yl}-phenyl)-cyclopentanecarboxylic acid,
3-{6-[2-(2,4-dichloro-phenyl)-ethylamino]-2-methoxy-pyrimidin-4-yl}-benzoic acid 2-morpholin-4-yl-ethyl ester,
3-{6-[2-(2,4-dichloro-phenyl)-ethylamino]-2-methoxy-pyrimidin-4-yl}-benzoic acid 2-(4-methyl-piperazin-1-yl)-ethyl ester,
3-{6-[2-(2,4-dichloro-phenyl)-ethylamino]-2-methoxy-pyrimidin-4-yl}-benzoic acid ethyl ester,
(3-{6-[2-(2,4-dichloro-phenyl)-ethylamino]-2-methoxy-pyrimidin-4-yl}-phenyl)-methanol,
(3'-Chloro-4'-{2-[6-(3-hydroxymethyl-phenyl)-2-methoxy-pyrimidin-4-ylamino]-ethyl}-biphenyl-3-yl)-methanol,
2-(3-{6-[2-(2,4-dichloro-phenyl)-ethylamino]-2-methoxy-pyrimidin-4-yl}-phenyl)-2-methyl-propionic acid methyl ester,
4-(3-{6-[2-(2,4-dichloro-phenyl)-ethylamino]-2-methoxy-pyrimidin-4-yl}-phenyl)-tetrahydro-pyran-4-carboxylic acid,
N-[4-(3-{6-[2-(2,4-dichloro-phenyl)-ethylamino]-2-methoxy-pyrimidin-4-yl}-phenyl)-tetrahydro-pyran-4-carbonyl]-methanesulfonamide,
4-(3-{6-[2-(2,4-dichloro-phenyl)-ethylamino]-2-methoxy-pyrimidin-4-yl}-phenyl)-tetrahydro-pyran-4-carboxylic acid ethyl ester;
(3-{6-[2-(2,4-dichloro-phenyl)-ethylamino]-2-methoxy-pyrimidin-4-yl}-phenyl)-difluoro-acetic ethanesulfonic acid [2-(3-{6-[2-(2,4-dichloro-phenyl)-ethylamino]-2-methoxy-pyrimidin-4-yl}-phenyl)-2,2-difluoro-acetyl]-amide,
(3-{6-[2-(2,4-dichloro-phenyl)-ethylamino]-2-methoxy-pyrimidin-4-yl}-phenyl)-difluoro-acetic acid ethyl ester,
(3-{6-[2-(2,4-dichloro-phenyl)-ethylamino]-2-methoxy-pyrimidin-4-yl}-phenyl)-acetonitrile,
(3-{6-[2-(2,4-dichloro-phenyl)-ethylamino]-2-methoxy-pyrimidin-4-yl}-phenyl)-difluoro-acetonitrile,
[2-(2,4-dichloro-phenyl)-ethyl]-(6-{3-[difluoro-(1H-tetrazol-5-yl)-methyl]-phenyl}-2-methoxy-pyrimidin-4-yl)-amine,
2-{3-[6-(indan-1-ylamino)-2-methoxy-pyrimidin-4-yl]-phenyl}-2-methyl-propionic acid,
2-{3-[6-(indan-2-ylamino)-2-methoxy-pyrimidin-4-yl]-phenyl}-2-methyl-propionic acid,
N-[4-(3-{2-methoxy-6-[2-(4-trifluoromethoxy-phenyl)-ethylamino]-pyrimidin-4-yl}-phenyl)-tetrahydro-pyran-4-carbonyl]-methanesulfonamide,
4-(3-{2-methoxy-6-[2-(4-trifluoromethoxy-phenyl)-ethylamino]-pyrimidin-4-yl}-phenyl)-tetrahydro-pyran-4-carboxylic acid methyl ester,
2-(3-{6-[2-(2,4-dichloro-phenyl)-ethylamino]-2-methoxymethyl-pyrimidin-4-yl}-phenyl)-2-methyl-propionic acid,
2-(3-{6-[2-(2,4-dichloro-phenyl)-ethylamino]-2-hydroxymethyl-pyrimidin-4-yl}-phenyl)-2-methyl-propionic acid,
5-{6-[2-(2,4-dichloro-phenyl)-ethylamino]-2-methoxy-pyrimidin-4-yl}-thiophene-2-carboxylic acid,
5-{2-methoxy-6-[2-(4-trifluoromethoxy-phenyl)-ethylamino]-pyrimidin-4-yl}-2,3-dihydro-benzofuran-2-carboxylic acid,
2-(3-{6-[2-(2,4-dichloro-phenyl)-ethylamino]-2-methoxy-pyrimidin-4-yl}-phenyl)-2-methyl-propionic acid 2,3-dihydroxy-propyl ester, 2-(3-{6-[(2,3-dihydro-benzofuran-2-ylmethyl)-amino]-2-methoxy-pyrimidin-4-yl}-phenyl)-2-methyl-propionic acid,
2-(3-{6-[(isochroman-1-ylmethyl)-amino]-2-methoxy-pyrimidin-4-yl}-phenyl)-2-methyl-propionic acid,
2-(3-{2-methoxy-6-[(4-methyl-3,4-dihydro-2H-benzo[1,4]oxazin-2-ylmethyl)-amino]-pyrimidin-4-yl}-phenyl)-2-methyl-propionic acid,
2-(3-{6-[(benzofuran-5-ylmethyl)-amino]-2-methoxy-pyrimidin-4-yl}-phenyl)-2-methyl-propionic acid,
N-(6-{6-[2-(2,4-dichloro-phenyl)-ethylamino]-2-methoxy-pyrimidin-4-yl}-benzothiazol-2-yl)-acetamide,
ethanesulfonic acid [2-(3-{6-[2-(2,4-dichloro-phenyl)-ethylamino]-2-methoxy-pyrimidin-4-yl}-phenyl)-2-methyl-propionyl]-amide,
N-[2-(3-{6-[2-(2,4-dichloro-phenyl)-ethylamino]-2-methoxy-pyrimidin-4-yl}-phenyl)-2-methyl-propionyl]-C-phenyl-methanesulfonamide,
2-(3-{6-[2-(2,4-dichloro-phenyl)-ethylamino]-2-methoxy-pyrimidin-4-yl}-phenyl)-2-methyl-1-morpholin-4-yl-propan-1-one,
2-(3-{6-[2-(2,4-dichloro-phenyl)-ethylamino]-2-methoxy-pyrimidin-4-yl}-phenyl)-N-(tetrahydro-pyran-4-yl)-isobutyramide,
2-(3-{6-[2-(2,4-dichloro-phenyl)-ethylamino]-2-methoxy-pyrimidin-4-yl}-phenyl)-N-(1H-tetrazol-5-yl)-isobutyramide,
[2-(2,4-dichloro-phenyl)-ethyl]-{2-methoxy-6-[3-(2H-tetrazol-5-yl)-piperidin-1-yl]-pyrimidin-4-yl}-amine,
1-{6-[2-(2,4-dichloro-phenyl)-ethylamino]-2-methoxy-pyrimidin-4-yl}-piperidine-4-carboxylic acid,
2-(2-Chloro-5-{6-[2-(2,4-dichloro-phenyl)-ethylamino]-2-methoxy-pyrimidin-4-yl}-phenyl)-propan-2-ol, or
2-(3-{6-[2-(2,4-dichloro-phenyl)-ethylamino]-2-methoxy-pyrimidin-4-yl}-4-fluoro-phenyl)-2-methyl-propionic acid,
or an N-oxide thereof, or an ester prodrug thereof, or a pharmaceutically acceptable salt, hydrate, or solvate thereof.

Another particular embodiment of the invention is a compound of Formula (I) or a pharmaceutical acceptable thereof, which is 3-{6-[2-(3-fluoro-4-methoxy-phenyl)-ethylamino]-2-methoxy-pyrimidin-4-yl}-benzonitrile, Example 1;
[6-(3-amino-phenyl)-2-methoxy-pyrimidin-4-yl]-[2-(4-methoxy-phenyl)-ethyl]amine, Example 2;
3-{2-methoxy-6-[2-(4-methoxy-phenyl)-ethylamino]-pyrimidin-4-yl}-benzenesulfonamide, Example 3;
3-{2-methoxy-6-[2-(4-methoxy-phenyl)-ethylamino]-pyrimidin-4-yl}-N-methyl-benzenesulfonamide, Example 4(a);
N-ethyl-3-{2-methoxy-6-[2-(4-methoxy-phenyl)-ethylamino]-pyrimidin-4-yl}-benzenesulfonamide, Example 4(b);
N-methoxycarbonyl-3-{2-methoxy-6-[2-(4-methoxy-phenyl)-ethylamino]-pyrimidin-4-yl}-benzenesulfonamide, Example 4(c);
6-(3-amino-phenyl)-2-methoxy-pyrimidin-4-yl]-[2-(4-trifluoromethoxy-phenyl)-ethyl]-amine, Example 5;
N-(3-{2-methoxy-6-[2-(4-trifluoromethoxy-phenyl)-ethylamino]-pyrimidin-4-yl}-phenyl)-acetamide, Example 6(a);
N-(3-{2-methoxy-6-[2-(4-methoxy-phenyl)-ethylamino]-pyrimidin-4-yl}-phenyl)-acetamide, Example 6(b);
(3-{2-methoxy-6-[2-(4-methoxy-phenyl)-ethylamino]-pyrimidin-4-yl}-phenyl)-carbamic acid ethyl ester, Example 6(c);
3-{6-[2-(2,4-difluoro-phenyl)-ethylamino]-2-methoxy-pyrimidin-4-yl}-benzoic acid, Example 7;
5-{2-methoxy-6-[2-(4-methoxy-phenyl)-ethylamino]-pyrimidin-4-yl}-thiophene-2-carboxylic acid trifluoroacetate, Example 8(a);
5-{2-methoxy-6-[2-(4-methoxy-phenyl)-ethylamino]-pyrimidin-4-yl}-thiophene-2-carbaldehyde, Example 8(b);
4-{2-methoxy-6-[2-(4-methoxy-phenyl)-ethylamino]-pyrimidin-4-yl}-thiophene-2-carbaldehyde, Example 8(c);
[6-(3,5-dimethyl-isoxazol-4-yl)-2-methoxy-pyrimidin-4-yl]-[2-(4-methoxy-phenyl)-ethyl]-amine, Example 8(d);
[2-methoxy-6-(5-methyl-thiophen-2-yl)-pyrimidin-4-yl]-[2-(4-methoxy-phenyl)-ethyl]-amine, Example 8(e);
[2-(4-methoxy-phenyl)-ethyl]-[2-methoxy-6-(1H-pyrazol-4-yl)-pyrimidin-4-yl]-amine, Example 8(f);
(6-isoquinolin-5-yl-2-methoxy-pyrimidin-4-yl)-[2-(4-methoxy-phenyl)-ethyl]-amine, Example 8(g);
(5-{2-methoxy-6-[2-(4-methoxy-phenyl)-ethylamino]-pyrimidin-4-yl}-thiophen-2-yl)-methanol, Example (9a);
(3-{2-methoxy-6-[2-(4-methoxy-phenyl)-ethylamino]-pyrimidin-4-yl}-thiophen-2-yl)-methanol, Example 9(b);
(3-{2-methoxy-6-[2-(4-methoxy-phenyl)-ethylamino]-pyrimidin-4-yl}-phenyl)-methanol, Example 9(c);
(3-{6-[2-(2-chloro-6-fluoro-phenyl)-ethylamino]-2-methoxy-pyrimidin-4-yl}-phenyl)-methanol, Example 9(d);
[2-(4-methoxy-phenyl)-ethyl]-(2-methoxy-6-quinolin-6-yl-pyrimidin-4-yl)-amine, Example 10(a);
[2-(4-methoxy-phenyl)-ethyl]-(2-methoxy-6-quinolin-3-yl-pyrimidin-4-yl)-amine, Example 10(b);
[6-(H-indol-5-yl)-2-methoxy-pyrimidin-4-yl]-[2-(4-methoxy-phenyl)-ethyl]-amine, Example 10(c);
N-(2-{2-methoxy-6-[2-(4-methoxy-phenyl)-ethylamino]-pyrimidin-4-yl}-phenyl)-methanesulfonamide, Example 10(d);
4-{2-methoxy-6-[2-(4-methoxy-phenyl)-ethylamino]-pyrimidin-4-yl}-benzamide, Example 10(e);
[2-methoxy-6-(1-methyl-1H-indol-5-yl)-pyrimidin-4-yl]-[2-(4-methoxy-phenyl)-ethyl]-amine, Example 10(f);
(6-benzo[b]thiophen-2-yl-2-methoxy-pyrimidin-4-yl)-[2-(4-methoxy-phenyl)-ethyl]-amine, Example 10(g);
1-(4-{2-methoxy-6-[2-(4-methoxy-phenyl)-ethylamino]-pyrimidin-4-yl}-phenyl)-ethanone, Example 10(h);
[6-(3-methanesulfonyl-phenyl)-2-methoxy-pyrimidin-4-yl]-[2-(4-methoxy-phenyl)-ethyl]-amine, Example 10(i);
[6-(2,3-dihydro-benzofuran-5-yl)-2-methoxy-pyrimidin-4-yl]-[2-(4-methoxy-phenyl)-ethyl]-amine, Example 10(j);
[2-methoxy-6-(4-morpholin-4-yl-phenyl)-pyrimidin-4-yl]-[2-(4-methoxy-phenyl)-ethyl]-amine, Example 10(k);
[6-(4-dimethylamino-phenyl)-2-methoxy-pyrimidin-4-yl]-[2-(4-methoxy-phenyl)-ethyl]-amine, Example 10(l);
2,2'-dimethoxy-N*6*,N*,6'*-bis-[2-(4-methoxy-phenyl)-ethyl]-[4,4']bipyrimidinyl-6,6'-diamine, Example 10(m);
[2-methoxy-6-(5-oxazol-5-yl-thiophen-2-yl)-pyrimidin-4-yl]-[2-(4-methoxy-phenyl)-ethyl]-amine, Example 11(a);
2-methoxy-6-(3-oxazol-5-yl-phenyl)-pyrimidin-4-yl]-[2-(4-methoxy-phenyl)-ethyl]-amine, Example 11(b);
[6-(5-difluoromethyl-thiophen-2-yl)-2-methoxy-pyrimidin-4-yl]-[2-(4-methoxy-phenyl)-ethyl]-amine, Example 12;
[2-(4-methoxy-phenyl)-ethyl]-[2-methoxy-6-(5-pyrrolidin-1-ylmethyl-thiophen-2-yl)-pyrimidin-4-yl]-amine, Example 13(a);
6-{4-fluoro-3-[(2-methoxy-ethylamino)-methyl]-phenyl}-2-methoxy-pyrimidin-4-yl)-[2-(4-methoxy-phenyl)-ethyl]-amine hydrochloride, Example 13(b);
4-[2-(3-{2-methoxy-6-[2-(4-methoxy-phenyl)-ethylamino]-pyrimidin-4-yl}-benzylamino)-ethyl]-phenol hydrochloride, Example 13(c);

N-(2-fluoro-5-{2-methoxy-6-[2-(4-methoxy-phenyl)-ethylamino]-pyrimidin-4-yl}-benzyl)-N',N'-dimethyl-ethane-1,2-diamine hydrochloride, Example 13(d);

[6-(1H-benzoimidazol-5-yl)-2-methoxy-pyrimidin-4-yl]-[2-(4-methoxy-phenyl)-ethyl]-amine, Example 14(a);

[6-(1H-benzotriazol-5-yl)-2-methoxy-pyrimidin-4-yl]-[2-(4-methoxy-phenyl)-ethyl]-amine, Example 14(b);

6-{2-methoxy-6-[2-(4-methoxy-phenyl)-ethylamino]-pyrimidin-4-yl}-3H-benzooxazol-2-one, Example 14(c);

3-{2-methoxy-6-[2-(4-methoxy-phenyl)-ethylamino]-pyrimidin-4-yl}-phenol hydrochloride, Example 15(a);

3-{6-[2-(2,4-dichloro-phenyl)-ethylamino]-2-methoxy-pyrimidin-4-yl}-benzoic acid hydrochloride, Example 15(b);

3-{6-[2-(2-chloro-6-fluoro-phenyl)-ethylamino]-2-methoxy-pyrimidin-4-yl}-benzoic acid hydrochloride, Example 15(c);

2-(3-{6-[2-(2,4-dichloro-phenyl)-ethylamino]-2-methoxy-pyrimidin-4-yl}-phenyl)-2-methyl-propionic acid hydrochloride, Example 15(d);

[2-(3,4-dimethoxy-phenyl)-ethyl]-[6-(3,4-dimethoxy-phenyl)-2-methylsulfanyl-pyrimidin-4-yl]-amine, Example 16(a);

3-{6-[2-(3,4-dimethoxy-phenyl)-ethylamino]-2-methylsulfanyl-pyrimidin-4-yl}-benzoic acid, Example 16(b);

[2-(4-methoxy-phenyl)-ethyl]-[6-(3-methoxy-phenyl)-2-methylsulfanyl-pyrimidin-4-yl]-amine, Example 16(c);

[2-(3,4-dimethoxy-phenyl)-ethyl]-[6-(3,4-dimethoxy-phenyl)-2-isopropoxy-pyrimidin-4-yl]-amine, Example 17(a);

[6-(3,4-dimethoxy-phenyl)-2-ethoxy-pyrimidin-4-yl]-[2-(3,4-dimethoxy-phenyl)-ethyl]-amine, Example 17(b);

[2-ethyl-6-(3-methoxy-phenyl)-pyrimidin-4-yl]-[2-(4-methoxy-phenyl)-ethyl]-amine, Example 18;

6-(3-methoxy-phenyl)-N*4*-[2-(4-methoxy-phenyl)-ethyl]-N*2*,N*2*-dimethyl-pyrimidine-2,4-diamine hydrochloride, Example 19;

2-fluoro-5-{2-methoxy-6-[2-(4-methoxy-phenyl)-ethylamino]-pyrimidin-4-yl}-benzoic acid, Example 20(a);

3-{6-[2-(2-chloro-6-fluoro-phenyl)-ethylamino]-2-methoxy-pyrimidin-4-yl}-benzoic acid, Example 20(b);

2-methoxy-5-{2-methoxy-6-[2-(4-methoxy-phenyl)-ethylamino]-pyrimidin-4-yl}-benzoic acid, Example 20(c);

[2-methoxy-6-(1-oxy-pyridin-3-yl)-pyrimidin-4-yl]-[2-(4-methoxy-phenyl)-ethyl]-amine, Example 21(a);

[2-(2,2-difluoro-benzo[1,3]dioxol-5-yl)-ethyl]-[2-methoxy-6-(1-oxy-pyridin-3-yl)-pyrimidin-4-yl]-amine, Example 21(b);

2-(3-{2-methoxy-6-[2-(4-methoxy-phenyl)-ethylamino]-pyrimidin-4-yl}-phenoxy)-2-methyl-propionic acid ethyl ester, Example 22(a);

(3-{2-methoxy-6-[2-(4-methoxy-phenyl)-ethylamino]-pyrimidin-4-yl}-phenoxy)-acetic acid methyl ester, Example 22(b);

(3-{6-[2-(2,4-dichloro-phenyl)-ethylamino]-2-methoxy-pyrimidin-4-yl}-phenoxy)-acetic acid methyl ester, Example 22(c);

(5-{6-[2-(2-chloro-6-fluoro-phenyl)-ethylamino]-2-methoxy-pyrimidin-4-yl}-2-oxo-2H-pyridin-1-yl)-acetic acid methyl ester, Example 22(d);

(3-{6-[2-(2,4-dichloro-phenyl)-ethylamino]-2-methoxy-pyrimidin-4-yl}-phenoxy)-acetonitrile, Example 22(e);

(3-{6-[2-chloro-6-fluoro-phenyl)-ethylamino]-2-methoxy-pyrimidin-4-yl}-phenoxy)-acetonitrile, Example 22(f);

2-(3-{2-methoxy-6-[2-(4-methoxy-phenyl)-ethylamino]-pyrimidin-4-yl}-phenoxy)-2-methyl-propionic acid, Example 23(a);

(3-{2-methoxy-6-[2-(4-methoxy-phenyl)-ethylamino]-pyrimidin-4-yl}-phenoxy)-acetic acid, Example 23(b);

(5-{6-[2-(2-chloro-6-fluoro-phenyl)-ethylamino]-2-methoxy-pyrimidin-4-yl}-2-oxo-2H-pyridin-1-yl)-acetic acid, Example 23(c);

2-(3-{6-[2-(2,4-dichloro-phenyl)-ethylamino]-2-methoxy-pyrimidin-4-yl}-phenoxy)-2-methyl-propionic acid, Example 23(d);

2-chloro-5-{2-methoxy-6-[2-(4-methoxy-phenyl)-ethylamino]-pyrimidin-4-yl}-benzoic acid hydrochloride salt, Example 23(e);

[2-(4-methoxy-phenyl)-ethyl]-{2-methoxy-6-[3-(1H-tetrazol-5-yl)-phenyl]-pyrimidin-4-yl}-amine, Example 24(a);

[2-(4-methoxy-phenyl)-ethyl]-{2-methoxy-6-[3-(1H-tetrazol-5-ylmethyl)-phenyl]-pyrimidin-4-yl}-amine hydrochloride, Example 24(b);

{2-methoxy-6-[4-methoxy-3-(1H-tetrazol-5-yl)-phenyl]-pyrimidin-4-yl}-[2-(4-methoxy-phenyl)-ethyl]-amine, Example 24(c);

N-(3-{2-methoxy-6-[2-(4-methoxy-phenyl)-ethylamino]-pyrimidin-4-yl}-benzoyl)-methanesulfonamide, Example 25(a);

3-{6-[2-(3,4-dimethoxy-phenyl)-ethylamino]-2-methoxy-pyrimidin-4-yl}-N-(2-pyrrolidin-1-yl-ethyl)-benzamide, Example 25(b);

2-fluoro-5-{2-methoxy-6-[2-(4-methoxy-phenyl)-ethylamino]-pyrimidin-4-yl}-benzaldehyde oxime, Example 26(a);

3-{2-methoxy-6-[2-(4-methoxy-phenyl)-ethylamino]-pyrimidin-4-yl}-benzaldehyde oxime, Example 26(b);

2-methoxy-5-{2-methoxy-6-[2-(4-methoxy-phenyl)-ethylamino]-pyrimidin-4-yl}-benzaldehyde oxime, Example 26(c);

3-{2-methoxy-6-[2-(4-methoxy-phenyl)-ethylamino]-pyrimidin-4-yl}-thiophene-2-carbaldehyde oxime, Example 26(d);

1-(5-{2-methoxy-6-[2-(4-methoxy-phenyl)-ethylamino]-pyrimidin-4-yl}-thiophen-2-yl)-ethanone oxime, Example 26(e);

5-{2-methoxy-6-[2-(4-methoxy-phenyl)-ethylamino]-pyrimidin-4-yl}-thiophene-2-carbaldehyde oxime, Example 26(f);

[6-(3-aminomethyl-4-fluoro-phenyl)-2-methoxy-pyrimidin-4-yl]-[2-(4-methoxy-phenyl)-ethyl]-amine hydrochloride, Example 27;

N-(2-Fluoro-5-{2-methoxy-6-[2-(4-methoxy-phenyl)-ethylamino]-pyrimidin-4-yl}-benzyl)-2-methoxy-acetamide hydrochloride, Example 28;

[2-methoxy-6-(3-methoxy-phenyl)-pyrimidin-4-yl]-[2-(4-methoxy-phenyl)-2-methyl-propyl]-amine, Example 29;

[2-(2-chloro-6-fluoro-phenyl)-ethyl]-[6-(6-methoxy-pyridin-3-yl)-2-methylsulfanyl-pyrimidin-4-yl]-amine, Example (30);

5-{6-[2-(2-chloro-6-fluoro-phenyl)-ethylamino]-2-methylsulfanyl-pyrimidin-4-yl}-1H-pyridin-2-one, Example 31;

5-{6-[2-(2-chloro-6-fluoro-phenyl)-ethylamino]-2-methoxy-pyrimidin-4-yl}-1H-pyridin-2-one, Example 32;

5-{6-[2-(2-chloro-6-fluoro-phenyl)-ethylamino]-2-methoxy-pyrimidin-4-yl}-1-(5-oxo-4,5-dihydro-[1,3,4]oxadiazol-2-ylmethyl)-1H-pyridin-2-one, Example 33;

3-(3-{6-[2-(2,4-dichloro-phenyl)-ethylamino]-2-methoxy-pyrimidin-4-yl-phenoxymethyl)-4H-[1,2,4]oxadiazol-5-one hydrochloride, Example 34(a);

3-(3-{6-[2-(2-chloro-6-fluoro-phenyl)-ethylamino]-2-methoxy-pyrimidin-4-yl}-benzyl)-4H-[1,2,4]oxadiazol-5-one hydrochloride, Example 34(b);

3-(3-{6-[2-(2-chloro-6-fluoro-phenyl)-ethylamino]-2-methoxy-pyrimidin-4-yl}-phenoxymethyl)-4H-[1,2,4]oxadiazol-5-one hydrochloride, Example 34(c);
3-{2-methoxy-6-[2-(4-methoxy-phenyl)-ethylamino]-pyrimidin-4-yl}-benzoic acid, Example 35(a);
3-{2-methoxy-6-[2-(4-trifluoromethoxy-phenyl)-ethylamino]-pyrimidin-4-yl}-benzoic acid, Example 35(b)];
[2-(3,4-dimethoxy-phenyl)-ethyl]-(2-methoxy-6-thiophen-2-yl-pyrimidin-4-yl)amine, Example 35(c);
[2-(3,4-dimethoxy-phenyl)-ethyl]-(6-furan-2-yl-2-methoxy-pyrimidin-4-yl)-amine, Example 35(d);
(6-biphenyl-4-yl-2-methoxy-pyrimidin-4-yl)-[2-(3,4-dimethoxy-phenyl)-ethyl]-amine, Example 35(e);
3-{6-[2-(4-fluoro-phenyl)-ethylamino]-2-methoxy-pyrimidin-4-yl}-benzoic acid hydrochloride, Example 35(f);
3-{2-methoxy-6-[2-(4-methoxy-phenyl)-ethylamino]-pyrimidin-4-yl}-benzamide, Example 35(g);
1-(3-{2-methoxy-6-[2-(4-methoxy-phenyl)-ethylamino]-pyrimidin-4-yl}-phenyl)-ethanone, Example 35(h);
3-{6-[2-(2,4-dichloro-phenyl)-ethylamino]-2-methoxy-pyrimidin-4-yl}-phenol, Example 35(i);
2-fluoro-5-{2-methoxy-6-[2-(4-methoxy-phenyl)-ethylamino]-pyrimidin-4-yl}-benzaldehyde, Example 35(j);
3-{6-[2-(3,4-dimethoxy-phenyl)-ethylamino]-2-methoxy-pyrimidin-4-yl}-benzoic acid, Example 35(k);
3-{2-methoxy-6-[2-(4-methoxy-phenyl)-ethylamino]-pyrimidin-4-yl}-thiophene-2-carbaldehyde, Example 35(l);
1-(5-{2-methoxy-6-[2-(4-methoxy-phenyl)-ethylamino]-pyrimidin-4-yl}-thiophen-2-yl)-ethanone, Example 35(m);
3-{6-[2-(4-chlorophenyl)-ethylamino]-2-methoxy-pyrimidin-4-yl}-benzoic acid hydrochloride, Example 35(n);
[2-methoxy-6-(6-methoxy-pyridin-3-yl)-pyrimidin-4-yl]-[2-(4-methoxy-phenyl)-ethyl]-amine, Example 35(o);
3-{2-methoxy-6-[2-(4-methoxy-phenyl)-ethylamino]-pyrimidin-4-yl}-phenol, Example 35(p);
[2-(4-methoxy-phenyl)-ethyl]-(2-methoxy-6-pyridin-4-yl-pyrimidin-4-yl)-amine, Example 35(q);
2-{2-methoxy-6-[2-(4-methoxy-phenyl)-ethylamino]-pyrimidin-4-yl}-phenol, Example 35(r);
(3-{2-methoxy-6-[2-(4-methoxy-phenyl)-ethylamino]-pyrimidin-4-yl}-phenyl)-acetonitrile, Example 35(s);
3-{2-methoxy-6-[2-(4-methoxy-phenyl)-ethylamino]-pyrimidin-4-yl}-benzonitrile, Example 35(t);
3-{2-methoxy-6-[2-(4-methoxy-phenyl)-ethylamino]-pyrimidin-4-yl}-benzaldehyde, Example 35(u);
3-{6-[2-(2-chloro-6-fluoro-phenyl)-ethylamino]-2-methoxy-pyrimidin-4-yl}-benzaldehyde, Example 35(v);
3-{6-[2-(2,4-dichloro-phenyl)-ethylamino]-2-methoxy-pyrimidin-4-yl}-benzoic acid, Example 35(w);
[2-methoxy-6-(pyridin-3-yl)-pyrimidin-4-yl]-[2-(4-methoxy-phenyl)-ethyl]-amine, Example 35(x);
2-methoxy-5-{2-methoxy-6-[2-(4-methoxy-phenyl)-ethylamino]-pyrimidin-4-yl}-benzaldehyde, Example 35(y);
2-chloro-5-{2-methoxy-6-[2-(4-methoxy-phenyl)-ethylamino]-pyrimidin-4-yl}-benzoic acid ethyl ester, Example 35(z);
{2-methoxy-6-[3-(3-methyl-[1,2,4]oxadiazol-5-yl)-phenyl]-pyrimidin-4-yl}-[2-(4-methoxy-phenyl)-ethyl]-amine, Example 36;
{2-methoxy-6-[3-(5-methyl-2H-[1,2,4]triazol-3-yl)-phenyl]-pyrimidin-4-yl}-[2-(4-methoxy-phenyl)-ethyl]-amine, Example 37;
{2-methoxy-6-[3-(3-methyl-isoxazol-5-yl)-phenyl]-pyrimidin-4-yl}-[2-(4-methoxy-phenyl)-ethyl]-amine, Example 38;
{2-methoxy-6-[3-(5-methyl-2H-pyrazol-3-yl)-phenyl]-pyrimidin-4-yl}-[2-(4-methoxy-phenyl)-ethyl]-amine, Example 39;
[2-(3-fluoro-4-methoxy-phenyl)-ethyl]-{2-methoxy-6-[3-(2H-tetrazol-5-yl)-phenyl]-pyrimidin-4-yl}-amine, Example 40;
1-ethyl-3-(3-{2-methoxy-6-[2-(4-methoxy-phenyl)-ethylamino]-pyrimidin-4-yl}-phenyl)-urea, Example 41;
2-(3-{6-[2-(2,4-dichloro-phenyl)-ethylamino]-2-methoxy-pyrimidin-4-yl}-phenoxy)-2-methyl-propionic acid ethyl ester, Example 42;
[2-(4-chloro-phenyl)-1-methyl-ethyl]-[6-(3,4-dimethoxy-phenyl)-2-methoxy-pyrimidin-4-yl]-amine, Example 43(a);
[2-methoxy-6-(3-methoxy-phenyl)-pyrimidin-4-yl]-[2-(4-nitro-phenyl)-ethyl]-amine, Example 43(b);
[2-methoxy-6-(3-methoxy-phenyl)-pyrimidin-4-yl]-[2-(4-trifluoromethoxy-phenyl)-ethyl]-amine, Example 43(c);
[2-(2-chloro-6-fluoro-phenyl)-ethyl]-[2-methoxy-6-(3-methoxy-phenyl)-pyrimidin-4-yl]-amine hydrochloride, Example 43(d);
[2-methoxy-6-(3-methoxy-phenyl)-pyrimidin-4-yl]-(2-thiophen-2-yl-ethyl)-amine hydrochloride, Example 43(e);
3-{2-[2-methoxy-6-(3-methoxy-phenyl)-pyrimidin-4-ylamino]-ethyl}1H-indol-5-ol, Example 43(f);
[2-(6-methoxy-1H-indol-3-yl)-ethyl]-[2-methoxy-6-(3-methoxy-phenyl)-pyrimidin-4-yl]-amine hydrochloride, Example 43(g);
[2-(5-methoxy-1H-indol-3-yl)-ethyl]-[2-methoxy-6-(3-methoxy-phenyl)-pyrimidin-4-yl]-amine hydrochloride, Example 43(h);
[2-methoxy-6-(3-methoxy-phenyl)-pyrimidin-4-yl]-(2-pyridin-3-yl-ethyl)-amine hydrochloride, Example 43(i);
[2-(4-amino-phenyl)-ethyl]-[2-methoxy-6-(3-methoxy-phenyl)-pyrimidin-4-yl]-amine hydrochloride, Example 43(j);
(4-methoxy-benzyl)-[2-methoxy-6-(3-methoxy-phenyl)-pyrimidin-4-yl]-amine hydrochloride, Example 43(k);
[2-methoxy-6-(3-methoxy-phenyl)-pyrimidin-4-yl]-(3-phenyl-propyl)-amine hydrochloride, Example 43(l);
[2-(1H-imidazol-4-yl)-ethyl]-[2-methoxy-6-(3-methoxy-phenyl)-pyrimidin-4-yl]-amine, Example 43(m);
(2S)-2-[2-methoxy-6-(3-methoxy-phenyl)-pyrimidin-4-ylamino]-3-(4-methoxy-phenyl)-propionic acid, Example 43(n);
[2-methoxy-6-(3-methoxy-phenyl)-pyrimidin-4-yl]-[2-(4-methoxy-phenyl)-ethyl]-amine, Example 43(o);
[2-methoxy-6-(5-methyl-[1,3,4]oxadiazol-2-yl)-pyrimidin-4-yl]-[2-(4-methoxy-phenyl)-ethyl]-amine, Example 44;
(2-methoxy-6-oxazol-5-yl-pyrimidin-4-yl)-[2-(4-methoxy-phenyl)-ethyl]-amine, Example 45;
3-{6-[2-(2,2-difluoro-benzo[1,3]dioxol-5-yl)-ethylamino]-2-methoxy-pyrimidin-4-yl}-benzoic acid, Example 46(a);
[2-(2,2-difluoro-benzo[1,3]dioxol-5-yl)-ethyl]-(2-methoxy-6-pyridin-3-yl-pyrimidin-4-yl)-amine hydrochloride, Example 46(b);
N-(3-{6-[2-(4-difluoromethoxy-phenyl)-ethylamino]-2-methoxy-pyrimidin-4-yl}-phenyl)-acetamide hydrochloride, Example 46(c);
[2-(4-difluoromethoxy-phenyl)-ethyl]-[6-(3-methanesulfonyl-phenyl)-2-methoxy-pyrimidin-4-yl]-amine hydrochloride, example 46(d);
3-{6-[2-(2-chloro-6-fluoro-phenyl)-ethylamino]-2-methoxy-pyrimidin-4-yl}-phenol, Example 46(e);
[2-(2,4-dichloro-phenyl)-ethyl]-(2-methyl-6-{3-[1-methyl-1-(1H-tetrazol-5-yl)-ethyl]-phenyl}-pyrimidin-4-yl)-amine hydrochloride, Example 47;

[2-Methoxy-6-(2-methoxy-benzyloxy)-pyrimidin-4-yl]-[2-(4-methoxy-phenyl)-ethyl]-amine hydrochloride, Examples 48;

2-(3-{6-[2-(2,4-dichloro-phenyl)-ethylamino]-2-methoxy-pyrimidin-4-yl}-phenyl)-propionic acid hydrochloride, Example 49(a);

2-(3-{6-[2-(2,4-dichloro-phenyl)-ethylamino]-2-methoxy-pyrimidin-4-yl}-phenyl)-2-methyl-propionic acid, Example 49(b);

2-(3-{6-[2-(2,4-dichloro-phenyl)-ethylamino]-2-methoxy-pyrimidin-4-yl}-phenyl)-2-methyl-propionic acid 1-ethoxycarbonyloxy-ethyl ester hydrochloride, Example 50;

2-(3-{6-[2-(2,4-dichloro-phenyl)-ethylamino]-2-methoxy-pyrimidin-4-yl}-phenyl)-2-methyl-propionic acid 2-dimethylamino-ethyl ester dihydrochloride, Example 51;

(5-{6-[2-(2-fluoro-4-trifluoromethyl-phenyl)-ethylamino]-2-methoxy-pyrimidin-4-yl}-1H-indol-3-yl)-acetic acid, Example 52;

[6-(1H-indol-6-yl)-2-methoxy-pyrimidin-4-yl]-[2-(4-methoxy-phenyl)-ethyl]-ammonium trifluoroacetate, Example 53(a);

[6-(1H-indazol-6-yl)-2-methoxy-pyrimidin-4-yl]-[2-(4-methoxy-phenyl)-ethyl]-amine, Example 53(b);

3-{6-[2-(2,6-dichloro-phenyl)-ethylamino]-2-methoxy-pyrimidin-4-yl}-benzoic acid, Example 53(c);

[2-(4-methoxy-phenyl)-ethyl]-{2-methoxy-6-[3-(1H-tetrazol-5-yl)-phenyl]-pyrimidin-4-yl}-amine, sodium salt, Example 54;

2-methoxy-5-{2-methoxy-6-[2-(4-methoxy-phenyl)-ethylamino]-pyrimidin-4-yl}-benzonitrile, Example 55;

(3-{6-[2-(2-chloro-6-fluoro-phenyl)-ethylamino]-2-methoxy-pyrimidin-4-yl}-benzyloxy)-acetic acid, Example 56;

Sodium 2-(3-{6-[2-(2,4-dichloro-phenyl)-ethylamino]-2-methoxy-pyrimidin-4-yl}-phenyl)-2-methyl-propionate, Example 57;

(3-{6-[2-(2,4-dichloro-phenyl)-ethylamino]-2-methoxy-pyrimidin-4-yl}-benzoylamino)-acetic acid ethyl ester, Example 58;

(3-{6-[2-(2,4-dichloro-phenyl)-ethylamino]-2-methoxy-pyrimidin-4-yl}-benzoylamino)-acetic acid, Example 59;

ethyl-carbamic acid 3-{6-[2-(2,4-dichloro-phenyl)-ethylamino]-2-methoxy-pyrimidin-4-yl}-phenyl ester, Example 60;

5-{2-methoxy-6-[2-(4-methoxy-phenyl)-ethylamino]-pyrimidin-4-yl}-thiophene-2-carboxylic acid, Example 61;

5-{2-methoxy-6-[2-(4-methoxy-phenyl)-ethylamino]-pyrimidin-4-yl}-thiophene-2-carboxylic acid methylamide trifluoroacetate, Example 62;

(3-{6-[2-(3,4-dimethoxy-phenyl)-ethylamino]-2-methoxy-pyrimidin-4-yloxy}-benzoic acid methyl ester, Examples 63;

N-[2-(3-{6-[2-(2-fluoro-4-trifluoromethyl-phenyl)-ethylamino]-2-methoxy-pyrimidin-4-yl}-phenyl)-ethyl]-2-methoxy-acetamide, Example 64;

N-[2-(3-{6-[2-(2-fluoro-4-trifluoromethyl-phenyl)-ethylamino]-2-methoxy-pyrimidin-4-yl}-phenyl)-ethyl]-acetamide hydrochloride, Example 65;

[2-(2-Fluoro-4-trifluoromethyl-phenyl)-ethyl]-[2-methoxy-6-(3-oxiranylmethoxy-phenyl)-pyrimidin-4-yl]-amine, Example 66;

2-{3-[6-(2,2-difluoro-2-phenyl-ethylamino)-2-methoxy-pyrimidin-4-yl]-phenyl}-2-methyl-propionic acid, Example 67;

2-[3-(2-methoxy-6-{2-[4-(5-methyl-[1,3,4]oxadiazol-2-yl)-phenyl]-ethylamino}-pyrimidin-4-yl)-phenyl]-2-methyl-propionic acid, Example 68;

5-(3-{6-[2-(3,4-difluoro-phenyl)-ethylamino]-2-methoxy-pyrimidin-4-yl}-phenoxymethyl)-1-ethyl-2,4-dihydro-[1,2,4]triazol-3-one, Example 69;

2-(2-fluoro-5-{2-methoxy-6-[2-(4-trifluoromethoxy-phenyl)-ethylamino]-pyrimidin-4-yl}-phenyl)-2-methyl-propionic acid, Example 70;

2-(3-{2-Methoxy-6-[(thiophen-3-ylmethyl)-amino]-pyrimidin-4-yl}-phenyl)-2-methyl-propionic acid, Example 71;

2-(3-{6-[(benzo[b]thiophen-2-ylmethyl)-amino]-2-methyl-pyrimidin-4-yl}-phenyl)-2-methyl-propionic acid, Example 72;

1-{6-[2-(2,4-dichloro-phenyl)-ethylamino]-2-methoxy-pyrimidin-4-yl}-piperidine-3-carboxylic acid, Example 73;

1-(3-{6-[2-(2,4-dichloro-phenyl)-ethylamino]-2-methoxy-pyrimidin-4-yl}-phenyl)-cyclopentanecarboxylic acid hydrochloride, Example 74;

3-{6-[2-(2,4-dichloro-phenyl)-ethylamino]-2-methoxy-pyrimidin-4-yl}-benzoic acid 2-morpholin-4-yl-ethyl ester, Example 75;

3-{6-[2-(2,4-dichloro-phenyl)-ethylamino]-2-methoxy-pyrimidin-4-yl}-benzoic acid 2-(4-methyl-piperazin-1-yl)-ethyl ester, Example 76;

3-{6-[2-(2,4-dichloro-phenyl)-ethylamino]-2-methoxy-pyrimidin-4-yl}-benzoic acid ethyl ester, Example 77;

(3-{6-[2-(2,4-dichloro-phenyl)-ethylamino]-2-methoxy-pyrimidin-4-yl}-phenyl)-methanol, Example 78(a);

(3'-chloro-4'-{2-[6-(3-hydroxymethyl-phenyl)-2-methoxy-pyrimidin-4-ylamino]-ethyl}-biphenyl-3-yl)-methanol, Example 78(b);

2-(3-{6-[2-(2,4-dichloro-phenyl)-ethylamino]-2-methoxy-pyrimidin-4-yl}-phenyl)-2-methyl-propionic acid methyl ester, Example 79;

4-(3-{6-[2-(2,4-dichloro-phenyl)-ethylamino]-2-methoxy-pyrimidin-4-yl}-phenyl)-tetrahydro-pyran-4-carboxylic acid, Example 80(a);

N-[4-(3-{6-[2-(2,4-dichloro-phenyl)-ethylamino]-2-methoxy-pyrimidin-4-yl}-phenyl)-tetrahydro-pyran-4-carbonyl]-methanesulfonamide, Example 80(b);

4-(3-{6-[2-(2,4-dichloro-phenyl)-ethylamino]-2-methoxy-pyrimidin-4-yl}-phenyl)-tetrahydro-pyran-4-carboxylic acid ethyl ester, Example 80(c);

(3-{6-[2-(2,4-dichloro-phenyl)-ethylamino]-2-methoxy-pyrimidin-4-yl}-phenyl)-difluoro-acetic acid, Example 81(a);

ethanesulfonic acid [2-(3-{6-[2-(2,4-dichloro-phenyl)-ethylamino]-2-methoxy-pyrimidin-4-yl}-phenyl)-2,2-difluoro-acetyl]-amide, Example 81(b);

(3-{6-[2-(2,4-dichloro-phenyl)-ethylamino]-2-methoxy-pyrimidin-4-yl}-phenyl)-difluoro-acetic acid ethyl ester, Example 81(c);

(3-{6-[2-(2,4-dichloro-phenyl)-ethylamino]-2-methoxy-pyrimidin-4-yl}-phenyl)-acetonitrile, Example 82(a);

(3-{6-[2-(2,4-dichloro-phenyl)-ethylamino]-2-methoxy-pyrimidin-4-yl}-phenyl)-difluoro-acetonitrile, Example 82(b);

[2-(2,4-dichloro-phenyl)-ethyl]-(6-{3-[difluoro-(1H-tetrazol-5-yl)-methyl]-phenyl}-2-methoxy-pyrimidin-4-yl)-amine, Example 82(c)

2-{3-[6-(indan-1-ylamino)-2-methoxy-pyrimidin-4-yl]-phenyl}-2-methyl-propionic acid, Example 83(a);

2-{3-[6-(indan-2-ylamino)-2-methoxy-pyrimidin-4-yl]-phenyl}-2-methyl-propionic acid, Example 83(b);

N-[4-(3-{2-methoxy-6-[2-(4-trifluoromethoxy-phenyl)-ethylamino]-pyrimidin-4-yl}-phenyl)-tetrahydro-pyran-4-carbonyl]-methanesulfonamide, Example 84(a);

4-(3-{2-methoxy-6-[2-(4-trifluoromethoxy-phenyl)-ethylamino]-pyrimidin-4-yl}-phenyl)-tetrahydro-pyran-4-carboxylic acid methyl ester, Example 84(b);

2-(3-{6-[2-(2,4-dichloro-phenyl)-ethylamino]-2-methoxymethyl-pyrimidin-4-yl}-phenyl)-2-methyl-propionic acid, Example 85;

2-(3-{6-[2-(2,4-dichloro-phenyl)-ethylamino]-2-hydroxymethyl-pyrimidin-4-yl}-phenyl)-2-methyl-propionic acid, Example 86;

5-{6-[2-(2,4-dichloro-phenyl)-ethylamino]-2-methoxy-pyrimidin-4-yl}-thiophene-2-carboxylic acid, Example 87;

5-{2-methoxy-6-[2-(4-trifluoromethoxy-phenyl)-ethylamino]-pyrimidin-4-yl}-2,3-dihydro-benzofuran-2-carboxylic acid hydrochloride, Example 88;

2-(3-{6-[2-(2,4-dichloro-phenyl)-ethylamino]-2-methoxy-pyrimidin-4-yl}-phenyl)-2-methyl-propionic acid 2,3-dihydroxy-propyl ester, Example 89;

2-(3-{6-[(2,3-dihydro-benzofuran-2-ylmethyl)-amino-]-2-methoxy-pyrimidin-4-yl}-phenyl)-2-methyl-propionic acid, Example 90;

2-(3-{6-[(isochroman-1-ylmethyl)-amino]-2-methoxy-pyrimidin-4-yl}-phenyl)-2-methyl-propionic acid, Example 91;

2-(3-{2-methoxy-6-[(4-methyl-3,4-dihydro-2H-benzo[1,4]oxazin-2-ylmethyl)-amino]-pyrimidin-4-yl}-phenyl)-2-methyl-propionic acid, Example 92;

2-(3-{6-[(benzofuran-5-ylmethyl)-amino]-2-methoxy-pyrimidin-4-yl}-phenyl)-2-methyl-propionic acid, Example 93;

N-(6-{6-[2-(2,4-dichloro-phenyl)-ethylamino]-2-methoxy-pyrimidin-4-yl}-benzothiazol-2-yl)-acetamide, Example 94;

ethanesulfonic acid [2-(3-{6-[2-(2,4-dichloro-phenyl)-ethylamino]-2-methoxy-pyrimidin-4-yl}-phenyl)-2-methyl-propionyl]-amide, Example 95(a);

N-[2-(3-{6-[2-(2,4-dichloro-phenyl)-ethylamino]-2-methoxy-pyrimidin-4-yl}-phenyl)-2-methyl-propionyl]-C-phenyl-methanesulfonamide, Example 95(b);

2-(3-{6-[2-(2,4-dichloro-phenyl)-ethylamino]-2-methoxy-pyrimidin-4-yl}-phenyl)-2-methyl-1-morpholin-4-yl-propan-1-one, Example 95(c);

2-(3-{6-[2-(2,4-dichloro-phenyl)-ethylamino]-2-methoxy-pyrimidin-4-yl}-phenyl)-N-(tetrahydro-pyran-4-yl)-isobutyramide, Example 95(d);

2-(3-{6-[2-(2,4-dichloro-phenyl)-ethylamino]-2-methoxy-pyrimidin-4-yl}-phenyl)-N-(1H-tetrazol-5-yl)-isobutyramide, Example 95(e);

[2-(2,4-dichloro-phenyl)-ethyl]-{2-methoxy-6-[3-(2H-tetrazol-5-yl)-piperidin-1-yl]-pyrimidin-4-yl}-amine, Example 96;

1-{6-[2-(2,4-dichloro-phenyl)-ethylamino]-2-methoxy-pyrimidin-4-yl}-piperidine-4-carboxylic acid, Example 97;

2-(2-chloro-5-{6-[2-(2,4-dichloro-phenyl)-ethylamino]-2-methoxy-pyrimidin-4-yl}-phenyl)-propan-2-ol, Example 98; or 2-(3-{6-[2-(2,4-dichloro-phenyl)-ethylamino]-2-methoxy-pyrimidin-4-yl}-4-fluoro-phenyl)-2-methyl-propionic acid hydrochloride, Example 99.

Another particular embodiment of the invention is a compound of Formula (I) or a pharmaceutically acceptable salt thereof, which is N-methoxycarbonyl-3-{2-methoxy-6-[2-(4-methoxy-phenyl)-ethylamino]-pyrimidin-4-yl}-benzenesulfonamide, Example 4(c);

3-{6-[2-(2,4-difluoro-phenyl)-ethylamino]-2-methoxy-pyrimidin-4-yl}-benzoic acid, Example 7;

5-{2-methoxy-6-[2-(4-methoxy-phenyl)-ethylamino]-pyrimidin-4-yl}-thiophene-2-carboxylic acid trifluoroacetate, Example 8(a);

5-{2-methoxy-6-[2-(4-methoxy-phenyl)-ethylamino]-pyrimidin-4-yl}-thiophene-2-carbaldehyde, Example 8(b);

(5-{2-methoxy-6-[2-(4-methoxy-phenyl)-ethylamino]-pyrimidin-4-yl}-thiophen-2-yl)-methanol, Example (9a);

(3-{2-methoxy-6-[2-(4-methoxy-phenyl)-ethylamino]-pyrimidin-4-yl}-phenyl)-methanol, Example 359(c);

[2-(4-methoxy-phenyl)-ethyl]-(2-methoxy-6-quinolin-6-yl-pyrimidin-4-yl)-amine, Example 10(a);

[2-(4-methoxy-phenyl)-ethyl]-(2-methoxy-6-quinolin-3-yl-pyrimidin-4-yl)-amine, Example 10(b);

[6-(1H-indol-5-yl)-2-methoxy-pyrimidin-4-yl]-[2-(4-methoxy-phenyl)-ethyl]-amine, Example 10(c);

[6-(1H-benzotriazol-5-yl)-2-methoxy-pyrimidin-4-yl]-[2-(4-methoxy-phenyl)-ethyl]-amine, Example 14(b);

3-{2-methoxy-6-[2-(4-methoxy-phenyl)-ethylamino]-pyrimidin-4-yl}-phenol hydrochloride, Example 15(a);

3-{6-[2-(2,4-dichloro-phenyl)-ethylamino]-2-methoxy-pyrimidin-4-yl}-benzoic acid hydrochloride, Example 15(b);

3-{6-[2-(2-chloro-6-fluoro-phenyl)-ethylamino]-2-methoxy-pyrimidin-4-yl}-benzoic acid hydrochloride, Example 15(c);

2-(3-{6-[2-(2,4-dichloro-phenyl)-ethylamino]-2-methoxy-pyrimidin-4-yl}-phenyl)-2-methyl-propionic acid hydrochloride, Example 15(d);

2-fluoro-5-{2-methoxy-6-[2-(4-methoxy-phenyl)-ethylamino]-pyrimidin-4-yl}-benzoic acid, Example 20(a);

3-{6-[2-(2-chloro-6-fluoro-phenyl)-ethylamino]-2-methoxy-pyrimidin-4-yl}-benzoic acid, Example 20(b);

2-methoxy-5-{2-methoxy-6-[2-(4-methoxy-phenyl)-ethylamino]-pyrimidin-4-yl}-benzoic acid, Example 20(c);

(3-{2-methoxy-6-[2-(4-methoxy-phenyl)-ethylamino]-pyrimidin-4-yl}-phenoxy)-acetic acid methyl ester, Example 22(b);

(3-{6-[2-(2,4-dichloro-phenyl)-ethylamino]-2-methoxy-pyrimidin-4-yl}-phenoxy)-acetic acid methyl ester, Example 22(c);

(3-{2-methoxy-6-[2-(4-methoxy-phenyl)-ethylamino]-pyrimidin-4-yl}-phenoxy)-acetic acid, Example 23(b);

(5-{6-[2-(2-chloro-6-fluoro-phenyl)-ethylamino]-2-methoxy-pyrimidin-4-yl}-2-oxo-2H-pyridin-1-yl)-acetic acid, Example 23(c);

2-(3-{6-[2-(2,4-dichloro-phenyl)-ethylamino]-2-methoxy-pyrimidin-4-yl}-phenoxy)-2-methyl-propionic acid, Example 23(d);

2-chloro-5-{2-methoxy-6-[2-(4-methoxy-phenyl)-ethylamino]-pyrimidin-4-yl}-benzoic acid hydrochloride salt, Example 23(e);

[2-(4-methoxy-phenyl)-ethyl]-{2-methoxy-6-[3-(1H-tetrazol-5-yl)-phenyl]-pyrimidin-4-yl}-amine, Example 24(a);

[2-(4-methoxy-phenyl)-ethyl]-{2-methoxy-6-[3-(1H-tetrazol-5-ylmethyl)-phenyl]-pyrimidin-4-yl}-amine hydrochloride, Example 24(b);

{2-methoxy-6-[4-methoxy-3-(1H-tetrazol-5-yl)-phenyl]-pyrimidin-4-yl}-[2-(4-methoxy-phenyl)-ethyl]-amine, Example 24(c);

N-(3-{2-methoxy-6-[2-(4-methoxy-phenyl)-ethylamino]-pyrimidin-4-yl}-benzoyl)-methanesulfonamide, Example 25(a);

3-{2-methoxy-6-[2-(4-methoxy-phenyl)-ethylamino]-pyrimidin-4-yl}-benzaldehyde oxime, Example 26(b);

3-{2-methoxy-6-[2-(4-methoxy-phenyl)-ethylamino]-pyrimidin-4-yl}-thiophene-2-carbaldehyde oxime, Example 26(d);

1-(5-{2-methoxy-6-[2-(4-methoxy-phenyl)-ethylamino]-pyrimidin-4-yl}-thiophen-2-yl)-ethanone oxime, Example 26(e);

5-{2-methoxy-6-[2-(4-methoxy-phenyl)-ethylamino]-pyrimidin-4-yl}-thiophene-2-carbaldehyde oxime, Example 26(f);

3-(3-{6-[2-(2,4-dichloro-phenyl)-ethylamino]-2-methoxy-pyrimidin-4-yl-phenoxymethyl)-4H-[1,2,4]oxadiazol-5-one hydrochloride, Example 34(a);

3-(3-{6-[2-(2-chloro-6-fluoro-phenyl)-ethylamino]-2-methoxy-pyrimidin-4-yl}-benzyl)-4H-[1,2,4]oxadiazol-5-one hydrochloride, Example 34(b);

3-(3-{6-[2-(2-chloro-6-fluoro-phenyl)-ethylamino]-2-methoxy-pyrimidin-4-yl}-phenoxymethyl)-4H-[1,2,4]oxadiazol-5-one hydrochloride, Example 34(c);

3-{2-methoxy-6-[2-(4-methoxy-phenyl)-ethylamino]-pyrimidin-4-yl}-benzoic acid, Example 35(a);

3-{6-[2-(4-fluoro-phenyl)-ethylamino]-2-methoxy-pyrimidin-4-yl}-benzoic acid hydrochloride, Example 35(f);

3-{6-[2-(2,4-dichloro-phenyl)-ethylamino]-2-methoxy-pyrimidin-4-yl}-phenol, Example 35(i);

3-{2-methoxy-6-[2-(4-methoxy-phenyl)-ethylamino]-pyrimidin-4-yl}-thiophene-2-carbaldehyde, Example 35(l);

3-{6-[2-(4-chlorophenyl)-ethylamino]-2-methoxy-pyrimidin-4-yl}-benzoic acid hydrochloride, Example 35(n);

3-{2-methoxy-6-[2-(4-methoxy-phenyl)-ethylamino]-pyrimidin-4-yl}-benzonitrile, Example 35(t);

3-{2-methoxy-6-[2-(4-methoxy-phenyl)-ethyl amino]-pyrimidin-4-yl}-benzaldehyde, Example 35(u);

3-{6-[2-(2,4-dichloro-phenyl)-ethylamino]-2-methoxy-pyrimidin-4-yl}-benzoic acid hydrochloride, Example 35(w);

[2-(3-fluoro-4-methoxy-phenyl)-ethyl]-{2-methoxy-6-[3-(2H-tetrazol-5-yl)-phenyl]-pyrimidin-4-yl}-amine, Example 40;

[2-methoxy-6-(3-methoxy-phenyl)-pyrimidin-4-yl]-[2-(4-nitro-phenyl)-ethyl]-amine, Example 43(b);

[2-methoxy-6-(3-methoxy-phenyl)-pyrimidin-4-yl]-[2-(4-methoxy-phenyl)-ethyl]-amine, Example 43(o);

[2-(2,4-dichloro-phenyl)-ethyl]-(2-methyl-6-{3-[1-methyl-1-(1H-tetrazol-5-yl)-ethyl]-phenyl}-pyrimidin-4-yl)-amine hydrochloride, example 47;

2-(3-{6-[2-(2,4-dichloro-phenyl)-ethylamino]-2-methoxy-pyrimidin-4-yl}-phenyl)-propionic acid hydrochloride, Example 49(a);

(5-{6-[2-(2-fluoro-4-trifluoromethyl-phenyl)-ethylamino]-2-methoxy-pyrimidin-4-yl}-1H-indol-3-yl)-acetic acid, Example 52;

[6-(H-indol-6-yl)-2-methoxy-pyrimidin-4-yl]-[2-(4-methoxy-phenyl)-ethyl]-ammonium trifluoroacetate, Example 53(a);

[6-(1H-indazol-6-yl)-2-methoxy-pyrimidin-4-yl]-[2-(4-methoxy-phenyl)-ethyl]-amine, Example 53(b);

3-{6-[2-(2,6-dichloro-phenyl)-ethylamino]-2-methoxy-pyrimidin-4-yl}-benzoic acid, Example 53(c);

[2-(4-methoxy-phenyl)-ethyl]-{2-methoxy-6-[3-(1H-tetrazol-5-yl)-phenyl]-pyrimidin-4-yl}-amine, sodium salt Example 54;

(3-{6-[2-(2-chloro-6-fluoro-phenyl)-ethylamino]-2-methoxy-pyrimidin-4-yl}-benzyloxy)-acetic acid, Example 56;

(3-{6-[2-(2,4-dichloro-phenyl)-ethylamino]-2-methoxy-pyrimidin-4-yl}-benzoylamino)-acetic acid, Example 59;

ethyl-carbamic acid 3-{6-[2-(2,4-dichloro-phenyl)-ethylamino]-2-methoxy-pyrimidin-4-yl}-phenyl ester, Example 60;

5-{2-methoxy-6-[2-(4-methoxy-phenyl)-ethylamino]-pyrimidin-4-yl}-thiophene-2-carboxylic acid methylamide trifluoroacetate, Example 62;

1-{6-[2-(2,4-dichloro-phenyl)-ethylamino]-2-methoxy-pyrimidin-4-yl}-piperidine-3-carboxylic acid, Example 73;

4-(3-{6-[2-(2,4-dichloro-phenyl)-ethylamino]-2-methoxy-pyrimidin-4-yl}-phenyl)-tetrahydro-pyran-4-carboxylic acid, Example 80(a);

N-[4-(3-{6-[2-(2,4-dichloro-phenyl)-ethylamino]-2-methoxy-pyrimidin-4-yl}-phenyl)-tetrahydro-pyran-4-carbonyl]-methanesulfonamide, Example 80(b);

(3-{6-[2-(2,4-dichloro-phenyl)-ethylamino]-2-methoxy-pyrimidin-4-yl}-phenyl)-difluoro-acetic acid, Example 81(a);

ethanesulfonic acid [2-(3-{6-[2-(2,4-dichloro-phenyl)-ethylamino]-2-methoxy-pyrimidin-4-yl}-phenyl)-2,2-difluoro-acetyl]-amide, Example 81(b);

[2-(2,4-dichloro-phenyl)-ethyl]-(6-{3-[difluoro-(1H-tetrazol-5-yl)-methyl]-phenyl}-2-methoxy-pyrimidin-4-yl)-amine, Example 82(c);

N-[4-(3-{2-methoxy-6-[2-(4-trifluoromethoxy-phenyl)-ethylamino]-pyrimidin-4-yl}-phenyl)-tetrahydro-pyran-4-carbonyl]-methanesulfonamide, Example 84(a);

ethanesulfonic acid [2-(3-{6-[2-(2,4-dichloro-phenyl)-ethylamino]-2-methoxy-pyrimidin-4-yl}-phenyl)-2-methyl-propionyl]-amide, Example 95(a);

N-[2-(3-{6-[2-(2,4-dichloro-phenyl)-ethylamino]-2-methoxy-pyrimidin-4-yl}-phenyl)-2-methyl-propionyl]-C-phenyl-methanesulfonamide, Example 95(b);

2-(3-{6-[2-(2,4-dichloro-phenyl)-ethylamino]-2-methoxy-pyrimidin-4-yl}-phenyl)-2-methyl-1-morpholin-4-yl-propan-1-one, Example 95(c);

2-{6-[2-(2,4-dichloro-phenyl)-ethylamino]-2-methoxy-pyrimidin-4-yl}-phenyl)-N-(tetrahydro-pyran-4-yl)-isobutyramide, Example 95(d);

2-(3-{6-[2-(2,4-dichloro-phenyl)-ethylamino]-2-methoxy-pyrimidin-4-yl}-phenyl)-N-(1H-tetrazol-5-yl)-isobutyramide, Example 95(e); or

[2-(2,4-dichloro-phenyl)-ethyl]-{2-methoxy-6-[3-(2H-tetrazol-5-yl)-piperidin-1-yl]-pyrimidin-4-yl}-amine, Example 96.

The compounds of present invention and the intermediates and starting materials used in their preparation are named in accordance with IUPAC rules of nomenclature in which the characteristic groups have decreasing priority for citation as the principle group as follows: acids, esters, amides, etc. Alternatively, the compounds are named by AutoNom 4 (Beilstein Information Systems, Inc.). [For example, a compound of Formula (I) wherein $R^1$ is methoxy, $L^1$ is ethylene, $L^2$ is a bond, $Cy^1$ is 3-(2H-tetrazol-5-yl)-phenyl, $Cy^2$ is 3-fluoro-4-methoxy-phenyl; that is, a compound having the following structure:

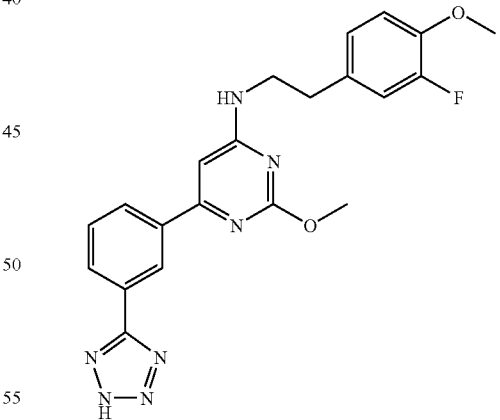

is named [2-(3-fluoro-4-methoxy-phenyl)-ethyl]-{2-methoxy-6-[3-(2H-tetrazol-5-yl)-phenyl]-pyrimidin-4-yl}-anine.

However, it is understood that, for a particular compound referred to by both a structural Formula and a nomenclature name, if the structural Formula and the nomenclature name are inconsistent with each other, the structural Formula takes the precedence over the nomenclature name.

The compounds of the invention exhibit prostaglandin D2 receptor antagonist activity and are useful a pharmacological acting agents. Accordingly, they are incorporated into pharmaceutical compositions and used in the treatment of patients suffering from certain medical disorders. Compounds within the scope of the present invention are antagonists of the prostaglandin D2 receptor, according to tests described in the literature and described in pharmacological testing section hereinafter, and which tests results are believed to correlate to pharmacological activity in humans and other mammals. Thus, in a further embodiment, the present invention provides compounds of the invention and compositions containing compounds of the invention for use in the treatment of a patient suffering from, or subject to, conditions, which can be ameliorated by the administration of a PGD2 antagonist. For example, compounds of the present invention could therefore be useful in the treatment of a variety of PGD2-mediated disorders including, but not limited to, allergic disease (such as allergic rhinitis, allergic conjunctivitis, atopic dermatitis, bronchial asthma and food allergy), systemic mastocytosis, disorders accompanied by systemic mast cell activation, anaphylaxis shock, bronchoconstriction, bronchitis, urticaria, eczema, diseases accompanied by itch (such as atopic dermatitis and urticaria), diseases (such as cataract, retinal detachment, inflammation, infection and sleeping disorders) which is generated secondarily as a result of behavior accompanied by itch (such as scratching and beating), inflammation, chronic obstructive pulmonary diseases, ischemic reperfusion injury, cerebrovascular accident, chronic rheumatoid arthritis, pleurisy, ulcerative colitis and the like.

Compounds of the present invention are further useful in treatments involving a combination therapy with:

(i) antihistamines, such as fexofenadine, loratadine and citirizine, for the treatment of allergic rhinitis;

(ii) leukotriene antagonists, such as montelukast and zafirlukast, for the treatment of allergic rhinitis, COPD, allergic dermatitis, allergic conjunctivitis etc—please specifically refer to the claims in WO 01/78697 A2;

(iii) beta agonists, such as albuterol, salbuterol and terbutaline, for the treatment of asthma, COPD, allergic dermatitis, allergic conjunctivitis etc;

(iv) antihistamines, such as fexofenadine, loratadine and citirizine, for the treatment of asthma, COPD, allergic dermatitis, allergic conjunctivitis etc;

(v) PDE4 (Phosphodiesterase 4) inhibitors, such as roflumilast and cilomilast, for the treatment of asthma, COPD, allergic dermatitis, allergic conjunctivitis etc; or (vi) with TP (Thromboxane A2 receptor) or CrTh2 (chemoattractant receptor-homologous molecule expressed on Th2 cells) antagonists, such as Ramatroban (BAY-u3405), for the treatment of COPD, allergic dermatitis, allergic conjunctivitis, etc.

A special embodiment of the therapeutic methods of the present invention is the treating of allergic rhinitis.

Another special embodiment of the therapeutic methods of the present invention is the treating of bronchial asthma.

According to a further feature of the invention there is provided a method for the treatment of a human or animal patient suffering from, or subject to, conditions which can be ameliorated by the administration of a prostaglandin D2 receptor antagonist, for example conditions as hereinbefore described, which comprises the administration to the patient of an effective amount of compound of the invention or a composition containing a compound of the invention. "Effective amount" is meant to describe an amount of compound of the present invention effective as a prostaglandin D2 receptor antagonist and thus producing the desired therapeutic effect.

References herein to treatment should be understood to include prophylactic therapy as well as treatment of established conditions.

The present invention also includes within its scope pharmaceutical compositions comprising at least one of the compounds of the invention in admixture with a pharmaceutically acceptable carrier.

In practice, the compound of the present invention may be administered in pharmaceutically acceptable dosage form to humans and other animals by topical or systemic administration, including oral, inhalational, rectal, nasal, buccal, sublingual, vaginal, colonic, parenteral (including subcutaneous, intramuscular, intravenous, intradermal, intrathecal and epidural), intracisternal and intraperitoneal. It will be appreciated that the preferred route may vary with for example the condition of the recipient.

"Pharmaceutically acceptable dosage forms" refers to dosage forms of the compound of the invention, and includes, for example, tablets, dragées, powders, elixirs, syrups, liquid preparations, including suspensions, sprays, inhalants tablets, lozenges, emulsions, solutions, granules, capsules and suppositories, as well as liquid preparations for injections, including liposome preparations. Techniques and formulations generally may be found in Remington's Pharmaceutical Sciences, Mack Publishing Co., Easton, Pa., latest edition.

A particular aspect of the invention provides for a compound according to the present invention to be administered in the form of a pharmaceutical composition. Pharmaceutical compositions, according to the present invention, comprise compounds of the present invention and pharmaceutically acceptable carriers.

Pharmaceutically acceptable carriers include at least one component selected from the group comprising pharmaceutically acceptable carriers, diluents, coatings, adjuvants, excipients, or vehicles, such as preserving agents, fillers, disintegrating agents, wetting agents, emulsifying agents, emulsion stabilizing agents, suspending agents, isotonic agents, sweetening agents, flavoring agents, perfuming agents, coloring agents, antibacterial agents, antifungal agents, other therapeutic agents, lubricating agents, adsorption delaying or promoting agents, and dispensing agents, depending on the nature of the mode of administration and dosage forms.

Exemplary suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances.

Exemplary antibacterial and antifungal agents for the prevention of the action of microorganisms include parabens, chlorobutanol, phenol, sorbic acid, and the like.

Exemplary isotonic agents include sugars, sodium chloride and the like.

Exemplary adsorption delaying agents to prolong absorption include aluminum monostearate and gelatin.

Exemplary adsorption promoting agents to enhance absorption include dimethyl sulfoxide and related analogs.

Exemplary diluents, solvents, vehicles, solubilizing agents, emulsifiers and emulsion stabilizers, include water, chloroform, sucrose, ethanol, isopropyl alcohol, ethyl carbonate, ethyl acetate, benzyl alcohol, tetrahydrofurfuryl alcohol, benzyl benzoate, polyols, propylene glycol, 1,3-butylene glycol, glycerol, polyethylene glycols, dimethylformamide, Tween® 60, Span® 60, cetostearyl alcohol, myristyl alcohol, glyceryl mono-stearate and sodium lauryl sulfate, fatty acid esters of sorbitan, vegetable oils (such as cottonseed oil, groundnut oil, corn germ oil, olive oil, castor oil and sesame oil) and injectable organic esters such as ethyl oleate, and the like, or suitable mixtures of these substances.

Exemplary excipients include lactose, milk sugar, sodium citrate, calcium carbonate and dicalcium phosphate.

Exemplary disintegrating agents include starch, alginic acids and certain complex silicates.

Exemplary lubricants include magnesium stearate, sodium lauryl sulfate, talc, as well as high molecular weight polyethylene glycols.

The choice of pharmaceutical acceptable carrier is generally determined in accordance with the chemical properties of the active compound such as solubility, the particular mode of administration and the provisions to be observed in pharmaceutical practice.

Pharmaceutical compositions of the present invention suitable for oral administration may be presented as discrete units such as a solid dosage form, such as capsules, cachets or tablets each containing a predetermined amount of the active ingredient, or as a powder or granules; as a liquid dosage form such as a solution or a suspension in an aqueous liquid or a non-aqueous liquid, or as an oil-in-water liquid emulsion or a water-in-oil liquid emulsion. The active ingredient may also be presented as a bolus, electuary or paste.

"Solid dosage form" means the dosage form of the compound of the invention is solid form, for example capsules, tablets, pills, powders, dragées or granules. In such solid dosage forms, the compound of the invention is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alginates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and $Na_2CO_3$, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, (i) lubricants, as for example, talc, calcium stearate, magnesium stearate, solid polyethylene glycols, sodium lauryl sulfate, (j) opacifying agents, (k) buffering agents, and agents which release the compound(s) of the invention in a certain part of the intestinal tract in a delayed manner.

A tablet may be made by compression or molding, optionally with one or more accessory ingredients. Compressed tables may be prepared by compressing in a suitable machine the active ingredient in a free-flowing form such as a powder or granules, optionally mixed with a binder, lubricant, inert diluent, preservative, surface active or dispersing agent. Excipients such as lactose, sodium citrate, calcium carbonate, dicalcium phosphate and disintegrating agents such as starch, alginic acids and certain complex silicates combined with lubricants such as magnesium stearate, sodium lauryl sulfate and talc may be used. A mixture of the powdered compounds moistened with an inert liquid diluent may be molded in a suitable machine to make molded tablets. The tablets may optionally be coated or scored and may be formulated so as to provide slow or controlled release of the active ingredient therein.

Solid compositions may also be employed as fillers in soft and hard-filled gelatin capsules using such excipients as lactose or milk sugar as well as high molecular weight polyethylene glycols, and the like.

If desired, and for more effective distribution, the compounds can be microencapsulated in, or attached to, a slow release or targeted delivery systems such as a biocompatible, biodegradable polymer matrices (e.g., poly(d,l-lactide co-glycolide)), liposomes, and microspheres and subcutaneously or intramuscularly injected by a technique called subcutaneous or intramuscular depot to provide continuous slow release of the compound(s) for a period of 2 weeks or longer. The compounds may be sterilized, for example, by filtration through a bacteria-retaining filter, or by incorporating sterilizing agents in the form of sterile solid compositions that can be dissolved in sterile water, or some other sterile injectable medium immediately before use.

"Liquid dosage form" means the dose of the active compound to be administered to the patient is in liquid form, for, example, pharmaceutically acceptable emulsions, solutions, suspensions, syrups and elixirs. In addition to the active compounds, the liquid dosage forms may contain inert diluents commonly used in the art, such solvents, solubilizing agents and emulsifiers.

When aqueous suspensions are used they can contain emulsifying agents or agents which facilitate suspension.

Pharmaceutical compositions suitable for topical administration means formulations that are in a form suitable to be administered topically to a patient. The formulation may be presented as a topical ointment, salves, powders, sprays and inhalants, gels (water or alcohol based), creams, as is generally known in the art, or incorporated into a matrix base for application in a patch, which would allow a controlled release of compound through the transdermal barrier. When formulated in an ointment, the active ingredients may be employed with either a paraffinic or a water-miscible ointment base. Alternatively, the active ingredients may be formulated in a cream with an oil-in-water cream base. Formulations suitable for topical administration in the eye include eye drops wherein the active ingredient is dissolved or suspended in a suitable carrier, especially an aqueous solvent for the active ingredient. Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

The oily phase of the emulsion pharmaceutical composition may be constituted from known ingredients in a known manner. While the phase may comprise merely an emulsifier (otherwise known as an emulgent), it desirably comprises a mixture of at least one emulsifier with a fat or an oil or with both a fat and an oil. In a particular embodiment, a hydrophilic emulsifier is included together with a lipophilic emulsifier that acts as a stabilizer. Together, the emulsifier(s) with or without stabilizer(s) make up the emulsifying wax, and the way together with the oil and fat make up the emulsifying ointment base which forms the oily dispersed phase of the cream formulations.

If desired, the aqueous phase of the cream base may include, for example, a least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound that enhances absorption or penetration of the active ingredient through the skin or other affected areas.

The choice of suitable oils or fats for a composition is based on achieving the desired properties. Thus a cream should preferably be a non-greasy, non-staining and washable product with suitable consistency to avoid leakage from tubes or other containers. Straight or branched chain, mono- or dibasic alkyl esters such as di-isopropyl myristate, decyl oleate, isopropyl palmitate, butyl stearate, 2-ethylhexyl palmitate or a blend of branched chain esters known as Crodamol CAP may be used. These may be used alone or in combination depending on the properties required. Alternatively, high melting point lipids such as white soft paraffin and/or liquid paraffin or other mineral oils can be used.

Pharmaceutical compositions suitable for rectal or vaginal administrations means formulations that are in a form suitable to be administered rectally or vaginally to a patient and containing at least one compound of the invention. Suppositories are a particular form for such formulations that can be prepared by mixing the compounds of this invention with suitable non-irritating excipients or carriers such as cocoa butter, polyethylene glycol or a suppository wax, which are solid at ordinary temperatures but liquid at body temperature and therefore, melt in the rectum or vaginal cavity and release the active component.

Pharmaceutical composition administered by injection may be by transmuscular, intravenous, intraperitoneal, and/or subcutaneous injection. The compositions of the present invention are formulated in liquid solutions, in particular in physiologically compatible buffers such as Hank's solution or Ringer's solution. In addition, the compositions may be formulated in solid form and redissolved or suspended immediately prior to use. Lyophilized forms are also included. The formulations are sterile and include emulsions, suspensions, aqueous and non-aqueous injection solutions, which may contain suspending agents and thickening agents and antioxidants, buffers, bacteriostats and solutes which render the formulation isotonic, and have a suitably adjusted pH, with the blood of the intended recipient.

Pharmaceutical composition of the present invention suitable for nasal or inhalational administration means compositions that are in a form suitable to be administered nasally or by inhalation to a patient. The composition may contain a carrier, in a powder form, having a particle size for example in the range 1 to 500 microns (including particle sizes in a range between 20 and 500 microns in increments of 5 microns such as 30 microns, 35 microns, etc.). Suitable compositions wherein the carrier is a liquid, for administration as for example a nasal spray or as nasal drops, include aqueous or oily solutions of the active ingredient. Compositions suitable for aerosol administration may be prepared according to conventional methods and may be delivered with other therapeutic agents. Metered dose inhalers are useful for administering compositions according to the invention for an inhalational therapy.

Actual dosage levels of active ingredient(s) in the compositions of the invention may be varied so as to obtain an amount of active ingredient(s) that is (are) effective to obtain a desired therapeutic response for a particular composition and method of administration for a patient. A selected dosage level for any particular patient therefore depends upon a variety of factors including the desired therapeutic effect, on the route of administration, on the desired duration of treatment, the etiology and severity of the disease, the patient's condition, weight, sex, diet and age, the type and potency of each active ingredient, rates of absorption, metabolism and/or excretion and other factors.

Total daily dose of the compounds of this invention administered to a patient in single or divided doses may be in amounts, for example, of from about 0.001 to about 100 mg/kg body weight daily and preferably 0.01 to 10 mg/kg/day. For example, in an adult, the doses are generally from about 0.01 to about 100, preferably about 0.01 to about 10, mg/kg body weight per day by inhalation, from about 0.01 to about 100, preferably 0.1 to 70, more especially 0.5 to 10, mg/kg body weight per day by oral administration, and from about 0.01 to about 50, preferably 0.01 to 10, mg/kg body weight per day by intravenous administration. The percentage of active ingredient in a composition may be varied, though it should constitute a proportion such that a suitable dosage shall be obtained. Dosage unit compositions may contain such amounts of such submultiples thereof as may be used to make up the daily dose. Obviously, several unit dosage forms may be administered at about the same time. A dosage may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. It goes without saying that, for other patients, it will be necessary to prescribe not more than one or two doses per day.

The formulations can be prepared in unit dosage form by any of the methods well known in the art of pharmacy. Such methods include the step of bringing into association the active ingredient with the carrier that constitutes one or more accessory ingredients. In general the formulations are prepared by uniformly and intimately bringing into association the active ingredient with liquid carriers or finely divided solid carriers or both, and then, if necessary, shaping the product.

The formulations may be presented in unit-dose or multi-dose containers, for example sealed ampoules and vials with elastomeric stoppers, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Compounds of the invention may be prepared by the application or adaptation of known methods, by which is meant methods used heretofore or described in the literature, for example those described by R. C. Larock in Comprehensive Organic Transformations, VCH publishers, 1989.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts, *Protecting Groups in Organic Synthesis*, 3rd edition, John Wiley & Sons, Inc., 1999. Suitable amine protecting groups include sulfonyl (e.g., tosyl), acyl (e.g., benzyloxycarbonyl or t-butoxycarbonyl) and arylalkyl (e.g., benzyl), which may be removed by hydrolysis or hydrogenolysis as appropriate. Other suitable amine protecting groups include trifluoroacetyl [—C(=O)CF$_3$] which may be removed by base catalyzed hydrolysis, or a solid phase resin bound benzyl group, such as a Merrifield resin bound 2,6-dimethoxybenzyl group (Ellman linker) or a 2,6-dimethoxy-4-[2-(polystyrylmethoxy)ethoxy]benzyl, which may be removed by acid catalyzed hydrolysis, for example with trifluoroacetic acid.

A compound of Formula (I), wherein R$^1$, Cy$^1$, Cy$^2$, L$^1$ and L$^2$ are as hereinbefore defined may be prepared by reaction of a compound of Formula (III), wherein L$^2$, R$^1$ and Cy$^1$ are as hereinbefore defined and X$^1$ is a halogen, preferably chlorine, or a triflate group, with an amine of Formula (IV), wherein L$^1$ and Cy$^2$ are as hereinbefore defined.

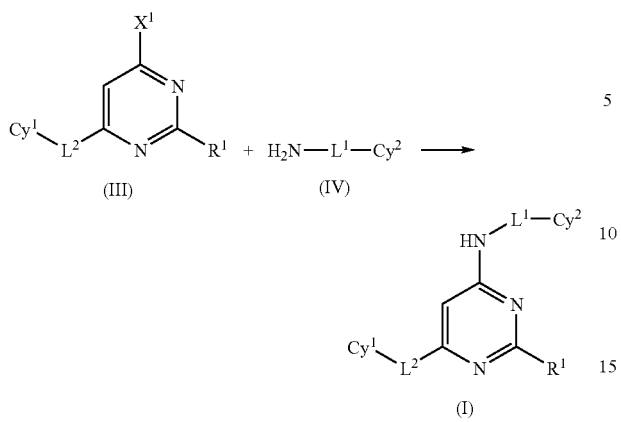

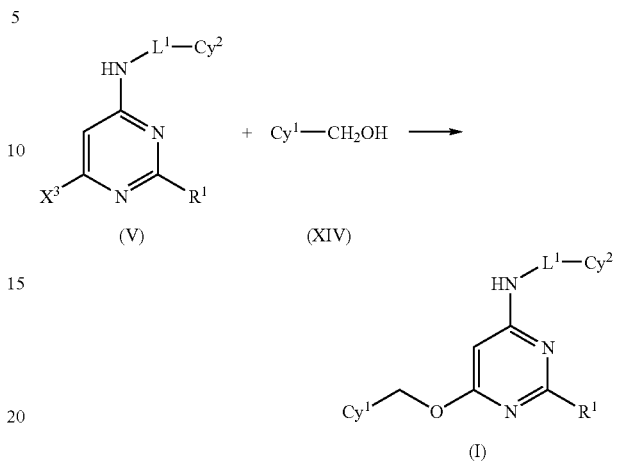

The reaction may conveniently be carried out for example in the presence of a suitable base, such as sodium bicarbonate, in an inert solvent, such as 1-methyl-2-pyrrolidinone, and at a temperature at about 160° C.

A compound of Formula (I), wherein $L^2$ is a bond and $R^1$, $Cy^1$, $Cy^2$ and $L^1$ are as hereinbefore defined may also be prepared by reaction of a compound of Formula (V), wherein $R^1$, $L^1$ and $Cy^2$ are as hereinbefore defined and $X^2$ is a halogen, preferably chlorine, or a triflate group, with a boronic acid of Formula (VI), or a boronic acid pinacol ester of formula (XVII), wherein $Cy^1$ is as hereinbefore defined.

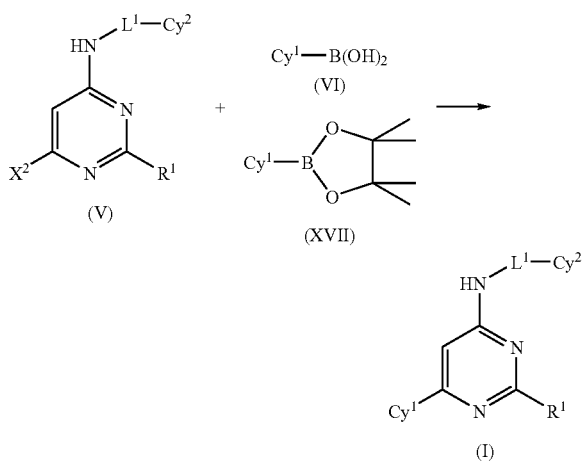

The coupling reaction may conveniently be carried out for example in the presence of a complex metal catalyst such as tetrakis(triphenylphosphine)palladium (0) and $Cs_2CO_3$, in an inert solvent, such as aqueous ethylene glycol dimethyl ether, and at a temperature at about 100° C. This reaction may also be conveniently carried out in a microwave oven at about 140° C. The coupling reaction may also be carried out in the presence of 1,1'-bis(diphenylphosphino)ferrocene-palladium (II) dichloride DCM complex and $Cs_2CO_3$, in an inert solvent, such as aqueous acetonitrile at a temperature up to about reflux temperature.

A compound of Formula (I), wherein $L^2$ is —$CH_2$—O— and $R^1$, $Cy^1$, $Cy^2$ and $L^1$ are as hereinbefore defined may also be prepared by reaction of a compound of Formula (V), wherein $R^1$, $L^1$ and $Cy^2$ are as hereinbefore defined and $X^3$ is a halogen, preferably chlorine, or a triflate group, with a compound of Formula (XIV), wherein $Cy^1$ is as hereinbefore defined. The reaction may be carried out in the presence of sodium hydride in an inert solvent, such as dimethylformamide, at a temperature up to reflux.

A compound of Formula (I), wherein $L^2$ is —O—, $R^1$ is ($C_1$-$C_4$)-alkylthio or ($C_1$-$C_4$)-alkyl, which is optionally substituted by one to three of same or different of halogen, hydroxy or alkoxy, $Cy^1$, $Cy^2$ and $L^1$ are as hereinbefore defined may also be prepared by reaction of a compound of Formula (XV), wherein $Cy^1$ is as hereinbefore defined and $X^4$ is a halogen, preferably chlorine, or a triflate group, with a compound of Formula (XVI), wherein $Cy^1$ is as hereinbefore defined. The reaction may conveniently be carried out for example in the presence of a suitable base, such as sodium bicarbonate or $Cs_2CO_3$, in an inert solvent, such as dimethylformamide, at a temperature up to reflux.

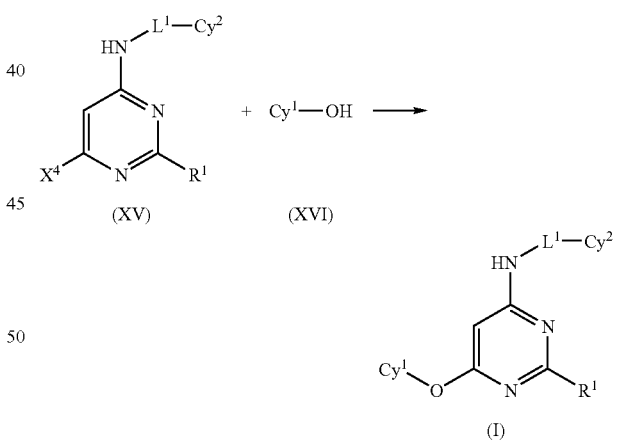

A compound of Formula (I), wherein $L^2$ is —O—, $R^1$ is —$NY^4Y^5$ or ($C_1$-$C_4$)-alkoxy, which is optionally substituted by one to three halogen, $Cy^1$, $Cy^2$ and $L^1$ are as hereinbefore defined may also be prepared by (i) oxidizing the corresponding compound of Formula (I), wherein $R^1$ is methylthio with an oxidizing reagent, such as 3-chloro-peroxybenzoic acid in an inert solvent, such as DCM, and at a temperature at about room temperature, and (ii) then reacting with an alkali metal alkoxide, such as a sodium alkoxide, or $HN^4Y^5$, in an inert solvent.

A compound of Formula (I), wherein $L^2$ is a bond, $Cy^1$ nitrogen-containing heterocyclyl that connects to the pyrimidine ring through its nitrogen ring atom, wherein the $Cy^1$ is optionally substituted one to three times by same or different $Cy^1$ substituents groups as hereinbefore defined, and $L^1$, $Cy^2$ and $R^1$ are as hereinbefore defined may be prepared by reaction of a corresponding compound of Formula (V), wherein $R^1$, $L^1$ and $Cy^2$ are as hereinbefore defined and $X^2$ is a halogen, preferably chlorine, with a corresponding compound of formula (XVIII), wherein $Cy^1$ is as hereinbefore defined.

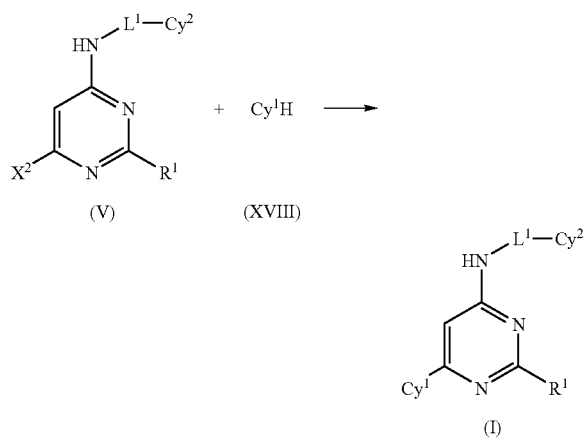

The reaction may conveniently be carried out for example in the presence of a suitable base, such as sodium bicarbonate or $K_2CO_3$, in an inert solvent, such as 1-methyl-2-pyrrolidinone, and at a temperature at about 140° C.

Compounds of the invention may also be prepared by interconversion of other compounds of the invention.

Thus, for example, compounds of Formula (I) in which $Cy^1$ is substituted by a carboxy group may be prepared by hydrolysis of the corresponding esters. The hydrolysis may conveniently be carried out by alkaline hydrolysis using a base, such as an alkali metal hydroxide, e.g. lithium hydroxide, or an alkali metal carbonate, e.g. $K_2CO_3$, in the presence of an aqueous/organic solvent mixture, using organic solvents such as dioxane, THF or methanol, at a temperature from about ambient to about reflux. The hydrolysis of the esters may also be carried out by acid hydrolysis using an inorganic acid, such as hydrochloric acid, in the presence of an aqueous/inert organic solvent mixture, using organic solvents such as dioxane or THF, at a temperature from about 50° C. to about 80° C.

As another example compounds of Formula (I) in which $Cy^1$ is substituted by a carboxy group may be prepared by acid catalyzed removal of the tert-butyl group of the corresponding tert-butyl esters using standard reaction conditions, for example reaction with trifluoroacetic acid at a temperature at about room temperature.

As another example compounds of Formula (I) in which $Cy^1$ is substituted by a carboxy group may be prepared by hydrogenation of the corresponding benzyl esters. The reaction may be carried out in the presence of ammonium formate and a suitable metal catalyst, e.g. palladium, supported on an inert carrier such as carbon, preferably in a solvent such as MeOH or EtOH and at a temperature at about reflux temperature. The reaction may alternatively be carried out in the presence of a suitable metal catalyst, e.g. platinum or palladium optionally supported on an inert carrier such as carbon, preferably in a solvent such as MeOH or EtOH.

As another example compounds of Formula (I) in which $Cy^1$ is substituted by a carboxy group may be prepared by oxidation of the corresponding compounds of Formula (I) in which $Cy^1$ is substituted by a formyl group. The reaction may be carried out using sodium dihydrogen phosphate monohydrate and sodium chlorite at a temperature at about room temperature.

As another example of the interconversion process, compounds of Formula (I) in which $Cy^1$ is substituted by a $Y^1Y^2N$—C(=O)— group may be prepared by coupling compounds of Formula (I), in which $Cy^1$ is substituted by a carboxy group, with an amine of Formula $Y^1Y^2NH$, to give an amide bond using standard peptide coupling procedures. Examples include (i) coupling in the presence of O-(7-azabenzotriazol-1-yl)-1,1,3,3-tetramethyluronium hexafluorophosphate and triethylamine (or diisopropylethylamine) in THF (or dimethylformamide) at room temperature, (ii) coupling in the presence of a carbodiimide, for example dicyclohexylcarbodiimide in the presence of triethylamine, (iii) treatment with 1-hydroxybenzotriazole and a carbodiimide, such as 1-(3-dimethylaminopropyl)-3-ethylcarbodiimide, in an inert solvent such as dimethylformamide and at a temperature at about room temperature. The coupling may also be brought about by reaction of compounds of Formula (I), in which $Cy^1$ is substituted by a carboxy group, with N-{(dimethylamino)(1H-1,2,3-triazaolo[4,5-b]pyridin-1-yl)methylene}-N-methylmethanaminium hexafluorophosphate N-oxide in the presence of a suitable base, such as diisopropylethylamine, in an inert solvent, such as dimethylformamide, and at a temperature at about room temperature, followed by reaction with an amine of Formula $Y^1Y^2NH$ (ammonium chloride can be used for the preparation of compounds of Formula (I) in which $Cy^1$ is substituted by a $H_2N$—C(=O)— group).

As another example of the interconversion process, compounds of Formula (I) in which $Cy^1$ is substituted by an alkyl-$SO_2$—NH—C(=O)— group may be prepared by coupling compounds of Formula (I), in which $Cy^1$ is substituted by a carboxy group, with an alkyl sulfonamide of Formula alkyl-$SO_2$—$NH_2$, to give an amide bond using standard peptide coupling procedures.

As another example of the interconversion process, compounds of Formula (I) in which $Cy^1$ is substituted by a $R^6$—C(=O)—N($R^5$)— group may be prepared by reaction of compounds of Formula (I), in which $Cy^1$ is substituted by a HN($R^5$)— group, with an acid chloride of Formula $R^6$—C(=O)—Cl in an inert solvent, such as DCM, and in the presence of a suitable base, such as triethylamine, at a temperature at about 0° C.

As another example of the interconversion process, compounds of Formula (I) in which $Cy^1$ is substituted by a $Y^1Y^2NSO_2$— group may be prepared by (i) reaction of compounds of Formula (I) in which $Cy^1$ is substituted by $H_2N$— with sodium nitrite in the presence of hydrochloric acid at a temperature at about 0° C., followed by treatment of the resulting diazonium salt with sulfur dioxide in the presence of copper chloride, and (ii) subsequent treatment of the resulting compounds of Formula (I) in which $Cy^1$ is substituted by a Cl—$SO_2$— with an amine of Formula $Y^1Y^2NH$ at a temperature at about 0° C.

As another example of the interconversion process, compounds of Formula (I) in which $Cy^1$ is substituted by an alkoxy-C(=O)—NH—$SO_2$— group may be prepared by reaction of compounds of Formula (I) in which $Cy^1$ is substituted by $H_2N$—$SO_2$— with an alkyl chloroformate in the presence of sodium hydride, in an inert solvent, such as THF, and at a temperature at about 0° C.

As another example of the interconversion process, compounds of Formula (I) in which $Cy^1$ is substituted by HOCH₂— group may be prepared by the reduction of corresponding compounds of Formula (I) in which Cy¹ is substituted by a $C_{1-4}$alkylO—C(=O)— group. The reduction may conveniently be carried out by means of reaction with lithium aluminum hydride, in an inert solvent, such as THF, and at a temperature from about room temperature to about reflux temperature.

As another example of the interconversion process, compounds of Formula (I) in which Cy¹ is substituted by HOCH₂— group may be prepared by the reduction of corresponding compounds of Formula (I) in which Cy¹ is substituted by a H—C(=O)— group. The reduction may conveniently be carried out by means of reaction with sodium borohydride, in an inert solvent, such as THF, and at a temperature from about 0° C. to about room temperature.

As another example of the interconversion process, compounds of Formula (I) in which Cy¹ is substituted by F₂CH— group may be prepared by reaction of corresponding compounds of Formula (I) in which Cy¹ is substituted by a H—C(=O)— group with diethylaminosulfur trifluoride, in an inert solvent, such as DCM, and at reflux temperature.

As another example of the interconversion process, compounds of Formula (I) in which Cy¹ is substituted by a R²—C(=N—OR³)— group, in which R² and R³ are both H, may be prepared by reaction corresponding compounds of Formula (I) in which Cy¹ is substituted by a formyl group with hydroxylamine hydrochloride in the presence of a suitable base, such as pyridine, and at a temperature at about room temperature. Compounds of Formula (I) in which Cy¹ is substituted by a R²—C(=N—OR³)— group, in which R³ is H and R² is alkyl may be similarly prepared from compounds of Formula (I) in which Cy¹ is substituted by a alkyl-CO— group.

As another example of the interconversion process, compounds of Formula (I) in which Cy¹ is substituted by a R⁷—NH—C(=O)—NH— group, in which R⁷ is as hereinbefore defined, may be prepared by reaction of the corresponding compounds of Formula (I), in which Cy¹ is substituted by an amino group, with an isocyanate of Formula R⁷N=C=O in an inert solvent, such as THF, and at a temperature at about room temperature.

As another example of the interconversion process, compounds of Formula (I) in which Cy¹ is substituted by

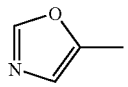

may be prepared by reaction of the corresponding compounds of Formula (I), in which Cy¹ is substituted by H—C(=O)— with tosylmethylisocyanide in the presence of K₂CO₃, in an inert solvent, such as MeOH and at a temperature at about reflux temperature.

As another example of the interconversion process, compounds of Formula (I) in which Cy¹ is substituted by

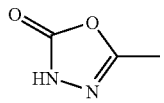

may be prepared by reaction of the corresponding compounds of Formula (I), in which Cy¹ is substituted by CH₃O—C(=O)—CH₂— with hydrazine, in an inert solvent, such as a mixture of MeOH and DCM, and at a temperature at about room temperature followed by treatment of the resulting hydrazide with 1,1-carbonyldiimidazole in the presence of triethylamine, in an inert solvent, such as N-methylpyrrolidine, and at room temperature.

As another example of the interconversion process, compounds of Formula (I) containing a

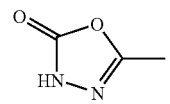

group may be prepared by reaction of the corresponding compounds of Formula (I) containing a NC—CH₂— group by (i) reaction with hydroxylamine hydrochloride in the presence of sodium methoxide, in an inert solvent, such as a mixture of MeOH and DCM, and at room temperature; (ii) reaction of the resulting N-hydroxy-acetamidine with 1,1-carbonyldiimidazole in the presence of 1,8-diazabicyclo[5,4,0]undec-7-ene, in an inert solvent, such as N-methylpyrrolidine, and at room temperature.

As another example of the interconversion process, compounds of Formula (I), wherein Cy¹ is substituted by a

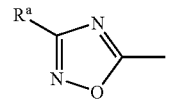

group, wherein Rᵃ is alkyl, may be prepared by reaction of the corresponding compounds of Formula (I), wherein Cy¹ is substituted by carboxy group, with compounds of Formula Rᵃ—C(=NH)—NHOH in the presence of TBTU followed by irradiation in a microwave oven at a temperature at about 140° C.

As another example of the interconversion process, compounds of Formula (I), wherein Cy¹ is substituted by a

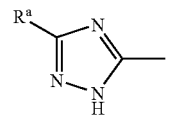

group, wherein Rᵃ is alkyl, may be prepared by reaction of the corresponding compounds of Formula (I), wherein Cy¹ is substituted by H₂N—C(=O)—, with compounds of Formula Rᵃ—C(OCH₃)₂—N(CH₃)₂ at a temperature at about 110° C. followed by reaction with hydrazine.

As another example of the interconversion process, compounds of Formula (I), wherein Cy¹ is substituted by a

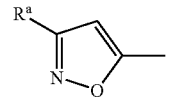

group, wherein Rᵃ is alkyl, may be prepared by reaction of the corresponding compounds of Formula (I), wherein Cy¹ is substituted by CH₃—C(=O)—, with compounds of Formula $R^a$—C(OCH$_3$)$_2$—N(CH$_3$)$_2$ at a temperature at about 90° C. followed by reaction with hydroxylamine.

As another example of the interconversion process, compounds of Formula (I) containing sulfoxide linkages may be prepared by the oxidation of corresponding compounds containing —S— linkages. For example, the oxidation may conveniently be carried out by means of reaction with a peroxyacid, e.g. 3-chloroperbenzoic acid, preferably in an inert solvent, e.g. DCM, preferably at or near room temperature, or alternatively by means of potassium hydrogen peroxomonosulfate in a medium such as aqueous methanol, buffered to about pH5, at temperatures between about 0° C. and room temperature. This latter method is preferred for compounds containing an acid-labile group.

As another example of the interconversion process, compounds of Formula (I) containing sulfone linkages may be prepared by the oxidation of corresponding compounds containing —S— or sulfoxide linkages. For example, the oxidation may conveniently be carried out by means of reaction with a peroxyacid, e.g. 3-chloroperbenzoic acid, preferably in an inert solvent, e.g. DCM, preferably at or near room temperature.

As another example of the interconversion process, compounds of Formula (I) in which there is a N-oxide group can be prepared by oxidation of the corresponding compounds containing a suitable tertiary nitrogen atom. For example, the oxidation may conveniently be carried out by means of reaction with a peroxyacid, e.g. 3-chloroperbenzoic acid, preferably in an inert solvent, e.g. DCM, preferably at or near room temperature.

As another example of the interconversion process, compounds of Formula (I) containing a cyano group may be prepared by reaction of the corresponding compounds of Formula (I) containing a —C(=O)—NH$_2$ group with phosphorus pentachloride in the presence of triethylamine. The reaction may conveniently be carried out in an inert solvent, such as THF, and at a temperature at about reflux temperature.

As another example of the interconversion process, compounds of Formula (I) containing a tetrazolyl group may be prepared by reaction of the corresponding compounds of Formula (I) containing a cyano group with azidotributyltin. The reaction may conveniently be carried out in an inert solvent, such as toluene, and at a temperature at about reflux temperature. Alternatively the reaction may be carried out using trimethylsilylazide and dibutyltinoxide in an inert solvent, such as toluene, and at a temperature at about 95° C.

As another example of the interconversion process, compounds of Formula (I), in which Cy$^1$ is substituted by hydroxy, may be prepared by reaction of the corresponding compounds of Formula (I), in which Cy$^1$ is substituted by methoxy, with a Lewis acid, such as boron tribromide, in an inert solvent, such as DCM and at a temperature from about 0° C. to about room temperature.

As another example of the interconversion process, compounds of Formula (I) in which Cy$^1$ is substituted by —OR$^a$ (in which R$^a$ is alkyl, which is optionally substituted by cycloalkyl, heterocyclyl, cycloalkenyl, heterocyclenyl, aryl, heteroaryl, or multicyclic alkaryl) may be prepared by alkylation the corresponding compounds of Formula (I) in which Cy$^1$ is substituted by hydroxy, with compounds of Formula (VII):

$$R^a—X^3 \quad (VII)$$

wherein R$^a$ is as just hereinbefore defined and X$^3$ is a halogen, preferably bromo atom, or a tosyl group, using standard alkylation conditions. The alkylation may for example be carried out in the presence of a base, such as an alkali metal carbonate (e.g. K$_2$CO$_3$ or Cs$_2$CO$_3$), an alkali metal alkoxide (e.g. potassium tertiary butoxide) or alkali metal hydride (e.g. sodium hydride), in dimethylformamide, or dimethyl sulfoxide, at a temperature from about 0° C. to about 100° C.

As another example of the interconversion process, compounds of Formula (I) in which Cy$^1$ is

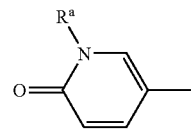

(in which R$^a$ is aryl, multicyclic alkaryl, cycloalkyl, heteroaryl, heterocyclyl; or alkyl, which is optionally substituted by cycloalkyl, cycloalkenyl, heterocyclyl, heterocyclenyl, aryl, heteroaryl or multicyclic alkaryl) may be prepared by alkylation the corresponding compounds of Formula (I) in which Cy$^1$ is

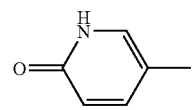

with compounds of Formula (VII), wherein R$^a$ is as just hereinbefore defined and X$^3$ is a halogen, preferably bromo atom, or a tosyl group, using standard alkylation conditions. The alkylation may for example be carried out in the presence of a base, such as an alkali metal carbonate (e.g. K$_2$CO$_3$ or Cs$_2$CO$_3$), an alkali metal alkoxide (e.g. potassium tertiary butoxide) or alkali metal hydride (e.g. sodium hydride), in dimethylformamide, or dimethyl sulfoxide, at a temperature from about 0° C. to about 100° C.

As another example of the interconversion process, compounds of Formula (I) in which Cy$^1$ is substituted by Y$^1$Y$^2$N—CH$_2$— may be prepared by reductive amination of the corresponding compounds of Formula (I), in which Cy$^1$ is substituted by H—C(=O)—, with an amine of Formula Y$^1$Y$^2$NH in the presence of sodium triacetoxyborohydride and acetic acid, in an inert solvent, such as a mixture of MeOH and 1,2-dichloroethane and at a temperature at about room temperature. The reductive amination may also be carried out in the presence of sodium cyanoborohydride or lithium cyanoborohydride, in methanol, and at a temperature at about room temperature.

As another example of the interconversion process, compounds of Formula (I) in which Cy$^1$ is substituted by H$_2$N—CH$_2$— may be prepared by reduction of the corresponding compounds of Formula (I), in which Cy$^1$ is substituted by H—C(=N—OH)—. The reduction may be carried out using zinc in the presence of acetic acid at room temperature.

As another example of the interconversion process, compounds of Formula (I) in which R$^1$ is alkoxy may be prepared by reaction of the corresponding compounds of Formula (I) in which R$^1$ is methanesulfonyl with the appropriate alcohol in the presence of sodium hydride. The reaction may conveniently be carried out in an inert solvent, such as dimethylformamide, and at a temperature form about 0° C. to about 20° C.

As another example of the interconversion process, compounds of Formula (I) in which R$^1$ is alkyl may be prepared by reaction of the corresponding compounds of Formula (I) in which R$^1$ is methanesulfonyl with the appropriate alkyl magnesium bromide. The reaction may conveniently be carried out in an inert solvent, such as THF, and at a temperature form about −50° C. to about 20° C.

As another example of the interconversion process, compounds of Formula (I) in which $R^1$ is dialkylamino may be prepared by reaction of the corresponding compounds of Formula (I) in which $R^1$ is methanesulfonyl with the appropriate dialkylamino. The reaction may conveniently be carried out in a microwave oven at a temperature at about 150° C., in inert solvent, such as methanol.

It will be appreciated that compounds of the present invention may contain asymmetric centers. These asymmetric centers may independently be in either the R or S configuration. It will be apparent to those skilled in the art that certain compounds of the invention may also exhibit geometrical isomerism. It is to be understood that the present invention includes individual geometrical isomers and stereoisomers and mixtures thereof, including racemic mixtures, of compounds of Formula (I) hereinabove. Such isomers can be separated from their mixtures, by the application or adaptation of known methods, for example chromatographic techniques and recrystallization techniques, or they are separately prepared from the appropriate isomers of their intermediates.

Intermediates of Formula (II), wherein $Cy^1$ is as hereinbefore defined, $R^1$ is alkylthio and $X^1$ is a chlorine atom, may be prepared by reaction of a dichloropyrimidine of Formula (IX), wherein R is $(C_1-C_4)$-alkyl, with a boronic acid of Formula (VI), wherein $Cy^1$ is as hereinbefore defined, in the presence of a complex metal catalyst such as tetrakis(triphenylphosphine)palladium (0) and $Cs_2CO_3$, using conditions described hereinbefore.

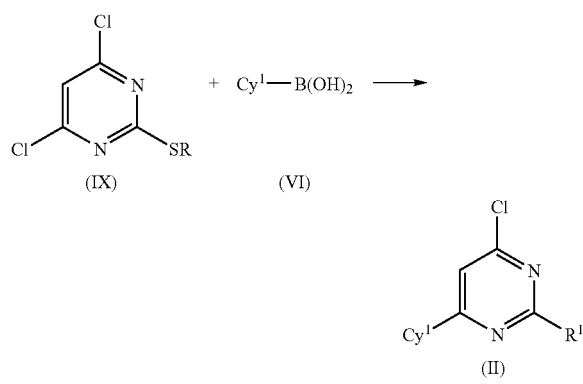

Intermediates of Formula (II), wherein $Cy^1$ is as hereinbefore defined, $R^1$ is $(C_1-C_4)$-alkoxy and $X^1$ is a chlorine atom, may be prepared from the corresponding intermediates of Formula (II) in which $R^1$ is $(C_1-C_4)$-alkylthio by (i) treatment of with meta-chloroperoxybenzoic acid in an inert solvent, such as DCM, and at a temperature at about room temperature, and (ii) reaction with an alkali metal alkoxide, such as a sodium alkoxide, in an inert solvent, such as ethylene glycol dimethyl ether.

Intermediates of Formula (V), wherein $L^1$ and $Cy^2$ are as hereinbefore defined, $R^1$ is $(C_1-C_4)$-alkoxy and $X^2$ is a chlorine atom, may be similarly prepared from the corresponding intermediates of Formula (V) in which $R^1$ is $(C_1-C_4)$-alkylthio.

Intermediates of Formula (V), wherein $L^1$ and $Cy^2$ are as hereinbefore defined, and $R^1$ is $(C_1-C_4)$-alkylthio or $(C_1-C_4)$-alkoxy, may be prepared by reaction of a dichloropyrimidine of Formula (X), wherein R is alkyl, with an amine of Formula (IV), wherein $L^1$ and $Cy^2$ are as hereinbefore defined, in the presence of a suitable base, such as sodium bicarbonate, in an inert solvent, such as ethanol, and at a temperature up to reflux temperature.

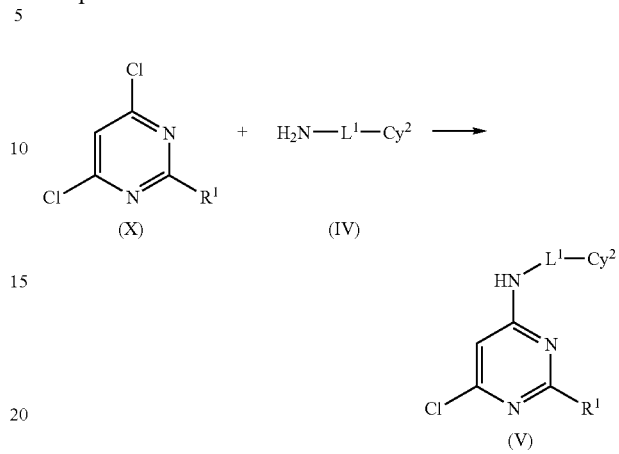

A subgenus of the intermediates of Formula (IV) in which $Cy^2$ is as hereinbefore defined and $L^1$ is ethylene, i.e. the intermediate of Formula (IV') may be prepared by (i) reaction of aryl- or heteroaryl aldehydes of Formula (XI), in which $Cy^2$ is as defined hereinbefore, with ammonium acetate in glacial acetic acid at a temperature at about 110° C. and (ii) reduction of the resulting 2-nitro-vinyl derivatives of Formula (XII) with lithium aluminum hydride, in an inert solvent, such as ether, and at a temperature at about 40° C.

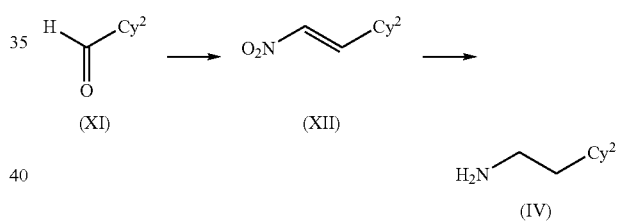

The intermediates of Formula (IV) in which $Cy^2$ is as hereinbefore defined and $L^1$ is ethylene may also be prepared by reduction of acetonitriles of Formula (XIII) using Raney nickel and ammonia. The reduction is conveniently carried out in water, at a temperature at about 50° C. in a Parr shaker at 50 PSI.

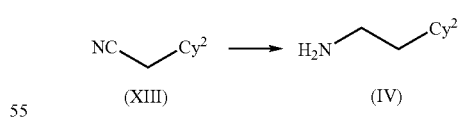

According to a further feature of the invention, acid addition salts of the compounds of this invention may be prepared by reaction of the free base with the appropriate acid, by the application or adaptation of known methods. For example, the acid addition salts of the compounds of this invention may be prepared either by dissolving the free base in water or aqueous alcohol solution or other suitable solvents containing the appropriate acid and isolating the salt by evaporating the solution, or by reacting the free base and acid in an organic solvent, in which case the salt separates directly or can be obtained by concentration of the solution.

For example, a choline salt of a compound of Formula (I), particularly of species described herein, can be prepared by the following method:

To a solution of a compound of Formula (I) (0.283 mmol) in MeOH (10 mL) is added 50% (w/w) aqueous choline solution (67 μL) and the mixture is stirred at room temperature for a few minutes. The mixture is concentrated in vacuo. The residue is dissolved in acetonitrile (2 mL). If necessary, the solution is filtered to remove any insoluble solid. The filtrate is concentrated in vacuo until crystals start to appear. EtOAc (~2 mL) is added and the mixture is warmed to 50-60° C. and then cooled down to room temperature. The crystals are filtered, washed with EtOAc and dried under vacuum at room temperature to afford the desired choline salt of the compound.

For example, a phosphoric acid salt of a compound of Formula (I), particularly of species described herein, can be prepared by the following method:

Phosphoric acid (3.21 mL, 1.49 N aqueous solution) is added to a solution of a compound of Formula (I) (4.56 mmol) in THF (45 mL). The mixture may become cloudy and is stirred for 10 minutes. If necessary, water is added drop-wise in intervals until the mixture is turned into clear solution. The mixture is continued for 1.5 hours at room temperature. The mixture is concentrated in vacuo, and the residue is recrystallized from acetone to afford the desired phosphoric acid salt of the compound.

For example, a sulfuric salt of a compound of Formula (I), particularly of species described herein, can be prepared by the following method:

A compound of Formula (I) (0.122 mmol) is dissolved in acetone (2 mL) with heat. Standard 1 N $H_2SO_4$ (1252 μL) is added to the solution. The mixture is heated with stirring and water is added dropwise to just give a clear solution while hot. The solution is allowed to cool to room temperature and the solvent is evaporated under a stream of nitrogen gas. The residue is dried in vacuo overnight at room temperature to afford the desired sulfuric acid salt of the compound.

The acid addition salts of the compounds of this invention can be regenerated from the salts by the application or adaptation of known methods. For example, parent compounds of the invention can be regenerated from their acid addition salts by treatment with an alkali, e.g. aqueous sodium bicarbonate solution or aqueous ammonia solution.

Compounds of this invention can be regenerated from their base addition salts by the application or adaptation of known methods. For example, parent compounds of the invention can be regenerated from their base addition salts by treatment with an acid, e.g. hydrochloric acid.

Compounds of the present invention may be conveniently prepared, or formed during the process of the invention, as solvates (e.g. hydrates). Hydrates of compounds of the present invention may be conveniently prepared by recrystallization from an aqueous/organic solvent mixture, using organic solvents such as dioxane, THF or methanol.

According to a further feature of the invention, base addition salts of the compounds of this invention may be prepared by reaction of the free acid with the appropriate base, by the application or adaptation of known methods. For example, the base addition salts of the compounds of this invention may be prepared either by dissolving the free acid in water or aqueous alcohol solution or other suitable solvents containing the appropriate base and isolating the salt by evaporating the solution, or by reacting the free acid and base in an organic solvent, in which case the salt separates directly or can be obtained by concentration of the solution.

The starting materials and intermediates may be prepared by the application or adaptation of known methods, for example methods as described in the Reference Examples or their obvious chemical equivalents.

The present invention is further exemplified, but not limited by, the following illustrative Examples and Intermediates.

High Pressure Liquid Chromatography—Mass Spectrometry (LCMS) experiments to determine retention times ($R_T$) and associated mass ions are performed using one of the following methods.

Method A: Experiments are performed on a Micromass Platform LC spectrometer with positive and negative ion electrospray and ELS/Diode array detection using a Phenomenex Luna C18(2) 30×4.6 mm column and a 2 ml/minute flow rate. The solvent system is 95% solvent A and 5% solvent B for the first 0.5 minutes followed by a gradient up to 5% solvent A and 95% solvent B over the next 4 minutes. The final solvent system is held constant for a further 0.5 minutes.

400 MHz $^1$H nuclear magnetic resonance spectra (NMR) are recorded at ambient temperature using a Varian Unity Inova (400 MHz) spectrometer with a triple resonance 5 mm probe. In the NMR chemical shifts (δ) are expressed ppm relative to tetramethylsilane. Chemical shifts values are indicated in parts per million (ppm) with reference to tetramethylsilane (TMS) as the internal standard.

Method A is applied to Examples 8(a)-(g), 9(a)-(b), 10(a)-(m), 11(a), 12, 13(a), 14(a)-(c), 26(d)-(f), 35(l)-(m), 61 and 62 to provide corresponding analytical data.

Method B: Mass Spectra (MS) are recorded using a Micromass LCT mass spectrometer. The method is positive electrospray ionization, scanning mass m/z from 100 to 1000. Liquid chromatography is performed on a Hewlett Packard 1100 Series Binary Pump & Degasser; stationary phase: phenomenex Synergi 2μ Hydro-RP 20×4.0 mm column, mobile phase: A=0.1% formic acid (FA) in water, B=0.1% FA in acetonitrile. Injection volume of 5 μL by CTC Analytical PAL System. Flow is 1 ml/minute. Gradient is 10% B to 90% B in 3 minutes and 90% B to 100% B in 2 minutes. Auxiliary detectors are: Hewlett Packard 1100 Series UV detector, wavelength=220 nm and Sedere SEDEX 75 Evaporative Light Scattering (ELS) detector temperature=46° C., Nitrogen pressure=4 bar.

300 MHz $^1$H nuclear magnetic resonance spectra (NMR) are recorded at ambient temperature using a Varian Mercury (300 MHz) spectrometer with an ASW 5 mm probe. In the NMR chemical shifts (δ) are expressed ppm relative to tetramethylsilane. Chemical shifts values are indicated in parts per million (ppm) with reference to tetramethylsilane (TMS) as the internal standard.

Method B is applied to the rest of Examples to provide corresponding analytical data.

As used in the examples and preparations that follow, the terms used therein shall have the meanings indicated: "kg" refers to kilograms, "g" refers to grams, "mg" refers to milligrams, "μg" refers to micrograms, "mol" refers to moles, "mmol" refers to millimoles, "M" refers to molar, "mM" refers to millimolar, "μM" refers to micromolar, "nM" refers to nanomolar, "L" refers to liters, "mL" or "ml" refers to milliliters, "μL" refers to microliters, "° C." refers to degrees Celsius, "mp" or "m.p." refers to melting point, "bp" or "b.p." refers to boiling point, "mm of Hg" refers to pressure in millimeters of mercury, "cm" refers to centimeters, "nm" refers to nanometers, "abs." refers to absolute, "conc." refers to concentrated, "c" refers to concentration in g/mL, "rt" refers to room temperature, "TLC" refers to thin layer chromatography, "HPLC" refers to high performance liquid chromatography, "i.p." refers to intraperitoneally, "i.v." refers to intravenously, "s"=singlet, "d"=doublet; "t"=triplet; "q"=quartet; "m"=multiplet, "dd"=doublet of doublets; "br"=broad, "LC"=liquid chromatograph, "MS"=mass spectrograph, "ESI/MS"=electrospray ionization/mass spectrograph, "$R_T$"=retention time, "M"=molecular ion, "PSI"=pounds per square inch, "DMSO"=Dimethyl sulfoxide, "DMF"=Dimethylformamide, "CDI"=1,1'-carbonyldiimidazole, "DCM"=dichloromethane, "HCl"=hydrochloric acid, "TBTU=O-(benzotriazol-1-yl)-N,N,N',N'-tetramethyluronium tetrafluoroborate", "PS-TBD"=1,5,7-triazabicyclo[4.4.0]dec-5-ene polystyrene, "PS-BEMP"=2-tert-butyl-imino-2-diethylamino-1,3-dimethyl-perhydro-1,3,2-diazaphosphorine polystyrene; "MP-carbonate"=Macroporous triethylammonium methylpolystyrene carbonate, "SPA"=Scintillation Proximity Assay, "ATTC"=American Type Culture Collection, "FBS"=Foetal Bovine Serum, "MEM"=Minimal Essential Medium, "CPM"=Counts Per Minute, "EtOAc"=ethyl acetate, "THF"=tetrahydrofuran, "MeOH"=methanol, "EtOH"=ethanol, "PBS"=Phosphate Buffered Saline, "TMD"=transmembrane domain, "IBMX"=3-isobutyl-1-methylxanthine, "cAMP"=cyclic adenosine monophosphate, "pddf"=1,1'-Bis(diphenylphosphino)ferrocene-palladium (II)dichloride DCM complex. "bis-(pinacolato)-diboron"=4,4,5,5,4',4',5',5'-Octamethyl-[2,2']bi[[1,3,2]dioxaborolanyl].

EXAMPLES

Example 1

3-{6-[2-(3-fluoro-4-methoxy-phenyl)-ethylamino]-2-methoxy-pyrimidin-4-yl}-benzonitrile Step 1. A solution of 3-fluoro-4-methoxybenzaldehyde [5.05 g, Intermediate (1)], nitromethane (5.3 mL) and ammonium acetate (6.3 g) in glacial acetic acid (60 mL) is heated at 110° C. for 16 hours, allowed to cool and poured into water (300 mL). The aqueous solution is extracted twice with EtOAc (200 mL). The combined extracts are washed with sodium bicarbonate solution (10%), with water, dried over sodium sulfate and evaporated affording 2-fluoro-1-methoxy-4-(2-nitro-vinyl)benzene [4.2 g, Intermediate (2)]. MS: 198 (M+H); $^1$H NMR (CDCl$_3$): δ 7.9 (1H, d, J=10 Hz); 7.5 (1H, d, 10 Hz); 7.3 (2H, m); 6.95-7.15 (1H, m); 4 (3H, s).

Step 2. A solution of 2-fluoro-1-methoxy-4-(2-nitro-vinyl)benzene (1.5 g, Intermediate (2)] in THF (50 mL) is treated dropwise with a solution of lithium aluminum hydride in ether (23 mL, 1M). The mixture is heated at 40° C. for 3 hours, cooled to room temperature, diluted with ether and quenched with Na$_2$SO$_4$.10H$_2$O (104 g). After standing at room temperature overnight the reaction mixture is filtered and the filtrate is evaporated. The residue is subjected to chromatography on silica gel eluting with EtOAc to give 2-(3-fluoro-4-methoxy-phenyl)-ethylamine [0.81 g, Intermediate (3)] as an oil. MS: 170 (M+H); $^1$H NMR (CDCl$_3$): 6.9-7 (3H, m); 3.85 (3H, s); 2.95 (2H, t); 2.7 (2H, t).

Step 3. A solution of 4,6-dichloro-2-methoxypyrimidine [0.7 g, Intermediate (4)], 2-(3-fluoro-4-methoxy-phenyl)-ethylamine [0.66 g, Intermediate (3)] and sodium bicarbonate (0.88 g) in EtOH (25 mL) is heated at 80° C. for three hours and poured into water (400 mL). The resulting solid is filtered and air dried affording (6-chloro-2-methoxy-pyrimidin-4-yl)-[2-(3-fluoro-4-methoxyphenyl)-ethyl]amine [1.1 g, Intermediate (5)]. MS: 312 (M+H); $^1$H NMR (CDCl$_3$): δ 6.9-7 (3H, m); 6.05 (1H, s); 3.95 (3H, s); 3.85 (3H, s); 3.6-3.7 (2H, m); 2.95 (2H, t).

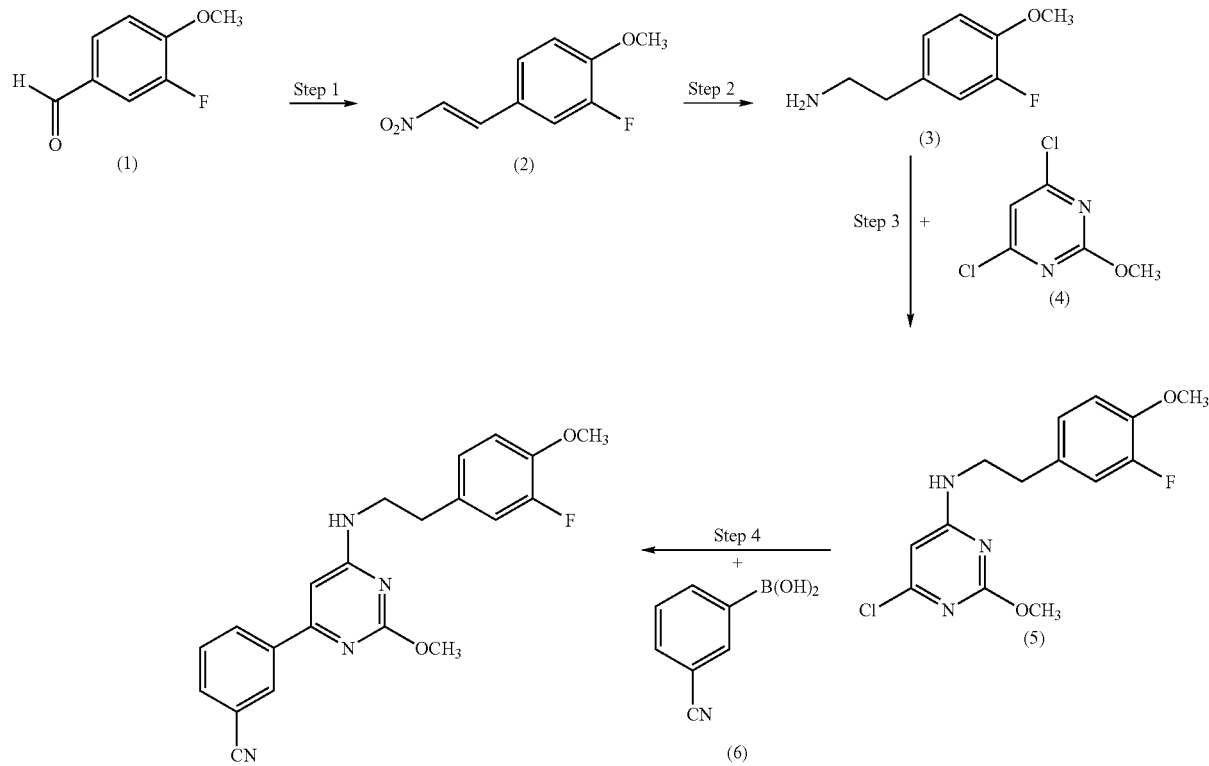

Step 4. (6-chloro-2-methoxy-pyrimidin-4-yl)-[2-(3-fluoro-4-methoxyphenyl)-ethyl]amine [1.6 g, Intermediate (5)], 3-cyano-phenylboronic acid [1.5 g, Intermediate (6)], Cs₂CO₃ (8.3 g) and tetrakis(triphenylphosphine)palladium (45 mg) in a solution of water (8 mL) and ethylene glycol dimethyl ether (32 mL) is heated at 90° C. for 16 hours. The solution is poured into water and extracted twice with EtOAc (200 mL). The combined extracts are dried over sodium sulfate, filtered, and evaporated. The residue is subjected to chromatography on silica gel eluting with EtOAc to give 3-{6-[2-(3-fluoro-4-methoxy-phenyl)-ethylamino]-2-methoxy-pyrimidin-4-yl}-benzonitrile [1.1 g, Example 1]. MS: 379 (M+H); ¹H NMR (CDCl₃): δ 8.3 (1H, s); 8.2 (1H, d (J=5.1 Hz)); 7.9 (1H, d (J=5.1 Hz)); 7.6 (1H, t); 7-7.2 (4H, m); 6.4 (1H, s); 5 (1H, m); 3.95 (3H, s); 3.8 (3H, s); 3.7 (2H, t); 3 (2H, t).

Example 2

[6-(3-Amino-phenyl)-2-methoxy-pyrimidin-4-yl]-[2-(4-methoxy-phenyl)-ethyl]amine

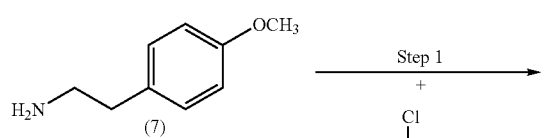

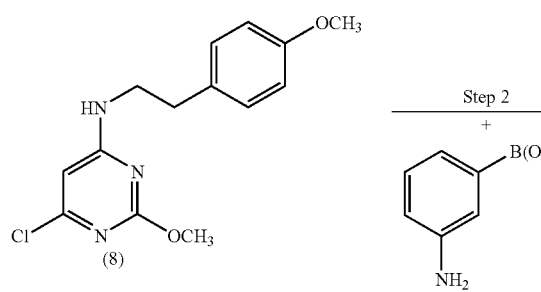

Step 1. Following procedures similar to those of Example 1, step 3, but using 4,6-dichloro-2-methoxypyrimidine [3.1 g, Intermediate (4)], 2-(4-methoxy-phenyl)-ethylamine [0.66 g, Intermediate (7)] and sodium bicarbonate (0.88 g) there is prepared (6-chloro-2-methoxy-pyrimidin-4-yl)-[2-(4-methoxy)-phenyl]-amine [5 g, Intermediate (8)]. MS: 294 (M+H); ¹H NMR (CDCl₃): δ 7.1 (2H, d, J=7); 6.8 (2H, d, J=7); 6 (1H, s); 3.95 (3H, s); 3.8 (3H, s); 3.5-3.6 (2H, m); 2.8 (2H, t).

Step 2. Following procedures similar to those of Example 1, step 4, but using (6-chloro-2-methoxy-pyrimidin-4-yl)-[2-(4-methoxyphenyl)-ethyl]amine [0.26 g, Intermediate (8)], 3-amino-phenylboronic acid [0.27 g, Intermediate (9)], Cs₂CO₃ (1.43 g), and tetrakis(triphenylphosphine)palladium (0) (6 mg) and carrying out the reaction at 90° C. for 16 hours there is prepared [6-(3-amino-phenyl)-2-methoxy-pyrimidin-4-yl]-[2-(4-methoxy-phenyl)-ethyl]amine [0.22 g, Example 2]. MS: 351 (M+H), ¹H NMR (CDCl₃): δ 7.2 (1H, s); 7-7.1 (4H, m); 6.8 (2H, d, J=7.0); 6 (1H, s); 3.95 (3H, s); 3.75 (3H, s); 3.5-3.6 (2H, m); 2.8 (2H, t).

Example 3

3-{2-Methoxy-6-[2-(4-methoxy-phenyl)-ethylamino]-pyrimidin-4-yl}-benzenesulfonamide

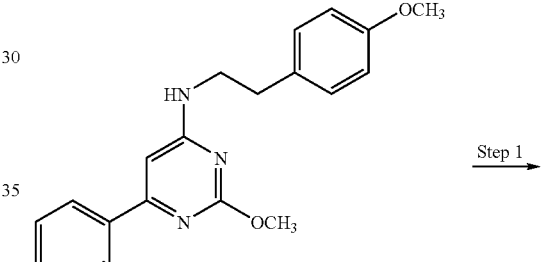

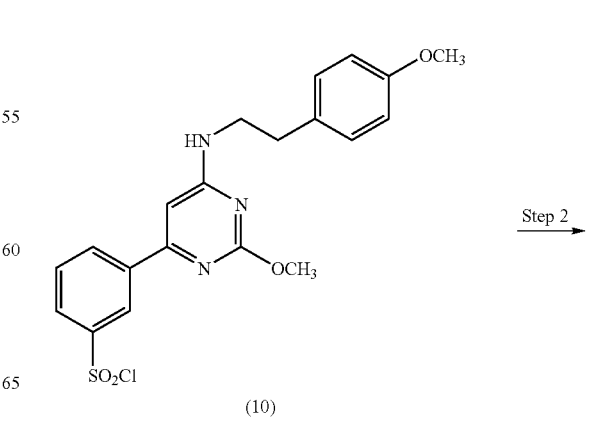

Example 4

(a) 3-{2-Methoxy-6-[2-(4-methoxy-phenyl)-ethylamino]-pyrimidin-4-yl}-N-methyl-benzenesulfonamide

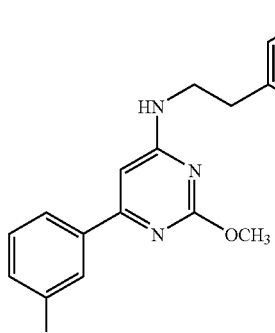

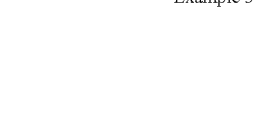

Example 3

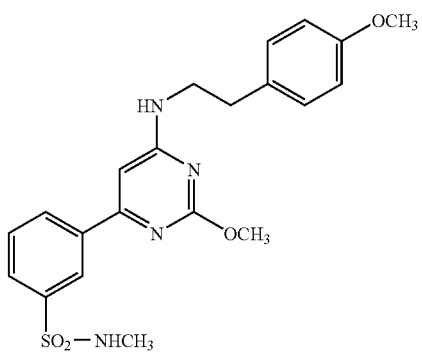

Step 1. [6-(3-Amino-phenyl)-2-methoxy-pyrimidin-4-yl]-[2-(4-methoxy-phenyl)-ethyl]amine [1.46 g, Example 2] in dimethylformamide (4 mL) is added to concentrated hydrochloric acid and crushed ice (8 mL), The mixture is cooled to 0° C., treated with dropwise sodium nitrite (0.32 g) in water (3 mL). After stirring at 0° C. for 15 minutes this mixture is treated with a solution of copper chloride (0.36 g) in a saturated solution of sulfur dioxide in acetic acid (15 mL) previously cooled to 0° C. The reaction mixture is allowed to reach room temperature over 30 minutes and poured into water. The resulting precipitate is filtered and air dried affording 3-{2-methoxy-6-[2-(4-methoxy-phenyl)-ethylamino]-pyrimidin-4-yl}-benzenesulfonylchloride [0.4 g, Intermediate (10)]. $^1$H NMR [(CD$_3$)$_2$SO]: δ 8 (1H, s); 7.7-7.8 (1H, m); 7.5 (1H, m); 7.2 (1H, s); 7.1 (2H, d, J=7.0); 6.8 (2H, d, J=7.0); 6.6 (1H, s); 4 (3H, s); 3.85 (3H, s); 3.7-3.8 (2H, m); 2.8 (2H, t).

Step 2. A mixture of 3-{2-methoxy-6-[2-(4-methoxy-phenyl)-ethylamino]-pyrimidin-4-yl}-benzenesulfonylchloride [0.2 g, Intermediate (10)] and triethylamine (0.3 mL) in dimethylformamide (5 mL) is cooled to 0° C. and treated with a solution of ammonia in 1,4-dioxane (5 mL, 0.5M). The solution is allowed to reach room temperature overnight and poured into water (100 mL). The mixture is extracted twice with EtOAc (100 mL). The combined extracts are washed with water, dried over sodium sulfate, filtered, and evaporated. The residue is subjected to chromatography on silica gel eluting with EtOAc to give 3-{2-methoxy-6-[2-(4-methoxy-phenyl)-ethylamino]-pyrimidin-4-yl}-benzenesulfonamide [140 mg, Example 3]. MS: 415 (M+H), $^1$H NMR [(CD$_3$)$_2$SO]: δ 8.4 (1H, s); 8.2 (1H, m); 7.9 (1H, d, J=3 Hz); 7.7 (1H, m); 7.4 (2H, m); 7.1 (2H, d, J=7 Hz); 6.8 (2H, d, J=7 Hz); 6.6 (1H, s); 3.9 (3H, s); 3.7 (3H, s); 3.5-3.6 (2H, m); 2.8 (2H, t). IC$_{50}$=2.9 nM A mixture of 3-{2-methoxy-6-[2-(4-methoxy-phenyl)-ethylamino]-pyrimidin-4-yl}-benzenesulfonylchloride [0.05 g, Intermediate (10)] and triethylamine (0.064 mL) in dimethylformamide (5 mL) is cooled to 0° C. and the treated with a solution of methylamine in THF (5 mL, 2M). The mixture is allowed to reach room temperature overnight, poured into water (100 mL). This mixture is extracted twice with EtOAc (100 mL). The combined extracts are washed with water, dried over sodium sulfate, filtered and evaporated. The residue is subjected to chromatography on silica gel eluting with EtOAc to give 3-{2-methoxy-6-[2-(4-methoxy-phenyl)-ethylamino]-pyrimidin-4-yl}-N-methyl-benzenesulfonamide [21.5 mg, Example 4(a)]. MS: 429 (M+H), $^1$H NMR [(CD$_3$)$_2$SO]: δ 8.4 (1H, s); 8.2 (1H, m); 7.85 (1H, d, J=3 Hz); 7.75-7.8 (1H, m); 7.5-7.6 (2H, m); 7.2 (2H, d, J=7 Hz); 6.95 (2H, d, J=7 Hz); 6.6 (1H, s); 3.9 (3H, s); 3.7 (3H, s); 3.5-3.6 (2H, m); 2.8 (2H, t); 2.45 (3H, d, J=2 Hz).

(b) N-Ethyl-3-{2-methoxy-6-[2-(4-methoxy-phenyl)-ethylamino]-pyrimidin-4-yl}-benzenesulfonamide

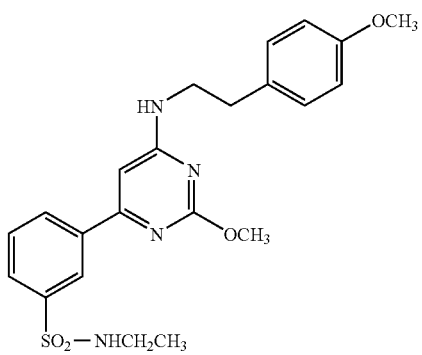

A mixture of 3-{2-methoxy-6-[2-(4-methoxy-phenyl)-ethylamino]-pyrimidin-4-yl}-benzenesulfonylchloride [0.065 g, Intermediate (10)] and triethylamine (0.25 mL) in dimethylformamide (3 mL) is cooled to 0° C. and the treated with a solution of ethylamine in MeOH (3 mL, 2 M). The mixture is allowed to reach room temperature overnight and poured into water (100 mL). This mixture is extracted twice with EtOAc (100 mL). The combined extracts are washed with water, dried over sodium sulfate, filtered and evaporated. The residue is subjected to chromatography on silica gel eluting with EtOAc to give N-ethyl-3-{2-methoxy-6-[2-(4-methoxy-phenyl)-ethylamino]-pyrimidin-4-yl}-benzenesulfonamide [20 mg, Example 4(b)]. MS: 443 (M+H), $^1$H NMR [(CD$_3$)$_2$SO]: δ 8.4 (1H, s); 8.2 (1H, m); 7.85 (1H, d, J=3 Hz); 7.75-7.8 (1H, m); 7.5-7.6 (2H, m); 7.2 (2H, d, J=7 Hz); 6.95 (2H, d, J=7 Hz); 6.6 (1H, s); 3.9 (3H, s); 3.7 (3H, s); 3.5-3.6 (2H, m); 2.8 (4H, m); 1 (3H, t). IC$_{50}$=6.6 nM (c) N-methoxycarbonyl-3-{2-methoxy-6-[2-(4-methoxy-phenyl)-ethylamino]-pyrimidin-4-yl}-benzenesulfonamide

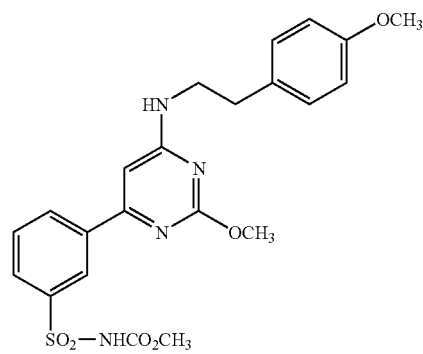

A solution of 3-{2-methoxy-6-[2-(4-methoxy-phenyl)-ethylamino]-pyrimidin-4-yl}-benzenesulfonamide [100 mg, Example 3] in THF (10 mL) is treated with sodium hydride (20 mg). The mixture is stirred at 0° C. for 60 minutes, treated with methyl chloroformate (1 mL) and stirring is continued 0° C. for a further 60 minutes. The reaction mixture is poured into water and extracted twice with EtOAc (50 mL). The combined extracts are washed with water, dried over sodium sulfate, filtered, and evaporated. The residue is subjected to chromatography on silica gel eluting with EtOAc in heptanes (1:1, v/v) to give N-methoxycarbonyl-3-{2-methoxy-6-[2-(4-methoxy-phenyl)-ethylamino]-pryrimidin-4-yl}-benzenesulfonamide [41 mg, Example 4(c)] as a solid. MS: 473 (M+H), $^1$H NMR [(CD$_3$)$_2$SO]: δ 12.2 (1H, s); 8.4 (1H, s); 8.15 (1H, m); 8 (1H, d, J=3 Hz); 7.65-7.8 (1H, m); 7.2 (2H, d, J=7 Hz); 6.9 (2H, d, J=7 Hz); 6.7 (1H, s); 3.9 (3H, s); 3.7 (3H, s); 3.5-3.6 (2H, m); 3.6 (3H, s); 2.8 (2H, t).

Example 5

[6-(3-amino-phenyl)-2-methoxy-pyrimidin-4-yl]-[2-(4-trifluoromethoxy-phenyl)-ethyl]-amine

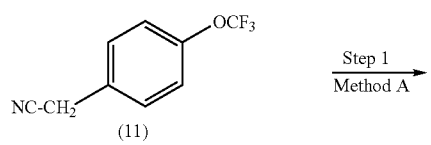

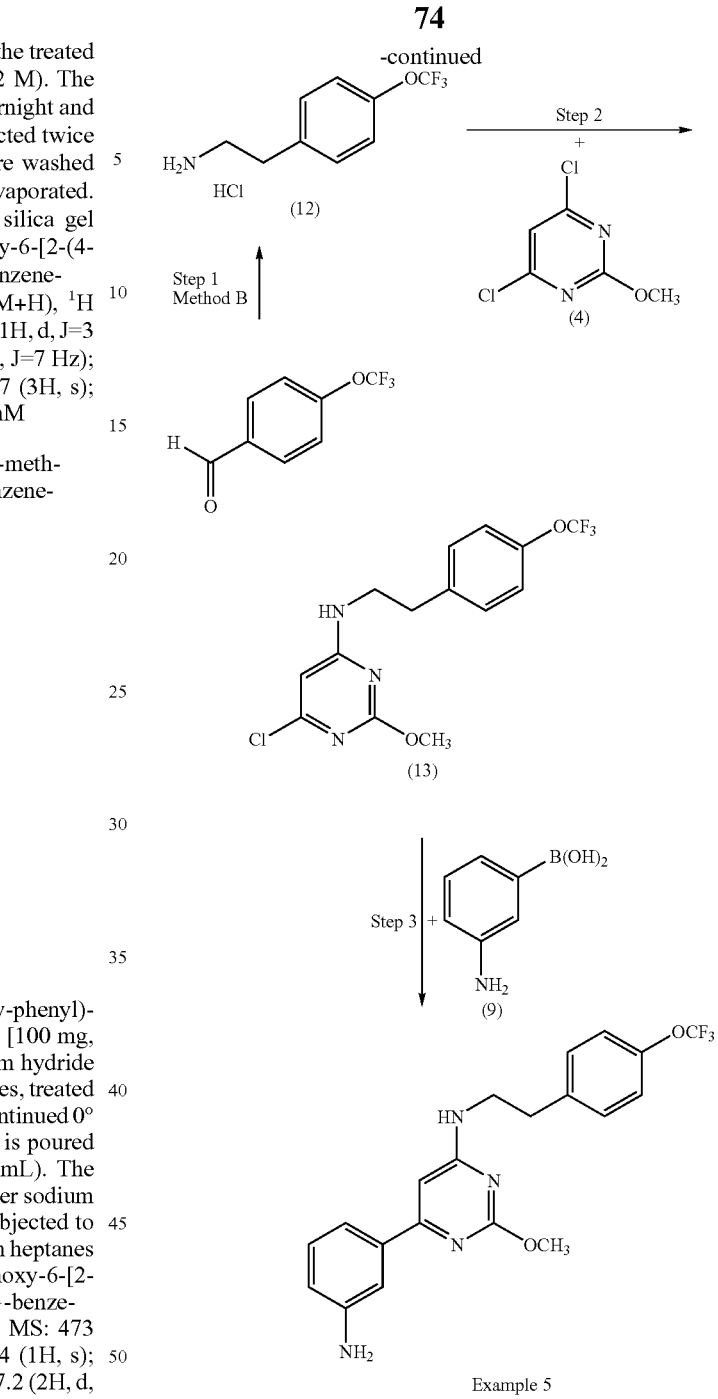

Example 5

Step 1.

Method A. A solution of (4-trifluoromethoxy-phenyl)-acetonitrile [5.05 g, Intermediate (11)] in MeOH (75 mL) is saturated with ammonia gas, and treated with Raney nickel in water (2 mL, 50%). The suspension is placed on Parr shaker at 50 PSI and 50° C. for 3 hours, and filtered through celite. The filtrate is evaporated and the residual oil is portioned between water and ethyl acetate. The organic phase is dried over sodium sulfate, filtered and evaporated. The residue is dissolved in MeOH and the solution treated with concentrated hydrochloric acid (1 mL) is added. The solution is evaporated in vacuo to a solid which is triturated with ether and air dried to give 2-(4-trifluoromethoxy-phenyl)-ethylamine hydrochloride [5.15 g, Intermediate (12)]. MS: 206

(M+H), $^1$H NMR (CDCl$_3$): δ 8.2 (2H, m); 7.4 (2H, d, J=5 Hz); 7.3 (2H, d, J=5 Hz); 3-3.1 (2H, m); 2.9-3 (2H, m).

Method B. A solution of (4-trifluoromethoxy benzaldehyde (1 g, 5.26 mmol) and nitromethane (0.96 g, 15.8 mmol) in acetic acid (10.6 mL) is treated with ammonium acetate (1.01 g, 13.2 mmol) is heated under microwave to 150° C. for 15 minutes. The reaction mixture is diluted with water, and extracted three times with DCM (50 mL). The combined extracts are washed sequentially with 2 N sodium hydroxide, water, and brine, dried over sodium sulfate and concentrated. The residue is subjected to silica gel chromatography to yield 4-trifluoromethoxy-(2-nitro-vinyl)-benzene (1.23 g) as a solid. A portion of 4-trifluoromethoxy-(2-nitro-vinyl)-benzene (0.504 g, 2.16 mmol) is hydrogenated with hydrogen in a balloon, 10% Pd/C (115 mg, 5 mol %) in MeOH (22 mL) containing concentrated hydrochloric acid (0.27 mL) at room temperature for 15 hours. The mixture is filtered and filtrate is concentrated to a solid that is washed with diethyl ether to obtain 2-(4-trifluoromethoxy-phenyl)-ethylamine hydrochloride [0.3 g, 57%, Intermediate (12)] as a solid. LC/MS: MS: 206 (M+H).

Step 2. Following procedures similar to those of Example 1, step 3, but using 4,6-dichloro-2-methoxypyrimidine [0.39 g, Intermediate (4)], 2-(4-trifluoromethoxy-phenyl)-ethylamine hydrochloride [0.38 g, Intermediate (12)] and sodium bicarbonate (0.74 g) there is prepared (6-chloro-2-methoxy-pyrimidin-4-yl)-[2-(4-trifluoromethoxy-phenyl)-ethyl]-amine [0.61 g, Intermediate (13)]. MS: 360 (M+H), $^1$H NMR (CDCl$_3$): δ 7.4 (2H, d, J=7 Hz); 7.3 (2H, d, J=7 Hz); 6.2 (1H, s); 3.8 (3H, s); 3.5-3.6 (2H, m); 2.8 (2H, t).

Step 3. Following procedures similar to those of Example 1, step 4, but using (6-chloro-2-methoxy-pyrimidin-4-yl)-[2-(4-trifluoromethoxyphenyl)-ethyl]amine [3.26 g, Intermediate (13)], 3-amino-phenylboronic acid [2.9 g, Intermediate (9)], Cs$_2$CO$_3$ (12.43 g) and tetrakis(triphenylphosphine) palladium (21 mg) in a solution of water (20 mL) and ethylene glycol dimethyl ether (80 mL) there is prepared [6-(3-amino-phenyl)-2-methoxy-pyrimidin-4-yl]-[2-(4-trifluoromethoxy-phenyl)-ethyl]-amine [3.5 g, Example 5]. MS: 405 (M+H), $^1$H NMR [(CD$_3$)$_2$SO]: δ 9.6 (2H, m); 8.2 (1H, s); 7.8 (1H, m); 7.6-7.7 (3H, m); 7.3-7.4 (3H, m); 7.2 (2H, d, J=3 Hz) 6.8 (1H, s); 4 (3H, s); 3.7-3.7 (2H, m); 2.9 (2H, t). IC$_{50}$=9.6 nM Example 6

(a) N-(3-{2-Methoxy-6-[2-(4-trifluoromethoxy-phenyl)-ethylamino]-pyrimidin-4-yl}-phenyl)-acetamide

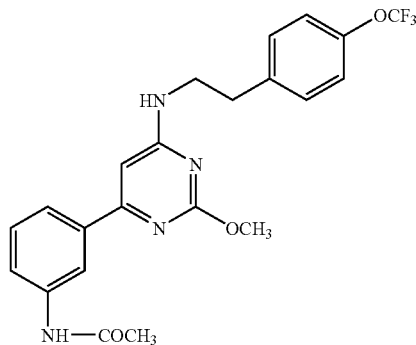

Example 6(a)

A solution of 6-(3-amino-phenyl)-2-methoxy-pyrimidin-4-yl]-[2-(4-trifluoromethoxy-phenyl)-ethyl]-amine [850 mg, Example 5] and triethylamine (0.32 mL) in DCM (10 mL) at 0° C. is treated with acetyl chloride (0.17 mL). After stirring at 0° C. for 1 hour the reaction mixture is poured into water and extracted twice with EtOAc (50 mL). The combined extracts are washed with water, dried over sodium sulfate, filtered, and evaporated. The residue is subjected to chromatography on silica gel eluting with EtOAc in heptanes (1:1, v/v) to give N-(3-{2-methoxy-6-[2-(4-trifluoromethoxy-phenyl)-ethylamino]-pyrimidin-4-yl}-phenyl)-acetamide [550 mg, Example 6(a)] as a solid. MS: 447 (M+H), $^1$H NMR [(CD$_3$)$_2$SO]: δ 10.4 (1H, s); 9.6 (1H, m); 8.2 (1H, s); 7.8 (1H, m); 7.7-7.8 (3H, m); 7.4-7.5 (3H, m); 7.2 (2H, d, J=3 Hz) 6.6 (1H, s); 4.05 (3H, s); 3.7-3.8 (2H, m); 3 (2H, t); 2.05 (3H, s). IC$_{50}$=4.8 nM (b) N-(3-{2-Methoxy-6-[2-(4-methoxy-phenyl)-ethylamino]-pyrimidin-4-yl}-phenyl)-acetamide

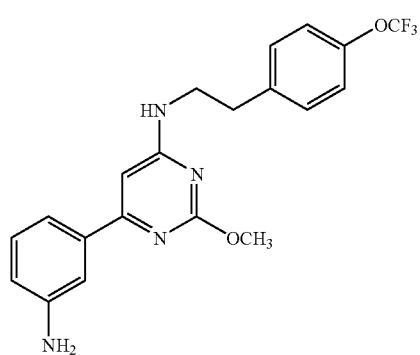

Example 5

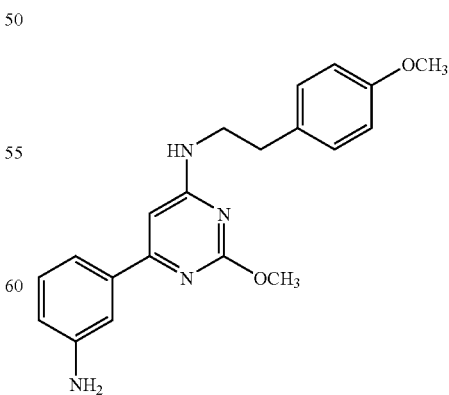

Example 2

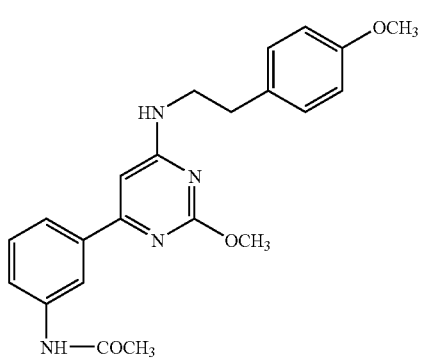

Example 6(b)

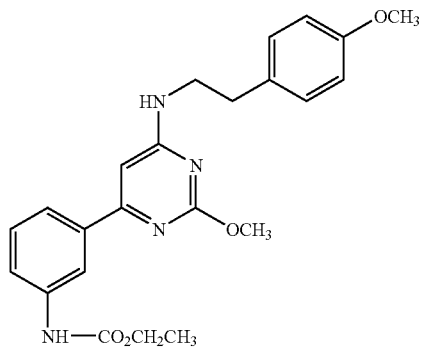

Example 6(c)

By proceeding in a similar manner to Example 6(b) but using [6-(3-amino-phenyl)-2-methoxy-pyrimidin-4-yl]-[2-(4-methoxy-phenyl)-ethyl]-amine [169 mg, Example 2] and ethyl chloroformate (47 μL), and subjected the reaction product to flash column chromatography on silica gel (10 g) eluting with 20 to 40% EtOAc in heptane) there is prepared (3-{2-methoxy-6-[2-(4-methoxy-phenyl)-ethylamino]-pyrimidin-4-yl}-phenyl)-carbamic acid ethyl ester [40.1 mg, 23%, Example 6(c)]. LCMS: $R_T$=2.84 minutes, MS: 423 (M+H).

To a solution of [6-(3-amino-phenyl)-2-methoxy-pyrimidin-4-yl]-[2-(4-methoxy-phenyl)-ethyl]-amine acetate [156 mg, 0.38 mmol, Example 2] in pyridine (1.3 mL) is added acetyl chloride (32 μL, 0.45 mmol). The reaction mixture is stirred for 3 hours at ambient temperature, quenched with the addition of water (20 mL), and extracted three times with EtOAc (20 mL). The combined extracts are washed four times with aqueous copper sulfate solution (10 mL), with water (10 mL), with brine (10 mL), dried over magnesium sulfate, filtered and concentrated by rotary evaporator. The resulting solid is subjected to flash column chromatography on silica gel (4.5 g) eluting with 3% MeOH in DCM to afford N-(3-{2-methoxy-6-[2-(4-methoxy-phenyl)-ethylamino]-pyrimidin-4-yl}-phenyl)-acetamide [51 mg, 34%, Example 6(b)]. LCMS: $R_T$=2.3 minutes, MS: 393 (M+H).

(c) (3-{2-Methoxy-6-[2-(4-methoxy-phenyl)-ethylamino]-pyrimidin-4-yl}-phenyl)-carbamic acid ethyl ester Example 7

3-{6-[2-(2,4-Difluoro-phenyl)-ethylamino]-2-methoxy-pyrimidin-4-yl}-benzoic acid

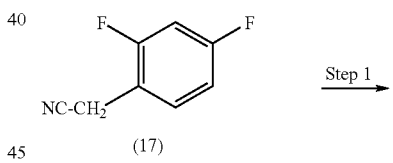

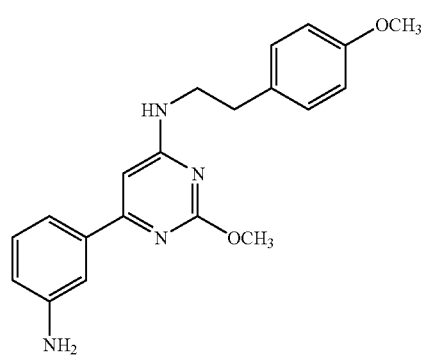

Example 2

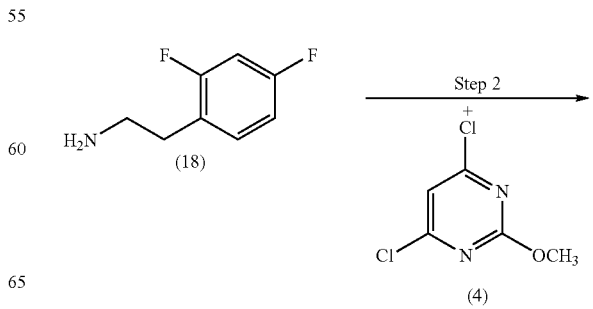

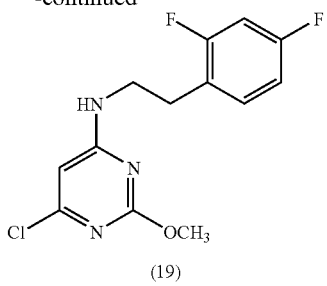

(19)

Step 3 +

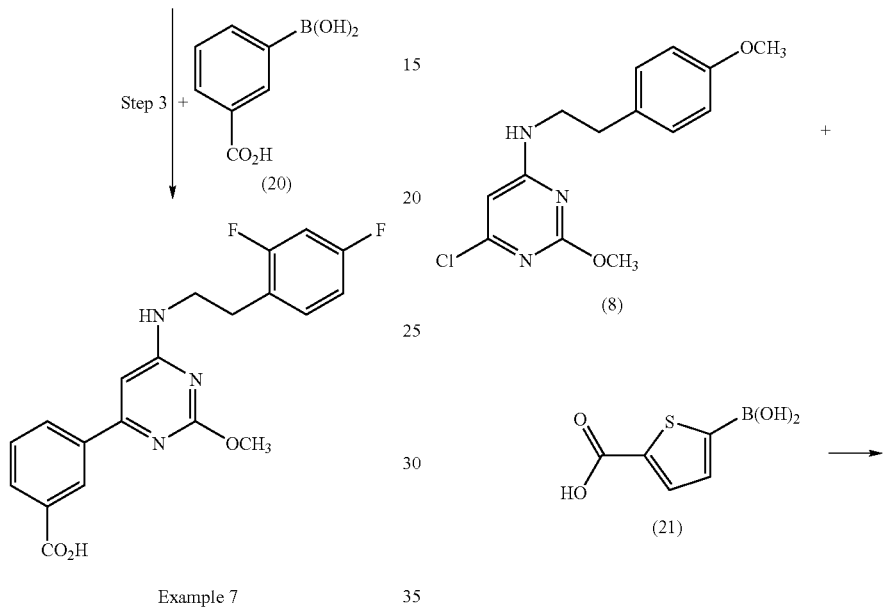

Step 1. Following, procedures similar to those of Example 5, step 1, but using (2,4-difluorophenyl)-acetonitrile [5.05 g, Intermediate (17)] there is prepared 2-(2,4-difluorophenyl)-ethylamine hydrochloride [4.8 g, Intermediate (18)]. MS: 158 (M+H), $^1$H NMR [(CD$_3$)$_2$SO]: δ 8.8 (1H, m); 7.3 (1H, s); 7.3 (1H, t); 6.9 (1H, t); 3.5-3.6 (2H, m); 2.8 (2H, t), Step 2. Following, procedures similar to those of Example 1, step 3, but using 4,6-dichloro-2-methoxypyrimidine [1.03 g, Intermediate (4)], 2-(2,4-difluorophenyl)-ethylamine hydrochloride [1.4 g, Intermediate (18)] and sodium bicarbonate (2.44 g) there is prepared (6-chloro-2-methoxy-pyrimidin-4-yl)-[2-(2,4-difluoro-phenyl)-ethyl]-amine [1.4 g, Intermediate (19)]. MS: 300 (M+H), $^1$H NMR [(CD$_3$)$_2$SO]: δ 8.8 (1H, m); 7.3-7.4 (1H, m); 7.3 (1H, t); 6.9 (1H, t); 6.2 (1H, s); 3.8 (3H, s); 3.5-3.6 (2H, m); 2.8 (2H, t).

Step 3. Following procedures similar to those of Example 1, step 3, but using (6-chloro-2-methoxy-pyrimidin-4-yl)-[2-(4-trifluoromethoxyphenyl)-ethyl]amine [220 mg, Intermediate (19)], 3-carboxyphenylboronic acid [240 mg, Intermediate (20)], CS$_2$CO$_3$ (1.2 g) and tetrakis(triphenylphosphine)palladium(0) (0.4 mg) there is prepared 3-{6-[2-(2,4-difluoro-phenyl)-ethylamino]-2-methoxy-pyrimidin-4-yl}-benzoic acid [93 mg, Example 7]. MS: 386 (M+H), $^1$H NMR [(CD$_3$)$_2$SO]: δ 8.45 (2H, m); 8-8.1 (3H, m); 7.6 (1H, d, J=3 Hz); 6.2 (1H, s); 4 (3H, s); 3.5-3.6 (2H, m); 2.9 (2H, t). IC$_{50}$=0.8 nM Example 8

(a) 5-{2-Methoxy-6-[2-(4-methoxy-phenyl)-ethylamino]-pyrimidin-4-yl}-thiophene-2-carboxylic acid trifluoroacetate

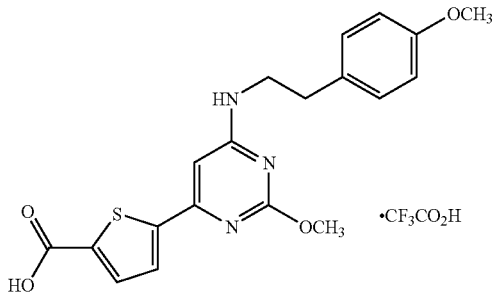

Example 8(a)

A mixture of (6-chloro-2-methoxy-pyrimidin-4-yl)-[2-(4-methoxy-phenyl)-ethyl]-amine [250 mg, 0.85 mmol, Intermediate (8) prepared as described in Example 2 step 1], 5-(dihydroxylboryl)-2-thiophenecarboxylic acid [200 mg, 1.16 mmol, Intermediate (21)], Cs$_2$CO$_3$ (760 mg, 1.87 mmol) 1,1'-bis(diphenylphosphino)ferrocene-palladium(II)dichloride DCM complex (54 mg, 0.066 mmol) in acetonitrile (4 mL) and water (4 mL) is degassed with vacuum/nitrogen several times and stirred at 90° C. for 4.5 hours. The reaction mixture is partitioned between EtOAc and water, separated the organic phase and dried over magnesium sulfate. The mixture is filtered and concentrated to provide a solid, which is subjected to flash column chromatography on silica gel eluting with a mixture of EtOAc and heptane. The material is recrystallized with MeOH and purified by HPLC (water/acetonitrile gradient) affording 5-{2-methoxy-6-[2-(4-methoxy-phenyl)-ethylamino]-pyrimidin-4-yl}-thiophene-2-carboxylic acid trifluoroacetate [34 mg. 10.4% yield, Example 8(a)]. LCMS: $R_T$=7.44 minutes; MS: 386 (M+H). $IC_{50}$=0.33 nM (b) 5-{2-methoxy-6-[2-(4-methoxy-phenyl)-ethylamino]-pyrimidin-4-yl}-thiophene-2-carbaldehyde

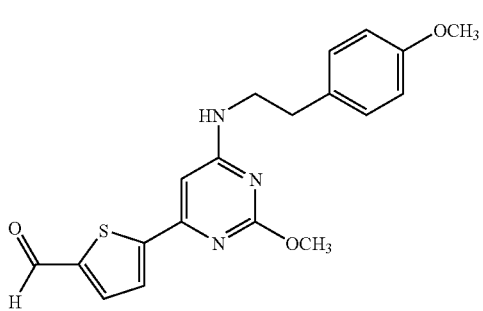

By proceeding in a similar manner as above in Example 8(a) but substituting 5-formyl-2-thiopheneboronic acid for 5-(dihydroxylboryl)-2-thiophenecarboxylic acid there is prepared 5-{2-methoxy-6-[2-(4-methoxy-phenyl)-ethylamino]-pyrimidin-4-yl}-thiophene-2-carbaldehyde [Example 8(b)]. $IC_{50}$=0.6 nM (c) 4-{2-Methoxy-6-[2-(4-methoxy-phenyl)-ethylamino]-pyrimidin-4-yl}-thiophene-2-carbaldehyde

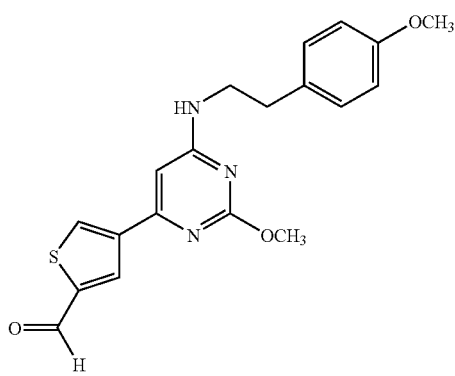

By proceeding in a similar manner as above in Example 8(a) but substituting 5-formyl-3-thiopheneboronic acid for 5-(dihydroxylboryl)-2-thiophenecarboxylic acid there is prepared 4-{2-methoxy-6-[2-(4-methoxy-phenyl)-ethylamino]-pyrimidin-4-yl}-thiophene-2-carbaldehyde [Example 8(c)].

(d) [6-(3,5-Dimethyl-isoxazol-4-yl)-2-methoxy-pyrimidin-4-yl]-[2-(4-methoxy-phenyl)-ethyl]-amine

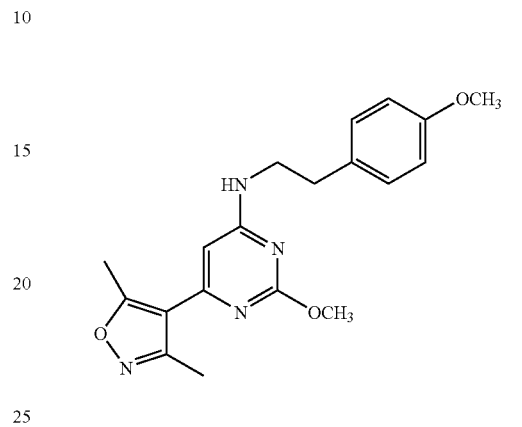

By proceeding in a similar manner as above in Example 8(a) but using (6-chloro-2-methoxy-pyrimidin-4-yl)-[2-(4-methoxy-phenyl)-ethyl]-amine (250 mg), 3,5-dimethylisoxazole-4-boronic acid (120 mg), $Cs_2CO_3$ (985 mg) and 1,1'-bis(diphenylphosphino)ferrocene-palladium(II)dichloride DCM complex (70 mg), there is prepared [6-(3,5-Dimethyl-isoxazol-4-yl)-2-methoxy-pyrimidin-4-yl]-[2-(4-methoxy-phenyl)-ethyl]-amine [Example 8(d)]. LCMS: $R_T$=6.49 minutes, MS: 355 (M+H). $IC_{50}$=1.9 nM (e) [2-Methoxy-6-(5-methyl-thiophen-2-yl)-pyrimidin-4-yl]-[2-(4-methoxy-phenyl)-ethyl]-amine

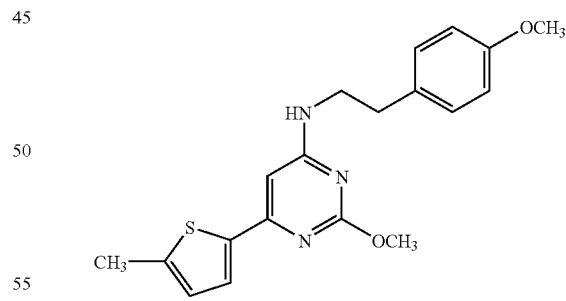

By proceeding in a similar manner as above in Example 8(a) but using (6-chloro-2-methoxy-pyrimidin-4-yl)-[2-(4-methoxy-phenyl)-ethyl]-amine (293.76 mg), 5-methylthiophene-2-boronic acid (290 mg), $Cs_2CO_3$ (1.181 g) and 1,1'-bis(diphenylphosphino)ferrocene-palladium (II) dichloride DCM complex (75 mg), and heating the reaction mixture at reflux temperature overnight, and subjecting the crude reaction product to flash column chromatography on silica gel eluting with a mixture of EtOAc and cyclohexane, there is prepared [2-methoxy-6-(5-methyl-thiophen-2-yl)-pyrimidin-4-yl]-[2-(4-methoxy-phenyl)-ethyl]-amine [252 mg, 70%, Example 8(e)]. LCMS: $R_T$=7.87 minutes, MS: 356 (M+H). $IC_{50}$=8.2 nM (f) [2-(4-Methoxy-phenyl)-ethyl]-[2-methoxy-6-(1H-pyrazol-4-yl)-pyrimidin-4-yl]-amine

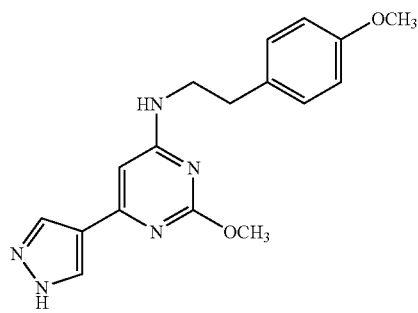

By proceeding in a similar manner as above in Example 8(a) but using (6-chloro-2-methoxy-pyrimidin-4-yl)-[2-(4-methoxy-phenyl)-ethyl]-amine (250 mg), 4-(4,4,5,5-tetramethyl-1,3,2-dioxaborolan-2-yl)-1H-pyrazole (329 mg), $Cs_2CO_3$ (985 mg) and 1,1'-bis(diphenylphosphino)ferrocene-palladium(II)dichloride DCM complex (70 mg), and heating the reaction mixture at 90° C. for 5 hours, and subjecting the crude reaction product to flash column chromatography on silica gel eluting with a mixture of EtOAc and cyclohexane, there is prepared [2-(4-methoxy-phenyl)-ethyl]-[2-methoxy-6-(1H-pyrazol-4-yl)-pyrimidin-4-yl]-amine [50 mg, 18%, Example 8(f)]. LCMS: $R_T$=5.04 minutes, MS: 326 (M+H). $IC_{50}$=26 nM (g) (6-Isoquinolin-5-yl-2-methoxy-pyrimidin-4-yl)-[2-(4-methoxy-phenyl)-ethyl]-amine

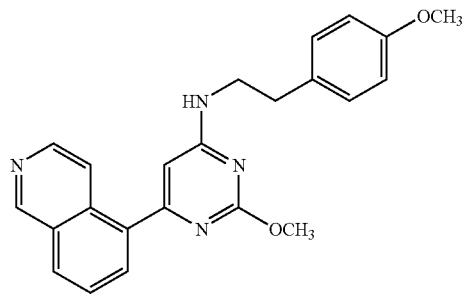

By proceeding in a similar manner as above in Example 8(a) but using (6-chloro-2-methoxy-pyrimidin-4-yl)-[2-(4-methoxy-phenyl)-ethyl]-amine (250 mg), 5-isoquinolineboronic acid (249 mg), $Cs_2CO_3$ (985 mg) and 1,1'-bis(diphenylphosphino)ferrocene-palladium(II)dichloride DCM complex (70 mg), and heating the reaction mixture at 90° C. for 5 hours, and subjecting the crude reaction product to flash column chromatography on silica gel eluting with a mixture of EtOAc and cyclohexane, there is prepared (6-isoquinolin-5-yl-2-methoxy-pyrimidin-4-yl)-[2-(4-methoxy-phenyl)-ethyl]-amine [163 mg, 50%, Example 8(g)]. LCMS: $R_T$=5.05 minutes, MS: 387 (M+H). $IC_{50}$=64 nM Example 9

(a) (5-{2-Methoxy-6-[2-(4-methoxy-phenyl)-ethylamino]-pyrimidin-4-yl}-thiophen-2-yl)-methanol

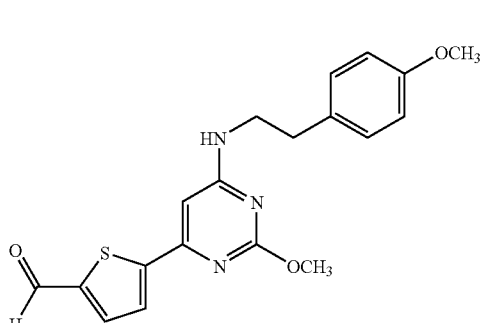

Example 8(b)

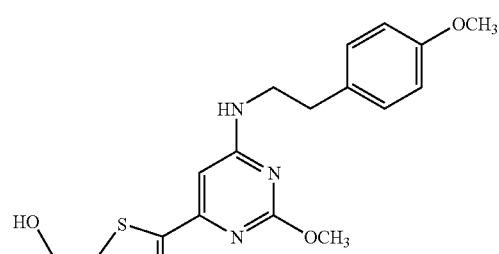

Example 9(a)

A mixture of 5-{2-methoxy-6-[2-(4-methoxy-phenyl)-ethylamino]-pyrimidin-4-yl}-thiophene-2-carbaldehyde [200 mg, 0.54 mmol, Example 8(b)] in MeOH (5 mL) and THF (5 mL) at 0° C. is treated with sodium borohydride (41 mg, 1.08 mmol). The mixture is stirred at ambient temperature for 1 hour and concentrated by rotary evaporator to remove the solvent. The residual solid is dissolved in water and the solution is extracted with ethyl acetate. The organic extract is dried over magnesium sulfate, filtered and concentrated to afford a solid which is subjected to flash column chromatography on silica gel eluting with a mixture of EtOAc and cyclohexane) to afford (5-{2-methoxy-6-[2-(4-methoxy-phenyl)-ethylamino]-pyrimidin-4-yl}-thiophen-2-yl)- methanol [75 mg, 37%, Example 9(a)] as a solid. LCMS: R$_T$=6.09 minutes; MS: 372 (M+H). IC$_{50}$=0.55 nM (b) (3-{2-Methoxy-6-[2-(4-methoxy-phenyl)-ethylamino]-pyrimidin-4-yl}-thiophen-2-yl)-methanol

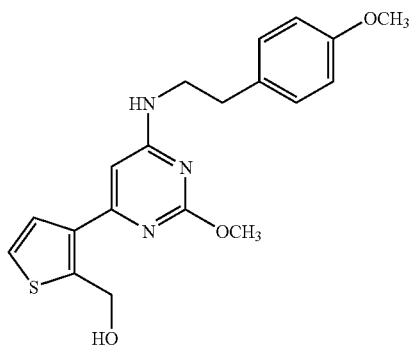

By proceeding in a similar manner as above in Example 9(a) but substituting 3-{2-methoxy-6-[2-(4-methoxy-phenyl)-ethylamino]-pyrimidin-4-yl}-thiophene-2-carbaldehyde [110 mg, 0.298 mmol, Example 35(l)] for 5-{2-methoxy-6-[2-(4-methoxy-phenyl)-ethylamino]-pyrimidin-4-yl}-thiophene-2-carbaldehyde acid, and subjecting the crude product to chromatography on a SCX column eluting with ammonia (2M) in MeOH and ethyl acetate, there is prepared (3-{2-methoxy-6-[2-(4-methoxy-phenyl)-ethylamino]-pyrimidin-4-yl}-thiophen-2-yl)-methanol [45 mg, 41%, Example 9(b)] as a solid. LCMS: R$_T$=5.87 minutes, MS: 372 (M+H). $^1$H NMR [400 MHz, (CD$_3$)$_2$SO] δ 7.48 (1H, s), 7.4 (1H, d, J=5.6 Hz), 7.35 (1H, s), 7.18 (2H, d, J=9.2 Hz), 6.85 (2H, d, J=9.2 Hz), 6.4 (1H, s), 5.9 (1H, t, J=5.6 Hz), 3.85 (3H, s), 3.72 (3H, s), 3.45 (2H, m), 2.8 (2H, t, J=6.8 Hz). IC$_{50}$=1.7 nM (c) (3-{2-Methoxy-6-[2-(4-methoxy-phenyl)-ethylamino]-pyrimidin-4-yl}-phenyl)-methanol

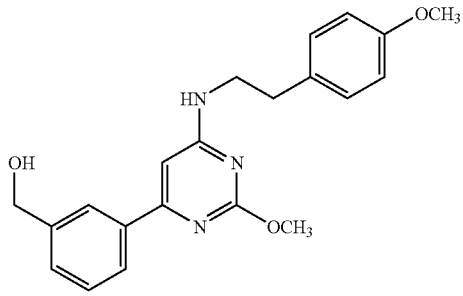

A solution of 3-{2-methoxy-6-[2-(4-methoxy-phenyl)-ethylamino]-pyrimidin-4-yl}-benzaldehyde [33 mg, 0.08 mmol, Example 35(u)] in a mixture of DCM (3 mL) and MeOH (1 mL) is treated with sodium borohydride (100 mg). After 10 minutes at 20° C., the mixture is concentrated, and extracted twice with EtOAc (10 mL). The combined extracts are dried over magnesium sulfate and filtered through a plug of silica gel to afford (3-{2-methoxy-6-[2-(4-methoxy-phenyl)-ethylamino]-pyrimidin-4-yl}-phenyl)-methanol [32 mg, 100%, Example 9(c)]. LCMS: R$_T$=2.18 minutes, MS: 366 (M+H).

(d) (3-{6-[2-(2-chloro-6-fluoro-phenyl)-ethylamino]-2-methoxy-pyrimidin-4-yl}-phenyl)-methanol

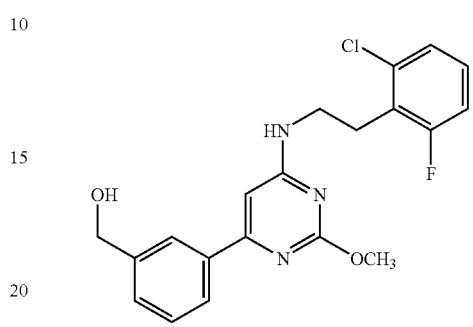

A solution of 3-{6-[2-(2-chloro-6-fluoro-phenyl)-ethylamino]-2-methoxy-pyrimidin-4-yl}-benzaldehyde [150 mg, 0.39 mmol, Example 35(v)], in DCM (4 mL) and MeOH (1 mL) is treated with sodium borohydride (74 mg, 1.95 mmol) at 0° C. After 1 hour at 20° C., the mixture is concentrated, and extracted twice with EtOAc (10 mL). The combined extracts are dried over magnesium sulfate and filtered through a plug of silica to afford (3-{6-[2-(2-chloro-6-fluoro-phenyl)-ethylamino]-2-methoxy-pyrimidin-4-yl}-phenyl)-methanol [110 mg, 73%, Example 9(d)]. LCMS: R$_T$=2.79 minutes, MS: 388 (M+H). IC$_{50}$=2.4 nM Example 10

(a) [2-(4-Methoxy-phenyl)-ethyl]-(2-methoxy-6-quinolin-6-yl-pyrimidin-4-yl)-amine

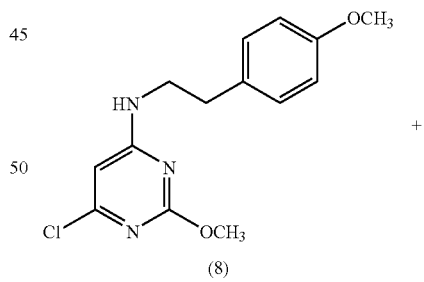

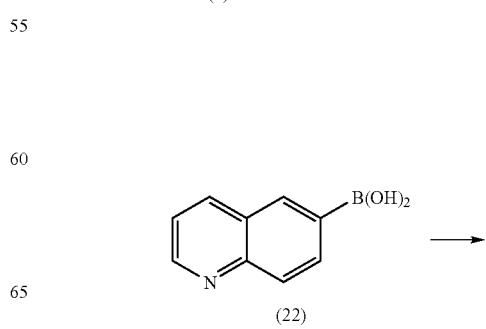

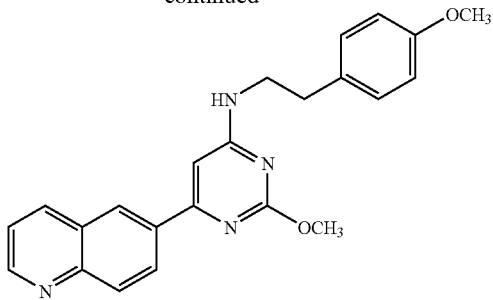

Example 10(a)

A mixture of (6-chloro-2-methoxy-pyrimidin-4-yl)-[2-(4-methoxy-phenyl)-ethyl]-amine (150 mg, 0.51 mmol, Intermediate (8) prepared as described in Example 2 step 1), quinoline-6-boronic acid [176 mg, 1.02 mmol, Intermediate (22)], $Cs_2CO_3$ (590 mg, 1.81 mmol) tetrakis(triphenylphosphine)palladium (0) (59 mg, 0.051 mmol), ethylene glycol dimethyl ether (4 mL) and water (1 mL) is placed in a microwave tube, sealed and evacuated and flushed with argon three times and irradiated in a microwave oven at 140° C. for 10 minutes. The reaction mixture is partitioned between EtOAc and water. The organic phase is separated, washed with saturated sodium bicarbonate solution, dried over magnesium sulfate and evaporated. The residual solid is subjected to flash column chromatography on silica gel eluting with a mixture of EtOAc and heptane. The material is recrystallized from MeOH to afford [2-(4-methoxy-phenyl)-ethyl]-(2-methoxy-6-quinolin-6-yl-pyrimidin-4-yl)-amine [140 mg, 71%, Example 10(a)] LCMS: $R_T$=5.97 minutes, MS: 387 (M+H). $IC_{50}$=0.6 nM (b) [2-(4-Methoxy-phenyl)-ethyl]-(2-methoxy-6-quinolin-3-yl-pyrimidin-4-yl)-amine

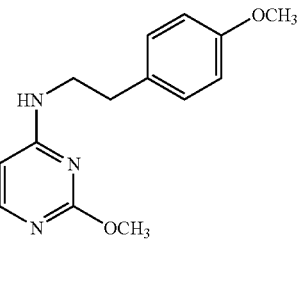

By proceeding in a similar manner as above in Example 10(a) but using (6-chloro-2-methoxy-pyrimidin-4-yl)-[2-(4-methoxy-phenyl)-ethyl]-amine (200 mg), 3-quinolineboronic acid (235 mg), $Cs_2CO_3$ (787 mg) and tetrakis(triphenylphosphine)palladium (0) (79 mg), and carrying out the reaction in a microwave oven at 140° C. for 6 minutes, there is prepared [2-(4-methoxy-phenyl)-ethyl]-(2-methoxy-6-quinolin-3-yl-pyrimidin-4-yl)-amine [156 mg, 59%, Example 10(b)]. LCMS: $R_T$=7.44 minutes, MS: 387 (M+H). $IC_{50}$=0.7 nM (c) [6-(1H-Indol-5-yl)-2-methoxy-pyrimidin-4-yl]-[2-(4-methoxy-phenyl)-ethyl]-amine

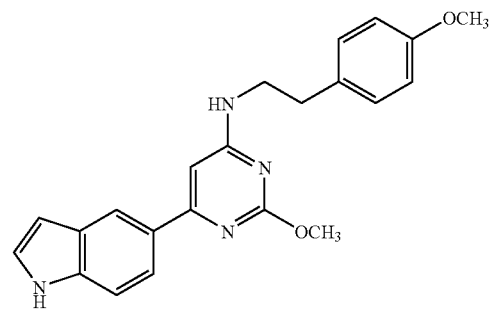

By proceeding in a similar manner as above in Example 10(a) but using (6-chloro-2-methoxy-pyrimidin-4-yl)-[2-(4-methoxy-phenyl)-ethyl]-amine (150 mg), 5-indolylboronic acid (165 mg), $Cs_2CO_3$ (590 mg) and tetrakis(triphenylphosphine)palladium(0) (58 mg), there is prepared [6-(1H-indol-5-yl)-2-methoxy-pyrimidin-4-yl]-[2-(4-methoxy-phenyl)-ethyl]-amine [Example 10(c)]. LCMS: $R_T$=6.3 minutes, MS: 375 (M+H). $^1H$ NMR [$(CD_3)_2SO$]: δ 8.22 (1H, s), 7.73 (1H, m), 7.45 (2H, d, J=9.2 Hz), 7.39 (2H, m), 7.19 (2H, d, J=9.2 Hz), 6.85 (2H, d, J=9.2 Hz), 6.6 (1H, s), 6.55 (1H, s), 3.9 (3H, s), 3.72 (3H, s), 3.55 (2H, m), 2.8 (2H, t, J=6.8 Hz). $IC_{50}$=0.7 nM (d) N-(2-{2-Methoxy-6-[2-(4-methoxy-phenyl)-ethylamino]-pyrimidin-4-yl}-phenyl)-methanesulfonamide

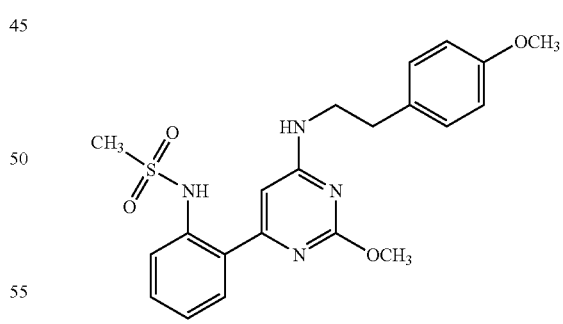

By proceeding in a similar manner as above in Example 10(a) but using (6-chloro-2-methoxy-pyrimidin-4-yl)-[2-(4-methoxy-phenyl)-ethyl]-amine (150 mg), 2-(methylsulfonylamino)phenylboronic acid (219 mg), $Cs_2CO_3$ (590 mg) and tetrakis(triphenylphosphine)palladium(0) (59 mg), and subjecting the crude reaction product to flash column chromatography on silica gel eluting with a mixture of EtOAc and cyclohexane there is prepared N-(2-{2-methoxy-6-[2-(4-methoxy-phenyl)-ethylamino]-pyrimidin-4-yl}-phenyl)- methanesulfonamide [115 mg, 53%, Example 10(d)]. LCMS: $R_T$=8.17 minutes, MS: 429 (M+H). $IC_{50}$=2 nM (e) 4-{2-Methoxy-6-[2-(4-methoxy-phenyl)-ethylamino]-pyrimidin-4-yl}-benzamide

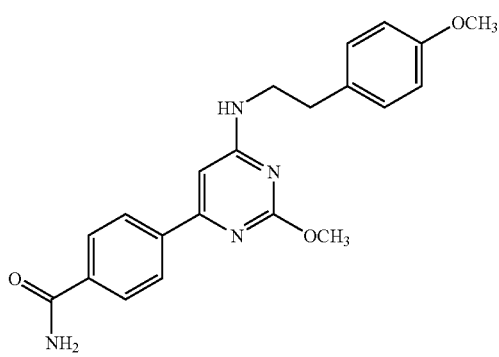

By proceeding in a similar manner as above in Example 10(a) but using (6-chloro-2-methoxy-pyrimidin-4-yl)-[2-(4-methoxy-phenyl)-ethyl]-amine (150 mg), (4-aminocarbonylphenyl)boronic acid (168 mg), $Cs_2CO_3$ (590 mg) and tetrakis(triphenylphosphine)palladium(0) (58 mg), and subjecting the crude reaction product to flash column chromatography on silica gel eluting with a mixtures of 20 to 100% EtOAc and cyclohexane, there is prepared 4-{2-methoxy-6-[2-(4-methoxy-phenyl)-ethylamino]-pyrimidin-4-yl}-benzamide [30 mg, 15.5%, Example 10(e)]. LCMS: $R_T$=5.32 minutes, MS: 379 (M+H). $IC_{50}$=2.3 nM (f) [2-Methoxy-6-(1-methyl-1H-indol-5-yl)-pyrimidin-4-yl]-[2-(4-methoxy-phenyl)-ethyl]-amine

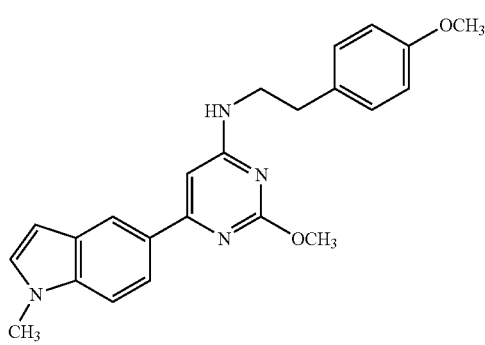

By proceeding, in a similar manner as above in Example 10(a) but using (6-chloro-2-methoxy-pyrimidin-4-yl)-[2-(4-methoxy-phenyl)-ethyl]-amine (150 mg), N-methylindole-5-boronic acid (178.5 mg), $Cs_2CO_3$ (590 mg) and tetrakis(triphenylphosphine)palladium (0) (58 mg), and subjecting the crude reaction product to flash column chromatography on silica gel eluting with a mixtures of 20 to 100% EtOAc and cyclohexane, there is prepared [2-methoxy-6-(1-methyl-1H-indol-5-yl)-pyrimidin-4-yl]-[2-(4-methoxy-phenyl)-ethyl]-amine [70 mg, 35%, Example 10(f)]. LCMS: $R_T$=6.75 minutes, MS: 389 (M+H). $^1$H NMR [$(CD_3)_2SO$]: δ 8.25 (1H, s), 7.78 (1H, s), 7.5 (1H, d, J=9.2 Hz), 7.38 (1H, d, J=2.3 Hz), 7.18 (2H, d, J=9.2 Hz), 6.85 (2H, d, J=9.2 Hz), 6.62 (1H, s), 6.55 (1H, d, J=2.3 Hz), 3.9 (3H, s), 3.82 (3H, s), 3.72 (3H, s), 3.45 (2H, m), 2.8 (2H, t, J=6.8 Hz).

(g) (6-Benzo[b]thiophen-2-yl-2-methoxy-pyrimidin-4-yl)-[2-(4-methoxy-phenyl)-ethyl]-amine

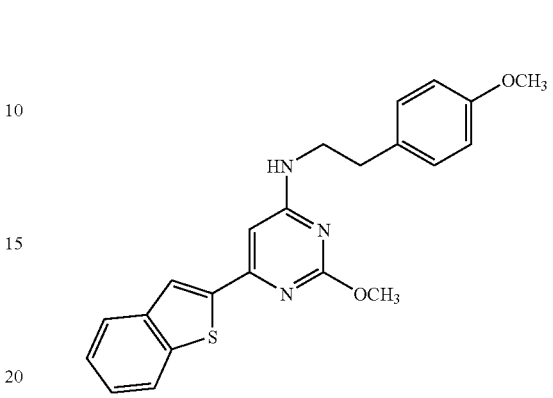

By proceeding in a similar manner as above in Example 10(a) but using (6-chloro-2-methoxy-pyrimidin-4-yl)-[2-(4-methoxy-phenyl)-ethyl]-amine (150 mg), benzo[b]thiophene-2-boronic acid (182 mg), $Cs_2CO_3$ (590 mg) and tetrakis(triphenylphosphine)palladium (0) (58 mg), and subjecting the crude reaction product to flash column chromatography on silica gel eluting with a mixtures of 20 to 100% EtOAc and cyclohexane, there is prepared (6-benzo[b]thiophen-2-yl-2-methoxy-pyrimidin-4-yl)-[2-(4-methoxy-phenyl)-ethyl]-amine [85 mg, 42% yield, Example 10(g)]. LCMS: $R_T$=10.39 minutes, MS: 392 (M+H). $IC_{50}$=5.1 nM (h) 1-(4-{2-Methoxy-6-[2-(4-methoxy-phenyl)-ethylamino]-pyrimidin-4-yl}-phenyl)-ethanone

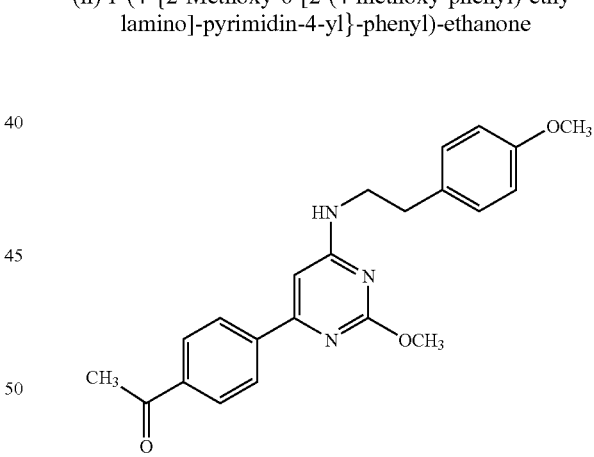

By proceeding in a similar manner as above in Example 10(a) but using (6-chloro-2-methoxy-pyrimidin-4-yl)-[2-(4-methoxy-phenyl)-ethyl]-amine (200 mg), 4-acetylphenylboronic acid (223 mg), $Cs_2CO_3$ (787 mg) and tetrakis(triphenylphosphine)palladium (0) (79 mg), and carrying out the reaction in a microwave oven at 140° C. for 6 minutes, and subjecting the crude reaction product to flash column chromatography on silica gel eluting with a mixture of EtOAc and cyclohexane, there is prepared 1-(4-{2-methoxy-6-[2-(4-methoxy-phenyl)-ethylamino]-pyrimidin-4-yl}-phenyl)-ethanone [160 mg, 62%, Example 10(h)]. LCMS: $R_T$=6.2 minutes, MS: 378 (M+H). $^1$H NMR [$(CD_3)_2SO$]: δ 8.1 (4H, m), 7.78 (1H, s), 7.62 (1H, s), 7.18 (2H, d, J=9.2 Hz), 6.85

(2H, d, J=9.2 Hz), 6.7 (1H, s), 3.9 (3H, s), 3.7 (3H, s), 3.55 (2H, m), 2.8 (2H, t, J=6.8 Hz), 2.6 (3H, s). IC$_{50}$=6.3 nM (i) [6-(3-Methanesulfonyl-phenyl)-2-methoxy-pyrimidin-4-yl]-[2-(4-methoxy-phenyl)-ethyl]-amine

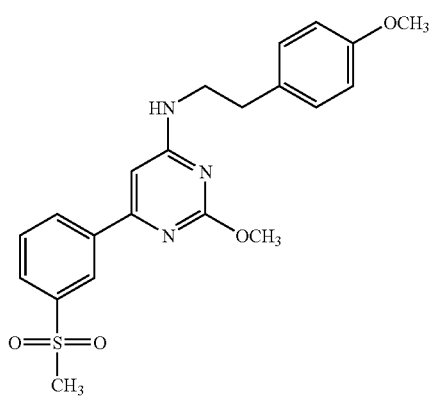

By proceeding in a similar manner as above in Example 10(a) but using (6-chloro-2-methoxy-pyrimidin-4-yl)-[2-(4-methoxy-phenyl)-ethyl]-amine (150 mg), 3-(methanesulfonyl)phenylboronic acid (204 mg), Cs$_2$CO$_3$ (590 mg) and tetrakis(triphenylphosphine)palladium (0) (59 mg), and subjecting the crude reaction product to flash column chromatography on silica gel eluting with a mixture of EtOAc and cyclohexane, there is prepared [6-(3-methanesulfonyl-phenyl)-2-methoxy-pyrimidin-4-yl]-[2-(4-methoxy-phenyl)-ethyl]-amine [142 mg, 67%, Example 10(i)]. LCMS: R$_T$=6.74 minutes, MS: 414 (M+H). $^1$H NMR [(CD$_3$)$_2$SO]: δ 8.45 (1H, s), 8.35 (1H, s), 8 (1H, d, J=9.2 Hz), 7.78 (1H, t, J=7.9 Hz), 7.65 (1H, s), 7.18 (2H, d, J=9.2 Hz), 6.85 (2H, d, J=9.2 Hz), 3.9 (3H, s), 3.7 (3H, s), 3.55 (2H, m), 3.25 (3H, s), 2.8 (2H, t, J=6.8 Hz). IC$_{50}$=7.3 nM (j) [6-(2,3-Dihydro-benzofuran-5-yl)-2-methoxy-pyrimidin-4-yl]-[2-(4-methoxy-phenyl)-ethyl]-amine

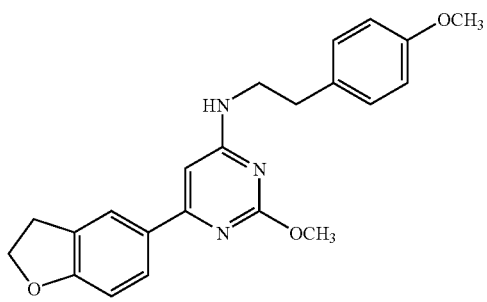

By proceeding in a similar manner as above in Example 10(a) but using (6-chloro-2-methoxy-pyrimidin-4-yl)-[2-(4-methoxy-phenyl)-ethyl]-amine (200 mg), 2,3-dihydro-1-benzofuran-5-ylboronic acid (223 mg), Cs$_2$CO$_3$ (787 mg) and tetrakis(triphenylphosphine)palladium (0) (79 mg), and carrying out the reaction in a microwave oven at 140° C. for 35 minutes, and subjecting the crude reaction product to flash column chromatography on silica gel eluting with a mixture of EtOAc and cyclohexane, there is prepared [6-(2,3-dihydro-benzofuran-5-yl)-2-methoxy-pyrimidin-4-yl]-[2-(4-methoxy-phenyl)-ethyl]-amine [165 mg, 64%, Example 10(j)]. LCMS: R$_T$=5.56 minutes, MS: 378 (M+H). $^1$H NMR [(CD$_3$)$_2$SO]: δ 8.9 (1H, s), 8.79 (1H, s), 7.4 (1H, s), 7.2 (1H, d, J=9.2 Hz), 6.85 (1H, t, J=9.2 Hz), 6.83 (2H, d, J=9.2 Hz), 6.5 (1H, s), 4.6 (2H, t, J=8 Hz), 3.85 (3H, s), 3.7 (3H, s), 3.55 (2H, m), 3.22 (2H, t, J=8 Hz), 2.8 (2H, t, J=6.8 Hz). IC$_{50}$=13 nM (k) [2-Methoxy-6-(4-morpholin-4-yl-phenyl)-pyrimidin-4-yl]-[2-(4-methoxy-phenyl)-ethyl]-amine

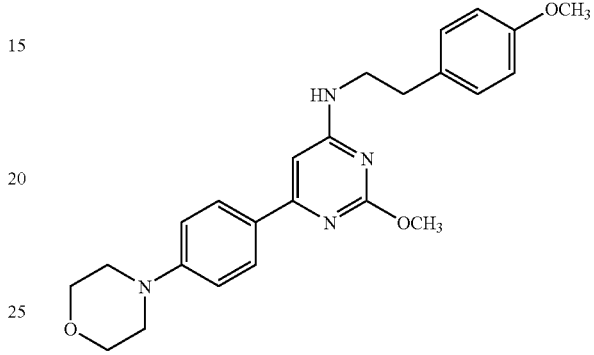

By proceeding in a similar manner as above in Example 10(a) but using (6-chloro-2-methoxy-pyrimidin-4-yl)-[2-(4-methoxy-phenyl)-ethyl]-amine (150 mg), 4-(morpholino)phenylboronic acid (211 mg), Cs$_2$CO$_3$ (590 mg) and tetrakis(triphenylphosphine)palladium (0) (59 mg), and carrying out the reaction in a microwave oven at 140° C. for 10 minutes and at 165° C. for 10 minutes, and subjecting the crude reaction product to flash column chromatography on silica gel eluting with a mixture of EtOAc and cyclohexane, there is prepared [2-methoxy-6-(4-morpholin-4-yl-phenyl)-pyrimidin-4-yl]-[2-(4-methoxy-phenyl)-ethyl]-amine [130 mg, 61%, Example 10(k)]. LCMS: R$_T$=6.28 minutes, MS: 421 (M+H). IC$_{50}$=13 nM (l) [6-(4-Dimethylamino-phenyl)-2-methoxy-pyrimidin-4-yl]-[2-(4-methoxy-phenyl)-ethyl]-amine

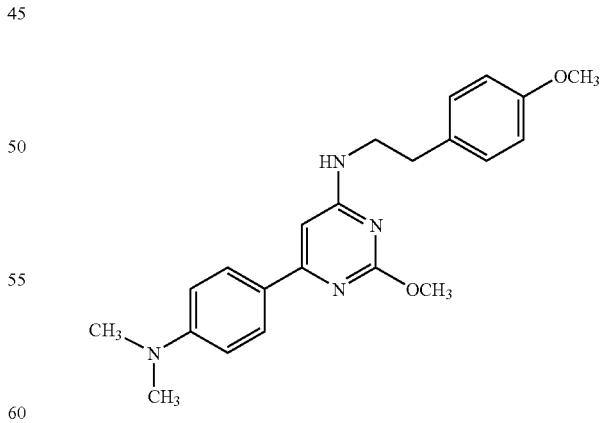

By proceeding in a similar manner as above in Example 10(a) but using (6-chloro-2-methoxy-pyrimidin-4-yl)-[2-(4-methoxy-phenyl)-ethyl]-amine (200 mg), 4-(N,N-dimethylamino)phenylboronic acid (224.4 mg), Cs$_2$CO$_3$ (787 mg) and tetrakis(triphenylphosphine)palladium(0) (79 mg), and subjecting the crude reaction product to flash column chromatography on silica gel eluting with a mixture of EtOAc and cyclohexane, followed by trituration with methanol, there is prepared [6-(4-dimethylamino-phenyl)-2-methoxy-pyrimidin-4-yl]-[2-(4-methoxy-phenyl)-ethyl]-amine [50 mg, 19%, Example 10(l)]. LCMS: $R_T$=5.77 minutes, MS: 379 (M+H). $IC_{50}$=42 nM (m) 2,2'-Dimethoxy-N*6*,N*6'*-bis-[2-(4-methoxy-phenyl)-ethyl]-[4,4']bipyrimidinyl-6,6'-diamine

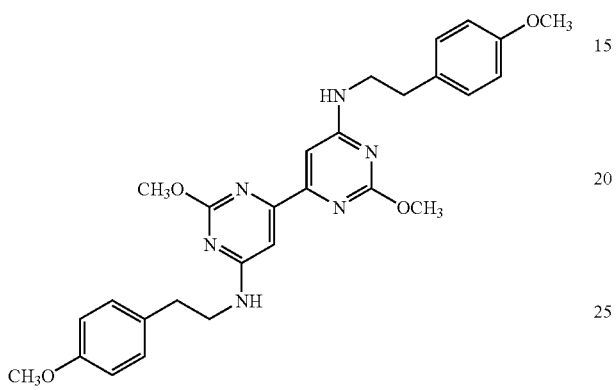

By proceeding in a similar manner as above in Example 10(a) but using (6-chloro-2-methoxy-pyrimidin-4-yl)-[2-(4-methoxy-phenyl)-ethyl]-amine (150 mg), (4-aminocarbonylphenyl)-boronic acid (168 mg), $Cs_2CO_3$ (590 mg) and tetrakis(triphenylphosphine)palladium (0) (58 mg), and subjecting the crude reaction product to flash column chromatography on silica under gradient elution conditions with 20 to 100% EtOAc in cyclohexane, followed by recrystallisation from methanol, there is prepared 2,2'-dimethoxy-N*6*,N*6'*-bis-[2-(4-methoxy-phenyl)-ethyl]-[4,4']bipyrimidinyl-6,6'-diamine [20 mg, 15%, Example 10(m)] as a side product. LCMS: $R_T$=8.13 minutes, MS: 517 (M+H).

Example 11

(a) [2-Methoxy-6-(5-oxazol-5-yl-thiophen-2-yl)-pyrimidin-4-yl]-[2-(4-methoxy-phenyl)-ethyl]-amine

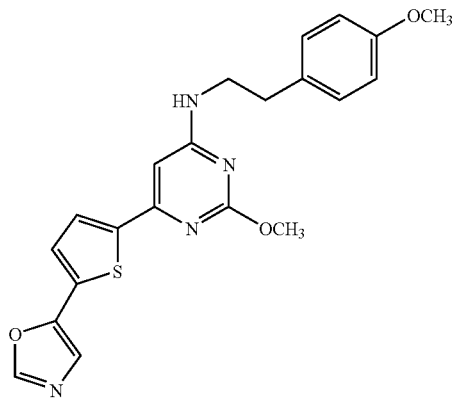

Example11(a)

A stirred mixture of 5-{2-methoxy-6-[2-(4-methoxy-phenyl)-ethylamino]-pyrimidin-4-yl}-thiophene-2-carbaldehyde [300 mg, 0.81 mmol, Example 8(b)], tosylmethylisocyanide (174 mg, 0.89 mmol), $K_2CO_3$ (246 mg 1.78 mmol) and MeOH (30 mL) is heated at reflux for 4 hours. The mixture is allowed to cool to ambient temperature, concentrated by rotary evaporator to remove the solvent. The residue is partitioned between EtOAc and water. The organic phase is dried over magnesium sulfate, filtered and concentrated. The residual solid is subjected to flash column chromatography on silica gel eluting with EtOAc and cyclohexane to afford [2-methoxy-6-(5-oxazol-5-yl-thiophen-2-yl)-pyrimidin-4-yl]-[2-(4-methoxy-phenyl)-ethyl]-amine [240 mg, 73%, Example 11(a)]. LCMS: $R_T$=8.99 minutes, MS: 409 (M+H). $IC_{50}$=2.3 nM (b) [2-Methoxy-6-(3-oxazol-5-yl-phenyl)-pyrimidin-4-yl]-[2-(4-methoxy-phenyl)-ethyl]-amine

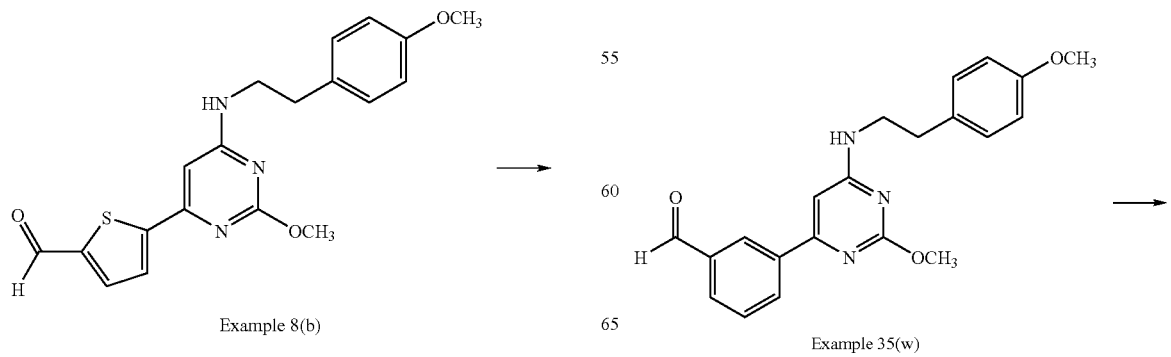

Example 8(b)      Example 35(w)

-continued

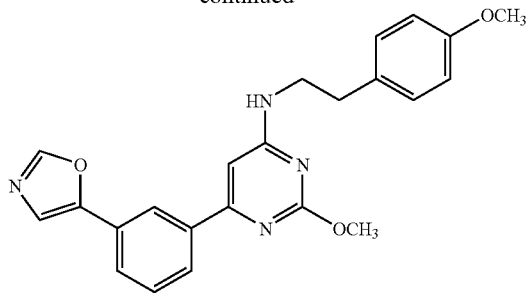

Example 11(b)

In a tube is combined 3-{2-methoxy-6-[2-(4-methoxy-phenyl)-ethylamino]-pyrimidin-4-yl}-benzaldehyde (200 mg, 0.55 mmol), tosylmethylisocyanide (119 mg, 0.61 mmol), Ambersep 900 OH resin (1 g), ethylene glycol dimethyl ether (3.5 mL) and water (3.5 mL). The tube is sealed and the mixture is heated to 85° C. and stirred for 18 hours. The mixture is allowed to cool to ambient temperature and filtered to remove the resin, and washed the resin with 10 mL methanol. The combined filtrate and washings are concentrated by rotary evaporator and the residue is subjected to flash column chromatography on silica gel eluting with 10 to 40% EtOAc in heptane gradient, to afford [2-methoxy-6-(3-oxazol-5-5-yl-phenyl)-pyrimidin-4-yl]-[2-(4-methoxy-phenyl)-ethyl]-amine [65 mg, 29.4%, Example 11(b)]. LCMS: $R_T$=2.59 minutes MS: 403 (M+H). $IC_{50}$=2.6 nM Example 12

[6-(5-Difluoromethyl-thiophen-2-yl)-2-methoxy-pyrimidin-4-yl]-[2-(4-methoxy-phenyl)-ethyl]-amine

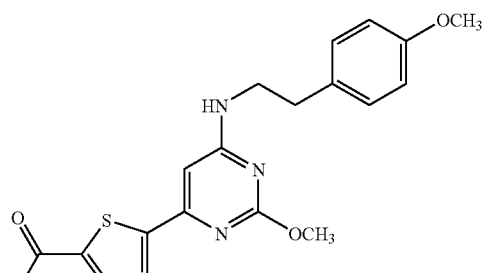

Example 8(b)

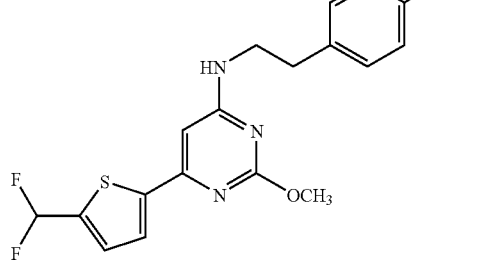

Example 12

A stirred mixture of 5-{2-methoxy-6-[2-(4-methoxy-phenyl)-ethylamino]-pyrimidin-4-yl}-thiophene-2-carbaldehyde [300 mg, 0.81 mmol, Example 8(b)] and diethylaminosulfur trifluoride (213 μL, 1.62 mmol) in DCM is heated to reflux for 4 hours. A further quantity of diethylaminosulfur trifluoride (106 μL, 0.81 mmol) is added and stirring at reflux is continued overnight. The reaction mixture is poured into water and extracted twice with DCM. The organic extracts are combined and dried over magnesium sulfate, filtered and concentrated. The residual solid is subjected to flash column chromatography on silica gel eluting with a mixture of EtOAc and cyclohexane to afford [6-(5-difluoromethyl-thiophen-2-16)-2-methoxy-pyrimidin-4-yl]-[2-(4-methoxy-phenyl)-ethyl]-amine [65 mg, 17%, Example 12]. LCMS: $R_T$=10.03 minutes, MS: 406 (M+H). $IC_{50}$=11 nM Example 13

(a) [2-(4-Methoxy-phenyl)-ethyl]-[2-methoxy-6-(5-pyrrolidin-1-ylmethyl-thiophen-2-yl)-pyrimidin-4-yl]-amine

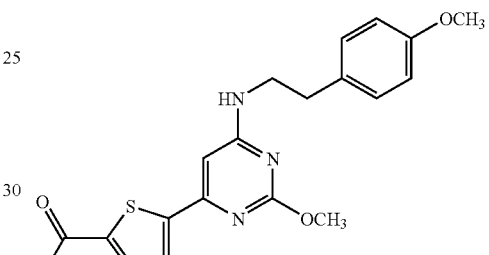

Example 8(b)

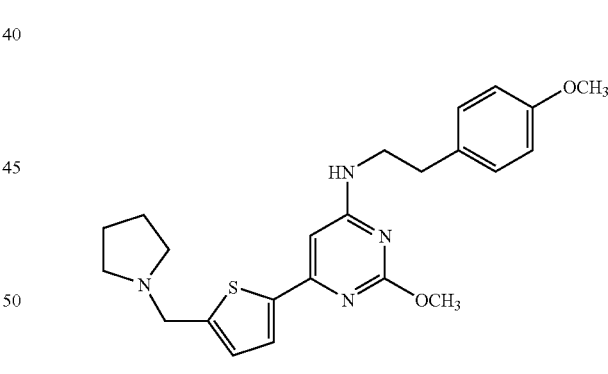

Example 13(a)

A mixture of 5-{2-methoxy-6-[2-(4-methoxy-phenyl)-ethylamino]-pyrimidin-4-yl}-thiophene-2-carbaldehyde [250 mg, 0.68 mmol, Example 8(b)], pyrrolidine (170 μL, 2.03 mmol) and sodium triacetoxyborohydride (502 mg, 2.37 mmol) in MeOH (10 mL) and 1,2-dichloroethane (10 mL) is treated with acetic Acid (116 mL, 2.03 mmol) to bring the pH to 6.0, stirred at ambient temperature for 6 hours, and treated with pyrrolidine (170 μL, 2.03 mmol) and sodium triacetoxyborohydride (502 mg, 2.37 mmol). The reaction mixture is stirred at ambient temperature overnight concentrated by rotary evaporator. The residual gum is partitioned between EtOAc and saturated sodium bicarbonate solution. The organic phase is separated, dried over magnesium sulfate, filtered and concentrated to provide a solid, which is subjected to flash column chromatography on silica gel eluting with a mixture of EtOAc and cyclohexane to afford [2-(4-methoxy-phenyl)-ethyl]-[2-methoxy-6-(5-pyrrolidin-1-ylmethyl-thiophen-2-yl)-pyrimidin-4-yl]-amine [202 mg, 70%, Example 13(a)]. LCMS: $R_T$=5.37 minutes, MS: 425 (M+H). $IC_{50}$=44 nM (b) (6-{4-Fluoro-3-[(2-methoxy-ethylamino)-methyl]-phenyl}-2-methoxy-pyrimidin-4-yl)-[2-(4-methoxy-phenyl)-ethyl]-amine hydrochloride

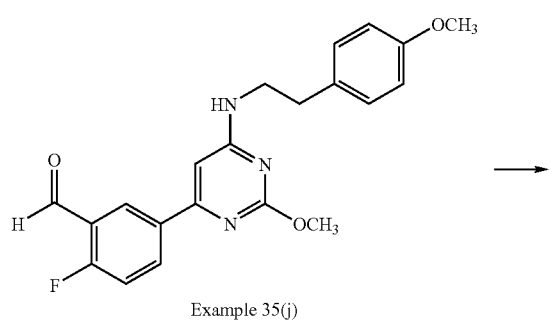

Example 35(j)

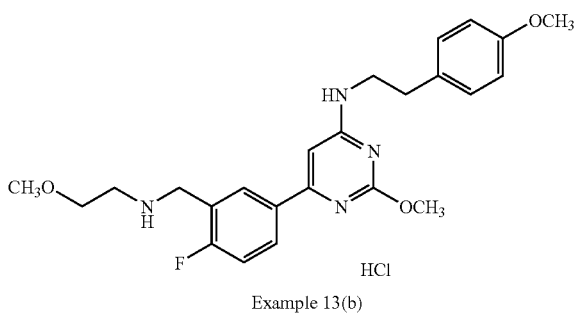

Example 13(b)

A mixture of 2-fluoro-5-{2-methoxy-6-[2-(4-methoxy-phenyl)-ethylamino]-pyrimidin-4-yl}-benzaldehyde [300 mg, 0.787 mmol, Example 35(j)], 2-methoxyethylamine (170 µL, 1.97 mmol), sodium triacetoxyborohydride (500 mg, 2.36 mmol) and 3 Å sieves (500 mg) in DCM (7 mL) is stirred at room temperature under a nitrogen atmosphere for 5 hours. The reaction mixture is filtered and the filter cake is washed with DCM (50 mL). The combined filtrate and washings are extracted with water (50 mL). The aqueous extract is extracted with DCM (50 mL). The new organic extract is washed with water (30 mL), with brine (30 mL), dried over sodium sulfate, filtered and concentrated by rotary evaporator. The resulting solid is subjected to flash column chromatography on silica (4.5 g) eluting with 0 to 8% MeOH in DCM gradient to afford a solid. This material is treated with hydrogen chloride in EtOAc and concentrated to afford (6-{4-fluoro-3-[(2-methoxy-ethylamino)-methyl]-phenyl}-2-methoxy-pyrimidin-4-yl)-[2-(4-methoxy-phenyl)-ethyl]-amine hydrochloride [260 mg, 75%, Example 13(b)] as a solid. LCMS: $R_T$=1.98 minutes, MS: 441 (M+H). $^1$H NMR (300 MHz, CDCl$_3$): δ 9.65 (1H, s), 8.27 (1H, s), 7.91 (1H, s), 7.47 (1H, t, J=0.03 Hz), 7.21 (2H, d, J=0.027 Hz), 6.85 (2H, d, J=0.027 Hz), 4.26 (2H, s), 4.03 (2H, s), 3.72 (6H, s), 3.31 (3H, s), 3.17 (2H, m), 2 (2H, t, J=0.024), 2.5 (2H, s).

(c) 4-[2-(3-{2-Methoxy-6-[2-(4-methoxy-phenyl)-ethylamino]-pyrimidin-4-yl}-benzylamino)-ethyl]-phenol hydrochloride

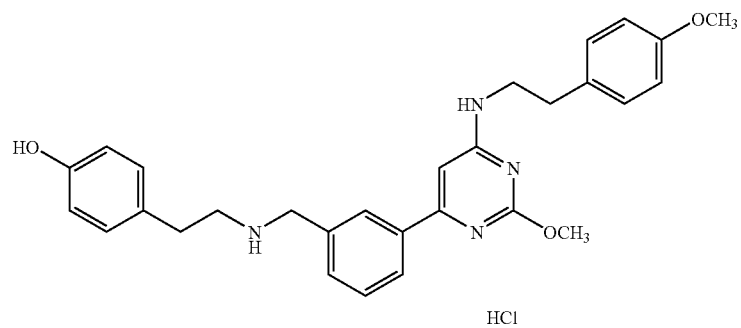

A mixture of 3-{2-methoxy-6-[2-(4-methoxy-phenyl)-ethylamino]-pyrimidin-4-yl}-benzaldehyde [80 mg, 0.22 mmol, Example 35(u)], 2-(4-hydroxy-phenyl)-ethylamine (45 mg, 0.33 mmol), sodium cyanoborohydride (16.6 mg, 0.264 mmol) and acetic acid (15 µL, 0.264 mmol) in EtOH (2 mL) is stirred at room temperature under a nitrogen atmosphere for 17 hours. The reaction mixture is poured into saturated sodium bicarbonate solution (10 mL), and extracted with EtOAc (15 mL). The extract is concentrated and the residue subjected to chromatography on silica gel, eluting with 5% ammonia in methanol. The material is treated with hydrogen chloride in EtOAc and concentrated to afford 4-[2-(3-{2-methoxy-6-[2-(4-methoxy-phenyl)-ethylamino]-pyrimidin-4-yl}-benzylamino)-ethyl]-phenol hydrochloride [55 mg, 51.5%, Example 13(c)] as a solid. LCMS: $R_T$=2.63 minutes, MS: 485 (M+H). $IC_{50}$=10 nM (d) N-(2-Fluoro-5-{2-methoxy-6-[2-(4-methoxy-phenyl)-ethylamino]-pyrimidin-4-yl}-benzyl)-N',N'-dimethyl-ethane-1,2-diamine hydrochloride

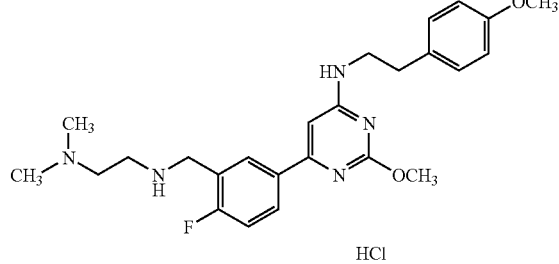

A mixture of 2-fluoro-5-{2-methoxy-6-[2-(4-methoxy-phenyl)-ethylamino]-pyrimidin-4-yl}-benzaldehyde [275 mg, 072 mmol, Example 35(j)], unsym-dimethylethylenediamine (217 μL, 1.97 mmol), sodium triacetoxyborohydride (500 mg, 2.36 mmol) and 3 Å sieves (500 mg) in DCM (7 mL) is stirred at room temperature under a nitrogen atmosphere for 5 hours. The reaction mixture is filtered and the filter cake is washed with DCM (50 mL). The combined filtrate and washings are extracted water with (50 mL) and the aqueous is extracted with DCM (50 mL). The new organic extract is washed with water (30 mL), with brine (30 mL), dried over sodium sulfate, filtered and concentrated by rotary evaporator. The resulting solid is subjected to flash column chromatography on silica (4.5 g) eluting with 0 to 7% MeOH in DCM gradient to afford a solid that is dissolved in methanol. This solution is treated with hydrogen chloride in EtOAc and concentrated to afford N-(2-fluoro-5-{2-methoxy-6-[2-(4-methoxy-phenyl)-ethylamino]-pyrimidin-4-yl}-benzyl)-N',N'-dimethyl-ethane-1,2-diamine hydrochloride [300 mg, 92%, Example 13(d)]. LCMS: $R_T$=2.04 minutes, MS: 454 (M+H). $IC_{50}$=56 nM Example 14

(a) [6-(1H-Benzoimidazol-1-yl)-2-methoxy-pyrimidin-4-yl]-[2-(4-methoxy-phenyl)-ethyl]-amine

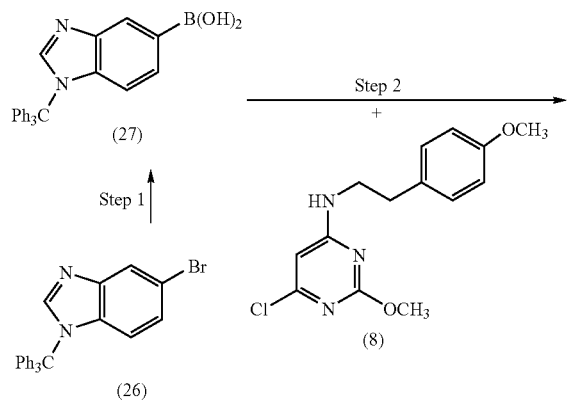

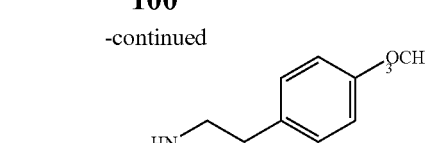

(28)

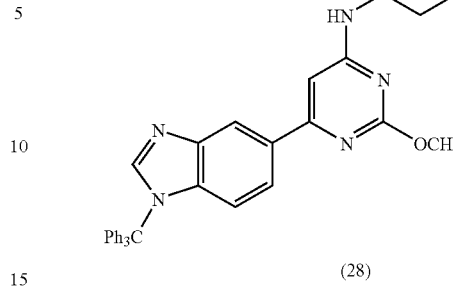

Step 3

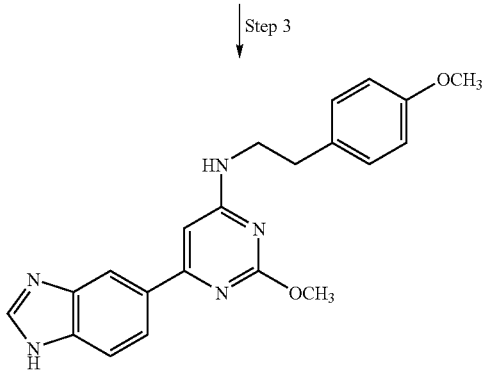

Example 14(a)

Step 1. A mixture of 5-bromo-1-trityl-1H-benzoimidazole [439 mg, 1 mmol, Intermediate (26), prepared as described in Tetrahedron 56, 3245-3253, 2000], bis(pinacolato)diboron (280 mg, 1.1 mmol), potassium acetate (393 mg, 4 mmol), 1,1'-bis(diphenylphosphino)ferrocene-palladium(II)dichloride DCM complex (82 mg, 0.1 mmol), and dimethylsulfoxide (8 mL) and degassed with vacuum/nitrogen several times, is stirred at 85° C. for 2 hours. The reaction mixture is partitioned between EtOAc and water. The organic phase is separated and the aqueous phase further extracted with ethyl acetate. The combined organic phases are dried over magnesium sulfate, filtered and concentrated to provide a solid, which is subjected to flash column chromatography on silica gel eluting with EtOAc and cyclohexane to afford 1-trityl-1H-benzoimidazol-5-ylboronic acid [500 mg, Intermediate (27)].

Step 2. By proceeding in a similar manner as above in Example 1 but substituting 1-trityl-1H-benzoimidazol-5-ylboronic acid [Intermediate (27)] for 5-(dihydroxylboryl)-2-thiophenecarboxylic acid there is prepared [2-(4-methoxyphenyl)-ethyl]-[2-methoxy-6-(1-trityl-1H-benzoimidazol-5-yl)-pyrimidin-4-yl]-amine [Intermediate (28)].

Step 3. A mixture of [2-(4-methoxy-phenyl)-ethyl]-[2-methoxy-6-(1-trityl-1H-benzoimidazol-5-yl)-pyrimidin-4-yl]-amine [300 mg, 0.485 mmol, Intermediate (28)], DCM (5 mL), trifluoroacetic acid (2 mL) and water (5%) is stirred at ambient temperature. The reaction mixture is concentrated by rotary evaporator to remove the solvent. The residue is taken up in saturated sodium bicarbonate solution and this solution is extracted with ethyl acetate. The extract is dried over magnesium sulfate, filtered and concentrated to provide a solid, which is subjected to flash column chromatography on silica gel eluting with 5% MeOH in DCM to afford [6-(1H-benzoimidazol-5-yl)-2-methoxy-pyrimidin-4-yl]-[2-(4-methoxy-phenyl)-ethyl]-amine [90 mg, 49%, Example 14(a)]. LCMS: $R_T$=4.73 minutes, MS: 376 (M+H). $IC_{50}$=2.7 nM (b) [6-(1H-Benzotriazol-5-yl)-2-methoxy-pyrimidin-4-yl]-[2-(4-methoxy-phenyl)-ethyl]-amine

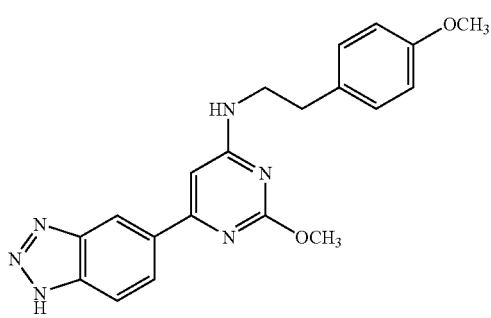

By proceeding in a similar manner as above in Example 14(a) but (i) substituting 5-bromo-1-trityl-1H-benzotriazole for 5-bromo-1-trityl-1H-benzoimidazole in Step 1 to obtain 1-trityl-1H-benzotriazol-5-ylboronic acid; (ii) substituting 1-trityl-1H-benzotriazol-5-ylboronic acid for 1-trityl-1H-benzoimidazol-5-ylboronic acid in step 2 to obtain [2-(4-methoxy-phenyl)-ethyl]-[2-methoxy-6-(1-trityl-1H-benzotriazol-5-yl)-pyrimidin-4-yl]-amine (130 mg, 0.21 mmol); (iii) substituting [2-(4-methoxy-phenyl)-ethyl]-[2-methoxy-6-(1-trityl-1H-benzotriazol-5-yl)-pyrimidin-4-yl]-amine for [2-(4-methoxy-phenyl)-ethyl]-[2-methoxy-6-(1-trityl-1H-benzoimidazol-5-yl)-pyrimidin-4-yl]-amine in step 3, there is prepared [6-(1H-benzotriazol-5-yl)-2-methoxy-pyrimidin-4-yl]-[2-(4-methoxy-phenyl)-ethyl]-amine [25 mg, 32%, Example 14(b)]. LCMS: $R_T$=5.65 minutes, MS: 377 (M+H). $^1$H NMR [(CD$_3$)$_2$SO]: δ 8.55 (1H, s), 7 (2H, m), 7.58 (1H, s), 7.22 (2H, d, J=9.2 Hz), 6.85 (2H, d, J=9.2 Hz), 6.75 (1H, s), 3.95 (3H, s), 3.72 (3H, s), 3.55 (2H, m), 2.8 (2H, t, J=6.8 Hz).

(c) 6-{2-Methoxy-6-[2-(4-methoxy-phenyl)-ethylamino]-pyrimidin-4-yl}-3H-benzooxazol-2-one

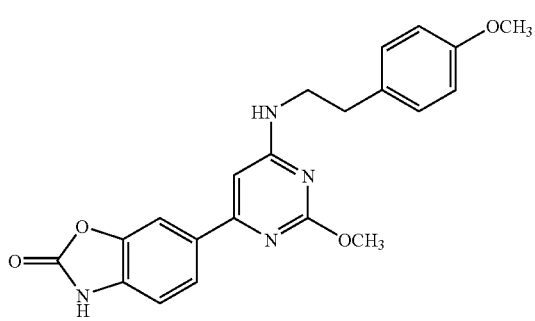

By proceeding in a similar manner as above in Example 14(a) but (i) substituting 5-bromo-1-trityl-1,3-dihydro-benzoimidazol-2-one for 5-bromo-1-trityl-1H-benzoimidazole in Step 1 to obtain 2-oxo-2,3-dihydro-benzooxazole-6-boronic acid; (iii) substituting 2-oxo-2,3-dihydro-benzooxazole-6-boronic acid for 1-trityl-1H-benzoimidazol-5-ylboronic acid in step 2 to obtain 6-{2-methoxy-6-[2-(4-methoxy-phenyl)-ethylamino]-pyrimidin-4-yl}-3-trityl-3H-benzooxazol-2-one; (iii) substituting 6-{2-methoxy-6-[2-(4-methoxy-phenyl)-ethyl amino]-pyrimidin-4-yl}-3-trityl-3H-benzooxazol-2-one ((52 mg) for [2-(4-methoxy-phenyl)-ethyl]-[2-methoxy-6-(1-trityl-1H-benzoimidazol-5-yl)-pyrimidin-4-yl]-amine in step 3, and subjecting the crude product to flash column chromatography on silica gel eluting with a mixture of EtOAc and cyclohexane, there is prepared 6-{2-methoxy-6-[2-(4-methoxy-phenyl)-ethylamino]-pyrimidin-4-yl}-3H-benzooxazol-2-one [19 mg, 59%, Example 14(c)]. LCMS: $R_T$=5.84 minutes. MS: 393 (M+H). $^1$H NMR [(CD$_3$)$_2$SO]: δ 11.8 (1H, s), 7.8 (1H, s), 7.5 (1H, s), 7.18 (1H, s), 7.18 (2H, d, J=9.2 Hz), 6.85 (2H, d, J=9.2 Hz), 6.6 (1H, s), 3.9 (3H, s), 3.7 (3H, s), 3.55 (2H, m), 2.8 (2H, t, J=6.8 Hz). $IC_{50}$=7 nM Example 15

(a) 3-{2-Methoxy-6-[2-(4-methoxy-phenyl)-ethylamino]-pyrimidin-4-yl}-phenol hydrochloride

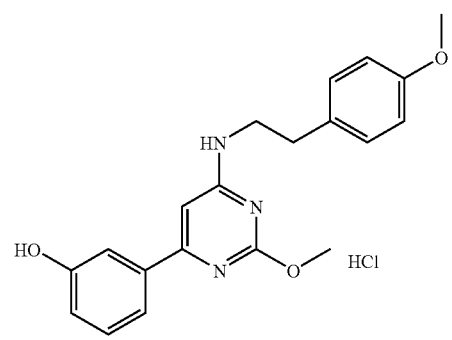

To a solution of 3-{2-Methoxy-6-[2-(4-methoxy-phenyl)-ethylamino]-pyrimidin-4-yl)}-phenol [0.3 g, Example 35(p)] in EtOAc is added a saturated solution of hydrogen chloride in EtOAc (3 mL) and the resulting precipitate is filtered, and dried to afford 3-{2-methoxy-6-[2-(4-methoxy-phenyl)-ethylamino]-pyrimidin-4-yl}-phenol hydrochloride [0.31 g, Example 15(a)] as a solid. LCMS: $R_T$=2.55 minutes, MS: 352 (M+H). $^1$H NMR [(CD$_3$)$_2$SO]: δ 10.1 (1H, brs), 9.6 (1H, brs), 7.64-7.54 (1H, m), 7.34 (1H, t, J=8.1 Hz), 7.21-7.12 (4H, m), 7.02 (1H, d, J=7.5 Hz), 6.85 (2H, d, J=8.4 Hz), 6.67 (1H, s), 4.06 (3H, s), 3.71 (3H, s), 3.7-3.6 (2H, m), 2.85 (2H, t, J=7.2 Hz). $IC_{50}$=0.1 nM (b) 3-{6-[2-(2,4-dichloro-phenyl)-ethylamino]-2-methoxy-pyrimidin-4-yl}-benzoic acid hydrochloride

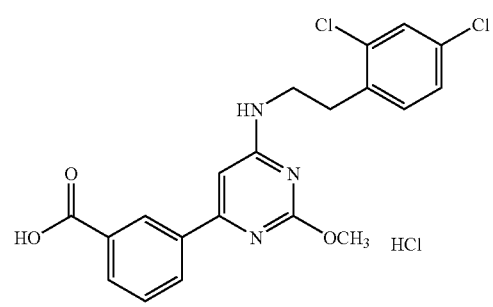

A suspension of 3-{6-[2-(2,4-dichloro-phenyl)-ethylamino]-2-methoxy-pyrimidin-4-yl}-benzoic acid [0.2 g, Example 35(w)] in DCM and MeOH is treated with a saturated solution of hydrogen chloride in EtOAc (0.5 mL), and chromatographed on silica gel eluting with 10% MeOH in DCM to provide the product, which is dissolved in acetonitrile/water/hydrochloric acid, and lyophilized to give 3-{6-[2-(2,4-dichloro-phenyl)-ethylamino]-2-methoxy-pyrimidin-4-yl}-benzoic acid hydrochloride [172 mg, Example 15(b)] as a solid. LCMS: $R_T$=2.72 minutes, MS: 417 (M+H).

(c) 3-{6-[2-(2-Chloro-6-fluoro-phenyl)-ethylamino]-2-methoxy-pyrimidin-4-yl}-benzoic acid hydrochloride

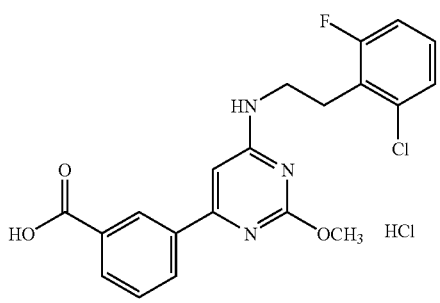

A solution of 3-{6-[2-(2-chloro-6-fluoro-phenyl)-ethylamino]-2-methoxy-pyrimidin-4-yl}-benzoic acid [0.1 g, Example 20(b)] in DCM and MeOH is treated with a saturated solution of hydrogen chloride in EtOAc (2 mL) and the mixture is concentrated, dissolved in acetonitrile and water, and lyophilized to afford 3-{6-[2-(2-chloro-6-fluoro-phenyl)-ethylamino]-2-methoxy-pyrimidin-4-yl}-benzoic acid hydrochloride [83 mg, Example 15(c)] as a solid. LCMS: $R_T$=2.85 minutes, MS: 402 (M+H).

(d) 2-(3-{6-[2-(2,4-Dichloro-phenyl)-ethylamino]-2-methoxy-pyrimidin-4-yl}-phenyl)-2-methyl-propionic acid hydrochloride

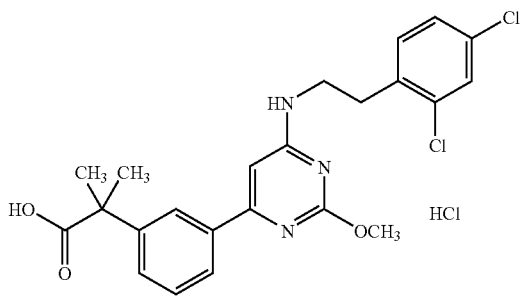

A solution of 2-(3-{6-[2-(2,4-dichloro-phenyl)-ethylamino]-2-methoxy-pyrimidin-4-yl}-phenyl)-2-methyl-propionic acid [4.3 g, 9.35 mmol, Example 49(b)] in MeOH is treated with 1 M hydrogen chloride in ether (18 mL). The mixture is evaporated and the resulting oil is dissolved in acetone (10 mL). After 2 minutes a solid precipitated. This is filtered giving 2-(3-{6-[2-(2,4-Dichloro-phenyl)-ethylamino]-2-methoxy-pyrimidin-4-yl}-phenyl)-2-methyl-propionic acid hydrochloride [4.043 g, 87%, Example 15(d)] as a solid. LC/MS: $R_T$=2.42 minutes, MS: 460 (M+H). $^1$H NMR [(CD$_3$)$_2$SO]: □ 12.4 (1H, br s), 7.36-7.8 (7H, m), 6.6 (1H, s), 4 (3H, s), 3.7 (2H, m), 3.02 (2H, m), 1.54 (6H, s). IC$_{50}$=0.3 nM Example 16

(a) [2-(3,4-Dimethoxy-phenyl)-ethyl]-[6-(3,4-dimethoxy-phenyl)-2-methylsulfanyl-pyrimidin-4-yl]-amine

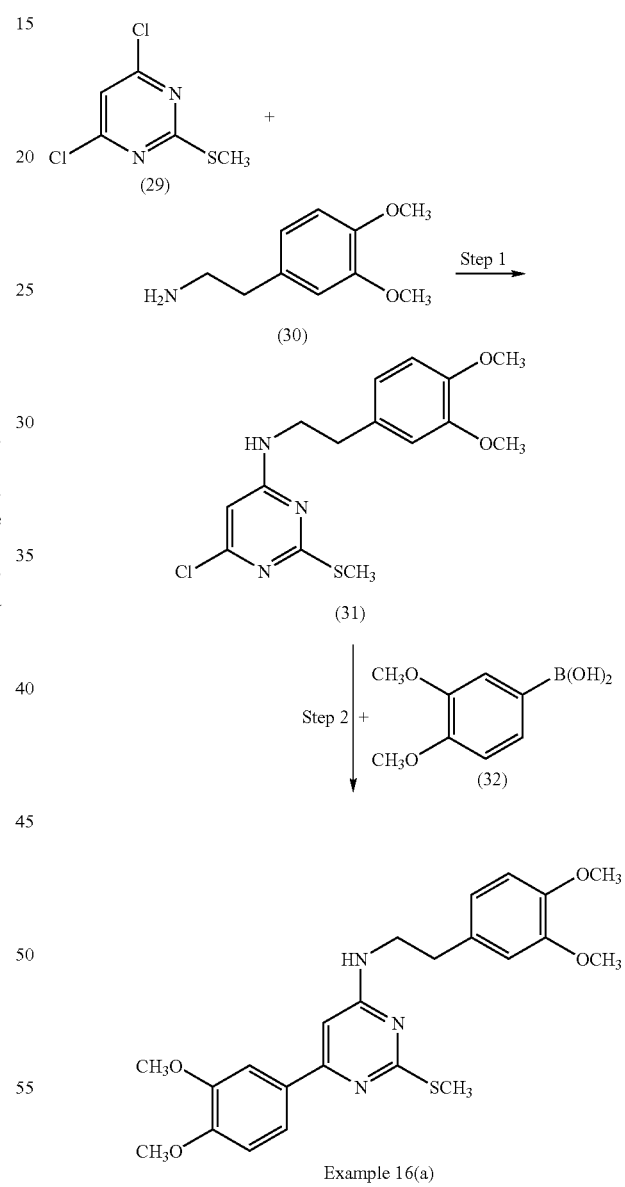

Example 16(a)

Step 1. A mixture of 4,6-dichloro-2-methylsulfanyl-pyrimidine [1 g, 5.1 mmol, Intermediate (29)], 3,4-dimethoxyphenyl ethylamine [0.98 g-, 54 mmol, Intermediate (30)], and sodium bicarbonate (0.86 g, 10 mmol) in EtOH (5 mL) is heated to reflux. After stirring, at 85° C. for 4 hours the mixture is diluted with water and filtered. The solid is washed with water, and dried to afford (6-chloro-2-methylsulfanylpyrimidin-4-yl)-[2-(3,4-dimethoxy-phenyl)-ethyl]-amine [1.8 g, Intermediate (31)]. LCMS: $R_T$=3.25 minutes, MS: 340 (M+H).

Step 2. By proceeding in a similar manner to Example 35(o) above but substituting commercially available 3,4-dimethoxy-phenyl-boronic acid [intermediate (32)] for 2-methoxy-5-pyridyl-boronic subjecting the crude reaction product to flash column chromatography on silica gel eluting with 50% EtOAc in heptane, there is prepared [2-(3,4-dimethoxy-phenyl)-ethyl]-[6-(3,4-dimethoxy-phenyl)-2-methylsulfanyl-pyrimidin-4-yl]-amine [0.73 g, Example 16(a)]. LCMS: $R_T$=2.72 minutes, MS: 442 (M+H).

(b) 3-{6-[2-(3,4-Dimethoxy-phenyl)-ethylamino]-2-methylsulfanyl-pyrimidin-4-yl}-benzoic acid

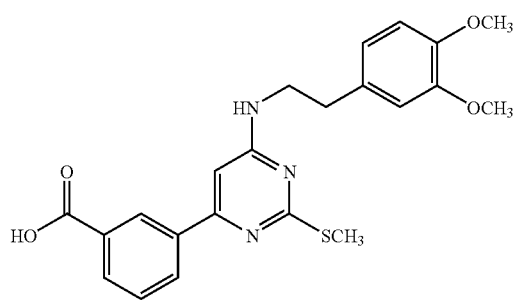

By proceeding in a similar manner to Example 16(a) above but using commercially available 3-carboxy-phenyl-boronic acid, and (6-chloro-2-methylsulfanyl-pyrimidin-4-yl)-[2-(3,4-dimethoxy-phenyl)-ethyl]-amine (0.57 g) in Step 2, and extracting the reaction mixture (adjusted to pH 2) with EtOAc followed by evaporation of the organic extract, there is prepared 3-{6-[2-(3,4-dimethoxy-phenyl)-ethylamino]-2-methylsulfanyl-pyrimidin-4-yl}-benzoic acid [0.48 g, Example 16(b)]. LCMS: $R_T$=2.75 minutes, MS: 426 (M+H). $IC_{50}$=243 nM (c) [2-(4-Methoxy-phenyl)-ethyl]-[6-(3-methoxy-phenyl)-2-methylsulfanyl-pyrimidin-4-yl]-amine

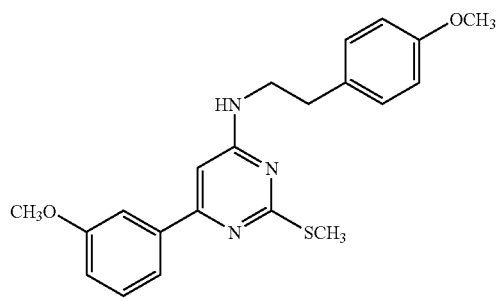

By proceeding in a similar manner to Example 16(a) above but (i) substituting 4-methoxy-phenylethylamine for 3,4-dimethoxy-phenylethylamine, in Step 1, to obtain (6-chloro-2-methylsulfanyl-pyrimidin-4-yl)-[2-(4-methoxy-phenyl)-ethyl]-amine [3 g, MS: 310 (M+H)] and (ii) substituting the (6-chloro-2-methylsulfanyl-pyrimidin-4-yl)-[2-(4-methoxy-phenyl)-ethyl]-amine (g), for (6-chloro-2-methoxy-pyrimidin-4-yl)-[2-(4-methoxy-phenyl)-ethyl]-amine, and substituting 3-methoxy-phenyl-boronic acid for 2-methoxy-5-pyridyl-boronic acid, in Step 2, and subjecting the crude product to short-path silica chromatography eluting with ethyl acetate, there is prepared [2-(4-methoxy-phenyl)-ethyl]-[6-(3-methoxy-phenyl)-2-methylsulfanyl-pyrimidin-4-yl]-amine [1.5 g, Example 16(c)]. MS: 382 (M+H).

Example 17

(a) [2-(3,4-Dimethoxy-phenyl)-ethyl]-[6-(3,4-dimethoxy-phenyl)-2-isopropoxy-pyrimidin-4-yl]-amine

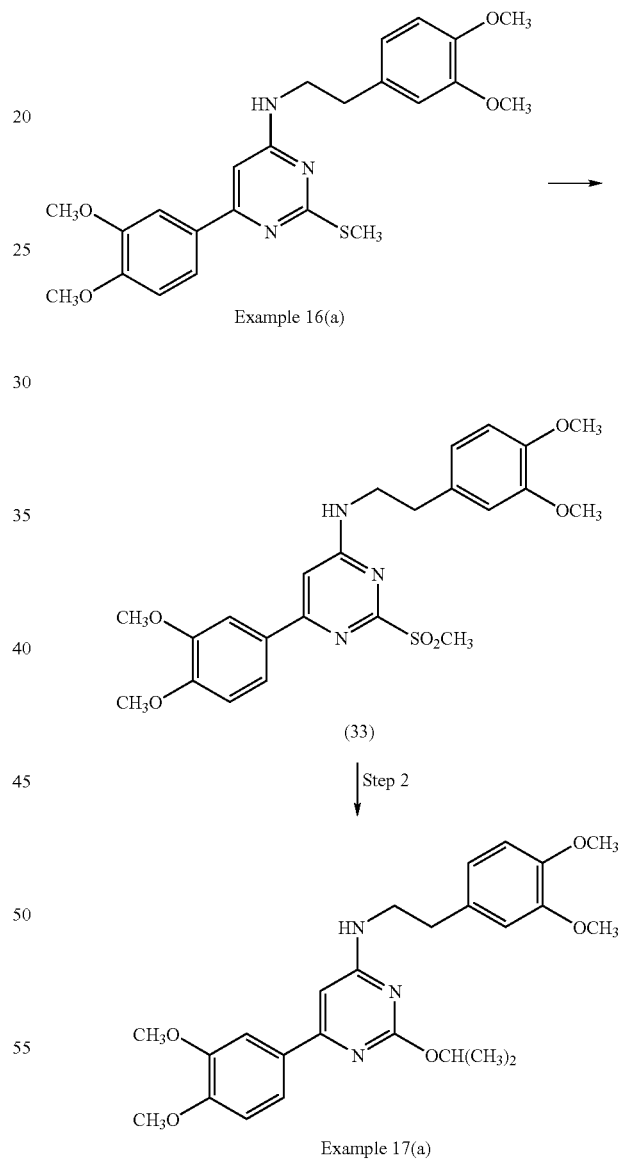

Step 1. A solution of [2-(3,4-dimethoxy-phenyl)-ethyl]-[6-(3,4-dimethoxy-phenyl)-2-methylsulfanyl-pyrimidin-4-yl]-amine [0.73 g, 1.68 mmol, Example 16(a)] in DCM (12 mL)

is treated with 3-chloroperoxybenzoic acid (70%, 0.9 g, 3.6 mmol). After 3 hours at 20° C., the mixture is quenched with 1 M sodium hydroxide solution (10 mL), and extracted twice with DCM (50 mL). The combined extracts are dried over magnesium sulfate, filtered, concentrated, and the residue subjected to chromatography on silica gel eluting with 70% EtOAc in heptane to afford [2-(3,4-dimethoxy-phenyl)-ethyl]-[6-(3,4-dimethoxy-phenyl)-2-methanesulfonyl-pyrimidin-4-yl]-amine [0.51 g, 64%, Intermediate (33)]. LCMS: $R_T$=2.97 minutes, MS: 474 (M+H).

Step 2. A solution of [2-(3,4-dimethoxy-phenyl)-ethyl]-[6-(3,4-dimethoxy-phenyl)-2-methanesulfonyl-pyrimidin-4-yl]-anine [200 mg, 0.42 mmol, Intermediate (33)], and isopropyl alcohol (1 mL) in N,N'-dimethylformamide (2 mL) at 0° C. is treated with sodium hydride (60%, 102 mg, 12.7 mmol). After 1 hour at 20° C., the mixture is concentrated, and extracted twice with EtOAc (50 mL). The combined extracts are washed twice with water, dried over magnesium sulfate, filtered, and concentrated. The residue is subjected to chromatography on silica gel eluting with 60% EtOAc in heptane to afford [2-(3,4-dimethoxy-phenyl)-ethyl]-[6-(3,4-dimethoxy-phenyl)-2-isopropoxy-pyrimidin-4-yl]-amine [0.15 g, 79%, Example 17(a)] LCMS: $R_T$=2.57 minutes, MS: 454 (M+H). $^1$H NMR (300 MHz, CDCl$_3$) □7.64 (1H, d, J=2.1 Hz), 7.55 (1H, dd, J=8.4, 2.4 Hz), 6.91 (1H, d, J=8.4 Hz), 6.86-6.76 (3H, m), 6.3 (1H, s), 5.43-5.34 (1H, m), 4.83 (1H, brs), 3.99 (3H, s), 3.95 (3H, s), 3.89 (3H, s), 3.75-3.65 (2H, m), 2.91 (2H, t, J=6.9 Hz) 1.45 (6H, d, J=6 Hz). IC$_{50}$=6728 nM (b) [6-(3,4-Dimethoxy-phenyl)-2-ethoxy-pyrimidin-4-yl]-[2-(3,4-dimethoxy-phenyl)-ethyl]-amine

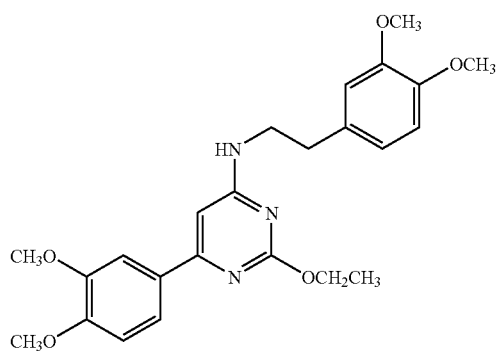

By proceeding in a similar manner to Example 17(a) above but substituting EtOH for isopropyl alcohol and 1,2-dimethoxyethane for N,N'-dimethylformamide in Step 2, and subjecting the crude product to a short-path silica gel filtration, there is prepared [6-(3,4-dimethoxy-phenyl)-2-ethoxy-pyrimidin-4-yl]-[2-(3,4-dimethoxy-phenyl)-ethyl]-amine [54 mg, Example 17(b)]. LCMS: $R_T$=2.62 minutes, MS: 440 (M+H). IC$_{50}$=655 nM Example 18

[2-Ethyl-6-(3-methoxy-phenyl)-pyrimidin-4-yl]-[2-(4-methoxy-phenyl)-ethyl]-amine

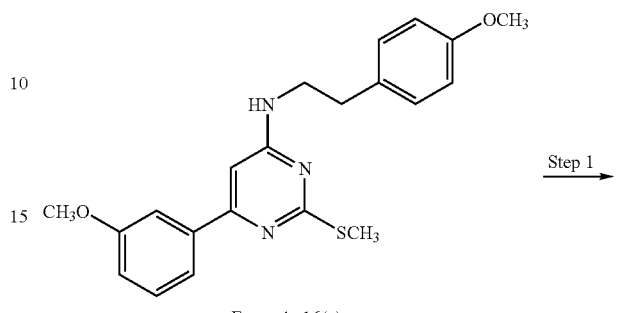

Example 16(c)

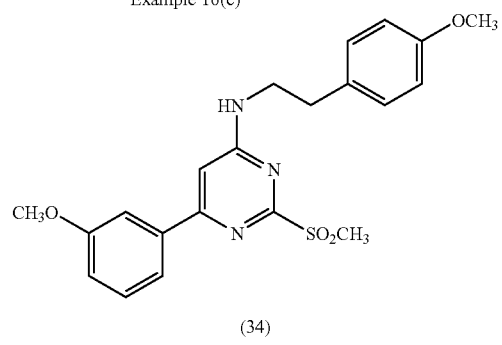

(34)

Step 2

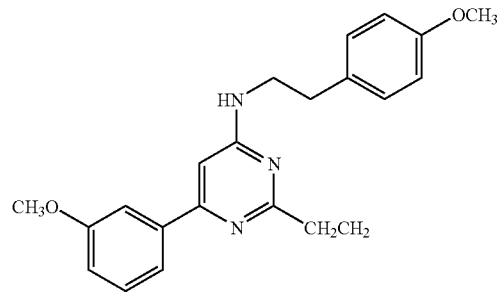

Example 18

Step 1. A solution of [2-(4-methoxy-phenyl)-ethyl]-[6-(3-methoxy-phenyl)-2-methylsulfanyl-pyrimidin-4-yl]-amine [1.5 g, 3.9 mmol, Example 16(c)] in DCM (30 mL) is treated with 3-chloroperoxybenzoic acid (70%, 2.1 g, 8.6 mmol). After 3 hours at 20° C., the mixture is filtered through basic alumina eluting with ethyl acetate, and the solution is concentrated. The residue is subjected to chromatography on silica gel eluting with 50% EtOAc in heptane to afford [2-methanesulfonyl-6-(3-methoxy-phenyl)-pyrimidin-4-yl]-[2-(4-methoxy-phenyl)-ethyl]-amine [1 g, 62%, Intermediate (34)] MS: 414 (M+H).

Step 2. A solution of [2-methanesulfonyl-6-(3-methoxy-phenyl)-pyrimidin-4-yl]-[2-(4-methoxy-phenyl)-ethyl]-amine [0.14 g, 0.34 mmol, Intermediate (34)] in THF (5 mL) is treated with a 1 M solution of ethyl magnesium bromide (5 mL, 5 mmol) at −50° C. The reaction mixture is allowed to warm to room temperature over 2 hours the treated with MeOH (0.5 mL), concentrated, and partitioned between EtOAc and water. The aqueous phase is further extracted with ethyl acetate. The residue is subjected to chromatography on silica gel eluting with 40% EtOAc in heptane to afford 12 ethyl-6-(3-methoxy-phenyl)-pyrimidin-4-yl]-[2-(4-methoxy-phenyl)-ethyl]-amine [89 mg, 72%, Example 18]. LCMS: $R_T$=2.38 minutes, MS: 364 (M+H). $IC_{50}$=219 nM Example 19

6-(3-Methoxy-phenyl)-N*4*-[2-(4-methoxy-phenyl)-ethyl]-N*2*,N*2*-dimethyl-pyrimidine-2,4-diamine hydrochloride

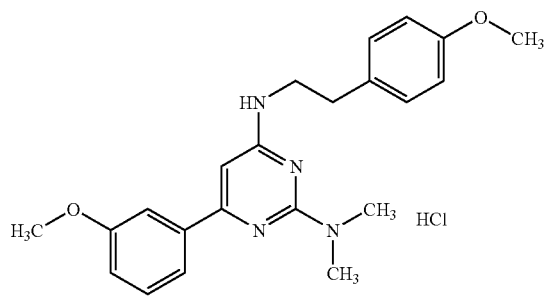

A solution of [2-methanesulfonyl-6-(3-methoxy-phenyl)-pyrimidin-4-yl]-[2-(4-methoxy-phenyl)-ethyl]-amine [200 mg, 0.42 mmol, Intermediate (34) prepared as in Example 18, step 1] in a 2M solution of dimethylamine in MeOH (2 mL, 4 mmol) is heated to 150° C. for 20 minutes in a Microwave. The mixture is concentrated, and the residue is subjected to chromatography on silica gel eluting with 70% EtOAc in heptane to afford 6-(3-methoxy-phenyl)-N*4*-[2-(4-methoxy-phenyl)-ethyl]-N*2*,N*2*-dimethyl-pyrimidine-2,4-diamine, which is treated with a solution of saturated hydrogen chloride in EtOAc (1 mL). The resulting precipitate is filtered and dried to afford 6-(3-methoxy-phenyl)-N*4*-[2-(4-methoxy-phenyl)-ethyl]-N*2*,N*2*-dimethyl-pyrimidine-2,4-diamine hydrochloride [0.11 g, 70%, Example 19] as a solid. LCMS: $R_T$=2.85 minutes, MS: 379 (M+H). $^1$H NMR (300 MHz, CD$_3$OD) □7.46 (1H, t, J=8.1 Hz), 7.26-7.1 (5H, m), 6.83 (2H, d, J=8.1 Hz), 6.27 (1H, s), 4.85 (1H, brs), 3.87 (3H, s), 3.74 (3H, s), 3.71 (2H, t, J=7.2 Hz), 3.28 (6H, s), 2.89 (2H, t, J=7.2 Hz). $IC_{50}$=4652 nM Example 20

(a) 2-Fluoro-5-{2-methoxy-6-[2-(4-methoxy-phenyl)-ethylamino]-pyrimidin-4-yl}-benzoic acid

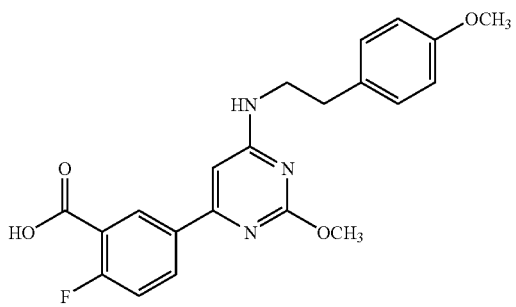

A solution of 2-fluoro-5-{2-methoxy-6-[2-(4-methoxy-phenyl)-ethylamino]-pyrimidin-4-yl}-benzaldehyde [120 mg, 0.31 mmol, Example 35(j)] and 2-methyl-2-butene (2.93 mL, 28 mmol) in t-butanol (4 mL) and THF (2 mL), is treated with a solution of sodium dihydrogen phosphate monohydrate (303 mg, 2.2 mmol) and sodium chlorite (0.28 g, 3.2 mmol) in water (2 mL) at room temperature. After 15 hours at 20° C., the mixture is concentrated and diluted with water. The mixture is adjusted to pH 3 and the resulting solid is filtered and dried to afford 2-fluoro-5-{2-methoxy-6-[2-(4-methoxy-phenyl)-ethylamino]-pyrimidin-4-yl}-benzoic acid. [118 mg, 96%, Example 20(a)]. LCMS: $R_T$=2.38 minutes, MS: 398 (M+H). $IC_{50}$=0.4 nM (b) 3-{6-[2-(2-Chloro-6-fluoro-phenyl)-ethylamino]-2-methoxy-pyrimidin-4-yl}-benzoic acid

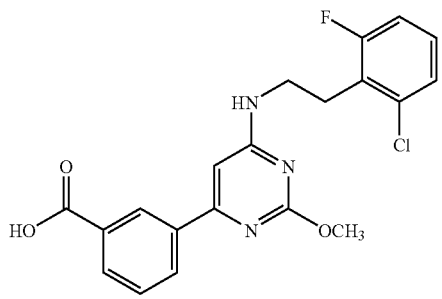

By proceeding in a similar manner to Example 20(a) above but substituting 3-{6-[2-(2-chloro-6-fluoro-phenyl)-ethylamino]-2-methoxy-pyrimidin-4-yl}-benzaldehyde [Example 35(v)] for 2-fluoro-5-{2-methoxy-6-[2-(4-methoxy-phenyl)-ethylamino]-pyrimidin-4-yl}-benzaldehyde, there is prepared 3-{6-[2-(2-chloro-6-fluoro-phenyl)-ethylamino]-2-methoxy-pyrimidin-4-yl}-benzoic acid [1 g, Example 20(b)]. LCMS: $R_T$=2.92 minutes, MS: 402 (M+H).

(c) 2-Methoxy-5-{2-methoxy-6-[2-(4-methoxy-phenyl)-ethylamino]-pyrimidin-4-yl}-benzoic acid

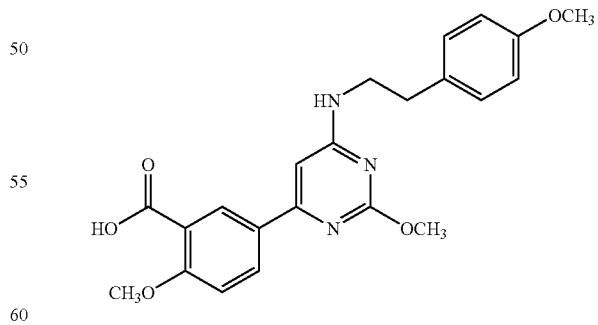

By proceeding in a similar manner to Example 20(a) above but substituting 2-methoxy-5-{2-methoxy-6-[2-(4-methoxy-phenyl)-ethylamino]-pyrimidin-4-yl}-benzaldehyde [120 mg, Example 35(y)] for 2-fluoro-5-{2-methoxy-6-[2-(4-methoxy-phenyl)-ethylamino]-pyrimidin-4-yl}-benzaldehyde, there is prepared 2-methoxy-5-{2-methoxy-6-[2-(4- methoxy-phenyl)-ethylamino]-pyrimidin-4-yl}-benzoic acid [150 mg, Example 20(c)]. LCMS: $R_T$=2.22 minutes, MS: 410 (M+H).

Example 21

(a) [2-Methoxy-6-(1-oxy-pyridin-3-yl)-pyrimidin-4-yl]-[2-(4-methoxy-phenyl)-ethyl]-amine

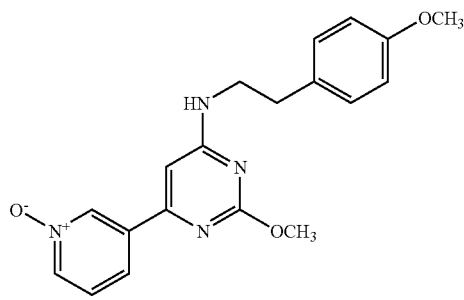

A solution of [2-methoxy-(6-pyridin-3-yl)-pyrimidin-4-yl]-[2-(4-methoxy-phenyl)-ethyl]-amine [0.24 g, 0.71 mmol, Example 35(x)] in DCM (10 mL) is treated with 3-chloroperoxybenzoic acid (70%, 0.21 g, 0.85 mmol). After 15 hours at 20° C., the mixture is quenched with 2 M sodium hydroxide solution (10 mL), and extracted twice with DCM (50 mL). The combined extracts are dried over magnesium sulfate, filtered, concentrated, and subjected to chromatography on silica gel eluting with 5% MeOH in DCM to afford [2-methoxy-6-(1-oxy-pyridin-3-yl)-pyrimidin-4-yl]-[2-(4-methoxy-phenyl)-ethyl]-amine [0.14 g, 56%, Example 21(a)] LCMS: $R_T$=2.69 minutes, MS: 353 (M+H). $IC_{50}$=149 nM (b) [2-(2,2-Difluoro-benzo[1,3]dioxol-5-yl)-ethyl]-[2-methoxy-6-(1-oxy-pyridin-3-yl)-pyrimidin-4-yl]-amine

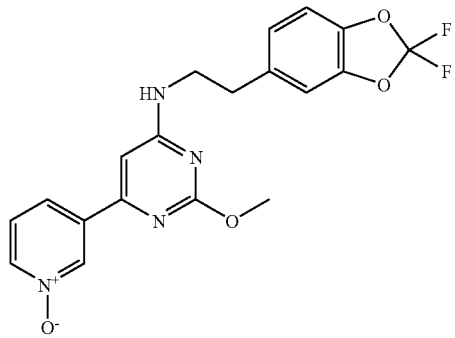

By proceeding in a similar manner to Example 21(a) but substituting [2-(2,2-difluoro-benzo[1,3]dioxol-5-yl)-ethyl]-(2-methoxy-6-pyridin-3-yl-pyrimidin-4-yl)-amine [21 mg, 0.0544 mmol, see example 46(b)] for [2-(4-methoxy-phenyl)-ethyl]-(2-methoxy-6-pyridin-3-yl-pyrimidin-4-yl)-amine with chloroform as solvent and subjecting the product to silica gel chromatography eluting with 0-10% MeOH in DCM, there is prepared [2-(2,2-difluoro-benzo[1,3]dioxol-5-yl)-ethyl]-[2-methoxy-6-(1-oxy-pyridin-3-yl)-pyrimidin-4-yl]-amine [20 mg, Example 21(b)] as a solid. LC/MS: $R_T$=2.85 minutes, MS: 403 (M+H). $^1$H NMR (300 MHz, CDCl$_3$): □8.8 (1H, s), 8.2 (1H, m), 7.84 (1H, m), 7.34 (1H, m), 6.86-7 (3H, m), 6.36 (1H, s), 5.36 (1H, br m), 3.99 (3H, s), 3.69 (2H, m), 2.96 (2H, m). $IC_{50}$=2155 nM

Example 22

(a) 2-(3-{2-Methoxy-6-[2-(4-methoxy-phenyl)-ethylamino]-pyrimidin-4-yl}-phenoxy)-2-methyl-propionic acid ethyl ester

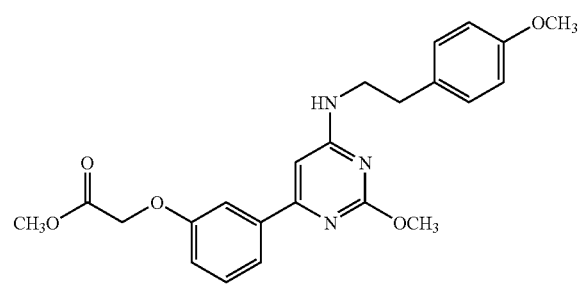

A mixture of 3-{2-methoxy-6-[2-(4-methoxy-phenyl)-ethylamino]-pyrimidin-4-yl}-phenol (400 mg, 1.14 mmol, Example 35(p)], Cs$_2$CO$_3$ (1.1 g, 3.41 mmol), and ethyl 2-bromo-2-methylpropionate (0.5 mL, 3.41 mmol) in N,N'-dimethylformamide (4 mL) is heated to 60° C. for 15 hours. The reaction mixture is diluted with water, and extracted with ethyl acetate. The extracts are dried over magnesium sulfate, filtered and concentrated. The residue is subjected to chromatography on silica gel eluting with 50% EtOAc in heptane to afford 2-(3-{2-methoxy-6-[2-(4-methoxy-phenyl)-ethylamino]-pyrimidin-4-yl}-phenoxy)-2-methyl-propionic acid ethyl ester [0.33 g, 62%, Example 22(a)]. LCMS: $R_T$=2.95 minutes, MS: 466 (M+H). $IC_{50}$=60 nM (b) (3-{2-Methoxy-6-[2-(4-methoxy-phenyl)-ethylamino]-pyrimidin-4-yl}-phenoxy)-acetic acid methyl ester By proceeding in a similar manner to Example 22(a) but substituting methyl bromoacetate for ethyl 2-bromo-2-methylpropionate, and carrying out the reaction at room temperature, there is prepared (3-{2-methoxy-6-[2-(4-methoxy-phenyl)-ethylamino]-pyrimidin-4-yl}-phenoxy)-acetic acid methyl ester [430 mg, Example 22(b)]. LCMS: $R_T$=2.52 minutes, MS: 424 (M+H).

(c) (3-{6-[2-(2,4-Dichloro-phenyl)-ethylamino]-2-methoxy-pyrimidin-4-yl}-phenoxy)-acetic acid methyl ester

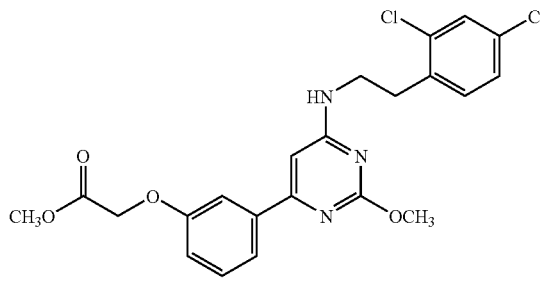

By proceeding in a similar manner to Example 22(a) but substituting methyl bromoacetate for ethyl 2-bromo-2-methylpropionate, and substituting 3-{6-[2-(2,4-dichloro-phenyl)-ethylamino]-2-methoxy-pyrimidin-4-yl}-phenol [Example 35(i)] for 3-{2-methoxy-6-[2-(4-methoxy-phenyl)-ethylamino]-pyrimidin-4-yl}-phenol, and carrying out the reaction at room temperature, there is prepared (3-{6-[2-(2,4-dichloro-phenyl)-ethylamino]-2-methoxy-pyrimidin-4-yl}-phenoxy)-acetic acid methyl ester [430 mg, Example 22(c)]. LCMS: $R_T$=2.88 minutes, MS: 462 (M+H). $IC_{50}$=0.6 nM

(d) (5-{6-[2-(2-Chloro-6-fluoro-phenyl)-ethylamino]-2-methoxy-pyrimidin-4-yl}-2-oxo-2H-pyridin-1-yl)-acetic acid methyl ester

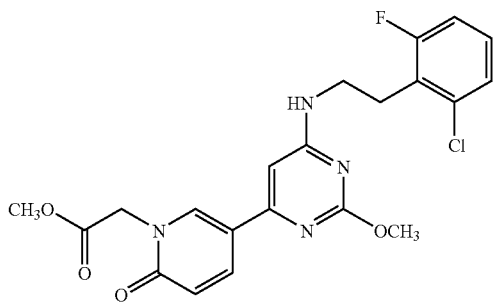

By proceeding in a similar manner to Example 22(a) but substituting methyl bromoacetate for ethyl 2-bromo-2-methylpropionate, and substituting 3-{6-[2-(2-chloro-6-fluoro-phenyl)-ethylamino]-2-methoxy-pyrimidin-4-yl}-1H-pyridin-2-one [Example 32] for 3-{2-methoxy-6-[2-(4-methoxy-phenyl)-ethylamino]-pyrimidin-4-yl}-phenol, and carrying out the reaction at room temperature, there is prepared (5-{6-[2-(2-chloro-6-fluoro-phenyl)-ethylamino]-2-methoxy-pyrimidin-4-yl}-2-oxo-2H-pyridin-1-yl)-acetic acid methyl ester [400 mg, Example 22(d)]. LCMS: $R_T$=2.89 minutes, MS: 447 (M+H). $IC_{50}$=14 nM

(e) (3-{6-[2-(2,4-Dichloro-phenyl)-ethylamino]-2-methoxy-pyrimidin-4-yl}-phenoxy)-acetonitrile

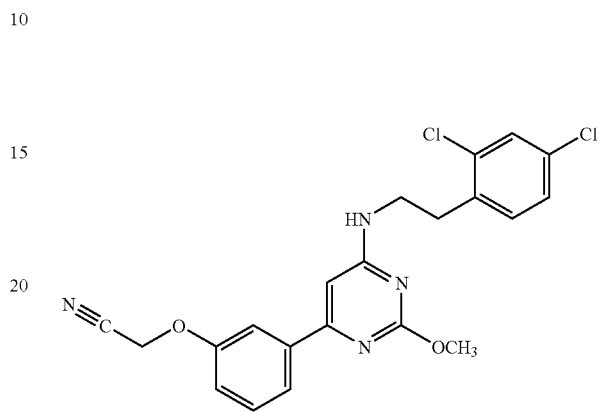

By proceeding in a similar manner to Example 22(a) but using bromoacetonitrile (0.11 mL, 1.5 mmol) and 3-{6-[2-(2,4-dichloro-phenyl)-ethylamino]-2-methoxy-pyrimidin-4-yl}-phenol (400 mg, 1.02 mmol, Example 35(i)], $Cs_2CO_3$ (0.98 g, 3 mmol) and N,N'-dimethylformamide (2 mL) and carrying out the reaction at room temperature there is prepared (3-{6-[2-(2,4-dichloro-phenyl)-ethylamino]-2-methoxy-pyrimidin-4-yl}-phenoxy)-acetonitrile [Example 22(e)]. MS: 429 (M+H). $IC_{50}$=0.4 nM

(f) (3-{6-[2-(2-chloro-6-fluoro-phenyl)-ethylamino]-2-methoxy-pyrimidin-4-yl}-phenoxy)-acetonitrile

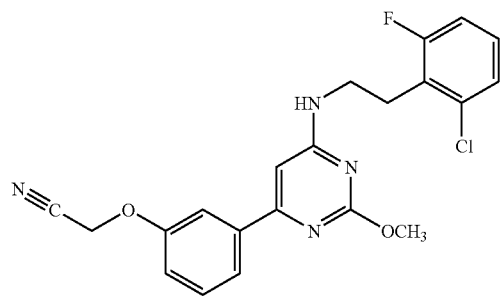

By proceeding in a similar manner to Example 22(a) but using bromoacetonitrile (0.11 mL, 1.5 mmol) and 3-{6-[2-(2-chloro-6-fluoro-phenyl)-ethylamino]-2-methoxy-pyrimidin-4-yl}-phenol [300 mg, Example 46(e)], $Cs_2CO_3$ (0.785 g) and N,N'-dimethylformamide (2.7 mL) and carrying out the reaction at room temperature there is prepared (3-{6-[2-

(2-chloro-6-fluoro-phenyl)-ethylamino]-2-methoxy-pyrimidin-4-yl}-phenoxy)-acetonitrile [300 mg, Example 22(f)] as a solid. LC/MS: 413 (M+H).

Example 23

(a) 2-(3-{2-Methoxy-6-[2-(4-methoxy-phenyl)-ethylamino]-pyrimidin-4-yl}-phenoxy)-2-methyl-propionic acid

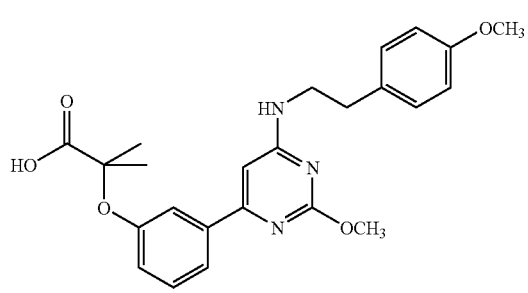

A solution of 2-(3-{2-methoxy-6-[2-(4-methoxy-phenyl)-ethylamino]-pyrimidin-4-yl}-phenoxy)-2-methyl-propionic acid ethyl ester [330 mg, 0.7 mmol, Example 22(a)] in a 2M solution of sodium hydroxide (5 mL, 10 mmol) in MeOH (4 mL), THF (2 mL) and water (4 mL) is heated to 60° C. for 30 minutes. After an additional 5 hours at room temperature, the mixture is concentrated, and diluted with water and ethyl acetate. The solution is acidified with dilute hydrochloric acid to pH, 2.0, and extracted with ethyl acetate. The extracts are dried over magnesium sulfate, filtered, and concentrated to afford 2-(3-{2-methoxy-6-[2-(4-methoxy-phenyl)-ethylamino]-pyrimidin-4-yl}-phenoxy)-2-methyl-propionic acid [0.21 g, 72%, Example 23(a)]. LCMS: $R_T$=2.47 minutes, MS: 438 (M+H).

(b) (3-{2-Methoxy-6-[2-(4-methoxy-phenyl)-ethylamino]-pyrimidin-4-yl}-phenoxy)-acetic acid

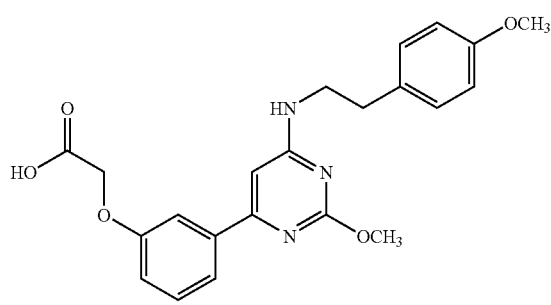

By proceeding in a similar manner to Example 23(a) but substituting (3-{2-methoxy-6-[2-(4-methoxy-phenyl)-ethylamino]-pyrimidin-4-yl}-phenoxy)-acetic acid methyl ester [Example 22(b)] for 2-(3-{2-methoxy-6-[2-(4-methoxy-phenyl)-ethylamino]-pyrimidin-4-yl}-phenoxy)-2-methyl-propionic acid ethyl ester, and carrying out the reaction at room temperature, there is prepared (3-{2-methoxy-6-[2-(4-methoxy-phenyl)-ethylamino]-pyrimidin-4-yl}-phenoxy)-acetic acid [297 mg, Example 23(b)]. LCMS: $R_T$=2.22 minutes, MS: 410 (M+H).

(c) (5-{6-[2-(2-Chloro-6-fluoro-phenyl)-ethylamino]-2-methoxy-pyrimidin-4-yl}-2-oxo-2H-pyridin-1-yl)-acetic acid

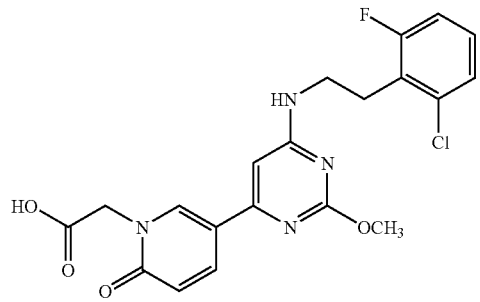

By proceeding in a similar manner to Example 23(a) but substituting (5-{6-[2-(2-chloro-6-fluoro-phenyl)-ethylamino]-2-methoxy-pyrimidin-4-yl}-2-oxo-2H-pyridin-1-yl)-acetic acid methyl ester [Example 22(d)] for 2-(3-{2-methoxy-6-[2-(4-methoxy-phenyl)-ethylamino]-pyrimidin-4-yl}-phenoxy)-2-methyl-propionic acid ethyl ester, and carrying out the reaction at room temperature, there is prepared (5-{6-[2-(2-chloro-6-fluoro-phenyl)-ethylamino]-2-methoxy-pyrimidin-4-yl}-2-oxo-2H-pyridin-1-yl)-acetic acid [79 mg, Example 23(c)]. LCMS: $R_T$=2.28 minutes, MS: 433 (M+H). $IC_{50}$=0.3 nM (d) 2-(3-{6-[2-(2,4-Dichloro-phenyl)-ethylamino]-2-methoxy-pyrimidin-4-yl}-phenoxy)-2-methyl-propionic acid

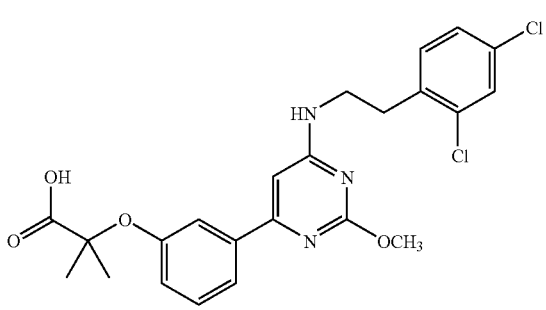

By proceeding in a similar manner to Example 23(a) but substituting 2-(3-{6-[2-(2,4-dichloro-phenyl)-ethylamino]-2-methoxy-pyrimidin-4-yl}-phenoxy)-2-methyl-propionic acid ethyl ester [410 mg, 0.81 mmol, Example 42] for 2-(3-{2-methoxy-6-[2-(4-methoxy-phenyl)-ethylamino]-pyrimidin-4-yl}-phenoxy)-2-methyl-propionic acid ethyl ester there is prepared 2-(3-{6-[2-(2,4-dichloro-phenyl)-ethylamino]-2-methoxy-pyrimidin-4-yl}-phenoxy)-2-methylpropionic acid [386 mg, 100%, Example 23(d)] as a solid. LCMS: $R_T$=2.63 minutes, MS: 476 (M+H).

(e) 2-Chloro-5-{2-methoxy-6-[2-(4-methoxy-phenyl)-ethylamino]-pyrimidin-4-yl}-benzoic acid hydrochloride salt

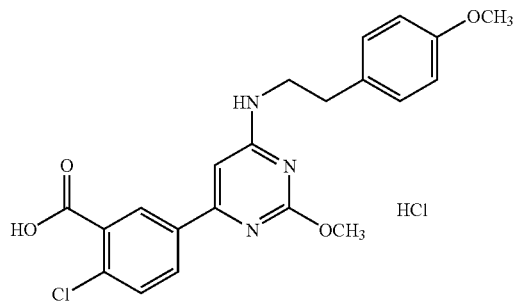

A solution of 2-chloro-5-{2-methoxy-6-[2-(4-methoxy-phenyl)-ethylamino]-pyrimidin-4-yl}-benzoic acid ethyl ester [120 mg, 0.27 mmol, Example 35(z)] and sodium hydroxide (2 mL, 4 mmol, 2M) in MeOH (8 mL) and water (2 mL) is stirred for 15 hours at 60° C. The mixture is concentrated, and diluted with water and ethyl acetate. The mixture is acidified with dilute hydrochloric acid to pH, 3, and extracted with ethyl acetate. The combined extracts are dried over magnesium sulfate, filtered, and concentrated. The residue is treated with saturated hydrogen chloride in EtOAc and concentrated to afford 2-chloro-5-{2-methoxy-6-[2-(4-methoxy-phenyl)-ethylamino]-pyrimidin-4-yl}-benzoic acid hydrochloride salt [101 mg, 82%, Example 23(e)]. LCMS: $R_T$=2.47 minutes, MS: 414 (M+H).

Example 24

(a) [2-(4-Methoxy-phenyl)-ethyl]-{2-methoxy-6-[3-(1H-tetrazol-5-yl)-phenyl]-pyrimidin-4-yl}-amine

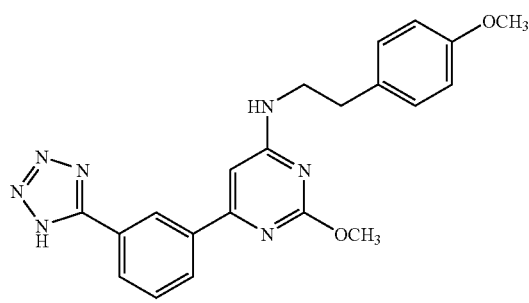

A solution of 3-{2-methoxy-6-[2-(4-methoxy-phenyl)-ethylamino]-pyrimidin-4-yl}-benzonitrile [0.12 g, 0.33 mmol, Example 35(t)], trimethylsilylazide (0.22 mL, 1.65 mmol) and dibutyltinoxide (41 mg, 0.16 mmol) in toluene (5 mL) is heated to 95° C. for 6 hours. The reaction mixture is concentrated, and partitioned between water and ethyl acetate. The aqueous phase solution is acidified with dilute hydrochloric acid to pH, 3.0, and extracted with ethyl acetate. The extracts are dried over magnesium sulfate, filtered and concentrated. The residue is subjected to chromatography on silica gel eluting with 5% MeOH in DCM to afford [2-(4-methoxy-phenyl)-ethyl]-{2-methoxy-6-[3-(1H-tetrazol-5-yl)-phenyl]-pyrimidin-4-yl}-amine [60 mg, 45%, Example 24(a)]. LCMS: $R_T$=2.65 minutes, MS: 404 (M+H).

(b) [2-(4-Methoxy-phenyl)-ethyl]-{2-methoxy-6-[3-(1H-tetrazol-5-ylmethyl)-phenyl]-pyrimidin-4-yl}-amine hydrochloride

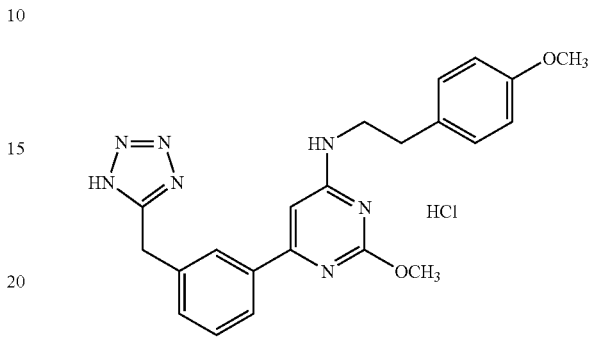

By proceeding in a similar manner to Example 24(a) above but substituting, (3-{2-methoxy-6-[2-(4-methoxy-phenyl)-ethylamino]-pyrimidin-4-yl}-phenyl)-acetonitrile [Example 35(s)] for 3-{2-methoxy-6-[2-(4-methoxy-phenyl)-ethylamino]-pyrimidin-4-yl}-benzonitrile, there is prepared [2-(4-methoxy-phenyl)-ethyl]-{2-methoxy-6-[3-(1H-tetrazol-5-ylmethyl)-phenyl]-pyrimidin-4-yl}-amine. This material is treated with a solution of hydrochloric acid in EtOAc followed by lyophilization to afford [2-(4-methoxy-phenyl)-ethyl]-{2-methoxy-6-[3-(1H-tetrazol-5-ylmethyl)-phenyl]-pyrimidin-4-yl}-amine hydrochloride (134 mg, Example 24(b)]. LCMS: $R_T$=2.62 minutes, MS: 418 (M+H). $^1$H NMR [300 MHz, (CD$_3$)$_2$SO]: ☐9.65 (1H, brs), 7.7-7.5 (4H, m), 7.2 (2H, d, J=8.4 Hz), 6.87 (2H, d, J=8.4 Hz), 6.68 (1H, s), 4.4 (2H, s), 4.08 (3H, s), 3.71 (3H, s), 3.6 (2H, m), 2.85 (2H, t, J=7.2 Hz). IC$_{50}$=0.1 nM (c) {2-Methoxy-6-[4-methoxy-3-(1H-tetrazol-5-yl)-phenyl]-pyrimidin-4-yl}-[2-(4-methoxy-phenyl)-ethyl]-amine

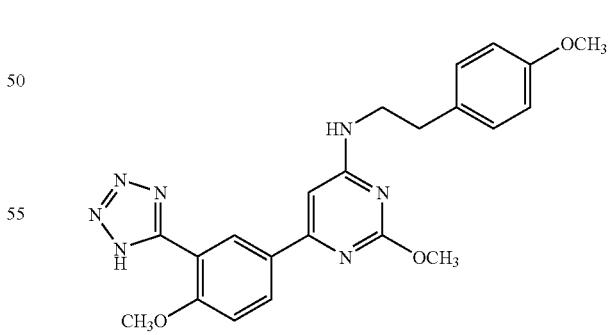

By proceeding in a similar manner to Example 24(a) above but substituting 2-methoxy-5-{2-methoxy-6-[2-(4-methoxy-phenyl)-ethylamino]-pyrimidin-4-yl}-benzonitrile [Example 55] for 3-{2-methoxy-6-[2-(4-methoxy-phenyl)-ethylamino]-pyrimidin-4-yl}-benzonitrile, there is prepared {2-methoxy-6-[4-methoxy-3-(1H-tetrazol-5-yl)-phenyl]-pyrimidin-4-yl}-[2-(4-methoxy-phenyl)-ethyl]-amine [310 mg, Example 24(c)]. LCMS: $R_T$=2.43 minutes, MS: 434 (M+H). $IC_{50}$=0.5 nM Example 25

(a) N-(3-{2-Methoxy-6-[2-(4-methoxy-phenyl)-ethylamino]-pyrimidin-4-yl}-benzoyl)-methanesulfonamide

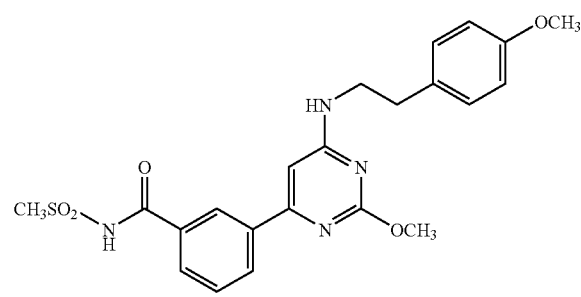

A solution of 3-{2-methoxy-6-[2-(4-methoxy-phenyl)-ethylamino]-pyrimidin-4-yl}-benzoic acid [100 mg, 0.26 mmol, Example 35(a)], methanesulfonamide (38 mg, 0.4 mmol), and dimethyl-pyridin-4-yl-amine (64 mg, 0.53 mmol) in DCM (5 mL) is treated with 1-(3-dimethylaminopropyl)-3-ethylcarbodiimide hydrochloride (101 mg, 0.53 mmol). After 8 hours at 20° C., the mixture is diluted with water, acidified (pH2 with citric acid), and extracted with DCM. The extracts are dried over magnesium sulfate, filtered and concentrated. The residue is subjected to chromatography on silica gel eluting with 10% MeOH in DCM to afford N-(3-{2-methoxy-6-[2-(4-methoxy-phenyl)-ethylamino]-pyrimidin-4-yl}-benzoyl)-methanesulfonamide [53 mg, 45%, Example 25(a)]. LCMS: $R_T$=2.35 minutes, MS: 457 (M+H). $^1$H NMR (300 MHz, $CDCl_3$) □8.3 (1H, s), 8.08 (1H, brs), 7.9 (1H, d, J=4.8 Hz), 7.34 (1H, brs), 7.12 (2H, d, J=8.4 Hz), 6.82 (2H, d, J=8.4 Hz), 6.46 (1H, brs), 6 (1H, brs), 3.91 (3H, s), 3.76 (3H, s), 3.61 (2H, brs), 3.31 (3H, s), 2.86 (2H, t, J=6.9 Hz).

(b) 3-{6-[2-(3,4-Dimethoxy-phenyl)-ethylamino]-2-methoxy-pyrimidin-4-yl}-N-(2-pyrrolidin-1-yl-ethyl)-benzamide

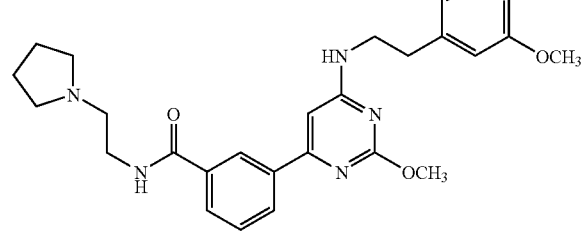

A solution of 3-{6-[2-(3,4-dimethoxy-phenyl)-ethylamino]-2-methoxy-pyrimidin-4-yl}-benzoic acid [0.15 mmol, Example 35(k)], hydroxybenzotriazole (41 mg, 0.3 mmol), 1-(3-dimethylaminopropyl)-3-ethylcarbodiimide hydrochloride (58 mg, 0.3 mmol), N-(2-aminoethyl)pyrrolidine (38 μL, 0.3 mmol) and N,N-diisopropylethylamine (105 μL, 0.6 mmol) in DCM (3 mL) is stirred at ambient temperature under a nitrogen atmosphere for 18 hours. The reaction is poured into water (20 mL) and extracted twice with EtOAc (25 mL). The organic extracts are combined and dried over magnesium sulfate, filtered and concentrated by rotary evaporator. The resulting solid is subjected to flash column chromatography on silica gel eluting with 10 to 60% EtOAc in heptane gradient to afford 3-{6-[2-(3,4-dimethoxy-phenyl)-ethylamino]-2-methoxy-pyrimidin-4-yl}-N-(2-pyrrolidin-1-yl-ethyl)-benzamide [18 mg, 24%, Example 25(b)]. LCMS: $R_T$=2.1 minutes, MS: 506 (M+H). $IC_{50}$=30 nM Example 26

(a) 2-Fluoro-5-{2-methoxy-6-[2-(4-methoxy-phenyl)-ethylamino]-pyrimidin-4-yl}-benzaldehyde oxime

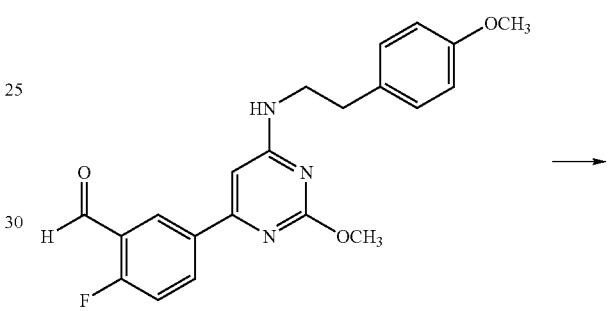

Example 35(j)

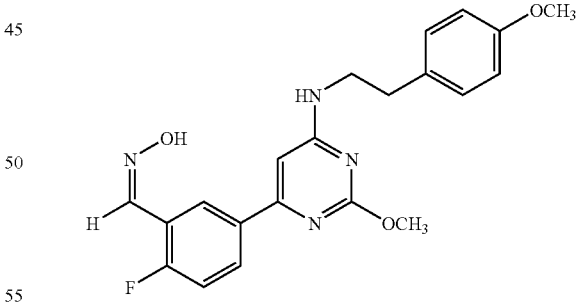

Example 26(a)

A mixture of 2-fluoro-5-{2-methoxy-6-[2-(4-methoxy-phenyl)-ethylamino]-pyrimidin-4-yl}-benzaldehyde [700 mg, 1.84 mmol, Example 35(j)], sodium acetate (2.5 g, 18.4 mmol) and hydroxylamine hydrochloride (1.3 g, 18.4 mmol) in EtOH (95%, 20 mL) is stirred for 20 hours at 20° C. The reaction mixture is concentrated, diluted with water, and extracted with ethyl acetate. The extracts are dried over magnesium sulfate, filtered through a plug of silica, and concentrated to afford 2-fluoro-5-{2-methoxy-6-[2-(4-methoxyphenyl)-ethylamino]-pyrimidin-4-yl}-benzaldehyde oxime [0.86 g, Example 26]. LCMS: $R_T$=2.53 minutes. MS: 397 (M+H). IC$_{50}$=4.5 nM (b) 3-{2-Methoxy-6-[2-(4-methoxy-phenyl)-ethylamino]-pyrimidin-4-yl}-benzaldehyde oxime

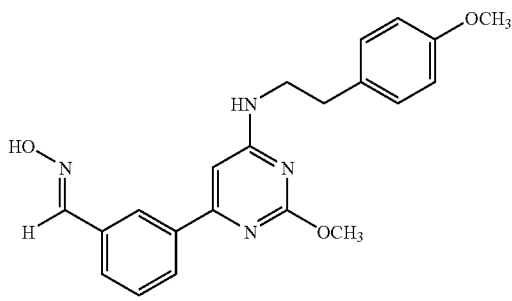

By proceeding in a similar manner to Example 26(a) above but: (i) substituting 3-{2-methoxy-6-[2-(4-methoxy-phenyl)-ethylamino]-pyrimidin-4-yl}-benzaldehyde [25 mg, Example 35(u)], for 2-fluoro-5-{2-methoxy-6-[2-(4-methoxy-phenyl)-ethylamino]-pyrimidin-4-yl}-benzaldehyde and carrying out the reaction for 6 hours at 20° C. there is prepared 3-{2-methoxy-6-[2-(4-methoxy-phenyl)-ethylamino]-pyrimidin-4-yl}-benzaldehyde oxime [15.2 mg, 58%, Example 26(b)]. LCMS: $R_T$=2.27 minutes, MS: 379 (M+H).

(c) 2-Methoxy-5-{2-methoxy-6-[2-(4-methoxy-phenyl)-ethylamino]-pyrimidin-4-yl}-benzaldehyde oxime

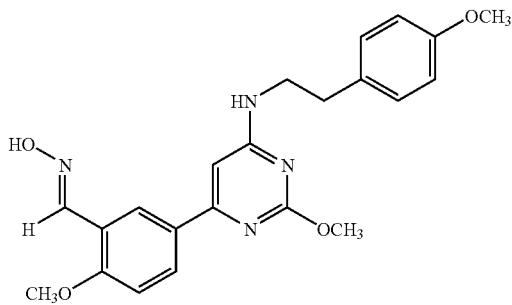

By proceeding in a similar manner to Example 26(a) above but substituting 2-methoxy-5-{2-methoxy-6-[2-(4-methoxy-phenyl)-ethylamino]-pyrimidin-4-yl}-benzaldehyde [510 mg, Example 35(y)] for 2-fluoro-5-{2-methoxy-6-[2-(4-methoxy-phenyl)-ethylamino]-pyrimidin-4-yl}-benzaldehyde and carrying out the reaction at 20° C. for 15 hours, there is prepared 2-methoxy-5-{2-methoxy-6-[2-(4-methoxy-phenyl)-ethylamino]-pyrimidin-4-yl}-benzaldehyde oxime [0.54 g, 100%, Example 26(c)]. LCMS: $R_T$=3.37 minutes, MS: 409 (M+H).

(d) 3-{2-Methoxy-6-[2-(4-methoxy-phenyl)-ethylamino]-pyrimidin-4-yl}-thiophene-2-carbaldehyde oxime

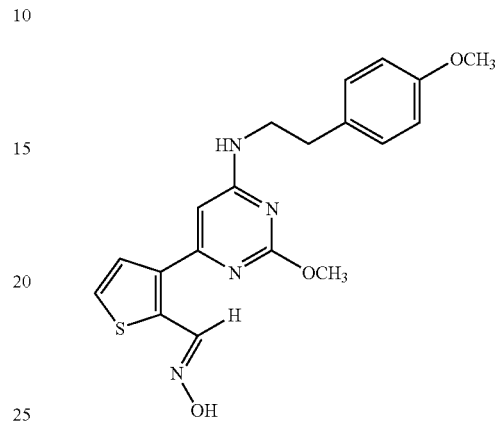

By proceeding in a similar manner to Example 26(a) above but substituting 3-{2-methoxy-6-[2-(4-methoxy-phenyl)-ethylamino]-pyrimidin-4-yl}-thiophene-2-carbaldehyde [105 mg, Example 35(l)] for 2-fluoro-5-{2-methoxy-6-[2-(4-methoxy-phenyl)-ethylamino]-pyrimidin-4-yl}-benzaldehyde, carrying out the reaction at reflux and subjecting the reaction product to chromatography loading with EtOAc and flushed with 2M Ammonia in methanol, there is prepared 3-{2-methoxy-6-[2-(4-methoxy-phenyl)-ethylamino]-pyrimidin-4-yl}-thiophene-2-carbaldehyde oxime [45 mg, 41%, Example 26(d)]. LCMS: $R_T$=6.28 minutes. MS: 385 (M+H). IC$_{50}$=0.4 nM (e) 1-(5-{2-Methoxy-6-[2-(4-methoxy-phenyl)-ethylamino]-pyrimidin-4-yl}-thiophen-2-yl)-ethanone oxime

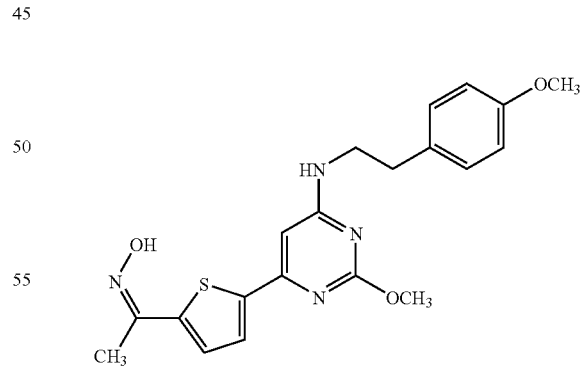

By proceeding in a similar manner to Example 26(a) above but substituting 1-(5-{2-methoxy-6-[2-(4-methoxy-phenyl)-ethylamino]-pyrimidin-4-yl}-thiophen-2-yl)-ethanone [Example 35(m)] for 2-fluoro-5-{2-methoxy-6-[2-(4-methoxy-phenyl)-ethylamino]-pyrimidin-4-yl}-benzaldehyde and carrying out the reaction at reflux for 4 hours there is prepared 1-(5-{2-methoxy-6-[2-(4-methoxy-phenyl)-ethylamino]-pyrimidin-4-yl}-thiophen-2-yl)-ethanone oxime [88 mg, 85%, Example 26(e)]. LCMS: $R_T$=7.77 minutes. MS: 399 (M+H). $IC_{50}$=0.8 nM (f) 5-{2-Methoxy-6-[2-(4-methoxy-phenyl)-ethylamino]-pyrimidin-4-yl}-thiophene-2-carbaldehyde oxime

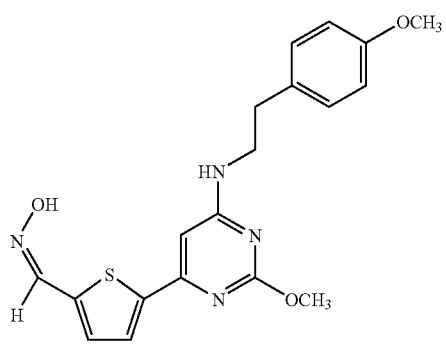

By proceeding in a similar manner to Example 26(a) above but substituting 5-{2-methoxy-6-[2-(4-methoxy-phenyl)-ethylamino]-pyrimidin-4-yl}-thiophene-2-carbaldehyde [200 mg, Example 8(b)] for 2-fluoro-5-{2-methoxy-6-[2-(4-methoxy-phenyl)-ethylamino]-pyrimidin-4-yl}-benzaldehyde, carrying out the reaction at reflux for 2 hours and subjecting the reaction product to chromatography on silica gel eluting with a mixture of EtOAc and cyclohexane there is prepared 5-{2-methoxy-6-[2-(4-methoxy-phenyl)-ethylamino]-pyrimidin-4-yl}-thiophene-2-carbaldehyde oxime [121 mg, 58%, Example 26(f)]. LCMS: $R_T$=7.2 minutes. MS: 385 (M+H).

Example 27

[6-(3-Aminomethyl-4-fluoro-phenyl)-2-methoxy-pyrimidin-4-yl]-[2-(4-methoxy-phenyl)-ethyl]-anine hydrochloride

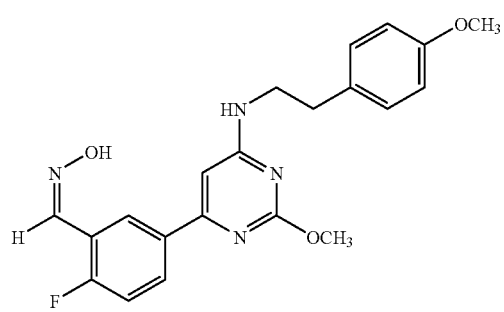

Example 26

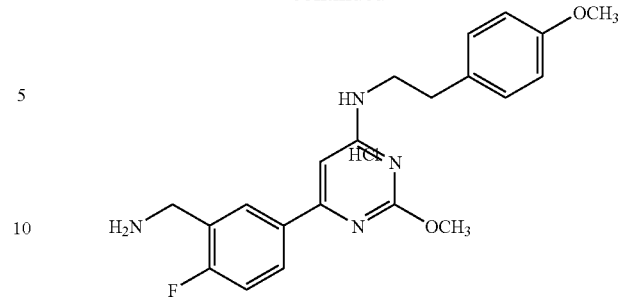

Example 27

A mixture of 2-fluoro-5-{2-methoxy-6-[2-(4-methoxy-phenyl)-ethylamino]-pyrimidin-4-yl}-benzaldehyde oxime [860 mg, Example 26(a)] in acetic acid (10 mL) is treated with zinc powder (0.6 g, 9.2 mmol). After 1 hour at 20° C., the reaction mixture is filtered through Celite, concentrated, diluted with 1 M sodium hydroxide solution, and extracted with ethyl acetate. The extracts are dried over magnesium sulfate, filtered, and subjected to chromatography on silica gel eluting with 10% MeOH in DCM to provide the free base, which is treated with saturated HCl in EtOAc afford [6-(3-aminomethyl-4-fluoro-phenyl)-2-methoxy-pyrimidin-4-yl]-[2-(4-methoxy-phenyl)-ethyl]-amine hydrochloride [720 mg, Example 27]. LCMS: $R_T$=1.88 minutes, MS: 383 (M+H). $IC_{50}$=41 nM Example 28

N-(2-Fluoro-5-{2-methoxy-6-[2-(4-methoxy-phenyl)-ethylamino]-pyrimidin-4-yl}-benzyl)-2-methoxy-acetamide hydrochloride

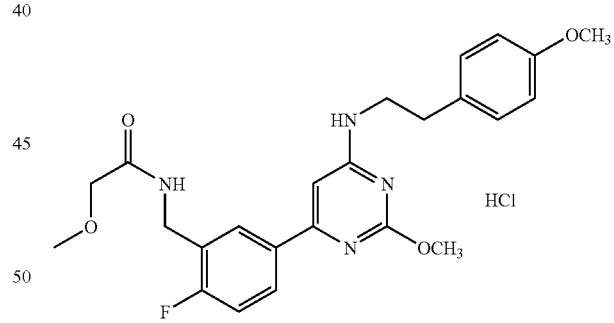

A solution of [6-(3-aminomethyl-4-fluoro-phenyl)-2-methoxy-pyrimidin-4-yl]-[2-(4-methoxy-phenyl)-ethyl]-amine [200 mg, 0.52 mmol, see example 27] and triethylamine (264 mg, 2.61 mmol) in DCM (5 mL) is treated with methoxyacetyl chloride (114 mg, 1.1 mmol) at 0° C. After 15 hours at 4° C. in a refrigerator, the mixture is quenched with water (10 mL) filtered through Chem-Elut. The filtrate is concentrated, and subjected to chromatography on silica gel eluting with 10% MeOH in DCM to give N-(2-fluoro-5-{2-methoxy-6-[2-(4-methoxy-phenyl)-ethylamino]-pyrimidin-4-yl}-benzyl)-2-methoxy-acetamide, which is treated with saturated solution of hydrogen chloride in EtOAc followed by lyophilization to afford N-(2-Fluoro-5-{2-methoxy-6-[2-(4-methoxy-phenyl)-ethylamino]-pyrimidin-4-yl}-benzyl)-2- methoxy-acetamide hydrochloride [190 mg, 74%, Example 28]. LCMS: $R_T$=2.35 minutes, MS: 455 (M+H). $IC_{50}$=9 nM Example 29

[2-Methoxy-6-(3-methoxy-phenyl)-pyrimidin-4-yl]-[2-(4-methoxy-phenyl)-2-methyl-propyl]-amine

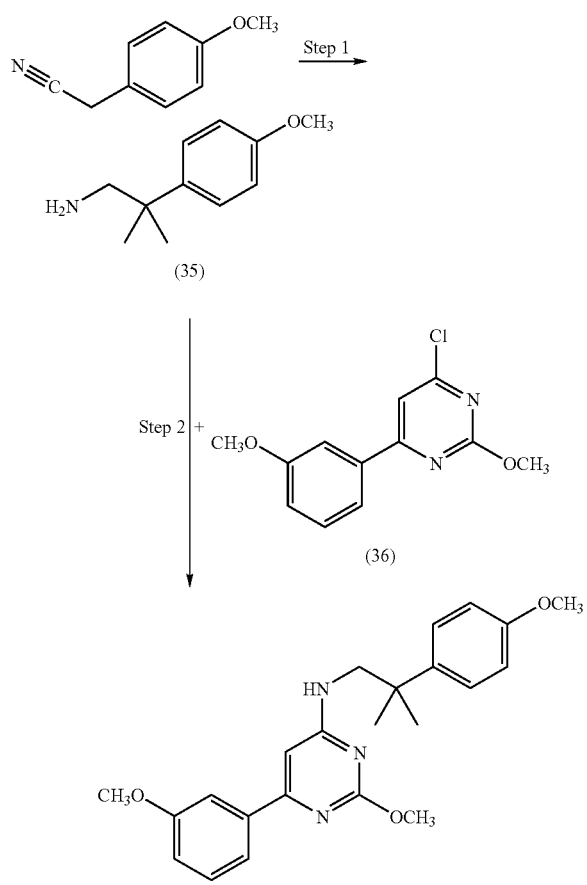

Example 29

Step 1. To a solution of (4-methoxy-phenyl)-acetonitrile [5 g, 34 mmol] in THF (40 mL), is added a 1.5 M solution of lithium diisopropylamide in cyclohexane (36 mL, 54 mmol) at −78° C. After 2 hours at −78° C., methyl iodide (3.4 g, 54 mmol) is added, and the mixture is allowed to warm to room temperature over 3 hours. After additional 12 hours at 20° C., the mixture is diluted with aqueous ammonium chloride solution, and extracted with ethyl acetate. The extracts are dried over magnesium sulfate, filtered and concentrated. The residue is subjected to chromatography on silica gel eluting with 40% EtOAc in heptane to afford a mixture of 2-(4-ethoxy-phenyl)-propionitrile and 2-(4-methoxy-phenyl)-2-methyl-propionitrile. To above mixture (5 g) in THF (20 mL) is add a 2 M solution of lithium aluminum hydride (35 mL, 70 mmol) at 0° C. After 12 hours at 20° C., the mixture is carefully quenched with 10% sodium hydroxide solution, and the white slurry is diluted with ether. The mixture is dried over magnesium sulfate, filtered and concentrated. The residue is subjected to chromatography on silica to afford 2-(4-methoxy-phenyl)-2-methyl-propylamine [2 g, 33%, Intermediate (35)]. MS: 180 (M+H).

Step 2. A mixture of 2-(4-methoxy-phenyl)-2-methyl-propylamine [172 mg, 0.96 mmol, Intermediate (35)], sodium bicarbonate (0.12 g), and 4-chloro-2-methoxy-6-(3-methoxy-phenyl)-pyrimidine [120 mg, 0.48 mmol, Intermediate (53)] in N-methylpyrrolidine (3 mL), is heated to 175° C. for 3 hours. The mixture is diluted with water, and extracted with ethyl acetate. The extracts are washed with water, dried over magnesium sulfate, filtered and concentrated. The residue is subjected to chromatography on silica gel eluting with 30% EtOAc in heptane to afford [2-methoxy-6-(3-methoxy-phenyl)-pyrimidin-4-yl]-[2-(4-methoxy-phenyl)-2-methyl-propyl]-amine [131 mg, 69%, Example 29]. LCMS: $R_T$=2.73 minutes, MS: 394 (M+H). $^1$H NMR (300 MHz, CDCl$_3$): □7.59 (1H, s), 7.51 (1H, d, J=7.8 Hz), 7.35-7.27 (3H, m), 6.96 (1H, dd, J=8.1, 2.4 Hz), 6.88 (2H, d, J=9 Hz), 6.31 (1H, s), 4.02 (3H, s), 3.86 (3H, s), 3.79 (3H, s), 3.62 (2H, brs), 1.4 (6H, s). $IC_{50}$=792 nM Example 30

[2-(2-Chloro-6-fluoro-phenyl)-ethyl]-[6-(6-methoxy-pyridin-3-yl)-2-methylsulfanyl-pyrimidin-4-yl]-amine

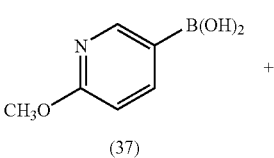

(37)

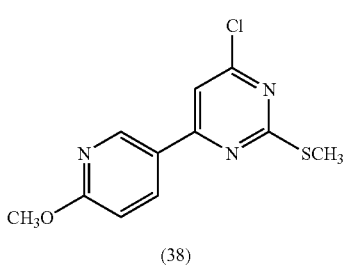

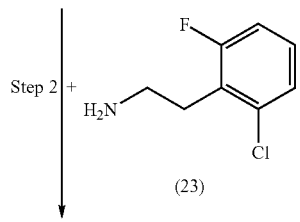

Example 30

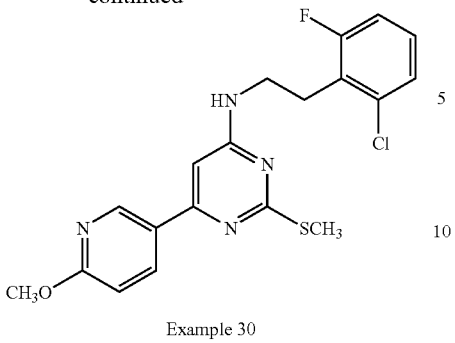

Example 30

Step 1. A mixture of 2-methoxy-5-pyridyl-boronic acid (600 mg, 2.04 mmol, Intermediate (37), prepared according to the procedure described in *J. Org. Chem.*, 67, 7541, 2002), 4,6-dichloro-2-methylsulfanyl-pyrimidine [700 mg, 3.59 mmol, Intermediate (29)], and $Cs_2CO_3$ (2.9 g, 8.97 mmol) in ethylene glycol dimethyl ether (8 mL) and water (2 mL) is degassed by bubbling with Argon gas for 5 minutes, and treated with tetrakis(triphenylphosphine)palladium(0) (207 mg, 0.18 mmol) at room temperature. After 3 hours at 85° C., the mixture is diluted with water (50 mL), and extracted twice with EtOAc (50 mL). The extracts are dried over magnesium sulfate, filtered, and concentrated to afford 4-chloro-6-(6-methoxy-pyridin-3-yl)-2-methylsulfanyl-pyrimidine [1.1 g, Intermediate (38)] as an oil. LCMS: $R_T$=3.72 minutes, MS: 268 (M+H).

Step 2. A mixture of 2-(2-chloro-6-fluoro-phenyl)-ethylamine [1.02 g, 5.88 mmol, Intermediate (23)], $Na_2CO_3$ (1.65 g, 19.6 mmol), and 4-chloro-6-(6-methoxy-pyridin-3-yl)-2-methylsulfanyl-pyrimidine [1.05 g, 3.92 mmol, Intermediate (38)] in N-methylpyrrolidine (10 mL), is heated to 175° C. for 3 hours. The reaction mixture is diluted with water, and extracted with ethyl acetate. The extracts are washed with water, dried over magnesium sulfate, filtered, and concentrated. The residue is subjected to short-path chromatography on silica gel eluting with EtOAc to afford [2-(2-chloro-6-fluoro-phenyl)-ethyl-]-[6-(6-methoxy-pyridin-3-yl)-2-methylsulfanyl-pryrimidin-4-yl]-amine [1.5 g, Example 30]. LCMS: $R_T$=3.37 minutes, MS: 405 (M+H).

Example 31

5-{6-[2-(2-Chloro-6-fluoro-phenyl)-ethylamino]-2-methylsulfanyl-pyrimidin-4-yl}-1H-pyridin-2-one

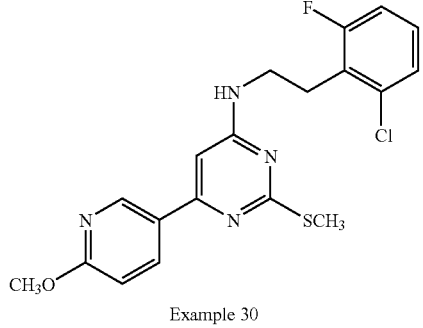

Example 30

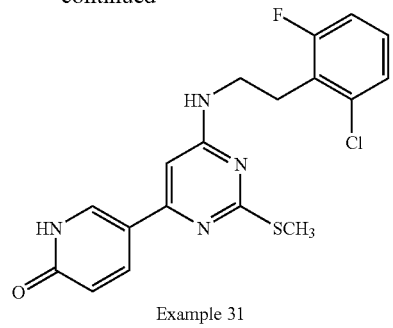

Example 31

A solution of [2-(2-chloro-6-fluoro-phenyl)-ethyl]-[6-(6-methoxy-pyridin-3-yl)-2-methylsulfanyl-pyrimidin-4-yl]-amine [1.5 g, 3.7 mmol, Example 30] and concentrated hydrochloric acid (5 mL) in EtOH (95%, 30 mL) is heated to 90° C. for 15 hours, and concentrated. The residue is diluted with water, and the pH of the solution is adjusted to 7. The resulting solid is filtered and dried to afford 5-{6-[2-(2-chloro-6-fluoro-phenyl)-ethylamino]-2-methylsulfanyl-pyrimidin-4-yl}-1H-pyridin-2-one [1.1 g, 76%, Example 31]. LCMS: $R_T$=3.12 minutes, MS: 391 (M+H).

Example 32

5-{6-[2-(2-chloro-6-fluoro-phenyl)-ethylamino]-2-methoxy-pyrimidin-4-yl}-1H-pyridin-2-one

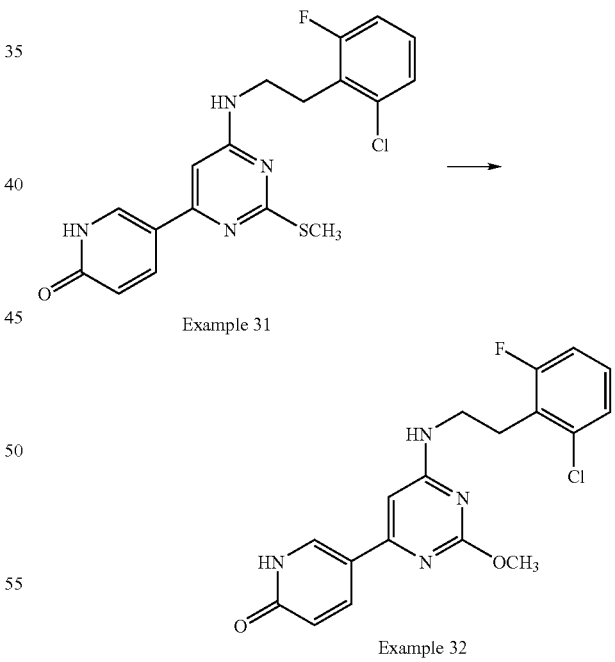

Example 31

Example 32

To a mixture of above 5-{6-[2-(2-chloro-6-fluoro-phenyl)-ethylamino]-2-methylsulfanyl-pyrimidin-4-yl}-1H-pyridin-2-one [1 g, 2.56 mmol, Example 31] in a mixture of MeOH (30 mL) and DCM (20 mL), is added 3-chloro-peroxybenzoic acid (70%, 1.32 g, 7.68 mmol) at room temperature. After 3 hours at 20° C., a 25% solution of sodium methoxide in MeOH (12 mL) is added at 0° C. After additional 1 hour, the mixture is concentrated, diluted with water, and neutralized with 3 M hydrochloric acid (pH 7). The resulting solid is filtered, and re-dissolved in a basic solution (pH 12). After acidifying into pH 3, the precipitate is filtered, and dried to give 5-{6-[2-(2-chloro-6-fluoro-phenyl)-ethylamino]-2-methoxy-pyrimidin-4-yl}-1H-pyridin-2-one [0.92 g, 96%, Example 32] as a solid. LCMS: $R_T$=2.23 minutes, MS: 375 (M+H).

Example 33

5-{6-[2-(2-Chloro-6-fluoro-phenyl)-ethylamino]-2-methoxy-pyrimidin-4-yl}-1-(5-oxo-4,5-dihydro-[1,3,4]oxadiazol-2-ylmethyl)-1H-pyridin-2-one

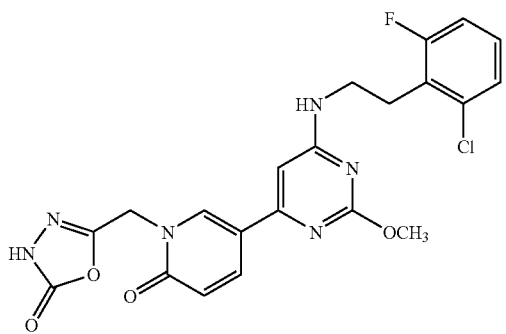

Step 1. A solution of (5-{6-[2-(2-chloro-6-fluoro-phenyl)-ethylamino]-2-methoxy-pyrimidin-4-yl}-2-oxo-2H-pyridin-1-yl)-acetic acid methyl ester [220 mg, 0.49 mmol, Example 22(d)] in a mixture of MeOH (5 mL) and DCM (2 mL) is treated with hydrazine hydrate (0.18 mL, 5.8 mmol). After 15 hours at 20° C., the mixture is concentrated to give (5-{6-[2-(2-chloro-6-fluoro-phenyl)-ethylamino]-2-methoxy-pyrimidin-4-yl}-2-oxo-2H-pyridin-1-yl)-acetic acid hydrazide. MS: 447 (M+H). This material is used without further purification.

Step 2. A mixture of (5-{6-[2-(2-chloro-6-fluoro-phenyl)-ethylamino]-2-methoxy-pyrimidin-4-yl}-2-oxo-2H-pyridin-1-yl)-acetic acid hydrazide and triethylamine (0.33 mL, 2.35 mmol) in N-methyl pyrrolidine (2 mL) is added 1,1-carbonyldiimidazole (0.29 g, 1.76 mmol) at room temperature. After 24 hours at 20° C., the mixture is diluted with water, and acidified with 1 M hydrochloric acid (pH 5.5). The resulting solid is filtered, washed with water/and ether, and dried to give 5-{6-[2-(2-chloro-6-fluoro-phenyl)-ethylamino]-2-methoxy-pyrimidin-4-yl}-1-(5-oxo-4,5-dihydro-[1,3,4]oxadiazol-2-ylmethyl)-1H-pyridin-2-one [108 mg, 47%, Example 33] as a solid. LCMS: $R_T$=2.76 minutes, MS: 473 (M+H). $IC_{50}$=1.2 nM

Example 34

(a) 3-(3-{6-[2-(2,4-Dichloro-phenyl)-ethylamino]-2-methoxy-pyrimidin-4-yl-phenoxymethyl)-4H-[1,2,4]oxadiazol-5-one hydrochloride

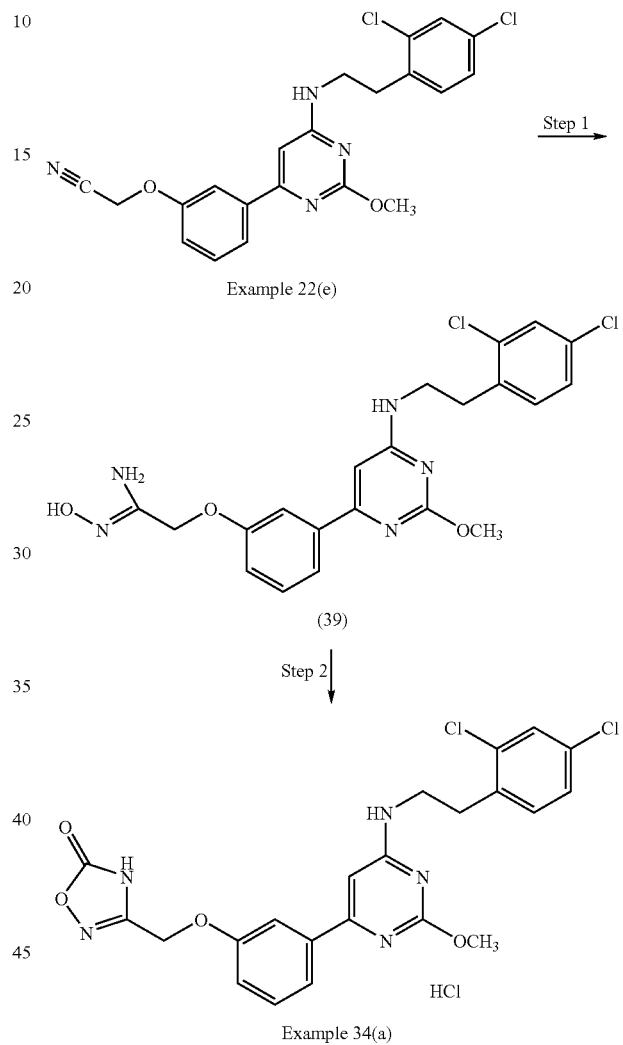

Step 1. A mixture of (3-{6-[2-(2,4-dichloro-phenyl)-ethylamino]-2-methoxy-pyrimidin-4-yl}-phenoxy)-acetonitrile [Example 22(e)] and hydroxylamine hydrochloride (1.4 g, 20 mmol) in MeOH (35 mL) and DCM (15 mL) is treated with a 25% solution of sodium methoxide in MeOH (3.4 mL, 15 mmol) at room temperature. After 24 hours at 20° C., the mixture is concentrated, diluted with water, and filtered to give 2-(3-{6-[2-(2,4-dichloro-phenyl)-ethylamino]-2-methoxy-pyrimidin-4-yl-phenoxy)-N-hydroxy-acetamidine [Intermediate (39)]. [MS: 462 (M+H)].

Step 2. A solution of 2-(3-{6-[2-(2,4-dichloro-phenyl)-ethylamino]-2-methoxy-pyrimidin-4-yl-phenoxy)-N-hydroxy-acetamidine [Intermediate (39)] and 1,8-diazabicyclo[5,4,0]undec-7-ene (0.61 mL, 4.1 mmol) in N-methylpyrrolidine (2 mL) is treated with 1,1-carbonyldiimidazole (0.5 g, 3.1 mmol) at room temperature. After 20 hours at 20° C., the reaction mixture is diluted with water, acidified with 1 M hydrochloric acid (pH 3.0), and extracted with ethyl acetate. The extracts are dried over magnesium sulfate, filtered, and concentrated to afford 3-(3-{6-[2-(2,4-dichloro-phenyl)-ethylamino]-2-methoxy-pyrimidin-4-yl-phenoxymethyl)-4H-[1,2,4]oxadiazol-5-one, which is treated with saturated hydrogen chloride in ethyl acetate lyophilized to provide 3-(3-{6-[2-(2,4-dichloro-phenyl)-ethylamino]-2-methoxy-pyrimidin-4-yl-phenoxymethyl)-4H-[1,2,4]oxadiazol-5-one hydrochloride [200 mg, Example 34(a)] as a solid. LCMS: $R_T$=2.73 minutes, MS: 488 (M+H).

(b) 3-(3-{6-[2-(2-Chloro-6-fluoro-phenyl)-ethylamino]-2-methoxy-pyrimidin-4-yl}-benzyl)-4H-[1,2,4]oxadiazol-5-one hydrochloride By proceeding in a similar manner to Example 34(a) above but: (i) substituting (3-{2-methoxy-6-[2-(2-chloro-6-fluoro-phenyl)-ethylamino]-pyrimidin-4-yl}-phenyl)-acetonitrile for (3-{6-[2-(2,4-dichloro-phenyl)-ethylamino]-2-methoxy-pyrimidin-4-yl}-phenoxy)-acetonitrile in Step 1, and carrying out the reaction at room temperature for 2 days (40% conversion) to give 2-(3-{6-[2-(2-chloro-6-fluoro-phenyl)-ethylamino]-2-methoxy-pyrimidin-4-yl}-phenyl)-N-hydroxy-acetamidine [Intermediate (40), MS: 430 (M+H)]; and (ii) substituting 2-(3-{6-[2-(2-chloro-6-fluoro-phenyl)-ethylamino]-2-methoxy-pyrimidin-4-yl}-phenyl)-N-hydroxy-acetamidine [Intermediate (40)] for 2-(3-{6-[2-(2,4-dichloro-phenyl)-ethylamino]-2-methoxy-pyrimidin-4-yl-phenoxy)-N-hydroxy-acetamidine in Step 2 there is prepared 3-(3-{6-[2-(2-chloro-6-fluoro-phenyl)-ethylamino]-2-methoxy-pyrimidin-4-yl}-benzyl)-4H-[1,2,4]oxadiazol-5-one hydrochloride [Example 34(b)]. LCMS: $R_T$=2.32 minutes, MS: 456 (M+H). IC$_{50}$=1 nM (c) 3-(3-{6-[2-(2-Chloro-6-fluoro-phenyl)-ethylamino]-2-methoxy-pyrimidin-4-yl}-phenoxymethyl)-4H-[1,2,4]oxadiazol-5-one hydrochloride

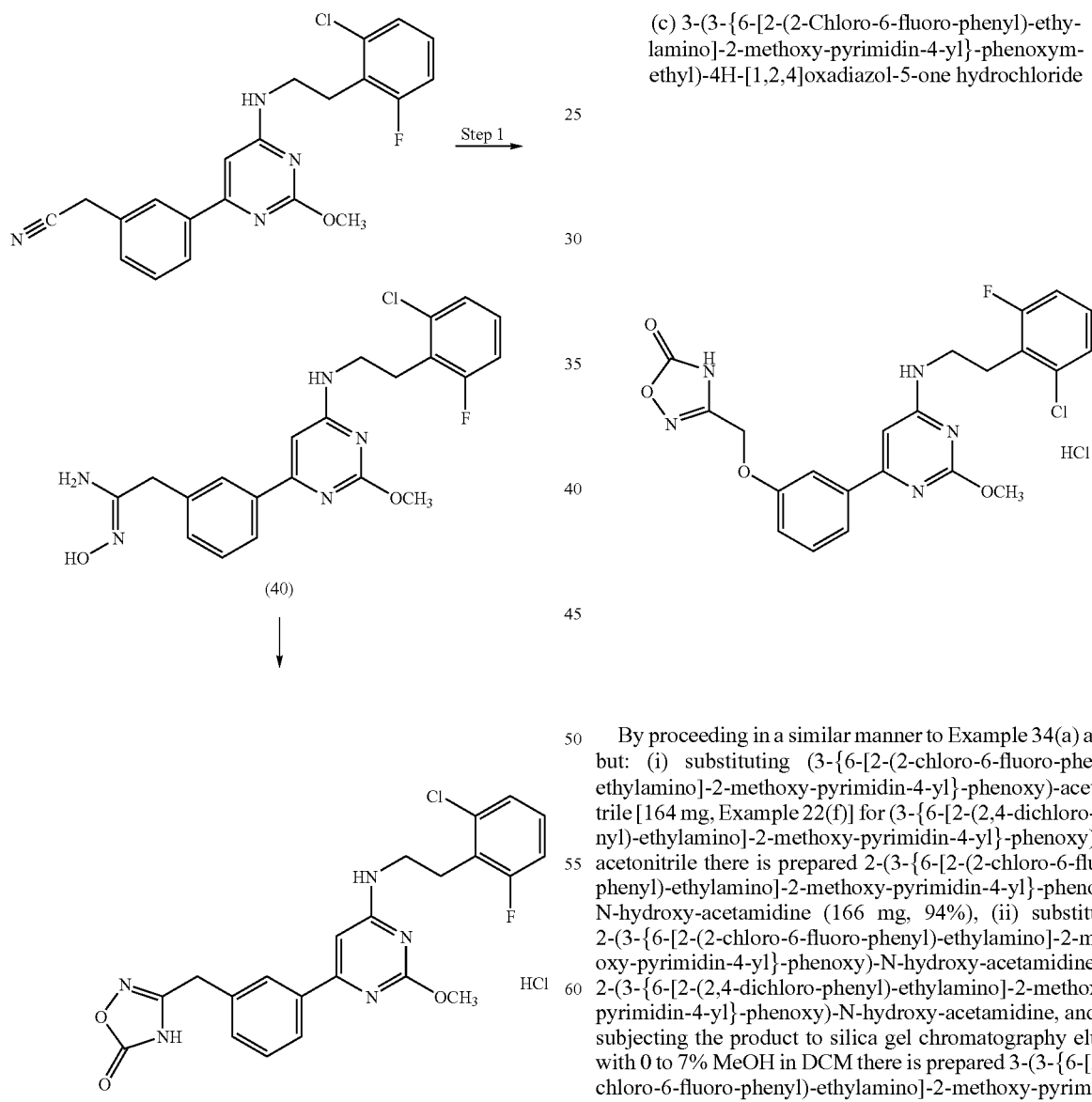

Example 34(b)

By proceeding in a similar manner to Example 34(a) above but: (i) substituting (3-{6-[2-(2-chloro-6-fluoro-phenyl)-ethylamino]-2-methoxy-pyrimidin-4-yl}-phenoxy)-acetonitrile [164 mg, Example 22(f)] for (3-{6-[2-(2,4-dichloro-phenyl)-ethylamino]-2-methoxy-pyrimidin-4-yl}-phenoxy)-acetonitrile there is prepared 2-(3-{6-[2-(2-chloro-6-fluoro-phenyl)-ethylamino]-2-methoxy-pyrimidin-4-yl}-phenoxy)-N-hydroxy-acetamidine (166 mg, 94%), (ii) substituting 2-(3-{6-[2-(2-chloro-6-fluoro-phenyl)-ethylamino]-2-methoxy-pyrimidin-4-yl}-phenoxy)-N-hydroxy-acetamidine for 2-(3-{6-[2-(2,4-dichloro-phenyl)-ethylamino]-2-methoxy-pyrimidin-4-yl}-phenoxy)-N-hydroxy-acetamidine, and (iii) subjecting the product to silica gel chromatography eluting with 0 to 7% MeOH in DCM there is prepared 3-(3-{6-[2-(2-chloro-6-fluoro-phenyl)-ethylamino]-2-methoxy-pyrimidin-4-yl}-phenoxymethyl)-4H-[1,2,4]oxadiazol-5-one hydrochloride [Example 34(c)] as a solid. LC/MS: $R_T$=2.4 minutes, MS: 472 (M+H). $^1$H NMR (300 MHz, (CD$_3$)$_2$SO): □12.82

(1H, br s), 7.18-7.55 (7H, m), 6.6 (1H, s), 5.18 (2H, s), 4 (3H, s), 3.68 (2H, m), 3.08 (2H, m). IC$_{50}$=0.3 nM

Example 35

(a) 3-{2-Methoxy-6-[2-(4-methoxy-phenyl)-ethylamino]-pyrimidin-4-yl}-benzoic acid

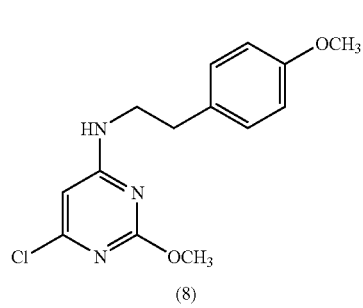

(8)

+

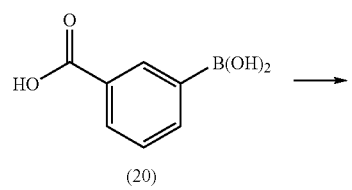

(20)

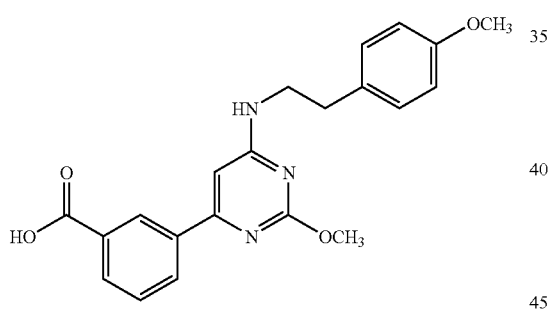

Example 35(a)

Argon is bubbled through a mixture of (6-chloro-2-methoxy-pyrimidin-4-yl)-[2-(4-methoxy-phenyl)-ethyl]-amine [300 mg, 1.02 mmol, Intermediate (8)], 3-carboxyphenyl boronic acid [339 mg, 2.04 mmol, Intermediate (20)], and Cs$_2$CO$_3$ (1.66 g, 5.1 mmol) in ethylene glycol dimethyl ether (8 mL) and water (2 mL), for a period of 5 minutes. To this mixture is added tetrakis(triphenylphosphine) palladium (0) (59 mg, 0.051 mmol) and the reaction vessel is sealed and heated to 90° C. After stirring for 17 hours the mixture is diluted with water (50 mL) and extracted with EtOAc (50 mL). The aqueous layer is acidified to pH 6 with 10% hydrochloric acid and extracted twice with EtOAc (50 mL). The organic extracts from the acidic solution are combined and dried over magnesium sulfate, filtered and concentrated to provide 3-{2-methoxy-6-[2-(4-methoxy-phenyl)-ethylamino]-pyrimidin-4-yl}-benzoic acid [350 mg, 90.4%, Example 35(a)] as a solid. LCMS: R$_T$=2.69 minutes, MS: 380 (M+H). $^1$H NMR [(CD$_3$)$_2$SO]: δ 8.52 (1H, s), 8.28 (3H, m), 8 (2H, m), 7.61 (2H, t, J=0.027 Hz), 7.47 (1H, m), 7.17 (2H, d, J=0.027 Hz), 6.85 (2H, d, J=0.027 Hz), 6.69 (1H, s), 3.89 (3H, s), 3.71 (3H, s), 2.8 (2H, t, J=0.024 Hz).

(b) 3-{2-Methoxy-6-[2-(4-trifluoromethoxy-phenyl)-ethylamino]-pyrimidin-4-yl}-benzoic acid

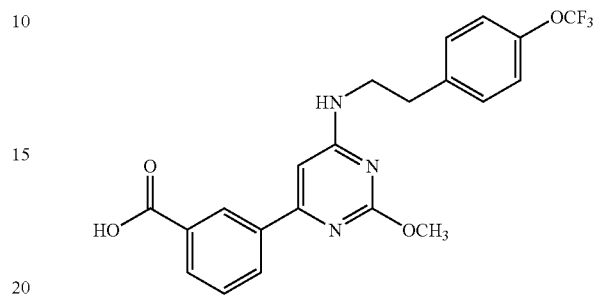

By proceeding in a similar manner as above in Example 35(a) but substituting (6-chloro-2-methoxy-pyrimidin-4-yl)-[2-(4-trifluoromethoxy-phenyl)-ethyl]-amine [503 mg, 1.45 mmol, Intermediate (13)] for (6-chloro-2-methoxy-pyrimidin-4-yl)-[2-(4-methoxy-phenyl)-ethyl]-amine and recrystallizing from EtOH there is prepared 3-{2-methoxy-6-[2-(4-trifluoromethoxy-phenyl)-ethylamino]-pyrimidin-4-yl}-benzoic acid [95 mg, 15%, Example 35(b)]. LCMS: R$_T$=2.93 minutes, MS: 434 (M+H).

(c) [2-(3,4-Dimethoxy-phenyl)-ethyl]-(2-methoxy-6-thiophen-2-yl-pyrimidin-4-yl)amine

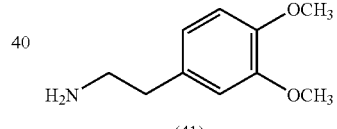

(41)

+

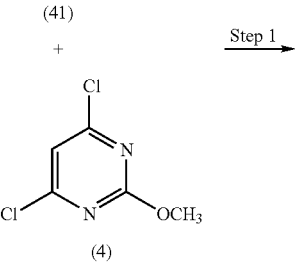

(4)

Step 1 →

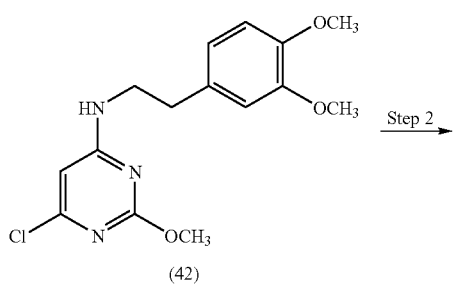

(42)

Step 2 →

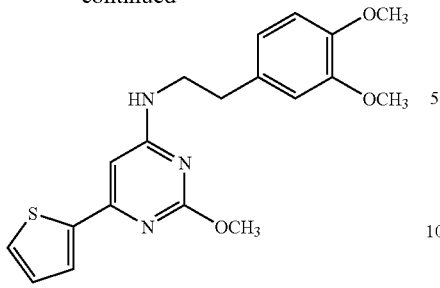

Example 35(c)

Step 1. By proceeding in a similar manner to that described in Example 1, Step 3, but substituting 2-(3,4-dimethoxy-phenyl)-ethylamine [Intermediate (41)] for 2-(3-fluoro-4-methoxy-phenyl)-ethylamine there is prepared (6-chloro-2-methoxy-pyrimidin-4-yl)-[2-(3,4-dimethoxy-phenyl)-ethyl]-amine [Intermediate (42)].

Step 2. By proceeding in a similar manner as above in Example 35(a) but (i) substituting (6-chloro-2-methoxy-pyrimidin-4-yl)-[2-(3,4-dimethoxy-phenyl)-ethyl]-amine [132 mg, 0.41 mmol, Intermediate (42)] for (6-chloro-2-methoxy-pyrimidin-4-yl)-[2-(4-methoxy-phenyl)-ethyl]-amine, and (ii) substituting 2-thiophene boronic acid (63 mg, 0.49 mmol) for 3-carboxyphenyl boronic acid, and (iii) subjecting the crude reaction product to flash column chromatography on silica gel eluting with 0 to 30% EtOAc in heptane gradient, there is prepared [2-(3,4-dimethoxy-phenyl)-ethyl]-(2-methoxy-6-thiophen-2-yl-pyrimidin-4-yl)amine [9.1 mg, 6%, Example 35(c)]. LCMS: $R_T$=2.56 minutes, MS: 372 (M+H).

(d) [2-(3,4-Dimethoxy-phenyl)-ethyl]-(6-furan-2-yl-2-methoxy-pyrimidin-4-yl)-amine

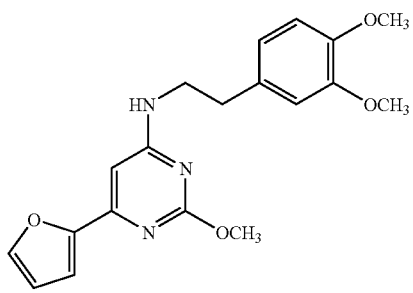

By proceeding in a similar manner as above in Example 35(a) but (i) substituting (6-chloro-2-methoxy-pyrimidin-4-yl)-[2-(3,4-dimethoxy-phenyl)-ethyl]-amine [100 mg, Intermediate (42)] for (6-chloro-2-methoxy-pyrimidin-4-yl)-[2-(4-methoxy-phenyl)-ethyl]-amine, and (ii) substituting 2-furan boronic acid (69 mg) for 3-carboxyphenyl boronic acid, and (iii) subjecting the crude reaction product to flash column chromatography on silica gel eluting with 0 to 30% EtOAc in heptane gradient, there is prepared [2-(3,4-dimethoxy-phenyl)-ethyl-]-(6-furan-2-yl-2-methoxy-pyrimidin-4-yl)-amine [32.4 mg, 30%, Example 35(d)]. LCMS: $R_T$=2.18 minutes, MS: 356 (M+H). $IC_{50}$=256 nM (e) (6-Biphenyl-4-yl-2-methoxy-pyrimidin-4-yl)-[2-(3,4-dimethoxy-phenyl)-ethyl]-amine

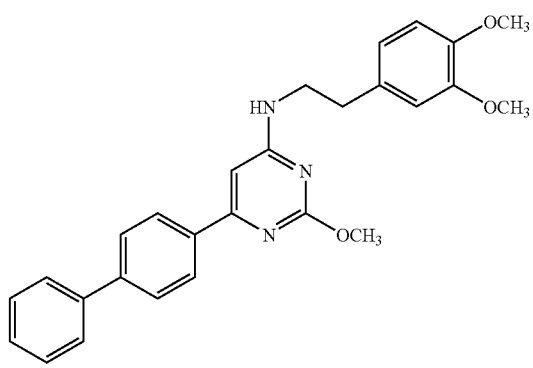

By proceeding in a similar manner as above in Example 35(a) but (i) substituting (6-chloro-2-methoxy-pyrimidin-4-yl)-[2-(3,4-dimethoxy-phenyl)-ethyl]-amine [100 mg, Intermediate (42)] for (6-chloro-2-methoxy-pyrimidin-4-yl)-[2-(4-methoxy-phenyl)-ethyl]-amine, and (ii) substituting 4-Biphenylboronic acid (122 mg) for 3-carboxyphenyl boronic acid, and (iii) subjecting the crude reaction product to flash column chromatography on silica (10 g) eluting with 20 to 60% EtOAc in heptane gradient, there is prepared (6-biphenyl-4-yl-2-methoxy-pyrimidin-4-yl)-[2-(3,4-dimethoxy-phenyl)-ethyl]-amine [79.7 mg, 58.6%, Example 35(e)]. LCMS: $R_T$=3.05 minutes, MS: 442 (M+H). $^1$H NMR (300 MHz, CDCl$_3$) δ 8.36 (1H, d, J=0.027 Hz), 8.09 (2H, d, J=0.027 Hz), 7.84 (1H, d, J=0.027 Hz), 7.78 (1H, d, J=0.027 Hz), 7.68 (9H, m), 7.45 (4H, m), 6.84 (1H, t, J=0.027 Hz), 6.79 (2H, m), 6.44 (1H, s), 4.93 (1H, s), 4.77 (1H, s), 4.07 (3H, s), 3.9 (6H, s), 3.72 (2H, m), 2.94 (2H, t, J=0.022 Hz). $IC_{50}$=369 nM (f) 3-{6-[2-(4-Fluoro-phenyl)-ethylamino]-2-methoxy-pyrimidin-4-yl}-benzoic acid hydrochloride

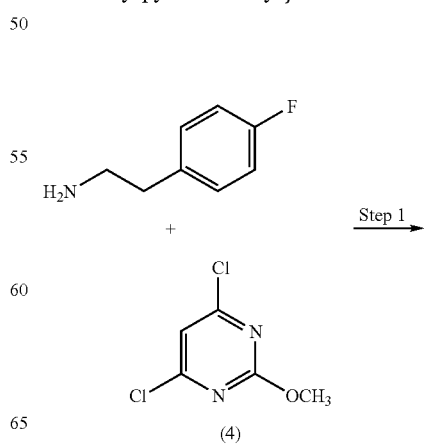

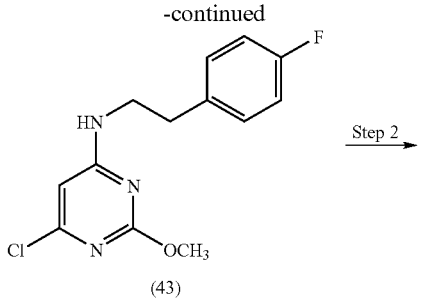

(43)

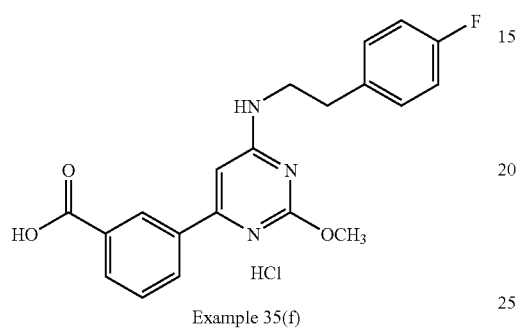

Example 35(f)

Step 1. By proceeding in a similar manner to that described in Example 1, Step 3, but substituting 2-(4-fluoro-phenyl)-ethylamine for 2-(3-fluoro-4-methoxy-phenyl)-ethylamine there is prepared (6-chloro-2-methoxy-pyrimidin-4-yl)-[2-(4-fluoro-phenyl)-ethyl]-amine [Intermediate (43)]. LCMS: $R_T$=3.22 minutes, MS: 282 (M+H).

Step 2. By proceeding in a similar manner as above in Example 35(a) but (i) substituting ((6-chloro-2-methoxy-pyrimidin-4-yl)-[2-(4-fluoro-phenyl)-ethyl]-amine [132 mg, 0.41 mmol, Intermediate (43)] for (6-chloro-2-methoxy-pyrimidin-4-yl)-[2-(4-methoxy-phenyl)-ethyl]-amine, and (ii) treating the product with hydrogen chloride in ethyl acetate, there is prepared 3-{6-[2-(4-fluoro-phenyl)-ethylamino]-2-methoxy-pyrimidin-4-yl}-benzoic acid hydrochloride [54 mg, 16.5%, Example 35(f)]. LCMS: $R_T$=2.47 minutes, MS: 368 (M+H).

(g) 3-{2-Methoxy-6-[2-(4-methoxy-phenyl)-ethylamino]-pyrimidin-4-yl}-benzamide

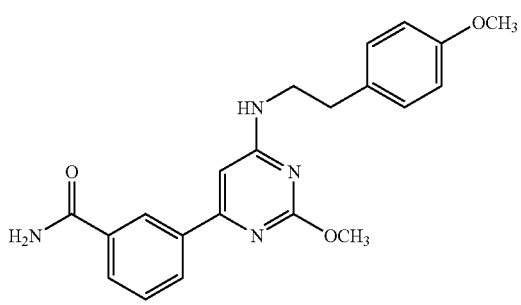

By proceeding in a similar manner as above in Example 35(a) but substituting (3-aminocarbonylphenyl)boronic acid for 3-carboxyphenyl boronic acid there is prepared 3-{2-methoxy-6-[2-(4-methoxy-phenyl)-ethylamino]-pyrimidin-4-yl}-benzamide [Example 35(g)].

(h) 1-(3-{2-Methoxy-6-[2-(4-methoxy-phenyl)-ethylamino]-pyrimidin-4-yl}-phenyl)-ethanone

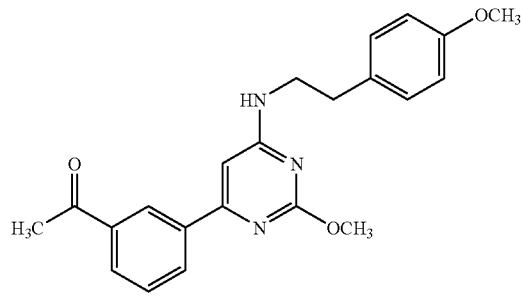

By proceeding in a similar manner as above in Example 35(a) but substituting 3-acetylphenylboronic acid for 3-carboxyphenyl boronic acid there is prepared 1-(3-{2-methoxy-6-[2-(4-methoxy-phenyl)-ethylamino]-pyrimidin-4-yl}-phenyl)-ethanone [Example 35(h)]. LCMS: $R_T$=2.57 minutes, MS: 378 (M+H). $IC_{50}$=5 nM (i) 3-{6-[2-(2,4-dichloro-phenyl)-ethylamino]-2-methoxy-pyrimidin-4-yl}-phenol

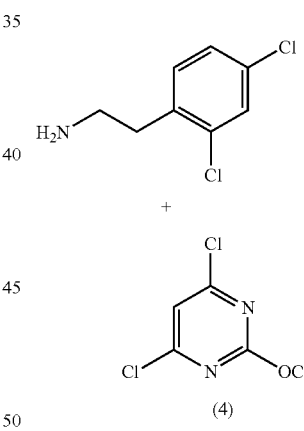

(4)

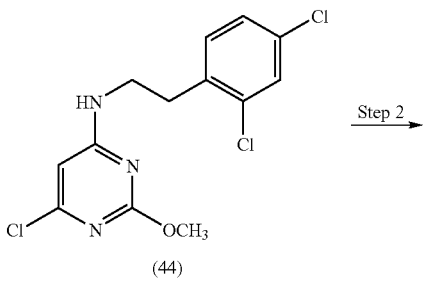

(44)

Example 35(i)

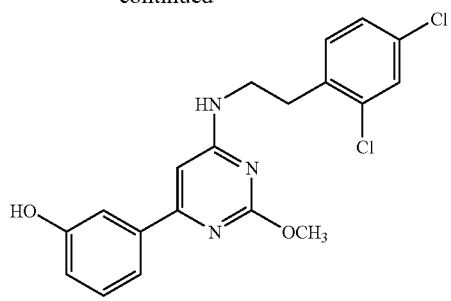

Step 1. By proceeding in a similar manner to that described in Example 1, Step 3, but substituting 2-(2,4-dichloro-phenyl)-ethylamine for 2-(3-fluoro-4-methoxy-phenyl)-ethylamine there is prepared (6-chloro-2-methoxy-pyrimidin-4-yl)-[2-(2,4-dichloro-phenyl)-ethyl]-amine [Intermediate (44)].

Step 2. By proceeding in a similar manner as above in Example 35(a) but (i) substituting (6-chloro-2-methoxy-pyrimidin-4-yl)-[2-(2,4-dichloro-phenyl)-ethyl]-amine [Intermediate (44)] for (6-chloro-2-methoxy-pyrimidin-4-yl)-[2-(4-methoxy-phenyl)-ethyl]-amine, and (ii) 3-hydroxyphenylboronic acid for 3-carboxyphenyl boronic acid there is prepared 3-{6-[2-(2,4-dichloro-phenyl)-ethylamino]-2-methoxy-pyrimidin-4-yl}-phenol [Example 35(i)]. LCMS: $R_T$=2.57 minutes, MS: 390 (M+H).

(j) 2-Fluoro-5-{2-methoxy-6-[2-(4-methoxy-phenyl)-ethylamino]-pyrimidin-4-yl}-benzaldehyde

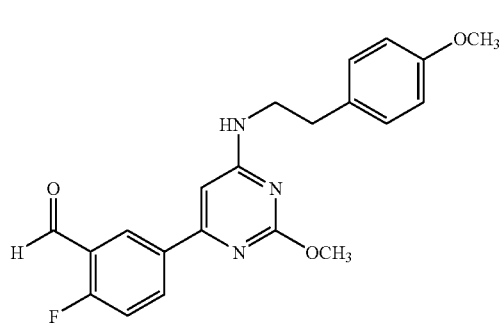

By proceeding in a similar manner as above in Example 35(a) but substituting 4-fluoro-3-formylbenzeneboronic acid for 3-carboxyphenyl boronic acid there is prepared 2-fluoro-5-{2-methoxy-6-[2-(4-methoxy-phenyl)-ethylamino]-pyrimidin-4-yl}-benzaldehyde [Example 35(j)]. LCMS: $R_T$=2.77 minutes, MS: 382 (M+H).

(k) 3-{6-[2-(3,4-Dimethoxy-phenyl)-ethylamino]-2-methoxy-pyrimidin-4-yl}-benzoic acid

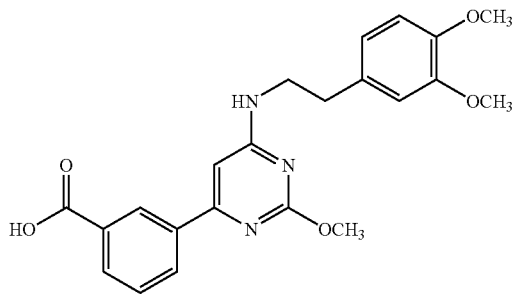

By proceeding in a similar manner as above in Example 35(a) by substituting (6-chloro-2-methoxy-pyrimidin-4-yl)-[2-(3,4-dimethoxy-phenyl)-ethyl]-amine for (6-chloro-2-methoxy-pyrimidin-4-yl)-[2-(4-methoxy-phenyl)-ethyl]-amine there is prepared 3-{6-[2-(3,4-dimethoxy-phenyl)-ethylamino]-2-methoxy-pyrimidin-4-yl}-benzoic acid [Example 35(k)]. LCMS: $R_T$=2.39 minutes, MS: 410 (M+H).

(l) 3-{2-Methoxy-6-[2-(4-methoxy-phenyl)-ethylamino]-pyrimidin-4-yl}-thiophene-2-carbaldehyde

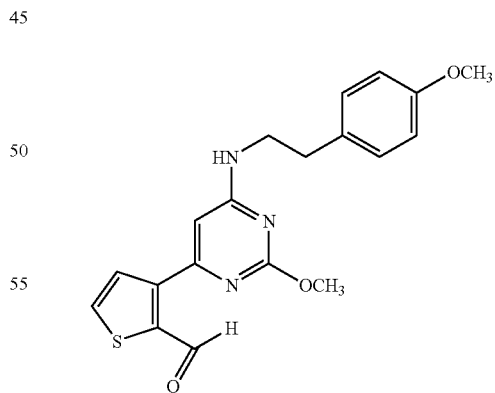

By proceeding in a similar manner as above in Example 35(a) by substituting 2-formyl-3-thiophene boronic acid (797 mg) for 3-carboxyphenyl boronic acid there is prepared 3-{2-methoxy-6-[2-(4-methoxy-phenyl)-ethylamino]-pyrimidin- 4-yl}-thiophene-2-carbaldehyde [450 mg (36%, Example 35(l)]. LCMS: $R_T$=7.42 minutes. MS: 370 (M+H).

(m) 1-(5-{2-Methoxy-6-[2-(4-methoxy-phenyl)-ethylamino]-pyrimidin-4-yl}-thiophen-2-yl)-ethanone

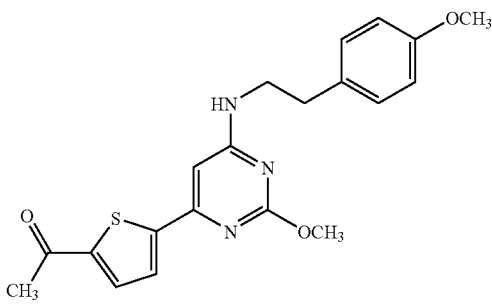

By proceeding in a similar manner as above in Example 35(a) but substituting 5-Acetyl-2-thiopheneboronic acid for 3-carboxyphenyl boronic acid there is prepared 1-(5-{2-methoxy-6-[2-(4-methoxy-phenyl)-ethylamino]-pyrimidin-4-yl}-thiophen-2-yl)-ethanone [200 mg, 51%, Example 35(m)]. $IC_{50}$=3.8 nM (n) 3-{6-[2-(4-chlorophenyl)-ethylamino]-2-methoxy-pyrimidin-4-yl}-benzoic acid hydrochloride

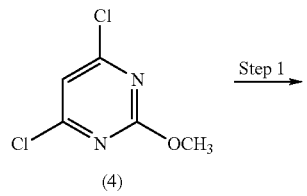

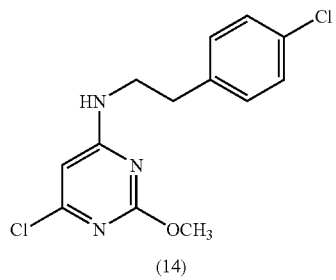

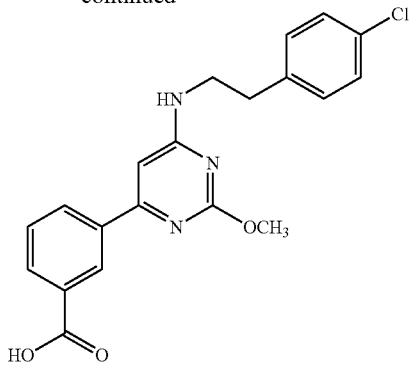

Example 35(n)

Step 1. A solution of 4,6-dichloro-2-methoxypyrimidine [0.7 g, Intermediate (4)], 2-(4-chlorophenyl)-ethylamine (0.66 g) and sodium bicarbonate (0.88 g) in EtOH (25 ml) is heated at 80° C. for three hours, poured into water (400 mL) and the solid is filtered and air dried affording (6-chloro-2-methoxy-pyrimidin-4-yl)-[2-(4-chlorophenyl)-ethyl]amine [1.1 g, Intermediate (14)]. MS: 299 (M+H). $^1$H NMR $(CD_3)_2$SO]: δ 8 (d, 2H, J=3 Hz); 7.4 (2H, d, J=3 Hz); 6.05 (1H, s); 4 (3H, s): 3.6-3.7 (2H, m); 2.95 (2H, t).

Step 2. By proceeding in a similar manner as above in Example 35(a) but substituting 6-chloro-2-methoxy-pyrimidin-4-yl)-[2-(4-chlorophenyl)-ethyl]amine [Intermediate (14)] for (6-chloro-2-methoxy-pyrimidin-4-yl)-[2-(4-methoxy-phenyl)-ethyl]-amine and treating the reaction product with 1.2 equivalents of hydrogen chloride in ether (IM) followed by evaporation and trituration with ether to there is prepared 3-{6-[2-(4-chlorophenyl)-ethylamino]-2-methoxy-pyrimidin-4-yl}-benzoic acid hydrochloride [1.1 g, Example 35(n)] as a solid. MS: 384 (M+H). $^1$H NMR (CDCl$_3$): δ 8.5 (1H, s); 8 (2H, d, J=5.1 Hz); 7.9 (1H, m); 7.6 (1H, t); 7.2-7.4 (4H, m); 6.6 (1H, s); 3.95 (3H, s); 3.7 (2H, t); 3 (2H, t). $IC_{50}$=0.6 nM (o) [2-Methoxy-6-(6-methoxy-pyridin-3-yl)-pyrimidin-4-yl]-[2-(4-methoxy-phenyl)-ethyl]-amine

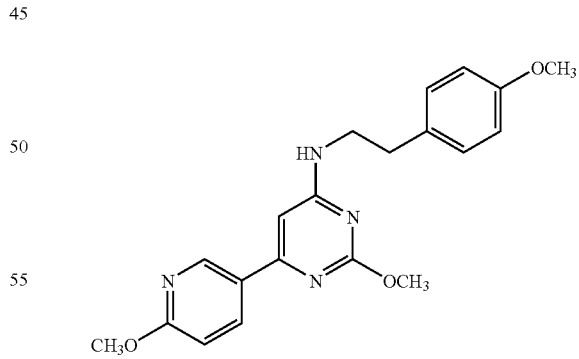

A mixture of (6-chloro-2-methoxy-pyrimidin-4-yl)-[2-(4-methoxy-phenyl)-ethyl]-amine (600 mg, 2.04 mmol), 2-methoxy-5-pyridyl-boronic acid (469 mg, 3.06 mmol, prepared according to the procedure described in *J. Org. Chem.*, 2002, 67, 7541), and Cs$_2$CO$_3$ (1.66 g, 5.11 mmol) in ethylene glycol dimethyl ether (8 mL) and water (2 mL), at room temperature, is degassed with argon gas for 5 minutes and treated with tetrakis(triphenylphosphine)palladium (0) (118 mg, 0.1 mmol). The mixture is heated at 85° C. for 5 hours, diluted with water (50 mL), and extracted twice with EtOAc (50 mL). The combined extracts are dried over magnesium sulfate, filtered and evaporated. The residue is subjected to chromatography on silica gel eluting with a mixture of EtOAc and heptane (1:1, v/v) affording [2-methoxy-6-(6-methoxy-pyridin-3-yl)-pyrimidin-4-yl]-[2-(4-methoxy-phenyl)-ethyl]-amine [0.75 g, 100%, Example 35(o)] as an oil. LCMS: $R_T$=2.74 minutes, MS: 367 (M+H). $^1$H NMR (300 MHz, CDCl$_3$): □08.78 (1H, d, J=2.1 Hz), 8.21 (1H, dd, J=8.7, 2.4 Hz), 7.16 (2H, d, J=8.4 Hz), 6.88 (1H, dd, J=8.7, 2.4 Hz), 6.82 (2H, d, J=8.4 Hz), 6.3 (1H, s), 4.95 (1H, brs), 4.03 (3H, s), 4.02 (3H, s), 3.82 (3H, s), 3.72-3.63 (2H, m), 2.92 (2H, t, J=6.9 Hz). $IC_{50}$=1.7 nM

(p) 3-{2-Methoxy-6-[2-(4-methoxy-phenyl)-ethylamino]-pyrimidin-4-yl}-phenol

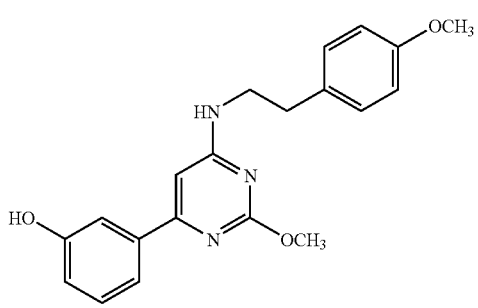

By proceeding in a similar manner as above in Example 35(o) but substituting commercially available 3-hydroxy-phenyl-boronic acid for 2-methoxy-5-pyridyl-boronic acid and subjecting the crude reaction product to short-path silica filtration, there is prepared 3-{2-methoxy-6-[2-(4-methoxy-phenyl)-ethylamino]-pyrimidin-4-yl}-phenol [1.1 g, Example 35(p)].

(q) [2-(4-Methoxy-phenyl)-ethyl]-(2-methoxy-6-pyridin-4-yl-pyrimidin-4-yl)-amine

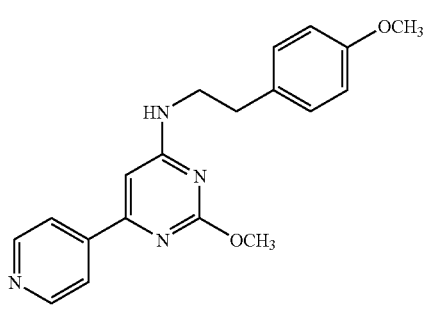

By proceeding in a similar manner as above in Example 35(o) but substituting commercially available 4-pyridyl-boronic acid for 2-methoxy-5-pyridyl-boronic, and subjecting the crude product to chromatography on silica gel eluting with MeOH in DCM (5:95, v/v), there is prepared [2-(4-methoxy-phenyl)-ethyl]-(2-methoxy-6-pyridin-4-yl-pyrimidin-4-yl)-amine [129 mg, Example 35(q)]. LCMS: $R_T$=2.35 minutes, MS: 337 (M+H). $IC_{50}$=8 nM

(r) 2-{2-Methoxy-6-[2-(4-methoxy-phenyl)-ethylamino]-pyrimidin-4-yl}-phenol

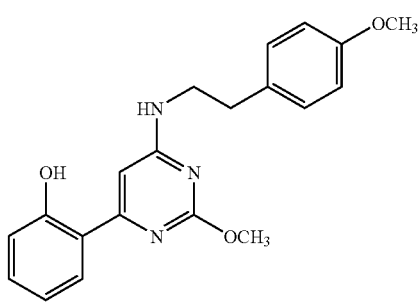

By proceeding in a similar manner as above in Example 35(o) but substituting commercially available 2-(4,4,5,5-tetramethyl-1,3,2-dioxaborolan-2-yl)phenol for 2-methoxy-5-pyridyl-boronic acid, and triturating the crude reaction product with ether, there is prepared 2-{2-methoxy-6-[2-(4-methoxy-phenyl)-ethylamino]-pyrimidin-4-yl}-phenol (143 mg, Example 35(r)] as a solid. LCMS: $R_T$=3.08 minutes, MS: 352 (M+H). $IC_{50}$=17 nM

(s) (3-{2-Methoxy-6-[2-(4-methoxy-phenyl)-ethylamino]-pyrimidin-4-yl}-phenyl)-acetonitrile

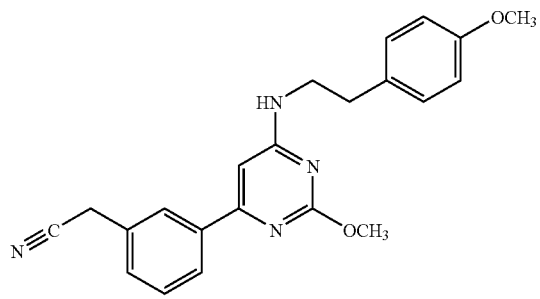

By proceeding in a similar manner as above in Example 35(o) but substituting commercially available (3-cyanomethyl-phenyl)-boronic acid, pinacol ester for 2-methoxy-5-pyridyl-boronic acid, and subjecting the crude product to chromatography on silica gel eluting with a mixture of 60% EtOAc in heptane, there is prepared (3-{2-methoxy-6-[2-(4-methoxy-phenyl)-ethylamino]-pyrimidin-4-yl}-phenyl)-acetonitrile [350 mg, Example 35(s)]. LCMS: $R_T$=2.48 minutes, MS: 375 (M+H). $IC_{50}$=6 nM (t) 3-{2-Methoxy-6-[2-(4-methoxy-phenyl)-ethylamino]-pyrimidin-4-yl}-benzonitrile

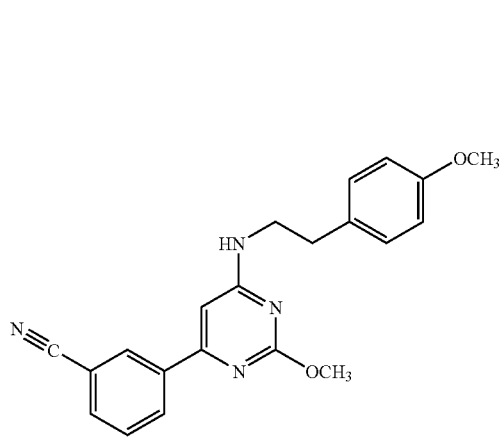

By proceeding in a similar manner as above in Example 35(o) but substituting commercially available 3-cyano-phenyl-boronic acid for 2-methoxy-5-pyridyl-boronic acid, and subjecting the crude product to chromatography on silica gel eluting with a mixture of 40% EtOAc in heptane, there is prepared 3-{2-methoxy-6-[2-(4-methoxy-phenyl)-ethylamino]-pyrimidin-4-yl}-benzonitrile [220 mg, Example 35(t)]. LCMS: $R_T$=3.15 minutes, MS: 361 (M+H). $IC_{50}$=0.9 nM (u) 3-{2-Methoxy-6-[2-(4-methoxy-phenyl)-ethylamino]-pyrimidin-4-yl}-benzaldehyde

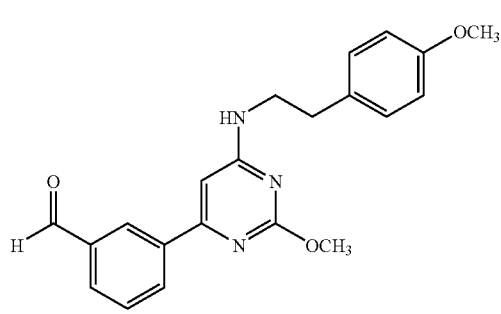

By proceeding in a similar manner as above in Example 35(o) but substituting commercially available 3-formyl-phenyl-boronic acid for 2-methoxy-5-pyridyl-boronic acid, and subjecting the crude product to chromatography on silica gel eluting with a mixture of 460% EtOAc in heptane, there is prepared 3-{2-methoxy-6-[2-(4-methoxy-phenyl)-ethylamino]-pyrimidin-4-yl}-benzaldehyde [12.4 mg, Example 35(u)]. LCMS: $R_T$=3.05 minutes, MS: 364 (M+H).

(v) 3-{6-[2-(2-Chloro-6-fluoro-phenyl)-ethylamino]-2-methoxy-pyrimidin-4-yl}-benzaldehyde

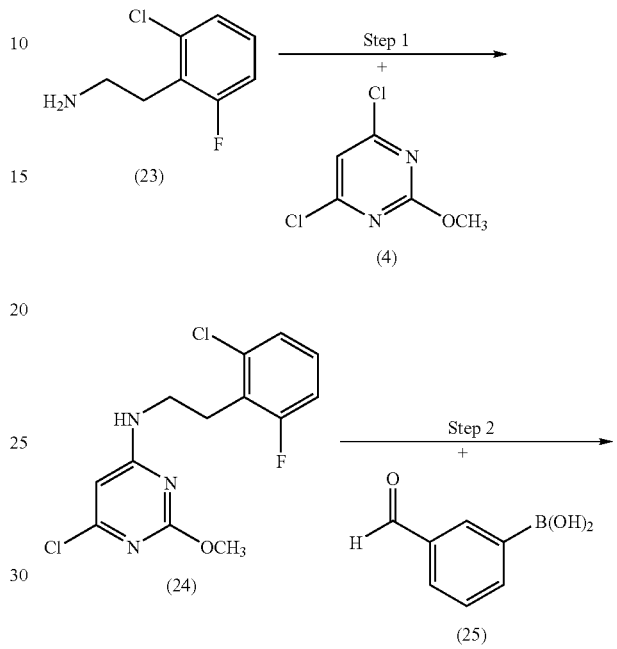

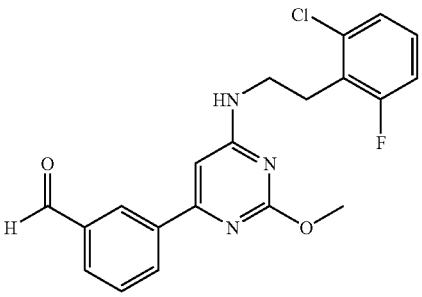

Example 35(v)

Step 1. Following procedures similar to those of Example 1, step 3, but using 4,6-dichloro-2-methoxypyrimidine [3.1 g, Intermediate (4)], 2-(2-chloro-6-fluoro-phenyl)-ethylamine (1.84 g, Intermediate (23)] and sodium bicarbonate (2.02 g) there is prepared (6-chloro-2-methoxy-pyrimidin-4-yl)-[2-(2-chloro-6-fluoro-phenyl)-ethyl]-amine [3.2 g, Intermediate (24)] as a white solid. LCMS: $R_T$=3.63 minutes, MS: 317 (M+H).

Step 2. By proceeding in a similar manner as above in Example 35(o) but substituting commercially available 3-formyl-phenyl-boronic acid [Intermediate (25)] for 2-methoxy-5-pyridyl-boronic acid, and (6-chloro-2-methoxy-pyrimidin-4-yl)-[2-(2-chloro-6-fluoro-phenyl)-ethyl]-amine [2 g, Intermediate (24) prepared in step 1], for (6-chloro-2-methoxy-pyrimidin-4-yl)-[2-(4-methoxy-phenyl)-ethyl]-amine, there is prepared 3-{6-[2-(2-chloro-6-fluoro-phenyl)-ethylamino]-2-methoxy-pyrimidin-4-yl}- benzaldehyde [2.76 g, Example 35(v)]. LCMS: R$_T$=3.2 minutes, MS: 386 (M+FI). IC$_{50}$=3.6 nM (w) 3-{6-[2-(2,4-Dichloro-phenyl)-ethylamino]-2-methoxy-pyrimidin-4-yl}-benzoic acid

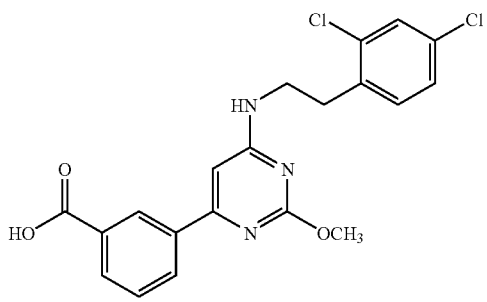

By proceeding in a similar manner as above in Example 35(o) but substituting commercially available 3-carboxy-phenyl-boronic acid for 2-methoxy-5-pyridyl-boronic acid, and (6-chloro-2-methoxy-pyrimidin-4-yl)-[2-(2,4-dichloro-phenyl)-ethyl]-amine [2 g, Intermediate (44)] for (6-chloro-2-methoxy-pyrimidin-4-yl)-[2-(4-methoxy-phenyl)-ethyl]-amine, and extracting the crude reaction mixture, adjusted to pH 2, with EtOAc there is prepared 3-{6-[2-(2,4-dichloro-phenyl)-ethylamino]-2-methoxy-pyrimidin-4-yl}-benzoic acid [2.5 g, Example 35(w)]. IC$_{50}$=0.3 nM (x) [2-Methoxy-6-(pyridin-3-yl)-pyrimidin-4-yl]-[2-(4-methoxy-phenyl)-ethyl]-amine

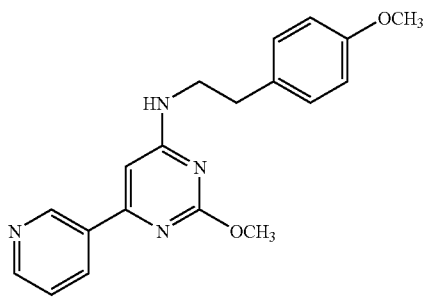

By proceeding in a similar manner as above in Example 35(o) but substituting commercially available 3-pyridyl-boronic acid for 2-methoxy-5-pyridyl-boronic acid, and subjecting the crude product to chromatography on silica gel eluting with 5% MeOH in DCM, there is prepared [2-methoxy-6-(pyridin-3-yl)-pyrimidin-4-yl]-[2-(4-methoxy-phe-nyl)-ethyl]-amine [45 mg, Example 35(x)]. LCMS: R$_T$=2.33 minutes, MS: 337 (M+H). IC$_{50}$=10 nM (y) 2-Methoxy-5-{2-methoxy-6-[2-(4-methoxy-phenyl)-ethylamino]-pyrimidin-4-yl}-benzaldehyde

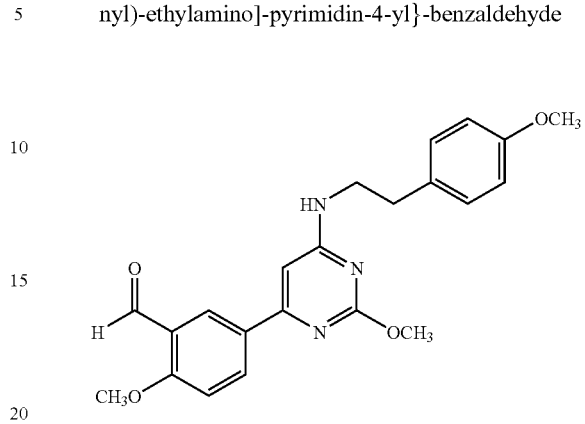

By proceeding in a similar manner as above in Example 35(o) but substituting commercially available 3-formyl-4-methoxy-boronic acid for 2-methoxy-5-pyridyl-boronic acid, and triturating the product with ether, there is prepared 2-methoxy-5-{2-methoxy-6-[2-(4-methoxy-phenyl)-ethylamino]-pyrimidin-4-yl}-benzaldehyde [780 mg, Example 35(y)]. LCMS: R$_T$=2.55 minutes, MS: 394 (M+H).

(z) 2-Chloro-5-{2-methoxy-6-[2-(4-methoxy-phenyl)-ethylamino]-pyrimidin-4-yl}-benzoic acid ethyl ester

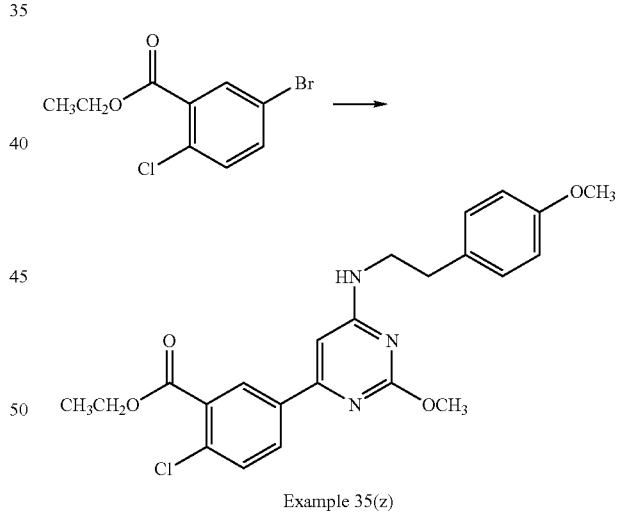

Example 35(z)

Step 1. Under a nitrogen atmosphere, a 50 mL round bottom flask is charged with bis(pinacolato)diborane (1.16 g, 4.55 mmol), potassium acetate (1.11 g, 11.4 mmol) and 5-bromo-2-chloro-benzoic acid ethyl ester (1 g, 3.79 mmol). After bubbling nitrogen through the mixture for 5 minutes, dichloro[1,1'-bis(diphenylphosphino)ferrocene]palladium DCM adduct [PdCl$_2$(dppf), 93 mg, 0.11 mmol] is added. The resulting mixture is heated to 60° C. for 2 hours, cooled to room temperature and poured into EtOAc (50 mL). This mixture is washed with water, with brine, dried over sodium sulfate, filtered and concentrated to give 2-chloro-5-(4,4,5,5-tetramethyl-[1,3,2]dioxaborolan-2-yl)-benzoic acid ethyl ester [LCMS: $R_T$=5.1 minutes, MS: 311 (M+H)] and the dimerized side product, 4,3'-Dichloro-biphenyl-3,4'-dicarboxylic acid diethyl ester in 2:1 ratio (0.65 g total). The crude mixture is used for a next step without further purification.

Step 2. By proceeding in a similar manner to Example 35(o) above but substituting the crude 2-chloro-5-(4,4,5,5-tetramethyl-[1,3,2]dioxaborolan-2-yl)-benzoic acid ethyl ester, prepared in step 1 above, for 2-methoxy-5-pyridyl-boronic acid, and carrying out a short-path silica gel filtration on the crude product, there is prepared 2-chloro-5-{2-methoxy-6-[2-(4-methoxy-phenyl)-ethylamino]-pyrimidin-4-yl}-benzoic acid ethyl ester [0.21 g, Example 35(z)]. LCMS: $R_T$=3.28 minutes, MS: 442 (M+H). $IC_{50}$=32 nM Example 36

{2-Methoxy-6-[3-(3-methyl-[1,2,4]oxadiazol-5-yl)-phenyl]-pyrimidin-4-yl}-[2-(4-methoxy-phenyl)-ethyl]-amine

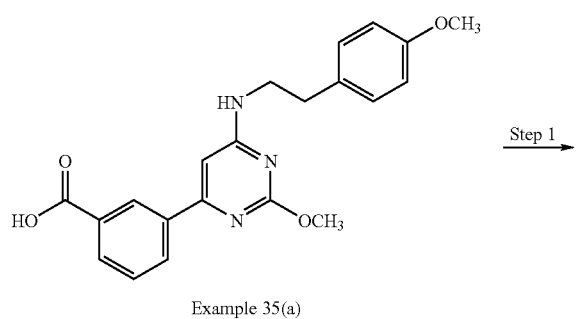

Example 35(a)

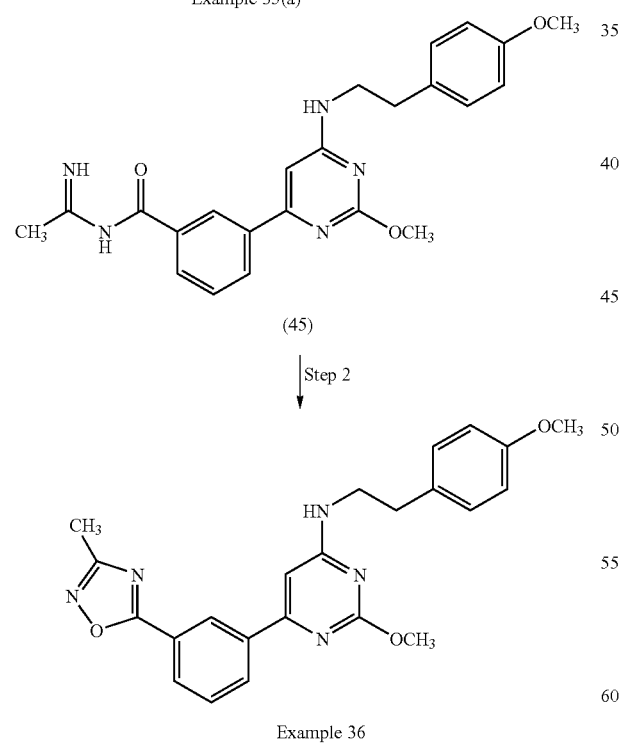

Step 1. To a solution of 3-{2-methoxy-6-[2-(4-methoxy-phenyl)-ethylamino]-pyrimidin-4-yl}-benzoic acid (200 mg, 0.53 mmol, Example 35(a)] in dimethylformamide (1.75 mL) is added diisopropylethylamine (0.23 mL, 1.33 mmol) followed by TBTU (205 mg, 0.64 mmol). Stirred the solution for 15 minutes before adding acetamide oxime (59 mg, 0.8 mmol). After 4 hours of stirring at ambient temperature the mixture is diluted with water (20 mL) and extracted twice with EtOAc (20 mL). The combined organic extracts are washed three times with water (20 mL), with brine (20 mL), dried over magnesium sulfate, filtered and concentrated by rotary evaporator to provide N-(1-imino-ethyl)-3-{2-methoxy-6-[2-(4-methoxy-phenyl)-ethylamino]-pyrimidin-4-yl}-benzamide [60 mg, 69%, Intermediate (45)].

Step 2. A solution of N-(1-imino-ethyl)-3-{2-methoxy-6-[2-(4-methoxy-phenyl)-ethylamino]-pyrimidin-4-yl}-benzamide [160 mg, 0.367 mmol, Intermediate (45)] in THF (2 mL) is irradiated in a microwave to 140° C. twice for 4 minutes. The reaction mixture is absorbed onto silica gel and subjected to flash column chromatography on silica gel (9 g) eluting with 0 to 50% EtOAc in heptane gradient, to afford {2-methoxy-6-[3-(3-methyl-[1.24]oxadiazol-5-yl)-phenyl]-pyrimidin-4-yl}-[2-(4-methoxy-phenyl)-ethyl]-amine [41 mg, 27%, Example 36]. LCMS: $R_T$=2.9 minutes, MS: 418 (M+H). $^1$H NMR (300 MHz, $CDCl_3$): δ 8.64 (1H, s), 8.26 (1H, dt, J=0.027, 0.0044 Hz), 8.15 (1H, dt, J=0.027, 0.0044 Hz), 7.59 (1H, t, J=0.026 Hz), 7.14 (2H, d, J=0.029 Hz), 6.86 (2H, d, J=0.029 Hz), 6.43 (1H, s), 4.94 (1H, s), 4.04 (3H, s), 3.78 (3H, s), 3.69 (2H, m), 2.9 (2H, t, J=0.022 Hz), 2.49 (3H, s). $IC_{50}$=2.6 nM Example 37

{2-Methoxy-6-[3-(5-methyl-2H-[1,2,4]triazol-3-yl)-phenyl]-pyrimidin-4-yl}-[2-(4-methoxy-phenyl)-ethyl]-amine

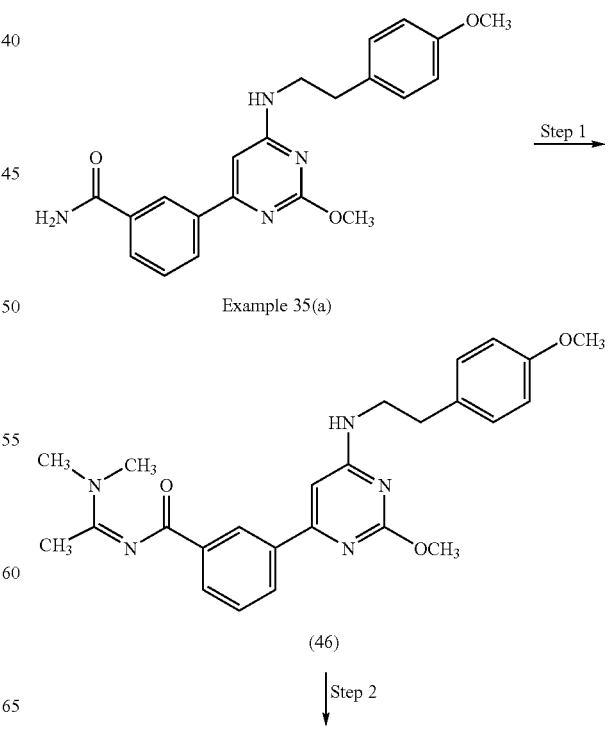

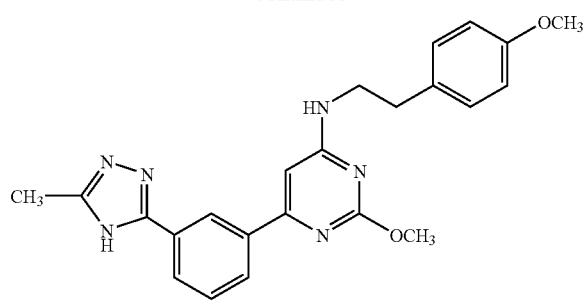

Example 37

Step 1. A mixture of 3-{2-methoxy-6-[2-(4-methoxy-phenyl)-ethylamino]-pyrimidin-4-yl}-benzamide [50 mg, 0.132 mmol, Example 35(g)] and dimethylacetamide dimethylacetal (2 mL) in a sealed tube and heated to 110° C. for 45 minutes. The mixture is concentrated by rotary evaporator to provide N-(1-dimethylamino-ethylidene)-3-{2-methoxy-6-[2-(4-methoxy-phenyl)-ethylamino]-pyrimidin-4-yl}-benzamide [Intermediate (46)] in quantitative yield.

Step 2. A solution of N-(1-dimethylamino-ethylidene)-3-{2-methoxy-6-[2-(4-methoxy-phenyl)-ethylamino]-pyrimidin-4-yl}-benzamide [0.132 mmol, Intermediate (46)] and hydrazine hydrate (15 µL, 0.48 mmol) in acetic acid (1 mL) is heated to 90° C. After stirring for 30 minutes removed from heat, quenched with saturated sodium bicarbonate solution (20 mL) and extracted twice with EtOAc (20 mL). The organic extracts are dried over magnesium sulfate, filtered and concentrated by rotary evaporator. The resulting oil is subjected to flash column chromatography on silica gel eluting with 40% EtOAc in heptane gradient to afford {2-methoxy-6-[3-(5-methyl-2H-[1,2,4]triazol-3-yl)-phenyl]-pyrimidin-4-yl}-[2-(4-methoxy-phenyl)-ethyl]-amine [38 mg, 69%, Example 37]. LCMS: $R_T$=2.59 minutes MS: 417 (M+H). $IC_{50}$=3.7 nM Example 38

{2-Methoxy-6-[3-(3-methyl-isoxazol-5-yl)-phenyl]-pyrimidin-4-yl}-[2-(4-methoxy-phenyl)-ethyl]-amine

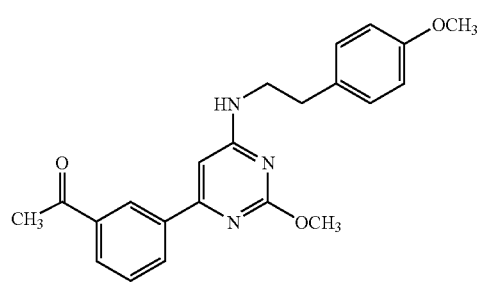

Example 35(h)

→ Step 1

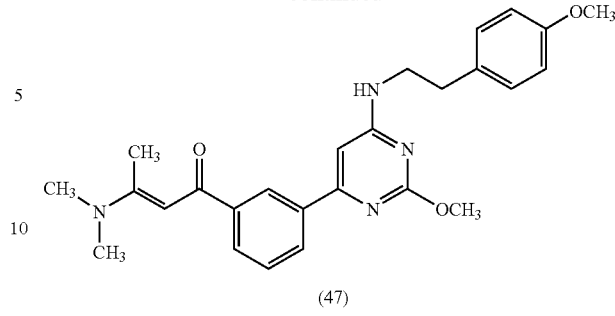

(47)

↓ Step 2

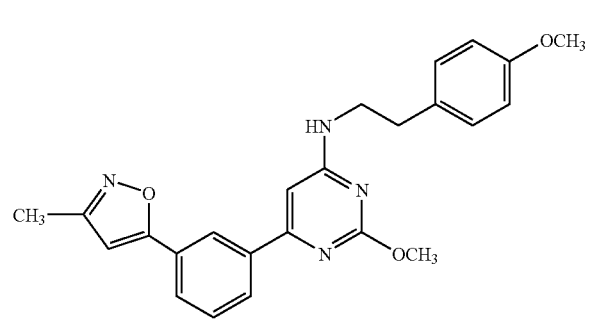

Example 38

Step 1. A mixture of 1-(3-{2-methoxy-6-[2-(4-methoxy-phenyl)-ethylamino]-pyrimidin-4-yl}-phenyl)-ethanone [125 mg, 0.33 mmol, Example 35(h)] and dimethylacetamide dimethylacetal (2 mL) in a round bottom flask is heated to 90° C. for 4 hours. The reaction mixture is treated with water (20 mL) and extracted three times with EtOAc (20 mL). The combined organics are dried over magnesium sulfate, filtered and concentrated by rotary evaporator to provide 3-dimethylamino-1-(3-{2-methoxy-6-[2-(4-methoxy-phenyl)-ethylamino]-pyrimidin-4-yl}-phenyl)-but-2-en-1-one [Intermediate (47)] in quantitative yield.

Step 2. In a sealed tube are combined 3-dimethylamino-1-(3-{2-methoxy-6-[2-(4-methoxy-phenyl)-ethylamino]-pyrimidin-4-yl}-phenyl)-but-2-en-1-one [60 mg, 0.134 mmol, Intermediate (47)], hydroxylamine hydrate (40 mg), and EtOH (3 mL). The mixture is heated at 95° C. with stirring for 6 hours concentrated. The resulting oil is subjected to flash column chromatography on silica gel eluting with 40% EtOAc in heptane to afford {2-methoxy-6-[3-(3-methyl-isoxazol-5-yl)-phenyl]-pyrimidin-4-yl}-[2-(4-methoxy-phenyl)-ethyl]-amine [56 mg, 100%, Example 38] as a solid. LCMS: $R_T$=2.82 minutes, MS: 417 (M+H). $IC_{50}$=6 nM

Example 39

{2-Methoxy-6-[3-(5-methyl-2H-pyrazol-3-yl)-phenyl]-pyrimidin-4-yl}-[2-(4-methoxy-phenyl)-ethyl]-amine

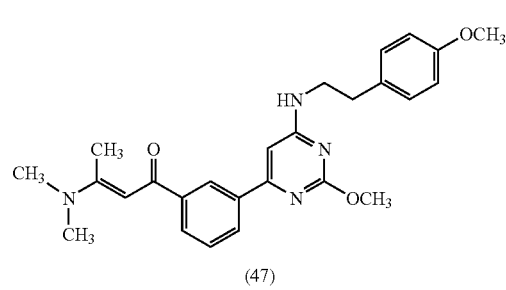

(47)

Example 40

[2-(3-Fluoro-4-methoxy-phenyl)-ethyl]-{2-methoxy-6-[3-(2H-tetrazol-5-yl)-phenyl]-pyrimidin-4-yl}-amine

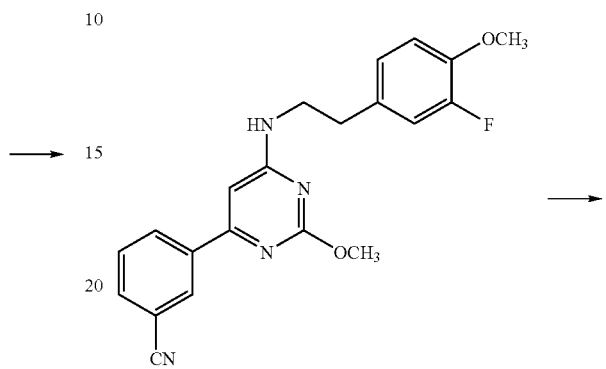

Example 1(a)

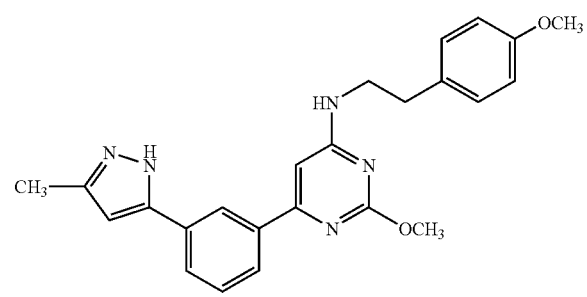

Example 39

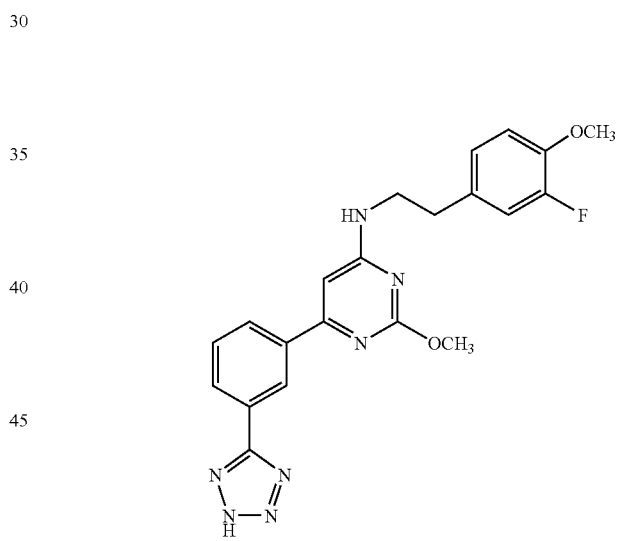

Example 40

In a sealed tube are combined 3-dimethylamino-1-(3-{2-methoxy-6-[2-(4-methoxy-phenyl)-ethylamino]-pyrimidin-4-yl}-phenyl)-but-2-en-1-one [147 mg, 0.33 mmol, Intermediate (47) prepared as described in Example 38, Step 1], hydrazine hydrate (200 µL), and EtOH (3 mL). Heated the mixture to 85° C. and stirred for 1.5 hours. The reaction mixture is concentrated to provide an oil which is subjected to flash column chromatography on silica gel eluting with 20 to 60% EtOAc in heptane gradient, to afford {2-methoxy-6-[3-(5-methyl-2H-pyrazol-3-yl)-phenyl]-pyrimidin-4-yl}-[2-(4-methoxy-phenyl)-ethyl]-amine [136 mg, 99%, Example 39]. LCMS: $R_f$=2.79 minutes, MS: 416 (M+H). $^1$H NMR (300 MHz, CDCl$_3$) δ 8.29 (1H, s), 7.9 (1H, d, J=0.027 Hz), 7.72 (1H, d, J=0.025 Hz), 7.4 (1H, t, J=0.026 Hz), 7.09 (2H, d, J=0.028 Hz), 6.82 (2H, d, J=0.028 Hz), 6.35 (2H, d, J=0.024 Hz), 5.18 (1H, s), 3.98 (3H, s), 3.75 (3H, s), 3.59 (2H, m), 2.83 (2H, t, J=0.023), 2.3 (3H, s).

A solution of 3-{6-[2-(3-fluoro-4-methoxy-phenyl)-ethylamino]-2-methoxy-pyrimidin-4-yl}-benzonitrile [1.5 g, Example 1] and tributyl tinazide (1.66 mL) in toluene (80 mL) is heated at 115° C. for 20 hours. The solution is cooled and treated with glacial acetic acid (20 mL) giving a white precipitate. The mixture is extracted twice with EtOAc (200 mL). The combined extracts are dried over sodium sulfate, filtered, and evaporated. The residue is subjected to chromatography on silica gel eluting with EtOAc to give [2-(3-fluoro-4-methoxy-phenyl)-ethyl]-{2-methoxy-6-[3-(2H-tetrazol-5-yl)-phenyl]-pyrimidin-4-yl}-amine (0.31 g, Example 40) as a solid. MS: 422 (M+H); $^1$H NMR (CDCl$_3$): δ 8.6 (1H, s); 8.1 (1H, d (J=5.1 Hz)); 7.9 (2H, m); 7.6 (1H, t); 7-7.2 (4H, m); 6.7

(1H, s); 3.95 (3H, s); 3.8 (3H, s); 3.6 (2H, t); 2.8 (2H, t); 1.6 (1H, m); 1.3 (1H, m). IC$_{50}$=0.4 nM

Example 41

1-Ethyl-3-(3-{2-methoxy-6-[2-(4-methoxy-phenyl)-ethylamino]-pyrimidin-4-yl}-phenyl)-urea

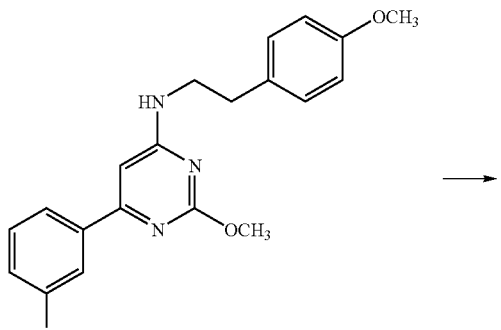

Example 2

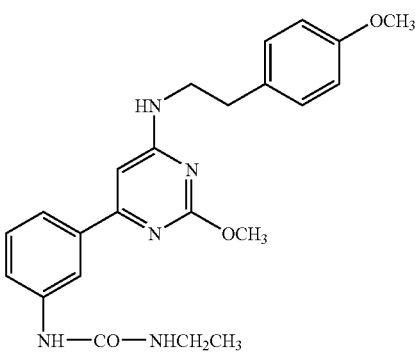

Example 41

To a solution of [6-(3-amino-phenyl)-2-methoxy-pyrimidin-4-yl]-[2-(4-methoxy-phenyl)-ethyl]-amine (184 mg, 0.45 mmol, Example 2) in pyridine (1.5 mL) is added ethyl isocyanate (43 µL, 0.54 mmol). The reaction mixture is stirred for 18 hours at ambient temperature, quenched with the addition of water (25 mL), and extracted four times with EtOAc (25 mL). The combined extracts and washed four times with aqueous copper sulfate solution (25 mL), with water (25 mL), with brine (25 mL), dried over magnesium sulfate, filtered and concentrated by rotary evaporator. The resulting solid is subjected to flash column chromatography on silica (4.5 g) eluting with 20 to 40% EtOAc in heptane to afford 1-ethyl-3-(3-{2-methoxy-6-[2-(4-methoxy-phenyl)-ethylamino]-pyrimidin-4-yl}-phenyl)-urea [98.3 mg, 52%, Example 41]. LCMS: R$_T$=2.68 minutes, MS: 422 (M+H). $^1$H NMR (300 MHz, CDCl$_3$) δ 8.11 (1H, d, J=0.17 Hz), 7.88 (2H, s), 7.62 (1H, d, J=0.026 Hz), 7.49 (1H, d, J=0.026 Hz), 7.18 (4H, m), 6.81 (2H, m), 6.22 (1H, d, J=0.08 Hz), 5.83 (1H, s), 5.35 (1H, s), 3.93 (3H, d, J=0.04 Hz), 3.73 (3H, d, J=0.012

Hz), 3.55 (2H, m), 3.19 (2H, q, J=0.022 Hz), 2.81 (2H, m), 2.13 (1H, s), 1.04 (2H, t, J=0.022 Hz). IC$_{50}$=7.6 nM

Example 42

2-(3-{6-[2-(2,4-Dichloro-phenyl)-ethylamino]-2-methoxy-pyrimidin-4-yl}-phenoxy)-2-methyl-propionic acid ethyl ester

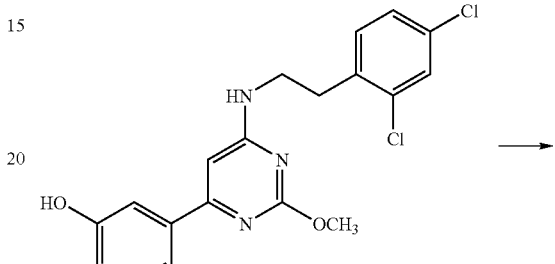

Example 35(i)

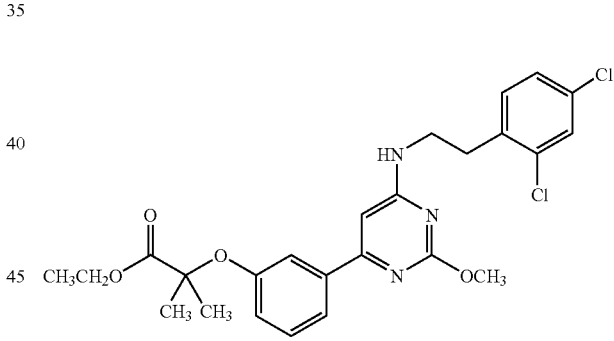

Example 42

A mixture of 3-{6-[2-(2,4-dichloro-phenyl)-ethylamino]-2-methoxy-pyrimidin-4-yl}-phenol [945 mg, 2.42 mmol, Example 35(i)], PS-TBD (3.38 g, 5 mmol), ethyl 2-bromoisobutyrate (888 mL, 605 mmol) and acetonitrile (20 mL) is heated to reflux and stirred for 2 hours. The heating is turned off and the mixture is stirred overnight at ambient temperature. The reaction mixture is filtered to remove the resin and the resin is washed with MeOH (20 mL) and with acetonitrile (20 mL). The combined filtrate and washings are concentrated by rotary evaporator. The residue is subjected to flash column chromatography on silica (40 g) eluting with 20 to 50% EtOAc in heptane gradient to afford 2-(3-{6-[2-(2,4-dichloro-phenyl)-ethylamino]-2-methoxy-pyrimidin-4-yl}-phenoxy)-2-methyl-propionic acid ethyl ester [450 mg, 37%, Example 42] as a solid. LCMS: R$_T$=2.9 minutes, MS: 504 (M+H).

Example 43

(a) [2-(4-Chloro-phenyl)-1-methyl-ethyl]-[6-(3,4-dimethoxy-phenyl)-2-methoxy-pyrimidin-4-yl]-amine

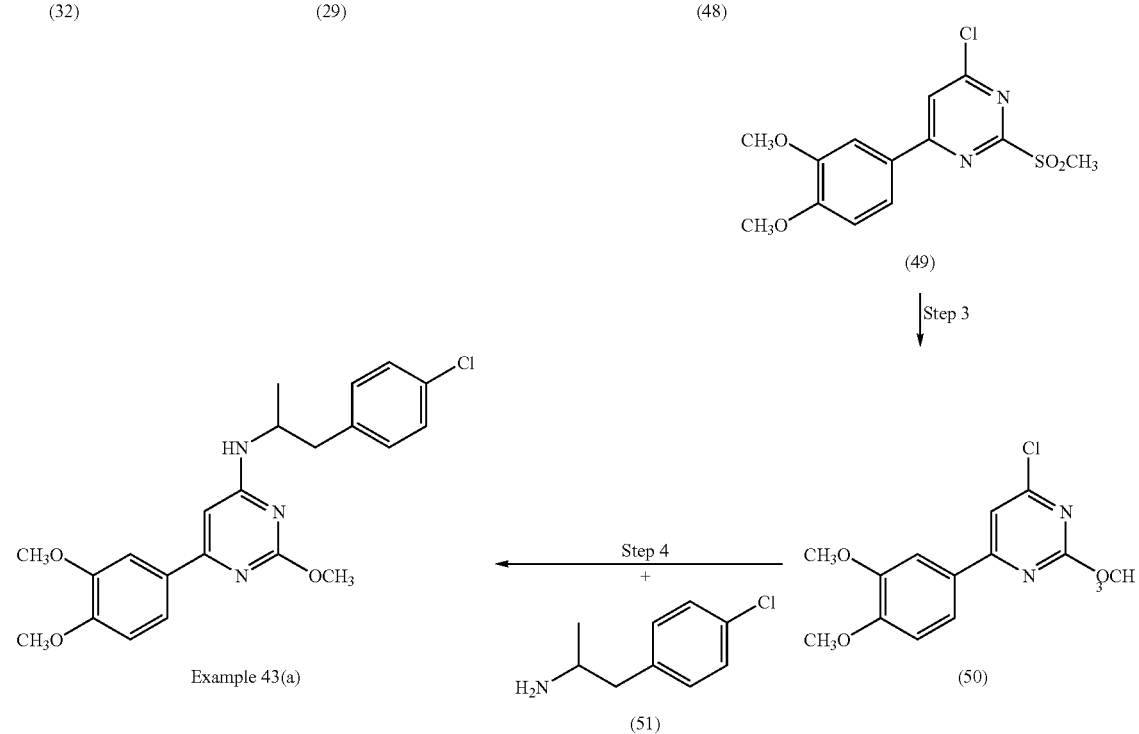

Step 1. Argon is bubbled through a mixture of 4,6-dichloro-2-(methylthio)pyrimidine [4.98 g, 25.55 mmol, Intermediate (29)], 3,4-dimethoxyphenylboronic acid [3.874 g, 21.29 mmol, Intermediate (32)], and $Cs_2CO_3$ (17.34 g, 53.23 mmol) in ethylene glycol dimethyl ether (56 mL) and water (14 mL), for a period of 15 minutes. To this mixture is added tetrakis (triphenylphosphine)palladium (0) (1.22 g, 1.06 mmol) the reaction vessel is heated to 100° C. After stirring overnight the mixture is diluted with water (250 mL) and extracted three times with EtOAc (100 mL). The organic extracts are combined, washed with brine (100 mL), and dried over magnesium sulfate. The mixture is filtered and concentrated to provide a solid that is dissolved in boiling isopropyl alcohol (40 mL) and allowed to cool to ambient temperature. After standing for 24 hours the solid is collected by filtration, washed with cold isopropyl alcohol and dried under high vacuum to afford 4-chloro-6-(3,4-dimethoxy-phenyl)-2-methylsulfanyl-pyrimidine [5.28 g, 83.5%, Intermediate (48)].

Step 2. A solution of 4-chloro-6-(3,4-dimethoxy-phenyl)-2-methylsulfanyl-pyrimidine [5.28 g, 0.0178 mol, Intermediate (48)] in DCM (120 mL) is chilled to 0° C. To the chilled solution is added 3-chloro-peroxybenzoic acid (9.66 g, 0.0392 mol). After 30 minutes the cooling bath is removed and the mixture is allowed to stir at ambient temperature overnight. The precipitate that formed is collected by filtration, washed with DCM (50 mL). The organic filtrate is washed with aqueous sodium hydroxide solution (150 mL, 2 N) and dried over magnesium sulfate. The mixture is filtered and concentrated to provide 4-chloro-6-(3,4-dimethoxy-phenyl)-2-methanesulfonyl-pyrimidine [5.05 g, 86%, Intermediate (49)] as a solid.

Step 3. A mixture of 4-chloro-6-(3,4-dimethoxy-phenyl)-2-methanesulfonyl-pyrimidine [5.05 g, 0.0154 mol, Intermediate (49)] in ethylene glycol dimethyl ether (100 mL) is chilled to 0° C. and added 25 wt % sodium methoxide in MeOH (1.32 mL, 0.0231 mol). After 15 minutes the reaction is allowed to warm to ambient temperature and stirred overnight. The mixture is concentrated to afford 4-chloro-6-(3,4-dimethoxy-phenyl)-2-methoxy-pyrimidine [4.3 g, 100%, Intermediate (50)]

Step 4. To a solution of 4-chloro-6-(3,4-dimethoxy-phenyl)-2-methoxy-pyrimidine [140 mg, 0.5 mmol, Intermediate (50)] and N,N-diisopropylethylamine (392 µL, 2.25 mmol) in THF (1.7 mL) is added DL-p-chloroamphetamine hydrochloride (154.6 mg, 0.75 mmol, Intermediate (51)]. The mixture is heated to reflux for 2 hours and quenched with water (20 mL)

and extracted twice with EtOAc (20 mL). The combined extracts are concentrated and the residue is subjected to flash column chromatography on silica gel eluting with 0 to 50% EtOAc in heptane gradient to afford [2-(4-chloro-phenyl)-1-methyl-ethyl]-[6-(3,4-dimethoxy-phenyl)-2-methoxy-pyrimidin-4-yl]-amine [52.7 mg, 25.5%, Example 43(a)]. LCMS: $R_T$=2.66 minutes, MS: 414 (M+H). $^1$H NMR (300 MHz, CDCl$_3$): δ 7.65 (1H, d, J=0.066 Hz), 7.53 (1H, dd, J=0.066, 0.028), 7.28 (2H, d, J=0.028 Hz), 7.14 (2H, d, J=0.028 Hz), 6.93 (1H, d, J=0.028 Hz), 6.31 (1H, s), 4.72 (1H, s), 4.34 (1H, s), 4.04 (3H, s), 3.99 (3H, s), 3.95 (3H, s), 2.89 (2H, qd, J=0.045, 0.022 Hz), 1.79 (1H, s), 1.24 (3H, d, J=0.22 Hz). IC$_{50}$=1726 nM (b) [2-Methoxy-6-(3-methoxy-phenyl)-pyrimidin-4-yl]-[2-(4-nitro-phenyl)-ethyl]-amine acid (10.06 g, 40.83 mmol) and stirred at room temperature for 4 hours. The reaction mixture is quenched with 2 N sodium hydroxide solution to pH=9, extracted with DCM (3×100 mL). The organic layers are combined and washed with 10 mL of brine and dried over sodium sulfate. The mixture is concentrated to provide 4-chloro-2-methanesulfonyl-6-(3-methoxy-phenyl)-pyrimidine [4.35 g, LC/MS: $R_T$=3.3 minutes, MS: 299 (M+H)] as a solid. 4.25 g of this material is dissolved in a mixture of MeOH (70 mL) and DCM (40 mL) and the solution is treated dropwise with sodium methoxide (25% wt in methanol, 3.58 mL, 15.64 mmol). The mixture is stirred at room temperature for 2 hours quenched with water (20 mL), concentrated to remove MeOH and DCM, and extracted three times with EtOAc (100 mL). The combined extracts are washed with 10 mL of brine and dried over sodium sulfate. The mixture is concentrated to provide a solid which is subjected to flash column chroma-

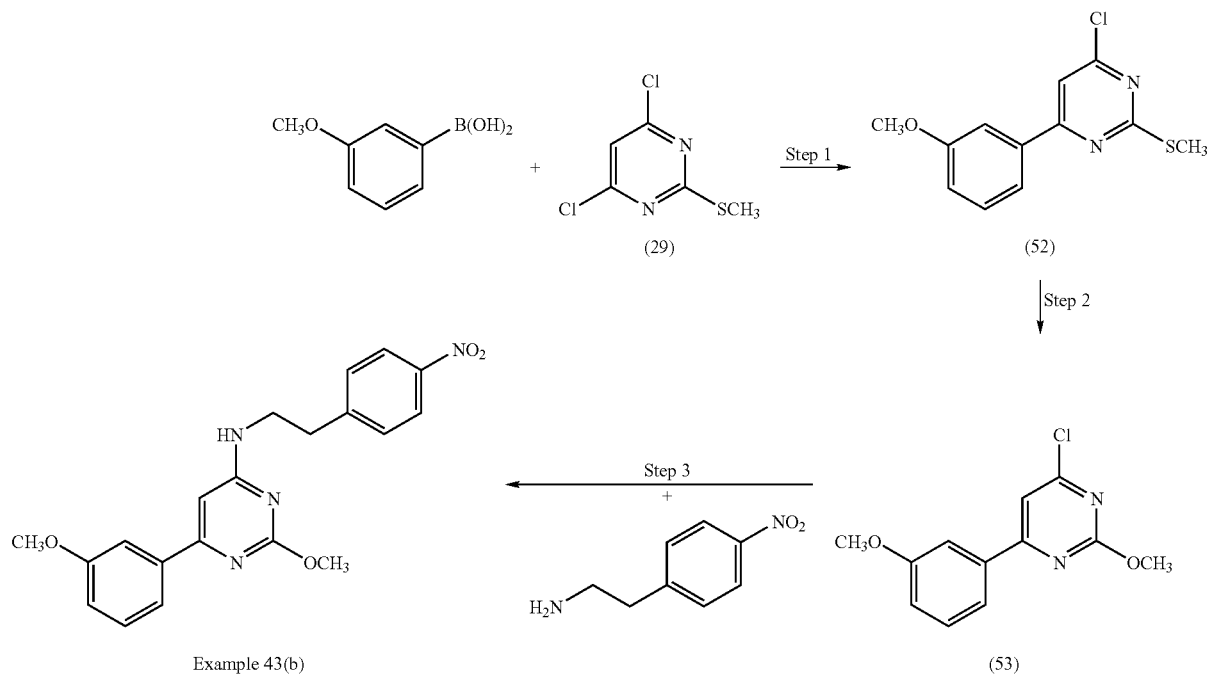

Example 43(b)

(53)

Step 1. To a mixture of 4,6-dichloro-2-methylsulfanyl-pyrimidine [4.9 g, 25.12 mmol, Intermediate (29)] and 3-methoxyphenylboronic acid [3.47 g, 22.84 mmol] in ethylene glycol dimethyl ether (40 mL) and water (10 mL), is added Cs$_2$CO$_3$ (18.6 g, 57.1 mmol). Nitrogen gas is bubbled through the mixture for 5 minutes before addition of tetrakis(triphenylphosphine)palladium (0) (1.32 g, 1.14 mmol). The reaction vessel is sealed and heated to 90° C. for 22 hours. The reaction mixture is quenched with 30 mL of water. Black precipitate is filtered, the filtrate is concentrated under vacuum and extracted three times with EtOAc (100 mL). The organic layers are combined and washed with 20 mL of brine and dried over sodium sulfate. The mixture is concentrated to provide an oil which is subjected to flash column chromatography (silica gel: 0-7% ethyl acetate/heptane) to afford 4-chloro-6-(3-methoxy-phenyl)-2-methylsulfanyl-pyrimidine [3.92 g, 64%, Intermediate (52)] as a solid. LC/MS: $R_T$=4.14 minutes, MS: 267 (M+H).

Step 2. To a solution of 4-chloro-6-(3-methoxy-phenyl)-2-methylsulfanyl-pyrimidine (3.63 g, 13.61 mmol, Intermediate (52)] in DCM (70 mL) is added 3-chloroperoxybenzoic tography (silica gel: 2-20% ethyl acetate/heptane) to afford 4-chloro-2-methoxy-6-(3-methoxy-phenyl)-pyrimidine [2.73 g, 80% yield for 2 steps, Intermediate (53)] as a solid. LC/MS: $R_T$=3.84 minutes MS: 251 (M+H).

Step 3. To a solution of 4-chloro-2-methoxy-6-(3-methoxy-phenyl)-pyrimidine [80 mg, 0.32 mmol, Intermediate (53)] and 2-(4-nitro-phenyl)-ethylamine hydrochloride (77.6 mg, 0.38 mmol) in EtOH (1.1 mL) is added diisopropylethylamine (0.139 mL, 0.80 mmol). The reaction mixture is heated under microwave at 170° C. for 45 minutes. Solvent is removed and residue is subjected to flash column chromatography (silica gel: 10-50% ethyl acetate/heptane) to afford [2-methoxy-6-(3-methoxy-phenyl)-pyrimidin-4-yl]-[2-(4-nitro-phenyl)-ethyl]-amine [62 mg, 51%, Example 43(b)] as a solid. LC/MS: $R_T$=2.57 minute, MS: 381 (M+H). $^1$H NMR (300 MHz, (CD$_3$)$_2$SO): □8.14 (2H, d, J=9.8 Hz), 7.53 (2H, d, J=9.8 Hz), 7.52 (3H, m), 7.38 (1H, t, J=8.6 Hz), 7.01 (1H, m), 6.58 (1H, s), 3.84 (3H, s), 3.79 (3H, s), 3.6 (2H, m), 2.99 (2H, m). IC$_{50}$=0.9 nM (c) [2-Methoxy-6-(3-methoxy-phenyl)-pyrimidin-4-yl]-[2-(4-trifluoromethoxy-phenyl)-ethyl]-amine

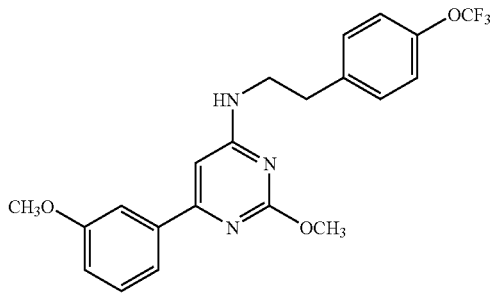

By proceeding in a similar manner to Example 43(b) above but substituting 2-(4-trifluoromethoxy-phenyl)-ethylamine [Intermediate 12] for 2-(4-nitro-phenyl)-ethylamine, acetonitrile for EtOH as solvent in Step 3, and carrying out the reaction in a microwave oven at 170° C. for 45 minutes, there is prepared [2-methoxy-6-[3]-methoxy-phenyl)-pyrimidin-4-yl]-[2-(4-trifluoromethoxy-phenyl)-ethyl]-amine [88 mg, 44%, Example 43(c)] as a solid. LC/MS: $R_T$=2.92 minutes, MS: 420 (M+H). $^1$H NMR (300 MHz, CDCl$_3$): □7.6 (H, m), 7.55 (1H, d, J=9 Hz), 7.52 (1H, t, J=7.4 Hz), 7.24 (2H, d, J=9.8 Hz), 7.16 (2H, d, J=9.8 Hz), 6.99 (1H, m), 6.36 (1H, s), 4.86 (1H, br s), 4.01 (3H, s), 3.86 (3H, s), 3.7 (2H, m), 2.96 (2H, m).

(d) [2-(2-Chloro-6-fluoro-phenyl)-ethyl]-[2-methoxy-6-(3-methoxy-phenyl)-pyrimidin-4-yl]-amine hydrochloride

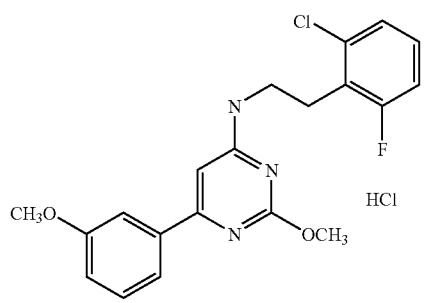

By proceeding in a similar manner to Example 43(b) but (i) substituting 2-(2-chloro-6-fluoro-phenyl)-ethylamine for 2-(4-nitro-phenyl)-ethylamine, acetonitrile for EtOH as solvent in Step 3 there is prepared [2-(2-chloro-6-fluoro-phenyl)-ethyl]-[2-methoxy-6-(3-methoxy-phenyl)-pyrimidin-4-yl]-amine which is dissolved in ether and treated with 1 M hydrogen chloride in ether to afford [2-(2-chloro-6-fluoro-phenyl)-ethyl]-[2-methoxy-6-(3-methoxy-phenyl)-pyrimidin-4-yl]-amine hydrochloride [51 mg, 60%, Example 43(d)] as a solid. LC/MS: $R_T$=2.82 minutes MS: 388 (M+H). $^1$H NMR [300 MHz, (CD$_3$)$_2$SO]: □7.12-7.48 (7H, m), 6.6 (1H, s), 3.99 (3H, s), 3.82 (3H, s), 3.67 (2H, m), 3.07 (2H, m).

(e) [2-Methoxy-6-(3-methoxy-phenyl)-pyrimidin-4-yl]-(2-thiophen-2-yl-ethyl)-amine hydrochloride

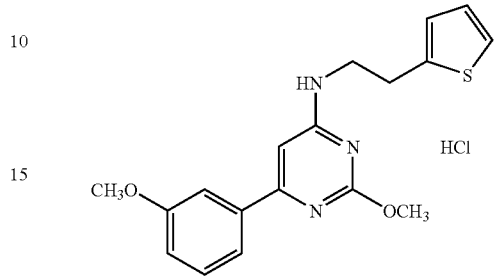

By proceeding in a similar manner to Example 43(b) but substituting 2-thiophen-2-yl-ethylamine for 2-(4-nitro-phenyl)-ethylamine, and substituting acetonitrile for EtOH as solvent in Step 3 there is prepared [2-methoxy-6-(3-methoxy-phenyl)-pyrimidin-4-yl]-(2-thiophen-2-yl-ethyl)-amine which is dissolved in ether and treated with 1 M hydrogen chloride in ether affording [2-methoxy-6-(3-methoxy-phenyl)-pyrimidin-4-yl]-(2-thiophen-2-yl-ethyl)-amine hydrochloride [33.7 mg, 45%, Example 43(e)] as a solid. LC/MS: $R_T$=2.52 minutes MS: 342 (M+H). $^1$H NMR [300 MHz, (CD$_3$)$_2$SO]: □7.32-7.5 (4H, m), 7.13 (1H, m), 6.96 (2H, m), 6.64 (1H, s), 4 (3H, s), 3.8 (3H, s), 3.7 (2H, m), 3.12 (2H, m). IC$_{50}$=9.7 nM (f) 3-{2-[2-Methoxy-6-(3-methoxy-phenyl)-pyrimidin-4-ylamino]-ethyl}-1H-indol-5-ol

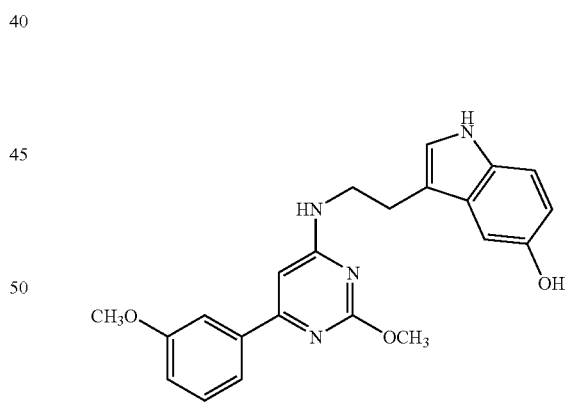

By proceeding in a similar manner to Example 1(a) but substituting 3-(2-amino-ethyl)-1H-indol-5-ol hydrochloride for 2-(4-nitro-phenyl)-ethylamine, and substituting acetonitrile for EtOH as solvent in Step 3, there is prepared 3-{2-[2-methoxy-6-(3-methoxy-phenyl)-pyrimidin-4-ylamino]-ethyl}-1H-indol-5-ol [19.5 mg, 25%, Example 43(f)] as a solid. LC/MS: $R_T$=2.13 minutes MS: 391 (M+H). $^1$H NMR [300 MHz, (CD$_3$)$_2$SO]: □10.46 (1H, s), 8.56 (1H, s), 7.48

(2H, m), 7.38 (1H, m), 6.99-7.12 (3H, m), 6.81 (1H, s), 6.58 (2H, m), 3.84 (3H, s), 3.79 (3H, s), 3.57 (2H, m), 2.84 (2H, m).

(g) [2-(6-Methoxy-1H-indol-3-yl)-ethyl]-[2-methoxy-6-(3-methoxy-phenyl)-pyrimidin-4-yl]-amine hydrochloride

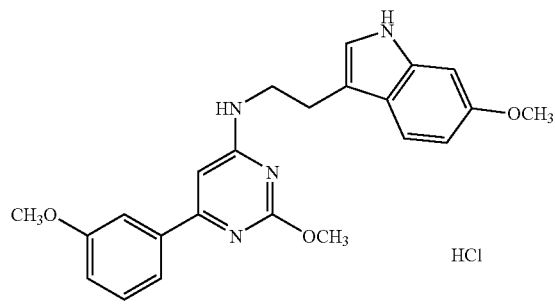

By proceeding in a similar manner to Example 43(b) but substituting 2-(6-methoxy-1H-indol-3-yl)-ethylamine for 2-(4-nitro-phenyl)-ethylamine, and substituting acetonitrile for EtOH as solvent in Step 3 there is prepared [2-(6-methoxy-1H-indol-3-yl)-ethyl]-[2-methoxy-6-(3-methoxy-phenyl)-pyrimidin-4-yl]-amine which is dissolved in ether and treated with 1 M hydrogen chloride in ether affording [2-(6-methoxy-1H-indol-3-yl)-ethyl]-2-methoxy-6-(3-methoxy-phenyl)-pyrimidin-4-yl]-amine hydrochloride [58.6 mg, 66%, Example 43(g)] as a solid. LC/MS: $R_T$=2.48 minutes MS: 405 (M+H). $^1$H NMR [300 MHz, (CD$_3$)$_2$SO]: □10.6 (1H, s), 7.3-7.5 (4H, m), 7.12 (1H, m), 7.02 (1H, m), 6.8 (1H, s), 6.61 (2H, m), 3.99 (3H, s), 3.8 (3H, s), 3.72 (3H, s), 3.58 (2H, m), 2.94 (2H, m). IC$_{50}$=104 nM (h) [2-(5-Methoxy-1H-indol-3-yl)-ethyl]-[2-methoxy-6-(3-methoxy-phenyl)-pyrimidin-4-yl]-amine hydrochloride

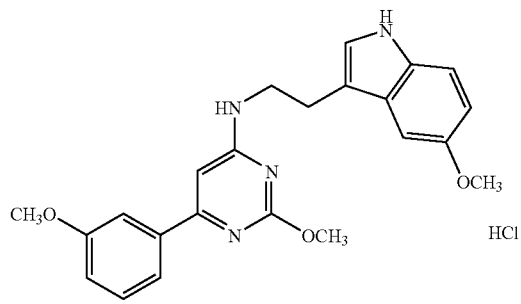

By proceeding in a similar manner to Example 43(b) but substituting 2-(5-methoxy-1H-indol-3-yl)-ethylamine for 2-(4-nitro-phenyl)-ethylamine, and substituting acetonitrile for EtOH as solvent in Step 3 there is prepared [2-(5-methoxy-1H-indol-3-yl)-ethyl]-[2-methoxy-6-(3-methoxy-phenyl)-pyrimidin-4-yl]-amine which is dissolved in ether and treated with 1 M hydrogen chloride in ether affording [2-(5-methoxy-1H-indol-3-yl)-ethyl]-[2-methoxy-6-(3-methoxy-phenyl)-pyrimidin-4-yl]-amine hydrochloride [52.1 mg, 59%, Example 43(h)] as a solid. LC/MS: $R_T$=2.45 minutes, MS: 405 (M+H). $^1$H NMR [300 MHz, (CD$_3$)$_2$SO]: □10.65 (1H, s), 7.41 (1H, m), 7.36 (2H, m), 7.2 (1H, m), 7.13 (2H, m), 7.01 (1H, m), 6.7 (1H, dd, J=9.6, 1.2 Hz), 6.6 (1H, s), 3.98 (3H, s), 3.8 (3H, s), 3.72 (3H, s), 3.56 (2H, m), 2.97 (2H, m).

(i) [2-Methoxy-6-(3-methoxy-phenyl)-pyrimidin-4-yl]-(2-pyridin-3-yl-ethyl)-amine hydrochloride

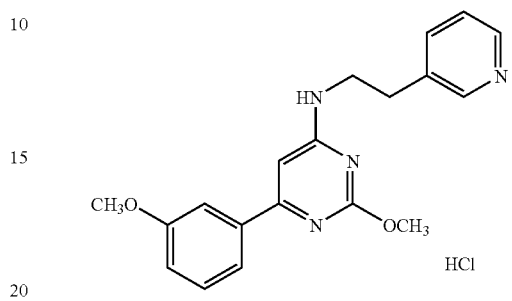

By proceeding in a similar manner to Example 43(b) but substituting 2-pyridin-3-yl-ethylamine for 2-(4-nitro-phenyl)-ethylamine, and substituting acetonitrile for EtOH as solvent in Step 3 there is prepared [2-methoxy-6-(3-methoxy-phenyl)-pyrimidin-4-yl]-(2-pyridin-3-yl-ethyl)-amine which is dissolved in ether and treated with 1 M hydrogen chloride in ether affording [2-methoxy-6-(3-methoxy-phenyl)-pyrimidin-4-yl]-(2-pyridin-3-yl-ethyl)-amine hydrochloride [33.2 mg, 45%, Example 43(i)] as a solid. LC/MS: $R_T$=1.53 minutes, MS: 337 (M+H). $^1$H NMR [300 MHz, (CD$_3$)$_2$SO]: □8.82 (1H, s), 8.76 (1H, m), 8.43 (1H, m), 7.95 (1H, m), 7.32-7.45 (3H, m), 7.11 (1H, m), 6.64 (1H, s), 3.98 (3H, s), 3.79 (3H, s), 3.76 (2H, m), 3.09 (2H, m). IC$_{50}$=248 nM (j) [2-(4-Amino-phenyl)-ethyl]-[2-methoxy-6-(3-methoxy-phenyl)-pyrimidin-4-yl]-amine hydrochloride

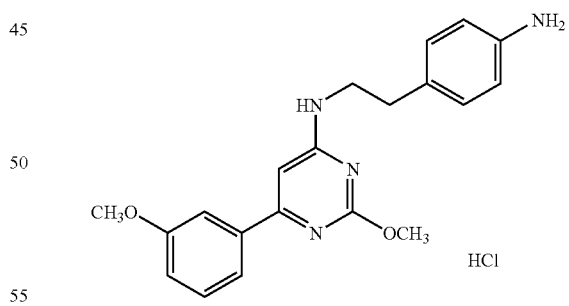

By proceeding in a similar manner to Example 43(b) but substituting 2-(4-amino-phenyl)-ethylamine for 2-(4-nitro-phenyl)-ethylamine, and substituting acetonitrile for EtOH as solvent in Step 3 there is prepared [2-(4-amino-phenyl)-ethyl]-[2-methoxy-6-(3-methoxy-phenyl)-pyrimidin-4-yl]-amine which is dissolved in ether and treated with 1 M hydrogen chloride in ether affording [2-(4-amino-phenyl)-ethyl]-[2-methoxy-6-(3-methoxy-phenyl)-pyrimidin-4-yl]-amine hydrochloride [52.4 mg, 68%, Example 43(j)] as a solid. LC/MS: $R_T$=1.72 minutes, MS: 351 (M+H). $^1$H NMR [300

MHz, (CD$_3$)$_2$SO]: □7.24-7.5 (7H, m), 7.08 (1H, m), 6.65 (1H, s), 4 (3H, s), 3.8 (3H, s), 3.64 (2H, m), 2.92 (2H, m).

(k) (4-Methoxy-benzyl)-[2-methoxy-6-(3-methoxy-phenyl)-pyrimidin-4-yl]-amine hydrochloride

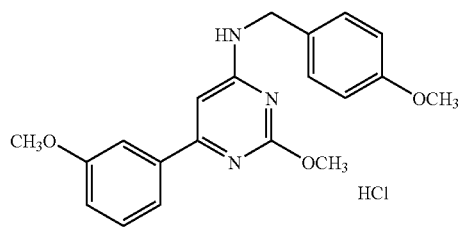

By proceeding in a similar manner to Example 43(b) but substituting 4-methoxy-benzylamine for 2-(4-nitro-phenyl)-ethylamine, and substituting acetonitrile for EtOH as solvent in Step 3 there is prepared (4-methoxy-benzyl)-[2-methoxy-6-(3-methoxy-phenyl)-pyrimidin-4-yl]-amine which is dissolved in ether and treated with 1 M hydrogen chloride in ether affording (4-methoxy-benzyl)-[2-methoxy-6-(3-methoxy-phenyl)-pyrimidin-4-yl]-amine hydrochloride [56.3 mg, 73%, Example 43(k)] as a solid. LC/MS: R$_T$=2.5 minutes, MS: 352 (M+H). $^1$H NMR [300 MHz, (CD$_3$)$_2$SO]: □7.36-7.5 (3H, m), 7.28 (2H, d, J=9.2 Hz), 7.1 (1H, m), 6.9 (2H, d, J=9.2 Hz), 6.65 (1H, s), 4.57 (2H, d, J=5 Hz), 4 (3H, s), 3.8 (3H, s), 3.72 (3H, s). IC$_{50}$=1073 nM

(l) [2-Methoxy-6-(3-methoxy-phenyl)-pyrimidin-4-yl]-(3-phenyl-propyl)-amine hydrochloride

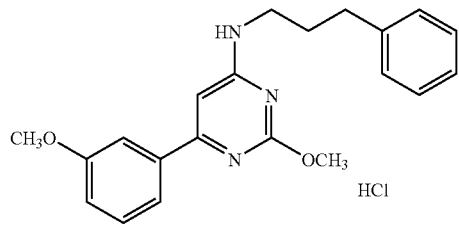

By proceeding in a similar manner to Example 43(b) but substituting 3-phenyl-propylamine for 2-(4-nitro-phenyl)-ethylamine, and substituting acetonitrile for EtOH as solvent in Step 3 there is prepared [2-methoxy-6-(3-methoxy-phenyl)-pyrimidin-4-yl]-(3-phenyl-propyl)-amine which is dissolved in ether and treated with 1 M hydrogen chloride in ether affording [2-methoxy-6-(3-methoxy-phenyl)-pyrimidin-4-yl]-(3-phenyl-propyl)-amine hydrochloride [60.6 mg, 79%, Example 43(l)] as a solid. LC/MS: R$_T$=2.65 minutes, MS: 350 (M+H). $^1$H NMR [300 MHz, (CD$_3$)$_2$SO]: □7.1-7.5 (9H, m), 6.62 (1H, s), 3.95 (3H, s), 3.8 (3H, s), 3.42 (2H, m), 2.64 (2H, m), 1.88 (2H, m). IC$_{50}$=1686 nM

(m) [2-(1H-Imidazol-4-yl)-ethyl]-[2-methoxy-6-(3-methoxy-phenyl)-pyrimidin-4-yl]-amine

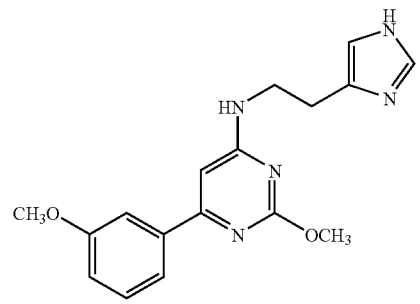

By proceeding in a similar manner to Example 43(b) but substituting 2-(1H-imidazol-4-yl)-ethylamine for 2-(4-nitro-phenyl)-ethylamine, and substituting acetonitrile for EtOH as solvent in Step 3 there is prepared [2-(1H-imidazol-4-yl)-ethyl]-[2-methoxy-6-(3-methoxy-phenyl)-pyrimidin-4-yl]-amine [39.2 mg, 54%, Example 43(m)] as a solid. LC/MS: R$_T$=1.45 minutes, MS: 326 (M+H). $^1$H NMR [300 MHz, (CD$_3$)$_2$SO]: □7.8 (1H, s), 7.52 (2H, m), 7.37 (1H, m), 7.01 (1H, m), 6.94 (1H, s), 6.6 (1H, s), 3.84 (3H, s), 3.79 (3H, s), 3.56 (2H, m), 2.79 (2H, m).

(n) (2S)-2-[2-Methoxy-6-(3-methoxy-phenyl)-pyridin-4-ylamino]-3-(4-methoxy-phenyl)-propionic acid

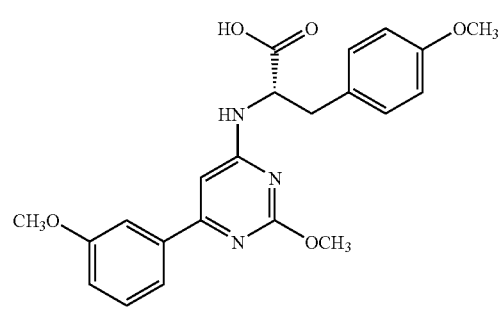

By proceeding in a similar manner to Example 43(b) but substituting L-O-methyl tyrosine for 2-(4-nitro-phenyl)-ethylamine in Step 3 there is prepared (2S)-2-[2-Methoxy-6-(3-methoxy-phenyl)-pyrimidin-4-ylamino]-3-(4-methoxy-phenyl)-propionic acid [40.2 mg, 45%, Example 43(n)] as a solid. LC/MS: R$_T$=2.38 minutes, MS: 410 (M+H). $^1$H NMR [300 MHz, (CD$_3$)$_2$SO]: □12 (1H, br s), 7.62 (1H, m), 7.49 (1H, m), 7.38 (1H, m), 7.18 (2H, m), 7 (1H, m), 6.8 (2H, m), 6.73 (1H, s), 4.59 (1H, m), 3.8 (3H, s), 3.78 (3H, s), 3.68 (3H, s), 3.1 (1H, m), 2.94 (1H, m). IC$_{50}$=548 nM (o) 2-Methoxy-6-(3-methoxy-phenyl)-pyrimidin-4-yl]-[2-(4-methoxy-phenyl)-ethyl]-amine

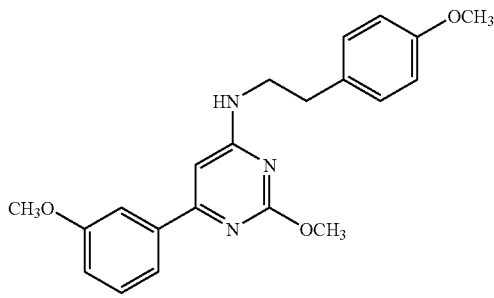

By proceeding in a similar manner to Example 43(b) but substituting 4-methoxyphenyl-ethylamine for 2-(4-nitrophenyl)-ethylamine, and substituting acetonitrile for EtOH as solvent in Step 3 there is prepared [2-methoxy-6-(3-methoxy-phenyl)-pyrimidin-4-yl]-[2-(4-methoxy-phenyl)-ethyl]-amine [58 mg, Example 43(o)].

Example 44

[2-Methoxy-6-(5-methyl-[1,3,4]oxadiazol-2-yl)-pyrimidin-4-yl]-[2-(4-methoxy-phenyl)-ethyl]-amine

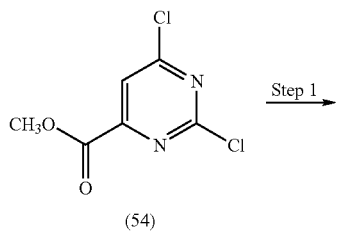

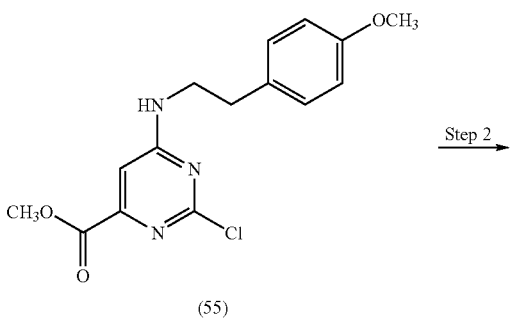

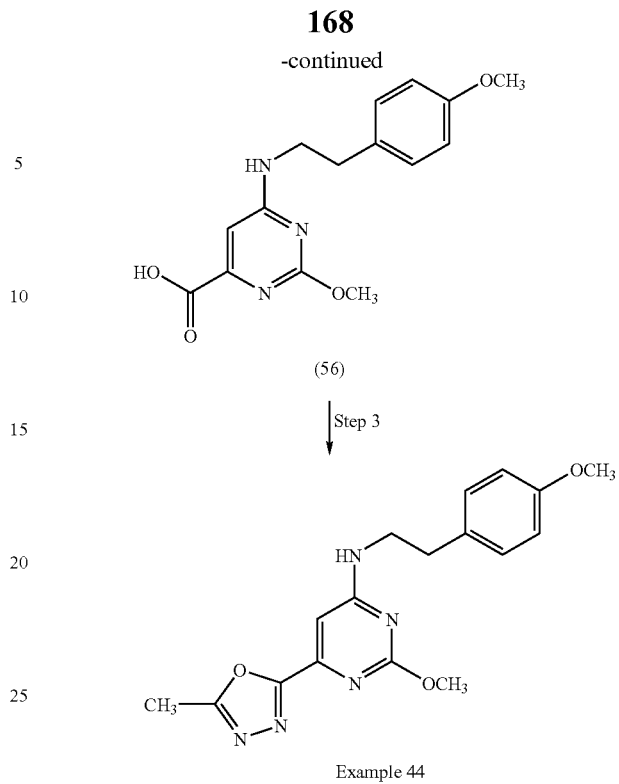

Example 44

Step 1. To a mixture of 2,6-dichloro-pyrimidine-4-carboxylic acid methyl ester [1 g, 4.83 mmol, Intermediate (54)] and N,N-diisopropylethylamine (1.27 mL, 7.25 mmol) in THF (16 mL) is added 2-(4-methoxyphenyl)-ethylamine (707 µL, 4.83 mmol). The resulting mixture is stirred at ambient temperature for 20 hours and poured into 50 mL water and extracted three times with 40 mL ethyl acetate. The organic extracts are combined and washed with 20 mL brine, dried over magnesium sulfate, filtered and concentrated to afford a solid which is purified via flash column chromatography on silica gel (35 g) eluting with 5 to 50% EtOAc in heptane gradient to afford 2-chloro-6-[2-(4-methoxy-phenyl)-ethylamino]-pyrimidine-4-carboxylic acid methyl ester [1 g, 64.5%, Intermediate (55)]. LCMS: R$_T$=2.9 minutes, MS: 322 (M+H).

Step 2. A mixture of 2-chloro-6-[2-(4-methoxy-phenyl)-ethylamino]-pyrimidine-4-carboxylic acid methyl ester [650 mg, 2.02 mmol, Intermediate (55)] 5M sodium methoxide in MeOH (20 mL, 10.1 mmol), in MeOH (10 mL) is heated to reflux and stirred for 5 hours. The heating is turned off and the mixture is stirred for 15 hours at room temperature and concentrated by rotary evaporator to remove the solvent. The solid is dissolved in water and the solution is acidified to pH 2 with the addition of 1N hydrochloric acid. Extracted three times with 75 mL EtOAc and concentrated the combined organic extracts to afford 2-methoxy-6-[2-(4-methoxy-phenyl)-ethylamino]-pyrimidine-4-carboxylic acid [390 mg, 64%, Intermediate (56)] as a solid. LCMS: R$_T$=1.99 minutes, MS: 304 (M+H).

Step 3. To a solution of 2-methoxy-6-[2-(4-methoxy-phenyl)-ethylamino]-pyrimidine-4-carboxylic acid [100 mg, 0.33 mmol, Intermediate (56)] in dimethylformamide (1 mL) is added N,N-diisopropylethylamine (145 µL, 0.83 mmol) followed by TBTU (128 mg, 0.4 mmol). Stirred the reaction mixture for 5 minutes before adding acetic hydrazide (37 mg, 0.5 mmol) and continued stirring the reaction mixture overnight at ambient temperature. The reaction mixture is poured into water (25 mL) and subsequently extracted three times with 25 mL ethyl acetate. The combined organic extracts are washed three times with 25 mL water, with 25 mL brine, dried over magnesium sulfate, filtered and concentrated by rotary evaporator. The material obtained is subjected to flash column chromatography on silica (10 g) eluting with 0 to 5% MeOH in DCM gradient to afford 2-methoxy-6-[2-(4-methoxy-phenyl)-ethylamino]-pyrimidine-4-carboxylic acid N'-acetyl-hydrazide (42 mg). A mixture of 2-methoxy-6-[2-(4-methoxy-phenyl)-ethylamino]-pyrimidine-4-carboxylic acid N'-acetyl-hydrazide (42 mg, 0.12 mmol), p-toluenesulfonyl-chloride (34 mg, 0.18 mmol) and PS-BEMP (218 mg, 0.48 mmol) in THF (1.5 mL) is irradiated in a microwave to 140° C. for 6 minutes. The material is filtered and absorbed onto silica gel and subjected to flash column chromatography on silica gel eluting with 10 to 50% EtOAc in heptane gradient to afford [2-methoxy-6-(5-methyl-[1,3,4]oxadiazol-2-yl)-pyrimidin-4-yl]-[2-(4-methoxy-phenyl)-ethyl]-amine [25.1 mg, 63%, Example 44]. LCMS: $R_T$=2.64 minutes, MS: 342 (M+H). $IC_{50}$=55 nM Example 45

(2-Methoxy-6-oxazol-5-yl-pyrimidin-4-yl)-[2-(4-methoxy-phenyl)-ethyl]-amine

Step 1. A mixture of 2-chloro-6-[2-(4-methoxy-phenyl)-ethylamino]-pyrimidine-4-carboxylic acid methyl ester [7.43 g, 23.09 mmol, Intermediate (55)] in dimethoxyethane (100 mL) is chilled in an ice/water bath to 3° C. and treated drop-wise via syringe with a solution of 2M lithium borohydride in THF (17.3 mL, 34.6 mmol) not allowing the reaction temperature to exceed 7° C. After complete addition stirring is continued at 5° C. for 1 hour. The reaction mixture is poured into ice/water (250 mL) and extracted four times EtOAc (100 mL). The combined organic extracts are washed with water (100 μL), them with brine (100 mL), dried over magnesium sulfate, filtered and concentrated by rotary evaporator to afford {2-chloro-6-[2-(4-methoxy-phenyl)-ethylamino]-pyrimidin-4-yl}-methanol [6.51 g, 96%, Intermediate (57)].

Step 2. A mixture of {2-chloro-6-[2-(4-methoxy-phenyl)-ethylamino]-pyrimidin-4-yl}-methanol (6.5 g mg, 22.1 mmol, Intermediate (57)] 25 wt % sodium methoxide in MeOH (15.2 mL, 66.3 mmol), in MeOH (20 mL) is heated to 90° C. and stirred for 3 hours and concentrated by rotary evaporator to remove the solvent. The solid is dissolved in water and the solution is acidified to pH 8 with the addition of saturated ammonium chloride solution. Extracted twice with 150 mL ethyl acetate, combined the extracts, Dried over magnesium sulfate, filtered and concentrated to afford {2-methoxy-6-[2-(4-methoxy-phenyl)-ethylamino]-pyrimi-

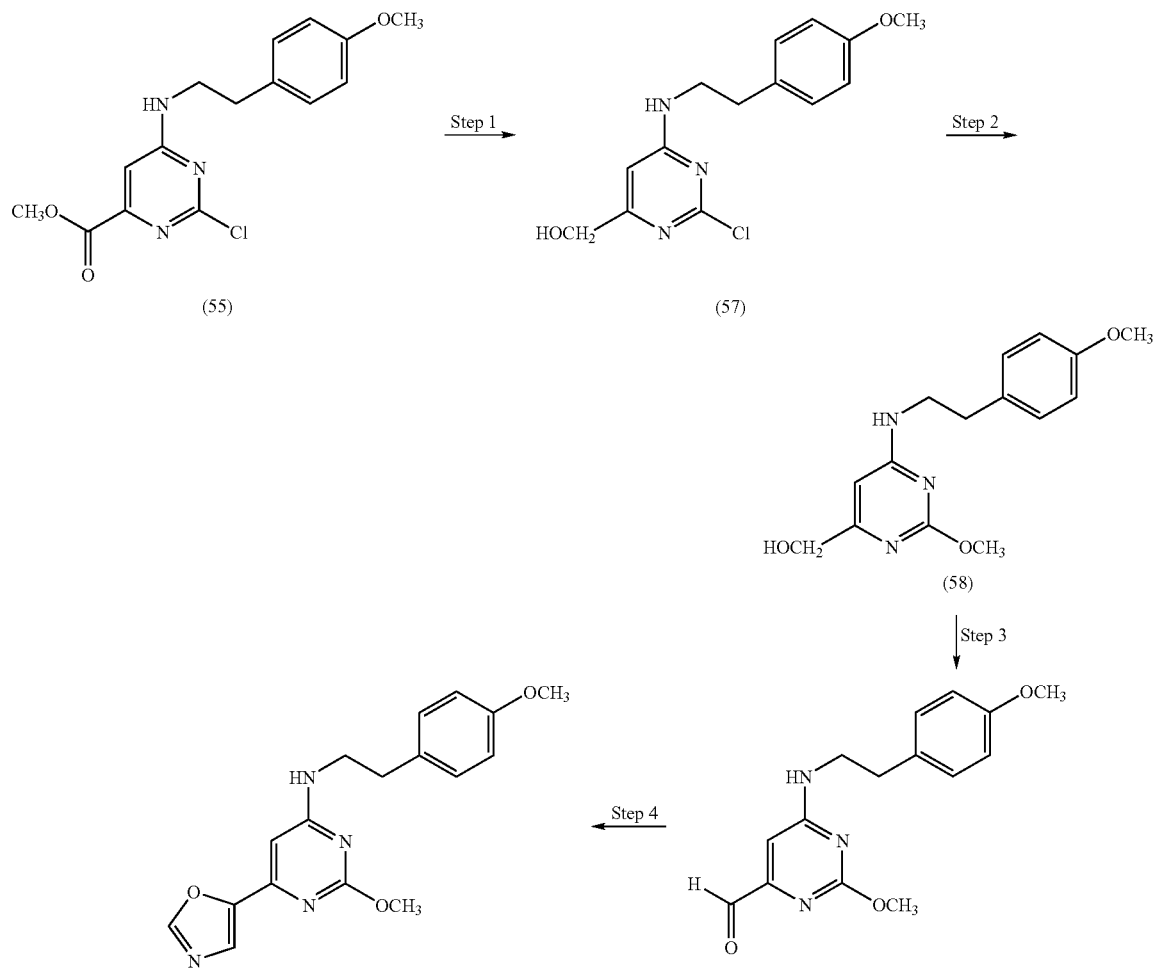

din-4-yl}-methanol [5.66 g, 88%, Intermediate (58)] as a solid. LCMS: $R_T$=2.35 minutes, MS: 290 (M+H).

Step 3. A solution of oxalyl chloride (305 μL, 3.55 mmol) in DCM (10 mL) is chilled to −78° C. To the chilled solution is added dropwise, dimethyl sulfoxide (492 μL, 6.92 mmol). After 10 minutes of stirring a solution of {2-methoxy-6-[2-(4-methoxy-phenyl)-ethylamino]-pyrimidin-4-yl}-methanol [500 mg, 1.73 mmol, Intermediate (58)] in DCM (7 mL) is added via syringe. The mixture is stirred at −78° C. for 30 minutes before adding triethylamine (1.95 mL, 13.84 mmol)

to flash column chromatography on silica gel eluting with 0 to 40% EtOAc in heptane gradient) to afford (2-methoxy-6-oxazol-5-yl-pyrimidin-4-yl)-[2-(4-methoxy-phenyl)-ethyl]-amine [11.6 mg, 8.5%, Example 45]. LCMS: $R_T$=2.57 minutes, MS: 327 (M+H). $IC_{50}$=7.8 nM Example 46

(a) 3-{6-[2-(2,2-Difluoro-benzo[1,3]dioxol-5-yl)-ethylamino]-2-methoxy-pyrimidin-4-yl}-benzoic acid

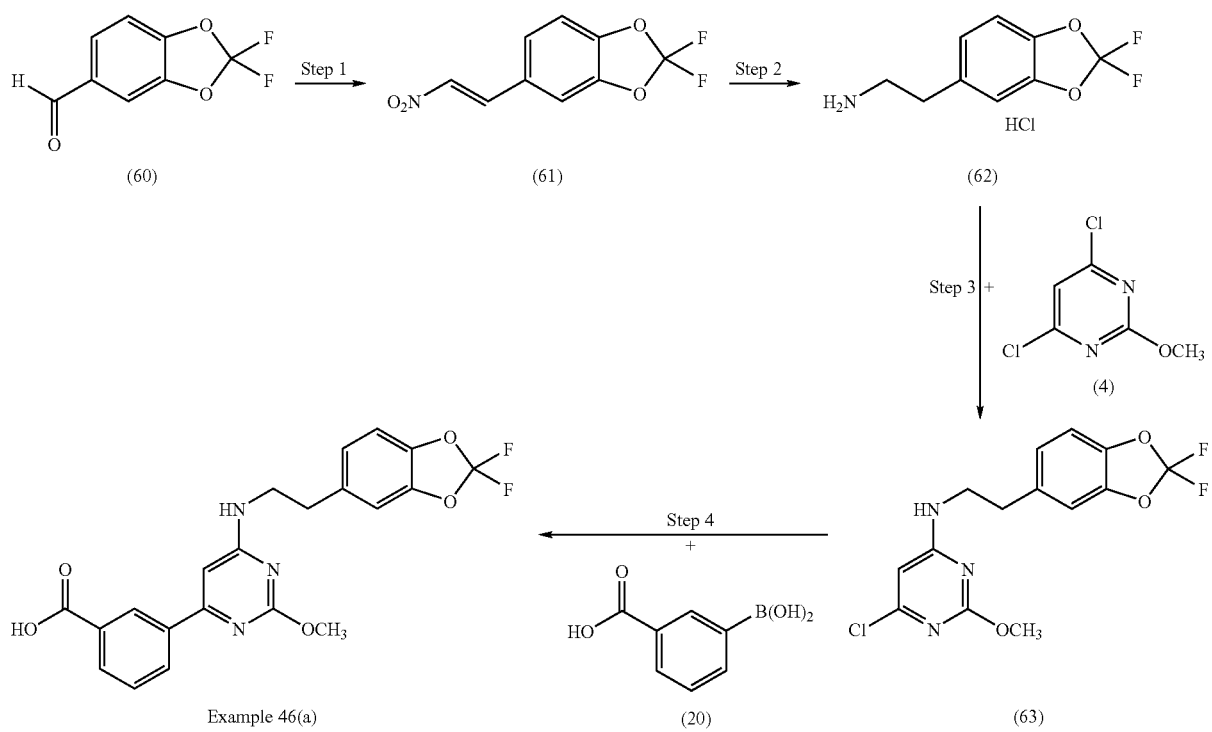

via syringe. After stirring for an additional 40 minutes at −78° C. the reaction is poured into water (30 mL) and this mixture is extracted twice with 30 mL DCM. The combined extracts are dried over magnesium sulfate, filtered and concentrated by rotary evaporator. The residue is taken up in toluene and re-concentrated and dried under high vacuum to afford 2-methoxy-6-[2-(4-methoxy-phenyl)-ethylamino]-pyrimidine-4-carbaldehyde [450 mg, 90.5%, Intermediate (59)].

Step 4. In a tube is combined 2-methoxy-6-[2-(4-methoxy-phenyl)-ethylamino]-pyrimidine-4-carbaldehyde [120 mg, 0.42 mmol, Intermediate (59)], tosylmethylisocyanide (90 mg, 0.46 mmol), Ambersep 900 OH resin (800 mg), ethylene glycol dimethyl ether (3.5 mL) and water (3.5 mL). The tube is sealed and the mixture is heated to 90° C. and stirred for 18 hours. The mixture is allowed to cool to ambient temperature and filtered to remove the resin, and the resin is washed with MeOH (10 mL). The combined filtrate and washings are concentrated by rotary evaporator and the residue is subjected Step 1. To a solution of 2,2-difluoro-benzo[1,3]dioxole-5-carbaldehyde [5.48 g, 29.44 mmol, Intermediate (60)] and nitromethane (4.78 mL, 88.32 mmol) in acetic acid (90 mL) is added ammonium acetate (5.67 g, 73.6 mmol). The reaction mixture is heated to reflux for 5.5 hours. Acetic acid is removed in vacuo and the residue is added water (20 mL) and extracted with DCM (3×50 mL), organic layers are combined and washed with 2 N sodium hydroxide, water and brine, dried over sodium sulfate and concentrated. The solid obtained is crystallized in methanol/DCM (1:1) to yield intermediate 2,2-difluoro-5-(2-nitro-vinyl)-benzo[1,3]dioxole [3.83 g, Intermediate (61)] as a solid.

Step 2. 2,2-difluoro-5-(2-nitro-vinyl)-benzo[1,3]dioxole (2 g, 8.73 mmol) is dissolved in THF (50 mL) and treated with lithium aluminum hydride (44 mL, 26.2 mmol, 1 M solution in THF) dropwise during 20 minutes at 0° C. The mixture is heated to reflux for 2 hours, quenched with water (2 mL) and 2 N sodium hydroxide (4 mL). The mixture is stirred for 5 minutes, filtered through a pad of Celite. The filtrate is concentrated treated with water and extracted three times with EtOAc (50 mL). The combined extracts are washed with brine, dried over sodium sulfate and the evaporated. The residue is dissolved in ether and treated with 1 M hydrogen chloride in ether affording 2-(2,2-difluoro-benzo[1,3]dioxol-5-yl)-ethylamine hydrochloride [1.04 g, 50%, Intermediate (62)] as a solid. LC/MS: MS: 202 (M+H).

Step 3. To a solution of 4,6-dichloro-2-methoxy-pyrimidine (0.606 g, 3.38 mmol, Intermediate (4)] and 2-(2,2-difluoro-benzo[1,3]dioxol-5-yl)-ethylamine hydrochloride (0.884 g, 3.72 mmol, Intermediate (62)]) in EtOH (11 mL) is added sodium bicarbonate (0.85 g, 10.14 mmol) and heated to reflux for 4 hours. The reaction mixture is filtered and filtrate is concentrated, residue solid is washed with small amount of EtOH to yield (6-chloro-2-methoxy-pyrimidin-4-yl)-[2-(2,2-difluoro-benzo[1,3]dioxol-5-yl)-ethyl]-amine [0.918 g, 79%, Intermediate (63)] as a solid. LC/MS: MS: 344 (M+H).

Step 4. A solution of (6-chloro-2-methoxy-pyrimidin-4-yl)-[2-(2,2-difluoro-benzo[1,3]dioxol-5-yl)-ethyl]-amine [150 mg, 0.437 mmol, Intermediate (63)] and 3-carboxyphenylboronic acid [87 mg, 0.524 mmol, Intermediate (20)] in acetonitrile (2 mL) and aqueous $Na_2CO_3$ solution (0.4 M, 2 mL) is degassed with nitrogen for 5 minutes before addition of tetrakis(triphenylphosphine)palladium(0) (25.2 mg, 5 mol %). The reaction vessel is sealed and heated under microwave to 130° C. for 20 minutes. To the reaction mixture is added 2 mL of water and pH is adjusted to about 6 using 6 N aqueous hydrochloric acid. This mixture is extracted three times with EtOAc (50 mL). The combined extracts are washed with brine, dried over sodium sulfate and concentrated to provide a solid which is redissolved in MeOH and DCM is added to precipitate a solid, 3-{6-[2-(2,2-difluoro-benzo[1,3]dioxol-5-yl)-ethylamino]-2-methoxy-pyrimidin-4-yl}-benzoic acid [166 mg, 88%, Example 46(a)]. LC/MS: $R_T$=2.67 minutes, MS: 430 (M+H). $^1$H NMR [300 MHz, $(CD_3)_2SO$]: □13.2 (1H, br s), 8.4 (1H, s), 8.06 (2H, m), 7.61 (1H, t, J=4.9 Hz), 7.36 (1H, s), 7.31 (1H, m), 7.06 (1H, m), 6.68 (1H, s), 3.99 (3H, s), 3.64 (2H, m), 2.9 (2H, m).

(b) [2-(2,2-Difluoro-benzo[1,3]-dioxol-5-yl)-ethyl]-(2-methoxy-6-pyridin-3-yl-pyrimidin-4-yl)-amine hydrochloride

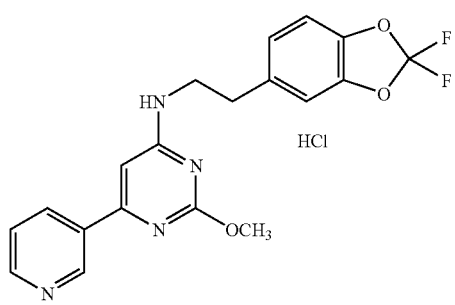

By proceeding in a similar manner to Example 46(a), but substituting 3-pyridylboronic acid for 3-carboxyphenylboronic acid in Step 4 and treating the crude reaction product with 1 M hydrogen chloride in ether, there is prepared [2-(2,2-difluoro-benzo[1,3]dioxol-5-yl)-ethyl]-(2-methoxy-6-pyridin-3-yl-pyrimidin-4-yl)-amine hydrochloride [132 mg, Example 46(b)] as a solid. LC/MS: $R_T$=2.72 minutes, MS: 387 (M+H). $^1$H NMR [300 MHz, $(CD_3)_2SO$]: □9.2 (1H, s), 8.84 (1H, m), 8.6 (1H, m), 7.85 (1H, m), 7.4 (1H, s), 7.36 (1H, d, J=9.6 Hz), 7.11 (1H, d, J=9.6 Hz), 6.78 (1H, s), 3.98 (3H, s), 3.62 (2H, m), 2.96 (2H, m). $IC_{50}$=212 nM (c) N-(3-{6-[2-(4-Difluoromethoxy-phenyl)-ethylamino]-2-methoxy-pyrimidin-4-yl}-phenyl)-acetamide hydrochloride

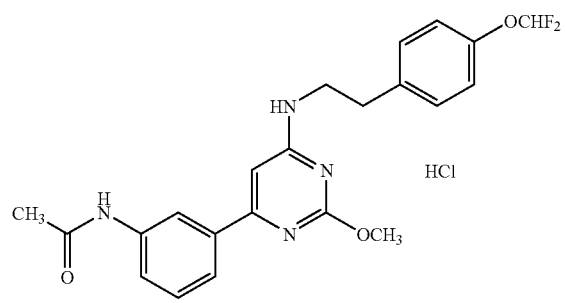

By proceeding in a similar manner to that described above for Steps 3 and 4 of Example 46(a), but (i) substituting 2-(4-difluoromethoxy-phenyl)-ethylamine hydrochloride [LC/MS: MS: 188, prepared by proceeding in a similar to Example 5, Step 1, method B, but substituting 4-difluoromethoxy benzaldehyde for 4-trifluoromethoxy benzaldehyde] for 2-(2,2-difluoro-benzo[1,3]dioxol-5-yl)-ethylamine hydrochloride in Step 3; (ii) substituting 3-acetamidophenylboronic acid for 3-carboxyphenylboronic acid in Step 4 and carrying out this reaction in a microwave oven at 130° C. for 23 minutes; and (iv) treating the reaction product with 1 M hydrogen chloride in ether, there is prepared N-(3-{6-[2-(4-difluoromethoxy-phenyl)-ethylamino]-2-methoxy-pyrimidin-4-yl}-phenyl)-acetamide hydrochloride [195 mg, Example 46(c)] as a solid. LC/MS: $R_T$=2.45 minutes, MS: 429 (M+H). $^1$H NMR [300 MHz, $(CD_3)_2SO$]: □10.22 (1H, br s), 8.18 (1H, s), 7.64 (1H, br s), 7.44 (1H, m), 7.36 (2H, d, J=9.2 Hz), 7.19 (1H, t, J=67.3 Hz), 7.12 (2H, d, J=9.2 Hz), 6.59 (1H, s), 4.01 (3H, s), 3.64 (2H, m), 2.9 (2H, m), 2.08 (3H, s). $IC_{50}$=4 nM (d) [2-(4-Difluoromethoxy-phenyl)-ethyl]-[6-(3-methanesulfonyl-phenyl)-2-methoxy-pyrimidin-4-yl]-amine hydrochloride

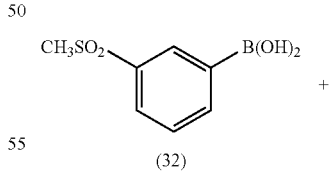

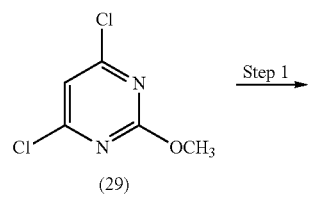

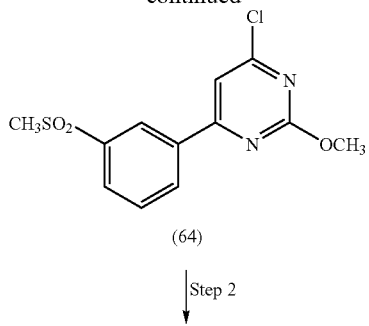

(64)

↓ Step 2

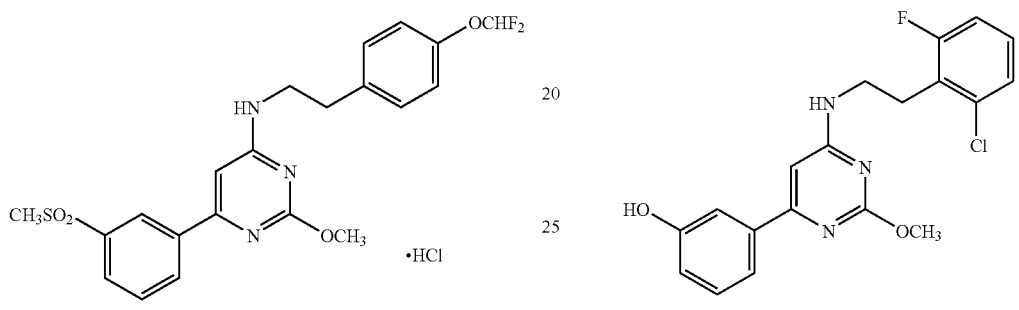

Example 46(d)

Step 1. By proceeding in a similar manner to Example 43(b), Step 1, but (i) substituting 3-methanesulfonyl-phenylboronic acid for 3-acetamidophenylboronic acid, and (ii) substituting 4,6-dichloro-2-methoxy-pyrimidine for 4,6-dichloro-2-methylsulfanyl-pyrimidine there is prepared 4-chloro-6-(3-methanesulfonyl-phenyl)-2-methoxy-pyrimidine [Intermediate (64)].

Step 2. By proceeding in a similar manner to Example 46(a), Step 3, but (i) substituting 4-chloro-6-(3-methanesulfonyl-phenyl)-2-methoxy-pyrimidine for 4,6-dichloro-2-methoxy-pyrimidine, (ii) substituting 2-(4-difluoromethoxy-phenyl)-ethylamine hydrochloride for 2-(2,2-difluoro-benzo[1,3]dioxol-5-yl)-ethylamine hydrochloride, and (iii) treating the product with 1 M hydrogen chloride in ether, there is prepared [2-(4-difluoromethoxy-phenyl)-ethyl]-[6-(3-methanesullonyl-phenyl)-2-methoxy-pyrimidin-4-yl]-amine hydrochloride [188 mg, example 46(d)]) as a solid. LC/MS: $R_T$=2.73 minutes, MS: 450 (M+H). $^1$H NMR [300 MHz, $(CD_3)_2SO$]: □8.39 (1H, br s), 8.21 (1H, br d, J=9 Hz), 8.08 (1H, d, J=9.4 Hz), 7.81 (1H, t, J=9.4 Hz), 7.35 (2H, d, J=9.6 Hz), 7.18 (1H, t, J=74.5 Hz), 7.12 (2H, d, J=9.6 Hz), 6.76 (1H, s), 4.01 (3H, s), 3.64 (2H, m), 3.28 (3H, s), 2.9 (2H, m). $IC_{50}$=17 nM (e) 3-{6-[2-(2-Chloro-6-fluoro-phenyl)-ethylamino]-2-methoxy-pyrimidin-4-yl}-phenol By proceeding in a similar manner to Example 46(a), Step 4, but (i) substituting [2-(2-chloro-6-fluoro-phenyl)-ethyl]-(6-chloro-2-methoxy-pyrimidin-4-yl)-amine [500 mg, 1.58 mmol, Intermediate (24)] for 4,6-dichloro-2-methoxy-pyrimidine and (ii) substituting 3-hydroxyphenyl boronic acid (240 mg, 1.74 mmol) for 3-carboxyphenylboronic acid there is prepared 3-{6-[2-(2-chloro-6-fluoro-phenyl)-ethylamino]-2-methoxy-pyrimidin-4-yl}-phenol [390 mg, 66%, Example 46(e)] as a solid.

Example 47

[2-(2,4-Dichloro-phenyl)-ethyl]-(2-methyl-6-{3-[1-methyl-1-(1H-tetrazol-5-yl)-ethyl]-phenyl}-pyrimidin-4-yl)-amine hydrochloride

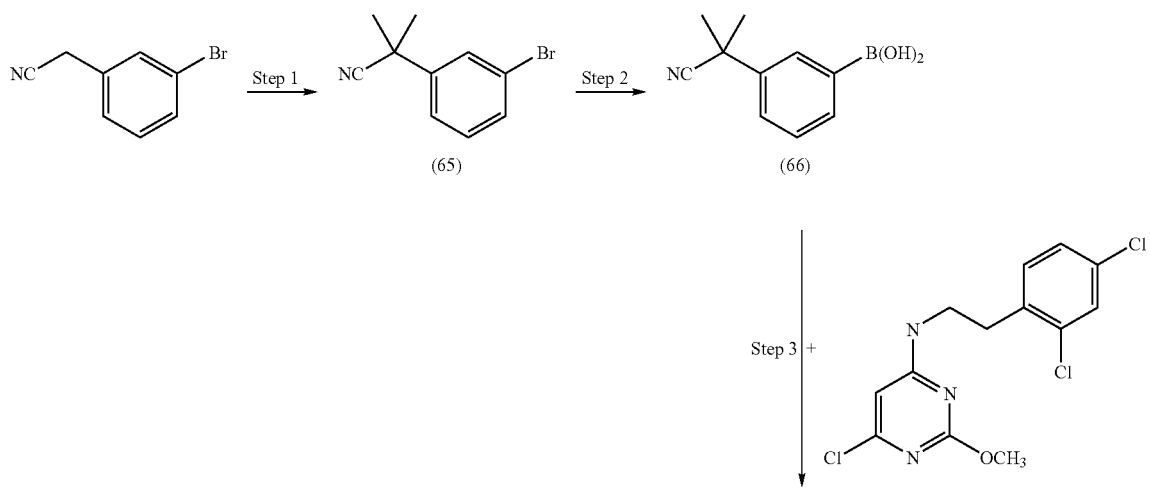

(65)  (66)

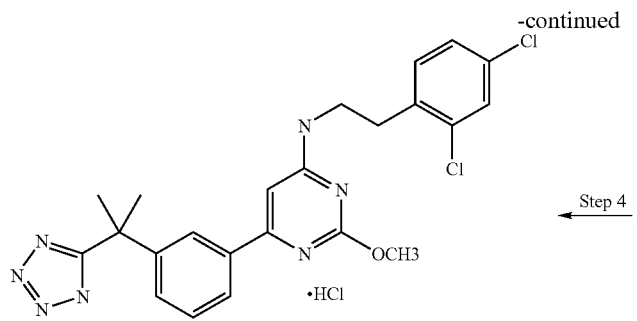

Example 47

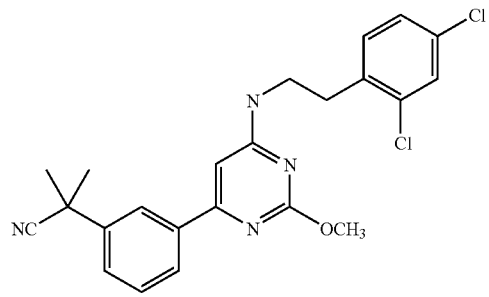

(67)

Step 1. To a solution of (3-bromo-phenyl)-acetonitrile (2.3 g, 11.77 mmol) in anhydrous THF (30 mL) is added potassium tert-butoxide (2.92 g, 25.89 mmol) at −40° C. Methyl iodide (1.95 mL, 29.43 mmol) is added in portions. The reaction mixture is allowed to warm up to room temperature, stirred for 15 hours, and quenched with 2N hydrochloric acid (10 mL), extracted with ethyl acetate. The organic layer is washed with brine, dried over sodium sulfate, concentrated, and purified via silica gel chromatography eluting with 0 to 50% EtOAc in heptane to give 2-(3-bromo-phenyl)-2-methyl-propionitrile (1.7 g) [Intermediate (65)] as an oil. MS: 225 (M+H).

Step 2. A solution of 2-(3-bromo-phenyl)-2-methyl-propionitrile [0.5 g, 2.2 mmol, Intermediate (65)] in toluene (8 mL) and THF (2 mL) is added triisopropyl borate (0.61 mL, 2.68 mmol) at −78° C. tert-Butyl lithium (1.7 M in pentane, 1.55 mL, 2.68 mmol) is added dropwise during 15 min. Reaction mixture is stirred at −78° C. for additional 1 hour, warmed up to −20° C. and quenched with 2N hydrochloric acid (10 mL). The reaction mixture is extracted with ether, combined ether layers are washed with brine, dried and concentrated to obtain 3-(cyano-dimethyl-methyl)-phenyl boronic acid (0.5 g) [Intermediate (66)] as an oil.

Step 3. By proceeding in a similar manner to Example 49(a), Step 3, but substituting 3-(cyano-dimethyl-methyl)-phenyl boronic acid [Intermediate (66)] for 3-(1-carboxy-ethyl)-phenyl boronic acid. 2-(3-{6-[2-(2,4-Dichloro-phenyl)-ethylamino]-2-methyl-pyrimidin-4-yl}-phenyl)-2-methyl-propionitrile [100 mg, Intermediate (67)] is obtained as a solid. LC/MS: $R_T$=2.74 minutes, MS: 441 (M+H).

Step 4. To a solution of 2-(3-{6-[2-(2,4-dichloro-phenyl)-ethylamino]-2-methyl-pyrimidin-4-yl}-phenyl)-2-methyl-propionitrile [50 mg, 0.11 mmol, Intermediate (67)] in α, α, α-trifluorotoluene (2 mL) is added azidotributyltin (0.251 mL, 0.88 mmol) and heated in microwave oven at 180° C. for 1.5 hours. Reaction mixture is concentrated and purified via silica gel chromatography eluting with 20 to 100% EtOAc in heptane to give [2-(2,4-dichloro-phenyl)-ethyl]-(2-methyl-6-{3-[1-methyl-1-(2H-tetrazol-5-yl)-ethyl]-phenyl}-pyrimidin-4-yl)-amine as a solid, which is treated with 1M hydrogen chloride in ether affording [2-(2,4-dichloro-phenyl)-ethyl]-(2-methyl-6-{3-[1-methyl-1-(2H-tetrazol-5-yl)-ethyl]-phenyl}-pyrimidin-4-yl)-amine hydrochloride [47 mg, 80%, Example 47] as a solid. LC/MS: $R_T$=2.47 minutes, MS: 484 (M+H). $^1$H NMR [300 MHz, (CD$_3$)$_2$SO]: □8.64 (1H, br s), 7.3-7.8 (7H, m), 6.56 (1H, s), 3.98 (3H, s), 3.64 (2H, m), 3 (2H, m), 1.8 (6H, s). IC$_{50}$=0.4 nM Example 48

[2-Methoxy-6-(2-methoxy-benzyloxy)-pyrimidin-4-yl]-[2-(4-methoxy-phenyl)-ethyl]-amine hydrochloride

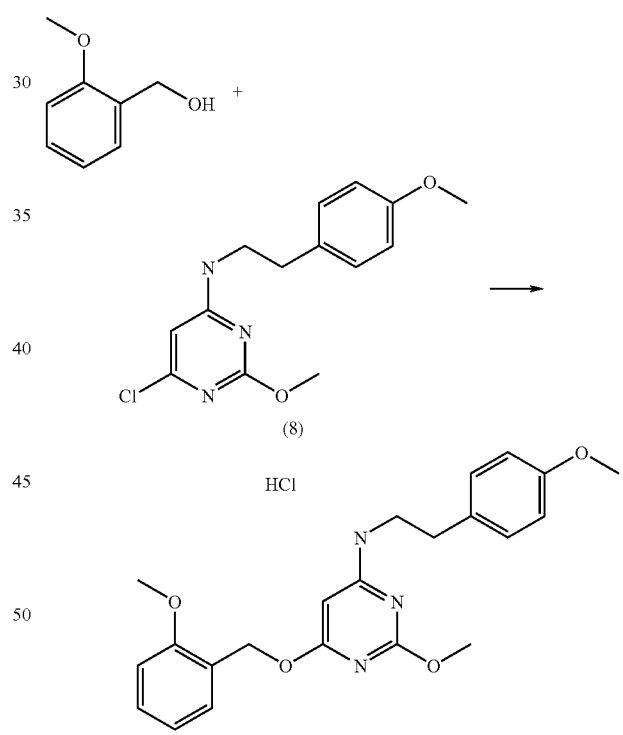

Example 48

To a suspension of (2-Methoxy-phenyl)-methanol (860 mg, 6.22 mmol), and sodium hydride (60%, 0.3 g) in DMF (10 mL) is add (6-Chloro-2-methoxy-pyrimidin-4-yl)-[2-(4-methoxy-phenyl)-ethyl]-amine [0.54 g, 1.8 mmol, Intermediate (8)] at 10° C. After 1 h at 60° C., the mixture is diluted with H$_2$O, and extracted with ethyl acetate. The extracts are dried (MgSO$_4$), filtered, concentrated, and chromatographed (SiO$_2$, 40% EtOAc in Heptane) to afford a non-separable mix of the product, [2-Methoxy-6-(2-methoxy-benzyloxy)-pyrimidin-4-yl]-[2-(4-methoxy-phenyl)-ethyl]-amine, and the disubstituted side product, [2,6-Bis-(2-methoxy-benzyloxy)-pyrimidin-4-yl]-[2-(4-methoxy-phenyl)-ethyl]-amine. To above mixture in CH$_2$Cl$_2$ is added a solution of HCl in EtOAc, and the mixture is concentrated, triturated (ether), and filtered to give 141 mg (19%) of 4-(2-Methoxy-benzyloxy)-6-[2-(4-methoxy-phenyl)-ethylamino]-pyrimidin-2-ol hydrochloride as a solid. LCMS: R$_T$=2.07 minutes, MS: 382 (M+H). The filtrate is concentrated, and chromatographed (silica gel, 40% EtOAc in Heptane) to afford [2-Methoxy-6-(2-methoxy-benzyloxy)-pyrimidin-4-yl]-[2-(4-methoxy-phenyl)-ethyl]-amine hydrochloride [39 mg, 5%, Example (48)] as an oil. LCMS: R$_T$=3.3 minutes, MS: 396 (M+H). IC$_{50}$=12 nM

Example 49

(a) 2-(3-{6-[2-(2,4-Dichloro-phenyl)-ethylamino]-2-methoxy-pyrimidin-4-yl}-phenyl)-propionic acid hydrochloride

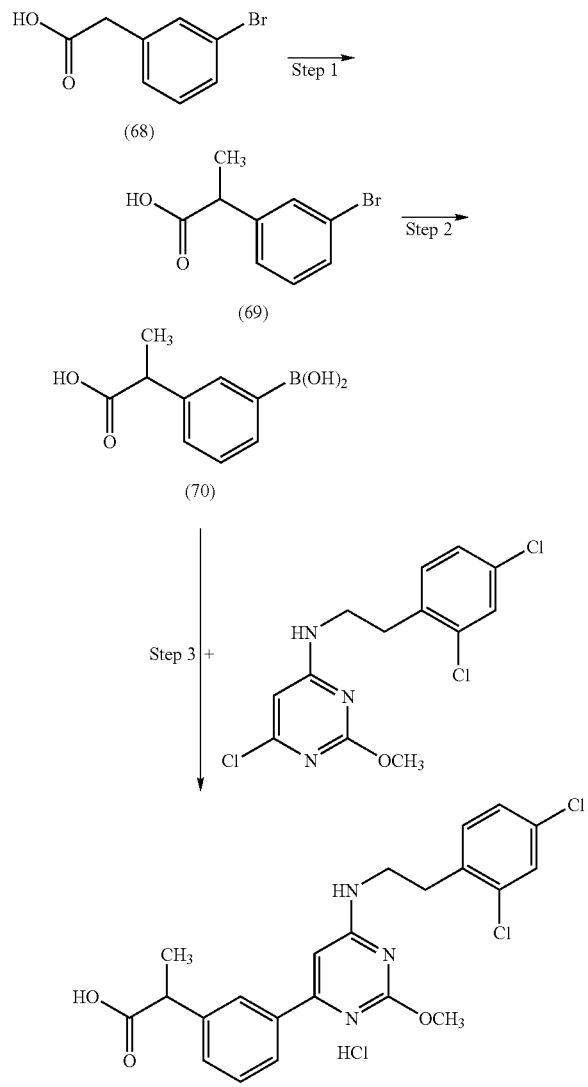

Step 1. A solution of LDA in THF/n-heptane/ethylbenzene (1.8M, 23.25 mL, 41.85 mmol) is cooled down to −78° C. and added a solution of 3-bromophenylacetic acid [3 g, 13.95 mmol, Intermediate (68)] in THF (7 mL) dropwise over 15 minutes. The mixture is stirred for 1 h at −78° C. and treated dropwise with methyl iodide (6.34 g, 44.64 mmol) over 15 minutes. The reaction mixture is warmed up to room temperature and after stirring overnight, the mixture is quenched with 2N hydrochloric acid and concentrated to remove THF. The residue is diluted with ether, washed twice with 2 N hydrochloric acid (20 mL) and extracted twice with 10% sodium hydroxide (20 mL). The combined sodium hydroxide extracts are acidified with 6 N hydrochloric acid to pH=1 and extracted three times with ether (50 mL). Combined organic extracts are washed with brine, dried over sodium sulfate and concentrated to obtain 2-(3-bromo-phenyl)-propionic acid [3 g, 100%, Intermediate (69)] as a solid, which is used without further purification. LC/MS: 229 (M+H).

Step 2. A solution of 2-(3-bromo-phenyl)-propionic acid [500 mg, 2.18 mmol, Intermediate (69)] in anhydrous ether (20 mL) is added tert-butyl lithium (1.7 M in pentane, 5.4 mL, 9.16 mmol) dropwise at −78° C. and this mixture is stirred for 30 minutes treated with tributyl borate (2.34 mL, 8.72 mmol). The reaction mixture is allowed to warm up to room temperature, stirred for 15 hours, diluted with ether, and quenched with 1 M H$_3$PO$_4$. After stirring for 30 minutes the ether layer is separated and extracted three times with 2 N sodium hydroxide (20 mL). The combined sodium hydroxide extracts are acidified with 6 N hydrochloric acid to pH=1 and extracted three times with ether (50 mL). The combined organic extracts are washed with brine, dried over sodium sulfate and concentrated to obtain 3-(1-carboxy-ethyl)-phenyl boronic acid [Intermediate (70)] as a solid, which is used without further purification.

Step 3. A solution of (6-chloro-2-methoxy-pyrimidin-4-yl)-[2-(2,4-dichloro-phenyl)-ethyl]-amine [170 mg, 0.51 mmol, Intermediate (44)] and 3-(1-carboxy-ethyl)-phenyl boronic acid [119 mg, 0.61 mmol, Intermediate (70)] in acetonitrile (2.5 mL) and aqueous Na$_2$CO$_3$ solution (0.4 M, 2.5 mL) is degassed with nitrogen for 5 minutes before addition of tetrakis(triphenylphosphine)palladium (0) (29.5 mg, 5 mol %). The reaction vessel is sealed and heated under microwave to 130° C. for 30 minutes. To the reaction mixture is added 2 mL of water, the pH is adjusted to about 7 using 2 N aqueous hydrochloric acid and this mixture is extracted three times with EtOAc (30 mL). The combined extracts are washed with brine, dried over sodium sulfate and concentrated. The resulting oil is subjected to silica gel chromatography eluting with 0 to 7% MeOH in DCM to give 2-(3-{6-[2-(2,4-dichloro-phenyl)-ethylamino]-2-methoxy-pyrimidin-4-yl}-phenyl)-propionic acid as a solid, which is treated with 1M hydrogen chloride in ether affording 2-(3-{6-[2-(2,4-dichloro-phenyl)-ethylamino]-2-methoxy-pyrimidin-4-yl}-phenyl)-propionic acid hydrochloride [122 mg, 50%, Example 49(a)] as a solid. LC/MS: R$_T$=2.47 minutes, MS: 446 (M+H). $^1$H NMR [300 MHz, (CD$_3$)$_2$SO]: □12.4

(1H, br s), 7.36-7.8 (7H, m), 6.6 (1H, s), 4 (3H, s), 3.78 (1H, q), 3.68 (2H, m), 3.02 (2H, m), 1.42 (3H, d). IC$_{50}$=1 nM (b) 2-(3-{6-[2-(2,4-Dichloro-phenyl)-ethylamino]-2-methoxy-pyrimidin-4-yl}-phenyl)-2-methyl-propionic acid

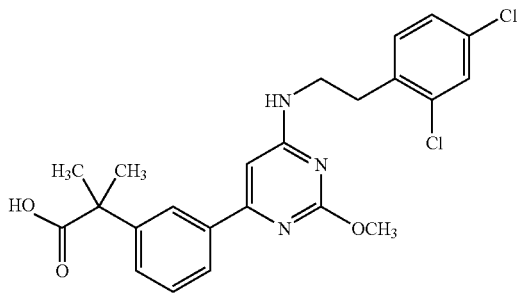

Step 1. To a solution of LDA in THF/n-heptane/ethylbenzene (1.8 M, 17 mL) at 0° C. is added a solution of 2-(3-bromo-phenyl)-propionic acid [3 g, 13.9 mmol, Intermediate (69)] in THF (5 mL) dropwise during 15 minutes. Stir for 1 hour, followed by addition of methyl iodide (4.93 g, 34.8 mmol) in THF (5 mL) dropwise during 10 min. The reaction mixture is stirred for 15 hours, quenched with 2N hydrochloric acid, concentrated in vacuo, and diluted with ether (150 mL). The ether layer is washed with 2N hydrochloric acid, extracted three times with 2N sodium hydroxide (50 mL), Combined sodium hydroxide layers are acidified with 6 N hydrochloric acid to pH=1 and extracted three times with ether (75 mL). Combined organic layers are washed with brine, dried over sodium sulfate and concentrated to obtain 2-(3-bromo-phenyl)-2-methyl-propionic acid as a solid (3.08 g, 91% yield), which is used without further purification. LC/MS: 243 (M+H)

Step 2. By proceeding in a similar manner to Example 49(a), Step 2, but substituting 2-(3-bromo-phenyl)-2-methyl-propionic acid for 2-(3-bromo-phenyl)-propionic acid. 3-(1-Carboxy-1-methyl-ethyl)-phenyl boronic acid is obtained as a semi-solid, which is used without further purification. LC/MS: 209 (M+H).

Step 3. By proceeding in a similar manner to Example 49(a), Step 3, but substituting 3-(1-carboxy-1-methyl-ethyl)-phenyl boronic acid for 3-(1-carboxy-ethyl)-phenyl boronic acid, 2-(3-{6-[2-(2,4-dichloro-phenyl)-ethylamino]-2-methoxy-pyrimidin-4-yl}-phenyl)-2-methyl-propionic acid [205 mg, 75%, Example 49(b)] is obtained as a solid. LC/MS: R$_T$=2.39 minutes, MS: 460.2 (M+H). $^1$H NMR [300 MHz, (CD$_3$)$_2$SO]: □12.38 (1H, s), 7.36-8 (7H, m), 6.58 (1H, s), 3.84 (3H, s), 3.58 (2H, m), 2.98 (2H, m), 1.54 (6H, s).

Example 50

2-(3-{6-[2-(2,4-Dichloro-phenyl)-ethylamino]-2-methoxy-pyrimidin-4-yl}-phenyl)-2-methyl-propionic acid 1-ethoxycarbonyloxy-ethyl ester hydrochloride

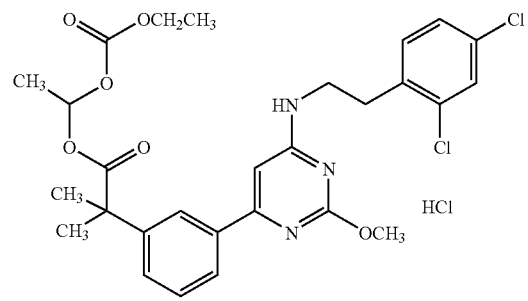

To a solution of 2-(3-{6-[2-(2,4-dichloro-phenyl)-ethylamino]-2-methoxy-pyrimidin-4-yl}-phenyl)-2-methyl-propionic acid [100 mg, 0.218 mmol, Example 49(b)] in dimethylformamide (2 mL) is added 1-chloroethyl ethyl carbonate (0.053 mL, 0.392 mmol) and Cs$_2$CO$_3$ (142 mg, 0.436 mmol). The mixture is heated under microwave at 110° C. for 10 minutes, quenched with water, and extracted with ethyl acetate. Combined organic layers are washed with brine, dried over sodium sulfate and concentrated. The residue is subjected to silica gel chromatography eluting with 0 to 40% EtOAc in heptane to obtain 2-(3-{6-[2-(2,4-dichloro-phenyl)-ethylamino]-2-methoxy-pyrimidin-4-yl}-phenyl)-2-methyl-propionic acid 1-ethoxycarbonyloxy-ethyl ester as an oil which is treated with 1M hydrogen chloride in ether affording 2-(3-{6-[2-(2,4-dichloro-phenyl)-ethylamino]-2-methoxy-pyrimidin-4-yl}-phenyl)-2-methyl-propionic acid 1-ethoxycarbonyloxy-ethyl ester hydrochloride [80 mg, 64%, Example 50] as a solid. LC/MS: R$_T$=2.94 minutes, MS: 576 (M+H). $^1$H NMR [300 MHz, (CD$_3$)$_2$SO]: □7.36-7.8 (7H, m), 6.64 (1H, q), 6.6 (1H, s), 4.05 (2H, q), 3.96 (3H, s), 3.68 (2H, m), 3 (2H, m), 1.57 (6H, s), 1.38 (3H, d), 1.15 (3H, t). IC$_{50}$=4 nM Example 51

2-(3-{6-[2-(2,4-Dichloro-phenyl)-ethylamino]-2-methoxy-pyrimidin-4-yl}-phenyl)-2-methyl-propionic acid 2-dimethylamino-ethyl ester dihydrochloride

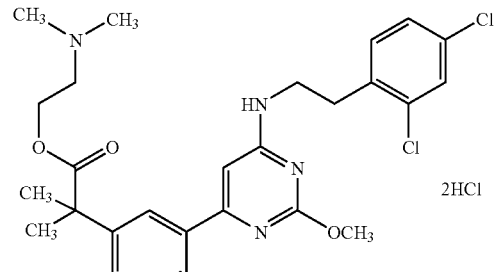

A solution of 2-(3-{6-[2-(2,4-dichloro-phenyl)-ethylamino]-2-methoxy-pyrimidin-4-yl}-phenyl)-2-methyl-propionic acid [100 mg, 0.218 mmol, Example 49(b)] in DCM (2 mL) is treated with HBTU (515.2 mg, 1.35 mmol). The mixture is stirred at room temperature for 2 hours and treated with 2-dimethylamino-ethanol (0.154 mL, 1.53 mmol). After stirring overnight, the mixture is quenched with water and extracted with ethyl acetate. The combined organic layers are washed with brine, dried over sodium sulfate and concentrated. The residue is subjected to silica gel chromatography eluting with 0 to 7.5% MeOH in DCM to obtain 2-(3-{6-[2-(2,4-dichloro-phenyl)-ethylamino]-2-methoxy-pyrimidin-4-yl}-phenyl)-2-methyl-propionic acid 2-dimethylamino-ethyl ester as an oil which is treated with 1M hydrogen chloride in ether affording 2-(3-{6-[2-(2,4-dichloro-phenyl)-ethylamino]-2-methoxy-pyrimidin-4-yl}-phenyl)-2-methyl-propionic acid 2-dimethylamino-ethyl ester dihydrochloride [88 mg, 67%, Example 51] as a solid. LC/MS: $R_f$=2.1 minutes, MS: 531 (M+H). $^1$H NMR [300 MHz, (CD$_3$)$_2$SO]: □10.16 (1H, br s), 7.3-7.82 (7H, m), 6.62 (1H, s), 4.37 (2H, m), 3.96 (3H, s), 3.68 (2H, m), 3.32 (2H, m), 3 (2H, m), 2.63 (6H, s), 1.6 (6H, s).

Example 52

(5-{6-[2-(2-Fluoro-4-trifluoromethyl-phenyl)-ethylamino]-2-methoxy-pyrimidin-4-yl}-1H-indol-3-yl)-acetic acid

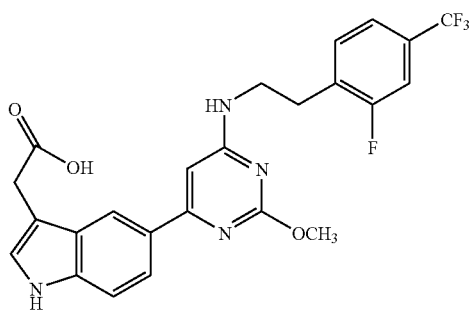

Step 1

(6-Chloro-2-methoxy-pyrimidin-4-yl)-[2-(2-fluoro-4-trifluoromethyl-phenyl)-ethyl]-amine

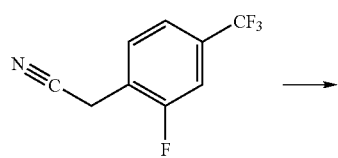

-continued

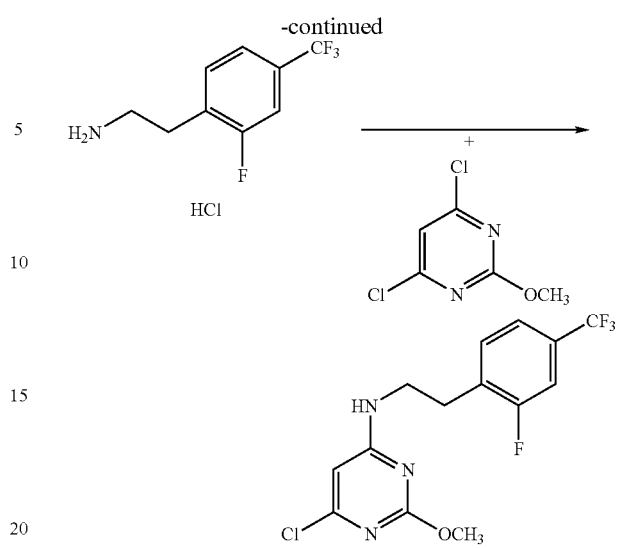

2-Fluoro-4-trifluoromethyl-phenyl acetonitrile (2 g, 9.85 mmol) is hydrogenated with H$_2$ in a balloon, 10% Pd/C (522 mg, 5 mol %) in 95% EtOH (50 mL) containing concentrated hydrochloric acid (1.64 mL) at room temperature for 15 hours. The mixture is filtered and filtrate is concentrated to a solid that is washed with diethyl ether to obtain 2-(2-fluoro-4-trifluoromethyl-phenyl)-ethylamine hydrochloride (1.88 g, 78%) as a solid. LC/MS: 208 (M+H). This compound (1.8 g, 8.7 mmol) is dissolved in EtOH (25 mL) and treated with 4,6-dichloro-2-methoxy-pyrimidine [1.3 g, 7.25 mmol, Intermediate (4)] and sodium bicarbonate (1.52 g, 18.13 mmol). The mixture is heated to reflux for 5 hours. Solid is filtered and EtOH is removed in vacuo. The residue is washed with small amount of DCM to obtain (6-chloro-2-methoxy-pyrimidin-4-yl)-[2-(2-fluoro-4-trifluoromethyl-phenyl)-ethyl]-amine (2.59 g, 76%) as a solid. LC/MS: 350 (M+H).

Step 2

3-Carboxymethyl-1H-indol-5-yl boronic acid

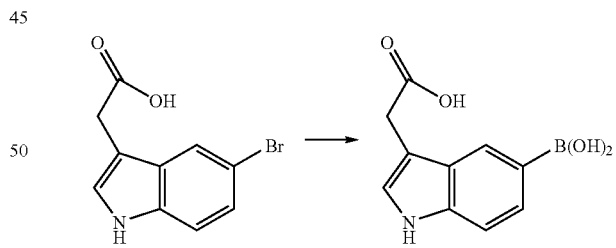

To a solution of (5-bromo-1H-indol-3-yl)-acetic acid (1 g, 3.94 mmol) in THF (66 mL) at −78° C. is added tert-butyl lithium (1.7 M in pentane, 11.6 mL, 19.7 mmol) dropwise and stirred at −78° C. for 30 minutes at −30° C. for 1 hour. Cooled down to −78° C. again and treated dropwise with triisopropyl borate (4.53 mL, 19.7 mmol). The reaction mixture is allowed to warm to room temperature during 1 hour quenched with 2N hydrochloric acid. This mixture is extracted with ether. The extract is dried over sodium sulfate and concentrate to obtain an oil which is subjected to silica gel chromatography affording 3-carboxymethyl-1H-indol-5-yl boronic acid (185 mg, 20%) as a solid.

Step 3

(5-{6-[2-(2-Fluoro-4-trifluoromethyl-phenyl)-ethylamino]-2-methoxy-pyrimidin-4-yl}-1H-indol-3-yl)-acetic acid

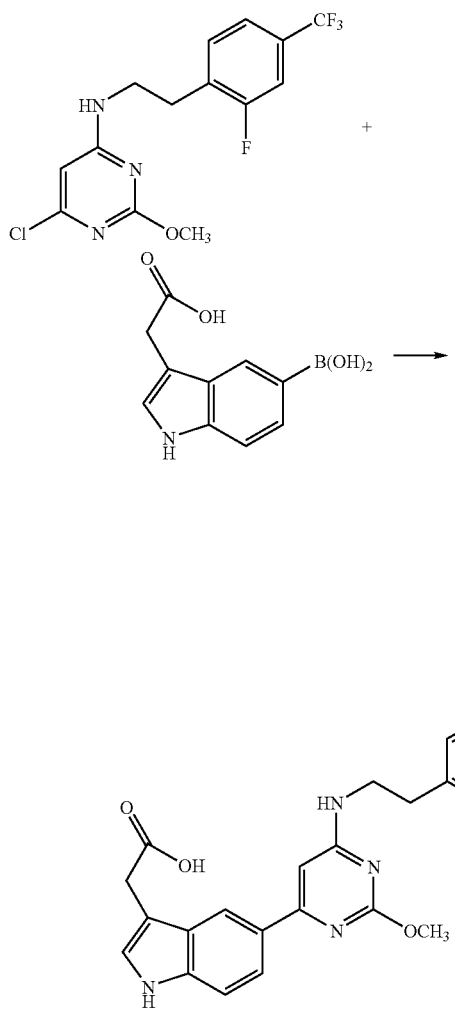

A solution of (6-chloro-2-methoxy-pyrimidin-4-yl)-[2-(2-fluoro-4-trifluoromethyl-phenyl)-ethyl]-amine (493 mg, 1.408 mmol) and 3-carboxymethyl-1H-indol-5-yl boronic acid (370 mg, 1.689 mmol) in toluene (9 mL), EtOH (4.5 mL) and water (1 mL) is added $Cs_2CO_3$ (1.146 g, 3.52 mmol) and degassed with nitrogen for 5 minutes before addition of tetrakis(triphenylphosphine)palladium (0) (81.3 mg, 5 mol %). The reaction vessel is sealed and heated under microwave to 130° C. for 15 minutes. To the reaction mixture is added 1N hydrochloric acid to adjust pH to about 2. This mixture is extracted three times with EtOAc (40 mL). The combined, extracts are washed with brine, dried over sodium sulfate and concentrated. The residue is subjected to silica gel chromatography to give (5-{6-[2-(2-fluoro-4-trifluoromethyl-phenyl)-ethylamino]-2-methoxy-pyrimidin-4-yl}-1H-indol-3-yl)-acetic acid [116 mg, 17%, Example 52] as a solid. LC/MS: $R_T$=2.57 minutes, MS: 489 (M+H). $^1$H NMR [300 MHz, $(CD_3)_2SO$]: □ 12.18 (1H, s), 11.05 (1H, s), 8.18 (1H, s), 7.24-7.76 (7H, m), 6.6 (1H, s), 3.87 (3H, s), 3.7 (2H, s), 3.6 (2H, m), 3 (2H, m). $IC_{50}$=0.4 nM Example 53

(a) [6-(1H-indol-6-yl)-2-methoxy-pyrimidin-4-yl]-[2-(4-methoxy-phenyl)-ethyl]-ammonium trifluoroacetate

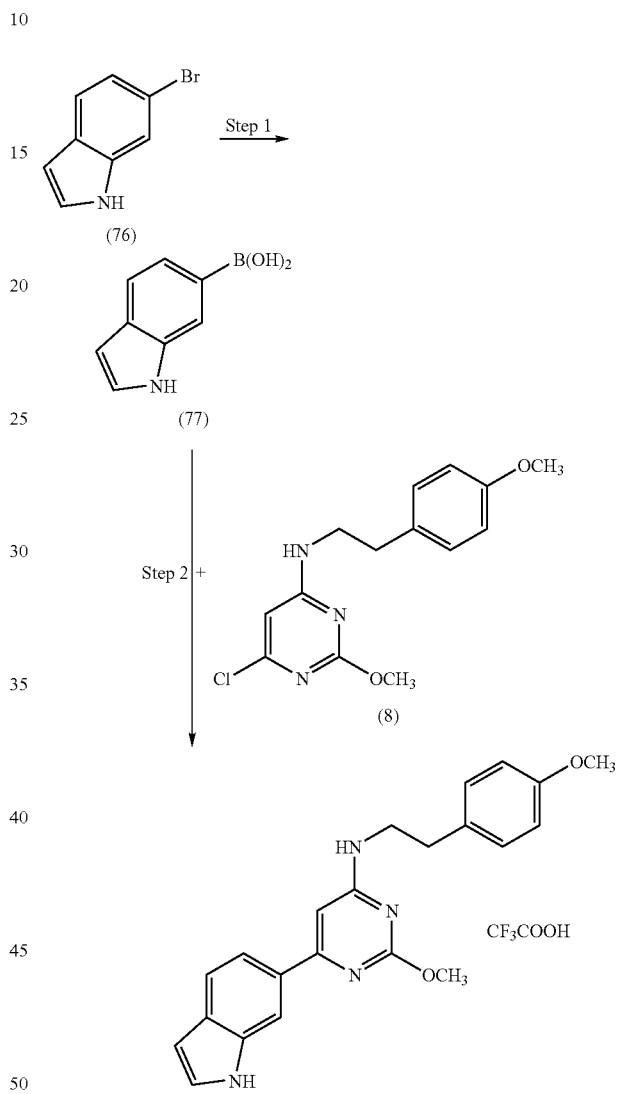

Example 53(a)

Step 1. A solution of 6-bromoindole (200 mg, 1.02 mmol) in anhydrous ether (4 mL), at −78° C., is treated dropwise with tert-butyllithium (1.7 M solution in pentane, 2 mL, 3.4 mmol). After stirring for 30 minutes the mixture is treated dropwise with tributyl borate (0.822 mL, 3.06 mmol) and allowed to warm up to room temperature. After stirring overnight the reaction mixture is diluted with ether, and this mixture is added in portions to phosphoric acid (15 mL, 1M), stirred for 30 minutes and extracted three times with ether (20 mL). The combined extracts are extracted three times with sodium hydroxide solution (20 mL, 1N). The combined sodium hydroxide extracts are acidified with phosphoric acid (1 M) to pH=2, extracted with ether. The combined ether extracts are washed with brine, dried over sodium sulfate and concentrated to obtain 1H-indol-6-yl-boronic acid [Intermediate (77)] as a solid, which is used for the next step without further purification.

Step 2. A mixture of (6-chloro-2-methoxy-pyrimidin-4-yl)-[2-(4-methoxy-phenyl)-ethyl]-amine [205.3 mg, 0.698 mmol, Intermediate (8)] and 1H-indol-6-yl-boronic acid [135 mg, 0.84 mmol, Intermediate (77)]) in acetonitrile (3.5 mL) and Na$_2$CO$_3$ solution (3.7 mL, 0.4 M) is degassed with nitrogen for 5 minutes and treated with tetrakis(triphenylphosphine)palladium (0) (40.5 mg, 0.035 mmol). The mixture is heated under microwave at 130° C. for 20 minutes and extracted three times with EtOAc (30 mL). The combined extracts are washed with saturated sodium bicarbonate solution, with brine, dried over sodium sulfate and concentrated to provide a residue which is subjected to Gilson prep. HPLC (C18 column, 5-100% acetonitrile/water, 0.1% trifluoroacetic acid) to afford [6-(1H-indol-6-yl)-2-methoxy-pyrimidin-4-yl]-[2-(4-methoxy-phenyl)-ethyl]-ammonium trifluoroacetate [87 mg, 33%, Example 53(a)] as an oil. LC/MS: R$_T$=2.47 minutes, MS: 375 (M+H). $^1$H NMR (300 MHz, CDCl$_3$): □10 (1H, br s), 8.14-6.2 (10H, m), 3.78 (3H, s), 3.73 (3H, s), 3.5 (2H, m), 2.8 (2H, m).

(b) [6-(1H-Indazol-6-yl)-2-methoxy-pyrimidin-4-yl]-[2-(4-methoxy-phenyl)-ethyl]-amine

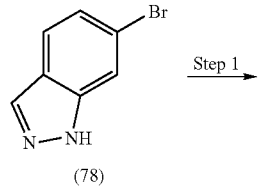

(78)

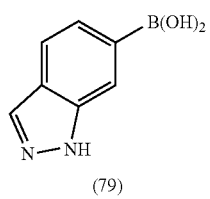

(79)

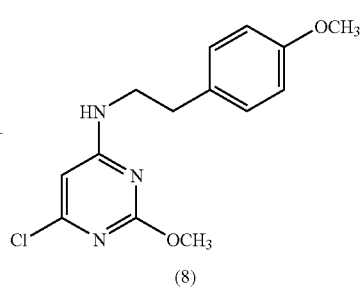

(8)

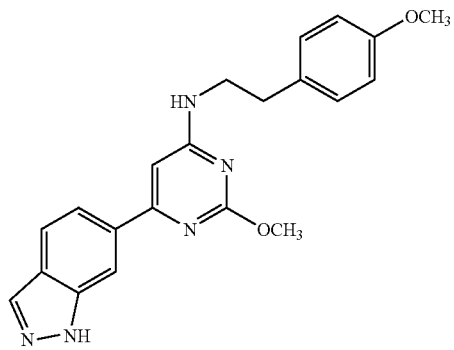

Example 53(b)

Step 1. By proceeding in a similar manner to Example 53(a), but substituting 6-bromo-1H-indazole for 6-bromoindole in Step 1 there is prepared 1H-indazol-6-yl-boronic acid [150 mg, Intermediate (79)] as a solid. This material is used for the next step without further purification.

Step 2. By proceeding in a similar manner to Example 53(a), but substituting 1H-indazol-6-yl-boronic acid [Intermediate (79)] for 1H-indol-6-yl-boronic acid in Step 2, and carrying out the reaction in toluene:EtOH:water (2.5 mL:1.3 mL:0.2 mL), there is prepared [6-(1H-Indazol-6-yl)-2-methoxy-pyrimidin-4-yl]-[2-(4-methoxy-phenyl)-ethyl]-amine [60 mg, Example 53(b)] as a solid. LC/MS: R$_T$=2.33 minutes, MS: 376 (M+H). $^1$H NMR [300 MHz, (CD$_3$)$_2$SO]: □13.2 (1H, s), 8.2 (1H, m), 8.1 (1H, s), 7.82 (1H, m), 7.68 (1H, m), 7.56 (1H, m), 7.2 (2H, d, J=8.6 Hz), 6.84 (2H, d, J=8.6 Hz), 6.7 (1H, s), 3.92 (3H, s), 3.7 (3H, s), 3.5 (2H, m), 2.8 (2H, m). IC$_{50}$=0.95 nM (c) 3-{6-[2-(2,6-Dichloro-phenyl)-ethylamino]-2-methoxy-pyrimidin-4-yl}-benzoic acid

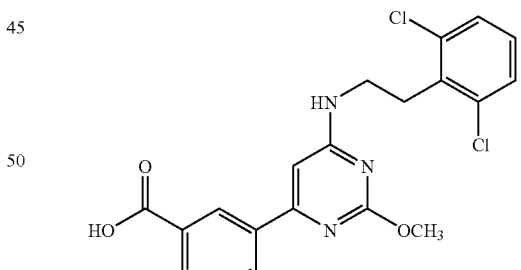

By proceeding in a similar manner to Example 53(a), Step 2, but substituting 3-carboxyboronic acid for 1H-indol-6-yl-boronic acid, and (6-chloro-2-methoxy-pyrimidin-4-yl)-[2-(2,6-dichloro-phenyl)-ethyl]-amine [Intermediate (44)] for (6-chloro-2-methoxy-pyrimidin-4-yl)-[2-(4-methoxy-phenyl)-ethyl]-amine, there is prepared 3-{6-[2-(2,6-dichloro-phenyl)-ethylamino]-2-methoxy-pyrimidin-4-yl}-benzoic acid [110 mg, Example 53(c)] as a solid. LC/MS: R$_T$=2.64 minutes, MS: 418 (M+H). $^1$H NMR [300 MHz, (CD$_3$)$_2$SO]: □13.2 (1H, br s), 8.54 (1H, s), 8.1 (1H, m), 8 (1H, m), 7.76

(1H, m), 7.6 (1H, m), 7.44 (2H, m), 7.26 (1H, m), 6.62 (1H, s), 3.86 (3H, s), 3.6 (2H, m), 3.22 (2H, m).

Example 54

[2-(4-Methoxy-phenyl)-ethyl]-{2-methoxy-6-[3-(1H-tetrazol-5-yl)-phenyl]-pyrimidin-4-yl}-amine, sodium salt

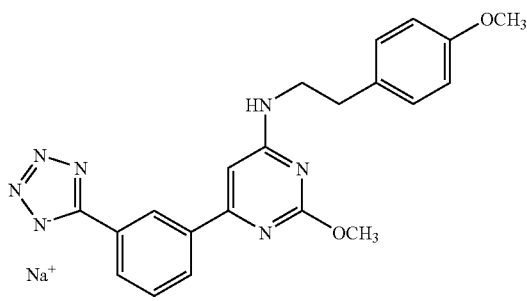

To a 0.5 M solution of sodium methoxide (10 mL, 5 mmol) in MeOH is added [2-(4-methoxy-phenyl)-ethyl]-{2-methoxy-6-[3-(1H-tetrazol-5-yl)-phenyl]-pyrimidin-4-yl}-amine [1.2 g, 2.97 mmol, Example 24(a)]. After 1 hour at room temperature the mixture is concentrated, filtered through a short pad of silica eluting with a mixture of MeOH and DCM (1:4, v/v), and triturated with a mixture of heptane and ether to afford [2-(4-methoxy-phenyl)-ethyl]-{2-methoxy-6-[3-(1H-tetrazol-5-yl)-phenyl]-pyrimidin-4-yl}-amine, sodium salt [1.13 g, 89%, Example 54] as a solid. LCMS: $R_T$=2.37 minutes, MS: 404 (M+H). $IC_{50}$=0.4 nM

Example 55

2-Methoxy-5-{2-methoxy-6-[2-(4-methoxy-phenyl)-ethylamino]-pyrimidin-4-yl}-benzonitrile

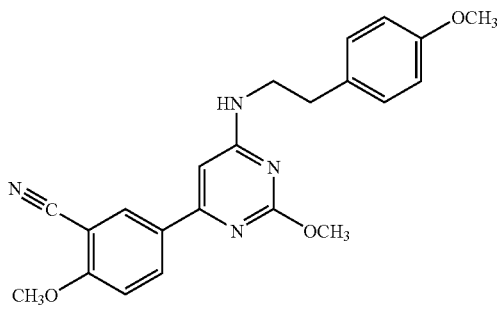

To a solution of 2-methoxy-5-{2-methoxy-6-[2-(4-methoxy-phenyl)-ethylamino]-pyrimidin-4-yl}-benzaldehyde oxime [0.49 g, 1.2 mmol, Example 26(c)], and triphenylphosphine (0.63 g, 2.4 mmol) in DCM (20 mL) is added N-chlorosuccinimide (0.32 g, 2.4 mmol) at 10° C. After 2 hours at 20° C., the mixture is concentrated, and subjected to chromatography on silica gel eluting with 5% to 10% MeOH in DCM to afford 2-methoxy-5-{2-methoxy-6-[2-(4-methoxy-phenyl)-ethylamino]-pyrimidin-4-yl}-benzonitrile [0.4 g, 85%, Example 55]. LCMS: $R_T$=2.75 minutes, MS: 391 (M+H).

Example 56

(3-{6-[2-(2-Chloro-6-fluoro-phenyl)-ethylamino]-2-methoxy-pyrimidin-4-yl}-benzyloxy)-acetic acid

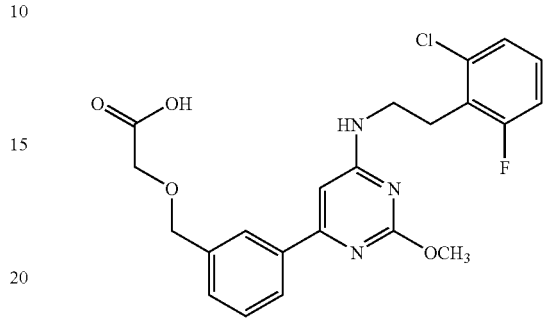

A solution of (3-{6-[2-(2-chloro-6-fluoro-phenyl)-ethylamino]-2-methoxy-pyrimidin-4-yl}-phenyl)-methanol (640 mg, 1.65 mmol) and bromo-acetic acid (0.25 g, 1.82 mmol) in N,N'-dimethylformamide (5 mL) is treated with sodium hydride (60%, 0.28 g, 6.94 mmol) at −30° C. The mixture is allowed to warm to room temperature over 1 hour, stirred for an additional 1 hour and quenched with water. The mixture is diluted with water, and washed with ether. The aqueous phase is acidified to pH 3.8 and the resulting solid is filtered and dried to give (3-{6-[2-(2-chloro-6-fluoro-phenyl)-ethylamino]-2-methoxy-pyrimidin-4-yl}-benzyloxy)-acetic acid [3.9 g, 53%, Example 56]. The filtrate is extracted with ethyl acetate, and the combined extracts are washed with water, dried over magnesium sulfate, and concentrated to afford additional quantity of (3-{6-[2-(2-chloro-6-fluoro-phenyl)-ethylamino]-2-methoxy-pyrimidin-4-yl}-benzyloxy)-acetic acid (0.43 g, Example 56). LCMS: $R_T$=2.43 minutes, MS: 446 (M+H). $IC_{50}$=0.6 nM

Example 57

Sodium; 2-(3-{6-[2-(2,4-dichloro-phenyl)-ethylamino]-2-methoxy-pyrimidin-4-yl}-phenyl)-2-methyl-propionate

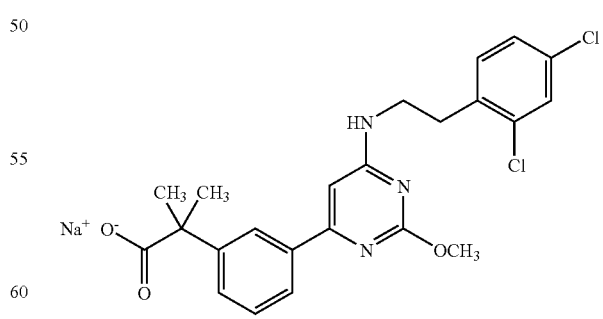

A solution of 2-(3-{6-[2-(2,4-dichloro-phenyl)-ethylamino]-2-methoxy-pyrimidin-4-yl}-phenyl)-2-methyl-propionic acid [540 mg, 1.17 mmol, Example 49(b)] in MeOH (60 mL) is treated with $Na_2CO_3$ (187 mg, 1.78 mmol) and the mixture is stirred for 15 hours. The reaction mixture is filtered and the filtrate is concentrated to dryness. To the residue is added a mixture of methanol, EtOAc and acetone. The insoluble material is filtered off and the filtrate is evaporated. The residue is again treated with a mixture of methanol, EtOAc and acetone, the insoluble material filtered off and the filtrate is evaporated. The residue is again treated with a mixture of methanol, EtOAc and acetone, the insoluble material filtered off and the filtrate is evaporated. To the residue is added MeOH (1 mL) and EtOAc (5 mL), followed by heptane until the solution turned cloudy and a solid is formed slowly. Heptane is repeatedly added until the solution stay clear. The mixture is filtered affording sodium 2-(3-{6-[2-(2,4-dichloro-phenyl)-ethylamino]-2-methoxy-pyrimidin-4-yl}-phenyl)-2-methyl-propionate as a crystalline. LC/MS: $R_T$=2.34 minutes, MS: 460 (M-Na$^+$ 2H)$^+$. $^1$H NMR [300 MHz, (CD$_3$)$_2$SO]: ☐ 7.97 (1H, br s), 7.24-7.7 (7H, m), 6.57 (1H, s), 3.86 (3H, s), 3.58 (2H, m), 2.98 (2H, m), 1.4 (6H, s).

Example 58

(3-{6-[2-(2,4-Dichloro-phenyl)-ethylamino]-2-methoxy-pyrimidin-4-yl}-benzoylamino)-acetic acid ethyl ester

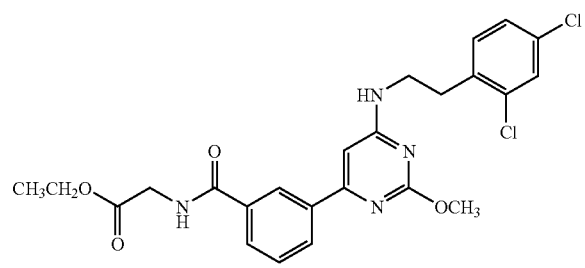

A mixture of 3-{6-[2-(2,4-dichloro-phenyl)-ethylamino]-2-methoxy-pyrimidin-4-yl}-benzoic acid [127 mg, 0.3 mmol, Example 35(w)], O-(benzotriazol-1-yl)-N,N,N'N'-tetramethyluronium tetrafluoroborate (116 mg, 0.36 mmol), diisopropylethylamine (131 μL, 0.75 mmol) and glycine ethyl ester hydrochloride (63 mg, 0.45 mmol) in dimethylformamide (3 mL) is stirred at ambient temperature for 18 hours. The mixture is poured into water and extracted three times with EtOAc (20 mL). The organic extracts are combined and washed twice with water (20 mL), dried over magnesium sulfate, filtered and concentrated by rotary evaporator to provide a solid. The solid is absorbed onto silica and subjected to flash column chromatography on silica (40 g) eluting with 0% to 50% ethyl acetate/heptane gradient, to afford (3-{6-[2-(2,4-dichloro-phenyl)-ethylamino]-2-methoxy-pyrimidin-4-yl}-benzoylamino)-acetic acid ethyl ester [120 mg, 79%, Example 58]. MS: 503 (M+H).

Example 59

(3-{6-[2-(2,4-Dichloro-phenyl)-ethylamino]-2-methoxy-pyrimidin-4-yl}-benzoylamino)-acetic acid

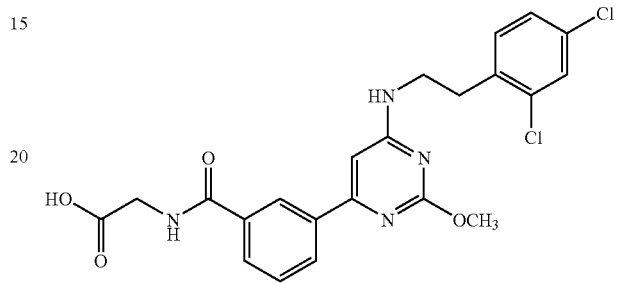

A mixture of (3-{6-[2-(2,4-dichloro-phenyl)-ethylamino]-2-methoxy-pyrimidin-4-yl}-benzoylamino)-acetic acid ethyl ester [120 mg, 0.24 mmol, Example 58], lithium hydroxide (20 mg, 0.48 mmol) in THF (1 mL), MeOH (1 mL) and water (1 mL) is stirred for 20 hours at ambient temperature. The mixture is acidified to pH 1 with 10% hydrochloric acid and extracted three times with EtOAc (25 mL). The organic extracts are combined and dried over magnesium sulfate, filtered and concentrated by rotary evaporator to provide (3-{6-[2-(2,4-dichloro-phenyl)-ethylamino]-2-methoxy-pyrimidin-4-yl}-benzoylamino)-acetic acid [49 mg, 43%, Example 59]. LCMS: $R_T$=2.77 minutes, MS: 475 (M+H). IC$_{50}$=0.8 nM Example 60

Ethyl-carbamic acid 3-{6-[2-(2,4-dichloro-phenyl)-ethylamino]-2-methoxy-pyrimidin-4-yl}-phenyl ester

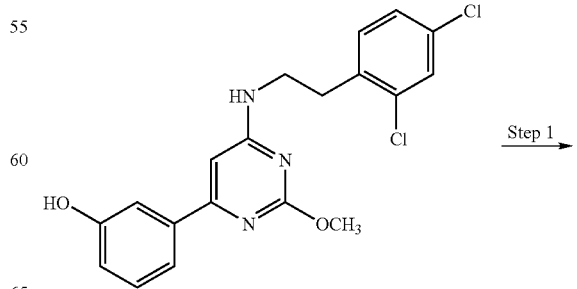

Example 35(i)

-continued

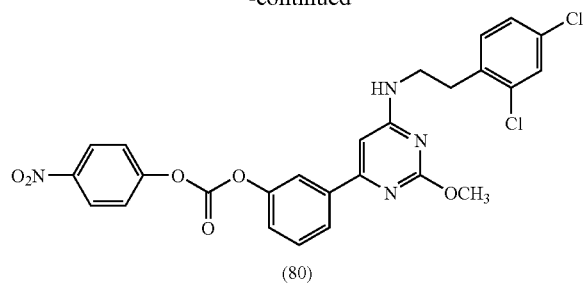

(80)

↓ Step 2

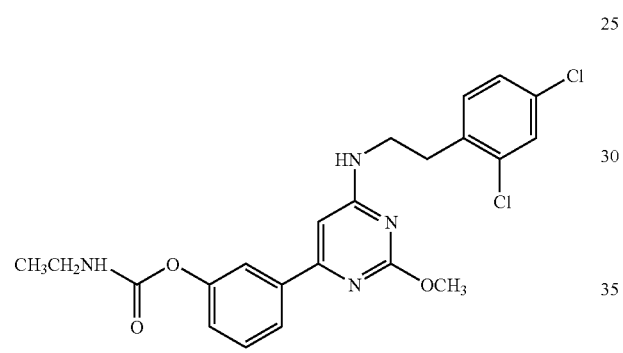

Example 60

Step 1. A mixture of 3-{6-[2-(2,4-dichloro-phenyl)-ethylamino]-2-methoxy-pyrimidin-4-yl}-phenol [220 mg, 0.51 mmol, Example 35(i)], diisopropylethylamine (178 μL, 0.75 mmol) and 4-nitrophenylchloroformate (123 mg, 0.61 mmol) in DCM (3 mL) is stirred at ambient temperature for 2 hours. The mixture is poured into water (25 mL) and extracted twice with EtOAc (25 mL). The organic extracts are combined and washed twice with water (25 mL) and once with brine (25 mL), the dried over magnesium sulfate, filtered and concentrated by rotary evaporator to provide carbonic acid 3-{6-[2-(2,4-dichloro-phenyl)-ethylamino]-2-methoxy-pyrimidin-4-yl}-phenyl ester 4-nitro-phenyl ester [291 mg, 102%, Intermediate (80)]. MS: 555 (M+H).

Step 2. A mixture of carbonic acid 3-{6-[2-(2,4-dichlorophenyl)-ethylamino]-2-methoxy-pyrimidin-4-yl}-phenyl ester 4-nitro-phenyl ester [291 mg, 0.52 mmol, Intermediate (80)] and 2 M ethylamine in MeOH (0.65 mL, 1.3 mmol) in DCM is stirred for 20 hours at ambient temperature. The precipitate that formed is collected by filtration and washed with DCM and dried under vacuum to afford ethyl-carbamic acid 3-{6-[2-(2,4-dichloro-phenyl)-ethylamino]-2-methoxy-pyrimidin-4-yl}-phenyl ester [80 mg, 33.3%, Example 60]. LCMS: $R_T$=1.31 minutes MS: 461 (M+H). $IC_{50}$=0.5 nM Example 61

5-{2-Methoxy-6-[2-(4-methoxy-phenyl)-ethylamino]-pyrimidin-4-yl}-thiophene-2-carboxylic acid

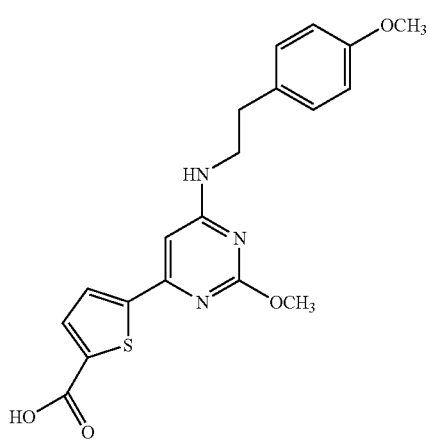

To a solution of 5-{2-methoxy-6-[2-(4-methoxy-phenyl)-ethylamino]-pyrimidin-4-yl}-thiophene-2-carbaldehyde [700 mg, 1.895 mmol, Example 8(b)] in acetone (20 mL) is added a solution of potassium permanganate (898 mg, 5.684 mmol) and $NaH_2PO_4 \cdot H_2O$ (79 mg, 0.568 mmol) in water (20 mL) followed by the addition of silica gel (4 g). The mixture is allowed to stir at ambient temperature for 6 hours, allowed to stand overnight, evaporated to remove the acetone and extracted several times with ethyl acetate. The organic extracts are combined and dried over magnesium sulfate, filtered and concentrated. The residual crude product is dissolved in refluxing acetonitrile and the solids that formed upon cooling are collected by filtration to afford 5-{2-methoxy-6-[2-(4-methoxy-phenyl)-ethylamino]-pyrimidin-4-yl}-thiophene-2-carboxylic acid [362 mg, 50%, Example 61].

Example 62

5-{2-Methoxy-6-[2-(4-methoxy-phenyl)-ethylamino]-pyrimidin-4-yl}-thiophene-2-carboxylic acid methylamide trifluoroacetate

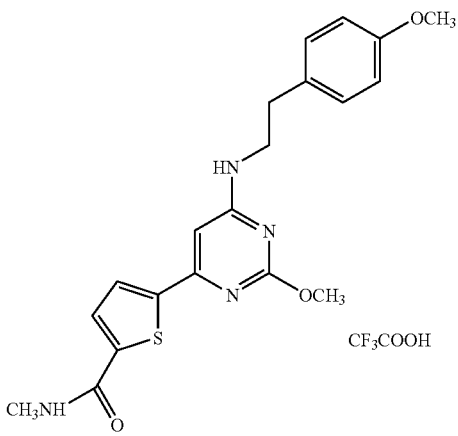

To a solution of 5-{2-methoxy-6-[2-(4-methoxy-phenyl)-ethylamino]-pyrimidin-4-yl}-thiophene-2-carboxylic acid [168 mg, 0.45 mmol, Example 61] in dimethylformamide (15 mL) and DCM (15 mL) is added 2.0M methylamine in THF (275 mL, 0.55 mmol) followed by the addition of 2-(7-aza-1H-benzotriazole-1-yl)-1,1,3,3-tetramethyluronium hexafluorophosphate (224 mg, 0.59 mmol) and diisopropylethylamine (254 mL, 1.46 mmol). The mixture is stirred at ambient temperature for 5 hours and diluted with DCM and washed several times with water. The organic layer is dried over magnesium sulfate, filtered and concentrated to afford the crude product. The material is purified twice by HPLC to afford 5-{2-methoxy-6-[2-(4-methoxy-phenyl)-ethylamino]-pyrimidin-4-yl}-thiophene-2-carboxylic acid methylamide trifluoroacetate, [29 mg, 13%, Example 62]. LCMS: $R_T$=6.96 minutes. MS: 399 (M+H). $IC_5$=0.3 nM

Example 63

(3-{6-[2-(3,4-Dimethoxy-phenyl)-ethylamino]-2-methoxy-pyrimidin-4-yloxy}-benzoic acid methyl ester

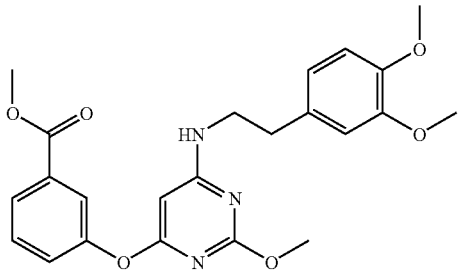

Step 1. A mixture of (6-chloro-2-methylsulfanyl-pyrimidin-4-yl)-[2-(3,4-dimethoxy-phenyl)-ethyl]-amine [250 mg, 0.74 mmol, Intermediate (31)], 3-hydroxy-benzoic acid ethyl ester (0.18 g, 1.1 mmol), and $Cs_2CO_3$ (0.48 g, 1.48 mmol) in DMF (4 mL) is heated to 90° C. for 15 h. The mixture is diluted with water, and extracted with EtOAc. The extracts are washed (water), dried ($MgSO_4$), filtered, concentrated, and chromatographed (silica gel, 30% EtOAc in Heptane) to afford 3-{6-[2-(3,4-dimethoxy-phenyl)-ethylamino]-2-methylsulfanyl-pyrimidin-4-yloxy}-benzoic acid ethyl ester [0.29 g, 83%, Intermediate (71)]. LCMS: $R_T$=3.7 minutes, MS: 470 (M+H).

Step 2. To a mixture of above 3-{6-[2-(3,4-dimethoxy-phenyl)-ethylamino]-2-methylsulfanyl-pyrimidin-4-yloxy}-benzoic acid methyl ester [0.25 g, 0.53 mmol, Intermediate (71)] in $CH_2Cl_2$ (5 mL), is added 3-chloro-peroxybenzoic acid (70%, 0.26 g, 1.06 mmol). After 2 h at 20° C., the mixture is treated with a resin-bound carbonate (MP carbonate, 3 mmol/g, 1 g, 3 mmol), and stirred for 2 h at 20° C. A short-path silica gel chromatography (EtOAc) provided 3-{6-[2-(3,4-dimethoxy-phenyl)-ethylamino]-2-methanesulfonyl-pyrimidin-4-yloxy}-benzoic acid ethyl ester [0.2 g, 75%, Intermediate (72)]. LCMS: $R_T$=3.2 minutes, MS: 502 (M+H).

Step 3

To a solution of above 3-{6-[2-(3,4-Dimethoxy-phenyl)-ethylamino]-2-methanesulfonyl-pyrimidin-4-yloxy}-benzoic acid ethyl ester [180 mg, 0.36 mmol, Intermediate (72)] in 1,2-dimethoxyethane (5 mL) is added a 25% solution of sodium methoxide (3 mL). After 1 h at 20° C., the mixture is filtered through a plug of $SiO_2$ (EtOAc). The filtrate is concentrated to give 3-{6-[2-(3,4-dimethoxy-phenyl)-ethylamino]-2-methoxy-pyrimidin-4-yloxy}-benzoic acid methyl ester [70 mg, 44%, Example (63)]. LCMS: $R_T$=3.34 minutes, MS: 440 (M+H). $IC_{50}$=6254 nM

Example 64

N-[2-(3-{6-[2-(2-Fluoro-4-trifluoromethyl-phenyl)-ethylamino]-2-methoxy-pyrimidin-4-yl}-phenyl)-ethyl]-2-methoxy-acetamide

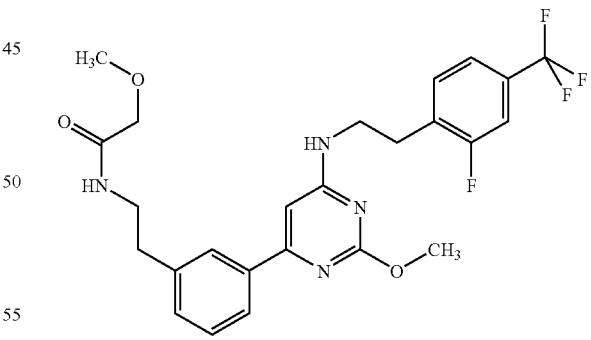

Step 1. A mixture of (6-chloro-2-methoxy-pyrimidin-4-yl)-[2-(2-fluoro-4-trifluoromethyl-phenyl)-ethyl]-amine [800 mg, 2.29 mmol, see Example 52, step 1], (3-cyanomethyl-phenyl)-boronic acid, pinacol ester (563 mg, 3.43 mmol), and $Cs_2CO_3$ (1.86 g, 5.72 mmol) in ethylene glycol dimethyl ether (15 mL) and water (4 mL) is degassed by bubbling with Argon gas for 5 minutes, and treated with tetrakis(triphenylphosphine)palladium(0) (132 mg, 0.11 mmol) at room temperature. After 1 h at 85° C., the mixture is diluted with water (50 mL), and extracted with EtOAc (2×50 mL). The extracts are dried (MgSO$_4$), filtered through a pad of SiO$_2$, and concentrated to afford (3-{6-[2-(2-fluoro-4-trifluoromethyl-phenyl)-ethylamino]-2-methoxy-pyrimidin-4-yl}-phenyl)-acetonitrile (1.2 g). LCMS: R$_T$=2.47 minutes, 92% purity. MS: 431 (M+H).

Step 2. A solution of (3-{6-[2-(2-fluoro-4-trifluoromethyl-phenyl)-ethylamino]-2-methoxy-pyrimidin-4-yl}-phenyl)-acetonitrile (660 mg, 1.53 mmol) in MeOH (20 mL) and concentrated HCl (2 mL) is degassed by bubbling with Argon gas for 5 minutes, and treated with palladium hydroxide on carbon (0.4 g) at room temperature. The mixture is hydrogenated for 15 h at room temperature under hydrogen balloon, filtered through celite, and concentrated in a rotavap. The residue is diluted with water, basified with NaOH solution, and extracted with EtOAc. The extracts are dried (MgSO$_4$), filtered, and concentrated to afford {6-[3-(2-amino-ethyl)-phenyl]-2-methoxy-pyrimidin-4-yl}-[2-(2-fluoro-4-trifluoromethyl-phenyl)-ethyl]-amine (0.55 g). LCMS: R$_T$=1.85 minutes; MS: 435 (M+H).

Step 3. A solution of {6-[3-(2-amino-ethyl)-phenyl]-2-methoxy-pyrimidin-4-yl}-[2-(2-fluoro-4-trifluoromethyl-phenyl)-ethyl]-amine (150 mg, 0.35 mmol) and triethylamine (0.24 mL, 1.73 mmol) in DCM (5 mL) is treated with methoxyacetyl chloride (75 mg, 0.69 mmol) at 10° C. After 10 minutes at 10° C., the mixture is quenched with aqueous NaHCO$_3$ solution (8 mL), and filtered through Chem-Elut with CH$_2$Cl$_2$ washing (10 mL). The filtrate is concentrated, and subjected to chromatography on silica gel eluting with 80% EtOAc in heptane to 5% MeOH in CH$_2$Cl$_2$ to give N-[2-(3-{6-[2-(2-fluoro-4-trifluoromethyl-phenyl)-ethylamino]-2-methoxy-pyrimidin-4-yl}-phenyl)-ethyl]-2-methoxy-acetamide, which is treated with saturated solution of hydrogen chloride in EtOAc followed by lyophilization to afford N-[2-(3-{6-[2-(2-fluoro-4-trifluoromethyl-phenyl)-ethylamino]-2-methoxy-pyrimidin-4-yl}-phenyl)-ethyl]-2-methoxy-acetamide hydrochloride [76 mg, Example 64]. LCMS: R$_T$=2.24 minutes, MS: 507 (M+H). $^1$H NMR (300 MHz, CDCl3) □9.35 (1H, s), 7.9 (1H, brs), 7.6-7.4 (7H, m), 6.65 (1H, s), 4 (3H, s), 3.76 (3H, s), 3.8-3.7 (2H, m), 3.4 (2H, q, J=6.9 Hz), 3.25 (2H, s), 3.06 (2H, t, J=6.6 Hz), 2.82 (2H, t, J=7.5 Hz). IC$_{50}$=56 nM Example 65

N-[2-(3-{6-[2-(2-Fluoro-4-trifluoromethyl-phenyl)-ethylamino]-2-methoxy-pyrimidin-4-yl}-phenyl)-ethyl]-acetamide hydrochloride

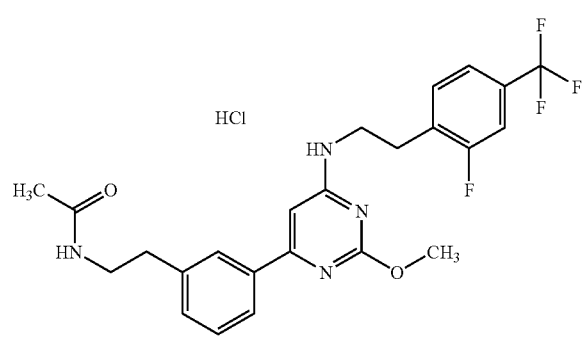

A solution of {6-[3-(2-amino-ethyl)-phenyl]-2-methoxy-pyrimidin-4-yl}-[2-(2-fluoro-4-trifluoromethyl-phenyl)-ethyl]-amine [150 mg, 0.35 mmol, see Example 64, step 2] and triethylamine (0.24 mL, 1.73 mmol) in DCM (5 mL) is treated with acetyl chloride (54 mg, 0.69 mmol) at 10° C. After 10 min at 10° C., the mixture is quenched with aqueous NaHCO$_3$ solution (8 mL), and filtered through Chem-Elut with CH$_2$Cl$_2$ washing (10 mL). The filtrate is concentrated, and subjected to chromatography on silica gel eluting with 80% EtOAc in Heptane to 5% MeOH in CH$_2$Cl$_2$ to give N-[2-(3-{6-[2-(2-fluoro-4-trifluoromethyl-phenyl)-ethylamino]-2-methoxy-pyrimidin-4-yl}-phenyl)-ethyl]-acetamide, which is treated with saturated solution of hydrogen chloride in EtOAc followed by lyophilization to afford N-[2-(3-{6-[2-(2-fluoro-4-trifluoromethyl-phenyl)-ethylamino]-2-methoxy-pyrimidin-4-yl}-phenyl)-ethyl]-acetamide hydrochloride [70 mg, Example 65]. LCMS: R$_T$=2.2 minutes, MS: 477 (M+H); $^1$H NMR (300 MHz, CDCl$_3$) □9.1 (1H, s), 7.95 (1H, brs), 7.7-7.4 (7H, m), 6.65 (1H, s), 4 (3H, s), 3.8-3.75 (2H, m), 3.3 (2H, q, J=6.9 Hz), 3.04 (2H, t, J=6.6 Hz), 2.78 (2H, t, J=7.5 Hz), 2.49 (3H, s). IC$_{50}$=37 nM Example 66

[2-(2-Fluoro-4-trifluoromethyl-phenyl)-ethyl]-[2-methoxy-6-(3-oxiranylmethoxy-phenyl)-pyrimidin-4-yl]-amine

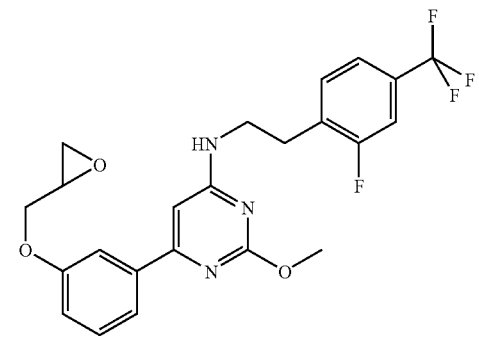

Step 1. A mixture of (6-chloro-2-methoxy-pyrimidin-4-yl)-[2-(2-fluoro-4-trifluoromethyl-phenyl)-ethyl]-amine [1.47 g, 4.2 mmol, see Example 52, step 1], (3-hydroxyphenyl)-boronic acid, (637 mg, 4.62 mmol), and Cs$_2$CO$_3$ (3.4 g, 10.5 mmol) in ethylene glycol dimethyl ether (20 mL) and water (4 mL) is degassed by bubbling with Argon gas for 5 minutes, and treated with tetrakis(triphenylphosphine)palladium(0) (243 mg, 0.21 mmol) at room temperature. After 15 h at 85° C., the mixture is diluted with water (50 mL), and extracted with EtOAc (2×50 mL). The extracts are dried (MgSO$_4$), filtered through a pad of SiO$_2$, and concentrated to afford 3-{6-[2-(2-fluoro-4-trifluoromethyl-phenyl)-ethylamino]-2-methoxy-pyrimidin-4-yl}-phenol (2 g). LCMS: R$_T$=2.32 minutes; MS: 408 (M+H).

Step 2. To a suspension of 3-{6-[2-(2-fluoro-4-trifluoromethyl-phenyl)-ethylamino]-2-methoxy-pyrimidin-4-yl}-phenol (280 mg, 0.68 mmol), and Cs$_2$CO$_3$ (0.44 g, 1.36 mmol) in DMF (2 mL) is added epichlorohydrin (80 μL, 1.02 mmol) at room temperature. After 4 h at 20° C., the mixture is diluted with water (10 mL), and extracted with EtOAc (2×10 mL). The extracts are washed with water (2×20 mL), dried (MgSO$_4$), filtered, and concentrated. The residue is chromatographed on SiO$_2$ eluting with 50% EtOAc in heptane to afford [2-(2-fluoro-4-trifluoromethyl-phenyl)-ethyl]-[2- methoxy-6-(3-oxiranylmethoxy-phenyl)-pyrimidin-4-yl]-amine [0.16 g, Example 66]. LCMS: $R_T$=2.62 minutes; MS: 464 (M+H).

Example 67

2-{3-[6-(2,2-Difluoro-2-phenyl-ethylamino)-2-methoxy-pyrimidin-4-yl]-phenyl}-2-methyl-propionic acid

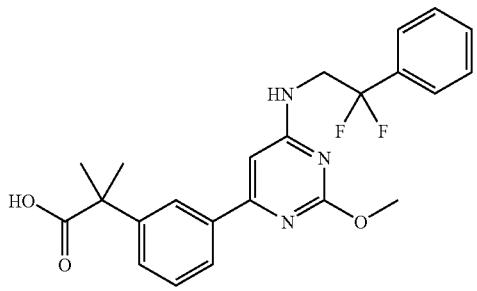

Step 1. To a solution of ethyl benzoylformate (0.36 g, 2 mmol) in CH$_2$Cl$_2$ (10 mL) is added Deoxo-Fluor (1.1 mL, 6 mmol) at 10° C. After 20 h at 20° C., the mixture is quenched with water (10 mL), and poured into Chem-Elut with CH$_2$Cl$_2$ washing (10 mL). The filtrate is concentrated to give difluoro-phenyl-acetic acid ethyl ester, which is used for next step without further purification.

Step 2. A solution of the above difluoro-phenyl-acetic acid ethyl ester and NH$_3$ in MeOH (7 M, 10 mL) is heated to 60° C. for 2 h in a pressure tube. The mixture is cooled to room temperature, and concentrated to afford 2,2-difluoro-2-phenyl-acetamide (0.33 g). LCMS: $R_T$=1.7 minutes; MS: 172 (M+H).

Step 3. To a s solution of 2,2-difluoro-2-phenyl-acetamide (0.76 g, 4.4 mmol) in THF (5 mL) is added Borane in THF (1 M, 20 mL, 20 mmole) at 10° C. After 70° C. for 20 h, the mixture is quenched with water (10 mL), concentrated, and chromatographed on SiO$_2$ eluting with 90% EtOAc in heptane to afford 2,2-difluoro-2-phenyl-ethylamine (0.58 g). LCMS: $R_T$ 0.92 minutes; MS: 158 (M+H); $^1$H NMR (300 MHz, CDCl$_3$) □7.57-7.45 (5H, m), 3.2 (2H, t).

Step 4. A mixture of 4,6-dichloro-2-methoxy-pyrimidine (0.66 g, 3.69 mmol), 2,2-difluoro-2-phenyl-ethylamine (0.58 g, 3.69 mmol), and NaHCO$_3$ (0.93 g, 11.1 mmol) in 95% EtOH (10 mL) is heated to reflux. After stirred at 85° C. for 5 h. The mixture is diluted with water, filtered, washed (water), and dried to afford (6-chloro-2-methoxy-pyrimidin-4-yl)-(2,2-difluoro-2-phenyl-ethyl)-amine as a solid (0.58 g). LCMS: $R_T$=3.17 minutes; MS: 300 (M+H). $^1$H NMR (300 MHz, CDCl$_3$) □7.57-7.45 (5H, m), 6.1 (1H, s), 5.2 (1H, s), 4.2-4 (2H, m), 3.92 (3H, s).

Step 5. A mixture of (6-chloro-2-methoxy-pyrimidin-4-yl)-(2,2-difluoro-2-phenyl-ethyl)-amine (0.19 g, 0.62 mmol), 3-(1-carboxy-1-methyl-ethyl)-phenyl boronic acid [190 mg, 0.94 mmol, see Example 49(b), step 2], and Cs$_2$CO$_3$ (0.51 g, 1.6 mmol) in ethylene glycol dimethyl ether (10 mL) and water (2 mL) is degassed by bubbling with Argon gas for 5 minutes, and treated with tetrakis(triphenylphosphine)palladium(0) (36 mg, 0.03 mmol) at room temperature. After 6 h at 85° C., the mixture is diluted with water (15 mL), and extracted with EtOAc (2×20 mL). The extracts are dried (MgSO$_4$), filtered, and concentrated. The residue is chromatographed on SiO$_2$ eluting with 70% EtOAc in heptane to afford 2-{3-[6-(2,2-difluoro-2-phenyl-ethylamino)-2-methoxy-pyrimidin-4-yl]-phenyl}-2-methyl-propionic acid [0.28 g Example 67]. LCMS: $R_T$=2.82 minutes; MS: 428 (M+H); $^1$H NMR (300 MHz, CDCl$_3$) 9.6 (1H, s), 8 (1H, s), 7.81 (1H, d, J=7.5 Hz), 7.5-7.4 (7H, m), 6.4 (1H, s), 4.2-4 (2H, m), 3.96 (3H, s), 1.65 (6H, s). IC$_{50}$=38 nM

Example 68

2-[3-(2-Methoxy-6-{2-[4-(5-methyl-[1,3,4]oxadiazol-2-yl)-phenyl]-ethylamino}-pyrimidin-4-yl)-phenyl]-2-methyl-propionic acid

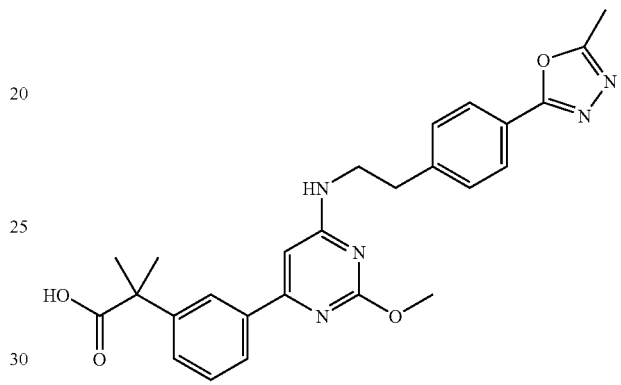

Step 1. To a solution of 4-[2-(6-chloro-2-methoxy-pyrimidin-4-ylamino)-ethyl]-benzoic acid (0.41 g, 1.33 mmol), acetic acid hydrazide (0.1 g, 2 mmol), and triethylamine (0.7 mL, 3.99 mmol) in DMF (3 mL) is added [(benzotriazol-1-yloxy)-dimethylamino-methylene]-dimethyl-ammonium tetrafluoro borate (0.51 g, 1.6 mmol) at room temperature. After 15 h at 20° C., the solid is filtered, and washed with water to afford 4-[2-(6-chloro-2-methoxy-pyrimidin-4-ylamino)-ethyl]-benzoic acid N'-acetyl-hydrazide (267 mg). The filtrate is extracted with EtOAc, and concentrated to afford additional amount of 4-[2-(6-chloro-2-methoxy-pyrimidin-4-ylamino)-ethyl]-benzoic acid N'-acetyl-hydrazide (100 mg). LCMS: $R_T$=2 minutes; MS: 364 (M+H).

Step 2. A mixture of 4-[2-(6-chloro-2-methoxy-pyrimidin-4-ylamino)-ethyl]-benzoic acid N'-acetyl-hydrazide (0.2 g, 0.55 mmol), and Burgess reagent (0.39 g, 1.65 mmol) in THF (6 mL) is placed in a microwave reactor. After 5 min at 130° C., the mixture is concentrated in a rotavap, and subjected to a chromatography eluting with 10% MeOH in CH$_2$Cl$_2$ to afford (6-chloro-2-methoxy-pyrimidin-4-yl)-{2-[4-(5-methyl-[1,3,4]oxadiazol-2-yl)-phenyl]-ethyl}-amine (160 mg). LCMS: $R_T$=2.29 minutes; MS: 346 (M+H).

Step 3. A mixture of (6-chloro-2-methoxy-pyrimidin-4-yl)-{2-[4-(5-methyl-[1,3,4]oxadiazol-2-yl)-phenyl]-ethyl}-amine (0.16 g, 0.46 mmol), 3-(1-carboxy-1-methyl-ethyl)-phenyl boronic acid, [125 mg, 0.6 mmol, see Example 49(b), step 2], and Cs$_2$CO$_3$ (0.37 g, 1.15 mmol) in ethylene glycol dimethyl ether (8 mL), acetonitrile (10 mL), and water (2 mL) is degassed by bubbling with Argon gas for 5 minutes, and treated with 1,1'-bis(diphenylphosphino)ferrocene palladium (II) chloride (20 mg) at room temperature. After 3 h at 85° C., the mixture is diluted with water (15 mL), and extracted with EtOAc (2×15 mL). The extracts are dried (MgSO$_4$), filtered, and concentrated. The residue is chromatographed on SiO$_2$ eluting with 80% EtOAc in heptane to afford 2-[3-(2-methoxy-6-{2-[4-(5-methyl-1,3,4]oxadiazol-2-yl)-phenyl]-ethylamino}-pyrimidin-4-yl)-phenyl]-2-methyl-propionic acid [55 mg, Example 68]. LCMS: $R_T$=1.82 minutes; MS: 474 (M+H); $^1$H NMR (300 MHz, CDCl$_3$) □ 7.98-7.81 (4H, m), 7.5-7.27 (4H, m), 6.33 (1H, s), 3.97 (3H, s), 3.72-3.6 (2H, m), 2.92 (2H, t, J=6.5 Hz), 2.6 (3H, s), 1.6 (6H, s).

Example 69

5-(3-{6-[2-(3,4-Difluoro-phenyl)-ethylamino]-2-methoxy-pyrimidin-4-yl}-phenoxymethyl)-1-ethyl-2,4-dihydro-[1,2,4]triazol-3-one

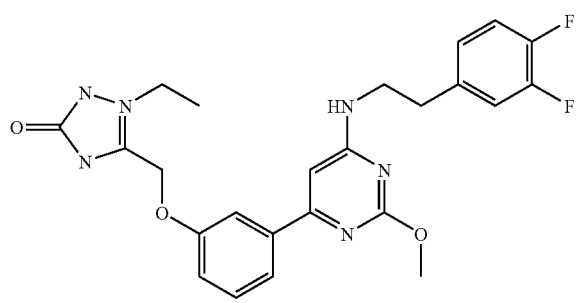

Step 1. A solution of 3,4-difluorobenzaldehyde (5.05 g), nitromethane (5.3 mL) and ammonium acetate (6.3 g) in glacial acetic acid (60 mL) is heated at 110° C. for 16 hours, allowed to cool and poured into water (300 mL). The solution is extracted with EtOAc (2×200 mL). The combined extract is washed with 10% NaHCO$_3$, water and dried over sodium sulfate, filtered and evaporated in vacuo to afford 1,2-difluoro-4-(2-nitro-vinyl)benzene (4.2 g). MS: 198 (M+H); $^1$H NMR (300 MHz, CDCl$_3$) □7.9 (1H, d, J=10 Hz); 7.5 (1H, d, 10 Hz); 7.3 (2H, m); 6.95-7.15 (1H, m).

Step 2. To a solution of 1,2-difluoro-4-(2-nitro-vinyl)benzene (1.5 g) in THF (50 mL) is added dropwise lithium aluminum hydride (23 mL, 1M in ether) and the solution is heated at 40° C. for 3 hours. The solution is cooled, diluted with ether and quenched with Na$_2$SO$_4$.10H2O (104 g) overnight. The solid is filtered, and the solution is evaporated in vacuo and chromatographed on silica gel eluting with EtOAc to afford 2-(3,4-difluoro-phenyl)-ethylamine (0.81 g). MS: 170 (M+H); $^1$H NMR (300 MHz, CDCl$_3$) □6.9-7 (3H, m); 2.95 (2H, t); 2.7 (2H, t).

Step 3. A solution of 4,6-dichloro-2-methoxypyrimidine (0.7 g), 2-(3,4-difluoro-phenyl)-ethylamine (0.66 g) and sodium bicarbonate (0.88 g) in EtOH (25 mL) is heated at 80° C. for three hours, poured into water (400 mL) and the solid is filtered and air dried to afford (6-chloro-2-methoxy-pyrimidin-4-yl)-[2-(3,4-difluoro-phenyl)-ethyl]-amine (1.1 g). MS: 312 (M+H); $^1$H NMR (300 MHz, CDCl$_3$) □6.9-7 (3H, m); 6.05 (1H, s); 3.95 (3H, s); 3.6-3.7 (2H, m); 2.95 (2H, t).

Step 4: A solution of (6-chloro-2-methoxy-pyrimidin-4-yl)-[2-(3,4-difluoro-phenyl)-ethyl]-amine (1.6 g), 3-cyanophenylboronic acid (1.5 g), Cs$_2$CO$_3$ (8.3 g) and tetrakis(triphenylphosphine)palladium (0) (45 mg) in water (8 mL) and DME (32 mL) is heated at 90° C. for 16 hours. The solution is poured into water and extracted with EtOAc (2×200 mL). The combined extract is dried over sodium sulfate, filtered, evaporated in vacuo and chromatographed on silica gel eluting with EtOAc to afford 3-{6-[2-(3,4-difluoro-phenyl)-ethylamino]-2-methoxy-pyrimidin-4-yl}-phenol (1.1 g). MS: 379 (M+H); $^1$H NMR (300 MHz, CDCl$_3$) □8.3 (1H, s); 8.2 (1H, d, J=5.1 Hz); 7.9 (1H, d (J=5.1 Hz)); 7.6 (1H, t); 7-7.2 (4H, m); 6.4 (1H, s); 5 (1H, m); 3.95 (3H, s); 3.7 (2H, t); 3 (2H, t).

Step 5. A solution of methylglyoxylate (11 g) and hydrazine hydrate (4.7 g) in MeOH (10 mL) is stirred at room temperature for 16 hours. The solution is concentrated and put under high vacuum for 3 hours. The residue is suspended in THF (200 mL) and ethylisocyanate (8.5 mL) is added. The mixture is stirred at room temperature for 16 hours. The solid is filtered and washed with diethyl ether to afford N-(2-hydroxyacetyl)-N-ethylcarbamidosemicarbazide (19 g). $^1$H NMR (300 MHz, DMSO-d$_6$) □9.2 (m, 1H); 8.6 (s, 1H); 6.3 (m, 1H); 3.9 (d, 2H, J=0.3); 3 (q, 2H); 1 (d, 3H, J=0.4).

Step 6. N-(2-hydroxyacetyl)-N-ethylcarbamidosemicarbazide (19 g) is suspended in a solution of NaOH (5.32 g) in water (60 mL) and EtOH (240 mL). The suspension is heated at 82° C. for 20 hours. The solution is acidified to pH=6 with concentrated HCl (22 mL) and concentrated to an oil. A portion of the oil (1.51 g) is suspended in acetonitrile (60 mL) and thionyl chloride (0.94 mL) is added dropwise. The solution is stirred at room temperature for 20 hours and concentrated to a solid, which is triturated with Et$_2$O/heptanes and filtered under nitrogen to afford 5-chloromethyl-4-ethyl-2,4-dihydro-[1,2,4]-triazol-3-one (1.52 g). $^1$H NMR (300 MHz, CDCl$_3$) □9.9 (m, 1H); 4.5 (s, 2H); 3.8 (t, 3H); 1.4 (d, 3H, J=0.3).

Step 7. A mixture of 3-{6-[2-(3-fluoro-4-methoxy-phenyl)-ethylamino]-2-methoxy-pyrimidin-4-yl}-phenol (0.4 g) and K$_2$CO$_3$ (0.46 g) in MeOH (25 mL) is heated to reflux for 30 minutes. The suspension is cooled to 0° C. and 5-chloromethyl-4-ethyl-2,4-dihydro-[1,2,4]triazol-3-one (0.12 g) is added and the solution is stirred at 0° C. for 30 minutes. The solution is acidified to pH=6 with glacial acetic acid and is extracted with EtOAc (3×100 mL). The combined organic layer is dried over Na$_2$SO$_4$, filtered and evaporated in vacuo. The residue is chromatographed on silica gel eluting with 5% MeOH in EtOAc to afford 5-(3-{6-[2-(3,4-difluoro-phenyl)-ethylamino]-2-methoxy-pyrimidin-4-yl}-phenoxymethyl)-1-ethyl-2,4-dihydro-[1,2,4]triazol-3-one (185 mg, Example 69). MS: 483 (M+H); $^1$H NMR (300 MHz, DMSO-d$_6$) 0111.8 (s, 1H); 7.5-7.8 (m, 3H); 7.2-7.4 (m, 2H); 7-7.2 (m, 2H); 6.6 (s, 1H); 5.1 (s, 2H); 3.9 (s, 3H); 3.7 (q, 2H); 3.5 (m, 2H); 2.9 (t, 2H); 1.2 (d, 3H). IC$_{50}$=143 nM Example 70

2-(2-Fluoro-5-{2-methoxy-6-[2-(4-trifluoromethoxy-phenyl)-ethylamino]-pyrimidin-4-yl}-phenyl)-2-methyl-propionic acid

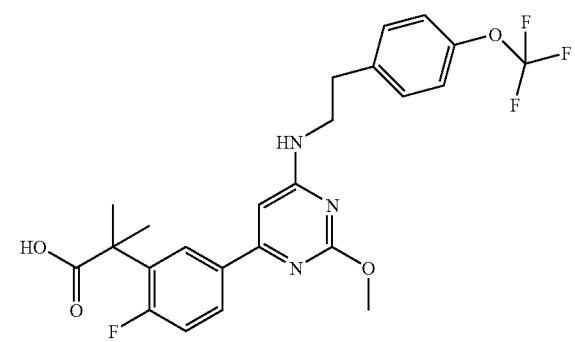

Step 1. To a solution of 5-bromo-2-fluorophenylacetic acid (5 g) in MeOH (200 mL) is added concentrated sulfuric acid (2 mL) and the solution is heated at 64° C. for 16 hours. The solution is evaporated in vacuo and the residue is taken up in EtOAc and washed with 10% sodium bicarbonate, brine and dried over sodium sulfate. The solution is filtered and evaporated in vacuo to afford (5-bromo-2-fluoro-phenyl)-acetic acid methyl ester (5.1 g). $^1$H NMR (300 MHz, CDCl$_3$) □7.3-7.5 (m, 2H); 6.9 (m, 1H); 3.9 (s, 3H).

Step 2. A solution of (5-bromo-2-fluoro-phenyl)-acetic acid methyl ester (3.5 g) in THF (50 mL) is cooled to −70° C. and KOtBu (36 mL, 1M in THF) is added dropwise while maintaining the temperature below −65° C. At −78° C. iodomethane (2.5 mL) is added in one portion and 18-crown-6 (0.45 g) is added. The solution is stirred at −78° C. for 30 minutes and allowed to warm to room temperature for 16 hours. The solution is poured into water (300 mL) and extracted with EtOAc (2×150 mL). The combined organic extract is washed with brine, dried over sodium sulfate, filtered and evaporated in vacuo. The residue is chromatographed on silica gel eluting with 20% EtOAc in heptane to afford 2-(5-bromo-2-fluoro-phenyl)-2-methyl-propionic acid methyl ester (3.7 g). MS: 276 (M+H); $^1$H NMR (300 MHz, CDCl$_3$) □7.3-7.5 (m, 2H); 6.9 (m, 1H); 3.85 (s, 3H); 1.6 (s, 6H).

Step 3. A solution of 2-(5-bromo-2-fluoro-phenyl)-2-methyl-propionic acid methyl ester (5.15 g), bis-(pinacolato)-diboron (5.24 g), Pd dppf (0.3 g) and KOAc (3.67 g) in DMSO (2 mL) and THF (200 mL) is heated at 84° C. for 16 hours. The solution is cooled to 5° C. and a solution of potassium hydroxide (16.6 g) in water (150 mL) is added. The solution is stirred at room temperature for 30 minutes and filtered. The filtrate is acidified to pH=6 with glacial acetic acid (19 mL) and extracted with EtOAc (2×200 mL). The combined extract is washed with brine, dried over sodium sulfate, filtered and evaporated in vacuo to afford 2-[2-fluoro-5-(4,4,5,5-tetramethyl-[1,3,2]dioxaborolan-2-yl)-phenyl]-2-methyl-propionic acid methyl ester (5.3 g). MS: 323 (M+H); $^1$H NMR (CDCl$_3$) □7.3-7.5 (m, 2H); 6.9 (m, 1H); 3.85 (s, 3H); 1.6 (s, 6H); 1.4 (s, 12H).

Step 4. A solution of (6-chloro-2-methoxy-pyrimidin-4-yl)-[2-(4-trifluoromethoxyphenyl)-ethyl]amine (1.6 g), 2-[2-fluoro-5-(4,4,5,5-tetramethyl-[1,3,2]dioxaborolan-2-yl)-phenyl]-2-methyl-propionic acid methyl ester (0.63 g), Cs$_2$CO$_3$ (11.6 g) and tetrakis(triphenylphosphine)palladium (0) (33 mg) in water (8 mL) and DME (32 mL) is heated at 90° C. for 16 hours. The solution is poured into water and extracted with EtOAc (2×200 mL). The combined extract is dried over sodium sulfate, filtered, evaporated in vacuo and chromatographed on silica gel eluting with EtOAc to afford 2-(2-fluoro-5-{2-methoxy-6-[2-(4-trifluoromethoxy-phenyl)-ethylamino]-pyrimidin-4-yl}-phenyl)-2-methyl-propionic acid methyl ester (300 mg). MS: 508 (M+H); $^1$H NMR (300 MHz, CD$_3$OD) □7.8, (d, 1H, J=0.3 Hz); 7.7 (m, 1H); 7.4 (d, 2H, J=0.4 Hz); 7.2-7.3 (m, 4H); 6.6 (s, 1H); 4.2 (s, 3H); 4 (s, 3H); 3.9 (m, 2H); 3.05 (t, 2H); 1.65 (s, 6H).

Step 5: A mixture of 2-(2-fluoro-5-{2-methoxy-6-[2-(4-trifluoromethoxy-phenyl)-ethylamino]-pyrimidin-4-yl}-phenyl)-2-methyl-propionic acid methyl ester (should this be the right starting material? 1.9 g) and sodium hydroxide (2.46 g) in water (19 mL), MeOH (19 mL) and THF (19 mL) is stirred at 40° C. for 40 hours. The solution is evaporated in vacuo and acidified to pH=6 with concentrated HCl (1.6 mL). The solid is filtered, air dried and chromatographed on silica gel eluting with 50% EtOAc in heptane to afford 2-(2-fluoro-5-{2-methoxy-6-[2-(4-trifluoromethoxy-phenyl)-ethylamino]-pyrimidin-4-yl}-phenyl)-2-methyl-propionic acid (1.12 g, Example 70). MS: 494 (M+H); $^1$H NMR (300 MHz, CD$_3$OD) 07.8, (d, 1H, J=0.3 Hz); 7.7 (m, 1H); 7.4 (d, 2H, J=0.4 Hz); 7.2-7.3 (m, 4H); 6.6 (s, 1H); 4.2 (s, 3H); 3.9 (m, 2H); 3.05 (t, 2H); 1.65 (s, 6H). IC$_{50}$=193 mM Example 71

2-(3-{2-Methoxy-6-[(thiophen-3-ylmethyl)-amino]-pyrimidin-4-yl}-phenyl)-2-methyl-propionic acid

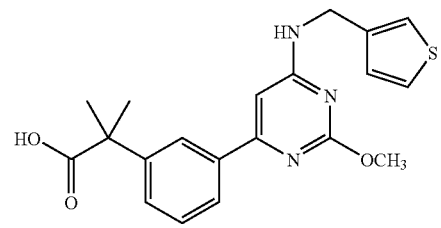

Step 1. By proceeding in a similar manner to that described in Example 1, Step 3, but substituting C-thiophen-3-yl-methylamine for 2-(3-fluoro-4-methoxy-phenyl)-ethylamine there is prepared (6-chloro-2-methoxy-pyrimidin-4-yl)-thiophen-3-ylmethyl-amine.

Step 2. Argon is bubbled through a mixture of (6-chloro-2-methoxy-pyrimidin-4-yl)-thiophen-3-ylmethyl-amine (216 mg, 0.84 mmol), 3-(1-carboxy-1-methyl-ethyl)-phenyl boronic acid [312 mg, 1.5 mmol, see Example 49(b) step 2], Cs$_2$CO$_3$ (821 mg, 2.52 mmol), and tetrakis(triphenylphosphine)palladium (0) (92 mg, 0.08 mmol) in ethylene glycol dimethyl ether (2.5 mL) and water (0.5 mL), for a period of 10 minutes. The reaction vessel is sealed and heated to 90° C. After stirring for 6 hours the heating is turned off and the mixture is allowed to cool to ambient temperature upon standing for 24 hours. The mixture is diluted with water (40 mL) and extracted twice with EtOAc (25 mL). The organic extracts are combined and dried over magnesium sulfate, filtered and concentrated to afford 2-(3-{2-methoxy-6-[(thiophen-3-ylmethyl)-amino]-pyrimidin-4-yl}-phenyl)-2-methyl-propionic acid [15 mg, 4.6%, Example 71] as a solid. LCMS R$_T$=1.94 minutes, MS: 384 (M+H). IC$_{50}$=393 nM Example 72

2-(3-{6-[(Benzo[b]thiophen-2-ylmethyl)-amino]-2-methyl-pyrimidin-4-yl}-phenyl)-2-methyl-propionic acid

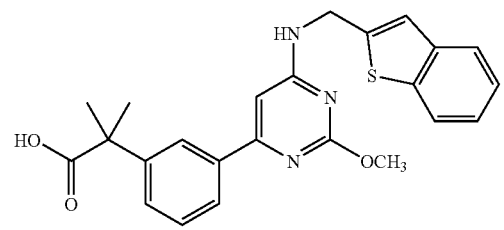

Step 1. By proceeding in a similar manner to that described in Example 1, Step 3, but substituting benzo[b]thiophen-2-yl-methylamine for 2-(3-fluoro-4-methoxy-phenyl)-ethylamine there is prepared benzo[b]thiophen-2-ylmethyl-(6-chloro-2-methyl-pyrimidin-4-yl)-amine.

Step 2. Argon is bubbled through a mixture of benzo[b]thiophen-2-ylmethyl-(6-chloro-2-methyl-pyrimidin-4-yl)-amine [247 mg, 0.81 mmol], 3-(1-carboxy-1-methyl-ethyl)-phenyl boronic acid [304 mg, 1.46 mmol, see Example 49(b) step 2], $Cs_2CO_3$ (792 mg, 2.43 mmol), and tetrakis(triphenylphosphine)palladium (0) (92 mg, 0.08 mmol) in ethylene glycol dimethyl ether (2.5 mL) and water (0.5 mL), for a period of 10 minutes. The reaction vessel is sealed and heated to 90° C. After stirring for 6 hours the heating is turned off and the mixture is allowed to cool to ambient temperature upon standing for 24 hours. The mixture is diluted with water (20 mL) and extracted twice with EtOAc (30 mL). The organic extracts are combined and dried over magnesium sulfate, filtered and concentrated to afford 2-(3-{6-[(benzo[b]thiophen-2-ylmethyl)-amino]-2-methyl-pyrimidin-4-yl}-phenyl)-2-methyl-propionic acid [51.6 mg, 14.7%, Example 72] as a solid. LCMS $R_T$=2.27 minutes, MS: 434 (M+H).

Example 73

1-{6-[2-(2,4-Dichloro-phenyl)-ethylamino]-2-methoxy-pyrimidin-4-yl}-piperidine-3-carboxylic acid

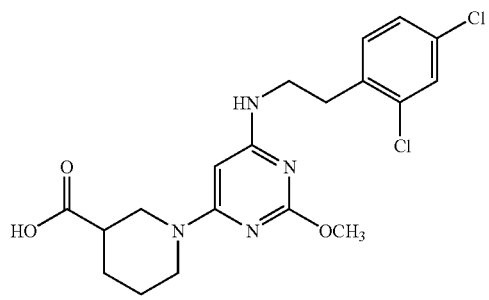

In a tube is combined (6-chloro-2-methoxy-pyrimidin-4-yl)-[2-(2,4-dichloro-phenyl)-ethyl]-amine [200 mg, 0.6 mmol, Intermediate (44)], nipecotic acid (194 mg, 1.5 mmol), $K_2CO_3$ (249 mg, 1.8 mmol) and 1-methyl-2-pyrrolidinone (2.5 mL). The tube is sealed and heated to 140° C. and stirred for hours. The mixture is allowed to cool to ambient temperature, stand for 12 hours, diluted with water (20 mL) and acidified using 3M HCl. A precipitate forms and is collected by filtration and dried under high vacuum to afford 1-{6-[2-(2,4-dichloro-phenyl)-ethylamino]-2-methoxy-pyrimidin-4-yl}-piperidine-3-carboxylic acid [121 mg, 47%, Example 73] as a solid. LCMS $R_T$=2.15 minutes, MS: 425 (M+H). $IC_{50}$=0.8 nM Example 74

1-(3-{6-[2-(2,4-Dichloro-phenyl)-ethylamino]-2-methoxy-pyrimidin-4-yl}-phenyl)-cyclopentanecarboxylic acid hydrochloride

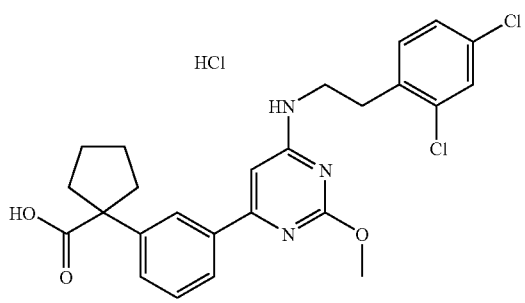

Step 1. HCl is bubbled through a solution of 3-bromophenyl acetic acid (10.5 g, 46.5 mmol) in EtOH (70 mL) chilled at 0° C. for 5 minutes. The flask is capped and stirred at ambient temperature for 5 hours. The mixture is concentrated. The residue is taken up with water (80 mL) and extracted twice with EtOAc (70 mL). The organic extracts are combined and dried over magnesium sulfate, filtered and concentrated to afford (3-bromo-phenyl)-acetic acid ethyl ester [10.55 g, 93.4%] as an oil, which is used without further purification.

Step 2. Sodium hydride (60% in oil, 1.07 g, 26.8 mmol) is added to a solution of (3-bromo-phenyl)-acetic acid ethyl ester [2.59 g, 10.7 mmol] and 18-crown-6 (catalytic amount) in N,N'-dimethylformamide (50 mL). The mixture is stirred for 25 minutes and 1,4-dibromobutane (1.41 mL, 11.8 mmol) is added dropwise via syringe. The mixture is stirred for 18 hours at ambient temperature, diluted with water (100 mL) and extracted thrice with EtOAc (60 mL). The organic extracts are combined and dried over magnesium sulfate, filtered and concentrated to afford 1-(3-bromo-phenyl)-cyclopentanecarboxylic acid ethyl ester [2.9 g, 91%] as an oil, which is used without further purification.

Step 3. A mixture of 1-(3-bromo-phenyl)-cyclopentanecarboxylic acid ethyl ester [3.42 g, 11.51 mmol], lithium hydroxide (579 mg, 13.81 mmol), THF (13 mL), MeOH (13 mL) and water (13 mL) is vigorously stirred for 18 hours. The mixture is concentrated and the residue is diluted with water (50 mL). The aqueous mixture is acidified with concentrated HCl to pH 1 and extracted twice with EtOAc (50 mL). The organic extracts are combined and dried over magnesium sulfate, filtered and concentrated to afford 1-(3-bromo-phenyl)-cyclopentanecarboxylic acid [2.5 g, 80.6%] as a solid, which is used without further purification.

Step 4. A solution of n-butyl lithium (2.5 M in hexanes, 5 mL, 12.48 mmol) in THF (30 mL) is chilled to −78° C., and a solution of 1-(3-bromo-phenyl)-cyclopentanecarboxylic acid [1.05 g, 3.9 mmol] in THF (10 mL) is added dropwise via syringe. The solution is stirred at temperature for 45 minutes and treated with tributyl borate (3.2 mL, 11.7 mmol). The reaction mixture is allowed to stir for 2.5 hours and then diluted with water (60 mL), acidified with 3M HCl and extracted twice with EtOAc (50 mL). The organic extracts are combined and dried over magnesium sulfate, filtered and concentrated to afford 3-(1-carboxy-cyclopentyl)-phenylboronic acid as a solid, which is used without further purification.

Step 5. Argon is bubbled through a mixture of (6-chloro-2-methoxy-pyrimidin-4-yl)-[2-(2,4-dichloro-phenyl)-ethyl]-amine [330 mg, 0.99 mmol], 3-(1-carboxy-cyclopentyl)-phenylboronic acid [580 mg, 2.48 mmol] and $Cs_2CO_3$ (808 mg, 2.48 mmol) in ethylene glycol dimethyl ether (4 mL) and water (1 mL), for a period of 5 minutes. To this mixture is added tetrakis(triphenylphosphine)palladium (0) (116 mg, 0.1 mmol) and the reaction vessel is sealed and heated to 90° C. After stirring for 8 hours the mixture is diluted with water (30 mL) acidified to pH 1 with concentrated HCl and extracted thrice with EtOAc (30 mL). The organic extracts are combined and dried over magnesium sulfate, filtered and concentrated to afford 1-(3-{6-[2-(2,4-dichloro-phenyl)-ethylamino]-2-methoxy-pyrimidin-4-yl}-phenyl)-cyclopentanecarboxylic acid as a solid that is treated with HCl in ethyl acetate. The material is then dissolved in acetone (5 mL) and heptane (15 mL) is added and allowed to stand at ambient temperature for 16 hours. The solvent is decanted from the crystals and dried under high vacuum to provide 1-(3-{6-[2-(2,4-dichloro-phenyl)-ethylamino]-2-methoxy-pyrimidin-4-yl}-phenyl)-cyclopentanecarboxylic acid hydrochloride [48 mg, 9%, Example 74] as a solid. LCMS $R_T$=2.54 minutes, MS: 486 (M+H). $IC_{50}$=0.5 nM Example 75

3-{6-[2-(2,4-Dichloro-phenyl)-ethylamino]-2-methoxy-pyrimidin-4-yl}-benzoic acid 2-morpholin-4-yl-ethyl ester

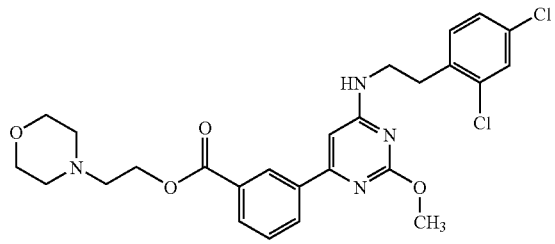

4-Dimethylaminopyridine (4.4 mg, 0.036 mmol) is added to a stirred solution of 3-{6-[2-(2,4-dichloro-phenyl)-ethylamino]-2-methoxy-pyrimidin-4-yl}-benzoic acid (100 mg, 0.24 mmol), N-(2-hydroxyethyl) morpholine (29.07 μL, 0.24 mmol) and 1,3-dicyclohexylcarbodiimide (0.31 mL, 1 M solution in DCM) in dry THF/DCM (6 mL, 1:1) and the reaction mixture is stirred for 5.5 hours at room temperature under nitrogen atmosphere. The mixture is filtered over a pad of Celite and the filtrate concentrated under reduced pressure. The residue is dissolved EtOAc (30 mL), washed with saturated aqueous sodium bicarbonate and brine, dried over sodium sulfate, filtered and concentrated under reduced pressure. The crude residue is purified by chromatography ($SiO_2$ packed column) eluting with ethyl acetate/heptane to afford 3-{6-[2-(2,4-dichloro-phenyl)-ethylamino]-2-methoxy-pyrimidin-4-yl}-benzoic acid 2-morpholin-4-yl-ethyl ester (56 mg, Example 75). LCMS: $R_T$=2.07 minutes, MS: 534 (M+H); $^1$H NMR, (300 MHz, $CDCl_3$): □8.62 (1H, s), 8.3 (1H, d, J=3.5 Hz), 8.1 (1H, d, J=3.5 Hz), 7.55 (1H, t, J=3.5 Hz), 7.42 (1H, s), 7.2 (2H, s), 6.48 (1H, s), 5.04 (1H, b), 4.5 (2H, t, J=2 Hz), 4.05 (3H, s), 3.72 (6H, t, J=2 Hz), 3.1 (2H, t, J=2 Hz), 2.8 (2H, t, 2 Hz), 2.6 (4H, t, 2 Hz).

Example 76

3-{6-[2-(2,4-Dichloro-phenyl)-ethylamino]-2-methoxy-pyrimidin-4-yl}-benzoic acid 2-(4-methyl-piperazin-1-yl)-ethyl ester

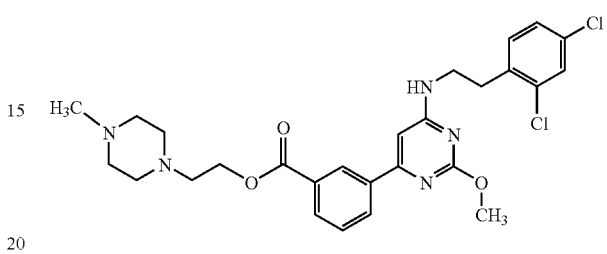

By proceeding in a similar manner as Example 75 but substituting 1-(2-hydroxyethyl)-4-methyl-piperazine for N-(2-hydroxyethyl) morpholine, there is prepared 3-{6-[2-(2,4-dichloro-phenyl)-ethylamino]-2-methoxy-pyrimidin-4-yl}-benzoic acid 2-(4-methyl-piperazin-1-yl)-ethyl ester (47 mg, Example 76). LCMS: $R_T$=2.04 minutes, MS: 545 (M+H); $^1$H NMR, (300 MHz, $CDCl_3$): □8.6 (1H, s), 8.3 (1H, d, J=3.5 Hz), 8.1 (1H, d, J=3.5 Hz), 7.55 (1H, t, J=3.5 Hz), 7.42 (1H, s), 7.2 (2H, s), 6.48 (1H, s), 5.15 (1H, b), 4.5 (2H, t, J=2 Hz), 4.05 (3H, s), 3.72 (2H, b), 3.1 (2H, t, J=2 Hz), 2.85 (2H, t, 2 Hz), 2.7 (4H, b), 2.5 (4H, b), 2.3 (3H, s). $IC_{50}$=7 nM Example 77

3-{6-[2-(2,4-Dichloro-phenyl)-ethylamino]-2-methoxy-pyrimidin-4-yl}-benzoic acid ethyl ester

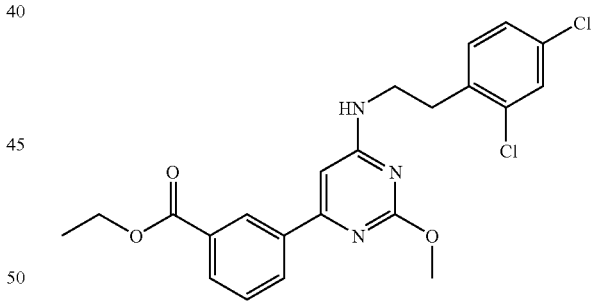

$Cs_2CO_3$ solution (407 mg, 1.25 mmol in 2 mL water) is added to a stirred solution of (6-chloro-2-methoxy-pyrimidin-4-yl)-[2-(2,4-dichloro-phenyl)-ethyl]-amine (166 mg, 0.5 mmol) and ethylcarbonylphenyl boronic acid (135.8 mg, 0.7 mmol) in 1,2-dimethoxyethane (5 mL). The mixture is degassed over nitrogen for 10 minutes, tetrakis(triphenylphosphine)palladium (0) (23 mg, 0.02 mmol) is added and the reaction mixture is refluxed at 90° C. for 6 hours. The reaction is cooled to room temperature, diluted with water (10 mL), filtered over a pad of Celite and the volatiles are removed under reduced pressure. The aqueous pH is adjusted to neutral (0.1 N HCl) and extracted twice with ethyl acetate. The combined extracts are washed with brine and water, dried over magnesium sulfate, filtered and concentrated in reduced pressure. The crude residue is purified by chromatography (SiO$_2$ packed column), eluting with 5-15% Ethyl acetate/DCM to afford 3-{6-[2-(2,4-dichloro-phenyl)-ethylamino]-2-methoxy-pyrimidin-4-yl}-benzoic acid ethyl ester (48 mg, Example 77). LCMS: R$_T$=2.95 minutes, MS: 447 (M+H); $^1$H NMR, (300 MHz, CDCl$_3$): □8.65 (1H, s), 8.3 (1H, d, J=3.5 Hz), 8.15 (1H, d, J=3.5 Hz), 7.55 (1H, t, J=3.5 Hz), 7.45 (1H, s), 7.25 (2H, s), 6.5 (1H, s), 4.95 (1H, b), 4.45 (2H, q, J=3.5 Hz), 4.05 (3H, s), 3.75 (2H, b), 3.1 (2H, t, J=3.5 Hz), 1.45 (3H, t, 3.5 Hz). IC$_{50}$=149 nM Example 78

(a) (3-{6-[2-(2,4-Dichloro-phenyl)-ethylamino]-2-methoxy-pyrimidin-4-yl}-phenyl)-methanol

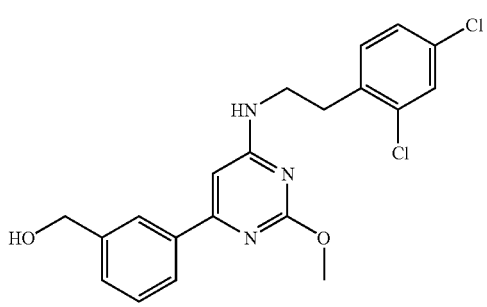

(b) (3'-Chloro-4'-{2-[6-(3-hydroxymethyl-phenyl)-2-methoxy-pyrimidin-4-ylamino]-ethyl}-biphenyl-3-yl)-methanol

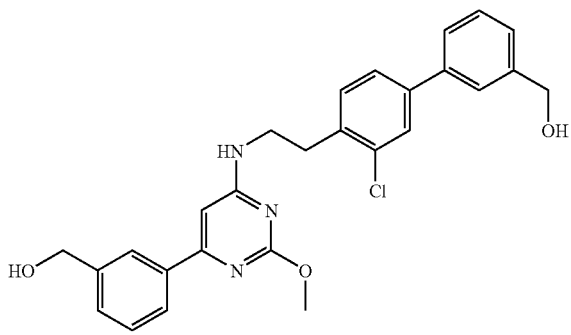

In a hard walled glass tube, a solution of (6-chloro-2-methoxy-pyrimidin-4-yl)-[2-(2,4-dichloro-phenyl)-ethyl]-amine (250 mg, 0.75 mmol), 3-(hydroxymethyl)phenylboronic acid (137 mg, 0.9 mmol) and Na$_2$CO$_3$ (79.7 mg, 0.75 mmol) in acetonitrile/water (6 mL, 2:1) is degassed over nitrogen for 10 minutes. Tetrakis(triphenylphosphine)palladium (0) (43.5 mg, 0.04 mmol) is added and the tube is sealed and set in a microwave for 25 minutes at 130° C. The reaction is dilute with 25 mL of water and extracted twice with ethyl acetate. The combined organic extracts are washed with brine, dried over sodium sulfate, filtered and concentrate in reduced pressure. The residue is purified by chromatography (SiO$_2$ packed column), eluted with EtOAc/DCM to afford (3-{6-[2-(2,4-dichloro-phenyl)-ethylamino]-2-methoxy-pyrimidin-4-yl}-phenyl)-methanol [165 mg, Example 78 (a)]. LCMS: R$_T$=2.24 minutes, MS: 405 (M+H); $^1$H NMR (300 MHz, CDCl$_3$): □8.05 (1H, s), 7.95 (1H, b)), 7.48 (3H, b), 7.42 (1H, s), 7.2 (1H, s), 6.45 (1H, s), 4.95 (1H, b), 4.78 (2H, b), 4.05 (3H, s), 3.72 (2H, b), 3.1 (2H, t, J=3.5 Hz); and to afford (3'-chloro-4'-{2-[6-(3-hydroxymethyl-phenyl)-2-methoxy-pyrimidin-4-ylamino]-ethyl}-biphenyl-3-yl)-methanol [110 mg, Example 78(b)]. LCMS: R$_T$=2.12 minutes, MS: 477 (M+H).

Example 79

2-(3-{6-[2-(2,4-Dichloro-phenyl)-ethylamino]-2-methoxy-pyrimidin-4-yl}-phenyl)-2-methyl-propionic acid methyl ester

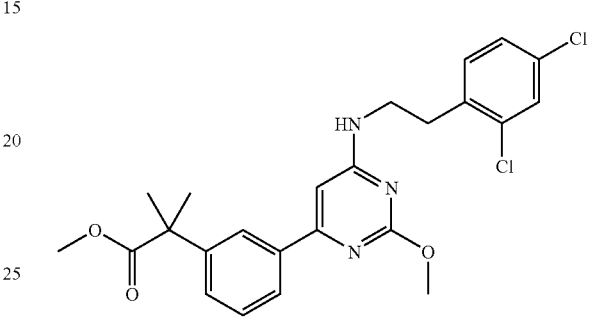

Hydrochloric acid (81.46 μL, 4M solution in 1,4-dioxane, 0.33 mmol) is added to a stirred solution of 2-(3-{6-[2-(2,4-dichloro-phenyl)-ethylamino]-2-methoxy-pyrimidin-4-yl}-phenyl)-2-methyl-propionic acid [100 mg, 0.22 mmol, Example 49(b)] in MeOH (8 mL), and the reaction mixture is stirred overnight at 65° C. The reaction is cooled to room temperature and concentrated in vacuo. The residue is purified by chromatography to afford 2-(3-{6-[2-(2,4-dichloro-phenyl)-ethylamino]-2-methoxy-pyrimidin-4-yl}-phenyl)-2-methyl-propionic acid methyl ester (34 mg, Example 79). LCMS: R$_T$=2.79 minutes; MS: 475 (M+H); $^1$H NMR (300 MHz, CDCl$_3$): □7.98 (1H, s), 7.88 (1H, b), 7.42 (3H, d, J=2 Hz), 7.2 (2H, s), 6.4 (1H, s), 5.08 (1H, b), 4.05 (3H, s), 3.7 (2H, b), 3.65 (3H, s), 3.1 (2H, t, J=2 Hz), 1.65 (6H, s).

Example 80

(a) 4-(3-{6-[2-(2,4-Dichloro-phenyl)-ethylamino]-2-methoxy-pyrimidin-4-yl}-phenyl)-tetrahydro-pyran-4-carboxylic acid

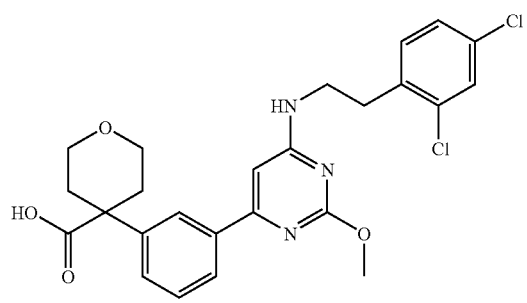

Step 1. Hydrogen chloride is bubbled through MeOH (80 mL) and the solution is stirred at 0° C. for 10 minutes. (3-bromo-phenyl)-acetic acid (30 g, 139.5 mmol) is added in portions and the reaction is stirred overnight, while warming to room temperature. The solution is concentrated in vacuo and the residue is dissolved in EtOAc (200 mL), washed with saturated aqueous sodium bicarbonate and brine, dried over sodium sulfate, filtered and concentrated in vacuo to afford (3-bromo-phenyl)-acetic acid methyl ester (32 g) used in the next step without further purification. MS: 230 (M+H); $^1$H NMR (300 MHz, CDCl$_3$): □7.45 (2H, m), 7.25 (2H, m), 3.72 (3H, s), 3.6 (2H, s).

Step 2. A solution of (3-bromo-phenyl)-acetic acid methyl ester (0.6 g, 2.62 mmol) in dry N,N'-dimethylformamide is added to a stirred suspension of sodium hydride (60% in mineral oil, 0.26 g, 6.55 mmol) in dry N,N'-dimethylformamide at 0° C. and stirring is continued for 20 minutes. A solution of bis(2-bromoethyl)ether (0.39 mL, 3.14 mmol) in N,N-dimethylformamide is added drop-wise and the reaction mixture is stirred overnight, while warming to room temperature. The reaction is quenched with water, extracted twice with ethyl acetate, the combined extracts is washed with brine and water, dried over sodium sulfate, filtered and concentrated in vacuo to afford 4-(3-bromo-phenyl)-tetrahydro-pyran-4-carboxylic acid methyl ester (610 mg) used in the next step without further purification. LCMS: R$_T$=2.81 minutes; MS: 299, 301 (M+H).

Step 3. Lithium hydroxide (0.21 g, 5.01 mmol) is added to a solution of 4-(3-bromo-phenyl)-tetrahydro-pyran-4-carboxylic acid methyl ester (0.5 g, 1.67 mmol) in methanol/water (8 mL, 3:1) and the reaction mixture is stirred for 5 hours at 65° C. The mixture is diluted with water and the volatiles are removed in vacuo. The aqueous is extracted once with diethyl ether, acidified to pH 2, and extracted twice with ethyl acetate. The combined extracts is dried over magnesium sulfate, filtered and concentrated in vacuo to afford 4-(3-bromo-phenyl)-tetrahydro-pyran-4-carboxylic acid (445 mg) sed in the next step without further purification. LCMS: R$_T$=1.9 minutes; MS: 283 (M−H).

Step 4. n-Butyllithium (2 M in pentane, 3.18 mL) is added to dry pentane (25 mL) at −78° C., under nitrogen atmosphere followed by drop-wise addition of a solution of 4-(3-bromo-phenyl)-tetrahydro-pyran-4-carboxylic acid (0.7 g, 2.45 mmol) in THF and the mixture is stirred at −78° C. for 2 hours. The reaction is quenched with tributyl borate (1.97 mL, 7.35 mmol) and stirring is continued for 1.5 hours, while warming to −20° C. The reaction is diluted with water and the volatiles are removed in vacuo. The aqueous is extracted once with diethyl ether, acidified to pH 2 (1 N HCl) and extracted twice with ethyl acetate. The combined extracts is dried over magnesium sulfate, filtered and concentrated in vacuo. The residue is dissolved in DCM (15 mL), heptane (200 mL) is added drop-wise and the mixture is stirred for 1.5 hours. The precipitate is suction filtered and air dried to afford 3-(4-tetrahydro-pyran-4-carboxylic acid)-phenylboronic acid (420 mg). LCMS: R$_T$=1.16 minutes; MS: 249 (M−H).

Step 5. Cs$_2$CO$_3$ solution (1.5 g, 4.6 mmol in 15 mL of water) is added to a stirred solution of (6-chloro-2-methoxy-pyrimidin-4-yl)-[2-(2,4-dichloro-phenyl)-ethyl]-amine (0.61 g, 1.84 mmol) and 3-(4-tetrahydro-pyran-4-carboxylic acid)-phenylboronic acid (0.6 g, 2.4 mmol) in 1,2-dimethoxyethane (45 mL). The mixture is degassed over nitrogen for 10 minutes, tetrakis(triphenylphosphine)palladium (0) (64 mg, 0.03 mmol) is added and the reaction mixture is refluxed at 90° C. overnight. The reaction is cooled to room temperature, diluted with water (150 mL), filtered over a pad of celite and the volatiles are removed in vacuo. The aqueous solution is slowly acidified (pH 4-5, 0.1N HCl) with vigorous stirring, which is continued for 2 hours. The formed precipitate is suction filtered and air dried to afford 4-(3-{6-[2-(2,4-dichloro-phenyl)-ethylamino]-2-methoxy-pyrimidin-4-yl}-phenyl)-tetrahydro-pyran-4-carboxylic acid [605 mg, Example 80(a)]. LCMS: Rt=2.26 minutes, MS: 502. 504 (M+H), H' NMR [300 MHz, (CD$_3$SO)$_2$SO]: □12.75 (1H, b) 8 (1H, s), 7.8 (1H, b), 7.55 (2H, b), 7.45 (2H, s), 7.35 (2H, s), 6.55 (1H, s), 3.85 (3H, s), 3.82 (2H, m), 3.5 (4H, m), 2.95 (2H, t, J=2 Hz), 2.4 (2H, m), 1.85 (2H, m). IC$_{50}$=0.05 nM (b) N-[4-(3-{6-[2-(2,4-Dichloro-phenyl)-ethylamino]-2-methoxy-pyrimidin-4-yl}-phenyl)-tetrahydro-pyran-4-carbonyl]-methanesulfonamide

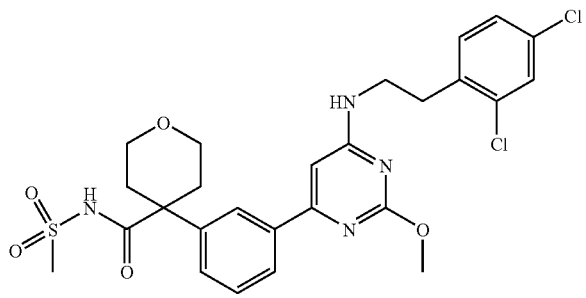

N-(3-dimethylaminopropyl)-N-ethylcarbodiimide hydrochloride (60.4 mg, 0.31 mmol) is added to a stirred ice cold solution of 4-(3-{6-[2-(2,4-dichloro-phenyl)-ethylamino]-2-methoxy-pyrimidin-4-yl}-phenyl)-tetrahydro-pyran-4-carboxylic acid [150 mg, 0.3 mmol, Example 80(a)], methanesulfonamide (30 mg, 0.31 mmol) and 4-dimethylaminopyridine (38.5 mg, 0.3 mmol) in dry DCM under nitrogen and the reaction mixture is stirred overnight, while warming to room temperature. The mixture is concentrated in vacuo, the residue is dissolved in ethyl acetate, washed with 0.1N HCl, brine and water, dried over sodium sulfate, filtered and concentrated in vacuo. The residue is purified by chromatography (SiO$_2$ packed column), eluting with ethyl acetate/heptane to afford N-[4-(3-{6-[2-(2,4-dichloro-phenyl)-ethylamino]-2-methoxy-pyrimidin-4-yl}-phenyl)-tetrahydro-pyran-4-carbonyl]-methanesulfonamide [65 mg, Example 80(b)]. LCMS: R$_T$=2.54 minutes; MS: 579, 581 (M+H); $^1$H NMR (300 MHz, CDCl$_3$): □8 (1H, s), 7.85 (1H, d, J=3.5 Hz), 7.45 (3H, m), 7.2 (2H, s), 6.4 (1H, s), 5.38 (1H, b), 4 (3H, s), 3.65-3.9 (6H, m), 3.2 (3H, s), 3.08 (2H, t, J=3.5 Hz), 2.45 (2H, b), 2.18 (2H, m). IC$_{50}$<1 nM (c) 4-(3-{-[2-(2,4-Dichloro-phenyl)-ethylamino]-2-methoxy-pyrimidin-4-yl}-phenyl)-tetrahydro-pyran-4-carboxylic acid ethyl ester

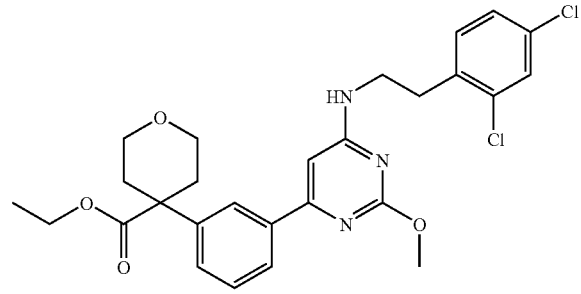

Hydrogen chloride (4 M in 1,4-dioxane, 20 μL, 0.08 mmol) is added to a solution of 4-(3-{6-[2-(2,4-dichloro-phenyl)-ethylamino]-2-methoxy-pyrimidin-4-yl}-phenyl)-tetrahydro-pyran-4-carboxylic acid [20 mg, 0.04 mmol, Example 80(a)] in ethyl alcohol (4 mL) and the reaction mixture is stirred overnight at 75° C. The reaction is cooled to room temperature, quenched with water, extracted twice with ethyl acetate. The combined extracts are dried over sodium sulfate, filtered and concentrated in vacuo. The residue is purified by chromatography (SiO₂ packed column), eluting with ethyl acetate/heptane to afford 4-(3-{6-[2-(2,4-dichloro-phenyl)-ethylamino]-2-methoxy-pyrimidin-4-yl}-phenyl)-tetrahydro-pyran-4-carboxylic acid ethyl ester [16 mg, Example 80(c)]. LCMS: $R_T$=2.74 minutes; MS: 530, 532 (M+H); $^1$H NMR (300 MHz, CDCl₃): □8.05 (1H, s), 7.9 (1H, d, J=3.5 Hz), 7.4-7.55 (3H, m), 7.2 (2H, s), 6.4 (1H, s), 5 (1H, b), 4.18 (2H, q, J=2 Hz), 4.05 (3H, s), 3.98 (2H, m), 3.75 (2H, b), 3.65 (2H, t, J=3.5 Hz), 3.1 (2H, t, J=2 Hz), 2.6 (2H, d, J=4 Hz), 2.1 (2H, m), 1.2 (3H, t, J=2 Hz). $IC_{50}$=223 nM Example 81

(a) (3-{6-[2-(2,4-Dichloro-phenyl)-ethylamino]-2-methoxy-pyrimidin-4-yl}-phenyl)-difluoro-acetic acid

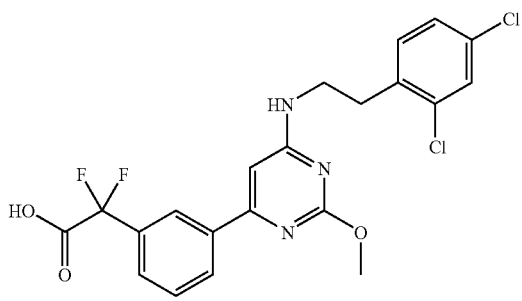

Step 1. By proceeding in a similar manner as Example 80(a), step 1, but substituting ethyl alcohol for methyl alcohol to afford (3-bromo-phenyl)-acetic acid ethyl ester. LCMS: $R_T$=1.82 minutes; MS: 243, 245 (M+H).

Step 2. Sodium bis(trimethylsilyl)-amide (1 M in THF, 27.14 mL, 27.14 mmol) is added drop-wise to (3-bromo-phenyl)-acetic acid ethyl ester (3 g, 12.34 mmol) in dry THF at −78° C. under nitrogen and the solution is stirred for 20 minutes. A solution of N-fluorobenzenesulfonimide (8.56 g, 27.14 mmol) in THF is added drop-wise and the reaction mixture is stirred at −78° C. for 3.5 hours. The reaction is quenched with HCl (0.02 N, 150 mL), extracted twice with DCM. The combined extracts are washed with water, dried over magnesium sulfate, filtered and concentrated in vacuo to afford (3-bromo-phenyl)-difluoro-acetic acid ethyl ester (2.7 g), which is used in the next step without further purification. LCMS: $R_T$=3.07 minutes; MS: 279, 281 (M+H); $^1$H NMR (300 MHz, CDCl₃): δ7.95 (1H, s), 7.65 (1H, d, J=3.5 Hz), 7.55 (1H, d, J=3.5 Hz), 7.35 (1H, t, J=3.5 Hz), 4.35 (2H, q, J=2.5 Hz), 1.32 (3H, t, J=2.5 Hz).

Step 3. Lithium hydroxide (0.13 g, 3.12 mmol) is added to a solution of (3-bromo-phenyl)-difluoro-acetic acid ethyl ester (0.29 g, 1.04 mmol) in methanol/water (8 mL, 3:1) and the reaction mixture is stirred overnight at room temperature. The mixture is diluted with water and volatiles are removed in vacuo. The aqueous is extracted once with diethyl ether, acidified to pH 2, and extracted twice with ethyl acetate. The combined extracts are dried over magnesium sulfate, filtered and concentrated in vacuo to afford (3-bromo-phenyl)-difluoro-acetic acid (250 mg), which is used in the next step without further purification. LCMS: $R_T$=2.26 minutes; MS: 249, 251(M−H).

Step 4. n-Butyllithium (2 M in pentane, 5.18 mL, 10.35 mmol) is added to dry pentane (30 mL) at −78° C. under nitrogen followed by drop-wise addition of a solution of (3-bromo-phenyl)-difluoro-acetic acid (1 g, 3.98 mmol) in THF and the mixture is stirred at −78° C. for 2 hours. The reaction is quenched with tributyl borate (3.2 mL, 11.94 mmol) and stirred for 1.5 hours, while warming to −20° C. The reaction is diluted with water and volatiles are removed in vacuo. The aqueous is extracted once with diethyl ether, acidified to pH 2 (1 N HCl) and extracted twice with ethyl acetate. The combined extracts are dried over magnesium sulfate, filtered and concentrated in vacuo. The residue is dissolved in DCM (15 mL), heptane (200 mL) is added drop-wise and the mixture is stirred for 1.5 hours. The precipitate is suction filtered and air dried to afford 3-(difluoro-acetic acid) phenyl boronic acid (310 mg). LCMS: $R_T$=0.68 minutes, MS: 215 (M−H).

Step 5. Cs₂CO₃ solution (0.41 g, 1.25 mmol in 4 mL of water) is added to a stirred solution of (6-chloro-2-methoxy-pyrimidin-4-yl)-[2-(2,4-dichloro-phenyl)-ethyl]-amine (0.17 g, 0.5 mmol) and 3-(difluoro-acetic acid)phenyl boronic acid (0.13 g, 0.6 mmol) in 1,2-dimethoxyethane (20 mL). The mixture is degassed over nitrogen for 10 minutes, tetrakis(triphenylphosphine)palladium (0) (23 mg, 0.02 mmol) is added and the reaction mixture is refluxed at 90° C. overnight. The reaction is cooled to room temperature, diluted with water (150 mL), filtered over a pad of celite and the volatiles removed it vacuo. The aqueous is slowly acidified (pH 4-5, 0.1 N HCl) and the mixture is stirred for 2 hours. The formed precipitate is suction filtered and air dried to afford (3-{6-[2-(2,4-dichloro-phenyl)-ethylamino]-2-methoxy-pyrimidin-4-yl}-phenyl)-difluoro-acetic acid [160 mg, Example 81(a)] LCMS: $R_T$=2.19 minutes; MS: 468, 470 (M+H); $^1$H NMR [300 MHz, (CD₃)₂SO]: □8.08 (2H, b), 7.7 (2H, m), 7.55 (1H, s), 7.35 (2H, s), 6.65 (1H, s), 3.92 (3H, s), 3.65 (2H, b), 3 (2H, t, J=2 Hz). $IC_{50}$=0.02 nM (b) Ethanesulfonic acid [2-(3-{6-[2-(2,4-dichloro-phenyl)-ethylamino]-2-methoxy-pyrimidin-4-yl}-phenyl)-2,2-difluoro-acetyl]-amide

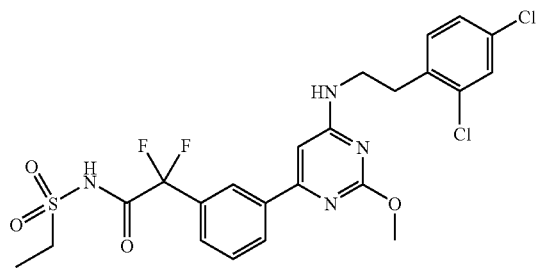

N-(3-dimethylaminopropyl)-N-ethylcarbodiimide hydrochloride (43 mg, 0.22 mmol) is added to a stirred ice cold solution of (3-{6-[2-(2,4-dichloro-phenyl)-ethylamino]-2-methoxy-pyrimidin-4-yl}-phenyl)-difluoro-acetic acid [100 mg, 0.21 mmol, Example 81 (a)], ethanesulfonamide (24.5 mg, 0.22 mmol) and 4-dimethylaminopyridine (26.1 mg, 0.21 mmol) in dry DCM under nitrogen. The reaction mixture is stirred at room temperature overnight at 60° C. The mixture is concentrated in vacuo, the residue is dissolved in ethyl acetate, washed with 0.1 N HCl, brine and water, dried over sodium sulfate, filtered and concentrated in vacuo. The residue is purified by chromatography to afford ethanesulfonic acid [2-(3-{6-[2-(2,4-dichloro-phenyl)-ethylamino]-2-methoxy-pyrimidin-4-yl}-phenyl)-2,2-difluoro-acetyl]-amide [35 mg, Example 81(b)]. LCMS: $R_T$=2.31 minutes; MS: 559, 561 (M+H); $^1$H NMR [300 MHz, CD$_3$OD]: □8.18 (1H, b), 8.05 (1H, b), 7.75 (1H, d, J=4 Hz), 7.5 (1H, t, J=4 Hz), 7.42 (1H, s), 7.28 (2H, q, J=4 Hz), 6.55 (1H, s), 3.95 (3H, s), 3.7 (2H, b), 3.18 (2H, q, J=4 Hz), 3.08 (2H, t, J=3.5 Hz), 1.15 (3H, t, J=4 Hz). IC$_{50}$=0.1 nM (c) (3-{6-[2-(2,4-Dichloro-phenyl)-ethylamino]-2-methoxy-pyrimidin-4-yl}-phenyl)-difluoro-acetic acid ethyl ester

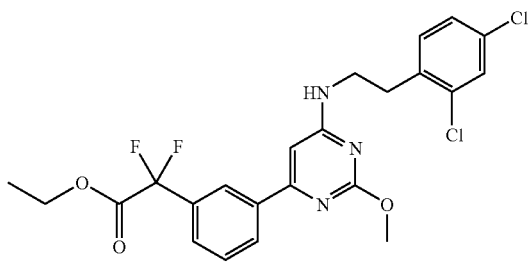

Hydrogen chloride (4 M in 1,4-dioxane, 52 μL, 2.1 mmol) is added to a solution of (3-{6-[2-(2,4-dichloro-phenyl)-ethylamino]-2-methoxy-pyrimidin-4-yl}-phenyl)-difluoro-acetic acid [65 mg, 0.14 mmol, Example 81(a)] in ethyl alcohol (6 mL) and the reaction mixture is stirred overnight at 65° C. The reaction is cooled to room temperature, quenched with water, extracted twice with ethyl acetate. The combined extracts are dried over sodium sulfate, filtered and concentrated in vacuo. The residue is purified by chromatography to afford (3-{6-[2-(2,4-dichloro-phenyl)-ethylamino]-2-methoxy-pyrimidin-4-yl}-phenyl)-difluoro-acetic acid ethyl ester [18 mg, Example 81(c)]. LCMS: $R_T$=3.19 minutes; MS: 496, 498 (M+H); $^1$H NMR [300 MHz, CDCl$_3$]: □8.18 (2H, d, J=3.5 Hz), 7.7 (1H, d, J=3.5 Hz), 7.55 (1H, t, J=3.5 Hz), 7.4 (1H, s), 7.42 (1H, s), 7.18 (2H, s), 6.45 (1H, s), 5.08 (1H, b), 4.3 (2H, q, J=4 Hz), 4.05 (3H, s), 3.72 (2H, b), 3.08 (2H, t, J=3.5 Hz), 1.3 (3H, t, J=4 Hz).

Example 82

(a) (3-{6-[2-(2,4-Dichloro-phenyl)-ethylamino]-2-methoxy-pyrimidin-4-yl}-phenyl)-acetonitrile

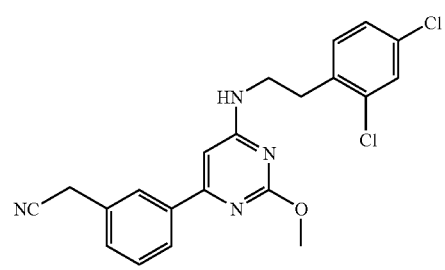

Cs$_2$CO$_3$ solution (1.63 g, 5 mmol in 4 mL of water) is added to a stirred solution of (6-chloro-2-methoxy-pyrimidin-4-yl)-[2-(2,4-dichloro-phenyl)-ethyl]-amine (0.66 g, 2 mmol) and cyanomethylphenyl boronic acid (0.68 g, 2.8 mmol) in 1,2-dimethoxyethane (8 mL). The mixture is degassed over nitrogen for 10 minutes, tetrakis(triphenylphosphine)palladium (0) (46 mg, 0.04 mmol) is added and the reaction mixture is refluxed at 90° C. overnight. The reaction is cooled to room temperature, diluted with water (100 mL) and stirred for 45 minutes. The formed precipitate is filtered. The solid is purified by chromatography (SiO$_2$ packed column), eluting with ethyl acetate/heptane to afford (3-{6-[2-(2,4-dichloro-phenyl)-ethylamino]-2-methoxy-pyrimidin-4-yl}-phenyl)-acetonitrile [585 mg, Example 82(a)]. LCMS: $R_T$=2.47 minutes; MS: 413,415 (M+H).

(b) (3-{6-[2-(2,4-Dichloro-phenyl)-ethylamino]-2-methoxy-pyrimidin-4-yl}-phenyl)-difluoro-acetonitrile

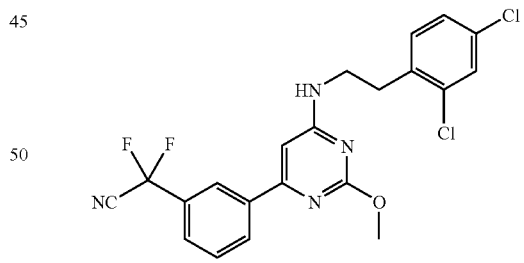

Sodium bis(trimethylsilyl)-amide (1 M in THF, 0.53 mL, 0.53 mmol) is added drop-wise to a stirred solution of (3-{6-[2-(2,4-dichloro-phenyl)-ethylamino]-2-methoxy-pyrimidin-4-yl}-phenyl)-acetonitrile (0.1 g, 0.24 mmol) in dry THF at −78° C. under nitrogen atmosphere and stirring continued for 20 minutes. A solution of N-fluorobenzenesulfonimide (0.17 g, 0.53 mmol) in THF is then added drop-wise and the reaction mixture is stirred at −78° C. for 3 hours. The reaction is diluted with water, extracted twice with ethyl acetate. The combined extracts are dried over sodium sulfate, filtered and concentrated in vacuo. The residue is purified by chromatography (SiO$_2$ packed column), eluting with ethyl acetate/heptane to afford (3-{6-[2-(2,4-dichloro-phenyl)-ethylamino]-2-methoxy-pyrimidin-4-yl}-phenyl)-difluoro-acetonitrile [15 mg, Example 82(b)]. LCMS: $R_T$=3.34 minutes; MS: 449, 451 (M+H).

(c) [2-(2,4-Dichloro-phenyl)-ethyl]-(6-{3-[difluoro-(1H-tetrazol-5-yl)-methyl]-phenyl)-2-methoxy-pyrimidin-4-yl}-amine

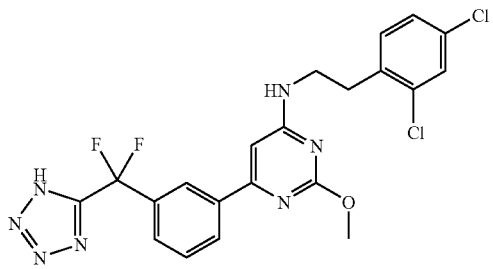

Sodium azide (10 mg, 0.15 mmol) is added to a stirred solution of (3-{6-[2-(2,4-dichloro-phenyl)-ethylamino]-2-methoxy-pyrimidin-4-yl}-phenyl)-difluoro-acetonitrile (50 mg, 0.11 mmol) in N,N'-dimethylformamide (4 mL) and the reaction is stirred for 4 hours at 80° C. The reaction is quenched with water, acidified to pH 2 (0.05 N HCl), extracted twice with ethyl acetate. The combined extracts is dried over sodium sulfate, filtered and concentrated in vacuo. The residue is diluted in toluene and concentrated in vacuo to afford [2-(2,4-dichloro-phenyl)-ethyl]-(6-{3-[difluoro-(1H-tetrazol-5-yl)-methyl]-phenyl}-2-methoxy-pyrimidin-4-yl)-amine [45 mg, Example 82(c)]. LCMS: $R_T$=2.29 minutes, LCMS: 492, 494 (M+H). IC$_{50}$=0.1 nM Example 83

(a) 2-{3-[6-(Indan-1-ylamino)-2-methoxy-pyrimidin-4-yl]-phenyl}-2-methyl-propionic acid

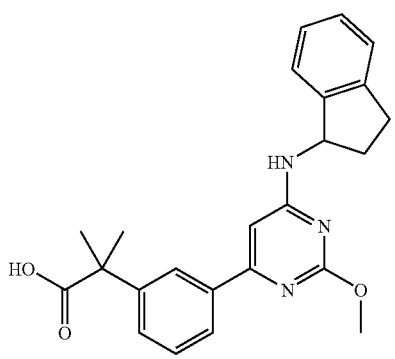

Step 1. A solution of 4,6-dichloro-2-methoxypyrimidine (1 g, 5.59 mmol), 2-aminoindan (0.72 mL, 5.59 mmol) and sodium bicarbonate (0.7 g, 8.38 mmol) in EtOH (25 mL) is refluxed overnight. The reaction is cooled to room temperature, quenched with water (100 mL) and stirred for one hour. The formed precipitate is suction filtered and air dried to afford (6-chloro-2-methoxy-pyrimidin-4-yl)-indan-1-yl-amine (1.5 g). LCMS: $R_T$=3.35 minutes, LCMS: 276, 278 (M+H).

Step 2. Cs$_2$CO$_3$ solution (0.32 g, 1 mmol, in 2 mL of water) is added to a stirred solution of (6-chloro-2-methoxy-pyrimidin-4-yl)-indan-1-yl-amine (0.11 g, 0.4 mmol) and 3-(2-methylpropionic acid)phenylboronic acid (0.1 g, 0.48 mmol) in 1,2-dimethoxyethane (8 mL). The mixture is degassed over nitrogen for 10 minutes, tetrakis(triphenylphosphine)palladium (0) (18.49 mg, 0.02 mmol) is added and the reaction mixture is refluxed overnight. The reaction is cooled to room temperature, diluted with water (60 mL), filtered over a pad of celite and the volatiles are removed in vacuo. The aqueous is acidified (pH 4-5, 0.1N HCl), extracted twice with ethyl acetate. The combined organic extracts are dried over magnesium sulfate, filtered and concentrated in vacuo. The residue is purified by chromatography (SiO$_2$ packed column), eluting with ethyl acetate/DCM to afford 2-{3-[6-(indan-1-ylamino)-2-methoxy-pyrimidin-4-yl]-phenyl}-2-methyl-propionic acid [74 mg, Example 83(a)]. LCMS: $R_T$=2.27 minutes; LCMS: 404 (M+H). IC$_{50}$=83 nM (b) 2-{3-[6-(Indan-2-ylamino)-2-methoxy-pyrimidin-4-yl]-phenyl}-2-methyl-propionic acid

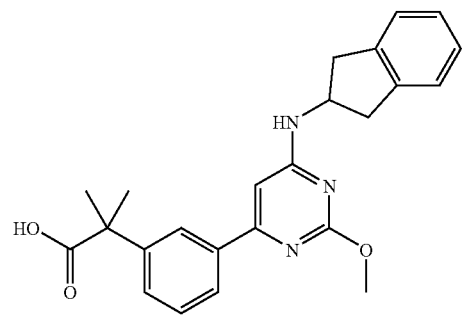

Step 1. By proceeding in a similar manner as on Example 83(a), step 1, but substituting 1-aminoindan for 2-aminoindan to afford (6-chloro-2-methoxy-pyrimidin-4-yl)-indan-2-yl-amine. LCMS: $R_T$=3.35 minutes; MS: 276, 278 (M+H).

Step 2. By proceeding in a similar manner as on Example 83(a), step 2, but substituting (6-chloro-2-methoxy-pyrimidin-4-yl)-indan-2-yl-amine for (6-chloro-2-methoxy-pyrimidin-4-yl)-indan-1-yl-amine to afford 2-{3-[6-(indan-2-ylamino)-2-methoxy-pyrimidin-4-yl]-phenyl}-2-methyl-propionic acid. LCMS: $R_T$=2.53 minutes, MS: 404 (M+H).

Example 84

(a) N-[4-(3-{2-Methoxy-6-[2-(4-trifluoromethoxy-phenyl)-ethylamino]-pyrimidin-4-yl}-phenyl)-tetrahydro-pyran-4-carbonyl]-methanesulfonamide

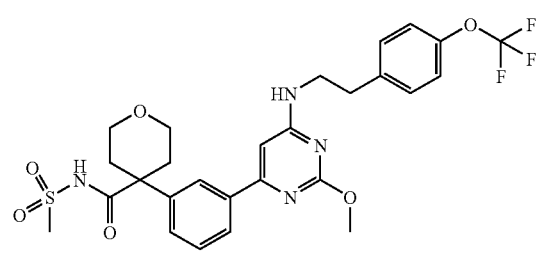

N-(3-dimethylaminopropyl)-N-ethylcarbodiimide hydrochloride (39 mg, 0.2 mmol) is added to a stirred ice cold solution of N-[4-(3-{2-methoxy-6-[2-(4-trifluoromethoxy-phenyl)-ethylamino]-pyrimidin-4-yl}-phenyl)-tetrahydro-pyran-4-carboxylic acid (100 mg, 0.19 mmol), methanesulfonamide (19.3 mg, 0.2 mmol) and 4-dimethylaminopyridine (23.6 mg, 0.19 mmol) in dry DCM under nitrogen. The reaction mixture is stirred overnight at room temperature and concentrated in vacuo. The residue is dissolved in ethyl acetate, washed with 0.1N HCl, brine and water, dried over sodium sulfate, filtered and concentrated in vacuo. The residue is purified by chromatography ($SiO_2$ packed column), eluting with ethyl acetate/heptane to afford N-[4-(3-{2-methoxy-6-[2-(4-trifluoromethoxy-phenyl)-ethylamino]-pyrimidin-4-yl}-phenyl)-tetrahydro-pyran-4-carbonyl]-methanesulfonamide [86 mg, Example 84(a)]. LCMS: $R_T$=2.52 minutes, LCMS: 595 (M+H). $IC_{50}$=0.7 nM (b) 4-(3-{2-Methoxy-6-[2-(4-trifluoromethoxy-phenyl)-ethylamino]-pyrimidin-4-yl}-phenyl)-tetrahydro-pyran-4-carboxylic acid methyl ester

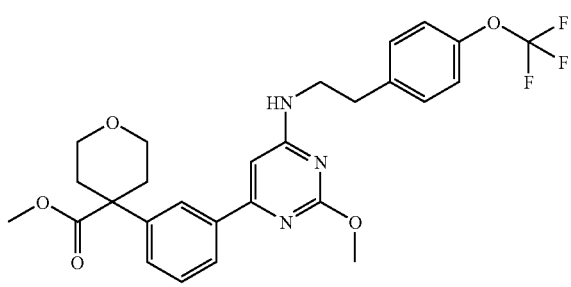

Hydrogen chloride (4 M in 1,4-dioxane, 43.5 µL, 0.17 mmol) is added to a solution of N-[4-(3-{2-methoxy-6-[2-(4-trifluoromethoxy-phenyl)-ethylamino]-pyrimidin-4-yl}-phenyl)-tetrahydro-pyran-4-carboxylic acid (45 mg, 0.09 mmol) in methyl alcohol (4 mL) and the reaction mixture is stirred overnight at 70° C. The reaction is cooled to room temperature, quenched with water. The volatiles are removed in vacuo. The aqueous is extracted twice with ethyl acetate. The combined extracts are dried over sodium sulfate, filtered and concentrated in vacuo. The residue is purified by chromatography ($SiO_2$ packed column), eluted with ethyl acetate/heptane to afford 4-(3-{2-methoxy-6-[2-(4-trifluoromethoxy-phenyl)-ethylamino]-pyrimidin-4-yl}-phenyl)-tetrahydro-pyran-4-carboxylic acid methyl ester [86 mg, Example 84(b)]. LCMS: $R_T$=2.48 minutes, MS: 532 (M+H). $IC_{50}$=70 nM Example 85

2-(3-{6-[2-(2,4-Dichloro-phenyl)-ethylamino]-2-methoxymethyl-pyrimidin-4-yl}-phenyl)-2-methyl-propionic acid

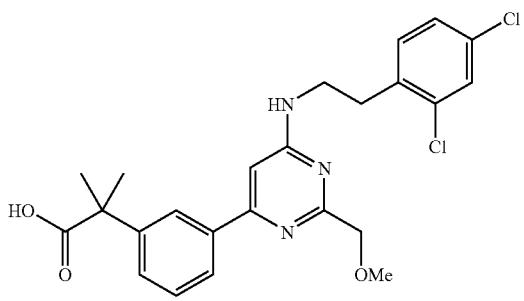

Step 1. Hydrochloric acid gas is bubbled through a solution of methoxyacetonitrile (26 g, 0.37 mol) in EtOH (22 mL) and diethyl ether (118 mL), which is chilled to −10° C. for twenty minutes. The reaction vessel is capped and stirred for 17 hours at ambient temperature. The mixture is cooled to −10° C. The solid that forms is collected by filtration, washed with diethyl ether and air dried to afford 2-methoxy-acetimidic acid ethyl ester hydrochloride (49.3 g, 87%) as a solid.

Step 2. Ammonia gas is bubbled through a solution of 2-methoxy-acetimidic acid ethyl ester hydrochloride (49.3 g, 0.32 mol) in EtOH (240 mL), which is chilled to −10° C. for twenty minutes. The reaction vessel is capped and stirred for 17 hours at ambient temperature. The mixture is concentrated in vacuo to afford 2-Methoxy-acetamidine hydrochloride (35 g, 88%) as a solid.

Step 3. To a solution of 2-methoxy-acetamidine hydrochloride (20.18 g, 0.16 mol) and diethylmalonate (24.6 mL, 0.16 mol) in EtOH (150 mL) is added 60% dispersion of sodium hydride in oil (14.3 g, 0.36 mol). The mixture is heated to reflux and stirred for 16 hours. The mixture is concentrated in vacuo and the residue is diluted with water (100 mL) and extracted with EtOAc (75 mL). The aqueous layer is acidified to pH 3 with HCl and extracted thrice with EtOAc (75 mL). The organic extracts from acidic solution are combined and dried over magnesium sulfate, filtered and concentrated to afford 2-methoxymethyl-pyrimidine-4,6-diol (20 g, 80%) as an oil.

Step 4. A solution of 2-methoxymethyl-pyrimidine-4,6-diol (2.3 g, 14.7 mmol), triethylamine (2.9 mL, 20.58 mmol), and phosphorous oxychloride (8.8 mL, 94.08 mmol) is heated to reflux for 1.5 hours. The mixture is concentrated in vacuo and the residue is poured onto ice (100 mL) and extracted three times with EtOAc (75 mL). The organic extracts are combined and dried over magnesium sulfate, filtered and concentrated to afford 4,6-dichloro-2-methoxymethyl-pyrimidine (2 g, 70%) as an oil.

Step 5. A solution of 4,6-dichloro-2-methoxymethyl-pyrimidine (250 mg, 1.3 mmol), 2-(2,4-dichloro-phenyl)-ethylamine (196 µL, 1.3 mmol), and sodium bicarbonate (218 mg, 2.6 mmol) in EtOH (5 mL) is heated at 80° C. for three hours and poured into water (20 mL) and extracted thrice with EtOAc (30 mL). The organic extracts are combined and dried over magnesium sulfate, filtered and evaporated. The residue is subjected to chromatography on silica gel eluting with 30% ethyl acetate:heptane to afford (6-chloro-2-methoxymethyl-pyrimidin-4-yl)-[2-(2,4-dichloro-phenyl)-ethyl]-amine (200 mg, 44%) as a solid.

Step 6. Argon is bubbled through a mixture of (6-chloro-2-methoxymethyl-pyrimidin-4-yl)-[2-(2,4-dichloro-phenyl)-ethyl]-amine (200 mg, 0.58 mmol), 3-(1-carboxy-1-methyl-ethyl)-phenyl boronic acid [266 mg, 1.28 mmol, see Example 49(b) step 2], $Cs_2CO_3$ (1.56 g, 2.52 mmol), and tetrakis(triphenylphosphine)palladium (0) (69 mg, 0.06 mmol) in ethylene glycol dimethyl ether (4 mL) and water (1 mL), for a period of 10 minutes. The reaction vessel is sealed and heated to 90° C. After stirring for 16 hours the mixture is diluted with water (40 mL) and extracted twice with EtOAc (25 mL). The organic extracts are combined and dried over magnesium sulfate, filtered and evaporated. The residue is subjected to chromatography on silica gel eluting with 40% ethyl acetate:heptane to afford 2-(3-{6-[2-(2,4-dichloro-phenyl)-ethylamino]-2-methoxymethyl-pyrimidin-4-yl}-phenyl)-2-methyl-propionic acid [165 mg, 60%, Example 85] as a solid. LCMS $R_T$=2.59 minutes, MS: 474 (M+H). $IC_{50}$=2.7 nM Example 86

2-(3-{6-[2-(2,4-Dichloro-phenyl)-ethylamino]-2-hydroxymethyl-pyrimidin-4-yl}-phenyl)-2-methyl-propionic acid

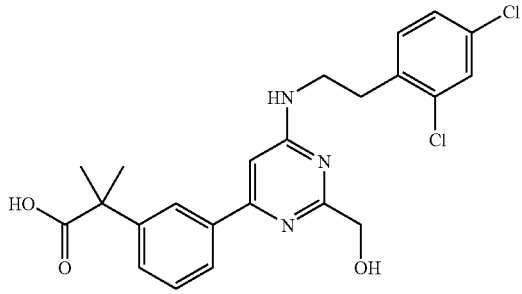

Step 1. A mixture of 4,6-dichloro-2-methylsulfanyl-pyrimidine (2.66 g, 13.6 mmol), 2-(2,4-dichloro-phenyl)-ethylamine (2.26 mL, 15 mmol) and sodium bicarbonate (2.29 g, 27.2 mmol) in EtOH (35 mL) is heated to 85° C. for 1 hour and poured into water (100 mL). The solid precipitate is collected by filtration and dissolved in hot EtOH (75 mL). After cooling overnight the crystals that formed are collected by filtration and dried to afford (6-chloro-2-methylsulfanyl-pyrimidin-4-yl)-[2-(2,4-dichloro-phenyl)-ethyl]-amine (3.43 g, 72%) as a solid.

Step 2. A mixture of (6-chloro-2-methylsulfanyl-pyrimidin-4-yl)-[2-(2,4-dichloro-phenyl)-ethyl]-amine (3.36 g, 9.64 mmol) in DCM (100 mL) is chilled to 0° C. and 70% 3-chloroperoxybenzoic acid (5.99 g, 24.29 mmol) is added portionwise. The mixture is stirred at 0° C. for 3 hours and warmed up to ambient temperature for 15 hours. The mixture is filtered to remove the precipitate and washed with DCM (100 mL). The filtrate is washed twice with 3N NaOH (40 mL), dried over magnesium sulfate, filtered and evaporated to afford (6-chloro-2-methanesulfonyl-pyrimidin-4-yl)-[2-(2,4-dichloro-phenyl)-ethyl]-amine (3.04 g, 83%) as a solid.

Step 3. A solution of (6-chloro-2-methanesulfonyl-pyrimidin-4-yl)-[2-(2,4-dichloro-phenyl)-ethyl]-amine (821 mg, 2.16 mmol) in THF (15 mL) is cooled to 0° C. A 1 M solution of vinyl magnesium bromide in THF (5.4 mL, 5.4 mmol) is added and the mixture is stirred for 30 minutes before adding water (30 mL) and extracted thrice with EtOAc (50 mL). The organic extracts are combined and dried over magnesium sulfate, filtered and evaporated. The residue is subjected to chromatography on silica gel eluting with 30% ethyl acetate: heptane to afford (6-chloro-2-vinyl-pyrimidin-4-yl)-[2-(2,4-dichloro-phenyl)-ethyl]-amine (600 mg) as a solid.

Step 4. To a solution of (6-chloro-2-vinyl-pyrimidin-4-yl)-[2-(2,4-dichloro-phenyl)-ethyl]-amine (240 mg, 0.73 mmol) in THF (2 mL), acetone (2 mL) and water (2 mL) is added 4-methylmorpholine N-oxide (342 mg, 2.92 mmol) followed by osmium tetroxide (153 μL, 0.015 mmol). After stirring the mixture at room temperature for 17 hours a solution of sodium bisulfite (728 mg, 7 mmol) in water (15 mL) is added and extracted twice with EtOAc (25 mL). The organic extracts are combined and dried over magnesium sulfate, filtered and concentrated to afford 1-{4-chloro-6-[2-(2,4-dichloro-phenyl)-ethylamino]-pyrimidin-2-yl}-ethane-1,2-diol (320 mg) as a solid.

Step 5. To a mixture of 1-{4-chloro-6-[2-(2,4-dichloro-phenyl)-ethylamino]-pyrimidin-2-yl}-ethane-1,2-diol (320 mg, 0.88 mmol) in MeOH (5 mL) and water (5 mL) is added sodium meta-periodate (567 mg, 2.65 mmol) and stirred for 16 hours before adding water (50 mL), and extracted thrice with EtOAc (30 mL). The organic extracts are combined and dried over magnesium sulfate, filtered and concentrated to afford 4-chloro-6-[2-(2,4-dichloro-phenyl)-ethylamino]-pyrimidine-2-carbaldehyde (270 mg, 93%) as a solid.

Step 6. To a solution of 4-chloro-6-[2-(2,4-dichloro-phenyl)-ethylamino]-pyrimidine-2-carbaldehyde (70 mg, 0.21 mmol) in MeOH (4 mL) is added sodium borohydride (24 mg, 0.63 mmol). The mixture is stirred for 4 hours at ambient temperature. Water (20 mL) is added and the mixture is extracted thrice with ethyl acetate (25 mL). The organic extracts are combined and dried over magnesium sulfate, filtered and concentrated to afford {4-chloro-6-[2-(2,4-dichloro-phenyl)-ethylamino]-pyrimidin-2-yl}-methanol (67 mg) as a solid.

Step 7. Argon is bubbled through a mixture of {4-chloro-6-[2-(2,4-dichloro-phenyl)-ethylamino]-pyrimidin-2-yl}-methanol (67 mg, 0.2 mmol), 3-(1-Carboxy-1-methyl-ethyl)-phenyl boronic acid [92 mg, 0.44 mmol, see Example 49(b) step 2], $Cs_2CO_3$ (197 mg, 0.6 mmol), and tetrakis(triphenylphosphine)palladium (0) (16.3 mg, 0.014 mmol) in ethylene glycol dimethyl ether (1.6 mL) and water (0.4 mL), for a period of 10 minutes. The reaction vessel is sealed and heated to 90° C. After stirring for 16 hours the mixture is diluted with water (25 mL), brought to pH 4 with HCl and extracted thrice with EtOAc (25 mL). The organic extracts are combined and dried over magnesium sulfate, filtered and concentrated to afford 2-(3-{6-[2-(2,4-dichloro-phenyl)-ethylamino]-2-hydroxymethyl-pyrimidin-4-yl}-phenyl)-2-methyl-propionic acid [16.5 mg, 18%, Example 86] as a solid. LCMS $R_T$=2.47 minutes, MS: 460 (M+H). $IC_{50}$=71 nM

Example 87

5-{6-[2-(2,4-Dichloro-phenyl)-ethylamino]-2-methoxy-pyrimidin-4-yl}-thiophene-2-carboxylic acid

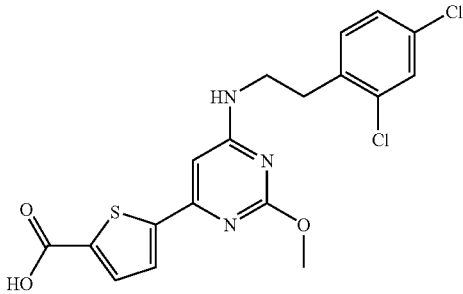

Step 1. 5-(Dihydroxyboryl)-2-thiophenecarboxylic acid (527 mg, 3.1 mmol) and 2,2-dimethyl-propane-1,3-diol (361 mg, 3.4 mmol) are stirred in THF (10 mL) for 19 hours and concentrated in vacuo to afford 5-(5,5-dimethyl-[1,3,2]dioxaborinan-2-yl)-thiophene-2-carboxylic acid (748 mg) as a solid. LCMS: $R_T$=1.15 minutes; $^1$H NMR [300 MHz, (CD$_3$)$_2$SO]: □13.15 (1H, s); 7.7 (1H, m); 7.45 (1H, m); 3.75 (4H, s); 0.95 (6H, s).

Step 2. A mixture of (6-chloro-2-methoxy-pyrimidin-4-yl)-[2-(2,4-dichloro-phenyl)-ethyl]-amine [277 mg, 0.83 mmol, Intermediate (44)], 5-(5,5-dimethyl-[1,3,2]dioxaborinan-2-yl)-thiophene-2-carboxylic acid (300 mg, 1.25 mmol), cesium fluoride (378 mg, 2.5 mmol) and tetrakis(triphenylphosphine) palladium (77 mg, 0.07 mmol) in water (2 mL) and ethylene glycol dimethyl ether (8 mL) is degassed with bubbling nitrogen for 5 minutes and is heated at 85° C. for 16 hours. The reaction mixture is cooled, diluted with water (150 mL) and brine (50 mL), and extracted three times with EtOAc (150 mL) and the extracts are concentrated in vacuo. The residue is subjected to flash column chromatography on silica (10 g) eluting with 0 to 15% MeOH in ethyl acetate. The product is triturated twice with heptanes (5 mL) and twice with ether (5 mL) and dried to afford 5-{6-[2-(2,4-dichloro-phenyl)-ethylamino]-2-methoxy-pyrimidin-4-yl}-thiophene-2-carboxylic acid (189 mg, Example 87) as a solid. MS: 424 (M+H); $^1$H NMR [300 MHz, (CD$_3$)$_2$SO]: δ 13.2 (1H, s); 7.7 (3H, m); 7.6 (1H, s); 7.35 (2H, s); 6.6 (1H, s); 4.85 (3H, s); 3.6 (2H, m); 3 (2H, t). IC$_{50}$=0.16 nM

Example 88

5-{2-Methoxy-6-[2-(4-trifluoromethoxy-phenyl)-ethylamino]-pyrimidin-4-yl}-2,3-dihydro-benzofuran-2-carboxylic acid hydrochloride

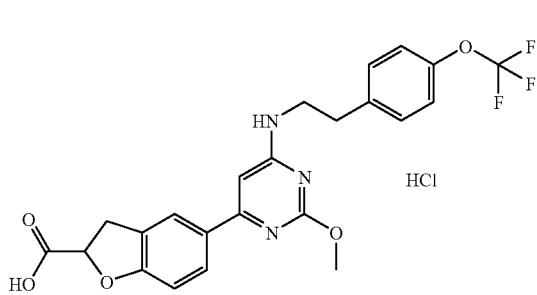

Step 1. To a solution of 2,3-dihydro-benzofuran-2-carboxylic acid (510 mg, 3.11 mmol) in glacial acetic acid (4 mL) is added bromine (497 mg, 3.11 mmol) dropwise. After 16 hours, the reaction is quenched with water (100 mL) and sodium bisulfite (1 g, 9.6 mmol) and extracted twice with EtOAc (100 mL). The extracts are concentrated in vacuo and dried under high vacuum to afford 5-bromo-2,3-dihydro-benzofuran-2-carboxylic acid (811 mg) as a solid. MS: 241 (M+H), $^1$H NMR [300 MHz, (CD$_3$)$_2$SO]: δ 13.05 (1H, s); 7.4 (1H, s); 7.25 (1H, d); 6.8 (1H, m); 5.25 (1H, q), 3.55 (1H, dd); 3.25 (1H, m).

Step 2. A mixture of 5-bromo-2,3-dihydro-benzofuran-2-carboxylic acid (0.74 g, 2.83 mmol), bis(pinacolato)diboron (1.51 g, 5.94 mmol), potassium acetate (1.47 g, 15 mmol), and 1,1'-bis(diphenylphosphino)ferrocene-palladium(II) dichloride DCM complex (115 mg, 0.14 mmol) in dimethylsulfoxide (10 mL) is degassed with bubbling nitrogen for 5 minutes. The mixture is heated to 90° C. for 16 hours. The reaction mixture is cooled, diluted with water (200 mL) and brine (25 mL), and filtered through Celite followed by water (200 mL) and EtOAc (200 mL). The filtrate is extracted twice with EtOAc (200 mL) and the extracts are concentrated in vacuo. The residue is subjected to flash column chromatography on silica (4 g) eluting with 80 to 100% EtOAc in heptane to afford 5-(4,4,5,5-tetramethyl-[1,3,2]dioxaborolan-2-yl)-2,3-dihydro-benzofuran-2-carboxylic acid (715 mg) as an oil. MS: 289 (M–H), $^1$H NMR [300 MHz, (CD$_3$)$_2$SO]: δ 13.05 (1H, s); 7.5 (2H, m); 6.8 (1H, m); 5.2 (1H, m); 3.6 (1H, m); 3.3 (1H, m); 1.05 (12H, s).

Step 3. A mixture of (6-chloro-2-methoxy-pyrimidin-4-yl)-[2(4-trifluoromethoxyphenyl)-ethyl]amine [475 mg, 1.36 mmol, Intermediate (13)], 5-(4,4,5,5-tetramethyl-[1,3,2]dioxaborolan-2-yl)-2,3-dihydro-benzofuran-2-carboxylic acid (266 mg, 0.91 mmol), Cs$_2$CO$_3$ (1.19 g, 3.6 mmol) and tetrakis(triphenylphosphine)palladium (146 mg, 0.13 mmol) in water (2 mL) and ethylene glycol dimethyl ether (8 mL) is degassed with bubbling nitrogen for 5 minutes and heated at 60° C. for 23 hours. The reaction mixture is cooled, diluted with water (200 mL) and brine (50 mL), and acidified with 1N hydrochloric acid to pH 5. The mixture is extracted three times with EtOAc (150 mL) and the extracts are concentrated in vacuo. The residue is subjected to flash column chromatography on silica (5 g) eluting with 0 to 20% MeOH in ethyl acetate. The product is dissolved in ether and treated with 1 M hydrogen chloride in ether to afford 5-{2-methoxy-6-[2-(4-trifluoromethoxy-phenyl)-ethylamino]-pyrimidin-4-yl}-2,3-dihydro-benzofuran-2-carboxylic acid hydrochloride (148 mg, Example 88) as a solid. MS: 476 (M+H); LCMS: $R_T$=2.78 minutes, MS: 474 (M–H). IC$_{50}$=3.1 nM

Example 89

2-(3-{6-[2-(2,4-Dichloro-phenyl)-ethylamino]-2-methoxy-pyrimidin-4-yl}-phenyl)-2-methyl-propionic acid 2,3-dihydroxy-propyl ester

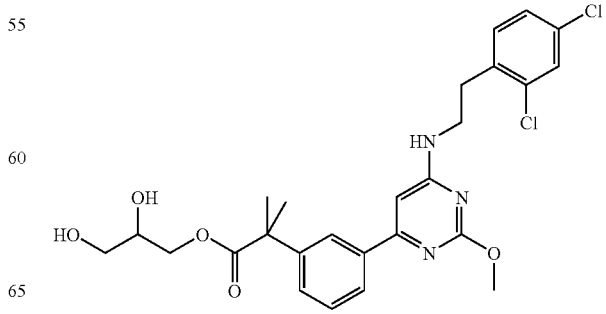

To a solution of 2-(3-{6-[2-(2,4-dichloro-phenyl)-ethylamino]-2-methoxy-pyrimidin-4-yl}-phenyl)-2-methyl-propionic acid [145 mg, 0.315 mmol, Example 49(b)] in N,N'-dimethylformamide (4 mL) is added (2,2-dimethyl-[1,3]dioxolan-4-yl)-methanol [62 mg, 0.472 mmol] and TBTU (151 mg, 0.472 mmol) followed by triethylamine (1 mL). The reaction mixture is stirred for 16 hours at ambient temperature, quenched with the addition of water (200 mL) and brine (25 mL) and extracted twice with EtOAc (200 mL). The extracts are concentrated in vacuo and the residue is stirred in MeOH (4 mL). 1 N hydrochloric acid is added (4 mL). After one hour the reaction is poured into water (150 mL) and extracted twice with EtOAc (150 mL). The extracts are concentrated and the residue is subjected to flash column chromatography on silica (4 g) eluting with 60 to 80% EtOAc in heptane to afford 2-(3-{6-[2-(2,4-dichloro-phenyl)-ethylamino]-2-methoxy-pyrimidin-4-yl}-phenyl)-2-methyl-propionic acid 2,3-dihydroxy-propyl ester (135 mg, Example 89) as an oil. MS: 534 (M+H), $^1$H NMR [300 MHz, (CD$_3$)$_2$SO]: δ 7.9 (1H, s); 7.8 (1H, s); 7.6 (2H, s); 7.45 (2H, m); 7.35 (2H, s); 6.6 (1H, s); 4.8 (1H, d); 4.55 (1H, t); 4.05 (1H, m); 3.9 (1H, m); 3.85 (3H, s); 3.6 (3H, m); 3.25 (2H, t); 2.95 (2H, t), 1.5 (6H, s). IC$_{50}$=18 nM Example 90

2-(3-{6-[(2,3-Dihydro-benzofuran-2-ylmethyl)-amino]-2-methoxy-pyrimidin-4-yl}-phenyl)-2-methyl-propionic acid

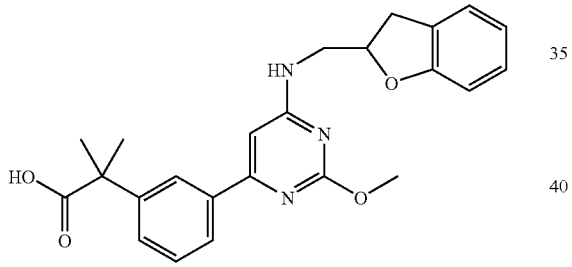

Step 1. To a mixture of (2,3-dihydro-benzofuran-2-yl)-methanol (1.65 g, 11 mmol), phthalimide (3.24 g, 22 mmol), and triphenylphosphine (5.77 g, 22 mmol) in THF (40 mL) is added diethyl azodicarboxylate (3.46 mL, 22 mmol) at −10° C., and the mixture is allowed to warm to room temperature. After 20 h at rt, the mixture is concentrated in vacuo, and the residue is chromatographed on SiO$_2$ (40% EtOAc in heptane) to afford 2-(2,3-dihydro-benzofuran-2-ylmethyl)-isoindole-1,3-dione (3.58 g). LCMS: R$_T$=2.64 minutes; MS: 280 (M+H).

Step 2. To a solution of 2-(2,3-dihydro-benzofuran-2-ylmethyl)-isoindole-1,3-dione (0.97 g, 3.47 mmol) in MeOH (15 mL) and CH$_2$Cl$_2$ (5 mL) is added hydrazine (0.55 mL, 17.4 mmol). After 20 h at rt, the mixture is filtered off and the filtrate is concentrated. The residue is diluted with water (50 mL), and extracted with CH$_2$Cl$_2$ (2×50 mL). The extracts are dried (MgSO$_4$), filtered, and concentrated to afford C-(2,3-dihydro-benzofuran-2-yl)-methylamine, which is used for a next step without further purification. LCMS: R$_T$=1.25 minutes; MS: 150 (M+H).

Step 3. A mixture of 4,6-dichloro-2-methoxy-pyrimidine (0.41 g, 2.3 mmol), C-(2,3-dihydro-benzofuran-2-yl)-methylamine (0.52 g, 3.47 mmol), and NaHCO$_3$ (0.97 g, 12 mmol) in EtOH (7 mL) is heated to reflux for 3 h. The mixture is diluted with water (8 mL), filtered, washed (water). The solid is dissolved in EtOAc, dried (MgSO$_4$), filtered, and concentrated in vacuo to afford (6-chloro-2-methoxy-pyrimidin-4-yl)-(2,3-dihydro-benzofuran-2-ylmethyl)-amine (0.5 g) as a solid. LCMS: R$_T$=2.59 minutes; MS: 292 (M+H).

Step 4. A mixture of (6-chloro-2-methoxy-pyrimidin-4-yl)-(2,3-dihydro-benzofuran-2-ylmethyl)-amine (167 mg, 0.57 mmol), 3-(1-carboxy-1-methyl-ethyl)-phenyl-boronic acid (155 mg, 0.75 mmol), and Cs$_2$CO$_3$ (0.46 g, 1.43 mmol) in ethylene glycol dimethyl ether (8 mL) and water (2 mL) is degassed by bubbling with Ar gas for 5 minutes, and treated with tetrakis(triphenylphosphine) palladium(0) (33 mg, 0.03 mmol) at room temperature. The mixture is heated at 85° C. for 3 h. The mixture is diluted with H$_2$O (20 mL), and extracted with EtOAc (10 mL). The aqueous layer is separated, acidified to pH 2.5 with 1M HCl solution, and extracted with EtOAc (2×10 mL). The extracts are dried (MgSO$_4$), filtered through a short pad of SiO$_2$ to afford 2-(3-{6-[(2,3-dihydro-benzofuran-2-ylmethyl)-amino]-2-methoxy-pyrimidin-4-yl}-phenyl)-2-methyl-propionic acid (139 mg, Example 90). LCMS: R$_T$=2.05 minutes; MS: 420 (M+H); $^1$H NMR (300 MHz, DMSO-d$_6$) □12.4 (1H, s), 8.05-7.8 (2H, m), 7.5-7.1 (5H, m), 6.8-6.75 (2H, m), 5 (1H, s), 4 (3H, brs), 3.65 (2H, brs), 3.4-2.95 (2H, m), 1.48 (6H, s).

Example 91

2-(3-{6-[(Isochroman-1-ylmethyl)-amino]-2-methoxy-pyrimidin-4-yl}-phenyl)-2-methyl-propionic acid

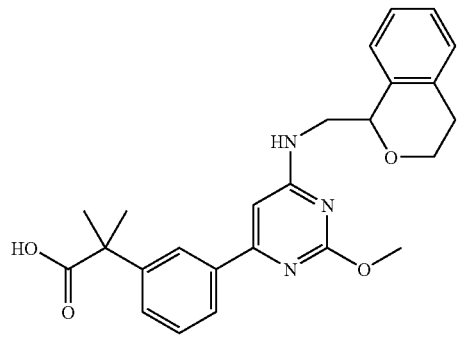

Step 1: A mixture of 4,6-dichloro-2-methoxy-pyrimidine (0.45 g, 2.5 mmol), C-isochroman-1-yl-methylamine (0.53 g, 3.2 mmol), and NaHCO$_3$ (0.63 g, 7.5 mmol) in EtOH (5 mL) is heated to reflux for 4 h. The mixture is diluted with water, concentrated in vacuo. The residue is partitioned between EtOAc and water, and extracted with EtOAc. The extracts are dried (Na$_2$SO$_4$), and concentrated to afford (6-chloro-2-methoxy-pyrimidin-4-yl)-isochroman-1-ylmethyl-amine (0.84 g). LCMS: R$_T$=2.94 minutes; MS: 306 (M+H).

Step 2. A mixture of (6-chloro-2-methoxy-pyrimidin-4-yl)-isochroman-1-ylmethyl-amine (141 mg, 0.46 mmol), 3-(1-carboxy-1-methyl-ethyl)-phenyl-boronic acid (125 mg, 0.6 mmol), and Cs$_2$CO$_3$ (0.37 g, 1.15 mmol) in ethylene glycol dimethyl ether (8 mL) and water (2 mL) is degassed by bubbling with Ar gas for 5 minutes, and treated with tetrakis (triphenylphosphine)palladium(0) (27 mg, 0.023 mmol) at room temperature. The mixture is heated at 85° C. for 3 h. The mixture is diluted with H$_2$O (20 mL), and extracted with EtOAc (20 mL). The aqueous layer is separated, acidified to pH 2.5 with 1M HCl solution, and extracted with EtOAc (2×30 mL). The extracts are dried (MgSO$_4$), filtered through a short pad of SiO$_2$ to afford 2-(3-{6-[(isochroman-1-ylmethyl)-amino]-2-methoxy-pyrimidin-4-yl}-phenyl)-2-methyl-propionic acid (189 mg, Example 91). LCMS: R$_T$=2.03 minutes; MS: 434 (M+H); $^1$H NMR (300 MHz, CDCl$_3$) □9.8 (1H, s), 8.02 (1H, s), 7.82 (1H, d, J=6 Hz), 7.5-7.1 (6H, m), 6.43 (1H, s) 5(1H), 4 (3H, s), 3.85-3.75 (1H, m), 3.65-3.55 (1H, m), 3.04-2.95 (1H, m), 2.75 (1H), 1.8 (6H, s). IC$_{50}$=23 nM

Example 92

2-(3-{2-Methoxy-6-[(4-methyl-3,4-dihydro-2H-benzo[1,4]oxazin-2-ylmethyl)-amino]-pyrimidin-4-yl}-phenyl)-2-methyl-propionic acid

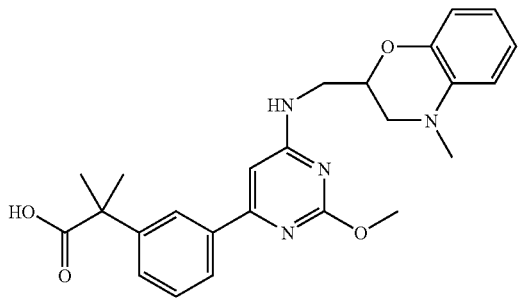

Step 1. A mixture of 4,6-dichloro-2-methoxy-pyrimidine (0.27 g, 1.48 mmol), C-(4-methyl-3,4-dihydro-2H-benzo[1,4]oxazin-2-yl)-methylamine (0.22 g, 1.23 mmol), and NaHCO$_3$ (0.62 g, 7.4 mmol) in EtOH (7 mL) is heated to reflux for 5 h. The mixture is concentrated in vacuo. The residue is partitioned between EtOAc and water, and extracted with EtOAc. The extracts are dried (Na$_2$SO$_4$), and concentrated to afford (6-chloro-2-methoxy-pyrimidin-4-yl)-(4-methyl-3,4-dihydro-2H-benzo[1,4]oxazin-2-ylmethyl)-amine (0.39 g). LCMS: R$_T$=3.27 minutes; MS: 321 (M+H).

Step 2. A mixture of (6-chloro-2-methoxy-pyrimidin-4-yl)-(4-methyl-3,4-dihydro-2H-benzo[1,4]oxazin-2-ylmethyl)-amine (200 mg, 0.62 mmol), 3-(1-carboxy-1-methyl-ethyl)-phenyl-boronic acid (190 mg, 0.94 mmol), and Cs$_2$CO$_3$ (0.51 g, 1.6 mmol) in ethylene glycol dimethyl ether (10 mL) and water (2 mL) is degassed by bubbling with Ar gas for 5 minutes, and treated with tetrakis(triphenylphosphine)palladium(0) (36 mg, 0.03 mmol) at room temperature. The mixture is heated at 85° C. for 6 h. The mixture is diluted with H$_2$O (20 mL), and extracted with EtOAc (20 mL). The aqueous layer is separated, acidified to pH 3 with 1M HCl solution, and extracted with EtOAc (2×30 mL). The extracts are dried (MgSO$_4$), filtered, and concentrated. The residue is chromatographed on SiO$_2$ (70% EtOAc in heptane) to afford 2-(3-{2-methoxy-6-[(4-methyl-3,4-dihydro-2H-benzo[1,4]oxazin-2-ylmethyl)-amino]-pyrimidin-4-yl}-phenyl)-2-methyl-propionic acid (190 mg, Example 92). LCMS: R$_T$=2.59 minutes; MS: 449 (M+H). IC$_{50}$=278 nM

Example 93

2-(3-{6-[(Benzofuran-5-ylmethyl)-amino]-2-methoxy-pyrimidin-4-yl}-phenyl)-2-methyl-propionic acid

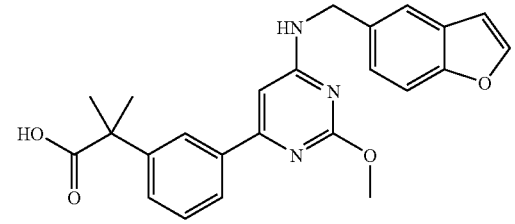

Step 1. By proceeding in a similar manner to that described in Example 1, Step 3, but substituting C-benzofuran-5-yl-methylamine for 2-(3-fluoro-4-methoxy-phenyl)-ethylamine there is prepared benzofuran-5-ylmethyl-(6-chloro-2-methoxy-pyrimidin-4-yl)-amine.

Step 2. Argon is bubbled through a mixture of benzofuran-5-ylmethyl-(6-chloro-2-methyoxy-pyrimidin-4-yl)-amine (100 mg, 0.35 mmol), 3-(1-carboxy-1-methyl-ethyl)-phenyl boronic acid [131 mg, 0.63 mmol, see Example 49(b) step 2], Cs$_2$CO$_3$ (342 mg, 1.05 mmol), and tetrakis(triphenylphosphine)palladium (0) (46 mg, 0.04 mmol) in ethylene glycol dimethyl ether (1.7 mL) and water (0.3 mL), for a period of 10 minutes. The reaction vessel is sealed and heated to 90° C. After stirring for 6 hours the heating is turned off and the mixture is allowed to cool to ambient temperature upon standing for 24 hours. The mixture is diluted with water (20 mL) and extracted twice with EtOAc (30 μL). The organic extracts are combined and dried over magnesium sulfate, filtered and concentrated to afford 2-(3-{6-[(benzofuran-5-ylmethyl)-amino]-2-methyoxy-pyrimidin-4-yl}-phenyl)-2-methyl-propionic acid [50 mg, 34%, Example 93] as a solid. LCMS R$_T$=2.05 minutes, MS: 418 (M+H).

Example 94

N-(6-{6-[2-(2,4-Dichloro-phenyl)-ethylamino]-2-methoxy-pyrimidin-4-yl}-benzothiazol-2-yl)-acetamide

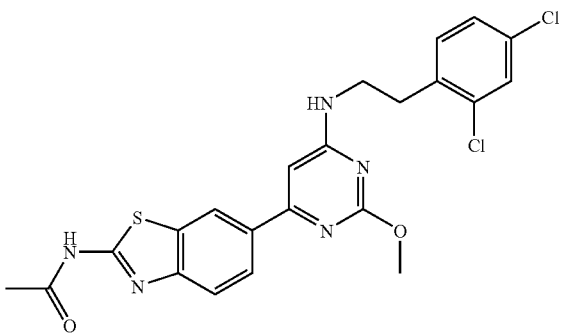

Step 1: To a solution of 2-amino-6-bromobenzothiazole (10 g, 43.65 mmol) and triethylamine (12.2 mL, 87.3 mmol) and N,N-dimethylaminopyridine (269 mg) in THF (100 mL) is added acetyl chloride (4.7 mL). After stirring for 17 hours water (100 mL) is added and the mixture is extracted twice with EtOAc (75 mL). The organic extracts are combined and dried over magnesium sulfate, filtered and concentrated to afford N-(6-bromo-benzothiazol-2-yl)-acetamide (8.79 g, 74%) as a solid.

Step 2: Argon is bubbled through a mixture of N-(6-bromo-benzothiazol-2-yl)-acetamide (5 g, 0.018 mol), bis(pinacolato)diboron (9.6 g, 0.038 mol), potassium acetate (9.3 g, 0.095 mol), and 1,1'-bis(diphenylphosphino)ferrocene-palladium (II)dichloride (816 mg, 1 mmol) in dimethylsulfoxide (60 mL) for a period of 10 minutes. The reaction vessel is sealed and heated to 90° C. After stirring for 18 hours the mixture is diluted with water (200 mL) and extracted twice with EtOAc (100 mL). The organic extracts are combined and dried over magnesium sulfate, filtered and evaporated. The residue is subjected to chromatography on silica gel eluting with 70% ethyl acetate:heptane to afford N-[6-(4,4,5,5-tetramethyl-[1,3,2]dioxaborolan-2-yl)-benzothiazol-2-yl]-acetamide (5.06 g, 88.3%) as a solid.

Step 3: Argon is bubbled through a mixture of N-[6-(4,4,5,5-tetramethyl-[1,3,2]dioxaborolan-2-yl)-benzothiazol-2-yl]-acetamide (1.12 g, 3.52 mmol), 2-methoxy-4,6-dichloro-pyrimidine (700 mg, 3.91 mmol), Na₂CO₃ (625 mg, 5.9 mmol), and bis(triphenylphosphine)palladium(II) chloride (280 mg, 0.4 mmol), in dimethoxyethane (8 mL), water (3.4 mL) and EtOH (2.2 mL) for 10 minutes. The mixture is irradiated by microwave at 160° C. for 10 minutes added water (20 mL) and extracted with EtOAc (40 mL). The organic extracts are combined and dried over magnesium sulfate, filtered and concentrated to afford N-[6-(6-chloro-2-methoxy-pyrimidin-4-yl)-benzothiazol-2-yl]-acetamide (160 mg) as a solid.

Step 4: A mixture of N-[6-(6-chloro-2-methoxy-pyrimidin-4-yl)-benzothiazol-2-yl]-acetamide (160 mg, 0.48 mmol), 2-(2,4-dichloro-phenyl)-ethylamine (362 µL, 2.4 mmol), and K₂CO₃ (359 mg, 2.6 mmol) in N-methylpyrrolidinone (2.6 mL) is heated to 140° C. Water (20 mL) is added after 1 hour of heating and extracted with EtOAc (20 mL). The organic extracts are combined and dried over magnesium sulfate, filtered and evaporated. This residue is subjected to chromatography on silica gel eluting with 90% ethyl acetate: heptane to afford a solid which is triturated with 1:1 methanol:ethyl acetate. The solid is collected to afford N-(6-{6-[2-(2,4-dichloro-phenyl)-ethylamino]-2-methoxy-pyrimidin-4-yl}-benzothiazol-2-yl)-acetamide [31 mg, 13%, Example 94]. LCMS R$_T$=2.49 minutes, MS: 488 (M+H). IC$_{50}$=11 nM Example 95

(a) Ethanesulfonic acid [2-(3-{6-[2-(2,4-dichloro-phenyl)-ethylamino]-2-methoxy-pyrimidin-4-yl}-phenyl)-2-methyl-propionyl]-amide

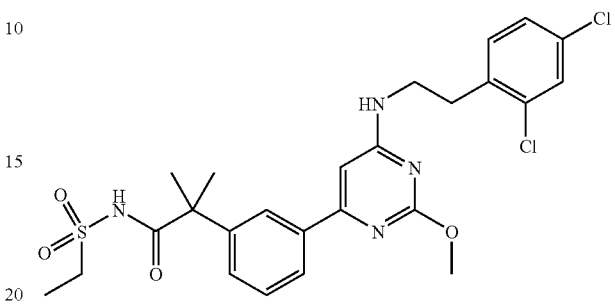

N-(3-dimethylaminopropyl)-N-ethylcarbodimide hydrochloride (44 mg, 0.23 mmol) is added to a stirred ice cold solution of 2-(3-{6-[2-(2,4-dichloro-phenyl)-ethylamino]-2-methoxy-pyrimidin-4-yl}-phenyl)-2-methyl-propionic acid (100 mg, 0.22 mmol), ethanesulfonamide (25 mg, 0.23 mmol) and 4-Dimethylaminopyridine (27 mg, 0.22 mmol) in dry DCM under nitrogen atmosphere. The ice bath is removed and the reaction mixture is stirred overnight at 60° C. The volatiles are removed under reduced pressure, the residue is dissolved in ethyl acetate, washed with 0.1 N HCl, brine and water, dried over sodium sulfate, filtered and concentrated under reduced pressure. The crude residue is purified by chromatography (SiO₂ packed column), eluting with EtOAc/DCM to afford ethanesulfonic acid [2-(3-{6-[2-(2,4-dichloro-phenyl)-ethylamino]-2-methoxy-pyrimidin-4-yl}-phenyl)-2-methyl-propionyl]-amide [67 mg, Example 95(a)]. LCMS: R$_T$=2.49 minutes, MS: 551, 553 (M+H).

(b) N-[2-(3-{6-[2-(2,4-Dichloro-phenyl)-ethylamino]-2-methoxy-pyrimidin-4-yl}-phenyl)-2-methyl-propionyl]-C-phenyl-methanesulfonamide

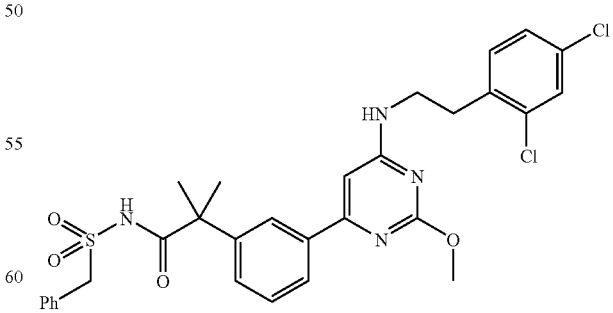

By proceeding in a similar manner as Example 95(a), but substituting phenyl-methanesulfonamide for ethanesulfonamide to afford N-[2-(3-{6-[2-(2,4-dichloro-phenyl)-ethylamino]-2-methoxy-pyrimidin-4-yl}-phenyl)-2-methyl-propionyl]-C-phenyl-methanesulfonamide [105 mg, Example 95(b)]LCMS: $R_T$=2.83 minutes, MS: 613, 615 (M+H). $IC_{50}$=2 nM (c) 2-(3-{6-[2-(2,4-Dichloro-phenyl)-ethylamino]-2-methoxy-pyrimidin-4-yl}-phenyl)-2-methyl-1-morpholin-4-yl-propan-1-one

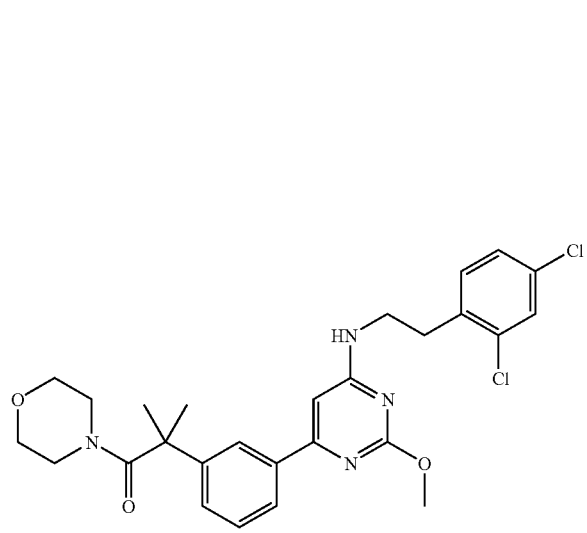

By proceeding in a similar manner as Example 95(a), but substituting morpholine for ethanesulfonamide to afford 2-(3-{6-[2-(2,4-dichloro-phenyl)-ethylamino]-2-methoxy-pyrimidin-4-yl}-phenyl)-2-methyl-1-morpholin-4-yl-propan-1-one [93 mg, Example 95(c)]. LCMS: $R_T$=2.35 minutes, MS: 529, 531 (M+H). $IC_{50}$=281 nM (d) 2-(3-{6-[2-(2,4-Dichloro-phenyl)-ethylamino]-2-methoxy-pyrimidin-4-yl}-phenyl)-N-(tetrahydro-pyran-4-yl)-isobutyramide

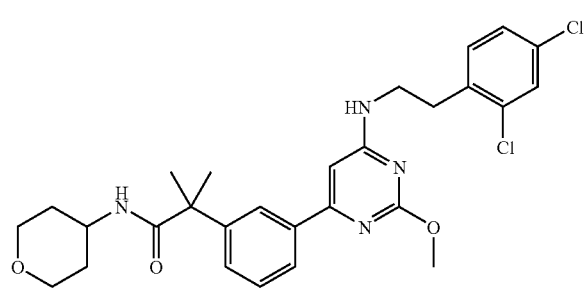

By proceeding in a similar manner as Example 95(a), but substituting tetrahydro-pyran-4-ylamine for ethanesulfonamide to afford 2-(3-{6-[2-(2,4-dichloro-phenyl)-ethylamino]-2-methoxy-pyrimidin-4-yl}-phenyl)-N-(tetrahydro-pyran-4-yl)-isobutyramide [55 mg, Example 95(d)]. LCMS: $R_T$=2.3 minutes, MS: 543, 545 (M+H). $IC_{50}$=278 nM (e) 2-(3-{6-[2-(2,4-Dichloro-phenyl)-ethylamino]-2-methoxy-pyrimidin-4-yl}-phenyl)-N-(1H-tetrazol-5-yl)-isobutyramide

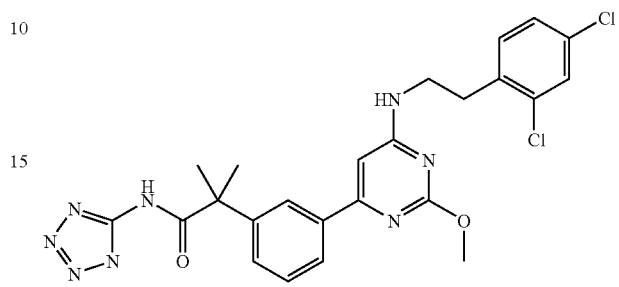

By proceeding in a similar manner as Example 95(a), but substituting 1H-tetrazol-5-ylamine for ethanesulfonamide to afford 2-(3-{6-[2-(2,4-Dichloro-phenyl)-ethylamino]-2-methoxy-pyrimidin-4-yl}-phenyl)-N-(1H-tetrazol-5-yl)-isobutyramide [106 mg, Example 95(e)]. LCMS: $R_T$=2.02 minutes, MS: 527, 529 (M+H). $IC_{50}$<1 nM Example 96

[2-(2,4-Dichloro-phenyl)-ethyl]-{2-methoxy-6-[3-(2H-tetrazol-5-yl)-piperidin 1-yl]-pyrimidin-4-yl}-amine

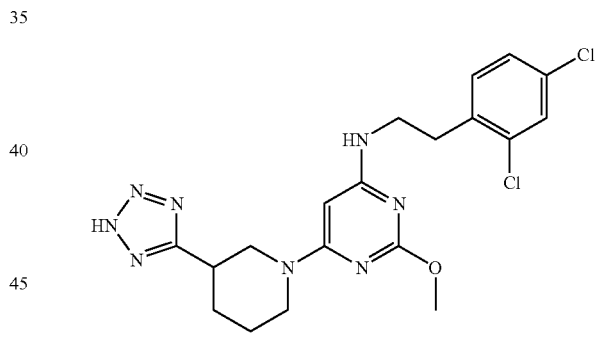

Step 1. To a mixture of 3-cyano-piperidine-1-carboxylic acid benzyl ester (1 g, 4.1 mmol), and dibutyltinoxide (153 mg, 0.6 mmol) in toluene (8 mL) is added trimethylsilylazide (1.1 mL, 8.2 mmol) at room temperature. After the mixture is heated at 95° C. for 15 h, more trimethylsilylazide (2 mL, 15 mmol) is added and the stirring is continued for 6 h at 95° C. The mixture is concentrated, and the resulting solid is triturated with heptane (30 mL) and filtered to afford 3-(1H-tetrazol-5-yl)-piperidine-1-carboxylic acid benzyl ester (1 g). LCMS: $R_T$=2.31 minutes, MS: 288 (M+H).

Step 2. To a solution of 3-(1H-tetrazol-5-yl)-piperidine-1-carboxylic acid benzyl ester (1 g, 3.5 mmol) in MeOH (20 mL) is added Pd on carbon (10%, 150 mg) at room temperature. The mixture is charged with Ar gas a few times before attaching a hydrogen gas balloon. After 30 h at 20° C., the mixture is filtered, and concentrated to afford 3-(1H-tetrazol-5-yl)-piperidine. LCMS: $R_T$=0.54 minutes, MS: 154 (M+H).

Step 3: A mixture of (6-chloro-2-methoxy-pyrimidin-4-yl)-[2-(2,4-dichloro-phenyl)-ethyl]-amine [300 mg, 0.9 mmol], 3-(1H-tetrazol-5-yl)-piperidine [383 mg, 2.25 mmol] and K$_2$CO$_3$ (373 mg, 2.7 mmol) in N-methylpyrollidinone (5 mL) is heated at 140° C. for 16 hours. The mixture is diluted with water (50 mL), acidified to pH 3 with 10% HCl and extracted three times with EtOAc (40 mL). The organic extracts from the acidic layer are combined and dried over magnesium sulfate, filtered and concentrated. The residue is subjected to chromatography on silica gel eluting with 15% ethyl methanol:DCM to afford an oil which is diluted with water (20 mL). A solid is formed and collected by filtration to afford [2-(2,4-dichloro-phenyl)-ethyl]-{2-methoxy-6-[3-(2H-tetrazol-5-yl)-piperidin-1-yl]-pyrimidin-4-yl}-amine [303 mg, 75%, Example 96] as a solid. LCMS: R$_T$=1.95 minutes, MS: 449 (M+H). IC$_{50}$=5 nM Example 97

1-{6-[2-(2,4-Dichloro-phenyl)-ethylamino]-2-methoxy-pyrimidin-4-yl}-piperidine-4-carboxylic acid

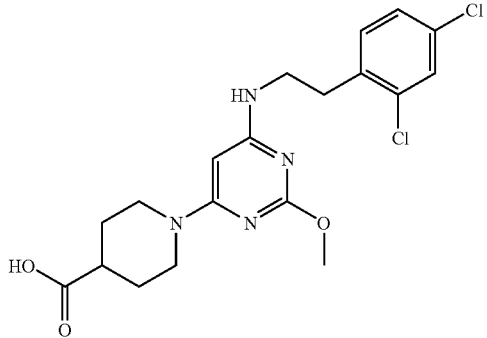

Step 1: A mixture of 2-methoxy-3,6-dichloropyrimidine (635 mg, 3.55 mmol), isonipecotic hydrochloride (706 mg, 4.26 mmol) and sodium bicarbonate (895 mg, 10.65 mmol) in EtOH (12 mL) is heated at 90° C. for 15 hours. The mixture is concentrated, and the residue is taken up in water (30 mL) and extracted three times with EtOAc (25 mL). The aqueous solution is acidified to pH 3 with 10% citric acid and extracted three times with EtOAc (25 mL). The organic extracts from the acidic layer are combined and dried over magnesium sulfate, filtered and concentrated to afford 1-(6-chloro-2-methoxy-pyrimidin-4-yl)-piperidine-4-carboxylic acid [680 mg, 70%] as a solid.

Step 2: To a solution of 1-(6-chloro-2-methoxy-pyrimidin-4-yl)-piperidine-4-carboxylic acid [131 mg, 0.48 mmol] in MeOH (1 mL) and toluene (1 mL) is added a solution of 2 M diazomethane in diethylether (0.48 mL, 0.96 mmol). The solution is stirred for 2 h at ambient temperature and concentrated. The residue is subjected to chromatography on silica gel eluting with 40% ethyl acetate:heptane to afford 1-(6-chloro-2-methoxy-pyrimidin-4-yl)-piperidine-4-carboxylic acid methyl ester [103 mg, 75%] as a solid.

Step 3: In a tube is combined 1-(6-chloro-2-methoxy-pyrimidin-4-yl)-piperidine-4-carboxylic acid methyl ester [103 mg, 0.36 mmol], 2-(2,4-dichloro-phenyl)-ethylamine (0.163 mL, 1.08 mmol), sodium bicarbonate (181 mg, 2.16 mmol) and N-methylpyrrolidinone (2 mL). The mixture is heated at 140° C. for 12 h. Additional 2-(2,4-dichloro-phenyl)-ethylamine (0.2 mL, 1.33 mmol) is added and heating at 140° C. is continued for another 12 h. The mixture is diluted with water (30 mL) and extracted twice with EtOAc (30 mL). The organic extracts are washed twice with water (40 mL) and once with brine (30 mL), combined, dried over magnesium sulfate, filtered and concentrated. The residue is subjected to chromatography on silica gel eluting with 40% ethyl acetate:heptane to afford 1-{6-[2-(2,4-dichloro-phenyl)-ethylamino]-2-methoxy-pyrimidin-4-yl}-piperidine-4-carboxylic acid methyl ester [70 mg, 44%] as a solid.

Step 4: A solution of 1-{6-[2-(2,4-dichloro-phenyl)-ethylamino]-2-methoxy-pyrimidin-4-yl}-piperidine-4-carboxylic acid methyl ester [70 mg, 0.16 mmol] and a 2 M solution of lithium hydroxide (1 mL, 2 mmol) in MeOH (1 mL) and THF (1 mL) is stirred at ambient temperature for 15 hours. The mixture is concentrated, and the residue is taken up with water, acidified to pH 2 with the addition of 10% HCl and extracted twice with EtOAc (20 mL). The organic extracts from the acidic layer are combined and dried over magnesium sulfate, filtered and concentrated to afford 1-{6-[2-(2,4-dichloro-phenyl)-ethylamino]-2-methoxy-pyrimidin-4-yl}-piperidine-4-carboxylic acid [26 mg, 38%, Example 97] as a solid. LCMS R$_T$=2.02 minutes, MS: 425 (M+H). IC$_{50}$=7 nM Example 98

2-(2-Chloro-5-{6-[2-(2,4-dichloro-phenyl)-ethylamino]-2-methoxy-pyrimidin-4-yl}-phenyl)-propan-2-ol

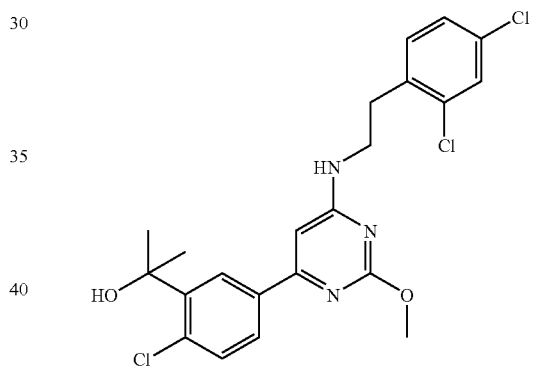

Step 1. To a suspension of 5-bromo-2-chlorobenzoic acid (5 g) in MeOH (200 mL) is added concentrated sulfuric acid (2 mL) and the mixture is heated at 64° C. for 16 h. The solution is evaporated in vacuo. The residue is taken up in EtOAc and washed with 10% sodium bicarbonate, brine and dried over sodium sulfate. The solution is filtered and evaporated in vacuo to afford 5-bromo-2-chloro-benzoic acid methyl ester (5.1 g). $^1$H NMR (300 MHz, CDCl$_3$) □7.3-7.5 (m, 2H); 6.9 (m, 1H); 3.9 (s, 3H).

Step 2. To a solution of 5-bromo-2-chloro-benzoic acid methyl ester (5 g) in diethyl ether (200 mL) cooled to −70° C. is added 3 M methylmagnesium bromide in THF (20 mL) dropwise. The solution is stirred at −78° C. for 2 h and allowed to warm to room temperature for 16 hours. The solution is cooled to 0° C. and 1 N HCl (100 mL) is added dropwise. The mixture is extracted with EtOAc (2×150 mL). The combined organic layer is washed with brine, dried over sodium sulfate, filtered and evaporated in vacuo. The residue is chromatographed on silica gel eluting with 20% EtOAc in heptane to afford 2-(5 bromo-2-chloro-phenyl)-propan-2-ol (4.56 g). MS: 250 (M+H); $^1$H NMR (300 MHz, CDCl$_3$) □7.8 (m, 1H); 7.5 (m, 1H); 7.2 (m, 1H); 4.4 (s, 1H); 1.6 (s, 6H).

Step 3. A solution of 2-(5-bromo-2-chloro-phenyl)-propan-2-ol (1.72 g), bis-(pinacolato)-diboron (1.94 g), Pd dppf (10 g) and KOAc (1.33 g) in a solution of DMSO (30 mL) is heated at 90° C. for 16 hours. The solution is cooled to 5° C. and a solution of KOH (16.6 g) in water (150 mL) is added. The solution is stirred at room temperature for 30 minutes and filtered. The solution is diluted with water (200 mL) and extracted with EtOAc (2×200 mL). The organic layer is washed with brine, dried over sodium sulfate, filtered and evaporated in vacuo to afford 2-[2-chloro-5-(4,4,5,5-tetramethyl-[1,3,2]dioxaborolan-2-yl)-phenyl]-propan-2-ol. $^1$H NMR (300 MHz, DMSO) □7.8 (m, 1H); 7.5 (m, 1H); 7.2 (m, 1H); 4.4 (s, 1H); 1.6 (s, 6H); 1.4 (s, 12H).

Step 4. A solution of (6-chloro-2-methoxy-pyrimidin-4-yl)-[2-(2,4-dichlorophenyl)ethyl]amine (0.58 g), 2-[2-chloro-5-(4,4,5,5-tetramethyl-[1,3,2]dioxaborolan-2-yl)-phenyl]-propan-2-ol (0.63 g), Cs$_2$CO$_3$ (1.36 g) and tetrakis(triphenylphosphine)palladium (0) (50 mg) in water (8 mL)/DME (32 mL) is heated at 90° C. for 16 h. The solution is poured into water and extracted with EtOAc (2×200 mL). The organic layer is dried over sodium sulfate, filtered, evaporated in vacuo. The residue is chromatographed on silica gel eluting with EtOAc to afford 2-(2-chloro-5-{6-[2-(2,4-dichloro-phenyl)-ethylamino]-2-methoxy-pyrimidin-4-yl}-phenyl)-propan-2-ol (162 mg, Example 98). MS: 466 (M+H); $^1$H NMR (300 MHz, DMSO) □8.2 (m, 1H); 7.8, (d, 1H, J=0.3 Hz); 7.5-7.7 (m, 2H); 7.4 (d, 2H, J=0.4 Hz); 7.3 (m, 1H); 7.3 (s, 1H); 6.6 (s, 1H) 4.2 (s, 3H); 4 (s, 3H); 3.8 (m, 2H); 3.05 (t, 2H); 1.55 (s, 6H). IC$_{50}$=110 nM Example 99

2-(3-{6-[2-(2,4-Dichloro-phenyl)-ethylamino]-2-methoxy-pyrimidin-4-yl}-4-fluoro-phenyl)-2-methyl-propionic acid hydrochloride

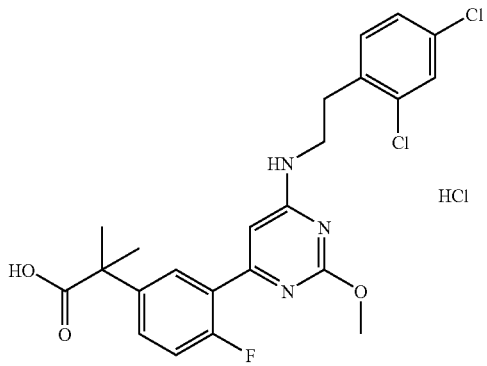

A solution of (6-chloro-2-methoxy-pyrimidin-4-yl)-[2-(2,4-dichlorophenyl)-ethyl]amine (0.24 g), 2-[4-fluoro-3-(4,4,5,5-tetramethyl-[1,3,2]dioxaborolan-2-yl)-phenyl]-2-methyl-propionic acid (0.4 g), Cs$_2$CO$_3$ (1.01 g) and tetrakis(triphenylphosphine)palladium (0) (100 mg) in water (20 mL)/DME (80 mL) is heated at 90° C. for 16 h. The solution is poured into water and extracted with EtOAc (2×200 mL). The organic layer is dried over sodium sulfate, filtered, evaporated in vacuo. The residue is chromatographed on silica gel eluting with EtOAc to afford 2-(3-{6-[2-(2,4-dichloro-phenyl)-ethylamino]-2-methoxy-pyrimidin-4-yl}-4-fluoro-phenyl)-2-methyl-propionic acid (100 mg), which is dissolved in THF (4 mL) and treated with 4 N HCl in 1,4-dioxane (1 mL). The mixture is concentrated in vacuo and the residue is suspended in ether (25 mL). The solid is formed and filtered under nitrogen to afford 2-(3-{6-[2-(2,4-Dichloro-phenyl)-ethylamino]-2-methoxy-pyrimidin-4-yl}-4-fluoro-phenyl)-2-methyl-propionic acid hydrochloride (67 mg, Example 99). MS: 478 (M+H); $^1$H NMR (300 MHz, NMR, CD$_3$OD) □7.8, (d, 1H, J=0.3 Hz); 7.4 (m, 2H); 7.35 (s, 1H); 7-7.15 (m, 4H); 6.6 (s, 1H); 4.2 (s, 3H); 3.6 (m, 2H); 3.05 (t, 2H); 1.65 (s, 6H). IC50=0.5 nM Pharmacological Testing The inhibitory effects of the compounds according to the invention are assessed in a human DP functional assay. A cAMP assay is employed using the human cell line LS174T, which expresses the endogenous DP receptor. The protocol is similar to that described previously (Wright D H, Ford-Hutchinson A W, Chadee K, Metters K M, The human prostanoid DP receptor stimulates mucin secretion in LS174T cells, *Br J Pharmacol.* 131(8):1537-45 (2000)).

Protocol for SPA cAMP Assay in Human LS174 T Cells

Materials

PGD2 (Cayman Chemical Cat#12010)
    IBMX (Sigma Cat#5879)
    cAMP SPA direct screening assay system (Amersham code RPA 559)
    96-well cell plates (Wallac Cat#1450-516)
    Wallac 1450 Microplate Trilux scintillation counter (PerkinElmer)
    Plate sealers
    Eppendorf tubes
    Dulbecco's Phosphate-Buffered Saline (PBS) (Invitrogen Cat#14040-133)
    Distilled water
    Vortex
    Magnetic stirrer and stirrer bars Reagent Preparation:

All reagents should be allowed to equilibrate to room temperature before reconstitution.

1× Assay Buffer

Transfer the contents of the bottle to a 500 mL graduated cylinder by repeated washing with distilled water. Adjust the final volume to 500 mL with distilled water and mix thoroughly.

Lysis Reagent 1 & 2

Dissolve each of the lysis reagents 1 and 2 in 200 mL assay buffer respectively. Leave at room temperature for 20 minutes to dissolve.

SPA Anti-Rabbit Beads

Add 30 mL of lysis buffer 2 to the bottle. Gently shake the bottle for 5 minutes.

Antiserum

Add 15 mL of lysis buffer 2 to each vial, and gently mix until the contents are completely dissolved.

Tracer (I$^{125}$-cAMP)

Add 14 mL lysis buffer 2 to each vial and gently mix until the contents are completely dissolved.

Preparation of Immunoreagent

1) Add equal volumes of tracer, antiserum and SPA anti-rabbit reagent to a bottle, ensuring that a sufficient volume of this mixture is prepared for the desired number of wells (150 μL/well).
2) Mix thoroughly.
3) This immunoreagent solution should be freshly prepared before each assay and not re-used.

Standard

1) Add 1 mL lysis buffer 1 and gently mix until contents are completely dissolved.

2) The final solution contains cAMP at a concentration of 512 pmol/mL.
3) Label 7 polypropylene or polystyrene tubes, 0.2 pmol, 0.4 pmol, 0.8 pmol, 1.6 pmol, 3.2 pmol, 6.4 pmol and 12.8 pmol.
4) Pipette 500 µL of lysis buffer 1 into all the tubes.
5) Into the 12.8 pmol tube pipette 500 µL of stock standard (512 pmol/mL) and mix thoroughly. Transfer 500 µL from 12.8 pmol tube to the 6.4 pmol tube and mix thoroughly. Repeat this doubling dilution successively with the remaining tubes.
6) 50 µL aliquots in duplicate from each serial dilution and the stock standard will give rise to 8 standard levels of cAMP ranging from 0.2-25.6 pmol standard Compound Dilution Buffer Add 50 µL of 1 mM IBMX into 100 mL PBS to make a final concentration of 100 µM and sonicate at 30° C. for 20 minutes.

PGD2 Preparation

Dissolve 1 mg PGD2 (FW, 352.5) in 284 µL DMSO to make 10 mM stock solution and store at 20° C. Before each assay, it is freshly prepared. Add 3 mL of 10 mM stock solution to 20 mL DMSO, mix it thoroughly, and transfer 10 mL to 40 mL PBS.

Compound Dilution

Compound dilution is carried out in Biomex 2000 (Beckman) using Method 1_cAMP DP 11 points.

5 µL of each compound from the 10 mM stock compound plates is transferred to the wells of a 96-well plate respectively as below.

|   | 1 | 2 | 3 | 4 | 5 | 6 | 7 | 8 | 9 | 10 | 11 | 12 |
|---|---|---|---|---|---|---|---|---|---|----|----|----|
| A | 1 | | | | | | | | | | | |
| B | 2 | | | | | | | | | | | |
| C | 3 | | | | | | | | | | | |
| D | 4 | | | | | | | | | | | |
| E | 5 | | | | | | | | | | | |
| F | 6 | | | | | | | | | | | |
| G | 7 | | | | | | | | | | | |
| H | reference | | | | | | | | | | | |

Fill the plate with 45 µL of DMSO except column 7 is filled with 28 µL DMSO. Pipette column 1 thoroughly, and transfer 12 µL into column 7 parallel. Perform 1:10 serial dilution from column 1 to column 6 and from column 7 to column 11 by transfer 5 µL to 45 µL DMSO to make following concentrations:

| First plate | Final concentration |
|---|---|
| Column 12 | 0 |
| Column 11 | 0.03 µM |
| Column 10 | 0.3 µM |
| Column 9 | 3 µM |
| Column 8 | 0.03 mM |
| Column 7 | 0.3 mM |
| Column 6 | 0.01 µM |
| Column 5 | 0.1 µM |
| Column 4 | 1 µM |
| Column 3 | 0.01 mM |
| Column 2 | 0.1 mM |
| Column 1 | 1 mM |

Fill a new 96-well plate with 247.5 µL of compound dilution buffer. Transfer 2.5 µL of serially diluted compounds from above plate to the new plate (1:100 dilution) as following:

| First plate | Second plate | Final concentration |
|---|---|---|
| Column 12 | Column 1 | 0 |
| Column 6 | Column 2 | 0.1 nM |
| Column 11 | Column 3 | 0.3 nM |
| Column 5 | Column 4 | 1 nM |
| Column 10 | Column 5 | 3 nM |
| Column 4 | Column 6 | 0.01 µM |
| Column 9 | Column 7 | 0.03 µM |
| Column 3 | Column 8 | 0.1 µM |
| Column 8 | Column 9 | 0.3 µM |
| Column 2 | Column 10 | 1 µM |
| Column 7 | Column 11 | 3 µM |
| Column 1 | Column 12 | 10 µM |

Cell Growth

1. LS174 T are always grown in MEM (ATCC Cat#30-2003), 10% FBS (ATCC Cat#30-2020) and additional 2 mM L-glutamine, at 37° C. and 5% $CO_2$.
2. Warm 0.05% Trypsin and Versine (Invitrogen Cat#25300-054) at 37° C. water bath.
3. Remove growth medium from cells. Cells in T165 flask are washed twice with 4 mL Trypsin followed by incubation at 37° C. and 5% $CO_2$ for 3 minutes.
4. Add 10 mL of medium and pipette thoroughly to separate the cells and count the cells.
5. Bring the cell density to $2.25 \times 10^5$ cells/ml and seed 200 µL cells/well (45,000 cells/well) in 96-well plates 1 day before the assay.

Assay Procedure

Day 1

Seed 45,000 cells/well in 200 µL medium in 96-well plates. Incubate the cell plate at 37° C., 5% $CO_2$ and 95% humidity overnight.

Day 2

1. Perform compound dilution.
2. Prepare assay buffer, lysis buffer 1 & 2, $PGD_2$ and standard.
3. Aspirate media from the cells and add 100 µL of compound solution using Zymark Sciclone-ALH/FD protocol cAMP DP.
4. Incubate the cells at 37° C., 5% $CO_2$ and 95% humidity for 15 minutes.
5. Add 5 µL of 300 nM PGD2 (20×15 nM final concentration) into each well using Zymark protocol cAMP DP PGD2, and incubate the cells at 37° C., 5% $CO_2$ and 95% humidity for additional 15 minutes.
6. Aspirate media from the cells and add 50 µL of lysis buffer 1 using Zymark protocol cAMP DP lysis, and incubate at room temperature with shaking for 30 minutes.
7. Add 150 µL immunoreagent to all wells (a total volume of 200 µL/well).
8. Seal the plates and shake for 2 minutes, put into the chamber of the Wallac microtitre plate µ scintillation counter for 16 hours.

Day 3

Count the amount of [$^{125}$I] cAMP for 2 minutes in 1450 Trilux scintillation counter.

Data Processing

Set Up Standard Curve of cAMP Versus CPM.

TABLE 1

| cAMP (pmol/mL) | CPM | | Average CPM |
|---|---|---|---|
| 0.2 | 5725 | 5769 | 5530 |
| 0.4 | 5367 | 5259 | 6317 |
| 0.8 | 4695 | 4796 | 6507 |
| 1.6 | 4251 | 4178 | 6581 |
| 3.2 | 3434 | 3429 | 6601 |
| 6.4 | 2758 | 2716 | 6711 |
| 12.8 | 2094 | 2054 | 6680 |
| 25.6 | 1531 | 1573 | 6653 |

The cAMP concentrations (pmol/mL) of unknown samples are calculated from a standard curve of cAMP versus CPM. % inhibition is calculated using the following formula:

$$\% \text{ Inhibition} = \frac{(\text{pmol of control} - \text{pmol of sample}) \times 100}{\text{pmol of control (cells + PGD2 only)}}$$

Results

Compounds within the scope of the invention produce 50% inhibition in the SPA cAMP assay in human LS174 T cells at concentrations within the range of about 0.1 nanomolar to about 10 micromolar. Preferred compounds within the scope of the invention produce 50% inhibition in the SPA cAMP assay in human LS174 T cells at concentrations within the range of about 0.1 to about 100 nanomolar. More preferred compounds within the scope of the invention produce 50% inhibition in the SPA cAMP assay in human LS174 T cells at concentrations within the range of about 0.1 to about 30 nanomolar.

We claim:

1. A compound of Formula (I)

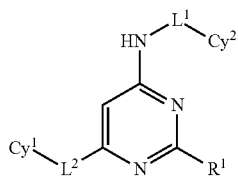

(I)

wherein:

(A) $Cy^1$ is cycloalkyl, heterocyclyl, cycloalkenyl, heterocyclenyl, heteroaryl, aryl, or multicyclic alkaryl, each of which is optionally substituted by one to three of same or different following $Cy^1$ substituent groups consisting of:
acyl, cyano, halogen, nitro, carboxy, hydroxy, alkylthio, alkylsulfonyl, alkylsulfinyl, cycloalkyl, heterocyclyl, cycloalkenyl, heterocyclenyl, aryl, heteroaryl, multicyclic alkaryl, aroyl, arylalkoxycarbonyl, arylalkylthio, aryloxy, aryloxycarbonyl, arylsulfinyl, arylsulfonyl, arylthio, heteroaryloxy, heteroarylalkoxycarbonyl, N-methoxysulfamoyl, $R^2$—C(=N—OR$^3$)—, $Y^1Y^2N$—, $Y^1Y^2NC(=O)$—, $Y^1Y^2NC(=O)$—O—, $Y^1Y^2NSO_2$—, alkyl-O—C(=O)—($C_2$-$C_6$)-alkylene-$Z^1$—, $Y^1Y^2N$—C(=O)—($C_1$-$C_6$)-alkylene-$Z^1$—, $Y^1Y^2N$—($C_2$-$C_6$)alkylene-$Z^1$—, alkyl-C(=O)—N(R$^5$)—$SO_2$—, alkyl-O—C(=O)—N(R$^5$)—, alkyl-O—C(=O)—N(R$^5$)—$SO_2$—, alkyl-O—N(R$^5$)—$SO_2$—, alkyl-O—N(R$^5$)—C(=O)—, alkyl-$SO_2$—N(R$^5$)—C(=O)—, aryl-$SO_2$—N(R$^5$)—C(=O)—, alkyl-$SO_2$—N(R$^5$)—, $R^6$—C(=O)—N(R$^5$)—, $R^7$—NH—C(=O)—NH—;

alkenyl, which is optionally substituted by alkoxy or hydroxy;

alkoxycarbonyl, which is optionally substituted by $Y^1Y^2N$—;

alkynyl, which is optionally substituted by hydroxy or alkoxy;

alkyl, which is optionally substituted by one to three of same or different of halogen, carboxy, cyano, hydroxy, $Y^1Y^2N$—, $Y^1Y^2N$—C(=O)—, $H_2N$—C(=NH)—NH—O—, $R^6$—C(=O)—N(R$^5$)—, alkyl-O—C(=O)—N(R$^5$)—, alkyl-$SO_2$—N(R$^5$)—, $R^8$—$SO_2$—N(R$^5$)—C(=O)—, aryl-N(R$^5$)—C(=O)—, heteroaryl-N(R$^5$)—C(=O)—, heterocyclyl-N(R$^5$)—C(=O)—, alkoxycarbonyl, cycloalkyl, heterocyclyl, cycloalkenyl, heterocyclenyl, aryl, heteroaryl, multicyclic alkaryl; alkoxy, which is optionally substituted by carboxy, aryl or heteroaryl; or alkoxycarbonyl, which is optionally substituted by $Y^1Y^2N$—; and alkoxy, which is optionally substituted by one to three of same of different of carboxy, alkoxycarbonyl, cyano, halogen, —NY$^1$Y$^2$, $Y^1Y^2N$—C(=O)—, cycloalkyl, heterocyclyl, cycloalkenyl, heterocyclenyl, aryl, heteroaryl, or multicyclic alkaryl;

wherein the aryl or heteroaryl moieties in the $Cy^1$ substituent groups are optionally independently substituted by hydroxy, amino, alkyl, alkoxy, carboxy, alkoxycarbonyl or $R^8$—$SO_2$—N(R$^5$)—C(=O)—;

and, wherein the cycloalkyl, cycloalkenyl, heterocyclyl, heterocyclenyl or multicyclic alkaryl moieties in the $Cy^1$ substituent groups independently is optionally substituted by hydroxy, amino, alkyl, alkoxy, oxo, carboxy, alkoxycarbonyl or $R^8$—$SO_2$—N(R$^5$)—C(=O)—;

and further provided that when $Cy^1$ is cycloalkyl, cycloalkenyl, heterocyclyl, heterocyclenyl or multicyclic alkaryl, each of which independently may also be substituted by oxo;

(B) $Cy^2$ is cycloalkenyl, heterocyclenyl, aryl, heteroaryl, or multicyclic alkaryl, each of which independently is optionally substituted by one to three of same or different of same or different of alkoxy, ($C_1$-$C_3$)-alkyl, hydroxy, cyano, halogen, haloalkoxy, haloalkyl, nitro, $Y^1Y^2N$—, $Y^1Y^2N$—$SO_2$—, aryl or heteroaryl, wherein the aryl is optionally substituted by alkyl or hydroxyalkyl, and the heteroaryl is optionally substituted by alkyl;

(C) $L^1$ is a straight- or branched-chain alkylene containing from 1 to 6 carbon atoms and is optionally substituted by carboxy or hydroxy; or $L^1$ is —CH$_2$—($C_1$-$C_5$)haloalkylene, or $L^1$ is cycloalkylene containing from 3 to 7 carbon atoms and is optionally substituted by hydroxy; or $L^1$ and $Cy^2$ together represent arylcycloalkyl or cycloalkylaryl;

(D) $R^1$ is ($C_1$-$C_4$)-alkoxy which is optionally substituted by one to three halogen;

(E) $L^2$ is bond, —O— or —CH$_2$—O—;

and wherein:

$R^2$, $R^3$, $R^4$ and $R^5$ are each independently H or alkyl, $R^6$ is alkyl, which is optionally substituted by hydroxy or alkoxy;

$R^7$ is H or alkyl;

$R^8$ is alkyl, aryl, arylalkyl, heteroaryl, heteroarylalkyl, wherein the aryl or heteroaryl moiety is optionally substituted by halogen;

Y¹ and Y² are each independently hydrogen, or alkyl, which is optionally substituted by one to three of same or different of carboxy, alkoxycarbonyl, alkoxy, hydroxy, amino, alkylamino, dialkylamino, cycloalkyl, cycloalkenyl, heterocyclyl, heterocyclenyl, aryl, heteroaryl or multicyclic alkaryl; wherein the aryl and heteroaryl independently is optionally substituted by hydroxy, amino, alkyl or alkoxy, and wherein the cycloalkyl, heterocyclyl, cycloalkenyl, heterocyclenyl and multicyclic alkaryl independently is optionally substituted by hydroxy, amino, alkyl, alkoxy or oxo; or Y¹ and Y² taken together with the nitrogen atom to which they are attached, form a nitrogen-containing three to seven member saturated heterocyclyl that optionally contains a further heteroatom selected from O, S, or NY³, wherein Y³ is hydrogen or alkyl, and wherein the heterocyclyl is optionally substituted by one to three of same or different of carboxy, hydroxy, hydroxyalkyl, oxo, amino, alkylamino or dialkylamino;

Z¹ is C(=O)—N(R⁴), NR⁴ or S(O)$_n$; and n is 0, 1 or 2;

provided that when R¹ is methoxy, L¹ is —CH$_2$—CH$_2$—, L² is a bond and Cy² is 2,4-dichlorophenyl, then Cy¹ is not 1-methyl-2-ethyloxycarbonyl-indol-5-yl;

and further provided that the compound is not 2-(3-{6-[2-(2,4-dichloro-phenyl)-ethylamino]-2-methoxy-pyrimidin-4-yl}-phenyl)-2-methyl-propionic acid;

or an N-oxide thereof, or a pharmaceutically acceptable salt or hydrate thereof.

2. The compound according to claim 1, wherein R¹ is methoxy, ethoxy or 2,2,2-trifluoroethoxy; or an N-oxide thereof, or a pharmaceutically acceptable salt or hydrate thereof.

3. The compound according to claim 1, wherein Cy¹ is phenyl, benzimidazolyl, benzo[1,3]dioxolyl, benzothiazolyl, benzo[b]thiophenyl, 1H-benzotriazolyl, 2,3-dihydro-benzo[1,4]dioxanyl, 2,3-dihydro-benzofuranyl, 3,4-dihydro-2H-benzo[1,4]oxazinyl, furanyl, imidazolyl, 1H-indazolyl, indolinyl, indolyl, isoquinolinyl, isoxazolyl, oxadiazolyl, oxazolyl, 2-oxo-1H-pyridinyl, phenyl, pyrazolyl, pyridyl, thiazolyl, quinolinyl, thienyl or piperidinyl, wherein each of which independently is optionally substituted by one to three of the same or different Cy¹ substituent groups; or an N-oxide thereof, or a pharmaceutically acceptable salt or hydrate thereof.

4. The compound according to claim 1, wherein Cy¹ is phenyl, benzimidazol-2-yl, benzimidazol-5-yl, benzo[1,3]dioxol-5-yl, benzothiazol-6-yl, benzo[b]thiophen-2-yl, benzo[b]thiophen-3-yl, 1H-benzotriazol-6-yl, 2,3-dihydro-benzo[1,4]dioxin-6-yl, 2,3-dihydrobenzofuran-5-yl, 3,4-dihydro-2H-benzo[1,4]oxazin-7-yl, furan-2-yl, furan-3-yl, imidazol-1-yl, 1H-indazol-6-yl, indolin-5-yl, indol-3-yl, indol-5-yl, indol-6-yl isoquinolin-5-yl, isoxazol-4-yl, [1,2,4]oxadiazol-5-yl, [1,3,4]oxadiazol-2-yl, oxazol-5-yl, 2-oxo-1H-pyridin-5-yl, phenyl, pyrazol-1-yl, pyrazol-3-yl, pyrazol-4-yl, pyrid-3-yl, pyrid-4-yl, thiazol-2-yl, quinolin-3-yl, quinolin-6-yl, quinolin-8-yl, thien-2-yl, thien-3-yl, or piperidin-1-yl, each of which is optionally substituted by one to three of the same or different Cy¹ substituent groups; or an N-oxide thereof, or a pharmaceutically acceptable salt or hydrate thereof.

5. The compound according to claim 1, wherein Cy² is phenyl, cyclohexenyl, benzo[1,3]dioxolyl, benzofuranyl, 2,3-dihydro-benzofuranyl, 3,4-dihydro-2H-benzo[1,4]oxazinyl, benzo[b]thiophenyl, imidazolyl, indolyl, isochromanyl, phenyl, naphthalenyl, pyridyl or thienyl, each of which is optionally substituted by one to three of same or different substituents of alkoxy, (C$_1$-C$_3$)-alkyl, hydroxy, cyano, halogen, haloalkoxy, haloalkyl, nitro, Y¹Y²N—, Y¹Y²N—SO$_2$—, aryl or heteroaryl, wherein the aryl is optionally substituted by alkyl or hydroxyalkyl, and the heteroaryl is optionally substituted by alkyl; or an N-oxide thereof, or a pharmaceutically acceptable salt or hydrate thereof.

6. The compound according to claim 1, wherein Cy² is phenyl, cyclohex-1-enyl, benzo[1,3]dioxol-5-yl, benzofuran-6-yl, 2,3-dihydro-benzofuran-2-yl, 3,4-dihydro-2H-benzo[1,4]oxazin-2-yl, benzo[b]thiophen-2-yl, imidazol-4-yl, 1H-indol-3-yl, 1H-indol-5-yl, naphthalene-2-yl, isochroman-1-yl, pyridin-2-yl, pyridin-3-yl, pyridin-4-yl or thien-2-yl, each of which is optionally substituted by one to three of the same or different substituents of alkoxy, (C$_1$-C$_3$)-alkyl, hydroxy, cyano, halogen, haloalkoxy, haloalkyl, nitro, Y¹Y²N—, Y¹Y²N—SO$_2$—, aryl or heteroaryl, wherein the aryl is optionally substituted by alkyl or hydroxyalkyl, and the heteroaryl is optionally substituted by alkyl; or an N-oxide thereof, or a pharmaceutically acceptable salt or hydrate thereof.

7. The compound according to claim 1, wherein L¹ is —CH$_2$—, —CH$_2$—CH$_2$—, —CH$_2$—CH$_2$—CH$_2$—, —CH$_2$—CH$_2$—CH$_2$—CH$_2$—, —CH$_2$—CH(CH$_3$)—, —CH$_2$—C(CH$_3$)$_2$—, —CH(CH$_3$)—CH$_2$—, —CH$_2$—CH(OH)—, —CH(CO$_2$H)—CH$_2$—, —CH$_2$—CF$_2$—,

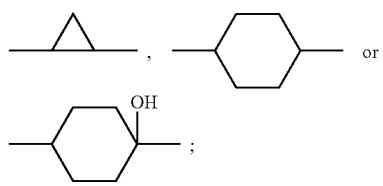

or an N-oxide thereof, or a pharmaceutically acceptable salt or hydrate thereof.

8. The compound according to claim 1, wherein L¹ and Cy² together represent indan-1-yl or indan-2-yl; or an N-oxide thereof, or a pharmaceutically acceptable salt or hydrate thereof.

9. The compound according to claim 1, wherein L¹ is —CH$_2$—CH$_2$—; or an N-oxide thereof, or a pharmaceutically acceptable salt or hydrate thereof.

10. The compound according to claim 1, wherein L¹ is —CH$_2$—CF$_2$—; or an N-oxide thereof, or a pharmaceutically acceptable salt or hydrate thereof.

11. The compound according to claim 1, wherein Cy¹ is unsubstituted phenyl or phenyl substituted by one to three of same or different substituent groups of:

acyl, alkylsulfinyl, alkylsulfonyl, carboxy, cyano, halo, heteroaroyl, heterocyclenyl, hydroxy, nitro, R²—C(=N—OR³)—, Y¹Y²N—, Y¹Y²NC(=O)—, Y¹Y²NC(=O)—O—, Y¹Y²NSO$_2$—, Y¹Y²N—C(=O)—(C$_1$-C$_6$)-alkylene-Z¹—, alkyl-C(=O)—N(R⁵)—SO$_2$—, alkyl-O—C(=O)—N(R⁵)—, alkyl-O—C(=O)—N(R⁵)—SO$_2$—, alkyl-O—N(R⁵)—C(=O)—, alkyl-O—N(R⁵)—SO$_2$—, alkyl-SO$_2$—N(R⁵)—C(=O)—, aryl-SO$_2$—N(R⁵)—C(=O)—, alkyl-SO$_2$—N(R⁵)—, R⁶—C(=O)—N(R⁵)—, alkyl-NH—C(=O)—NH—;

alkoxy, which is optionally substituted by one to three of same or different of carboxy or heteroaryl; or alkyl, which is optionally substituted by one to three of same or different of halogen, carboxy, aryl, heteroaryl multicyclic alkaryl, cyano, hydroxy, Y¹Y²N—, H$_2$N—C(=NH)—NH—O—, R⁶—C(=O)—N(R⁵)—, R⁶—N(R⁵)—C(=O)—, alkyl-O—C(=O)—N(R⁵)—, alkyl-SO₂—N(R⁵)—, R⁸—SO₂—N(R⁵)—C(=O)—, H₂N—C(=NH)—NH—O—; or alkoxy, which is optionally substituted by carboxy or heteroaryl;

wherein the aryl or heteroaryl moieties in the substituent groups are optionally independently substituted by hydroxy, amino, alkyl, alkoxy, carboxy, alkoxycarbonyl or R⁸—SO₂—N(R⁵)—C(=O)—;

and, wherein the heterocyclenyl or multicyclic alkaryl moieties in the substituent groups independently is optionally substituted by hydroxy, amino, alkyl, alkoxy, carboxy, alkoxycarbonyl, R⁸—SO₂—N(R⁵)—C(=O)— or oxo;

or an N-oxide thereof, or a pharmaceutically acceptable salt or hydrate thereof.

12. The compound according to claim 1, wherein Cy¹ is benzimidazol-2-yl, benzimidazol-5-yl, benzo[1,3]dioxol-5-yl, benzothiazol-6-yl, benzo[b]thiophen-2-yl, benzo[b]thiophen-3-yl, 1H-benzotriazol-6-yl, 2,3-dihydro-benzo[1,4]dioxin-6-yl, 2,3-dihydrobenzofuran-5-yl, 3,4-dihydro-2H-benzo[1,4]oxazin-7-yl, furan-2-yl, furan-3-yl, imidazol-1-yl, 1H-indazol-6-yl, indolin-5-yl, indol-3-yl, indol-5-yl, indol-6-yl isoquinolin-5-yl, isoxazol-4-yl, [1,2,4]oxadiazol-5-yl, [1,3,4]oxadiazol-2-yl, oxazol-5-yl, 2-oxo-1H-pyridin-5-yl), phenyl, pyrazol-1-yl, pyrazol-3-yl, pyrazol-4-yl, pyrid-3-yl, pyrid-4-yl, thiazol-2-yl, quinolin-3-yl, quinolin-6-yl, quinolin-8-yl, thien-2-yl, thien-3-yl or piperidin-1-yl, each of which is optionally substituted by one to three of the same or different substituent groups of lower alkanoyl, lower alkoxy, carboxy, cyano, halogen, R²—C(=N—OR³)—Y¹Y²N—, Y¹Y²NC(=O)—, heteroaryl; or loweralkyl, which is optionally substituted by one to three of same or different of halogen, carboxy, heteroaryl, hydroxy, or Y¹Y²N—; wherein the heteroaryl moieties in substituent groups are optionally independently substituted by hydroxy, amino, alkyl or alkoxy; or an N-oxide thereof, or a pharmaceutically acceptable salt or hydrate thereof.

13. The compound according to claim 1, wherein Cy¹ is benzimidazol-2-yl, benzimidazol-5-yl, benzo[1,3]dioxol-5-yl, benzothiazol-6-yl, benzo[b]thiophen-2-yl, benzo[b]thiophen-3-yl, 1H-benzotriazol-6-yl, 2,3-dihydro-benzo[1,4]dioxin-6-yl, 2,3-dihydrobenzofuran-5-yl, 3,4-dihydro-2H-benzo[1,4]oxazin-7-yl, furan-2-yl, furan-3-yl, imidazol-1-yl, 1H-indazol-6-yl, indolin-5-yl, indol-3-yl, indol-5-yl, indol-6-yl isoquinolin-5-yl, isoxazol-4-yl, [1,2,4]oxadiazol-5-yl, [1,3,4]oxadiazol-2-yl, oxazol-5-yl, 2-oxo-1H-pyridin-5-yl, phenyl, pyrazol-1-yl, pyrazol-3-yl, pyrazol-4-yl, pyrid-3-yl, pyrid-4-yl, thiazol-2-yl, quinolin-3-yl, quinolin-6-yl, quinolin-8-yl, thien-2-yl, thien-3-yl or piperidin-1-yl, each of which is optionally substituted by one to three of the same or different substituent groups of formyl, acetyl, methoxy, carboxy, cyano, chloro, methyl, —CHF₂—, oxazol-5-yl, tetrazol-5-yl, HO₂C—CH₂—, HOCH₂—, HO—CH(CH₃)—, H—C(=N—OH)—, H—C(=N—OCH₃)—, CH₃—C(=N—OH)—, CH₃—C(=N—OCH₃)—, H₂N—CH₂—, CH₃NHCH₂—, CH₃OCH₂CH₂NHCH₂—, CH₃NH—C(=O)—,

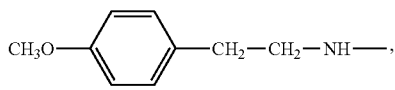

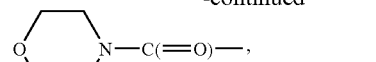

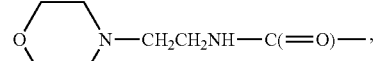

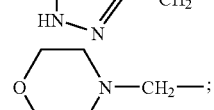

or an N-oxide thereof, or a pharmaceutically acceptable salt or hydrate thereof.

14. The compound according to claim 1, wherein Cy¹ is phenyl or phenyl substituted by one to three of the same or different groups of formyl, acetyl, methoxy, chloro, fluoro, hydroxy, nitro, cyano, carboxy, CH₃O—CH=CH—, CH₃—SO—, CH₃SO₂—, CH₃CH₂SO₂—, HO₂C—CH₂—O—, HO₂C—C(CH₃)₂—O—,

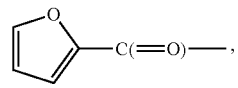

5-amino-[1,3,4]oxadiazol-2-yl, 3-methyl-isoxazol-5-yl, 3-methyl-[1,2,4]oxadiazol-5-yl, 5-methyl-[1,3,4]oxadiazol-2-yl, 2-methyl-2H-tetrazol-5-yl, 1-methyl-1H-tetrazol-5-yl, 5-methyl-2H-[1,2,4]triazol-3-yl, 3H-[1,3,4]oxadiazol-2-one, oxazol-5-yl, tetrazol-5-yl, 1H-tetrazol-5-ylmethyl, 1-methyl-1-(1H-tetrazol-5-yl)-ethyl,

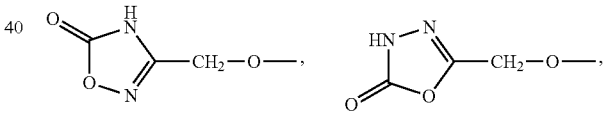

3H-[1,3,4]oxadiazol-2-one, H—C(=N—OH)—, CH₃—C(=N—OH)—, H₂N—, (CH₃)₂N—,

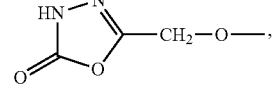

CH₃OCH₂CH₂NH—,

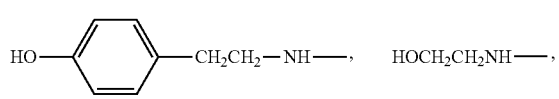

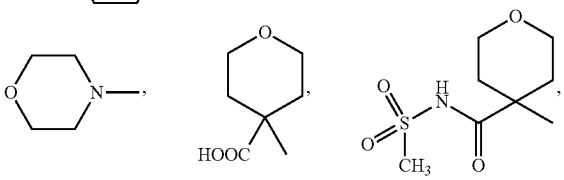

-continued

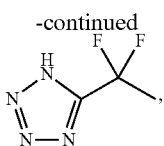

HO₂C—CF₂—,  CH₃CH₂SO₂NHC(=O)—C(CH₃)₂—, PhCH₂SO₂NHC(=O)—C(CH₃)₂—,  CH₃CH₂SO₂NHC(=O)—CF₂—,  H₂N—C(=O)—,  CH₃NHC(=O)—, (CH₃)₂NC(=O)—, (CH₃)₂NCH₂CH₂NH—C(=O)—, HO₂CCH₂NH—C(=O)—,  HO₂CCH(CH₃)NH—C(=O)—, HO₂CCH(CH{CH₃}₂)NH—C(=O)—, HO₂CCH(CH₂CH{CH₃}₂)NH—C(=O)—,

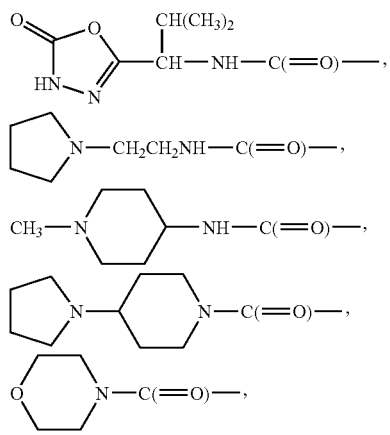

CH₃CH₂NH—C(=O)—O—,  H₂N—SO₂—, CH₃NHSO₂—, CH₃CH₂NHSO₂—, (CH₃)₂CHNH—SO₂—, CH₃CH₂NH—C(=O)—CH₂—O—,  (CH₃)₂CHNH—C(=O)—CH₂—O—,  (CH₃)₂NCH₂CH₂NH—C(=O)—C(CH₃)₂—O—, CH₃—C(=O)—NH—SO₂—, CH₃CH₂—O—C(=O)—NH—,  CH₃—O—C(=O)—NH—SO₂—, CH₃—O—N(CH₃)—C(=O)—,  CH₃—O—NH—SO₂—, CH₃—SO₂—NH—C(=O)—,  CH₃—SO₂—N(CH₃)—C(=O)—,

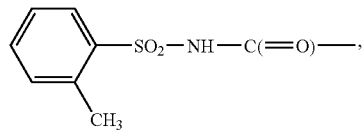

CH₃—SO₂—NH—,  CH₃—C(=O)—NH—,  CH₃O—CH₂—C(=O)—NH—,  CH₃CH₂NH—C(=O)—NH—, HO₂C—CH₂CH₂—,  HO₂C—CH(CH₃)—,  HO₂C—C(CH₃)₂—, HO₂C—CH₂—O—CH₂—, benzyl, NC—CH₂—,

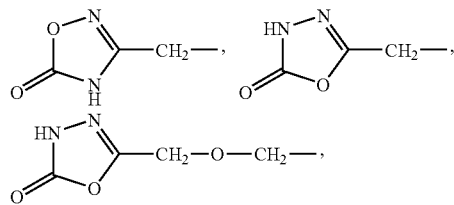

HOCH₂—,  HOCH₂CH₂—,  HO—CH(CH₃)—,  HO—C(CH₃)₂—,  H₂NCH₂—,  (CH₃)₂NCH₂CH₂NHCH₂—, HO₂C—CH(CH₂Ph)—NHCH₂—, HO₂C—CH(CH₂OH)—NHCH₂—,

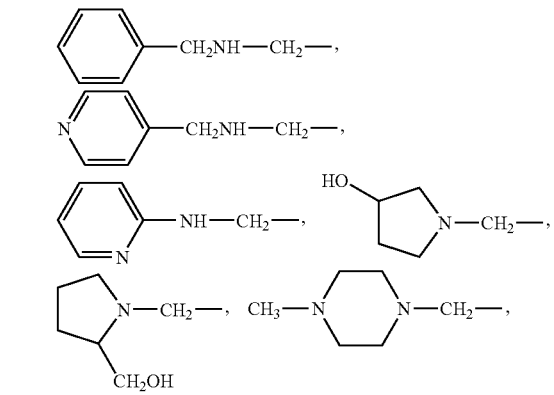

H₂N—C(=NH)—NH—O—CH₂—,  CH₃OCH₂—C(=O)—NH—CH₂—,  HOCH₂—NH—C(=O)—CH₂—, CH₃—C(=O)—NH—CH₂—,  CH₃—C(=O)—NH—CH₂CH₂—,  HOCH₂CH₂—NH—C(=O)—CH₂CH₂—, CH₃—O—C(=O)—NH—CH₂—,  CH₃SO₂—NH—CH₂—, H₂N—C(=NH)—NH—O—CH₂—,

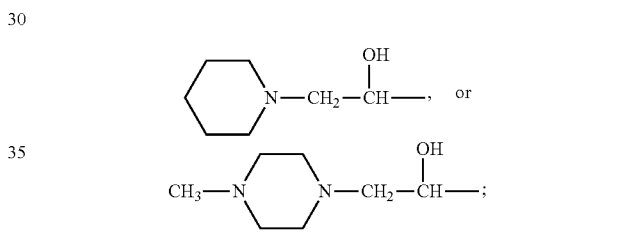

or an N-oxide thereof, or a pharmaceutically acceptable salt or hydrate thereof.

15. The compound according to claim 1 wherein $Cy^2$ is cyclohex-1-enyl; or an N-oxide thereof, or a pharmaceutically acceptable salt or hydrate thereof.

16. The compound according to claim 1 wherein $Cy^2$ is naphthyl or phenyl, each of which is optionally substituted by one to three of the same or different groups of alkoxy, ($C_1$-$C_3$)-alkyl, hydroxy, cyano, halogen, haloalkoxy, haloalkyl, nitro, $Y^1Y^2N$—, $Y^1Y^2N$—$SO_2$—, aryl or heteroaryl, wherein the aryl is optionally substituted by alkyl or hydroxyalkyl, and the heteroaryl is optionally substituted by alkyl; or an N-oxide thereof, or a pharmaceutically acceptable salt or hydrate thereof.

17. The compound according to claim 1 wherein $Cy^2$ is naphthyl or phenyl, each of which is optionally substituted by one to three of same or different groups of methoxy, ethoxy, methyl, ethyl, bromo, chloro, fluoro, F₂HCO—, F₃CO—, F₃C—, amino, H₂N—SO₂—, cyano, hydroxy, nitro or 5-methyl-[1,3,4]oxadiazol-2-yl; or an N-oxide thereof, or a pharmaceutically acceptable salt or hydrate thereof.

18. The compound according to claim 1 wherein $Cy^2$ is benzo[1,3]dioxol-5-yl, 1H-indol-3-yl, 1H-indol-5-yl, imidazol-4-yl, 1H-indol-3-yl, pyridin-2-yl, pyridin-3-yl, pyridin-4-yl, or thien-2-yl, each of which is optionally substituted by one to three of same or different groups of alkoxy, halo, or hydroxy; or an N-oxide thereof, or a pharmaceutically acceptable salt or hydrate thereof.

19. The compound according to claim 1 wherein $L^2$ is a bond; or an N-oxide thereof, or a pharmaceutically acceptable salt or hydrate thereof.

20. The compound according to claim 1 wherein the compound is of Formula (II)

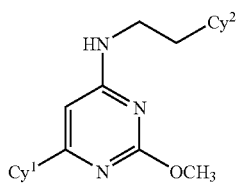

(II)

or an N-oxide thereof, or a pharmaceutically acceptable salt or hydrate thereof.

21. The compound according to claim 20 wherein $Cy^1$ is phenyl or phenyl substituted by one to three of same or different substituent groups of:

acyl, alkylsulfonyl, carboxy, cyano, halo, heteroaryl, hydroxy, heterocyclyl, $R^2$—C(=N—OR$^3$)—, $Y^1Y^2N$—, $Y^1Y^2NC(=O)$—, $Y^1Y^2NC(=O)$—O—, $Y^1Y^2N$—SO$_2$—, $Y^1Y^2N$—C(=O)—(C$_1$-C$_6$)-alkylene-Z$^1$—, alkyl-C(=O)—N(R$^5$)—SO$_2$—, alkyl-O—C(=O)—N(R$^5$)—SO$_2$—, alkyl-O—N(R$^5$)—SO$_2$—, alkyl-SO$_2$—N(R$^5$)—C(=O)—, alkyl-SO$_2$—N(R$^5$)—, $R^6$—C(=O)—N(R$^5$)—, alkyl-NH—C(=O)—NH—;

alkenyl, which is optionally substituted by alkoxy;

alkoxy, which is optionally substituted by carboxy or heteroaryl; or alkyl, which is optionally substituted by halogen, carboxy, cyano, heteroaryl, hydroxy, $R^6$—C(=O)—N(R$^5$)—, $R^8$—SO$_2$—N(R$^5$)—C(=O)—; or alkoxy, which is optionally substituted by carboxy;

wherein the heterocyclyl moieties in the substituent groups are optionally independently substituted by hydroxy, amino, alkyl, alkoxy, oxo, carboxy, alkoxycarbonyl or $R^8$—SO$_2$—N(R$^5$)—C(=O)—; and the heteroaryl moieties in the substituent groups are optionally independently substituted by hydroxy, amino, alkyl, alkoxy, carboxy, alkoxycarbonyl or $R^8$—SO$_2$—N(R$^5$)—C(=O)—;

or an N-oxide thereof, or a pharmaceutically acceptable salt or hydrate thereof.

22. The compound according to claim 20 wherein $Cy^1$ is phenyl or phenyl substituted by one to three of same or different substituent groups of formyl, acetyl, cyano, methoxy, chloro, fluoro, hydroxy, carboxy, 5-amino-[1,3,4]oxadiazol-2-yl, 3-methyl-isoxazol-5-yl, 3-methyl-[1,2,4]oxadiazol-5-yl, 5-methyl-[1,3,4]oxadiazol-2-yl, 2-methyl-2H-tetrazol-5-yl, 5-methyl-2H-[1,2,4]triazol-3-yl, oxazol-5-yl, tetrazol-5-yl, 1H-tetrazol-5-ylmethyl, 1-methyl-1-(1H-tetrazol-5-yl)-ethyl, H$_2$N—, CH$_3$—NHC(=O)—, CH$_3$CH$_2$NH—C(=O)—CH$_2$O—CH=CH—, CH$_3$SO$_2$—, CH$_3$CH$_2$SO$_2$—, HO$_2$C—CH$_2$—O—, HO$_2$C—C(CH$_3$)$_2$—O—, H—C(=N—OH)—, CH$_3$—C(=N—OH)—, CH$_3$OCH$_2$CH$_2$NH—, H$_2$N—SO$_2$—, CH$_3$NHSO$_2$—, CH$_3$CH$_2$NHSO$_2$—, (CH$_3$)$_2$CHNH—SO$_2$—, CH$_3$CH$_2$NH—C(=O)—CH$_2$—O—, (CH$_3$)$_2$CHNH—C(=O)—CH$_2$—O—, CH$_3$—C(=O)—NH—SO$_2$—, CH$_3$—O—C(=O)—NH—SO$_2$—, CH$_3$—O—NH—SO$_2$—, CH$_3$—SO$_2$—NH—C(=O)—, CH$_3$—SO$_2$—N(CH$_3$)—C(=O)—, CH$_3$—SO$_2$—NH—, CH$_3$—C(=O)—NH—, CH$_3$O—CH$_2$—C(=O)—NH—, CH$_3$CH$_2$NH—C(=O)—NH—, HO$_2$C—CH$_2$CH$_2$—, HO$_2$C—CH(CH$_3$)—, HO$_2$C—C(CH$_3$)$_2$—, HO$_2$C—CH$_2$—O—CH$_2$—, HOCH$_2$—, HO—CH(CH$_3$)—, HO—C(CH$_3$)$_2$—, NC—CH$_2$—, CH$_3$OCH$_2$—C(=O)—NH—CH$_2$—,

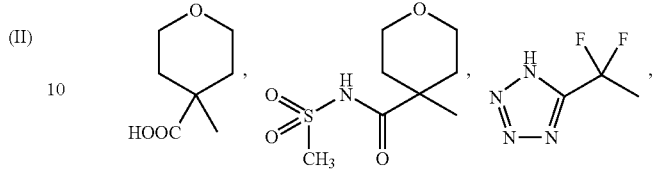

HO$_2$C—CF$_2$—, CH$_3$CH$_2$SO$_2$NHC(=O)—C(CH$_3$)$_2$—, PhCH$_2$SO$_2$NHC(=O)—C(CH$_3$)$_2$—, CH$_3$CH$_2$SO$_2$NHC(=O)—CF$_2$—,

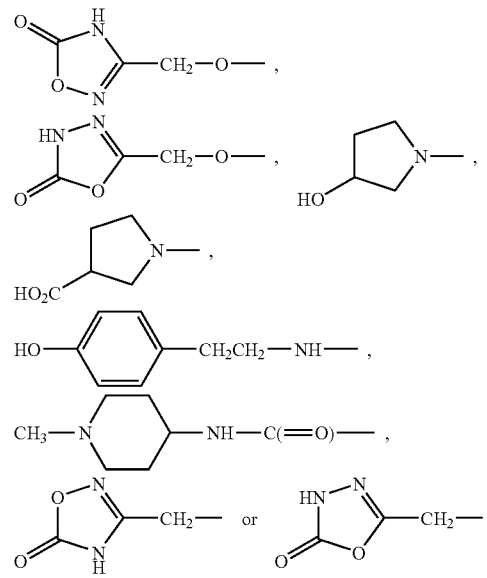

or an N-oxide thereof, or a pharmaceutically acceptable salt or hydrate thereof.

23. The compound according to claim 20 wherein $Cy^1$ is benzimidazol-2-yl, benzimidazol-5-yl, benzo[1,3]dioxol-5-yl, benzothiazol-6-yl, benzo[b]thiophen-2-yl, benzo[b]thiophen-3-yl, 1H-benzotriazol-6-yl, 2,3-dihydro-benzo[1,4]dioxin-6-yl, 2,3-dihydrobenzofuran-5-yl, 3,4-dihydro-2H-benzo[1,4]oxazin-7-yl, furan-2-yl, furan-3-yl, imidazol-1-yl, 1H-indazol-6-yl, indolin-5-yl, indol-3-yl, indol-5-yl, indol-6-yl isoquinolin-5-yl, isoxazol-4-yl, [1,2,4]oxadiazol-5-yl, [1,3,4]oxadiazol-2-yl, oxazol-5-yl, 2-oxo-1H-pyridin-5-yl, phenyl, pyrazol-1-yl, pyrazol-3-yl, pyrazol-4-yl, pyrid-3-yl, pyrid-4-yl, thiazol-2-yl, quinolin-3-yl, quinolin-6-yl, quinolin-8-yl, thien-2-yl, thien-3-yl or piperidin-1-yl, each of which is optionally substituted with one to three of same or different substituent groups of:

acyl, carboxy, heteroaryl, $R^2$—C(=N—OR$^3$)—, $Y^1Y^2NC(=O)$—; or alkyl, which is optionally substituted by carboxy, heteroaryl or hydroxy;

wherein the heteroaryl moieties in the substituent groups are optionally independently substituted by hydroxy, amino, alkyl or alkoxy;

or an N-oxide thereof, or a pharmaceutically acceptable salt or hydrate thereof.

24. The compound according to claim 20 wherein $Cy^1$ is benzimidazol-2-yl, benzimidazol-5-yl, benzo[1,3]dioxol-5-yl, benzothiazol-6-yl, benzo[b]thiophen-2-yl, benzo[b]thiophen-3-yl, 1H-benzotriazol-6-yl, 2,3-dihydro-benzo[1,4]dioxin-6-yl, 2,3-dihydrobenzofuran-5-yl, 3,4-dihydro-2H-benzo[1,4]oxazin-7-yl, furan-2-yl, furan-3-yl, imidazol-1-yl, 1H-indazol-6-yl, indolin-5-yl, indol-3-yl, indol-5-yl, indol-6-yl isoquinolin-5-yl, isoxazol-4-yl, [1,2,4]oxadiazol-5-yl, [1,3,4]oxadiazol-2-yl, oxazol-5-yl, 2-oxo-1H-pyridin-5-yl, phenyl, pyrazol-1-yl, pyrazol-3-yl, pyrazol-4-yl, pyrid-3-yl, pyrid-4-yl, thiazol-2-yl, quinolin-3-yl, quinolin-6-yl, quinolin-8-yl, thien-2-yl, thien-3-yl or piperidin-1-yl, each of which is optionally substituted with one to three of same or different substituent groups of formyl, acetyl, methyl, methoxy, carboxy, oxazol-5-yl, tetrazol-5-yl, $HO_2C—CH_2—$, $HOCH_2—$, $HO—CH(CH_3)—$, $H—C(=N—OH)—$, $H—C(=N—OCH_3)—$, $CH_3—C(=N—OH)—$, $CH_3—C(=N—OCH_3)—$, $CH_3NH—C(=O)—$,

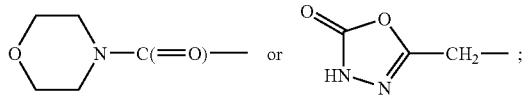

or an N-oxide thereof, or a pharmaceutically acceptable salt or hydrate thereof.

25. The compound according to claim 20 wherein $Cy^2$ is naphthyl or phenyl, each of which is optionally substituted with one to three of same or different substituent groups of alkoxy, $(C_1-C_3)$-alkyl, hydroxy, cyano, halogen, haloalkoxy, haloalkyl, nitro, $Y^1Y^2N—$, $Y^1Y^2N—SO_2—$, aryl or heteroaryl, wherein the aryl is optionally substituted by alkyl or hydroxyalkyl, and the heteroaryl is optionally substituted by alkyl; or an N-oxide thereof, or a pharmaceutically acceptable salt or hydrate thereof.

26. The compound according to claim 20 wherein $Cy^2$ is naphthyl or phenyl, each of which is optionally substituted with one to three of same or different substituent groups of methoxy, methyl, ethyl, cyano, bromo, chloro, fluoro, $F_2HCO—$, $F_3CO—$, $F_3C—$, nitro or 5-methyl-[1,3,4]oxadiazol-2-yl; or an N-oxide thereof, or a pharmaceutically acceptable salt or hydrate thereof.

27. The compound according to claim 20 wherein $Cy^2$ is cyclohex-1-enyl, benzo[1,3]dioxol-5-yl, benzofuran-6-yl, 2,3-dihydro-benzofuran-2-yl, 3,4-dihydro-2H-benzo[1,4]oxazin-2-yl, benzo[b]thiophen-2-yl, imidazol-4-yl, 1H-indol-3-yl, 1H-indol-5-yl, naphthalene-2-yl, isochroman-1-yl, pyridin-2-yl, pyridin-3-yl, pyridin-4-yl or thien-2-yl; or an N-oxide thereof, or a pharmaceutically acceptable salt or hydrate thereof.

28. The compound according to claim 20 wherein $Cy^2$ is benzo[1,3]dioxol-5-yl, 2,2-difluoro-benzo[1,3]dioxol-5-yl pyridin-4-yl or thien-2-yl; or an N-oxide thereof, or a pharmaceutically acceptable salt or hydrate thereof.

29. The compound according to claim 20 wherein $Cy^1$ is phenyl, which is optionally substituted with one to three same or different substituent groups of:
acyl, carboxy, cyano, halo, heteroaryl, heterocyclyl, hydroxy, $R^2—C(=N—OR^3)—$, $Y^1Y^2NC(=O)—$, $Y^1Y^2NC(=O)—O—$, alkyl-O—C(=O)—N(R^5)—SO_2—$, alkyl-SO_2—N(R^5)—C(=O)—$;
alkoxy, which is optionally substituted by carboxy or heteroaryl; or alkyl, which is optionally substituted by halogen, carboxy, heteroaryl, hydroxy, $R^6—C(=O)—N(R^5)—$, $R^8—SO_2—N(R^5)—C(=O)—$; or alkoxy, which is optionally substituted by carboxy;
wherein
the heterocyclyl moieties in the substituent groups are optionally independently substituted by hydroxy, amino, alkyl, alkoxy, oxo, carboxy, alkoxycarbonyl or $R^8—SO_2—N(R^5)—C(=O)—$;
the heteroaryl moieties in the substituent groups are optionally independently substituted by hydroxy, amino, alkyl, alkoxy, carboxy, alkoxycarbonyl or $R^8—SO_2—N(R^5)—C(=O)—$;
or an N-oxide thereof, or a pharmaceutically acceptable salt or hydrate thereof.

30. The compound according to claim 20 wherein $Cy^1$ is phenyl, which is optionally substituted with one to three of same or different substituent groups of formyl, methoxy, carboxy, chloro, fluoro, cyano, tetrazol-5-yl, 1H-tetrazol-5-ylmethyl, $HO_2C—CH_2—O—$, $HO_2C—C(CH_3)_2—O—$, $H—C(=N—OH)—$, $CH_3NHC(=O)—$, $CH_3CH_2NH—C(=O)—O—$, $CH_3—O—C(=O)—NH—SO_2—$, $CH_3—SO_2—NH—C(=O)—$, $HO_2C—CH(CH_3)—$, $HO_2C—C(CH_3)_2—$, $HO_2C—CH_2—O—CH_2—$, $HOCH_2—$,

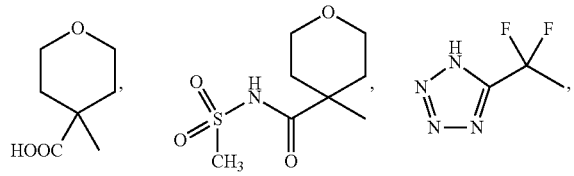

$HO_2C—CF_2—$, $CH_3CH_2SO_2NHC(=O)—C(CH_3)_2—$, $PhCH_2SO_2NHC(=O)—C(CH_3)_2—$, $CH_3CH_2SO_2NHC(=O)—CF_2—$,

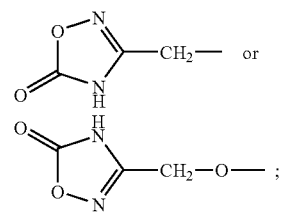

or an N-oxide thereof, or a pharmaceutically acceptable salt or hydrate thereof.

31. The compound according to claim 20 wherein $Cy^1$ is:

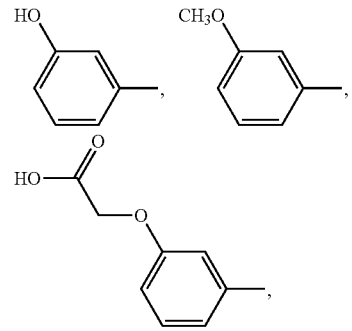

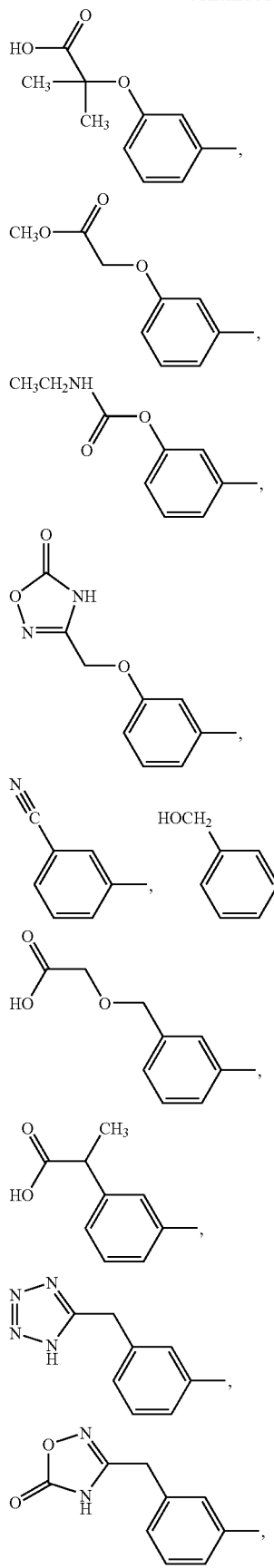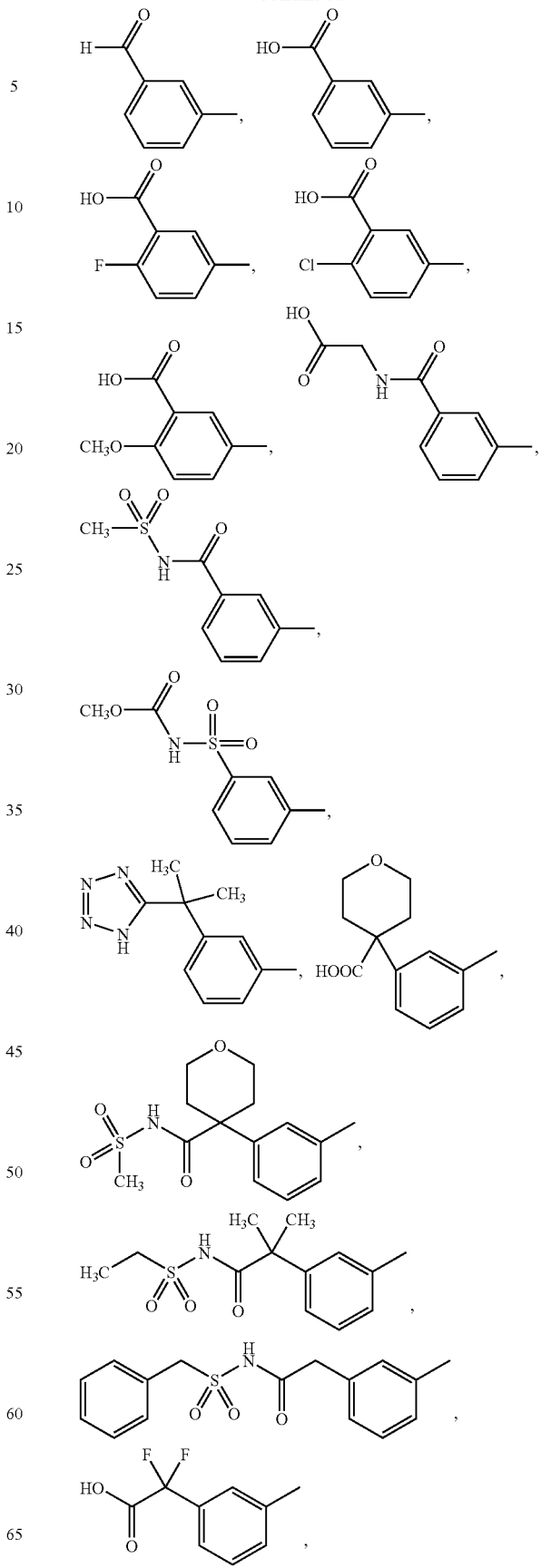

-continued

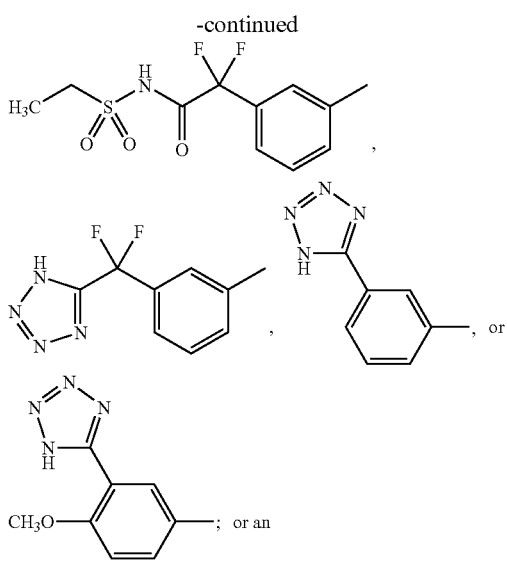

; or an

N-oxide thereof, or a pharmaceutically acceptable salt or hydrate thereof.

32. The compound according to claim 20 wherein $Cy^1$ is 1H-benzotriazol-6-yl, 1H-indazol-6-yl, indol-5-yl, indol-6-yl, 2-oxo-1H-pyridin-5-yl, quinolin-6-yl, quinolin-3-yl, thien-2-yl, thien-3-yl or 1-piperidin-1-yl, each of which is optionally substituted by one to three of same or different groups of acyl, carboxy, tetrazol-5-yl; $R^2$—C(=N—OR$^3$)—, $Y^1Y^2$NC(=O)—; or alkyl, which is optionally substituted by carboxy or hydroxy; or an N-oxide thereof, or a pharmaceutically acceptable salt or hydrate thereof.

33. The compound according to claim 20 wherein $Cy^1$ is 1H-benzotriazol-6-yl, 1H-indazol-6-yl, indol-5-yl, indol-6-yl, 2-oxo-1H-pyridin-5-yl, quinolin-6-yl, quinolin-3-yl, thien-2-yl, thien-3-yl or 1-piperidin-1-yl, each of which is optionally substituted by one to three of same or different groups of formyl, carboxy, tetrazol-5-yl, H—C(=N—OH)—, $CH_3$—C(=N—OH)—, $CH_3$—NH—C(=O)—, $HO_2$C—$CH_2$—, or HO—$CH_2$—; or an N-oxide thereof, or a pharmaceutically acceptable salt or hydrate thereof.

34. The compound according to claim 20 wherein $Cy^1$ is:

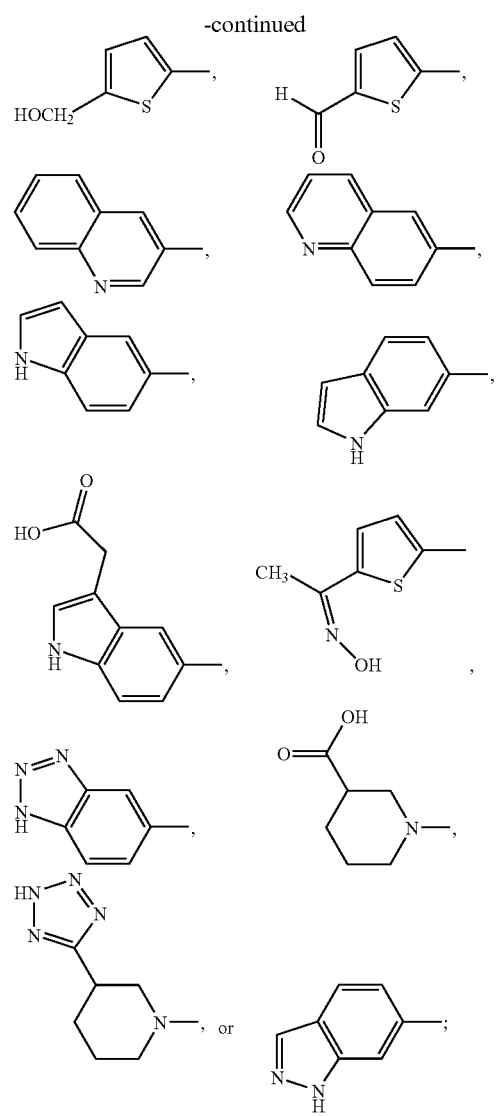

or an N-oxide thereof, or a pharmaceutically acceptable salt or hydrate thereof.

35. The compound according to claim 20 wherein $Cy^2$ is 4-chlorophenyl, 2,4-dichlorophenyl, 2,6-dichlorophenyl, 2,6-difluorophenyl, 2-fluoro-6-chlorophenyl, 3-fluoro-4-methoxyphenyl, 4-fluorophenyl, 2-fluoro-4-trifluoromethylphenyl, 4-methoxyphenyl, 4-nitrophenyl, 2,2-difluoro-benzo[1,3]dioxol-5-yl or 4-trifluoromethoxyphenyl; or an N-oxide thereof, or a pharmaceutically acceptable salt or hydrate thereof.

36. The compound according to claim 1, which is
3-{6-[2-(3-fluoro-4-methoxy-phenyl)-ethylamino]-2-methoxy-pyrimidin-4-yl}-benzonitrile,
[6-(3-amino-phenyl)-2-methoxy-pyrimidin-4-yl]-[2-(4-methoxy-phenyl)-ethyl]amine,
3-{2-methoxy-6-[2-(4-methoxy-phenyl)-ethylamino]-pyrimidin-4-yl}-benzenesulfonamide,
3-{2-methoxy-6-[2-(4-methoxy-phenyl)-ethylamino]-pyrimidin-4-yl}-N-methyl-benzenesulfonamide,
N-ethyl-3-{2-methoxy-6-[2-(4-methoxy-phenyl)-ethylamino]-pyrimidin-4-yl}-benzenesulfonamide,
N-methoxycarbonyl-3-{2-methoxy-6-[2-(4-methoxy-phenyl)-ethylamino]-pyrimidin-4-yl}-benzenesulfonamide, 6-(3-amino-phenyl)-2-methoxy-pyrimidin-4-yl]-[2-(4-trifluoromethoxy-phenyl)-ethyl]-amine,
N-(3-{2-methoxy-6-[2-(4-trifluoromethoxy-phenyl)-ethylamino]-pyrimidin-4-yl}-phenyl)-acetamide,
N-(3-{2-methoxy-6-[2-(4-methoxy-phenyl)-ethylamino]-pyrimidin-4-yl}-phenyl)-acetamide,
(3-{2-methoxy-6-[2-(4-methoxy-phenyl)-ethylamino]-pyrimidin-4-yl}-phenyl)-carbamic acid ethyl ester,
3-{6-[2-(2,4-difluoro-phenyl)-ethylamino]-2-methoxy-pyrimidin-4-yl}-benzoic acid,
5-{2-methoxy-6-[2-(4-methoxy-phenyl)-ethylamino]-pyrimidin-4-yl}-thiophene-2-carboxylic acid
5-{2-methoxy-6-[2-(4-methoxy-phenyl)-ethylamino]-pyrimidin-4-yl}-thiophene-2-carbaldehyde,
4-{2-methoxy-6-[2-(4-methoxy-phenyl)-ethylamino]-pyrimidin-4-yl}-thiophene-2-carbaldehyde,
[6-(3,5-dimethyl-isoxazol-4-yl)-2-methoxy-pyrimidin-4-yl]-[2-(4-methoxy-phenyl)-ethyl]-amine,
[2-methoxy-6-(5-methyl-thiophen-2-yl)-pyrimidin-4-yl]-[2-(4-methoxy-phenyl)-ethyl]-amine,
[2-(4-methoxy-phenyl)-ethyl]-[2-methoxy-6-(1-pyrazol-4-yl)-pyrimidin-4-yl]-amine,
(6-isoquinolin-5-yl-2-methoxy-pyrimidin-4-yl)-[2-(4-methoxy-phenyl)-ethyl]-amine,
(5-{2-methoxy-6-[2-(4-methoxy-phenyl)-ethylamino]-pyrimidin-4-yl}-thiophen-2-yl)-methanol,
(3-{2-methoxy-6-[2-(4-methoxy-phenyl)-ethylamino]-pyrimidin-4-yl}-thiophen-2-yl)-methanol,
(3-{2-methoxy-6-[2-(4-methoxy-phenyl)-ethylamino]-pyrimidin-4-yl}-phenyl)-methanol,
(3-{6-[2-(2-chloro-6-fluoro-phenyl)-ethylamino]-2-methoxy-pyrimidin-4-yl}-phenyl)-methanol,
[2-(4-methoxy-phenyl)-ethyl]-(2-methoxy-6-quinolin-6-yl-pyrimidin-4-yl)-amine,
[2-(4-methoxy-phenyl)-ethyl]-(2-methoxy-6-quinolin-3-yl-pyrimidin-4-yl)-amine,
[6-(1H-indol-5-yl)-2-methoxy-pyrimidin-4-yl]-[2-(4-methoxy-phenyl)-ethyl]-amine,
N-(2-{2-methoxy-6-[2-(4-methoxy-phenyl)-ethylamino]-pyrimidin-4-yl}-phenyl)-methanesulfonamide,
4-{2-methoxy-6-[2-(4-methoxy-phenyl)-ethylamino]-pyrimidin-4-yl}-benzamide,
[2-methoxy-6-(1-methyl-1-indol-5-yl)-pyrimidin-4-yl]-[2-(4-methoxy-phenyl)-ethyl]-amine,
(6-benzo[b]thiophen-2-yl-2-methoxy-pyrimidin-4-yl)-[2-(4-methoxy-phenyl)-ethyl]-amine,
1-(4-{2-methoxy-6-[2-(4-methoxy-phenyl)-ethylamino]-pyrimidin-4-yl}-phenyl)-ethanone,
[6-(3-methanesulfonyl-phenyl)-2-methoxy-pyrimidin-4-yl]-[2-(4-methoxy-phenyl)-ethyl]-amine,
[6-(2,3-dihydro-benzofuran-5-yl)-2-methoxy-pyrimidin-4-yl]-[2-(4-methoxy-phenyl)-ethyl]-amine,
[2-methoxy-6-(4-morpholin-4-yl-phenyl)-pyrimidin-4-yl]-[2-(4-methoxy-phenyl)-ethyl]-amine,
[6-(4-dimethylamino-phenyl)-2-methoxy-pyrimidin-4-yl]-[2-(4-methoxy-phenyl)-ethyl]-amine,
[2-methoxy-6-(5-oxazol-5-yl-thiophen-2-yl)-pyrimidin-4-yl]-[2-(4-methoxy-phenyl)-ethyl]-amine,
2-methoxy-6-(3-oxazol-5-yl-phenyl)-pyrimidin-4-yl]-[2-(4-methoxy-phenyl)-ethyl]-amine,
[6-(5-difluoromethyl-thiophen-2-yl)-2-methoxy-pyrimidin-4-yl]-[2-(4-methoxy-phenyl)-ethyl]-amine,
[2-(4-methoxy-phenyl)-ethyl]-[2-methoxy-6-(5-pyrrolidin-1-ylmethyl-thiophen-2-yl)-pyrimidin-4-yl]-amine,
6-{4-fluoro-3-[(2-methoxy-ethylamino)-methyl]-phenyl}-2-methoxy-pyrimidin-4-yl)-[2-(4-methoxy-phenyl)-ethyl]-amine,
4-[2-(3-{2-methoxy-6-[2-(4-methoxy-phenyl)-ethylamino]-pyrimidin-4-yl}-benzylamino)-ethyl]-phenol,
N-(2-fluoro-5-{2-methoxy-6-[2-(4-methoxy-phenyl)-ethylamino]-pyrimidin-4-yl}-benzyl)-N',N'-dimethyl-ethane-1,2-diamine,
[6-(1H-benzoimidazol-5-yl)-2-methoxy-pyrimidin-4-yl]-[2-(4-methoxy-phenyl)-ethyl]-amine,
[6-(1H-benzotriazol-5-yl)-2-methoxy-pyrimidin-4-yl]-[2-(4-methoxy-phenyl)-ethyl]-amine,
[2-(3,4-dimethoxy-phenyl)-ethyl]-[6-(3,4-dimethoxy-phenyl)-2-isopropoxy-pyrimidin-4-yl]-amine,
[6-(3,4-dimethoxy-phenyl)-2-ethoxy-pyrimidin-4-yl]-[2-(3,4-dimethoxy-phenyl)-ethyl]-amine,
2-fluoro-5-{2-methoxy-6-[2-(4-methoxy-phenyl)-ethylamino]-pyrimidin-4-yl}-benzoic acid,
3-{6-[2-(2-chloro-6-fluoro-phenyl)-ethylamino]-2-methoxy-pyrimidin-4-yl}-benzoic acid,
2-methoxy-5-{2-methoxy-6-[2-(4-methoxy-phenyl)-ethylamino]-pyrimidin-4-yl}-benzoic acid,
[2-methoxy-6-(1-oxy-pyridin-3-yl)-pyrimidin-4-yl]-[2-(4-methoxy-phenyl)-ethyl]-amine,
[2-(2,2-difluoro-benzo[1,3]dioxol-5-yl)-ethyl]-[2-methoxy-6-(1-oxy-pyridin-3-yl)-pyrimidin-4-yl]-amine,
2-(3-{2-methoxy-6-[2-(4-methoxy-phenyl)-ethylamino]-pyrimidin-4-yl}-phenoxy)-2-methyl-propionic acid ethyl ester,
(3-{2-methoxy-6-[2-(4-methoxy-phenyl)-ethylamino]-pyrimidin-4-yl}-phenoxy)-acetic acid methyl ester,
(3-{6-[2-(2,4-dichloro-phenyl)-ethylamino]-2-methoxy-pyrimidin-4-yl}-phenoxy)-acetic acid methyl ester,
(5-{6-[2-(2-chloro-6-fluoro-phenyl)-ethylamino]-2-methoxy-pyrimidin-4-yl}-2-oxo-2H-pyridin-1-yl)-acetic acid methyl ester,
(3-{6-[2-(2,4-dichloro-phenyl)-ethylamino]-2-methoxy-pyrimidin-4-yl}-phenoxy)-acetonitrile,
(3-{6-[2-(2-chloro-6-fluoro-phenyl)-ethylamino]-2-methoxy-pyrimidin-4-yl}-phenoxy)-acetonitrile,
2-(3-{2-methoxy-6-[2-(4-methoxy-phenyl)-ethylamino]-pyrimidin-4-yl}-phenoxy)-2-methyl-propionic acid,
(3-{2-methoxy-6-[2-(4-methoxy-phenyl)-ethylamino]-pyrimidin-4-yl}-phenoxy)-acetic acid,
(5-{6-[2-(2-chloro-6-fluoro-phenyl)-ethylamino]-2-methoxy-pyrimidin-4-yl}-2-oxo-2H-pyridin-1-yl)-acetic acid,
2-(3-{6-[2-(2,4-dichloro-phenyl)-ethylamino]-2-methoxy-pyrimidin-4-yl}-phenoxy)-2-methyl-propionic acid,
2-chloro-5-{2-methoxy-6-[2-(4-methoxy-phenyl)-ethylamino]-pyrimidin-4-yl}-benzoic acid,
[2-(4-methoxy-phenyl)-ethyl]-{2-methoxy-6-[3-(1H-tetrazol-5-yl)-phenyl]-pyrimidin-4-yl}-amine,
[2-(4-methoxy-phenyl)-ethyl]-{2-methoxy-6-[3-(1H-tetrazol-5-ylmethyl)-phenyl]-pyrimidin-4-yl}-amine,
{2-methoxy-6-[4-methoxy-3-(1H-tetrazol-5-yl)-phenyl]-pyrimidin-4-yl}-[2-(4-methoxy-phenyl)-ethyl]-amine,
N-(3-{2-methoxy-6-[2-(4-methoxy-phenyl)-ethylamino]-pyrimidin-4-yl}-benzoyl)-methanesulfonamide,
3-{6-[2-(3,4-dimethoxy-phenyl)-ethylamino]-2-methoxy-pyrimidin-4-yl}-N-(2-pyrrolidin-1-yl-ethyl)-benzamide,
2-fluoro-5-{2-methoxy-6-[2-(4-methoxy-phenyl)-ethylamino]-pyrimidin-4-yl}-benzaldehyde oxime,
3-{2-methoxy-6-[2-(4-methoxy-phenyl)-ethylamino]-pyrimidin-4-yl}-benzaldehyde oxime,
2-methoxy-5-{2-methoxy-6-[2-(4-methoxy-phenyl)-ethylamino]-pyrimidin-4-yl}-benzaldehyde oxime, 3-{2-methoxy-6-[2-(4-methoxy-phenyl)-ethylamino]-pyrimidin-4-yl}-thiophene-2-carbaldehyde oxime,
1-(5-{2-methoxy-6-[2-(4-methoxy-phenyl)-ethylamino]-pyrimidin-4-yl}-thiophen-2-yl)-ethanone oxime,
5-{2-methoxy-6-[2-(4-methoxy-phenyl)-ethylamino]-pyrimidin-4-yl}-thiophene-2-carbaldehyde oxime,
[6-(3-aminomethyl-4-fluoro-phenyl)-2-methoxy-pyrimidin-4-yl]-[2-(4-methoxy-phenyl)-ethyl]-amine,
N-(2-Fluoro-5-{2-methoxy-6-[2-(4-methoxy-phenyl)-ethylamino]-pyrimidin-4-yl}-benzyl)-2-methoxy-acetamide,
[2-methoxy-6-(3-methoxy-phenyl)-pyrimidin-4-yl]-[2-(4-methoxy-phenyl)-2-methyl-propyl]-amine,
5-{6-[2-(2-chloro-6-fluoro-phenyl)-ethylamino]-2-methoxy-pyrimidin-4-yl}-1H-pyridin-2-one,
5-{6-[2-(2-chloro-6-fluoro-phenyl)-ethylamino]-2-methoxy-pyrimidin-4-yl}-1-(5-oxo-4,5-dihydro-[1,3,4]oxadiazol-2-ylmethyl)-1H-pyridin-2-one,
3-(3-{6-[2-(2,4-dichloro-phenyl)-ethylamino]-2-methoxy-pyrimidin-4-yl-phenoxymethyl)-4H-[1,2,4]oxadiazol-5-one,
3-(3-{6-[2-(2-chloro-6-fluoro-phenyl)-ethylamino]-2-methoxy-pyrimidin-4-yl}-benzyl)-4H-[1,2,4]oxadiazol-5-one,
3-(3-{6-[2-(2-chloro-6-fluoro-phenyl)-ethylamino]-2-methoxy-pyrimidin-4-yl}-phenoxymethyl)-4H-[1,2,4]oxadiazol-5-one,
3-{2-methoxy-6-[2-(4-methoxy-phenyl)-ethylamino]-pyrimidin-4-yl}-benzoic acid,
3-{2-methoxy-6-[2-(4-trifluoromethoxy-phenyl)-ethylamino]-pyrimidin-4-yl}-benzoic acid,
[2-(3,4-dimethoxy-phenyl)-ethyl]-(methoxy-6-thiophen-2-yl-pyrimidin-4-yl)amine,
[2-(3,4-dimethoxy-phenyl)-ethyl]-(6-furan-2-yl-2-methoxy-pyrimidin-4-yl)-amine,
(6-biphenyl-4-yl-2-methoxy-pyrimidin-4-yl)-[2-(3,4-dimethoxy-phenyl)-ethyl]-amine,
3-{6-[2-(4-fluoro-phenyl)-ethylamino]-2-methoxy-pyrimidin-4-yl}-benzoic acid,
3-{2-methoxy-6-[2-(4-methoxy-phenyl)-ethylamino]-pyrimidin-4-yl}-benzamide,
1-(3-{2-methoxy-6-[2-(4-methoxy-phenyl)-ethylamino]-pyrimidin-4-yl}-phenyl)-ethanone,
3-{6-[2-(2,4-dichloro-phenyl)-ethylamino]-2-methoxy-pyrimidin-4-yl}-phenol,
2-fluoro-5-{2-methoxy-6-[2-(4-methoxy-phenyl)-ethylamino]-pyrimidin-4-yl}-benzaldehyde,
3-{6-[2-(3,4-dimethoxy-phenyl)-ethylamino]-2-methoxy-pyrimidin-4-yl}-benzoic acid,
3-{2-methoxy-6-[2-(4-methoxy-phenyl)-ethylamino]-pyrimidin-4-yl}-thiophene-2-carbaldehyde,
1-(5-{2-methoxy-6-[2-(4-methoxy-phenyl)-ethylamino]-pyrimidin-4-yl}-thiophen-2-yl)-ethanone,
3-{6-[2-(4-chlorophenyl)-ethylamino]-2-methoxy-pyrimidin-4-yl}-benzoic acid,
[2-methoxy-6-(6-methoxy-pyridin-3-yl)-pyrimidin-4-yl]-[2-(4-methoxy-phenyl)-ethyl]-amine,
3-{2-methoxy-6-[2-(4-methoxy-phenyl)-ethylamino]-pyrimidin-4-yl}-phenol,
[2-(4-methoxy-phenyl)-ethyl]-(2-methoxy-6-pyridin-4-yl-pyrimidin-4-yl)-amine,
2-{2-methoxy-6-[2-(4-methoxy-phenyl)-ethylamino]-pyrimidin-4-yl}-phenol,
(3-{2-methoxy-6-[2-(4-methoxy-phenyl)-ethylamino]-pyrimidin-4-yl}-phenyl)-acetonitrile,
3-{2-methoxy-6-[2-(4-methoxy-phenyl)-ethylamino]-pyrimidin-4-yl}-benzonitrile,
3-{2-methoxy-6-[2-(4-methoxy-phenyl)-ethylamino]-pyrimidin-4-yl}-benzaldehyde,
3-{6-[2-(2-chloro-6-fluoro-phenyl)-ethylamino]-2-methoxy-pyrimidin-4-yl}-benzaldehyde,
3-{6-[2-(2,4-dichloro-phenyl)-ethylamino]-2-methoxy-pyrimidin-4-yl}-benzoic acid,
[2-methoxy-6-(pyridin-3-yl)-pyrimidin-4-yl]-[2-(4-methoxy-phenyl)-ethyl]-amine,
2-methoxy-5-{2-methoxy-6-[2-(4-methoxy-phenyl)-ethylamino]-pyrimidin-4-yl}-benzaldehyde,
2-chloro-5-{2-methoxy-6-[2-(4-methoxy-phenyl)-ethylamino]-pyrimidin-4-yl}-benzoic acid ethyl ester,
{2-methoxy-6-[3-(3-methyl-[1,2,4]oxadiazol-5-yl)-phenyl]-pyrimidin-4-yl}-[2-(4-methoxy-phenyl)-ethyl]-amine,
{2-methoxy-6-[3-(5-methyl-2H-[1,2,4]triazol-3-yl)-phenyl]-pyrimidin-4-yl}-[2-(4-methoxy-phenyl)-ethyl]-amine,
{2-methoxy-6-[3-(3-methyl-isoxazol-5-yl)-phenyl]-pyrimidin-4-yl}-[2-(4-methoxy-phenyl)-ethyl]-amine,
{2-methoxy-6-[3-(5-methyl-2H-pyrazol-3-yl)-phenyl]-pyrimidin-4-yl}-[2-(4-methoxy-phenyl)-ethyl]-amine,
[2-(3-fluoro-4-methoxy-phenyl)-ethyl]-{2-methoxy-6-[3-(2H-tetrazol-5-yl)-phenyl]-pyrimidin-4-yl}-amine,
1-ethyl-3-(3-{2-methoxy-6-[2-(4-methoxy-phenyl)-ethylamino]-pyrimidin-4-yl}-phenyl)-urea,
2-(3-{6-[2-(2,4-dichloro-phenyl)-ethylamino]-2-methoxy-pyrimidin-4-yl}-phenoxy)-2-methyl-propionic acid ethyl ester,
[2-(4-chloro-phenyl)-1-methyl-ethyl]-[6-(3,4-dimethoxy-phenyl)-2-methoxy-pyrimidin-4-yl]-amine,
[2-methoxy-6-(3-methoxy-phenyl)-pyrimidin-4-yl]-[2-(4-nitro-phenyl)-ethyl]-amine,
[2-methoxy-6-(3-methoxy-phenyl)-pyrimidin-4-yl]-[2-(4-trifluoromethoxy-phenyl)-ethyl]-amine,
[2-(2-chloro-6-fluoro-phenyl)-ethyl]-[2-methoxy-6-(3-methoxy-phenyl)-pyrimidin-4-yl]-amine,
[2-methoxy-6-(3-methoxy-phenyl)-pyrimidin-4-yl]-(2-thiophen-2-yl-ethyl)-amine,
3-{2-[2-methoxy-6-(3-methoxy-phenyl)-pyrimidin-4-ylamino]-ethyl}-1H-indol-5-ol,
[2-(6-methoxy-1H-indol-3-yl)-ethyl]-[2-methoxy-6-(3-methoxy-phenyl)-pyrimidin-4-yl]-amine,
[2-(5-methoxy-1H-indol-3-yl)-ethyl]-[2-methoxy-6-(3-methoxy-phenyl)-pyrimidin-4-yl]-amine,
[2-methoxy-6-(3-methoxy-phenyl)-pyrimidin-4-yl]-(2-pyridin-3-yl-ethyl)-amine,
[2-(4-amino-phenyl)-ethyl]-[2-methoxy-6-(3-methoxy-phenyl)-pyrimidin-4-yl]-amine,
(4-methoxy-benzyl)-[2-methoxy-6-(3-methoxy-phenyl)-pyrimidin-4-yl]-amine,
[2-methoxy-6-(3-methoxy-phenyl)-pyrimidin-4-yl]-(3-phenyl-propyl)-amine,
[2-(1H-imidazol-4-yl)-ethyl]-[2-methoxy-6-(3-methoxy-phenyl)-pyrimidin-4-yl]-amine,
(2S)-2-[2-methoxy-6-(3-methoxy-phenyl)-pyrimidin-4-ylamino]-3-(4-methoxy-phenyl)-propionic acid,
[2-methoxy-6-(3-methoxy-phenyl)-pyrimidin-4-yl]-[2-(4-methoxy-phenyl)-ethyl]-amine,
[2-methoxy-6-(5-methyl-[1,3,4]oxadiazol-2-yl)-pyrimidin-4-yl]-[2-(4-methoxy-phenyl)-ethyl]-amine,
(2-methoxy-6-oxazol-5-yl-pyrimidin-4-yl)-[2-(4-methoxy-phenyl)-ethyl]-amine;
3-{6-[2-(2,2-difluoro-benzo[1,3]dioxol-5-yl)-ethylamino]-2-methoxy-pyrimidin-4-yl}-benzoic acid,
[2-(2,2-difluoro-benzo[1,3]dioxol-5-yl)-ethyl]-(2-methoxy-6-pyridin-3-yl-pyrimidin-4-yl)-amine, N-(3-{6-[2-(4-difluoromethoxy-phenyl)-ethylamino]-2-methoxy-pyrimidin-4-yl}-phenyl)-acetamide,
[2-(4-difluoromethoxy-phenyl)-ethyl]-[6-(3-methanesulfonyl-phenyl)-2-methoxy-pyrimidin-4-yl]-amine,
3-{6-[2-(2-chloro-6-fluoro-phenyl)-ethylamino]-2-methoxy-pyrimidin-4-yl}-phenol,
[2-Methoxy-6-(2-methoxy-benzyloxy)-pyrimidin-4-yl]-[2-(4-methoxy-phenyl)-ethyl]-amine,
2-(3-{6-[2-(2,4-dichloro-phenyl)-ethylamino]-2-methoxy-pyrimidin-4-yl}-phenyl)-propionic acid,
(5-{6-[2-(2-fluoro-4-trifluoromethyl-phenyl)-ethylamino]-2-methoxy-pyrimidin-4-yl}-1H-indol-3-yl)-acetic acid,
[6-(1H-indol-6-yl)-2-methoxy-pyrimidin-4-yl]-[2-(4-methoxy-phenyl)-ethyl]-ammonium trifluoroacetate,
[6-(1H-indazol-6-yl)-2-methoxy-pyrimidin-4-yl]-[2-(4-methoxy-phenyl)-ethyl]-amine,
3-{6-[2-(2,6-dichloro-phenyl)-ethylamino]-2-methoxy-pyrimidin-4-yl}-benzoic acid,
2-methoxy-5-{2-methoxy-6-[2-(4-methoxy-phenyl)-ethylamino]-pyrimidin-4-yl}-benzonitrile,
(3-{6-[2-(2-chloro-6-fluoro-phenyl)-ethylamino]-2-methoxy-pyrimidin-4-yl}-benzyloxy)-acetic acid,
(3-{6-[2-(2,4-dichloro-phenyl)-ethylamino]-2-methoxy-pyrimidin-4-yl}-benzoylamino)-acetic acid ethyl ester,
(3-{6-[2-(2,4-dichloro-phenyl)-ethylamino]-2-methoxy-pyrimidin-4-yl}-benzoylamino)-acetic acid,
ethyl-carbamic acid 3-{6-[2-(2,4-dichloro-phenyl)-ethylamino]-2-methoxy-pyrimidin-4-yl}-phenyl ester,
5-{2-methoxy-6-[2-(4-methoxy-phenyl)-ethylamino]-pyrimidin-4-yl}-thiophene-2-carboxylic acid,
5-{2-methoxy-6-[2-(4-methoxy-phenyl)-ethylamino]-pyrimidin-4-yl}-thiophene-2-carboxylic acid methylamide,
(3-{6-[2-(3,4-dimethoxy-phenyl)-ethylamino]-2-methoxy-pyrimidin-4-yloxy}-benzoic acid methyl ester,
N-[2-(3-{6-[2-(2-fluoro-4-trifluoromethyl-phenyl)-ethylamino]-2-methoxy-pyrimidin-4-yl}-phenyl)-ethyl]-2-methoxy-acetamide,
N-[2-(3-{6-[2-(2-fluoro-4-trifluoromethyl-phenyl)-ethylamino]-2-methoxy-pyrimidin-4-yl}-phenyl)-ethyl]-acetamide,
[2-(2-fluoro-4-trifluoromethyl-phenyl)-ethyl]-[2-methoxy-6-(3-oxiranylmethoxy-phenyl)-pyrimidin-4-yl]-amine,
2-{3-[6-(2,2-difluoro-2-phenyl-ethylamino)-2-methoxy-pyrimidin-4-yl]-phenyl}-2-methyl-propionic acid,
2-[3-(2-methoxy-6-{2-[4-(5-methyl-[1,3,4]oxadiazol-2-yl)-phenyl]-ethylamino}-pyrimidin-4-yl)-phenyl]-2-methyl-propionic acid,
5-(3-{6-[2-(3,4-difluoro-phenyl)-ethylamino]-2-methoxy-pyrimidin-4-yl}-phenoxymethyl)-1-ethyl-2,4-dihydro-[1,2,4]triazol-3-one,
2-(2-fluoro-5-{2-methoxy-6-[2-(4-trifluoromethoxy-phenyl)-ethylamino]-pyrimidin-4-yl}-phenyl)-2-methyl-propionic acid,
2-(3-{2-methoxy-6-[(thiophen-3-ylmethyl)-amino]-pyrimidin-4-yl}-phenyl)-2-methyl-propionic acid,
1-{6-[2-(2,4-dichloro-phenyl)-ethylamino]-2-methoxy-pyrimidin-4-yl}-piperidine-3-carboxylic acid,
1-(3-{6-[2-(2,4-dichloro-phenyl)-ethylamino]-2-methoxy-pyrimidin-4-yl}-phenyl)-cyclopentanecarboxylic acid,
3-{6-[2-(2,4-dichloro-phenyl)-ethylamino]-2-methoxy-pyrimidin-4-yl}-benzoic acid 2-morpholin-4-yl-ethyl ester,
3-{6-[2-(2,4-dichloro-phenyl)-ethylamino]-2-methoxy-pyrimidin-4-yl}-benzoic acid 2-(4-methyl-piperazin-1-yl)-ethyl ester,
3-{6-[2-(2,4-dichloro-phenyl)-ethylamino]-2-methoxy-pyrimidin-4-yl}-benzoic acid ethyl ester,
(3-{6-[2-(2,4-dichloro-phenyl)-ethylamino]-2-methoxy-pyrimidin-4-yl}-phenyl)-methanol,
(3'-chloro-4'-{2-[6-(3-hydroxymethyl-phenyl)-2-methoxy-pyrimidin-4-ylamino]-ethyl}-biphenyl-3-yl)-methanol,
4-(3-{6-[2-(2,4-dichloro-phenyl)-ethylamino]-2-methoxy-pyrimidin-4-yl}-phenyl)-tetrahydro-pyran-4-carboxylic acid,
N-[4-(3-{6-[2-(2,4-dichloro-phenyl)-ethylamino]-2-methoxy-pyrimidin-4-yl}-phenyl)-tetrahydro-pyran-4-carbonyl]-methanesulfonamide,
4-(3-{6-[2-(2,4-dichloro-phenyl)-ethylamino]-2-methoxy-pyrimidin-4-yl}-phenyl)-tetrahydro-pyran-4-carboxylic acid ethyl ester,
(3-{6-[2-(2,4-dichloro-phenyl)-ethylamino]-2-methoxy-pyrimidin-4-yl}-phenyl)-difluoro-acetic acid,
ethanesulfonic acid [2-(3-{6-[2-(2,4-dichloro-phenyl)-ethylamino]-2-methoxy-pyrimidin-4-yl}-phenyl)-2,2-difluoro-acetyl]-amide,
(3-{6-[2-(2,4-dichloro-phenyl)-ethylamino]-2-methoxy-pyrimidin-4-yl}-phenyl)-difluoro-acetic acid ethyl ester,
(3-{6-[2-(2,4-dichloro-phenyl)-ethylamino]-2-methoxy-pyrimidin-4-yl}-phenyl)-acetonitrile,
(3-{6-[2-(2,4-dichloro-phenyl)-ethylamino]-2-methoxy-pyrimidin-4-yl}-phenyl)-difluoro-acetonitrile,
[2-(2,4-dichloro-phenyl)-ethyl]-(6-{3-[difluoro-(1H-tetrazol-5-yl)-methyl]-phenyl}-2-methoxy-pyrimidin-4-yl)-amine,
2-{3-[6-(indan-1-ylamino)-2-methoxy-pyrimidin-4-yl]-phenyl}-2-methyl-propionic acid,
2-{3-[6-(indan-2-ylamino)-2-methoxy-pyrimidin-4-yl]-phenyl}-2-methyl-propionic acid,
N-[4-(3-{2-methoxy-6-[2-(4-trifluoromethoxy-phenyl)-ethylamino]-pyrimidin-4-yl}-phenyl)-tetrahydro-pyran-4-carbonyl]-methanesulfonamide,
4-(3-{2-methoxy-6-[2-(4-trifluoromethoxy-phenyl)-ethylamino]-pyrimidin-4-yl}-phenyl)-tetrahydro-pyran-4-carboxylic acid methyl ester,
5-{6-[2-(2,4-dichloro-phenyl)-ethylamino]-2-methoxy-pyrimidin-4-yl}-thiophene-2-carboxylic acid,
5-{2-Methoxy-6-[2-(4-trifluoromethoxy-phenyl)-ethylamino]-pyrimidin-4-yl}-2,3-dihydro-benzofuran-2-carboxylic acid,
2-(3-{6-[(2,3-dihydro-benzofuran-2-ylmethyl)-amino]-2-methoxy-pyrimidin-4-yl}-phenyl)-2-methyl-propionic acid,
2-(3-{6-[(isochroman-1-ylmethyl)-amino]-2-methoxy-pyrimidin-4-yl}-phenyl)-2-methyl-propionic acid,
2-(3-{2-methoxy-6-[(4-methyl-3,4-dihydro-2H-benzo[1,4]oxazin-2-ylmethyl)-amino]-pyrimidin-4-yl}-phenyl)-2-methyl-propionic acid,
2-(3-{6-[(Benzofuran-5-ylmethyl)-amino]-2-methoxy-pyrimidin-4-yl}-phenyl)-2-methyl-propionic acid,
N-(6-{6-[2-(2,4-dichloro-phenyl)-ethylamino]-2-methoxy-pyrimidin-4-yl}-benzothiazol-2-yl)-acetamide,
ethanesulfonic acid [2-(3-{6-[2-(2,4-dichloro-phenyl)-ethylamino]-2-methoxy-pyrimidin-4-yl}-phenyl)-2-methyl-propionyl]-amide,
N-[2-(3-{6-[2-(2,4-dichloro-phenyl)-ethylamino]-2-methoxy-pyrimidin-4-yl}-phenyl)-2-methyl-propionyl]-C-phenyl-methanesulfonamide, 2-(3-{6-[2-(2,4-dichloro-phenyl)-ethylamino]-2-methoxy-pyrimidin-4-yl}-phenyl)-2-methyl-1-morpholin-4-yl-propan-1-one,
2-(3-{6-[2-(2,4-dichloro-phenyl)-ethylamino]-2-methoxy-pyrimidin-4-yl}-phenyl)-N-(tetrahydro-pyran-4-yl)-isobutyramide,
2-(3-{6-[2-(2,4-dichloro-phenyl)-ethylamino]-2-methoxy-pyrimidin-4-yl}-phenyl)-N-(1H-tetrazol-5-yl)-isobutyramide,
1-{6-[2-(2,4-dichloro-phenyl)-ethylamino]-2-methoxy-pyrimidin-4-yl}-piperidine-4-carboxylic acid,
2-(2-chloro-5-{6-[2-(2,4-dichloro-phenyl)-ethylamino]-2-methoxy-pyrimidin-4-yl}-phenyl)-propan-2-ol,
2-(3-{6-[2-(2,4-dichloro-phenyl)-ethylamino]-2-methoxy-pyrimidin-4-yl}-4-fluoro-phenyl)-2-methyl-propionic acid, or or an N-oxide thereof, or a pharmaceutically acceptable salt or hydrate thereof.

37. The compound or the pharmaceutically acceptable salt according to claim 1, which is:
3-{6-[2-(3-fluoro-4-methoxy-phenyl)-ethylamino]-2-methoxy-pyrimidin-4-yl}-benzonitrile;
[6-(3-amino-phenyl)-2-methoxy-pyrimidin-4-yl]-[2-(4-methoxy-phenyl)-ethyl]amine;
3-{2-methoxy-6-[2-(4-methoxy-phenyl)-ethylamino]-pyrimidin-4-yl}-benzenesulfonamide;
3-{2-methoxy-6-[2-(4-methoxy-phenyl)-ethylamino]-pyrimidin-4-yl}-N-methyl-benzenesulfonamide;
N-ethyl-3-{2-methoxy-6-[2-(4-methoxy-phenyl)-ethylamino]-pyrimidin-4-yl}-benzenesulfonamide;
N-methoxycarbonyl-3-{2-methoxy-6-[2-(4-methoxy-phenyl)-ethylamino]-pyrimidin-4-yl}-benzenesulfonamide;
6-(3-amino-phenyl)-2-methoxy-pyrimidin-4-yl]-[2-(4-trifluoromethoxy-phenyl)-ethyl]-amine;
N-(3-{2-methoxy-6-[2-(4-trifluoromethoxy-phenyl)-ethylamino]-pyrimidin-4-yl}-phenyl)-acetamide;
N-(3-{2-methoxy-6-[2-(4-methoxy-phenyl)-ethylamino]-pyrimidin-4-yl}-phenyl)-acetamide;
(3-{2-methoxy-6-[2-(4-methoxy-phenyl)-ethylamino]-pyrimidin-4-yl}-phenyl)-carbamic acid ethyl ester;
3-{6-[2-(2,4-difluoro-phenyl)-ethylamino]-2-methoxy-pyrimidin-4-yl}-benzoic acid;
5-{2-methoxy-6-[2-(4-methoxy-phenyl)-ethylamino]-pyrimidin-4-yl}-thiophene-2-carboxylic acid trifluoroacetate;
5-{2-methoxy-6-[2-(4-methoxy-phenyl)-ethylamino]-pyrimidin-4-yl}-thiophene-2-carbaldehyde;
4-{2-methoxy-6-[2-(4-methoxy-phenyl)-ethylamino]-pyrimidin-4-yl}-thiophene-2-carbaldehyde;
[6-(3,5-dimethyl-isoxazol-4-yl)-2-methoxy-pyrimidin-4-yl]-[2-(4-methoxy-phenyl)-ethyl]-amine;
[2-methoxy-6-(5-methyl-thiophen-2-yl)-pyrimidin-4-yl]-[2-(4-methoxy-phenyl)-ethyl]-amine;
[2-(4-methoxy-phenyl)-ethyl]-[2-methoxy-6-(1H-pyrazol-4-yl)-pyrimidin-4-yl]-amine;
(6-isoquinolin-5-yl-2-methoxy-pyrimidin-4-yl)-[2-(4-methoxy-phenyl)-ethyl]-amine;
(5-{2-methoxy-6-[2-(4-methoxy-phenyl)-ethylamino]-pyrimidin-4-yl}-thiophen-2-yl)-methanol;
(3-{2-methoxy-6-[2-(4-methoxy-phenyl)-ethylamino]-pyrimidin-4-yl}-thiophen-2-yl)-methanol;
(3-{2-methoxy-6-[2-(4-methoxy-phenyl)-ethylamino]-pyrimidin-4-yl}-phenyl)-methanol;
(3-{6-[2-(2-chloro-6-fluoro-phenyl)-ethylamino]-2-methoxy-pyrimidin-4-yl}-phenyl)-methanol;
[2-(4-methoxy-phenyl)-ethyl]-(2-methoxy-6-quinolin-6-yl-pyrimidin-4-yl)-amine;
[2-(4-methoxy-phenyl)-ethyl]-(2-methoxy-6-quinolin-3-yl-pyrimidin-4-yl)-amine;
[6-(1H-indol-5-yl)-2-methoxy-pyrimidin-4-yl]-[2-(4-methoxy-phenyl)-ethyl]-amine;
N-(2-{2-methoxy-6-[2-(4-methoxy-phenyl)-ethylamino]-pyrimidin-4-yl}-phenyl)-methanesulfonamide;
4-{2-methoxy-6-[2-(4-methoxy-phenyl)-ethylamino]-pyrimidin-4-yl}-benzamide;
[2-methoxy-6-(1-methyl-1H-indol-5-yl)-pyrimidin-4-yl]-[2-(4-methoxy-phenyl)-ethyl]-amine;
(6-benzo[b]thiophen-2-yl-2-methoxy-pyrimidin-4-yl)-[2-(4-methoxy-phenyl)-ethyl]-amine;
1-(4-{2-methoxy-6-[2-(4-methoxy-phenyl)-ethylamino]-pyrimidin-4-yl}-phenyl)-ethanone;
[6-(3-methanesulfonyl-phenyl)-2-methoxy-pyrimidin-4-yl]-[2-(4-methoxy-phenyl)-ethyl]-amine;
[6-(2,3-dihydro-benzofuran-5-yl)-2-methoxy-pyrimidin-4-yl]-[2-(4-methoxy-phenyl)-ethyl]-amine;
[2-methoxy-6-(4-morpholin-4-yl-phenyl)-pyrimidin-4-yl]-[2-(4-methoxy-phenyl)-ethyl]-amine;
[6-(4-dimethylamino-phenyl)-2-methoxy-pyrimidin-4-yl]-[2-(4-methoxy-phenyl)-ethyl]-amine;
[2-methoxy-6-(5-oxazol-5-yl-thiophen-2-yl)-pyrimidin-4-yl]-[2-(4-methoxy-phenyl)-ethyl]-amine;
2-methoxy-6-(3-oxazol-5-yl-phenyl)-pyrimidin-4-yl]-[2-(4-methoxy-phenyl)-ethyl]-amine;
[6-(5-difluoromethyl-thiophen-2-yl)-2-methoxy-pyrimidin-4-yl]-[2-(4-methoxy-phenyl)-ethyl]-amine;
[2-(4-methoxy-phenyl)-ethyl]-[2-methoxy-6-(5-pyrrolidin-1-ylmethyl-thiophen-2-yl)-pyrimidin-4-yl]-amine;
6-{4-fluoro-3-[(2-methoxy-ethylamino)-methyl]-phenyl}-2-methoxy-pyrimidin-4-yl)-[2-(4-methoxy-phenyl)-ethyl]-amine hydrochloride;
4-[2-(3-{2-methoxy-6-[2-(4-methoxy-phenyl)-ethylamino]-pyrimidin-4-yl}-benzylamino)-ethyl]-phenol hydrochloride;
N-(2-fluoro-5-{2-methoxy-6-[2-(4-methoxy-phenyl)-ethylamino]-pyrimidin-4-yl}-benzyl)-N',N'-dimethyl-ethane-1,2-diamine hydrochloride;
[6-(1H-benzoimidazol-5-yl)-2-methoxy-pyrimidin-4-yl]-[2-(4-methoxy-phenyl)-ethyl]-amine;
[6-(1H-benzotriazol-5-yl)-2-methoxy-pyrimidin-4-yl]-[2-(4-methoxy-phenyl)-ethyl]-amine;
6-{2-methoxy-6-[2-(4-methoxy-phenyl)-ethylamino]-pyrimidin-4-yl}-3H-benzooxazol-2-one;
3-{2-methoxy-6-[2-(4-methoxy-phenyl)-ethylamino]-pyrimidin-4-yl}-phenol hydrochloride;
3-{6-[2-(2,4-dichloro-phenyl)-ethylamino]-2-methoxy-pyrimidin-4-yl}-benzoic acid;
3-{6-[2-(2-chloro-6-fluoro-phenyl)-ethylamino]-2-methoxy-pyrimidin-4-yl}-benzoic acid hydrochloride;
-[2-(3,4-dimethoxy-phenyl)-ethyl]-[6-(3,4-dimethoxy-phenyl)-2-isopropoxy-pyrimidin-4-yl]-amine;
[6-(3,4-dimethoxy-phenyl)-2-ethoxy-pyrimidin-4-yl]-[2-(3,4-dimethoxy-phenyl)-ethyl]-amine;
2-fluoro-5-{2-methoxy-6-[2-(4-methoxy-phenyl)-ethylamino]-pyrimidin-4-yl}-benzoic acid;
3-{6-[2-(2-chloro-6-fluoro-phenyl)-ethylamino]-2-methoxy-pyrimidin-4-yl}-benzoic acid;
2-methoxy-5-{2-methoxy-6-[2-(4-methoxy-phenyl)-ethylamino]-pyrimidin-4-yl}-benzoic acid;
[2-methoxy-6-(1-oxy-pyridin-3-yl)-pyrimidin-4-yl]-[2-(4-methoxy-phenyl)-ethyl]-amine;
[2-(2,2-difluoro-benzo[1,3]dioxol-5-yl)-ethyl]-[2-methoxy-6-(1-oxy-pyridin-3-yl)-pyrimidin-4-yl]-amine;

2-(3-{2-methoxy-6-[2-(4-methoxy-phenyl)-ethylamino]-pyrimidin-4-yl}-phenoxy)-2-methyl-propionic acid ethyl ester;
(3-{2-methoxy-6-[2-(4-methoxy-phenyl)-ethylamino]-pyrimidin-4-yl}-phenoxy)-acetic acid methyl ester;
(3-{6-[2-(2,4-dichloro-phenyl)-ethylamino]-2-methoxy-pyrimidin-4-yl}-phenoxy)-acetic acid methyl ester;
(5-{6-[2-(2-chloro-6-fluoro-phenyl)-ethylamino]-2-methoxy-pyrimidin-4-yl}-2-oxo-2H-pyridin-1-yl)-acetic acid methyl ester;
(3-{6-[2-(2,4-dichloro-phenyl)-ethylamino]-2-methoxy-pyrimidin-4-yl}-phenoxy)-acetonitrile;
(3-{6-[2-(2-chloro-6-fluoro-phenyl)-ethylamino]-2-methoxy-pyrimidin-4-yl}-phenoxy)-acetonitrile;
2-(3-{2-methoxy-6-[2-(4-methoxy-phenyl)-ethylamino]-pyrimidin-4-yl}-phenoxy)-2-methyl-propionic acid;
(3-{2-methoxy-6-[2-(4-methoxy-phenyl)-ethylamino]-pyrimidin-4-yl}-phenoxy)-acetic acid;
(5-{6-[2-(2-chloro-6-fluoro-phenyl)-ethylamino]-2-methoxy-pyrimidin-4-yl}-2-oxo-2H-pyridin-1-yl)-acetic acid;
2-(3-{6-[2-(2,4-dichloro-phenyl)-ethylamino]-2-methoxy-pyrimidin-4-yl}-phenoxy)-2-methyl-propionic acid;
2-chloro-5-{2-methoxy-6-[2-(4-methoxy-phenyl)-ethylamino]-pyrimidin-4-yl}-benzoic acid hydrochloride salt;
[2-(4-methoxy-phenyl)-ethyl]-{2-methoxy-6-[3-(1H-tetrazol-5-yl)-phenyl]-pyrimidin-4-yl}-amine;
[2-(4-methoxy-phenyl)-ethyl]-{2-methoxy-6-[3-(1H-tetrazol-5-ylmethyl)-phenyl]-pyrimidin-4-yl}-amine hydrochloride;
{2-methoxy-6-[4-methoxy-3-(1H-tetrazol-5-yl)-phenyl]-pyrimidin-4-yl}-[2-(4-methoxy-phenyl)-ethyl]-amine;
N-(3-{2-methoxy-6-[2-(4-methoxy-phenyl)-ethylamino]-pyrimidin-4-yl}-benzoyl)-methanesulfonamide;
3-{6-[2-(3,4-dimethoxy-phenyl)-ethylamino]-2-methoxy-pyrimidin-4-yl}-N-(2-pyrrolidin-1-yl-ethyl)-benzamide;
2-fluoro-5-{2-methoxy-6-[2-(4-methoxy-phenyl)-ethylamino]-pyrimidin-4-yl}-benzaldehyde oxime;
3-{2-methoxy-6-[2-(4-methoxy-phenyl)-ethylamino]-pyrimidin-4-yl}-benzaldehyde oxime;
2-methoxy-5-{2-methoxy-6-[2-(4-methoxy-phenyl)-ethylamino]-pyrimidin-4-yl}-benzaldehyde oxime;
3-{2-methoxy-6-[2-(4-methoxy-phenyl)-ethylamino]-pyrimidin-4-yl}-thiophene-2-carbaldehyde oxime;
1-(5-{2-methoxy-6-[2-(4-methoxy-phenyl)-ethylamino]-pyrimidin-4-yl}-thiophen-2-yl)-ethanone oxime;
5-{2-methoxy-6-[2-(4-methoxy-phenyl)-ethylamino]-pyrimidin-4-yl}-thiophene-2-carbaldehyde oxime;
[6-(3-aminomethyl-4-fluoro-phenyl)-2-methoxy-pyrimidin-4-yl]-[2-(4-methoxy-phenyl)-ethyl]-amine hydrochloride;
N-(2-Fluoro-5-{2-methoxy-6-[2-(4-methoxy-phenyl)-ethylamino]-pyrimidin-4-yl}-benzyl)-2-methoxy-acetamide hydrochloride;
[2-methoxy-6-(3-methoxy-phenyl)-pyrimidin-4-yl]-[2-(4-methoxy-phenyl)-2-methyl-propyl]-amine;
5-{6-[2-(2-chloro-6-fluoro-phenyl)-ethylamino]-2-methoxy-pyrimidin-4-yl}-1H-pyridin-2-one;
5-{6-[2-(2-chloro-6-fluoro-phenyl)-ethylamino]-2-methoxy-pyrimidin-4-yl}-1-(5-oxo-4,5-dihydro-[1,3,4]oxadiazol-2-ylmethyl)-1H-pyridin-2-one;
3-(3-{6-[2-(2,4-dichloro-phenyl)-ethylamino]-2-methoxy-pyrimidin-4-yl-phenoxymethyl)-4H-[1,2,4]oxadiazol-5-one hydrochloride;
3-(3-{6-[2-(2-chloro-6-fluoro-phenyl)-ethylamino]-2-methoxy-pyrimidin-4-yl}-benzyl)-4H-[1,2,4]oxadiazol-5-one hydrochloride;
3-(3-{6-[2-(2-chloro-6-fluoro-phenyl)-ethylamino]-2-methoxy-pyrimidin-4-yl}-phenoxymethyl)-4H-[1,2,4]oxadiazol-5-one hydrochloride;
3-{2-methoxy-6-[2-(4-methoxy-phenyl)-ethylamino]-pyrimidin-4-yl}-benzoic acid;
3-{2-methoxy-6-[2-(4-trifluoromethoxy-phenyl)-ethylamino]-pyrimidin-4-yl}-benzoic acid;
[2-(3,4-dimethoxy-phenyl)-ethyl]-(2-methoxy-6-thiophen-2-yl-pyrimidin-4-yl)amine;
[2-(3,4-dimethoxy-phenyl)-ethyl]-(6-furan-2-yl-2-methoxy-pyrimidin-4-yl)-amine;
(6-biphenyl-4-yl-2-methoxy-pyrimidin-4-yl)-[2-(3,4-dimethoxy-phenyl)-ethyl]-amine;
3-{6-[2-(4-fluoro-phenyl)-ethylamino]-2-methoxy-pyrimidin-4-yl}-benzoic acid hydrochloride;
3-{2-methoxy-6-[2-(4-methoxy-phenyl)-ethylamino]-pyrimidin-4-yl}-benzamide;
1-(3-{2-methoxy-6-[2-(4-methoxy-phenyl)-ethylamino]-pyrimidin-4-yl}-phenyl)-ethanone;
3-{6-[2-(2,4-dichloro-phenyl)-ethylamino]-2-methoxy-pyrimidin-4-yl}-phenol hydrochloride;
2-fluoro-5-{2-methoxy-6-[2-(4-methoxy-phenyl)-ethylamino]-pyrimidin-4-yl}-benzaldehyde;
3-{6-[2-(3,4-dimethoxy-phenyl)-ethylamino]-2-methoxy-pyrimidin-4-yl}-benzoic acid;
3-{2-methoxy-6-[2-(4-methoxy-phenyl)-ethylamino]-pyrimidin-4-yl}-thiophene-2-carbaldehyde;
1-(5-{2-methoxy-6-[2-(4-methoxy-phenyl)-ethylamino]-pyrimidin-4-yl}-thiophen-2-yl)-ethanone;
3-{6-[2-(4-chlorophenyl)-ethylamino]-2-methoxy-pyrimidin-4-yl}-benzoic acid hydrochloride;
[2-methoxy-6-(6-methoxy-pyridin-3-yl)-pyrimidin-4-yl]-[2-(4-methoxy-phenyl)-ethyl]-amine;
3-{2-methoxy-6-[2-(4-methoxy-phenyl)-ethylamino]-pyrimidin-4-yl}-phenol;
3-{6-[2-(2,4-dichloro-phenyl)-ethylamino]-2-methoxy-pyrimidin-4-yl}-phenol;
[2-(4-methoxy-phenyl)-ethyl]-(2-methoxy-6-pyridin-4-yl-pyrimidin-4-yl)-amine;
2-{2-methoxy-6-[2-(4-methoxy-phenyl)-ethylamino]-pyrimidin-4-yl}-phenol;
(3-{2-methoxy-6-[2-(4-methoxy-phenyl)-ethylamino]-pyrimidin-4-yl}-phenyl)-acetonitrile;
3-{2-methoxy-6-[2-(4-methoxy-phenyl)-ethylamino]-pyrimidin-4-yl}-benzonitrile;
3-{2-methoxy-6-[2-(4-methoxy-phenyl)-ethylamino]-pyrimidin-4-yl}-benzaldehyde;
3-{6-[2-(2-chloro-6-fluoro-phenyl)-ethylamino]-2-methoxy-pyrimidin-4-yl}-benzaldehyde;
3-{6-[2-(2,4-dichloro-phenyl)-ethylamino]-2-methoxy-pyrimidin-4-yl}-benzoic acid;
[2-methoxy-6-(pyridin-3-yl)-pyrimidin-4-yl]-[2-(4-methoxy-phenyl)-ethyl]-amine;
2-methoxy-5-{2-methoxy-6-[2-(4-methoxy-phenyl)-ethylamino]-pyrimidin-4-yl}-benzaldehyde;
2-chloro-5-{2-methoxy-6-[2-(4-methoxy-phenyl)-ethylamino]-pyrimidin-4-yl}-benzoic acid ethyl ester;
{2-methoxy-6-[3-(3-methyl-[1,2,4]oxadiazol-5-yl)-phenyl]-pyrimidin-4-yl}-[2-(4-methoxy-phenyl)-ethyl]-amine;
{2-methoxy-6-[3-(5-methyl-2H-[1,2,4]triazol-3-yl)-phenyl]-pyrimidin-4-yl}-[2-(4-methoxy-phenyl)-ethyl]-amine;

{2-methoxy-6-[3-(3-methyl-isoxazol-5-yl)-phenyl]-pyrimidin-4-yl}-[2-(4-methoxy-phenyl)-ethyl]-amine;
{2-methoxy-6-[3-(5-methyl-2H-pyrazol-3-yl)-phenyl]-pyrimidin-4-yl}-[2-(4-methoxy-phenyl)-ethyl]-amine;
[2-(3-fluoro-4-methoxy-phenyl)-ethyl]-{2-methoxy-6-[3-(2H-tetrazol-5-yl)-phenyl]-pyrimidin-4-yl}-amine;
1-ethyl-3-(3-{2-methoxy-6-[2-(4-methoxy-phenyl)-ethylamino]-pyrimidin-4-yl}-phenyl)-urea;
2-(3-{6-[2-(2,4-dichloro-phenyl)-ethylamino]-2-methoxy-pyrimidin-4-yl}-phenoxy)-2-methyl-propionic acid ethyl ester;
[2-(4-chloro-phenyl)-1-methyl-ethyl]-[6-(3,4-dimethoxy-phenyl)-2-methoxy-pyrimidin-4-yl]-amine;
[2-methoxy-6-(3-methoxy-phenyl)-pyrimidin-4-yl]-[2-(4-nitro-phenyl)-ethyl]-amine;
[2-methoxy-6-(3-methoxy-phenyl)-pyrimidin-4-yl]-[2-(4-trifluoromethoxy-phenyl)-ethyl]-amine;
[2-(2-chloro-6-fluoro-phenyl)-ethyl]-[2-methoxy-6-(3-methoxy-phenyl)-pyrimidin-4-yl]-amine hydrochloride;
[2-methoxy-6-(3-methoxy-phenyl)-pyrimidin-4-yl]-(2-thiophen-2-yl-ethyl)-amine hydrochloride;
3-{2-[2-methoxy-6-(3-methoxy-phenyl)-pyrimidin-4-ylamino]-ethyl}-1H-indol-5-ol;
[2-(6-methoxy-1H-indol-3-yl)-ethyl]-[2-methoxy-6-(3-methoxy-phenyl)-pyrimidin-4-yl]-amine hydrochloride;
[2-(5-methoxy-1H-indol-3-yl)-ethyl]-[2-methoxy-6-(3-methoxy-phenyl)-pyrimidin-4-yl]-amine hydrochloride;
[2-methoxy-6-(3-methoxy-phenyl)-pyrimidin-4-yl]-(2-pyridin-3-yl-ethyl)-amine hydrochloride;
[2-(4-amino-phenyl)-ethyl]-[2-methoxy-6-(3-methoxy-phenyl)-pyrimidin-4-yl]-amine hydrochloride;
(4-methoxy-benzyl)-[2-methoxy-6-(3-methoxy-phenyl)-pyrimidin-4-yl]-amine hydrochloride;
[2-methoxy-6-(3-methoxy-phenyl)-pyrimidin-4-yl]-(3-phenyl-propyl)-amine hydrochloride;
[2-(1H-imidazol-4-yl)-ethyl]-[2-methoxy-6-(3-methoxy-phenyl)-pyrimidin-4-yl]-amine;
-2-[2-methoxy-6-(3-methoxy-phenyl)-pyrimidin-4-ylamino]-3-(4-methoxy-phenyl)-propionic acid;
[2-methoxy-6-(3-methoxy-phenyl)-pyrimidin-4-yl]-[2-(4-methoxy-phenyl)-ethyl]-amine;
[2-methoxy-6-(5-methyl-[1,3,4]oxadiazol-2-yl)-pyrimidin-4-yl]-[2-(4-methoxy-phenyl)-ethyl]-amine;
(2-methoxy-6-oxazol-5-yl-pyrimidin-4-yl)-[2-(4-methoxy-phenyl)-ethyl]-amine;
3-{6-[2-(2,2-difluoro-benzo[1,3]dioxol-5-yl)-ethylamino]-2-methoxy-pyrimidin-4-yl}-benzoic acid;
[2-(2,2-difluoro-benzo[1,3]dioxol-5-yl)-ethyl]-(2-methoxy-6-pyridin-3-yl-pyrimidin-4-yl)-amine hydrochloride;
N-(3-{6-[2-(4-difluoromethoxy-phenyl)-ethylamino]-2-methoxy-pyrimidin-4-yl}-phenyl)-acetamide hydrochloride;
[2-(4-difluoromethoxy-phenyl)-ethyl]-[6-(3-methanesulfonyl-phenyl)-2-methoxy-pyrimidin-4-yl]-amine hydrochloride;
3-{6-[2-(2-chloro-6-fluoro-phenyl)-ethylamino]-2-methoxy-pyrimidin-4-yl}-phenol;
2-(3-{6-[2-(2,4-dichloro-phenyl)-ethylamino]-2-methoxy-pyrimidin-4-yl}-phenyl)-propionic acid hydrochloride;
(5-{6-[2-(2-fluoro-4-trifluoromethyl-phenyl)-ethylamino]-2-methoxy-pyrimidin-4-yl}-1H-indol-3-yl)-acetic acid;
[6-(1H-indol-6-yl)-2-methoxy-pyrimidin-4-yl]-[2-(4-methoxy-phenyl)-ethyl]-ammonium trifluoroacetate;
[6-(1H-indazol-6-yl)-2-methoxy-pyrimidin-4-yl]-[2-(4-methoxy-phenyl)-ethyl]-amine;
3-{6-[2-(2,6-dichloro-phenyl)-ethylamino]-2-methoxy-pyrimidin-4-yl}-benzoic acid;
[2-(4-methoxy-phenyl)-ethyl]-{2-methoxy-6-[3-(1H-tetrazol-5-yl)-phenyl]-pyrimidin-4-yl}-amine, sodium salt;
2-methoxy-5-{2-methoxy-6-[2-(4-methoxy-phenyl)-ethylamino]-pyrimidin-4-yl}-benzonitrile;
(3-{6-[2-(2-chloro-6-fluoro-phenyl)-ethylamino]-2-methoxy-pyrimidin-4-yl}-benzyloxy)-acetic acid;
(3-{6-[2-(2,4-dichloro-phenyl)-ethylamino]-2-methoxy-pyrimidin-4-yl}-benzoylamino)-acetic acid ethyl ester;
(3-{6-[2-(2,4-dichloro-phenyl)-ethylamino]-2-methoxy-pyrimidin-4-yl}-benzoylamino)-acetic acid;
ethyl-carbamic acid 3-{6-[2-(2,4-dichloro-phenyl)-ethylamino]-2-methoxy-pyrimidin-4-yl}-phenyl ester;
5-{2-methoxy-6-[2-(4-methoxy-phenyl)-ethylamino]-pyrimidin-4-yl}-thiophene-2-carboxylic acid;
5-{2-methoxy-6-[2-(4-methoxy-phenyl)-ethylamino]-pyrimidin-4-yl}-thiophene-2-carboxylic acid methylamide trifluoroacetate,
[2-Methoxy-6-(2-methoxy-benzyloxy)-pyrimidin-4-yl]-[2-(4-methoxy-phenyl)-ethyl]-amine hydrochloride,
(3-{6-[2-(3,4-dimethoxy-phenyl)-ethylamino]-2-methoxy-pyrimidin-4-yloxy}-benzoic acid methyl ester,
N-[2-(3-{6-[2-(2-fluoro-4-trifluoromethyl-phenyl)-ethylamino]-2-methoxy-pyrimidin-4-yl}-phenyl)-ethyl]-2-methoxy-acetamide,
N-[2-(3-{6-[2-(2-fluoro-4-trifluoromethyl-phenyl)-ethylamino]-2-methoxy-pyrimidin-4-yl}-phenyl)-ethyl]-acetamide hydrochloride,
[2-(2-fluoro-4-trifluoromethyl-phenyl)-ethyl]-[2-methoxy-6-(3-oxiranylmethoxy-phenyl)-pyrimidin-4-yl]-amine,
2-{3-[6-(2,2-difluoro-2-phenyl-ethylamino)-2-methoxy-pyrimidin-4-yl]-phenyl}-2-methyl-propionic acid,
2-[3-(2-methoxy-6-{2-[4-(5-methyl-[1,3,4]oxadiazol-2-yl)-phenyl]-ethylamino}-pyrimidin-4-yl)-phenyl]-2-methyl-propionic acid,
5-(3-{6-[2-(3,4-difluoro-phenyl)-ethylamino]-2-methoxy-pyrimidin-4-yl}-phenoxymethyl)-1-ethyl-2,4-dihydro-[1,2,4]triazol-3-one,
2-(2-fluoro-5-{2-methoxy-6-[2-(4-trifluoromethoxy-phenyl)-ethylamino]-pyrimidin-4-yl}-phenyl)-2-methyl-propionic acid,
2-(3-{2-methoxy-6-[(thiophen-3-ylmethyl)-amino]-pyrimidin-4-yl}-phenyl)-2-methyl-propionic acid,
1-{6-[2-(2,4-dichloro-phenyl)-ethylamino]-2-methoxy-pyrimidin-4-yl}-piperidine-3-carboxylic acid,
1-(3-{6-[2-(2,4-dichloro-phenyl)-ethylamino]-2-methoxy-pyrimidin-4-yl}-phenyl)-cyclopentanecarboxylic acid hydrochloride,
3-{6-[2-(2,4-dichloro-phenyl)-ethylamino]-2-methoxy-pyrimidin-4-yl}-benzoic acid 2-morpholin-4-yl-ethyl ester,
3-{6-[2-(2,4-dichloro-phenyl)-ethylamino]-2-methoxy-pyrimidin-4-yl}-benzoic acid 2-(4-methyl-piperazin-1-yl)-ethyl ester,
3-{6-[2-(2,4-dichloro-phenyl)-ethylamino]-2-methoxy-pyrimidin-4-yl}-benzoic acid ethyl ester,
(3-{6-[2-(2,4-dichloro-phenyl)-ethylamino]-2-methoxy-pyrimidin-4-yl}-phenyl)-methanol, (3'-chloro-4'-{2-[6-(3-hydroxymethyl-phenyl)-2-methoxy-pyrimidin-4-ylamino]-ethyl}-biphenyl-3-yl)-methanol,
4-(3-{6-[2-(2,4-dichloro-phenyl)-ethylamino]-2-methoxy-pyrimidin-4-yl}-phenyl)-tetrahydro-pyran-4-carboxylic acid,
N-[4-(3-{6-[2-(2,4-dichloro-phenyl)-ethylamino]-2-methoxy-pyrimidin-4-yl}-phenyl)-tetrahydro-pyran-4-carbonyl]-methanesulfonamide,
4-(3-{6-[2-(2,4-dichloro-phenyl)-ethylamino]-2-methoxy-pyrimidin-4-yl}-phenyl)-tetrahydro-pyran-4-carboxylic acid ethyl ester,
(3-{6-[2-(2,4-dichloro-phenyl)-ethylamino]-2-methoxy-pyrimidin-4-yl}-phenyl)-difluoro-acetic acid,
ethanesulfonic acid[2-(3-{6-[2-(2,4-dichloro-phenyl)-ethylamino]-2-methoxy-pyrimidin-4-yl}-phenyl)-2,2-difluoro-acetyl]-amide,
(3-{6-[2-(2,4-dichloro-phenyl)-ethylamino]-2-methoxy-pyrimidin-4-yl}-phenyl)-difluoro-acetic acid ethyl ester,
(3-{6-[2-(2,4-dichloro-phenyl)-ethylamino]-2-methoxy-pyrimidin-4-yl}-phenyl)-acetonitrile,
(3-{6-[2-(2,4-dichloro-phenyl)-ethylamino]-2-methoxy-pyrimidin-4-yl}-phenyl)-difluoro-acetonitrile,
[2-(2,4-dichloro-phenyl)-ethyl]-(6-{3-[difluoro-(1H-tetrazol-5-yl)-methyl]-phenyl}-2-methoxy-pyrimidin-4-yl)-amine,
2-{3-[6-(Indan-1-ylamino)-2-methoxy-pyrimidin-4-yl]-phenyl}-2-methyl-propionic acid,
2-{3-[6-(Indan-2-ylamino)-2-methoxy-pyrimidin-4-yl]-phenyl}-2-methyl-propionic acid,
N-[4-(3-{2-Methoxy-6-[2-(4-trifluoromethoxy-phenyl)-ethylamino]-pyrimidin-4-yl}-phenyl)-tetrahydro-pyran-4-carbonyl]-methanesulfonamide,
4-(3-{2-Methoxy-6-[2-(4-trifluoromethoxy-phenyl)-ethylamino]-pyrimidin-4-yl}-phenyl)-tetrahydro-pyran-4-carboxylic acid methyl ester,
5-{6-[2-(2,4-dichloro-phenyl)-ethylamino]-2-methoxy-pyrimidin-4-yl}-thiophene-2-carboxylic acid,
5-{2-Methoxy-6-[2-(4-trifluoromethoxy-phenyl)-ethylamino]-pyrimidin-4-yl}-2,3-dihydro-benzofuran-2-carboxylic acid hydrochloride,
2-(3-{6-[(2,3-dihydro-benzofuran-2-ylmethyl)-amino]-2-methoxy-pyrimidin-4-yl}-phenyl)-2-methyl-propionic acid,
2-(3-{6-[(isochroman-1-ylmethyl)-amino]-2-methoxy-pyrimidin-4-yl}-phenyl)-2-methyl-propionic acid,
2-(3-{2-methoxy-6-[(4-methyl-3,4-dihydro-2H-benzo[1,4]oxazin-2-ylmethyl)-amino]-pyrimidin-4-yl}-phenyl)-2-methyl-propionic acid,
2-(3-{6-[(benzofuran-5-ylmethyl)-amino]-2-methoxy-pyrimidin-4-yl}-phenyl)-2-methyl-propionic acid,
N-(6-{6-[2-(2,4-dichloro-phenyl)-ethylamino]-2-methoxy-pyrimidin-4-yl}-benzothiazol-2-yl)-acetamide,
ethanesulfonic acid [2-(3-{6-[2-(2,4-dichloro-phenyl)-ethylamino]-2-methoxy-pyrimidin-4-yl}-phenyl)-2-methyl-propionyl]-amide,
N-[2-(3-{6-[2-(2,4-dichloro-phenyl)-ethylamino]-2-methoxy-pyrimidin-4-yl}-phenyl)-2-methyl-propionyl]-C-phenyl-methanesulfonamide,
2-(3-{6-[2-(2,4-dichloro-phenyl)-ethylamino]-2-methoxy-pyrimidin-4-yl}-phenyl)-2-methyl-1-morpholin-4-yl-propan-1-one,
2-(3-{6-[2-(2,4-dichloro-phenyl)-ethylamino]-2-methoxy-pyrimidin-4-yl}-phenyl)-N-(tetrahydro-pyran-4-yl)-isobutyramide,
2-(3-{6-[2-(2,4-dichloro-phenyl)-ethylamino]-2-methoxy-pyrimidin-4-yl}-phenyl)-N-(1H-tetrazol-5-yl)-isobutyramide,
1-{6-[2-(2,4-dichloro-phenyl)-ethylamino]-2-methoxy-pyrimidin-4-yl}-piperidine-4-carboxylic acid,
2-(2-chloro-5-{6-[2-(2,4-dichloro-phenyl)-ethylamino]-2-methoxy-pyrimidin-4-yl}-phenyl)-propan-2-ol, or
2-(3-{6-[2-(2,4-dichloro-phenyl)-ethylamino]-2-methoxy-pyrimidin-4-yl}-4-fluoro-phenyl)-2-methyl-propionic acid hydrochloride.

38. A pharmaceutical composition comprising a pharmaceutically effective dosage amount of the compound according to claim 1 or an N-oxide thereof, or a pharmaceutically acceptable salt or hydrate thereof, in admixture with a pharmaceutically acceptable carrier.

39. A pharmaceutical composition comprising a pharmaceutically effective amount of the compound according to claim 1 or an N-oxide thereof, or a pharmaceutically acceptable salt or hydrate thereof, and a compound selected from the group consisting of an antihistamine, a leukotriene antagonist, a beta agonist, a PDE4 inhibitor, a TP antagonist and a CrTh2 antagonist, in admixture with a pharmaceutically acceptable carrier.

40. The pharmaceutical composition according to claim 39, wherein the antihistamine is fexofenadine, loratadine or cetirizine, the leukotriene antagonist is montelukast or zafirlukast, the beta agonist is albuterol, salbuterol or terbutaline, the PDE4 inhibitor is roflumilast or cilomilast, the TP antagonist is ramatroban, and the CrTh2 antagonist is ramatroban.

* * * * *